United States Patent
Pinto et al.

(10) Patent No.: US 7,626,039 B2
(45) Date of Patent: Dec. 1, 2009

(54) ARYLPROPIONAMIDE, ARYLACRYLAMIDE, AYRLPROPYNAMIDE, OR ARYLMETHYLUREA ANALOGS AS FACTOR XIA INHIBITORS

(75) Inventors: Donald J. P. Pinto, Churchville, PA (US); Joanne M. Smallheer, Yardley, PA (US); James R. Corte, Lawrenceville, NJ (US); Zilun Hu, Jamison, PA (US); Cullen L. Cavallaro, Robbinsville, NJ (US); Paul J. Gilligan, Wilmington, DE (US); Mimi L. Quan, Yardley, PA (US); Leon M. Smith, II, Somerset, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 223 days.

(21) Appl. No.: 11/610,027

(22) Filed: Dec. 13, 2006

(65) Prior Publication Data

US 2008/0161373 A1 Jul. 3, 2008

Related U.S. Application Data

(60) Provisional application No. 60/750,130, filed on Dec. 14, 2005, provisional application No. 60/821,163, filed on Aug. 2, 2006, provisional application No. 60/865,211, filed on Nov. 10, 2006.

(51) Int. Cl.
*A61K 31/41* (2006.01)
(52) U.S. Cl. .............. 548/335.1; 548/343.1; 548/343.5; 548/311.1
(58) Field of Classification Search .................. None
See application file for complete search history.

(56) References Cited

U.S. PATENT DOCUMENTS

| | | | |
|---|---|---|---|
| 6,852,725 | B1 | 2/2005 | Thurieau et al. |
| 7,129,264 | B2 | 10/2006 | Smallheer et al. |
| 7,138,412 | B2 | 11/2006 | Quan et al. |
| 7,417,063 | B2 | 8/2008 | Smallheer et al. |
| 7,429,604 | B2 | 9/2008 | Corte et al. |
| 7,453,002 | B2 | 11/2008 | Hangeland et al. |
| 7,459,564 | B2 | 12/2008 | Corte et al. |
| 2004/0132788 | A1 | 7/2004 | Chabrier De Lassauniere et al. |
| 2004/0180855 | A1 | 9/2004 | Schumacher et al. |
| 2004/0186151 | A1* | 9/2004 | Mjalli et al. ............... 514/365 |
| 2004/0220206 | A1 | 11/2004 | Smallheer et al. |
| 2004/0235847 | A1 | 11/2004 | Quan et al. |
| 2005/0203143 | A1 | 9/2005 | Breslin et al. |
| 2005/0228000 | A1 | 10/2005 | Smallheer et al. |
| 2005/0282805 | A1 | 12/2005 | Hangeland et al. |
| 2006/0004013 | A1* | 1/2006 | Kimura et al. ............. 514/249 |
| 2006/0009455 | A1 | 1/2006 | Corte et al. |
| 2006/0154915 | A1 | 7/2006 | Corte et al. |

FOREIGN PATENT DOCUMENTS

| | | |
|---|---|---|
| WO | WO98/27108 | 11/1997 |
| WO | WO98/57951 A | 12/1998 |
| WO | WO99/64401 A | 12/1999 |
| WO | WO99/65942 A1 | 12/1999 |
| WO | WO01/02387 | 1/2001 |
| WO | WO01/27079 | 4/2001 |
| WO | WO02/10140 | 2/2002 |
| WO | WO2003/064440 A | 8/2003 |
| WO | WO2004/071448 A | 8/2004 |
| WO | WO 2004/071448 A2 * | 8/2004 |
| WO | WO2005/082895 A | 9/2005 |
| WO | WO2006/061638 | 6/2006 |
| WO | WO2007/070816 A2 | 6/2007 |
| WO | WO2007/070818 A1 | 6/2007 |

OTHER PUBLICATIONS

Vippagunta et al, "Crystalline Solids", Advanced Drug Delivery Reviews, vol. 48, pp. 3-26 (2001).*
Gavezzotti, "Are Crystal Structures Predictable?", Accounts of Chemical Research, vol. 27, pp. 309-314 (1994).*
U.S. Appl. No. 12/266,659, filed Nov. 7, 2008, James R. Corte.
U.S. Appl. No. 12/097,068, filed Jun. 12, 2008, Wei Han.
U.S. Appl. No. 12/097,080, filed Jun. 12, 2008, James R. Corte.
U.S. Appl. No. 12/097,068, filed Dec. 13, 2006, Wei Han.
U.S. Appl. No. 12/097,080, filed Dec. 13, 2006, James R. Corte.
Walsh, P.N., *Platelets and Factor XI Bypass the Contact System of Blood Coagulation*, Thromb. Haemostasis, 1999, vol. 82, pp. 234. 242.
Coleman, R., *Contact Activation Pathway*, Hemostasis and Thrombosis, pp. 103-122, 2001.

(Continued)

*Primary Examiner*—Kamal A Saeed
*Assistant Examiner*—Valerie Rodriguez-Garcia
(74) *Attorney, Agent, or Firm*—Jing G. Sun

(57) ABSTRACT

The present invention provides compounds of Formula (I):

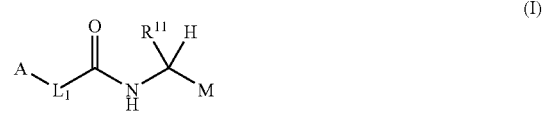

(I)

or a stereoisomer, tautomer, pharmaceutically acceptable salt or solvate form thereof, wherein the variables A, $L_1$, M and $R^{11}$ are as defined herein. The compounds of Formula (I) are selective inhibitors of serine protease enzymes of the coagulation cascade and/or contact activation system; for example thrombin, factor Xa, factor XIa, factor IXa, factor VIIa and/or plasma kallikrein. In particular, it relates to compounds that are selective factor XIa inhibitors or dual inhibitors of fXIa and plasma kallikrein. This invention also relates to pharmaceutical compositions comprising these compounds and methods of treating thromboembolic and/or inflammatory disorders using the same.

14 Claims, No Drawings

OTHER PUBLICATIONS

Schmaier A.H., *Contact Activation*, Thrombosis and Hemorrhage, pp. 105-128, 1998.

Galiani, D. *Activation of Factor IX by Factor XIa*, Trends Cardiovasc. Med., vol. 10, No. 5, pp. 198-204, 2000.

Bouma, B.N. et al., *Thrombin-Activatable Fibrinolysis Inhibitor*, Thromb. Res. 2001, vol. 101, 329-354.

Gailani D., *Gene Targeting in Hemostasis, Factor XI*, Frontiers in Bioscience, 2001, vol. 6, 201-207.

Gailani, D. et al., *A murine model of factor XI deficiency*, Blood Coagulation and Fibrinolysis, 1997, vol. 8, 134-144.

Minnema, M.C. et al., *Activation of Clotting Factors XI and IX in Patients with Acute Myocardial Infarction*, Arterioscler. Throb. Vasc. Biol., 2000, vol. 20, pp. 2489-2493.

Murakami T. et al., *Evaluation of Factor XIa-$\alpha_1$-Antitrypsin in Plasma, a Contact Phase-Activated Coagulation Factor-Inhibitor Complex, in Patients with Coronary Artery Disease*, Arterioscler Thromb. Vasc. Biol., 1995, vol. 15, pp. 1107-1113.

Meijers, J.C.M. et al, *High Levels of Coagulation Factor XI as a Risk Factor for Venous Thrombosis*, N. Engl. J. Med., 2000, vol. 342, pp. 696-701.

Hirsh, J. et al., *New anticoagulants*, Blood, Jan. 15, 2005, vol. 105, No. 2. pp. 453-463.

Hoffman, M., *A cell-based model of coagulation and the role of factor VIIal*, Blood Reviews (2003), 17, 51-55.

Shariat-Madar et al., *Blood*, Jul. 1, 2006, vol. 108, No. 1, pp. 192-199.

Renne, T. et al., *Defective thrombus formation in mice lacking coagulation factor* XII, J. Exp. Medicine 2005, vol. 202, pp. 271-281.

Kleinschnitz et al., *Targeting coagulation factor XII provides protection from pathological thrombosis in cerebral ischemia without interfering with hemostasis*, J. Expl. Medicine, 2006, vol. 203, 513-518.

Chan et al., *The Characterization of Mice with a Targeted Combined Deficiency of Protein C and Factor XI*, Amer. J. Pathology 2001, vol. 158, pp. 469-479.

Gruber et al., *Factor XI-dependence of surface- and tissue factor-initiated thrombus propagation in primates*, Blood 2003, vol. 102, pp. 953-955.

Rosen et al., *FXI is Essential for Thrombus Formation Following FeCl$_3$-induced Injury of the Carotid Artery in the Mouse*, Thromb. Haemost 2002; 87; 774-776.

Wang et al., *Effects of factor IX or factor XI deficiency on ferric chloride-induced carotid artery occlusion in mice*, Journal of Thrombosis and Haemostasis, 3: 695-702, (2005).

\* cited by examiner

ARYLPROPIONAMIDE, ARYLACRYLAMIDE, AYRLPROPYNAMIDE, OR ARYLMETHYLUREA ANALOGS AS FACTOR XIA INHIBITORS

CROSS-REFERENCE TO RELATED APPLICATIONS

The present application claims priority benefit of U.S. provisional applications Ser. No. 60/750,130, filed Dec. 14, 2005; Ser. No. 60/821,163, filed Aug. 2, 2006; and Ser. No. 60/865,211, filed Nov. 10, 2006, each of which is incorporated by reference herein.

FIELD OF THE INVENTION

The present invention relates generally to novel arylpropionamide, arylacrylamide, arylpropynamide, or arylmethylurea compounds, and analogues thereof, which are useful as selective inhibitors of serine protease enzymes of the coagulation cascade and/or contact activation system; for example thrombin, factor XIa, factor Xa, factor IXa and/or factor VIIa, and/or plasma kallikrein. In particular, it relates to compounds that are selective factor XIa inhibitors or dual inhibitors of fXIa and plasma kallikrein. This invention also relates to pharmaceutical compositions comprising these compounds and methods of using the same.

BACKGROUND OF THE INVENTION

Factor XIa is a plasma serine protease involved in the regulation of blood coagulation. While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thrombotic or thromboembolic disorders and include acute coronary syndrome, unstable angina, myocardial infarction, thrombosis in the cavity of the heart, ischemic stroke, deep vein thrombosis, peripheral occlusive arterial disease, transient ischemic attack, and pulmonary embolism. In addition, thrombosis occurs on artificial surfaces in contact with blood, including catheters and artificial heart valves. Therefore, drugs that inhibit blood coagulation, or anticoagulants, are "pivotal agents for prevention and treatment of thromboembolic disorders" (Hirsh, J. et al. *Blood* 2005, 105, 453-463). Thromboembolic disorders are the largest cause of mortality and disability in the industrialized world.

Blood coagulation is initiated in vivo by the binding of tissue factor (TF) to Factor VII (FVII) to generate Factor VIIa (FVIIa). The resulting TF:FVIIa complex activates Factor IX (FIX) and Factor X (FX) which leads to the production of Factor Xa (FXa). The FXa that is generated catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Walsh, P. N. *Thromb. Haemostasis.* 1999, 82, 234-242.) The resulting burst of thrombin coverts fibrinogen to fibrin, which polymerizes to form the structural framework of a blood clot, and activates platelets, which are a key cellular component of coagulation (Hoffman, M. *Blood Reviews* 2003, 17, S1-S5). Factor XIa plays a key role in propagating this amplification loop and is thus an attractive target for anti-thrombotic therapy.

An alternative way of initiation of coagulation is operative when blood is exposed to artificial surfaces (e.g., during hemodialysis, 'on-pump' cardiovascular surgery, vessel grafts, bacterial sepsis), on cell surfaces, cellular receptors, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al. *Blood* 2006, 108, 192-199). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R. *Contact Activation Pathway*, pages 103-122 in *Hemostasis and Thrombosis*, Lippincott Williams & Wilkins 2001; Schmaier A. H. *Contact Activation*, pages 105-128 in *Thrombosis and Hemorrhage,* 1998). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al. *J. Exp. Medicine* 2005, 202, 271-281; Kleinschmitz et al. *J. Exp.l Medicine,* 2006, 203, 513-518). The fact that factor XI is down-stream from factor XIIa, combined with the identical phenotype of the XII and XI deficient mice suggest that the contact activation system could play a major role in factor XI activation in vivo.

Factor XI is a zymogen of a trypsin-like serine protease and is present in plasma at a relatively low concentration. Proteolytic activation at an internal R369-I370 bond yields a heavy chain (369 amino acids) and a light chain (238 amino acids). The latter contains a typical trypsin-like catalytic triad (H413, D464, and S557). Activation of factor XI by thrombin is believed to occur on negatively charged surfaces, most likely on the surface of activated platelets. Platelets contain high affinity (0.8 nM) specific sites (130-500/platelet) for activated factor XI. After activation, factor XIa remains surface bound and recognizes factor IX as its normal macromolecular substrate. (Galiani, D. *Trends Cardiovasc. Med.* 2000, 10, 198-204.)

In addition to the feedback activation mechanisms described above, thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al. *Thromb. Res.* 2001, 101, 329-354.) Thus, inhibitors of factor XIa are expected to be anticoagulant and profibrinolytic.

Further evidence for the anti-thromboembolic effects of targeting factor XI is derived from mice deficient in factor XI. It has been demonstrated that complete fXI deficiency protected mice from ferric chloride (FeCl$_3$)-induced carotid artery thrombosis (Rosen et al. *Thromb Haemost* 2002, 87, 774-77; Wang et al., *J Thromb Haemost* 2005, 3, 695-702). Also, factor XI deficiency rescues the perinatal lethal phenotype of complete protein C deficiency (Chan et al., *Amer. J. Pathology* 2001, 158, 469-479). Furthermore, baboon cross-reactive, function blocking antibodies to human factor XI protect against baboon arterial—venous shunt thrombosis (Gruber et al., *Blood* 2003, 102, 953-955). Evidence for an antithrombotic effect of small molecule inhibitors of factor XIa is also disclosed in published U.S. Patent Application US20040180855A1. Taken together, these studies suggest that targeting factor XI will reduce the propensity for thrombotic and thromboembolic diseases.

Genetic evidence indicates that factor XI is not required for normal homeostasis, implying a superior safety profile of the factor XI mechanism compared to competing antithrombotic mechanisms. In contrast to hemophilia A (factor VIII deficiency) or hemophilia B (factor IX deficiency), mutations of the factor XI gene causing factor XI deficiency (hemophilia C) result in only a mild to moderate bleeding diathesis characterized primarily by postoperative or posttraumatic, but rarely spontaneous hemorrhage. Postoperative bleeding occurs mostly in tissue with high concentrations of endogenous fibrinolytic activity (e.g. oral cavity, and urogenital system). The majority of the cases are fortuitously identified by preoperative prolongation of APTT (intrinsic system) without any prior bleeding history.

The increased safety of inhibition of XIa as an anticoagulation therapy is further supported by the fact that Factor XI knock-out mice, which have no detectable factor XI protein, undergo normal development, and have a normal life span. No evidence for spontaneous bleeding has been noted. The APTT (intrinsic system) is prolonged in a gene dose-dependent fashion. Interestingly, even after severe stimulation of the coagulation system (tail transection), the bleeding time is not significantly prolonged compared to wild-type and heterozygous litter mates. (Gailani, D. *Frontiers in Bioscience* 2001, 6, 201-207; Gailani, D. et al. *Blood Coagulation and Fibrinolysis* 1997, 8, 134-144.) Taken together, these observations suggest that high levels of inhibition of factor XIa should be well tolerated. This is in contrast to gene targeting experiments with other coagulation factors.

In vivo activation of factor XI can be determined by complex formation with either C1 inhibitor or alpha 1 antitrypsin. In a study of 50 patients with acute myocardial infarction (AMI), approximately 25% of the patients had values above the upper normal range of the complex ELISA. This study can be viewed as evidence that at least in a subpopulation of patients with AMI, factor XI activation contributes to thrombin formation (Minnema, M. C. et al. *Arterioscler. Thromb. Vasc. Biol.* 2000, 20, 2489-2493). A second study establishes a positive correlation between the extent of coronary arteriosclerosis and factor XIa in complex with alpha 1 antitrypsin (Murakami, T. et al. *Arterioscler Thromb Vasc Biol* 1995, 15, 1107-1113.). In another study, Factor XI levels above the 90th percentile in patients were associated with a 2.2-fold increased risk for venous thrombosis (Meijers, J. C. M. et al. *N. Engl. J. Med.* 2000, 342, 696-701.).

Plasma kallikrein is a zymogen of a trypsin-like serine protease and is present in plasma at 35 to 50 µg/mL. The gene structure is similar to that of factor XI. Overall, the amino acid sequence of plasma kallikrein has 58% homology to factor XI. Proteolytic activation by factor XIIa at an internal I 389-R390 bond yields a heavy chain (371 amino acids) and a light chain (248 amino acids). The active site of plasma kallikrein is contained in the light chain. The light chain of plasma kallikrein reacts with protease inhibitors, including alpha 2 macroglobulin and C1-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Plasma kallikrein cleaves HMWK to liberate bradykinin. Bradykinin release results in increase of vascular permeability and vasodilation (for review, Coleman, R. Contact Activation Pathway, pages 103-122 in *Hemostasis and Thrombosis*, Lippincott Williams & Wilkins 2001; Schmaier A. H. *Contact Activation*, pages 105-128 in *Thrombosis and Hemorrhage*, 1998).

Proteins or peptides that reportedly inhibit Factor XIa are disclosed in WO 01/27079. There are advantages in using small organic compounds, however, in preparing pharmaceuticals, e.g., small compounds generally have better oral bioavailability and compatibility in making formulations to aid in delivery of the drug as compared with large proteins or peptides. Small molecule inhibitors of Factor XIa are disclosed in U.S. Patent Application Publications, e.g., US20040235847A1, US20040220206A1, US20050228000A1, US20060009455A1, and US20050282805A1.

In addition, it is also desirable to find new compounds with improved pharmacological characteristics compared with known serine protease inhibitors. For example, it is preferred to find new compounds with improved factor XIa inhibitory activity and selectivity for factor XIa versus other serine proteases. Also, it is preferred to find new compounds with improved plasma kallikrein inhibitory activity and selectivity for plasma kallikrein versus other serine proteases. It is also desirable and preferable to find compounds with advantageous and improved characteristics in one or more of the following categories, which are given as examples and are not intended to be limiting: (a) pharmacokinetic properties, including oral bioavailability; (b) pharmaceutical properties; (c) dosage requirements; (d) factors which decrease blood concentration peak-to-trough characteristics; (e) factors that increase the concentration of active drug at the receptor; (f) factors that decrease the liability for clinical drug-drug interactions; (g) factors that decrease the potential for adverse side-effects; and (h) factors that improve manufacturing costs or feasibility.

SUMMARY OF THE INVENTION

The present invention provides novel arylpropionamide, arylacrylamide, arylpropynamide, or arylmethylurea compounds, and analogues thereof, which are useful as selective inhibitors of serine protease enzymes, especially factor XIa and/or plasma kallikrein, or stereoisomers, tautomers, pharmaceutically acceptable salts, solvates, or prodrugs thereof.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for modulation of the coagulation cascade and/or the contact activation system comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating thromboembolic disorders comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating inflammatory diseases disorders comprising administering to a host in need of such treatment a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of a thrombotic or thromboembolic disorder.

The present invention also provides the use of the compounds of the present invention or stereoisomers, tautomers, pharmaceutically acceptable salts, solvates, or prodrugs thereof, for the manufacture of a medicament for the treatment of an inflammatory disorder.

These and other features of the invention will be set forth in the expanded form as the disclosure continues.

DETAILED DESCRIPTION OF THE INVENTION

In a first aspect, the present invention provides, inter alia, compounds of Formula (I):

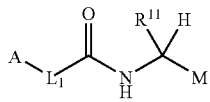

(I)

or stereoisomers, tautomers, pharmaceutically acceptable salts, solvates, or prodrugs thereof, wherein:

A is a $C_{3-10}$ carbocycle substituted with 0-1 $R^1$ and 0-3 $R^2$, or a 5- to 12-membered heterocycle comprising: carbon atoms and 1-4 heteroatoms selected from N, O, and $S(O)_p$, wherein said heterocycle is substituted with 0-1 $R^1$ and 0-3 $R^2$; provided that when A is a heterocycle containing one or more nitrogen atoms, A is not attached to $L_1$ via any of the nitrogen atoms on the A ring;

$L_1$ is —CH($R^5$)CH$_2$—, —CH(NR$^7$R$^8$)CH$_2$—, —C($R^5$)=CH—, —C≡C—, —OCH$_2$—, —CR$^5$R$^6$NH—, —CH$_2$O—, —SCH$_2$—, —SO$_2$CH$_2$—, —CH$_2$NR$^{10}$—, or —NHNH—;

provided that when $L_1$ is —CH$_2$O—, then A is other than an unsubstituted phenyl;

M is

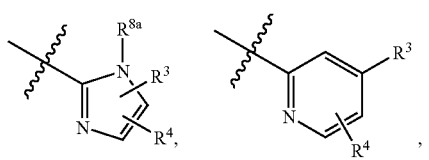

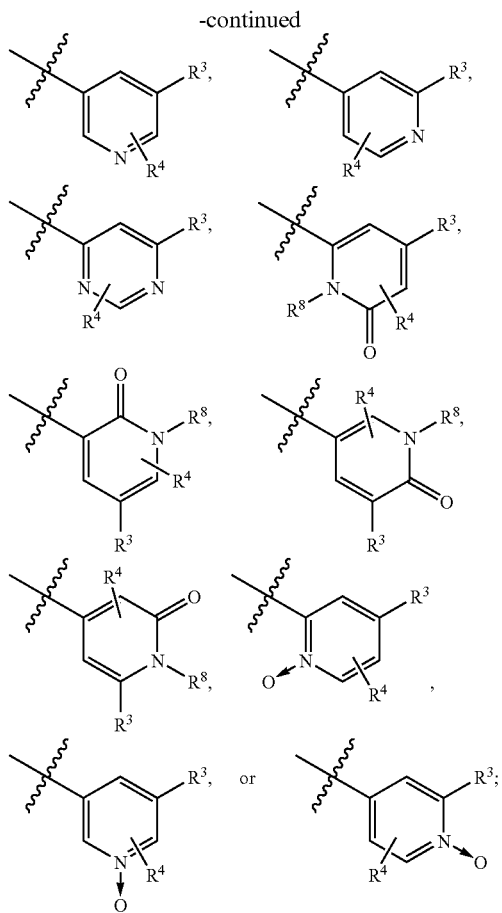

$R^1$ is, independently at each occurrence, F, Cl, Br, I, OCF$_3$, CF$_3$, —(CH$_2$)$_r$OR$^a$, —(CH$_2$)$_r$SR$^a$, CN, —(CH$_2$)$_r$NR$^7$R$^8$, —C(=NR$^8$)NR$^8$R$^9$, —C(O)NR$^8$R$^9$, —S(O)$_p$NR$^8$R$^9$, or C$_{1-6}$ alkyl substituted with 0-1 R$^{1a}$;

$R^{1a}$ is F, OCF$_3$, CF$_3$, OR$^a$, SR$^a$, CN, —NR$^7$R$^8$, —C(O)NR$^8$R$^9$, —NR$^8$C(O)R$^c$, —S(O)$_p$NR$^8$R$^9$, —NR$^8$SO$_2$R$^c$, or —(CF$_2$)$_r$CF$_3$;

$R^2$ is, independently at each occurrence, =O, F, Cl, Br, OCF$_3$, CF$_3$, CHF$_2$, CN, NO$_2$, —(CH$_2$)$_r$OR$^a$, —(CH$_2$)$_r$SR$^a$, —(CH$_2$)$_r$C(O)R$^a$, —(CH$_2$)$_r$C(O)OR$^a$, —(CH$_2$)$_r$OC(O)R$^a$, —(CH$_2$)$_r$NR$^7$R$^8$, —(CH$_2$)$_r$C(O)NR$^8$R$^9$, —(CH$_2$)$_r$NR$^8$C(O)R$^c$, —(CH$_2$)$_r$NR$^8$C(O)OR$^c$, —NR$^8$C(O)NR$^8$R$^c$, —S(O)$_p$NR$^8$R$^9$, —NR$^8$S(O)$_p$R$^c$, —S(O)R$^c$, —S(O)$_2$R$^c$, C$_{1-6}$ alkyl substituted with 0-1 R$^{2a}$, —(CH$_2$)$_r$-3-7 membered carbocycle optionally substituted with 0-2 R$^{2b}$, or —(CH$_2$)$_r$-5-7 membered heterocycle comprising carbon atoms and 1-4 heteroatoms selected from N, O, and S(O)$_p$, wherein said heterocycle is substituted with 0-2 R$^{2b}$;

alternately, when $R^1$ and $R^2$ groups are substituents on adjacent atoms they may be taken together with the atoms to which they are attached to form a 5- to 7-membered carbocycle or heterocycle comprising carbon atoms and 0-4 heteroatoms selected from N, O, and S(O)$_p$ and substituted with 0-2 R$^g$;

$R^{2a}$ is F, OCF$_3$, CF$_3$, OR$^a$, SR$^a$, CN, —NR$^7$R$^8$, —C(O)NR$^8$R$^9$, —NR$^8$C(O)R$^c$, —NR$^8$C(O)OR$^c$, —NR$^8$C(O)NR$^8$R$^c$, —S(O)$_p$NR$^8$R$^9$, —NR$^8$SO$_2$R$^c$, or —(CF$_2$)$_r$CF$_3$;

$R^{2b}$ is, independently at each occurrence, =O, F, Br, Cl, OCF$_3$, CF$_3$, —(CH$_2$)$_r$OR$^a$, —(CH$_2$)$_r$SR$^a$, —(CH$_2$)$_r$CN, —(CH$_2$)$_r$NR$^7$R$^8$, —(CH$_2$)$_r$C(O)OR$^a$, —(CH$_2$)$_r$OC(O)R$^a$, —(CH$_2$)$_r$C(O)NR$^8$R$^9$, —(CH$_2$)$_r$NR$^8$C(O)R$^c$, —(CH$_2$)$_r$NR$^8$C(O)OR$^c$, —(CH$_2$)$_r$S(O)$_p$NR$^8$R$^9$, —(CH$_2$)$_r$NR$^8$SO$_2$R$^c$, C$_{1-4}$ alkyl or —(CF$_2$)$_r$CF$_3$;

R$^3$ is, independently at each occurrence, —(CH$_2$)$_r$—C$_{3-10}$ carbocycle substituted with 0-3 R$^{3a}$ and 0-1 R$^{3d}$, or —(CH$_2$)$_r$-5- to 12-membered heterocycle comprising: carbon atoms and 1-4 heteroatoms selected from N, O, and S(O)$_p$, wherein said heterocycle is substituted with 0-3 R$^{3a}$ and 0-1 R$^{3d}$;

R$^{3a}$ is, independently at each occurrence, =O, =NR$^8$, F, Cl, Br, I, OCF$_3$, CF$_3$, —(CH$_2$)$_r$CN, NO$_2$, —(CH$_2$)$_r$OR$^{3b}$, —(CH$_2$)$_r$SR$^{3b}$, —(CH$_2$)$_r$NR$^7$R$^8$, —NHC(O)NR$^8$R$^9$, —(CH$_2$)$_r$C(O)OR$^{3b}$, —C(O)C$_{1-4}$ alkyl, —SO$_2$NHR$^{3b}$, —SO$_2$NHCO$_2$R$^{3c}$, —SO$_2$NHCO$_2$R$^{3c}$, —CONHSO$_2$R$^{3c}$, —(CH$_2$)$_r$NR$^8$C(O)R$^{3b}$, —(CH$_2$)$_r$NR$^8$CO$_2$R$^{3c}$, —(CH$_2$)$_r$S(O)$_p$NR$^8$R$^9$, —(CH$_2$)$_r$NR$^8$S(O)$_p$R$^{3c}$, —NHSO$_2$CF$_3$, —S(O)R$^{3c}$, —S(O)$_2$R$^{3c}$, —(CH$_2$)$_r$OC(O)R$^{3b}$, —(CH$_2$)$_r$C(O)NR$^8$R$^9$, —(CH$_2$)$_r$OC(O)NR$^8$R$^9$, —NHCOCF$_3$, —NHSO$_2$R$^{3c}$, —CONHOR$^{3b}$, C$_{1-4}$ haloalkyl, C$_{1-4}$ haloalkyloxy-, C$_{1-6}$ alkyl substituted by R$^{3e}$, C$_{2-6}$ alkenyl substituted by R$^{3e}$, C$_{1-6}$ alkynyl substituted by R$^{3e}$, C$_{3-6}$ cycloalkyl substituted by 0-1 R$^{3d}$, —(CH$_2$)$_r$—C$_{6-10}$ carbocycle substituted by 0-3 R$^{3d}$ or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{3d}$;

alternately, when two R$^{3a}$ groups are substituted on adjacent atoms, they can be taken together with the atoms to which they are attached to form a C$_{3-10}$ carbocycle substituted with 0-2 R$^{3d}$, or a 5- to 10-membered heterocycle comprising: carbon atoms and 1-4 heteroatoms selected from N, O, and S(O)$_p$, wherein said heterocycle is substituted with 0-2 R$^{3d}$;

R$^{3b}$ is, independently at each occurrence, H, C$_{1-6}$ alkyl substituted with 0-2 R$^{3d}$, C$_{2-6}$ alkenyl substituted with 0-2 R$^{3d}$, C$_{2-6}$ alkynyl substituted with 0-2 R$^{3d}$, —(CH$_2$)$_r$—C$_{3-10}$ carbocycle substituted with 0-3 R$^{3d}$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{3d}$;

R$^{3c}$ is, independently at each occurrence, C$_{1-6}$ alkyl substituted with 0-2 R$^{3d}$, C$_{2-6}$ alkenyl substituted with 0-2 R$^{3d}$, C$_{2-6}$ alkynyl substituted with 0-2 R$^{3d}$, —(CH$_2$)$_r$—C$_{3-10}$ carbocycle substituted with 0-3 R$^{3d}$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{3d}$;

R$^{3d}$ is, independently at each occurrence, H, =O, F, Cl, Br, CN, NO$_2$, —(CH$_2$)$_r$NR$^7$R$^8$, —(CH$_2$)$_r$OR$^a$, —C(O)R$^a$, —C(O)OR$^a$, —OC(O)R$^a$, —NR$^8$C(O)R$^c$, —C(O)NR$^8$R$^9$, —S(O)$_2$NR$^8$R$^9$, —NR$^7$R$^8$, —NR$^8$S(O)$_2$NR$^8$R$^9$, —NR$^8$S(O)$_2$R$^c$, —S(O)$_p$R$^c$, —(CF$_2$)$_r$CF$_3$, C$_{1-6}$ alkyl substituted with 0-2 R$^e$, C$_{2-6}$ alkenyl substituted with 0-2 R$^e$, C$_{2-6}$ alkynyl substituted with 0-2 R$^e$, —(CH$_2$)$_r$—C$_{3-10}$ carbocycle substituted with 0-3 R$^d$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^d$;

R$^{3e}$ is, independently at each occurrence, H, —(CH$_2$)$_r$OR$^a$, F, =O, CN, NO$_2$, —(CH$_2$)$_r$NR$^7$R$^8$, —C(O)R$^a$, —C(O)OR$^a$, —OC(O)R$^a$, —NR$^8$C(O)R$^c$, —C(O)NR$^8$R$^9$, —S(O)$_2$NR$^8$R$^9$, —NR$^8$S(O)$_2$NR$^8$R$^9$, —NR$^8$S(O)$_2$R$^c$, —S(O)$_p$R$^c$, —(CF$_2$)$_r$CF$_3$, —(CH$_2$)$_r$—C$_{3-10}$ carbocycle substituted with 0-3 R$^d$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^d$;

R$^4$ is, independently at each occurrence, H, F, Cl, Br, I, OCF$_3$, CF$_3$, CN, NO$_2$, —(CH$_2$)$_r$OR$^a$, —(CH$_2$)$_r$SR$^a$, —(CH$_2$)$_r$C(O)R$^a$, —(CH$_2$)$_r$C(O)OR$^a$, —OC(O)R$^a$, —(CH$_2$)$_r$NR$^7$R$^8$, —NR$^8$(CH$_2$)$_r$C(O)OR$^a$, —(CH$_2$)$_r$C(O) NR$^8$R$^9$, —(CH$_2$)$_r$NR$^8$C(O)R$^c$, —(CH$_2$)$_r$NR$^8$C(O)R$^b$, —(CH$_2$)$_r$NR$^8$C(O)NR$^8$R$^9$, —S(O)$_p$NR$^8$R$^9$, —NR$^8$S(O)$_p$R$^c$, —S(O)$_2$R$^c$, or C$_{1-4}$ alkyl substituted with 0-2 R$^{4a}$;

R$^{4a}$ is, independently at each occurrence, H, F, =O, C$_{1-6}$ alkyl, OR$^a$, SR$^a$, CF$_3$, CN, NO$_2$, —C(O)R$^a$, —C(O)OR$^a$, —NR$^7$R$^8$, —C(O)NR$^8$R$^9$, —NR$^8$C(O)R$^c$, —S(O)$_p$NR$^8$R$^9$, —NR$^8$S(O)$_p$R$^c$, —S(O)R$^c$, or —S(O)$_2$R$^c$;

R$^5$ is, independently at each occurrence, H, F, CF$_3$, —(CH$_2$)$_r$OR$^a$, =O, —(CH$_2$)$_r$NR$^7$R$^8$, —S(O)$_p$NR$^8$R$^9$, —(CH$_2$)$_r$CO$_2$R$^a$, —(CH$_2$)$_r$CONR$^8$R$^9$, or C$_{1-4}$ alkyl;

R$^6$ is, independently at each occurrence, H, F, or C$_{1-4}$ alkyl;

R$^7$ is, independently at each occurrence, H, C$_{1-6}$ alkyl, —(CH$_2$)$_n$—C$_{3-10}$ carbocycle, —(CH$_2$)$_n$-(5- to 10-membered heteroaryl), —C(O)R$^c$, —CHO, —C(O)$_2$R$^c$, —S(O)$_2$R$^c$, —CONR$^8$R$^c$, —OCONHR$^c$, —C(O)O—(C$_{1-4}$ alkyl)OC(O)—(C$_{1-4}$ alkyl), or —C(O)O—(C$_{1-4}$ alkyl)OC(O)—(C$_{6-10}$ aryl); wherein said alkyl, carbocycle, heteroaryl, and aryl are substituted with 0-2 R$^f$; wherein said heteroaryl comprises: carbon atoms and 1-4 heteroatoms selected from N, O, and S(O)$_p$;

R$^8$ is, independently at each occurrence, H, C$_{1-6}$ alkyl, —(CH$_2$)$_n$-phenyl, or —(CH$_2$)$_n$-5- to 10-membered heterocycle comprising: carbon atoms and 1-4 heteroatoms selected from N, O, and S(O)$_p$; wherein said alkyl, phenyl and heterocycle are optionally substituted with 0-2 R$^f$;

alternatively, R$^7$ and R$^8$, when attached to the same nitrogen, combine to form a 5- to 10-membered heterocycle comprising: carbon atoms and 0-3 additional heteroatoms selected from N, O, and S(O)$_p$, wherein said heterocycle is substituted with 0-2 R$^f$;

R$^{8a}$ is H or C$_{1-4}$ alkyl;

R$^9$ is, independently at each occurrence, H, C$_{1-6}$ alkyl, or —(CH$_2$)$_n$-phenyl; wherein said alkyl and phenyl are optionally substituted with 0-2 R$^f$;

alternatively, R$^8$ and R$^9$, when attached to the same nitrogen, combine to form a 5- to 12-membered heterocycle comprising: carbon atoms and 0-2 additional heteroatoms selected from N, O, and S(O)$_p$, wherein said heterocycle is substituted with 0-2 R$^d$;

R$^{10}$ is, independently at each occurrence, H or C$_{1-6}$ alkyl substituted with 0-3 R$^{10a}$;

R$^{10a}$ is, independently at each occurrence, H, =O, C$_{1-4}$ alkyl, OR$^a$, SR$^a$, F, CF$_3$, CN, NO$_2$, —C(O)R$^a$, —C(O)OR$^a$, —C(O)NR$^8$R$^9$, —NR$^8$C(O)R$^c$, —S(O)$_p$NR$^8$R$^9$, —NR$^8$S (O)$_p$R$^c$, or —S(O)$_p$R$^c$;

R$^{11}$ is C$_{1-4}$haloalkyl, —C(O)NR$^8$R$^9$, —CH$_2$C(O)NR$^8$R$^9$, —CH$_2$CH$_2$C(O)NR$^8$R$^9$, —C(O)R$^a$, —CH$_2$C(O)R$^a$, —CH$_2$CH$_2$C(O)R$^a$, —C(O)OR$^a$, —CH$_2$C(O)OR$^a$, —CH$_2$CH$_2$C(O)OR$^a$, C$_{1-6}$ alkyl substituted with 0-3 R$^{11c}$, C$_{2-6}$ alkenyl substituted with 0-3 R$^{11a}$, C$_{2-6}$ alkynyl substituted with 0-3 R$^{11a}$, —(CH$_2$)$_r$—C$_{3-10}$ carbocycle substituted with 0-3 R$^{11b}$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{11b}$;

R$^{11a}$ is, independently at each occurrence H, =O, OR$^a$, SR$^a$, F, CF$_3$, CN, NO$_2$, —C(O)R$^a$, —C(O)OR$^a$, —NR$^7$R$^8$, —C(O)NR$^8$R$^9$, —NR$^8$C(O)R$^c$, —NR$^8$C(O)OR$^c$, —NR$^8$CHO, —S(O)$_p$NR$^8$R$^9$, —NR$^8$S(O)$_p$R$^c$, —S(O)$_p$R$^c$, C$_{1-4}$ alkyl, C$_{3-6}$ cycloalkyl, C$_{1-4}$ haloalkyl, C$_{1-4}$ haloalkyloxy-, —(CH$_2$)$_r$—C$_{3-10}$ carbocycle substituted with 0-3 R$^d$, or —(CH$_2$)$_r$-5- to 10-membered heterocycle comprising carbon atoms and 1-4 heteroatoms selected from N, O, and S(O)$_p$, and substituted with 0-3 R$^d$;

R$^{11b}$ is, independently at each occurrence, H, =O, =NR$^8$, OR$^a$, —CH$_2$OR$^a$, F, Cl, Br, CN, NO$_2$, CF$_3$, OCF$_3$, OCHF$_2$, —C(CH$_3$)$_2$OR$^a$, —C(O)R$^a$, —C(O)OR$^a$, —NR$^7$R$^8$, —C(O)NR$^8$R$^9$, —NR$^7$C(O)R$^b$, —NR$^8$C(O)$_2$R$^c$, —S(O)$_p$NR$^8$R$^9$, —NR$^8$S(O)$_p$R$^c$, —S(O)$_p$R$^c$, C$_{1-6}$ alkyl, C$_{2-6}$ alkenyl, C$_{2-6}$ alkynyl, C$_{3-6}$ cycloalkyl, C$_{1-4}$ haloalkyl, C$_{1-4}$ haloalkyloxy-, —(CH$_2$)$_r$—C$_{3-10}$ carbocycle substituted with 0-3 R$^d$, or —(CH$_2$)$_r$-5- to 10-membered heterocycle comprising carbon atoms and 1-4 heteroatoms selected from N, O, and S(O)$_p$, and substituted with 0-3 R$^d$;

alternately, when two R$^{11b}$ groups are substituents on adjacent atoms they may be taken together with the atoms to which they are attached to form a 5- to 7-membered heterocycle comprising carbon atoms and 1-4 heteroatoms selected from N, O, and S(O)$_p$ and substituted with 0-2 R$^g$;

R$^{11c}$ is, independently at each occurrence H, =O, OR$^a$, SR$^a$, F, CF$_3$, CN, NO$_2$, —NR$^7$R$^8$, —NR$^8$C(O)R$^c$, —NR$^8$C(O)OR$^c$, —NR$^8$CHO, —S(O)$_p$NR$^8$R$^9$, —NR$^8$S(O)$_p$R$^c$, —S(O)$_p$R$^c$, C$_{1-4}$ alkyl, C$_{3-6}$ cycloalkyl, C$_{1-4}$ haloalkyl, C$_{1-4}$ haloalkyloxy-, —(CH$_2$)$_r$—C$_{3-10}$ carbocycle substituted with 0-3 R$^d$, or —(CH$_2$)$_r$-5- to 10-membered heterocycle comprising carbon atoms and 1-4 heteroatoms selected from N, O, and S(O)$_p$, and substituted with 0-3 R$^d$;

R$^a$ is, independently at each occurrence, H, CF$_3$, C$_{1-6}$ alkyl, —(CH$_2$)$_r$—C$_{3-7}$ cycloalkyl, —(CH$_2$)$_r$—C$_{6-10}$ aryl, or —(CH$_2$)$_r$-5- to 10-membered heterocycle comprising carbon atoms and 1-4 heteroatoms selected from N, O, and S(O)$_p$, wherein said cycloalkyl, aryl or heterocycle groups are optionally substituted with 0-2 R$^f$;

R$^b$ is, independently at each occurrence, CF$_3$, OH, C$_{1-4}$ alkoxy, C$_{1-6}$ alkyl, —(CH$_2$)$_r$—C$_{3-10}$ carbocycle substituted with 0-2 R$^d$, or —(CH$_2$)$_r$-5- to 10-membered heterocycle comprising: carbon atoms and 1-4 heteroatoms selected from N, O, and S(O)$_p$ and substituted with 0-3 R$^d$;

R$^c$ is, independently at each occurrence, CF$_3$, C$_{1-6}$ alkyl substituted with 0-2 R$^f$, C$_{3-6}$ cycloalkyl substituted with 0-2 R$^f$, C$_{6-10}$ aryl, 5- to 10-membered heteroaryl, (C$_{6-10}$ aryl)-C$_{1-4}$ alkyl, or (5- to 10-membered heteroaryl)-C$_{1-4}$ alkyl, wherein said aryl is substituted with 0-3 R$^f$ and said heteroaryl comprises: carbon atoms and 1-4 heteroatoms selected from N, O, and S(O)$_p$ and substituted with 0-3 R$^f$;

R$^d$ is, independently at each occurrence, H, =O, =NR$^8$, OR$^a$, F, Cl, Br, I, CN, NO$_2$, —NR$^7$R$^8$, —C(O)R$^a$, —C(O)OR$^a$, —OC(O)R$^a$, —NR$^8$C(O)R$^c$, —C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl substituted with 0-2 R$^e$, C$_{2-6}$ alkenyl substituted with 0-2 R$^e$, or C$_{2-6}$ alkynyl substituted with 0-2 R$^e$;

R$^e$ is, independently at each occurrence, =O, OR$^a$, F, Cl, Br, I, CN, NO$_2$, —NR$^7$R$^8$, —C(O)R$^a$, —C(O)OR$^a$, —NR$^8$C(O)R$^c$, —C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

R$^f$ is, independently at each occurrence, H, =O, —(CH$_2$)$_r$OR$^g$, F, Cl, Br, I, CN, NO$_2$, —NR$^g$R$^g$, —C(O)R$^g$, —C(O)OR$^g$, —NR$^g$C(O)R$^g$, —C(O)NR$^g$R$^g$, —SO$_2$NR$^g$R$^g$, —NR$^g$SO$_2$NR$^g$R$^g$, —NR$^g$SO$_2$—C$_{1-4}$ alkyl, —NR$^g$SO$_2$CF$_3$, —NR$^g$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, C$_{2-6}$ alkynyl, —(CH$_2$)$_n$-phenyl, or —(CH$_2$)$_n$-5- to 10-membered heterocycle comprising carbon atoms and 1-4 heteroatoms selected from N, O, and S(O)$_p$;

R$^g$ is, independently at each occurrence, H, C$_{1-6}$ alkyl, or —(CH$_2$)$_n$-phenyl;

n, at each occurrence, is selected from 0, 1, 2, 3, and 4;
p, at each occurrence, is selected from 0, 1, and 2; and
r, at each occurrence, is selected from 0, 1, 2, 3, and 4;
provided that:
when M is an imidazole ring, L$_1$ is —C(R$^5$R$^6$)NH— or —CH$_2$O—, and R$^3$ is unsubstituted phenyl, then R$^{11}$ is other than —CH$_2$-(3-indolyl);
M is an imidazole ring, L$_1$ is —CH=CH—, A is halogen substituted phenyl, and R$^{11}$ is —CH$_2$— (pyridyl), then R$^{3a}$ is other than morpholyl which is optionally substituted.

In a second aspect, the present invention includes compounds of Formula (I), or stereoisomers, tautomers, pharmaceutically acceptable salts, solvates, or prodrugs thereof, within the scope of the first aspect wherein:

R$^3$ is, independently at each occurrence, phenyl substituted with 0-3 R$^{3a}$ and 0-1 R$^{3d}$, naphthyl substituted with 0-3 R$^{3a}$ and 0-1 R$^{3d}$, 1,2,3,4-tetrahydronaphthyl substituted with 0-3 R$^{3a}$ and 0-1 R$^{3d}$, or —(CH$_2$)$_r$-5- to 12-membered heterocycle comprising: carbon atoms and 1-4 heteroatoms selected from N, O, and S(O)$_p$, wherein said heterocycle is substituted with 0-3 R$^{3a}$ and 0-1 R$^{3d}$;

R$^4$ is, independently at each occurrence, H, Me, Et, Pr, F, Cl, Br, I, OCF$_3$, CF$_3$, CN, NO$_2$, —(CH$_2$)$_r$OH, —(CH$_2$)$_r$C(O)OR$^a$, OR$^a$, SR$^a$, —C(O)R$^a$, —C(O)OR$^a$, —NR$^7$R$^8$, —(CH$_2$)$_r$NH$_2$, —NR$^8$(CH$_2$)$_r$C(O)OR$^a$, —(CH$_2$)$_r$C(O)NR$^8$R$^9$, —NR$^8$C(O)R$^c$, —NR$^8$C(O)OR$^c$, —NR$^8$C(O)NR$^8$R$^9$, —S(O)$_p$NR$^8$R$^9$, —NR$^8$S(O)$_p$R$^c$, or —S(O)$_2$R$^c$; and R$^{11}$ is C$_{1-4}$ haloalkyl, —CH$_2$C(O)NR$^8$R$^9$, —CH$_2$CH$_2$C(O)NR$^8$R$^9$, —CH$_2$C(O)R$^a$, —CH$_2$CH$_2$C(O)R$^a$, —CH$_2$C(O)OR$^a$, —CH$_2$CH$_2$C(O)OR$^a$, C$_{1-6}$ alkyl substituted with 0-2 R$^{11c}$, C$_{2-6}$ alkenyl substituted with 0-2 R$^{11a}$, C$_{2-6}$ alkynyl substituted with 0-2 R$^{11a}$, —(CH$_2$)$_r$—C$_{3-10}$ carbocycle substituted with 0-3 R$^{11b}$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{11b}$.

In a third aspect, the present invention includes compounds of Formula (I), or stereoisomers, tautomers, pharmaceutically acceptable salts, solvates, or prodrugs thereof, within the scope of the first aspect wherein:

R$^1$ is, independently at each occurrence, F, Cl, Br, I, OCF$_3$, CF$_3$, OCH$_3$, CH$_3$, Et, NH$_2$, —C(=NH)NH$_2$, —C(O)NH$_2$, —CH$_2$NH$_2$ or —SO$_2$NH$_2$;

R$^2$ is, independently at each occurrence, F, Cl, Br, CF$_3$, NO$_2$, —(CH$_2$)$_r$OR$^a$, —(CH$_2$)$_r$SR$^a$, —C(O)OR$^a$, —C(O)NR$^8$R$^9$, —NR$^8$C(O)R$^c$, —NR$^8$C(O)OR$^c$, —NR$^8$C(O)NR$^8$R$^c$, —S(O)$_p$NR$^8$R$^9$, —NR$^8$SO$_2$R$^c$, —NR$^7$R$^8$, —S(O)R$^c$, —S(O)$_2$R$^c$, C$_{1-6}$ alkyl substituted with 0-1 R$^{22}$, or a 5-7 membered heterocycle comprising carbon atoms and 1-4 heteroatoms selected from N, O, and S(O)$_p$, wherein said heterocycle is substituted with 0-2 R$^{2b}$;

alternately, when R$^1$ and R$^2$ groups are substituents on adjacent atoms they may be taken together with the atoms to which they are attached to form a 5- to 7-membered carbocycle or heterocycle comprising carbon atoms and 0-4 heteroatoms selected from N, O, and S(O)$_p$ and substituted with 0-2 R$^g$;

R$^3$ is, independently at each occurrence, phenyl substituted with 0-2 R$^{3a}$ and 0-1 R$^{3d}$, naphthyl substituted with 0-2 R$^{3a}$ and 0-1 R$^{3d}$, 1,2,3,4-tetrahydronaphthyl substituted with 0-2 R$^{3a}$ and 0-1 R$^{3d}$, or a 5- to 12-membered heterocycle substituted with 0-2 R$^{3a}$ and 0-1 R$^{3d}$, wherein said heterocycle is selected from: thiophene, furan, thiazole, tetrazole, pyridine, pyridone, pyrimidine, pyrrole, pyrazole, indole, 2-oxindole, isoindoline, indazole, 7-azaindole, benzofuran, benzothiophene, benzimidazole, benzisoxazole, benzoxazole, quinazoline, quinoline, isoquinoline, quinoxaline, phthalazine, dihydrophthalazine, dihydroisoquinoline, dihydroquinoline, dihydroquinolinone, dihydroindole, dihydrobenzimidazole, dihydrobenzoxazine, dihydroquinazoline, dihydroquinoxaline, benzothiazine, benzoxazine, tetrahydrobenzazepine, dihydroazabenzocycloheptene, and tetrahydroquinoline;

$R^{3a}$ is, independently at each occurrence, =O, F, Cl, Br, Me, CN, OH, OMe, —OC(O)(t-Bu), —CH$_2$OMe, CF$_3$, COMe, CO$_2$H, CO$_2$Me, —CH$_2$CO$_2$H, —(CH$_2$)$_2$CO$_2$H, —CH$_2$CO$_2$Me —CH$_2$CO$_2$Et, —CH$_2$CH$_2$CO$_2$Et, —CH$_2$CN, NH$_2$, —CH$_2$NH$_2$, —CH$_2$NMe$_2$, —NHCOMe, —NHCO$_2$Me, —NHCO$_2$Et, —NHCH$_2$CH$_2$CO$_2$H, —NHCO$_2$(i-Pr), —NHCO$_2$(i-Bu), —NHCO$_2$(t-Bu), —NHCO$_2$Bn, —NHCO$_2$CH$_2$CH$_2$OMe, —NHCO$_2$CH$_2$CH$_2$CH$_2$OMe, —NHCO$_2$CH$_2$CO$_2$H, —NHCO$_2$CH$_2$CH$_2$CO$_2$H, —NHCO$_2$CH$_2$CH$_2$OH, —NHCO$_2$CH$_2$CH$_2$NH$_2$, —NHCO$_2$CH$_2$-tetrahydrofuran-2-yl, —NHCO$_2$CH$_2$CH$_2$CH(Me)OMe, —NHCO$_2$CH$_2$CH$_2$C(O)NH$_2$, —NHC(O)NHCH$_2$CH$_2$-morpholino, —NHC(O)NHCH$_2$-pyrid-4-yl, —NHCO$_2$CH$_2$-pyrid-4-yl, —NHCO$_2$CH$_2$-pyrid-3-yl, —NHCO$_2$CH$_2$-pyrid-2-yl, —NHCO$_2$CH$_2$— (piperidin-4-yl), —NHC(O)NHCH$_2$CH$_2$-pyrid-4-yl, —NHCO$_2$CH$_2$CH$_2$-pyrid-4-yl, —NHCO$_2$CH$_2$CH$_2$-morpholino, —CH$_2$NHCO$_2$Me, —NHC(O)NHMe, —NHC(O)N(Me)$_2$, —NHC(O)NHCH$_2$CH$_2$OMe, 4-[(1-carbamoyl-cyclopropanecarbonyl)-amino]-, —NHSO$_2$Me, —SO$_2$NH$_2$, —SO$_2$NHMe, —SO$_2$NHCH$_2$CH$_2$OH, —SO$_2$NHCH$_2$CH$_2$OMe, —CONH$_2$, —CONHMe, —CON(Me)$_2$, —C(O)NHCH$_2$CH$_2$OMe, —CH$_2$CONH$_2$, —CO(N-morpholino), —NHCH$_2$CH$_2$(N-morpholino), —NR$^7$R$^8$, —NH(1H-imidazol-2-yl), 1H-tetrazol-5-yl, tetrazol-1-yl, pyrimidin-5-yl, N-morpholino, or —(CH$_2$)$_r$-5- to 6-membered heterocycle comprising: carbon atoms and 1-4 heteroatoms selected from N, O, and S(O)$_p$, wherein said heterocycle is substituted with 0-1 R$^{3d}$;

$R^4$ is, independently at each occurrence, H, F, Cl, Br, OH, OMe, NH$_2$, Me, Et, CF$_3$, —CH$_2$OH, —C(O)$_2$H, CO$_2$Me, CO$_2$Et, —C(O)NH$_2$, —C(O)NHMe, —C(O)N(Me)$_2$, or —CH$_2$CO$_2$H; and $R^{11}$ is C$_{1-4}$ haloalkyl, —CH$_2$C(O)NR$^8$R$^9$, —CH$_2$CH$_2$C(O)NR$^8$R$^9$, —CH$_2$C(O)R$^a$, —CH$_2$CH$_2$C(O)R$^a$, —CH$_2$C(O)OR$^a$, —CH$_2$CH$_2$C(O)OR$^a$, C$_{1-6}$ alkyl substituted with 0-2 R$^{11c}$, —(CH$_2$)$_r$-C$_{3-7}$ cycloalkyl substituted with 0-2 R$^{11b}$, —(CH$_2$)$_r$-indanyl substituted with 0-2 R$^{11b}$, —(CH$_2$)$_r$-indenyl substituted with 0-2 R$^{11b}$, —(CH$_2$)$_r$-phenyl substituted with 0-2 R$^{11b}$, —(CH$_2$)$_r$-naphthyl substituted with 0-2 R$^{11b}$, or —(CH$_2$)$_r$-5- to 10-membered heterocycle comprising carbon atoms and 1-4 heteroatoms selected from N, O, and S(O)$_p$, wherein said heterocycle is substituted with 0-2 R$^{11b}$.

In a fourth aspect, the present invention includes compounds of Formula (I), or stereoisomers, tautomers, pharmaceutically acceptable salts, solvates, or prodrugs thereof, wherein:

A is substituted with 0-1 R$^1$ and 0-3 R$^2$ and selected from: C$_{3-7}$ cycloalkyl, phenyl, naphthyl, 1,2,3,4-tetrahydronaphthyl, pyrrolidinyl, pyridyl, indazolyl, indolyl, imidazolyl, furanyl, thienyl, benzimidazolyl, benzisoxazolyl, benzothiazolyl, benzothiophenyl, 3,4-methylenedioxy-phenyl, oxazolyl, isoxazolyl, thiazolyl, isothiazolyl, and pyrazolyl;

L$_1$ is —CH$_2$CH$_2$—, —CH(NH$_2$)CH$_2$—, —CH(NHCOMe)CH$_2$—, —CH(NHCOEt)CH$_2$—, —CH(NHCO$_2$(t-Bu))CH$_2$—, —CH=CH—, —C(Me)=CH—, —C≡C—, —CH$_2$NH—, —CH(CH$_2$CO$_2$H)NH—, —CH$_2$O—, —NHNH—, —SCH$_2$—, —SO$_2$CH$_2$— or —OCH$_2$—;

M is

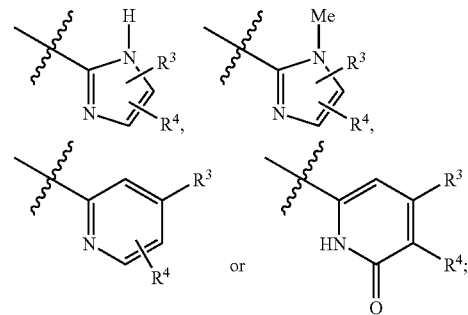

$R^1$ is, independently at each occurrence, F, Cl, Br, CF$_3$, NH$_2$, —CH$_2$NH$_2$, —C(=NH)NH$_2$, —C(O)NH$_2$, —SO$_2$NH$_2$, SR$^a$, OR$^a$, or C$_{1-6}$ alkyl substituted with 0-1 R$^{1a}$;

$R^2$ is, independently at each occurrence, =O, F, Cl, Br, CF$_3$, Me, Et, OR$^a$, CN, NO$_2$, NR$^7$R$^8$, —CH$_2$OMe, —SR$^2$, —CH$_2$SMe, —C(O)OR$^a$, —CH$_2$NR$^7$R$^8$, —SO$_2$NH$_2$, —SO$_2$Me, —NHSO$_2$R$^c$, —CH$_2$NHSO$_2$R$^c$, —C(O)NR$^8$R$^9$, —NHC(O)R$^c$, —CH$_2$NHC(O)R$^c$, —NHC(O)OR$^c$, —CH$_2$NHC(O)OR$^c$, —NHC(O)NHR$^c$, —CH$_2$NHC(O)NHR$^c$, or a 5-7 membered heterocycle substituted with 0-2 R$^{2b}$ and selected from: pyrrolidinyl, 2-oxo-1-pyrrolidinyl, piperidinyl, pyrazolyl, triazolyl, and tetrazolyl;

alternately, when R$^1$ and R$^2$ groups are substituents on adjacent atoms they may be taken together with the atoms to which they are attached to form a 5- to 6-membered heterocycle comprising carbon atoms and 0-4 heteroatoms selected from N, O, and S(O)$_p$;

$R^3$ is, independently at each occurrence, phenyl substituted with 0-2 R$^{3a}$, naphthyl substituted with 0-2 R$^{3a}$, 1,2,3,4-tetrahydro-naphthyl substituted with 0-3 R$^{3a}$ and 0-1 R$^{3d}$, or a 5- to 12-membered heterocycle comprising: carbon atoms and 1-2 heteroatoms selected from N, O, and S(O)$_p$, wherein said heterocycle is substituted with 0-2 R$^{3a}$;

$R^{3a}$ is, independently at each occurrence, =O, F, Cl, Br, Me, CN, OH, OMe, —OC(O)(t-Bu), CH$_2$OMe, CF$_3$, COMe, CO$_2$H, CO$_2$Me, —CH$_2$CO$_2$H, —(CH$_2$)$_2$CO$_2$H, —CH$_2$CO$_2$Me, —CH$_2$CO$_2$Et, —CH$_2$CH$_2$CO$_2$Et, —CH$_2$CN, NH$_2$, —CH$_2$NH$_2$, —CH$_2$NMe$_2$, —NHCOMe, —NHCO$_2$Me, —NHCO$_2$Et, —NHCH$_2$CH$_2$CO$_2$H, —NHCO$_2$(i-Pr), —NHCO$_2$(i-Bu), —NHCO$_2$(t-Bu), —NHCO$_2$Bn, —NHCO$_2$CH$_2$CH$_2$OMe, —NHCO$_2$CH$_2$CH$_2$CH$_2$OMe, —NHCO$_2$CH$_2$CO$_2$H, —NHCO$_2$CH$_2$CH$_2$CO$_2$H, —NHCO$_2$CH$_2$CH$_2$OH, —NHCO$_2$CH$_2$CH$_2$NH$_2$, —NHCO$_2$CH$_2$-tetrahydrofuran-2-yl, —NHCO$_2$CH$_2$CH$_2$CH(Me)OMe, —NHCO$_2$CH$_2$CH$_2$C(O)NH$_2$, —NHC(O)NHCH$_2$CH$_2$-morpholino, —NHC(O)NHCH$_2$-pyrid-4-yl, —NHCO$_2$CH$_2$-pyrid-4-yl, —NHCO$_2$CH$_2$-pyrid-3-yl, —NHCO$_2$CH$_2$-pyrid-2-yl, —NHCO$_2$CH$_2$—(piperidin-4-yl), —NHC(O)NH CH$_2$CH$_2$-pyrid-4-yl, —NHCO$_2$CH$_2$CH$_2$-pyrid-4-yl, —NHCO$_2$CH$_2$CH$_2$-morpholino, —CH$_2$NHCO$_2$Me, —NHC(O)NHMe, —NHC(O)N(Me)$_2$, —NHC(O)NHCH$_2$CH$_2$OMe, 4-[(1-carbamoyl-cyclopropanecarbonyl)-amino]-, —NHSO$_2$Me, —SO$_2$NH$_2$, —SO$_2$NHMe, —SO$_2$NHCH$_2$CH$_2$OH, —SO$_2$NHCH$_2$CH$_2$OMe, —CONH$_2$, —CONHMe, —CON(Me)$_2$, —C(O)NHCH$_2$CH$_2$OMe, —CH$_2$CONH$_2$, —CO(N-morpholino), —NHCH$_2$CH$_2$(N-morpholino), —NR$^7$R$^8$, —NH(1H-imidazol-2-yl), 1H-tetrazol-5-yl, tetrazol-1-yl, pyrimidin-5-yl, or N-morpholino, or —(CH$_2$)$_r$-5- to 6-membered heterocycle comprising: carbon atoms and 1-4 heteroatoms selected from N, O, and S(O)$_p$, wherein said heterocycle is substituted with 0-1 R$^{3d}$;

alternatively, two of R$^{3a}$ groups located on adjacent atoms, they can be taken together with the atoms to which they are attached to form a 5- to 10-membered heterocycle comprising: carbon atoms and 1-4 heteroatoms selected from N, O, and S(O)$_p$, wherein said heterocycle is substituted with 0-2 R$^{3d}$;

R$^4$ is, independently at each occurrence, H, F, Cl, Br, OMe, NH$_2$, CF$_3$, Me, Et, CO$_2$H, CO$_2$Me, or CO$_2$Et;

R$^{8a}$ is H, Me or Et;

R$^{11}$ is C$_{1-4}$ haloalkyl, —CH$_2$C(O)NR$^8$R$^9$, —CH$_2$CH$_2$C(O)NR$^8$R$^9$, —CH$_2$C(O)R$^a$, —CH$_2$CH$_2$C(O)R$^a$, —CH$_2$C(O)OR$^a$, —CH$_2$CH$_2$C(O)OR$^a$, C$_{1-6}$ alkyl substituted with 0-2 R$^{11c}$, —CH$_2$OBn, —CH$_2$SBn, —(CH$_2$)$_r$—C$_{3-7}$ cycloalkyl substituted with 0-2 R$^{11b}$, —(CH$_2$)$_r$-phenyl substituted with 0-2 R$^{11b}$, —(CH$_2$)$_r$-indanyl substituted with 0-2 R$^{11b}$, —(CH$_2$)$_r$-indenyl substituted with 0-2 R$^{11b}$, —(CH$_2$)$_r$-naphthyl substituted with 0-2 R$^{11b}$, or —(CH$_2$)$_r$-5- to 10-membered heteroaryl substituted with 0-2 R$^{11b}$ and selected from thiazolyl, oxazolyl, pyrazolyl, triazolyl, tetrazolyl, thiadiazolyl, isoxazolyl, imidazolyl, pyridyl, pyrimidinyl, pyrazinyl, pyridazinyl, indolyl, indazolyl, isoindolyl, indolinyl, isoindolinyl, benzimidazolyl, benzothiazolyl, benzotriazolyl, quinolinyl, isoquinolinyl, tetrahydroquinolinyl, tetrahydroisoquinolinyl, and 2,2-dioxo-2,3-dihydro-1H-2λ$^6$-benzo[c]thiophenyl;

R$^{11b}$ is, independently at each occurrence, H, =O, F, Cl, Br, CF$_3$, OH, OMe, OEt, —CH$_2$OH, —C(CH$_3$)$_2$OH, —CH$_2$OMe, O(i-Pr), OCF$_3$, OCHF$_2$, CN, OPh, OBn, NO$_2$, NH$_2$, —C(O)R$^a$, —C(O)OR$^a$, —C(O)NR$^7$R$^8$, —NR$^8$C(O)R$^c$, —NR$^8$C(O)$_2$R$^c$, —S(O)$_p$NR$^8$R$^9$, —NR$^8$S(O)$_p$R$^c$, —S(O)$_p$R$^c$, C$_{1-6}$ alkyl, or —(CH$_2$)$_r$—C$_{3-10}$ carbocycle substituted with 0-3 R$^d$; and alternately, when two R$^{11b}$ groups are substituents on adjacent atoms they may be taken together with the atoms to which they are attached to form a 5- to 7-membered heterocycle comprising carbon atoms and 1-4 heteroatoms selected from N, O, and S(O)$_p$ and substituted with 0-2 R$^g$.

In a fifth aspect, the present invention includes compounds of Formula (I), or stereoisomers, tautomers, pharmaceutically acceptable salts, solvates, or prodrugs thereof, wherein:

A is substituted with 0-2 R$^2$ and selected from:

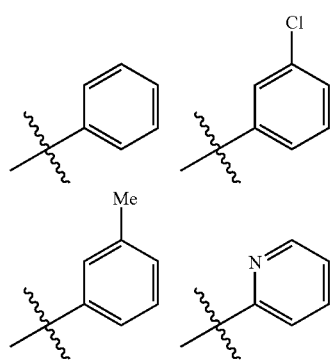

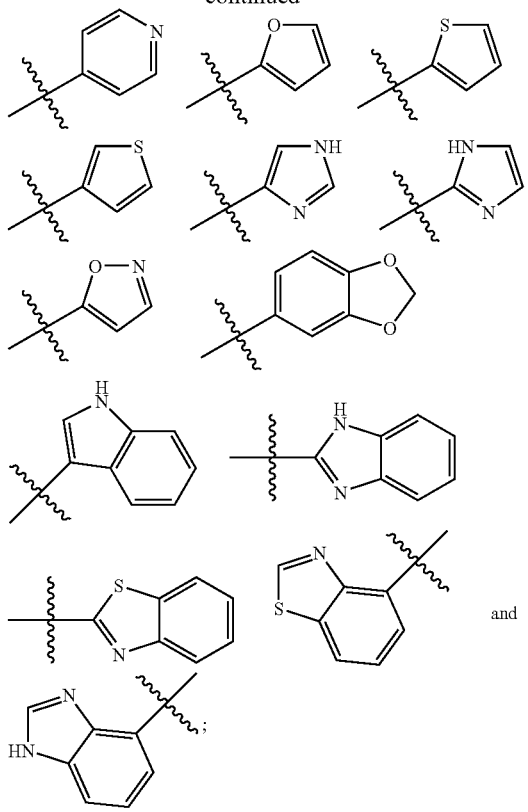

R$^2$ is, independently at each occurrence, =O, F, Cl, Br, Me, CF$_3$, OMe, OEt, OPh, OBn, SMe, SEt, S(n-Pr), SBn, —CH$_2$SMe, SO$_2$Me, NH$_2$, —CH$_2$NH$_2$, NO$_2$, CO$_2$H, CO$_2$Me, CONH$_2$, —CH$_2$NHCOPh, —NHCO$_2$Me, —CH$_2$NHCO$_2$Et, —CH$_2$NHCO$_2$(i-Pr), —CH$_2$NHCO$_2$(t-Bu), —CH$_2$NHCO$_2$Bn, —CH$_2$NHCO(CH$_2$)$_2$CO$_2$H, —CONHPh, —NHCONHMe, —CH$_2$NHCONHEt, —CH$_2$NHCONH(CH$_2$)$_2$CO$_2$Et, —CH$_2$NHCONHPh, —CH$_2$NHCONH(4-Cl-Ph), —CH$_2$NHCONHBn, —NHSO$_2$Me, —CH$_2$NHSO$_2$Me, —CH$_2$NHSO$_2$Et, —CH$_2$NHSO$_2$(n-Pr), —CH$_2$NHSO$_2$(i-Pr), —CH$_2$NHSO$_2$(n-pentyl), —CH$_2$NHSO$_2$Ph, —CH$_2$NHSO$_2$(4-NHCOMe-Ph), —CH$_2$NHSO$_2$(4-Cl—Bn), —CH$_2$NHSO$_2$CH$_2$CH$_2$Ph, —CH$_2$NHSO$_2$CH$_2$CH$_2$(2-Cl-Ph), —CH$_2$NHSO$_2$CH$_2$CH$_2$(3-Cl-Ph), —CH$_2$NHSO$_2$CH$_2$CH$_2$(4-Cl-Ph), —CH$_2$NHSO$_2$(3,4-dimethyl-isoxazol-4-yl), 1-pyrrolidinyl, 2-oxo-1-pyrrolidinyl, 3-carboxy-N-piperidinyl, pyrazol-1-yl, 4-carboxy-pyrazol-1-yl, 1,2,3-triazol-1-yl, 1,2,4-triazol-1-yl, 1,2,3-triazol-2-yl, 4-carboxy-1,2,3-triazol-1-yl, 4-(ethoxycarbonyl)-1,2,3-triazol-1-yl, tetrazol-1-yl, tetrazol-5-yl, 5-Me-tetrazol-1-yl, 5-CF$_3$-tetrazol-1-yl, or —OCH$_2$(2-tetrahydrofuranyl);

R$^3$ is, independently at each occurrence, phenyl substituted with 0-2 R$^{3a}$, naphthyl substituted with 0-2 R$^{3a}$, 1,2,3,4-tetrahydro-naphthyl substituted with 0-2 R$^{3a}$, or a 5- to 12-membered heterocycle substituted with 0-2 R$^{3a}$ and selected from: thiophene, furan, thiazole, tetrazole, pyridine, pyridinone, pyrimidine, pyrrole, pyrazole, indole, 2-oxindole, isoindolin-1-one, indazole, 1H-indazole-3-one, 7-azaindole, benzofuran, benzothiophene, benzimidazole, benzisoxazole, benzoxazole, quinazoline, quinoline, isoquinoline, 3H-quinazolin-4-one, phthalazine, 2H-phthalazin-1-one, 2H-3,4-dihydrophthalazin-1-one, 1H-quinolin-4-one, 1H-quinolin-2-one, 2H-3,4-dihydroisoquinolin-1-one, 3,4-dihydro-1H-quinolin-2-one, 1,3-dihydroindol-2-one, 3H-benzoxazol-2-one, 1,3-dihydrobenzimidazol-2-one, 1,4-dihydro-3,1-benzoxazin-2-one, 3,4-dihydro-1H-quinazolin-2-one, 1,3-dihydro-quinazoline-2,4-dione, 1,4-dihydro-quinoxaline-2,3-dione, 4H-benzo[1,4]thiazine-3-one, 2H-benzo[1,4]thiazin-3(4H)-one, 4H-1,4-benzoxazin-3-one, 1,3,4,5-tetrahydro-1-benzazepin-2-one, 1,3,4,5-tetrahydro-1,3-benzodiazepin-2-one, 8,9-dihydro-5H-7-oxa-5-aza-benzocyclohepten-6-one, benzimidazol-2-one, 1,3-dihydrobenzimidazol-2-one, 3H-benzoxazol-2-one, 3H-quinazolin-4-one, and 1,2,3,4-tetrahydroquinoline; and $R^4$ is, independently at each occurrence, H, Me, F, Br, Cl, $CF_3$, $CO_2H$, $CO_2Me$, or $CO_2Et$.

In a sixth aspect, the present invention includes compounds of Formula (I) or its stereoisomers, tautomers, pharmaceutically acceptable salts, solvates, or prodrugs thereof, within the scope of the first aspect wherein:

A is phenyl, 2-fluorophenyl, 3-fluorophenyl, 2-chlorophenyl, 3-chlorophenyl, 2-bromophenyl, 3-bromophenyl, 3-methylphenyl, 2-methoxyphenyl, 3-methoxyphenyl, 3-aminomethylphenyl, 4-aminomethylphenyl, 2-carboxy-5-chlorophenyl, 2-methoxycarbonyl-5-chlorophenyl, 2-(N-(methoxycarbonyl)-amino)-5-chlorophenyl, 2-(N-(ethoxycarbonyl)-aminomethyl)-5-chlorophenyl, 2-(N-(isopropoxycarbonyl)-aminomethyl)-5-chlorophenyl, 2-(N-(tert-butoxycarbonyl)-aminomethyl)-5-chlorophenyl, 2-(N-(phenylcarbonyl)-aminomethyl)-5-chlorophenyl, 2-(N-(benzoxycarbonyl)-aminomethyl)-5-chlorophenyl, 2-((N-(3-propanoic acid)carbonyl)-aminomethyl)-5-chlorophenyl, 2-(3-methylureido)-5-chlorophenyl, 2-(3-ethylureidomethyl)-5-chlorophenyl, 2-[3-(2-ethoxycarbonyl-ethyl)-ureidomethyl]-5-chlorophenyl, 2-(3-phenylureido)methyl)-5-chlorophenyl, 2-(3-(4-chlorophenyl)ureido)methyl)-5-chlorophenyl, 2-(3-benzylureido)methyl)-5-chlorophenyl, 2-(N-(methylsulfonyl)-amino)-5-chlorophenyl, 2-(N-(methylsulfonyl)-aminomethyl)-5-chlorophenyl, 2-(N-(ethylsulfonyl)-aminomethyl)-5-chlorophenyl, 2-(N-(n-propylsulfonyl)-aminomethyl)-5-chlorophenyl, 2-(N-(isopropylsulfonyl)-aminomethyl)-5-chlorophenyl, 2-(N-(n-pentylsulfonyl)-aminomethyl)-5-chlorophenyl, 2-(N-(phenylsulfonyl)-aminomethyl)-5-chlorophenyl, 2-((N-(4-methylcarbonylaminophenyl)sulfonyl)-aminomethyl)-5-chlorophenyl, 2-(N-(4-chlorobenzylsulfonyl)-aminomethyl)-5-chlorophenyl, 2-(N-(phenethylsulfonyl)-aminomethyl)-5-chlorophenyl, 2-(N-(2-chlorophenethylsulfonyl)-aminomethyl)-5-chlorophenyl, 2-(N-(3-chlorophenethylsulfonyl)-aminomethyl)-5-chlorophenyl, 2-(N-(4-chlorophenethylsulfonyl)-aminomethyl)-5-chlorophenyl, 2-(N-(3,4-dimethyl-isoxazol-4-yl)-aminomethyl)-5-chlorophenyl, 2-(N-(3,4-dimethyl-isoxazol-4-ylsulfonyl)-aminomethyl)-5-chlorophenyl, 3-carbamoylphenyl, 2,4-difluorophenyl, 2,5-difluorophenyl, 2,5-dichlorophenyl, 3,5-dichlorophenyl, 5-chloro-2-fluorophenyl, 3-chloro-2-fluorophenyl, 3-chloro-4-methylphenyl, 2-methyl-5-chlorophenyl, 2-methoxy-5-chlorophenyl, 2-ethoxy-5-chlorophenyl, 2-benzyloxy-5-chlorophenyl, 2-methylthio-5-chlorophenyl, 2-ethylthio-5-chlorophenyl, 2-propylthio-5-chlorophenyl, 2-benzylthio-5-chlorophenyl, 2-methylthiomethyl-5-chlorophenyl, 2-(2-oxo-1-pyrrolidinyl)-5-chlorophenyl, 3-trifluoromethyl-2-fluorophenyl, 2-trifluoromethyl-5-chlorophenyl, 5-bromo-2-fluorophenyl, 2-amino-5-chlorophenyl, 2-aminomethyl-5-chlorophenyl, 2-methylsulfonyl-5-chlorophenyl, 2-methylsulfonamide-5-chlorophenyl, 2-phenylcarbamoyl-5-chlorophenyl, 2-(3-carboxy-N-piperidinyl)-5-chlorophenyl, 2,6-difluoro-3-methylphenyl, 2-chloro-6-fluoro-3-methylphenyl, 2-fluoro-6-chloro-3-methylphenyl, 2,6-difluoro-3-chlorophenyl, 2,3-dichloro-6-aminophenyl, 2,3-dichloro-6-nitrophenyl, 2-phenoxyphenyl, 2-phenoxy-5-chlorophenyl, 2-(N-pyrrolidinyl)-5-chlorophenyl, 2-(pyrazol-1-yl)-5-chlorophenyl, 2-(4-carboxy-pyrazol-1-yl)-5-chlorophenyl, 2-(1,2,3-triazol-1-yl)-5-methylphenyl, 2-(1,2,3-triazol-1-yl)-5-chlorophenyl, 2-(1,2,3-triazol-2-yl)-5-chlorophenyl, 2-(1,2,4-triazol-1-yl)-5-chlorophenyl, 2-[(4-carboxy)-1,2,3-triazol-1-yl]-5-methylphenyl, 2-[(4-carboxy)-1,2,3-triazol-1-yl]-5-chlorophenyl, 2-[(4-ethoxycarbonyl)-1,2,3-triazol-1-yl]-5-chlorophenyl, 2-(tetrazol-1-yl)-5-methylphenyl, 2-(tetrazol-1-yl)-5-chlorophenyl, 2-(tetrazol-5-yl)-5-chlorophenyl, 2-(5-methyl-tetrazol-1-yl)-5-chlorophenyl, 2-(tetrazol-1-yl)-3-fluoro-5-chlorophenyl, 2-(tetrazol-1-yl)-3-fluoro-5-methylphenyl, 2-(5-methyltetrazol-1-yl)-5-chlorophenyl 2-(5-trifluoromethyl-tetrazol-1-yl)-5-chlorophenyl, 2-(2-tetrahydrofuranyl-methoxy)-5-chlorophenyl, 3,4-methylenedioxy-phenyl, cyclopentyl, 2-oxo-1-pyrrolidinyl, 2-furanyl, 2-thienyl, 3-thienyl, 5-chloro-2-thienyl, 5-chloro-3-thienyl, 2,5-dichloro-3-thienyl, 1-imidazolyl, 2-imidazolyl, 4-imidazolyl, 3-chloro-5-isoxazolyl, 4-pyridyl, 3-fluoro-2-pyridyl, 2(1H)-oxo-5-chloropyridin-1-yl, 1-indolyl, 3-indolyl, 2-benzimidazolyl, 6-chlorobenzimidazol-4-yl, 2-methyl-6-chlorobenzothiazol-4-yl or 2,6-dichlorobenzothiazol-4-yl;

$L_1$ is —$CH_2CH_2$—, —CH═CH—, —C(Me)═CH—, —C≡C—, —$CH_2NH$—, —$CH_2O$—, —NHNH—, —$SCH_2$—, —$SO_2CH_2$— or —$OCH_2$—;

$R^3$ is, independently at each occurrence, phenyl, 3-biphenyl, 4-biphenyl, 3-aminophenyl, 4-aminophenyl, 3-N,N-dimethylaminophenyl, 4-phenoxyphenyl, 4-benzyloxyphenyl, 4-(t-butoxymethyl)-phenyl, 4-methylsulfonylphenyl, 3-cyanophenyl, 4-cyanophenyl, 3-fluorophenyl, 4-fluorophenyl, 3-chlorophenyl, 4-chlorophenyl, 3-bromophenyl, 4-bromophenyl, 3-hydroxyphenyl, 4-hydroxyphenyl, 2-methoxyphenyl, 3-methoxyphenyl, 4-methoxyphenyl, 3-trifluoromethylphenyl, 4-trifluoromethylphenyl, 3-carboxyphenyl, 4-carboxyphenyl, 3-methoxycarbonylphenyl, 4-methoxycarbonylphenyl, 3-carboxymethylphenyl, 4-carboxymethylphenyl, 4-methoxycarbonylmethylphenyl, 3-ethoxycarbonylmethylphenyl, 4-ethoxycarbonylmethylphenyl, 4-ethoxycarbonylethylphenyl, 3-carbamoylphenyl, 4-carbamoylphenyl, 3-aminocarbonylmethylphenyl, 4-aminocarbonylmethylphenyl, 4-methylaminocarbonylphenyl, 4-dimethylaminocarbonylmethylphenyl, 4-amidinophenyl, 3-methylcarbonylaminophenyl, 4-methylcarbonylaminophenyl, 4-methoxycarbonylaminophenyl, 4-aminosulfonylphenyl, 3-methylsulfonylaminophenyl, 4-methylsulfonylamino, 2,4-difluorophenyl, 3-fluoro-4-cyanophenyl, 4-amino-3-carboxyphenyl, 4-amino-3-methoxycarbonylphenyl, 2,4-dichlorophenyl, 3-cyano-5-fluorophenyl, 3-fluoro-4-carbamoylphenyl, 3-carboxy-4-cyanophenyl, 3-phenyl-4-carbamoylphenyl, 4-(2-oxo-1-piperidino)-phenyl, thiazol-2-yl, thien-2-yl, 4-methoxycarbonyl-thiazol-2-yl, 4-carbamoyl-thiazol-2-yl, 1-benzyl-pyazol-4-yl, 5-phenyl-oxazol-2-yl, 5-carbamoyl-thien-2-yl, 5-carboxy-thien-2-yl, pyrid-2-yl, pyrid-3-yl, pyrid-4-yl, 6-amino-pyrid-3-yl, benzimidazol-2-yl, 6-methoxy-pyrid-3-yl, 1-methyl-benzimidazol-2-yl, benzoxazol-2-yl, benzothiazol-2-yl, 3-amino-benzisoxazol-6-yl, 3-amino-benzisoxazol-5-yl, indazol-5-yl, indazol-6-yl, 3-amino-indazol-5-yl, 3-hydroxy-indazol-5-yl, 3-amino-indazol-6-yl, 3-amino-1-methyl-indazol-6-yl, 3-amino-4-fluoro-indazol-6-yl, 3-amino-5-fluoro-indazol-6-yl, 3-amino-7-fluoro-indazol-6-yl, 4-imino-3,4-dihydro-2H-phthalazin-1-on-7-yl, 3-(5-tetrazolyl)-phenyl, 2,3-dihydroisoindol-1-on-6-yl, quinolin-5-yl, quinolin-6-yl, quinolin-8- yl, isoquinolin-5-yl, 2H-isoquinolin-1-on-6-yl, 2,4-diaminoquinazolin-7-yl, 4-NH$_2$-quinazolin-7-yl,
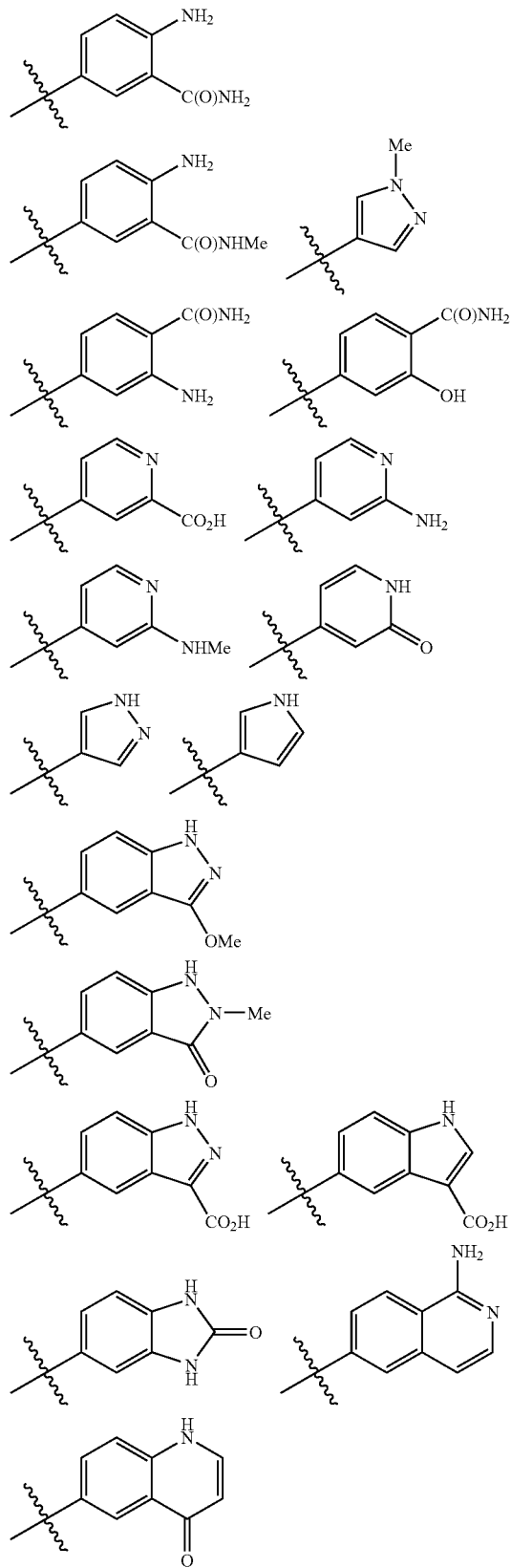
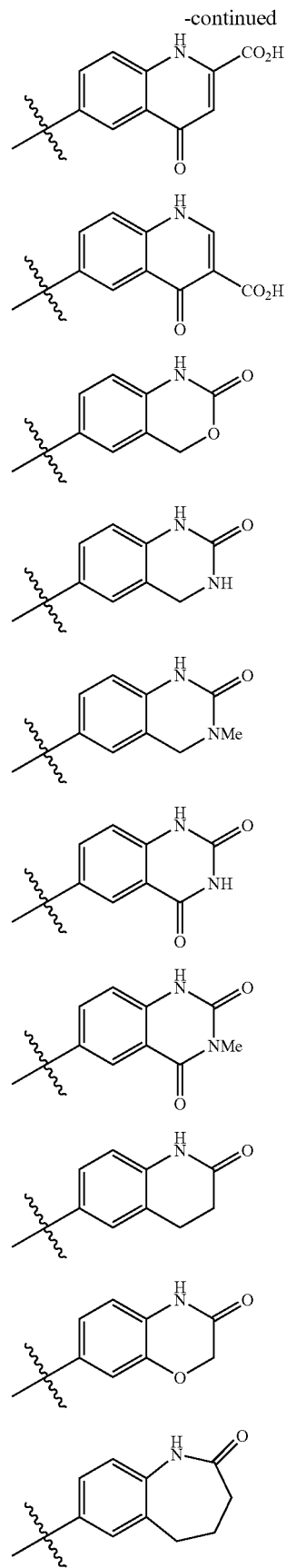
-continued

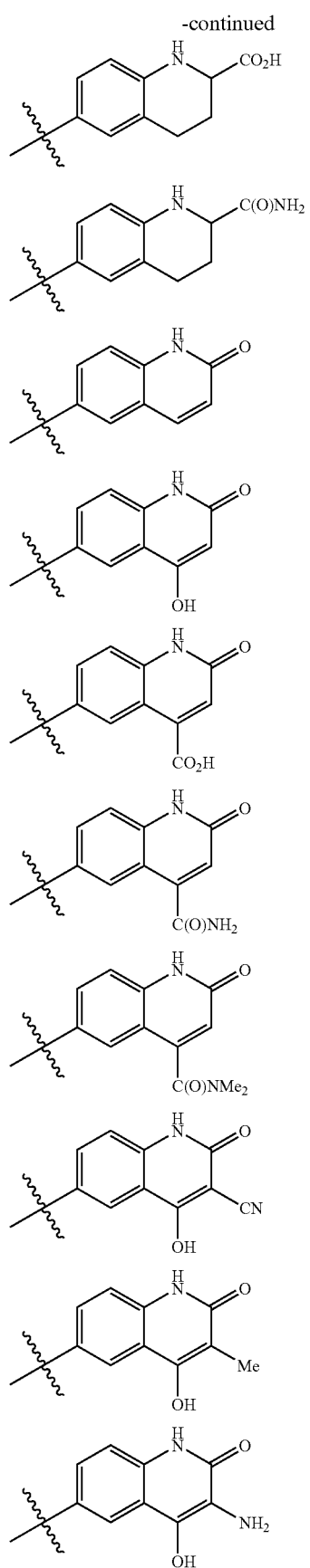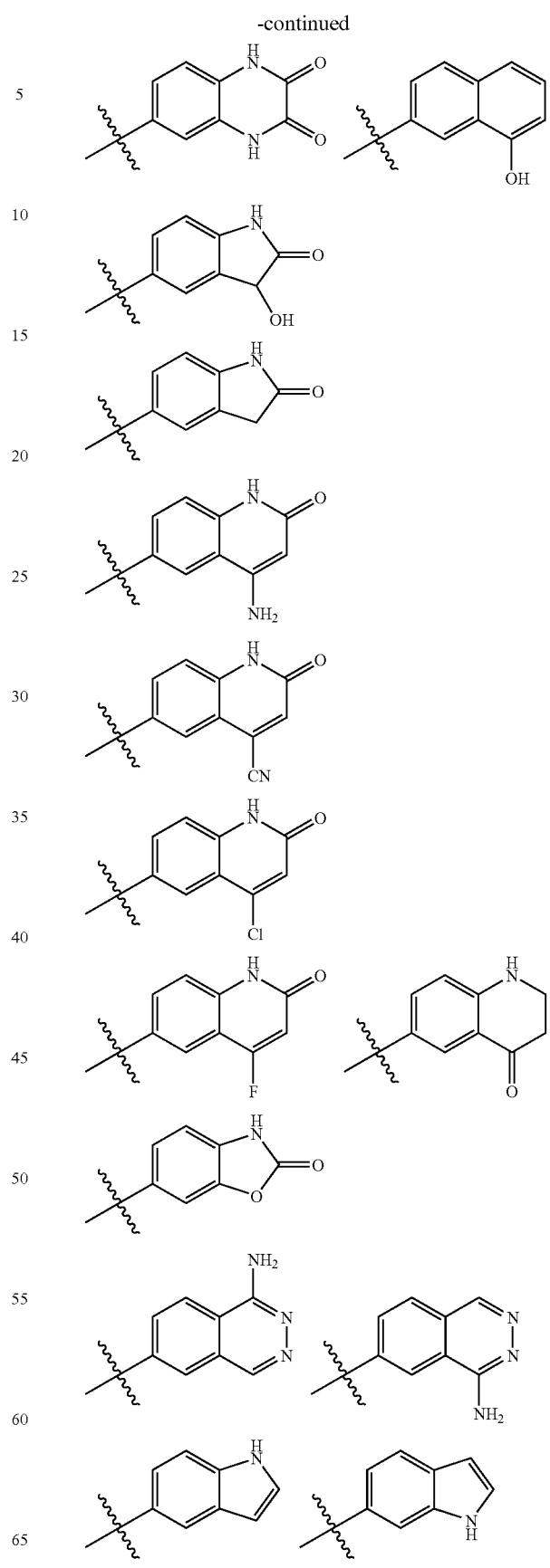

-continued
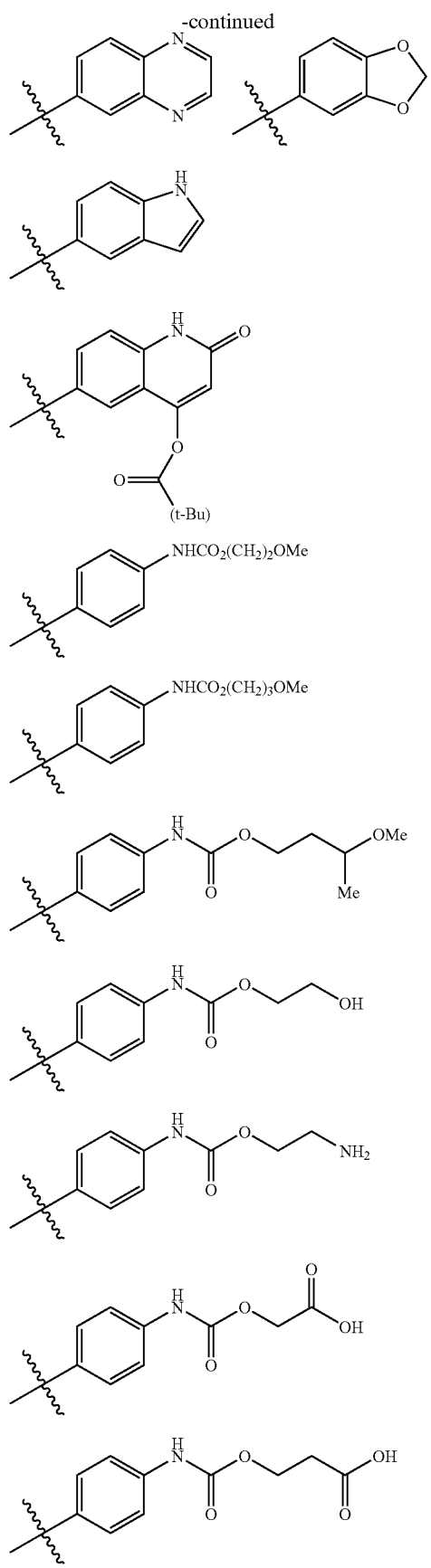
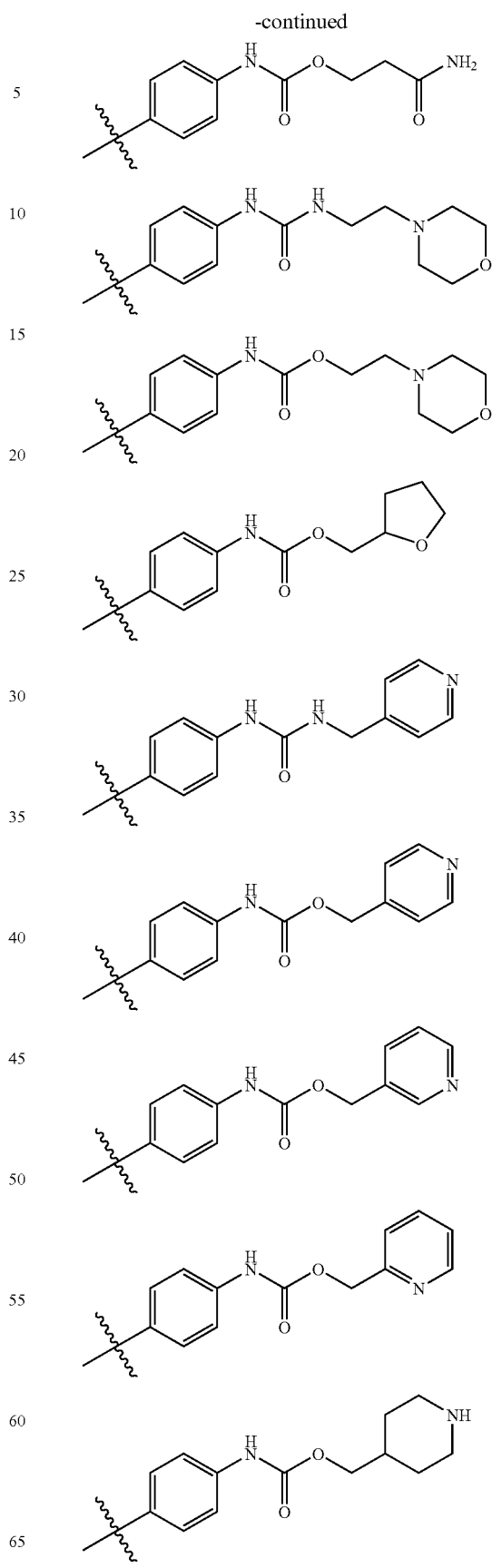

-continued

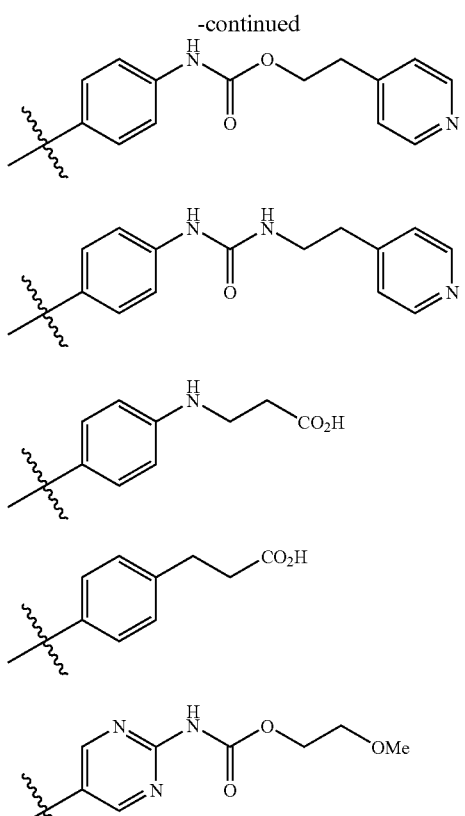

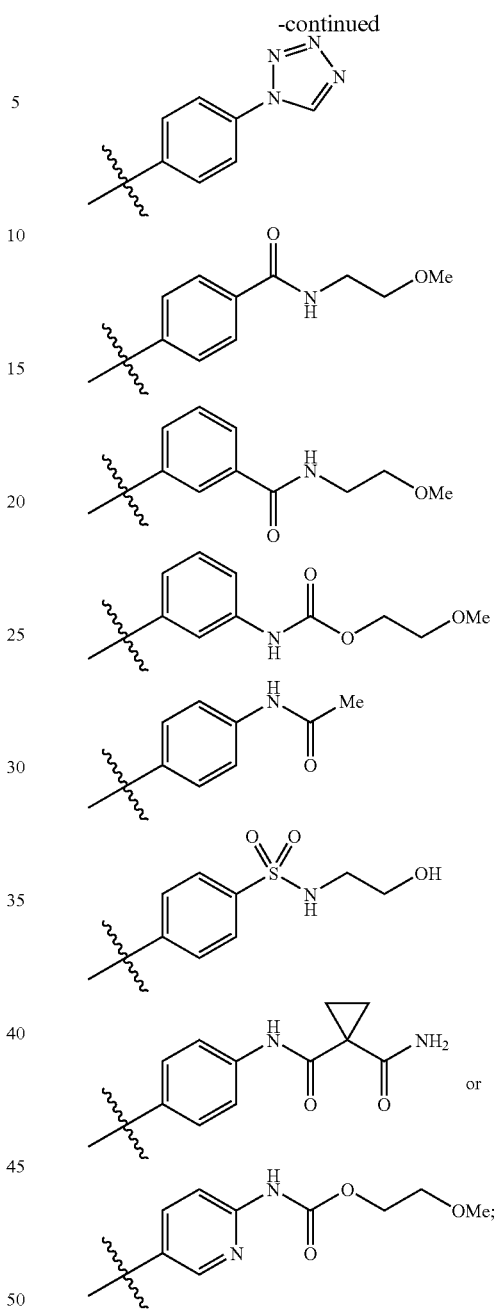

R[4] is, independently at each occurrence, H, Me, F, Br, Cl, CF$_3$, CO$_2$H, CO$_2$Me, or CO$_2$Et; and R[11] is methyl, n-propyl, n-butyl, neopentyl, cyclohexylmethyl, carboxymethyl, benzylaminocarbonylethyl, N-phenethylaminocarbonylethyl, N-benzyl-N-methylaminocarbonylethyl, N-[(pyridin-2-yl)methyl]aminocarbonylethyl, N-[(5-methylpyrazin-2-yl)methyl]aminoethyl, N-(thiazol-2-ylmethyl)aminocarbonylethyl, N-(cyclopropylmethyl)aminocarbonylmethyl, benzyl, phenethyl, 2-fluorobenzyl, 3-fluorobenzyl, 4-fluorobenzyl, 2-chlorobenzyl, 3-chlorobenzyl, 4-chlorobenzyl, 2-bromobenzyl, 3-bromobenzyl, 4-bromobenzyl, 3-carboxybenzyl, 3-carbamoylbenzyl, 3-(N-methylcarbamoyl)-benzyl, 3-(N-ethylcarbamoyl)-benzyl, 3-(N,N-dimethylcarbamoyl)-benzyl, 3-tetrazolyl-benzyl, 2-methylbenzyl, 3-methylbenzyl, 4-methylbenzyl, 3-trifluoromethylbenzyl, 4-trifluoromethylbenzyl, 2-aminobenzyl, 3-aminobenzyl, 2-nitrobenzyl, 3-nitrobenzyl, 4-nitrobenzyl, 3-methoxybenzyl, 4-methoxybenzyl, 3-difluoromethoxybenzyl, 2-trifluoromethoxybenzyl, 3-trifluoromethoxybenzyl, 2-phenoxybenzyl, 3-phenoxybenzyl, 2-benzyloxybenzyl, 3-benzyloxybenzyl, 4-benzyloxybenzyl, 4-phenylcarbonylbenzyl, 3-methoxycarbonylbenzyl, 3-methylcarbonylamino-benzyl, 2-phenylcarbonylamino-benzyl, 2-benzylcarbonylamino-benzyl, 3-benzylcarbonylamino-benzyl, 3-(benzoyl-methyl-amino)-benzyl, 3-(2-phenyl-ethyl)carbonylamino-benzyl, 2-phenylsulfonylamino-benzyl, 3-phenylsulfonylamino-benzyl, 3-[N-methyl-N-phenylaminosulfonyl]-benzyl, 3-[benzenesulfonyl-methyl-amino]-benzyl, 3-isobutylaminocarbonyl-benzyl, 3-t-butylcarbonylamino-benzyl, 3-isopentylaminocarbnoyl-benzyl, 3-(2-methylphenyl)carbamoyl-benzyl, 3-(3-methylphenyl)carbamoyl-benzyl, 3-(4-methylphenyl)carbamoyl-benzyl, 3-(4-fluorophenyl)carbamoyl-benzyl, 3-(1-naphthyl)carbamoyl-benzyl, 3-benzylcarbamoyl-benzyl, 3-(4-chlorophenyl)methylcarbamoyl-benzyl, 3-(4-methoxyphenyl)methylcarbamoyl-benzyl, 3-(2-phenylethyl)carbamoyl-benzyl, 3-[2-(4-methoxyphenyl)ethyl]carbamoyl-benzyl, 3-[2-(2-chlorophenyl)ethyl]carbamoyl-benzyl, 3-[2-(3-chlorophenyl)ethyl]carbamoyl-benzyl, 3-[2-(4-chlorophenyl)ethyl]carbamoyl-benzyl, 3-[methyl-(pyridin-2-ylethyl)]carbamoyl-benzyl 3-(3-phenylpropyl)carbamoyl-benzyl, 3-(ethyl-methyl-carbamoyl)-benzyl, 3-(isopropyl-methyl-carbamoyl)-benzyl, 3-(isobutyl-methyl-carbamoyl)-benzyl, 3-(methyl-phenyl-carbamoyl)-benzyl, 3-[(methyl-(3-methylphenyl)-carbamoyl]-benzyl, 3-[methyl-(4-methylphenyl)-carbamoyl]-benzyl, 3-(benzyl-methyl-carbamoyl)-benzyl, 3-[(3-chlorobenzyl)-methyl-carbamoyl]-benzyl, 3-[(4-chlorobenzyl)-methyl-carbamoyl]-benzyl, 3-[methyl-phenethyl-carbamoyl)]-benzyl, 3-(ethyl-phenyl-carbamoyl)-benzyl, 3-(piperidin-1-ylcarbonyl)-benzyl, 3-(4-phenyl-piperidin-1-ylcarbonyl)-benzyl, 3-(3,4-dihydro-2H-quinolin-1-ylcarbonyl)-benzyl, 3-[(2-methoxyethyl)-methyl-carbamoyl]-benzyl, 3-(4-methoxy-piperidin-1-ylcarbonyl)-benzyl, 3-(morpholin-4-ylcarbonyl)-benzyl, 3-(morpholin-4-ylsulfonyl)-benzyl, 3-[(N-(2-methoxyethyl), N-methylamino)sulfonyl]-benzyl, 3-(N,N-dimethylaminosulfonyl)-benzyl, 3-(azetidin-1-ylcarbonyl)-benzyl, 3-(3-methoxy-azetidin-1-ylcarbonyl)-benzyl, 3-(3-hydroxy-pyrrolidin-1-ylcarbonyl)-benzyl, 3-[(4-tetrahydropyranyl)methylcarbonyl]-benzyl, 3-[(2-hydroxyethyl)-methyl-carbamoyl]-benzyl, 3-(3-hydroxy-azetidin-1-ylcarbonyl)-benzyl, 3-(4-hydroxypiperidin-1-ylcarbonyl)-benzyl, 3-[4-(N,N-dimethylamino)-piperidin-1-ylcarbonyl]-benzyl, 3-(4-methyl-piperazin-1-ylcarbonyl)-benzyl, 3-[3-(N,N-dimethylamino)-pyrrolidin-1-ylcarbonyl]-benzyl, 2-phenyl-benzyl, 3-phenyl-benzyl, 4-phenyl-benzyl, 3-phenethyl-benzyl, benzyloxymethyl, benzylthiomethyl, 1-naphthylmethyl, 2-naphthylmethyl, thiazol-4-ylmethyl, pyrid-2-ylmethyl, pyrid-3-ylmethyl, pyrid-4-ylmethyl, 1-benzyl-imidazol-4-ylmethyl, benzothiazol-2-ylmethyl, 3-[(2,6-dimethylmorpholin-4-ylcarbonyl)-benzyl, (benzyloxycarbonyl)methyl, (1-methylpyrazol-3-yl)methyl, (1-methylpyrazol-4-yl)methyl, (1-methylpyrazol-5-yl)methyl, (3-methylpyrazol-5-yl)methyl, (1-ethylpyrazol-4-yl)methyl, (1-n-propylpyrazol-4-yl)methyl, (1-isopropylpyrazol-4-yl)methyl, 1-ethylpyrazol-3-ylmethyl, 3-pyrazolylmethyl, (4-chloro-3-methyl-5-pyrazolyl)methyl, (4-chloro-1,5-dimethyl-3-pyrazolyl)methyl, (4-chloro-1,3-dimethyl-5-pyrazolyl)methyl, (4-chloro-1-methyl-3-pyrazolyl)methyl, [1-(4-methoxybenzyl)-pyrazol-3-yl]methyl, (1,5-dimethylpyrazol-3-yl)methyl, (1,3-dimethylpyrazol-5-yl)methyl, [1-(4-methoxybenzyl)-5-methyl-pyrazol-3-yl]methyl, (3-trifluoromethylpyrazol-5-yl)methyl, [1-(4-methoxybenzyl)-3-trifluoromethylpyrazol-5-yl]methyl, [(1-methyl-5-methoxycarbonyl)-pyrazol-3-yl]methyl, [(1-methyl-5-carboxy)-pyrazol-3-yl]methyl, [(1-methyl-5-carbamoyl)-pyrazol-3-yl]methyl, [(5-methoxycarbonyl)-pyrrol-2-yl]methyl, thiazol-2-ylmethyl, thiazol-4-methyl, (2-methoxypyridin-3-yl)methyl, (6-methoxypyridin-3-yl)methyl, (4-(methoxycarbonyl)-oxazol-2-yl)methyl, morpholin-4-ylcarbonylmethyl, (2,6-dimethyl-morpholin-4-yl)carbonylmethyl, N-((5-methylpyrazin-2-yl)methyl)-aminocarbonylmethyl, 2-hydroxy-indan-5-ylmethyl, 4-methylpiperazin-1-ylcarbonylmethyl, piperazin-1-ylcarbonylmethyl, 4-methylcarbonylpiperazin-1-ylcarbonylmethyl, pyrrolidin-1-ylcarbonylmethyl, 2-methoxypyrrolidin-1-ylcarbonylmethyl, aziridin-1-ylcarbonylmethyl, [3-(4-methoxyphenoxy)-azetidin-1-yl]carbonylmethyl, 2-hydroxyethylaminocarbonylmethyl, 2-methoxyethylaminocarbonylmethyl, 2-ethoxyethylaminocarbonylmethyl, bis (2-methoxyethyl)aminocarbonylmethyl, 4-dimethylaminopyrrolidin-1-ylcarbonylmethyl, (3-phenyl-pyrrolidin-1-yl)carbonylmethyl, (3,3-dimethyl-piperidin-1-yl)carbonylmethyl, [2-(4-pyridyl)-pyrrolidin-1-yl]carbonylmethyl, 4-chlorophenylaminocarbonylmethyl, 3-chlorophenylcarbonylmethyl, N-methyl-N-benzylaminocarbonylmethyl, cyclopropylaminocarbonylmethyl, cyclopropylmethylaminocarbonylmethyl, cyclopentylaminocarbonylmethyl, (trans-2-phenylcyclopropyl)aminocarbonylmethyl, N,N-dimethylaminoethylaminocarbonylmethyl, N-((pyridin-2-yl)methyl)-aminocarbonylmethyl, N-((pyridin-3-yl)methyl)-aminocarbonylmethyl, N-((pyridin-4-yl)methyl)-aminocarbonylmethyl, N-((pyridin-2-yl)ethyl)-aminocarbonylmethyl, N-((6-oxo-1,6-dihydropyridin-3-yl)methyl)-aminocarbonylmethyl, (1,1-dioxo-1$\lambda^6$-thiomorpholin-4-yl)carbonylmethyl, (thiomorpholin-4-yl)carbonylmethyl, N-(tert-butoxycarbonyl)-1H-indol-3-ylmethyl, 1H-indol-3-ylmethyl, 2,2-dioxo-2,3-dihydro-1H-2$\lambda^6$-benzo[c]thiophen-5-ylmethyl, 4,4,4-trifluorobutyl, cyclopropylmethyl, (4-hydroxy)cyclohexylmethyl, 4-oxocyclohexylmethyl, 2-(t-butoxycarbonylamino)ethyl, 2-aminoethyl, (1,3-dihydro-isoindol-2-yl)carbonylmethyl, (4-acetyl-perhydro-1,4-diazepin-1-yl)carbonylmethyl, (4-(2-N,N-diethylaminoethyl)-perhydro-1,4-diazepin-1-yl)carbonylmethyl, (6-oxo-7,10-diaza-tricyclo[7.2.1.0$^{2,7}$]dodeca-2,4-dien-10-ylcarbonyl)methyl, (1,4-diaza-bicyclo[3.2.2]nonane-4-carbonyl)methyl, (5-t-butoxycarbonyl-2,5-diazabicyclo[2.2.1]heptane-2-carbonyl)methyl, (1-methyl-hexahydro-pyrrolo[1,2-a]pyrazin-2-ylcarbonyl)methyl,

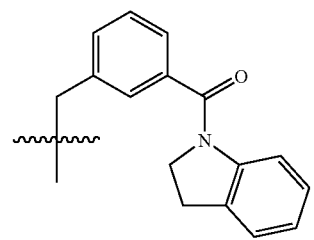

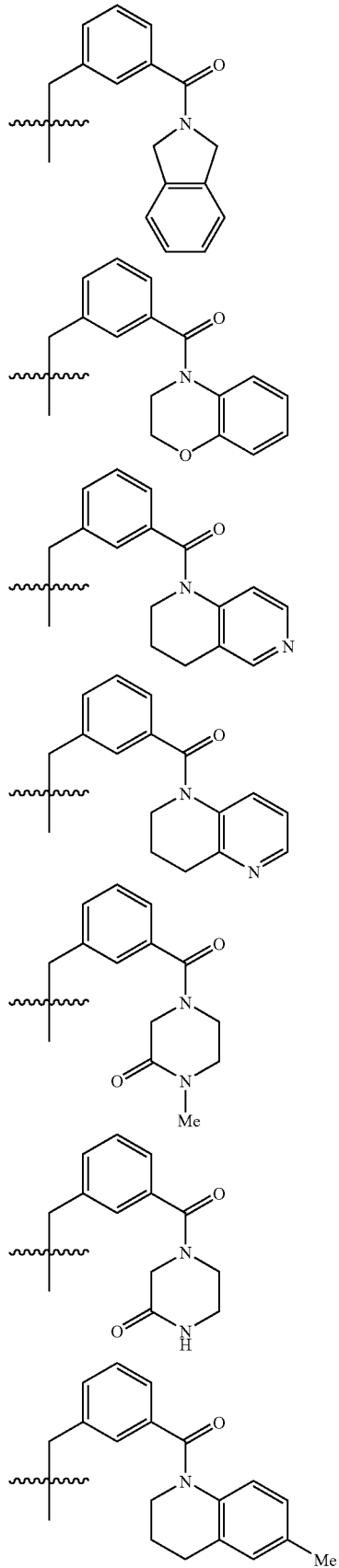

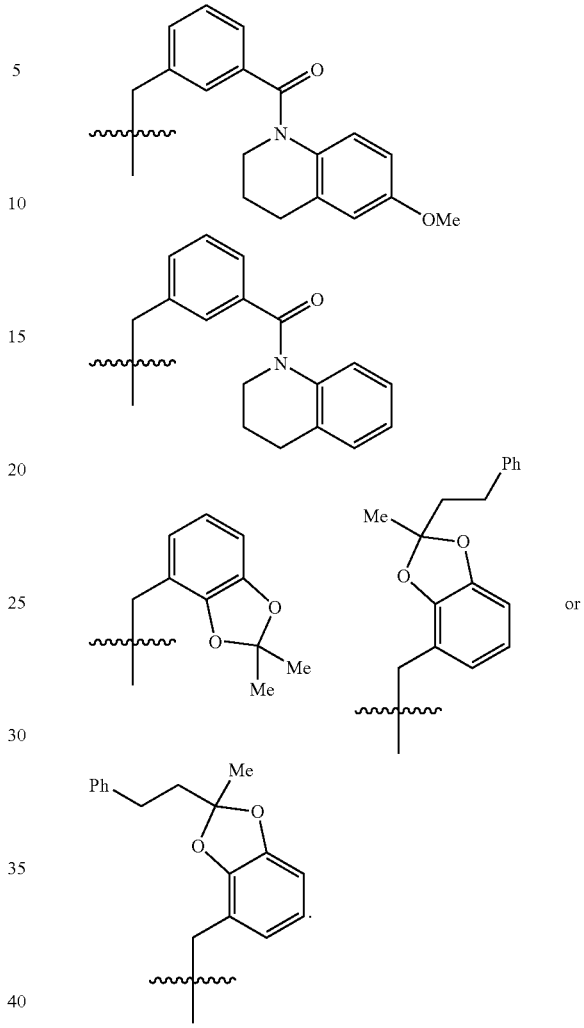

In a seventh aspect, the present invention includes compounds of Formula (I) or its stereoisomers, tautomers, pharmaceutically acceptable salts, solvates, or prodrugs thereof, within the scope of the first aspect wherein:

A is 3-chlorophenyl, 3-bromophenyl, 3-methylphenyl, 3-methoxyphenyl, 2,5-dichlorophenyl, 5-chloro-2-fluorophenyl, 5-bromo-2-fluorophenyl, 3-chloro-2-fluorophenyl, 2-methyl-5-chlorophenyl, 2-methoxy-5-chlorophenyl, 2-methylthio-5-chlorophenyl, 2-ethylthio-5-chlorophenyl, 2-propylthio-5-chlorophenyl, 2-benzylthio-5-chlorophenyl, 2-amino-5-chlorophenyl, 2-aminomethyl-5-chlorophenyl, 2,6-difluoro-3-methylphenyl, 2-chloro-6-fluoro-3-methylphenyl, 2-fluoro-6-chloro-3-methylphenyl, 2,6-difluoro-3-chlorophenyl, 2,3-dichloro-6-nitrophenyl, 5-chloro-2-thienyl, 3,4-methylenedioxyphenyl, 2-methoxycarbonyl-5-chlorophenyl, 6-chlorobenzimidazol-4-yl, 2-(1,2,3-triazol-1-yl)-5-methylphenyl, 2-(1,2,3-triazol-1-yl)-5-chlorophenyl, 2-(1,2,4-triazol-1-yl)-5-chlorophenyl, 2-(1,2,3-triazol-2-yl)-5-chlorophenyl, 2-[(4-carboxy)-1,2,3-triazol-1-yl]-5-chlorophenyl, 2-[(4-carboxy)-1,2,3-triazol-1-yl]-5-methylphenyl, 2-[(4-ethoxycarbonyl)-1,2,3-triazol-1-yl]-5-chlorophenyl, 2-(tetrazol-1-yl)-5-methylphenyl, 2-(tetrazol-1-yl)-5-chlorophenyl, 2-(tetrazol-1-yl)-3-fluoro-5-chlorophenyl, 2-(tetrazol-1-yl)-3-fluoro-5-methylphenyl, or 2-(5-methyltetrazol-1-yl)-5-chlorophenyl;

$L_1$ is —$CH_2CH_2$—, —CH═CH—, —C(Me)═CH—, —C≡C—, or —$CH_2$NH—;
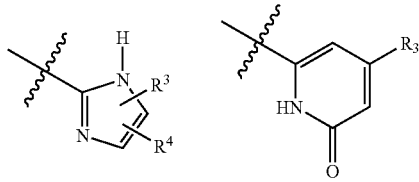
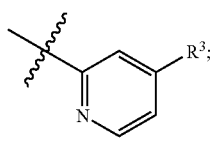
M is
$R^3$ is, independently at each occurrence,
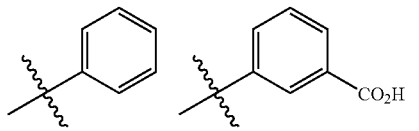
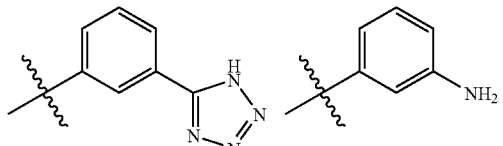
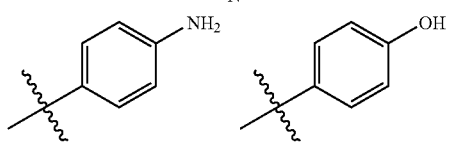
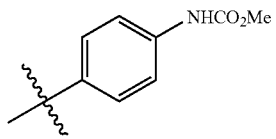
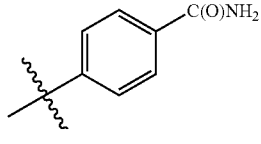
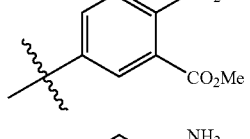
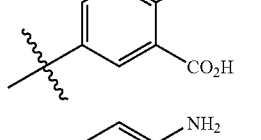
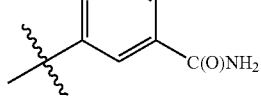
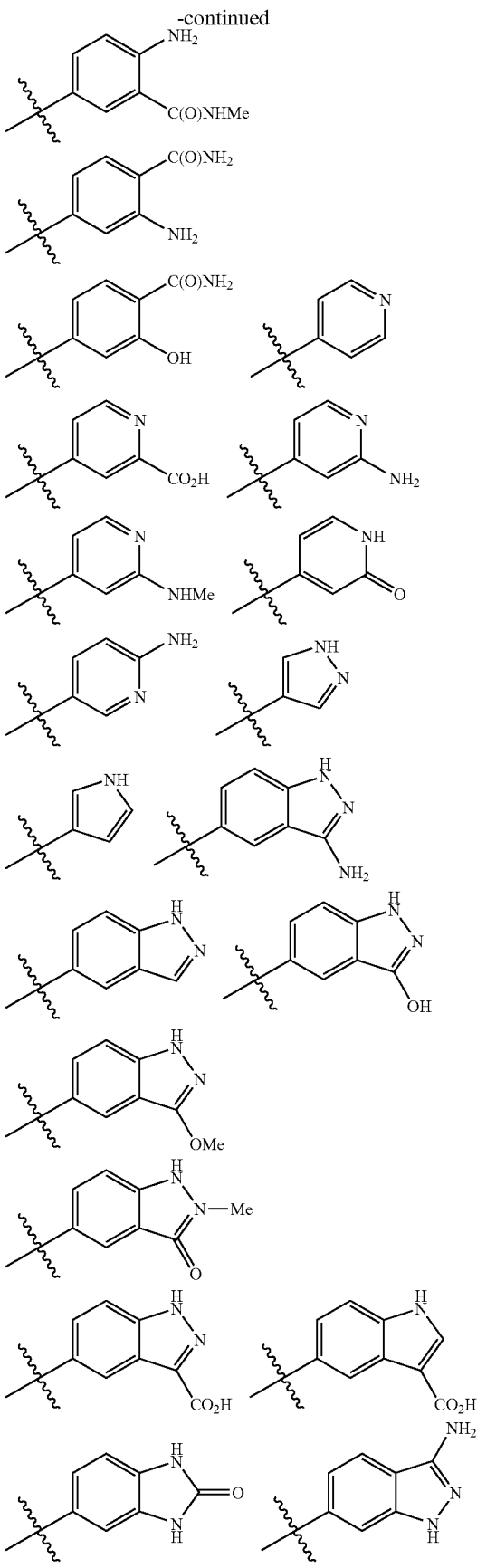

-continued
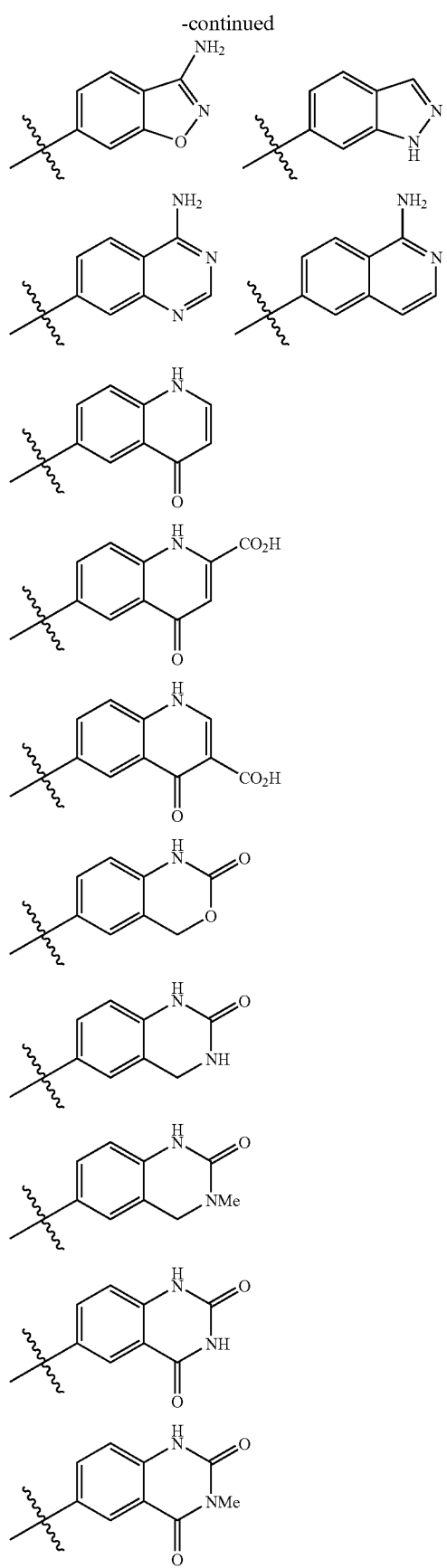
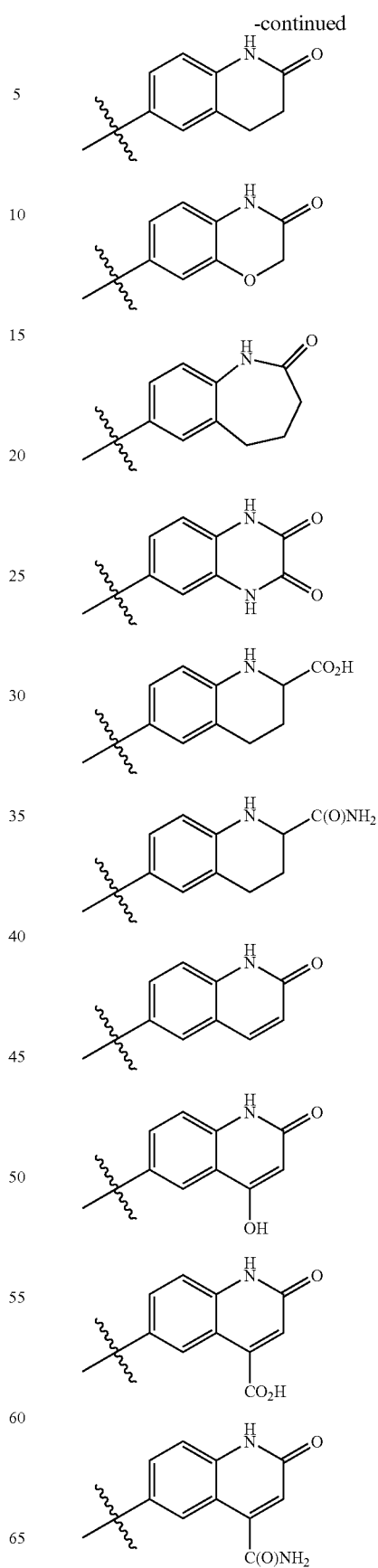

-continued
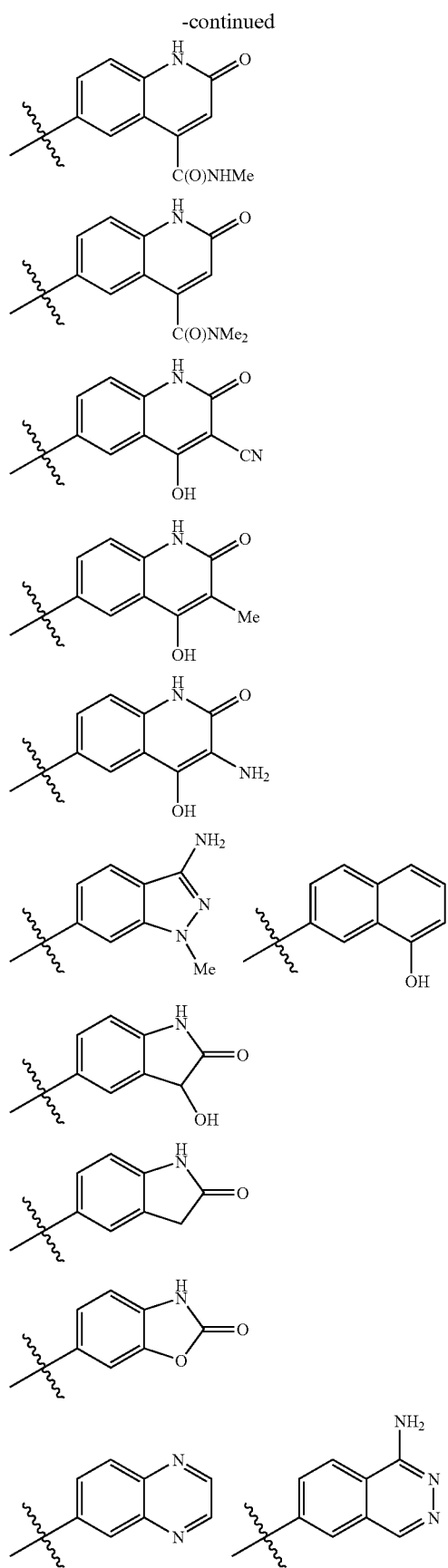
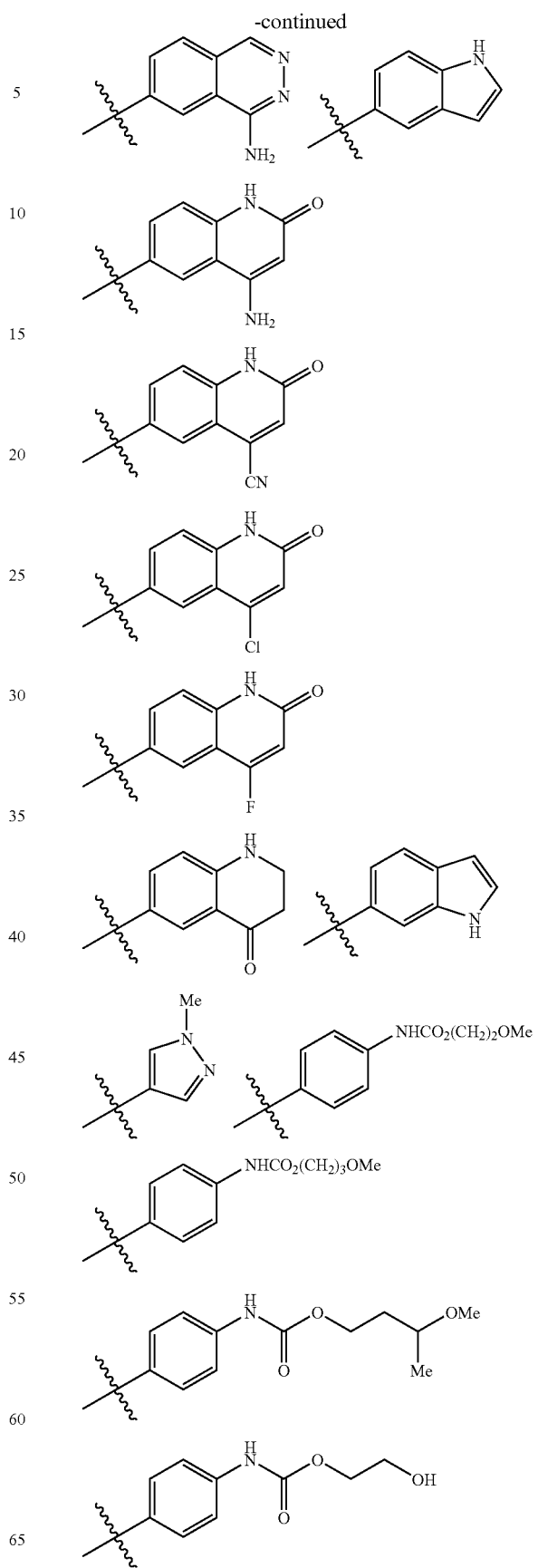

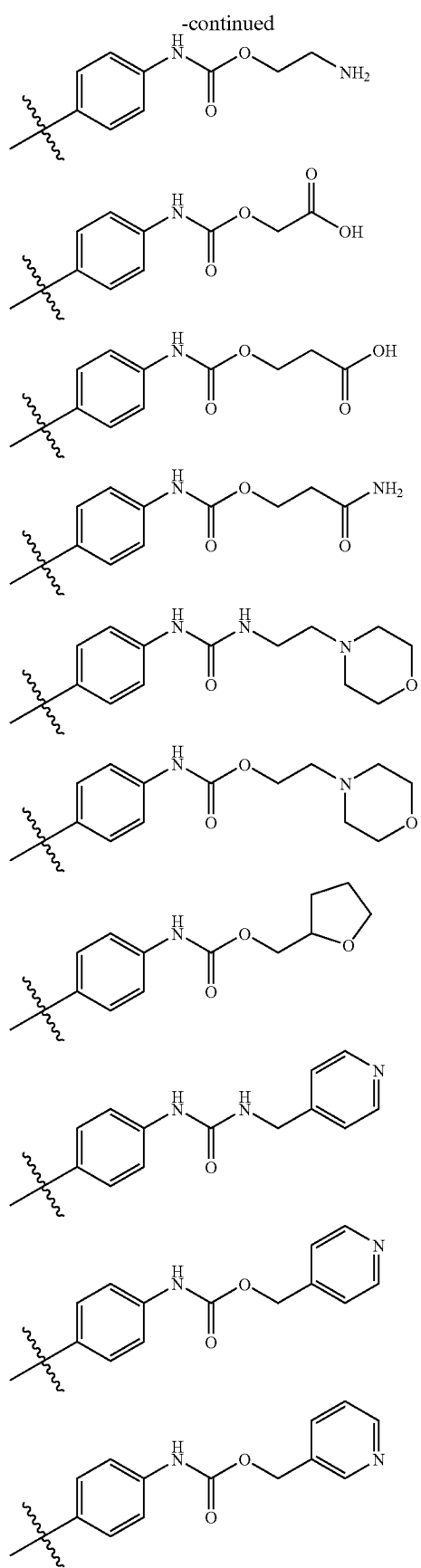
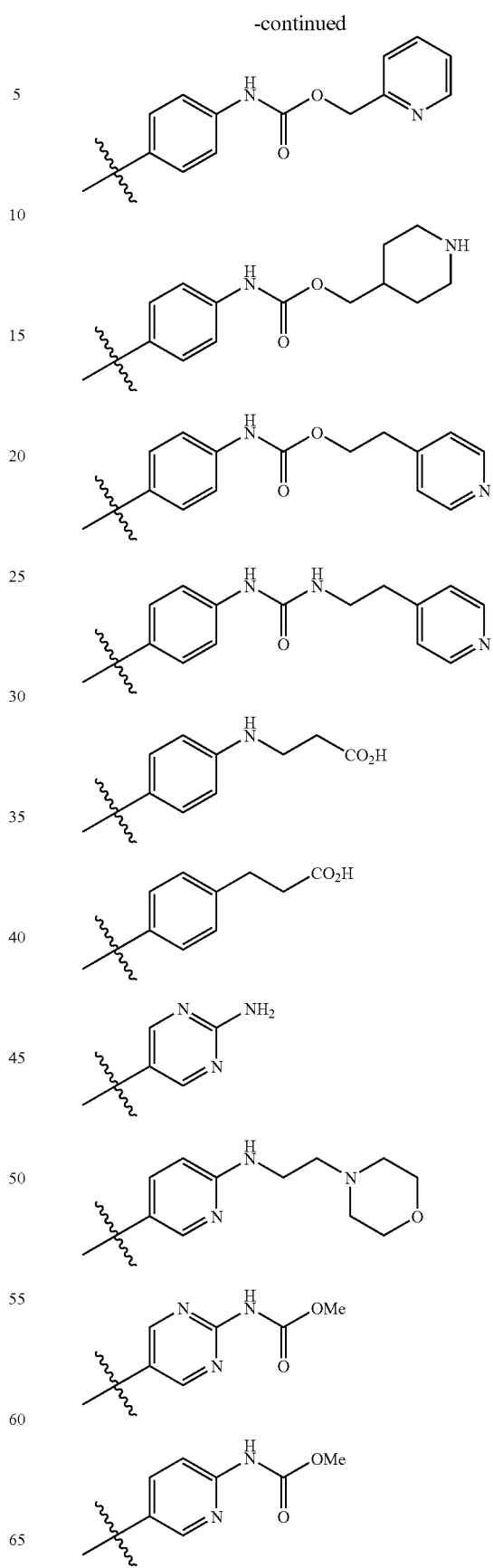

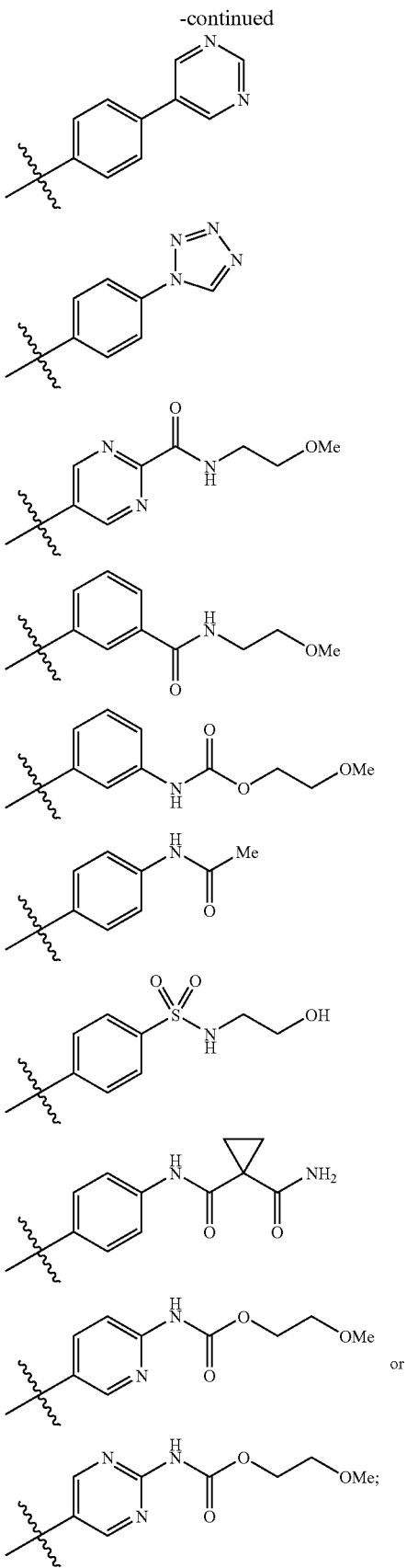

R[4] is H, Me or Cl; and

R[11] is methyl, n-butyl, carboxymethyl, cyclopropylmethyl, benzyl, 4-fluoro-benzyl, (benzyloxycarbonyl)methyl, 3-carboxy-benzyl, 3-carbamoyl-benzyl, 3-(N-methylcarbamoyl)-benzyl, 3-(N,N-dimethylcarbamoyl)-benzyl, (1-methylpyrazol-3-yl)methyl, (1-methylpyrazol-4-yl)methyl, (1-ethylpyrazol-4-yl)methyl, (1-n-propylpyrazol-4-yl)methyl, (1-isopropylpyrazol-4-yl)methyl, 1-ethylpyrazol-3-ylmethyl, 3-pyrazolylmethyl, 1-(4-methoxybenzyl)-pyrazol-3-yl]methyl, (1,5-dimethylpyrazol-3-yl)methyl, (1,3-dimethylpyrazol-5-yl)methyl, [1-(4-methoxybenzyl)-5-methyl-pyrazol-3-yl]methyl, (3-trifluoromethylpyrazol-5-yl)methyl, [1-(4-methoxybenzyl)-3-trifluoromethylpyrazol-5-yl]methyl, (3-methylpyrazol-5-yl)methyl, (1-methylpyrazol-5-yl)methyl, (2-methoxypyridin-3-yl)methyl, (6-methoxypyridin-3-yl)methyl, (4-(methoxycarbonyl)-oxazol-2-yl)methyl, morpholin-4-ylcarbonylmethyl, N-((5-methylpyrazin-2-yl)methyl)-aminocarbonylmethyl, N-((pyridin-2-yl)methyl)-aminocarbonylmethyl, N-((pyridin-3-yl)methyl)-aminocarbonylmethyl, N-((pyridin-4-yl)methyl)-aminocarbonylmethyl, N-((pyridin-2-yl)ethyl)-aminocarbonylmethyl, 4-methylpiperazin-1-ylcarbonylmethyl, 4-methylcarbonylpiperazin-1-ylcarbonylmethyl, pyrrolidin-1-ylcarbonylmethyl, 2-methoxypyrrolidin-1-ylcarbonylmethyl, aziridin-1-ylcarbonylmethyl, 2-hydroxyethylaminocarbonylmethyl, 2-methoxyethylaminocarbonylmethyl, bis(2-methoxyethyl)aminocarbonylmethyl, 4-dimethylaminopyrrolidin-1-ylcarbonylmethyl, 4-chlorophenylaminocarbonylmethyl, 3-chlorophenylcarbonylmethyl, N-methyl-N-benzylaminocarbonylmethyl, cyclopropylaminocarbonylmethyl, cyclopropylmethylaminocarbonylmethyl, cyclopentylaminocarbonylmethyl, (trans-2-phenylcyclopropyl)aminocarbonylmethyl, N,N-dimethylaminoethylaminocarbonylmethyl, 1-(1,1-dioxo-1λ[6]-thiomorpholin-4-yl)carbonylmethyl, N-(tert-butoxycarbonyl)-1H-indol-3-ylmethyl, 1H-indol-3-ylmethyl, 2,2-dioxo-2,3-dihydro-1H-2λ[6]-benzo[c]thiophen-5-ylmethyl, (4-hydroxy)cyclohexylmethyl or 4-oxo-cyclohexylmethyl, cyclohexylmethyl, phenethyl, 2-fluorobenzyl, 3-fluorobenzyl, 2-chlorobenzyl, 3-(N-ethylcarbamoyl)-benzyl, 3-methylbenzyl, 4-methylbenzyl, 3-methoxybenzyl, 3-difluoromethoxybenzyl, 3-trifluoromethoxy-benzyl, 3-methoxycarbonylbenzyl, 3-methylcarbonylamino-benzyl, 3-benzylcarbonylamino-benzyl, 3-(benzoyl-methyl-amino)-benzyl, 3-(2-phenylethyl)carbonylamino-benzyl, 2-phenylsulfonylamino-benzyl, 3-phenylsulfonylamino-benzyl, 3-[N-methyl, N-phenylaminosulfonyl]-benzyl, 3-(benzenesulfonyl-methyl-amino)-benzyl, 3-(2-methylphenyl)carbamoyl-benzyl, 3-(3-methylphenyl)carbamoyl-benzyl, 3-(4-methylphenyl)carbamoyl-benzyl, 3-(4-fluorophenyl)carbamoyl-benzyl, 3-(1-naphthyl)carbamoyl-benzyl, 3-benzylcarbamoyl-benzyl, 3-(4-chlorophenyl)methylcarbamoyl-benzyl, 3-(4-methoxyphenyl)methylcarbamoyl-benzyl, 3-(2-phenylethyl)carbamoyl-benzyl, 3-[2-(4-methoxyphenyl)ethyl]carbamoyl-benzyl, 3-[2-(2-chlorophenyl)ethyl]carbamoyl-benzyl, 3-[2-(3-chlorophenyl)ethyl]carbamoyl-benzyl, 3-[2-(4-chlorophenyl)ethyl]carbamoyl-benzyl, 3-[methyl-(pyridin-2-ylethyl)]carbamoyl-benzyl 3-(3-phenylpropyl)carbamoyl-benzyl, 3-(ethyl-methyl-carbamoyl)-benzyl, 3-(isopropyl-methyl-carbamoyl)-benzyl, 3-(isobutyl-methyl-carbamoyl)-benzyl, 3-(methyl-phenyl-carbamoyl)-benzyl, 3-[(methyl-(3-methylphenyl)-carbamoyl]-benzyl, 3-[methyl-(4-methylphenyl)-carbamoyl]-benzyl, 3-(benzyl-methyl-carbamoyl)-benzyl, 3-[(3-chlorobenzyl)-methyl-carbamoyl]-benzyl, 3-[(4-chlorobenzyl)-methyl-carbamoyl]-benzyl, 3-[methyl-phenethyl-carbamoyl)]-benzyl, 3-(ethyl-phenyl-carbamoyl)- benzyl, 3-(piperidin-1-ylcarbonyl)-benzyl, 3-(3,4-dihydro-2H-quinolin-1-ylcarbonyl)-benzyl, 3-[(2-methoxyethyl)-methyl-carbamoyl]-benzyl, 3-(4-methoxy-piperidin-1-ylcarbonyl)-benzyl, 3-(morpholin-4-ylcarbonyl)-benzyl, 3-(morpholin-4-ylsulfonyl)-benzyl, 3-[(N-(2-methoxyethyl), N-methylamino)sulfonyl]-benzyl, 3-(N,N-dimethylaminosulfonyl)-benzyl, 3-(azetidin-1-ylcarbonyl)-benzyl, 3-(3-methoxy-azetidin-1-ylcarbonyl)-benzyl, 3-(3-hydroxy-pyrrolidin-1-ylcarbonyl)-benzyl, 3-[(4-tetrahydropyranyl)methylcarbonyl]-benzyl, 3-[(2-hydroxyethyl)-methyl-carbamoyl]-benzyl, 3-(3-hydroxy-azetidin-1-ylcarbonyl)-benzyl, 3-(4-hydroxypiperidin-1-ylcarbonyl)-benzyl, 3-[4-(N,N-dimethylamino)-piperidin-1-ylcarbonyl]-benzyl, 3-(4-methyl-piperazin-1-ylcarbonyl)-benzyl, 3-[3-(N,N-dimethylamino)-pyrrolidin-1-ylcarbonyl]-benzyl, 1-naphthylmethyl, 2-naphthylmethyl, thiazol-4-ylmethyl, pyrid-2-ylmethyl, pyrid-3-ylmethyl, pyrid-4-ylmethyl, 1-benzyl-imidazol-4-ylmethyl, benzothiazol-2-ylmethyl, 3-[(2,6-dimethylmorpholin-1-ylcarbonyl)-benzyl, (benzyloxycarbonyl)methyl, (4-chloro-3-methyl-5-pyrazolyl)methyl, (4-chloro-1,5-dimethyl-3-pyrazolyl)methyl, (4-chloro-1,3-dimethyl-5-pyrazolyl)methyl, [(1-methyl-5-methoxycarbonyl)-pyrazol-3-yl]methyl, [(1-methyl-5-carboxy)-pyrazol-3-yl]methyl, [(1-methyl-5-carbamoyl)-pyrazol-3-yl]methyl, [(5-methoxycarbonyl)-pyrrol-2-yl]methyl, thiazol-2-ylmethyl, thiazol-4-methyl, 2-hydroxyindan-5-ylmethyl, 2-ethoxyethylaminocarbonylmethyl, 4,4,4-trifluorobutyl, N-((6-oxo-1,6-dihydropyridin-3-yl)methyl)-aminocarbonylmethyl, (thiomorpholin-4-yl)carbonylmethyl, (2,6-dimethyl-morpholin-4-yl)carbonylmethyl, piperazin-1-ylcarbonylmethyl, (4-chloro-1-methyl-3-pyrazolyl)methyl,

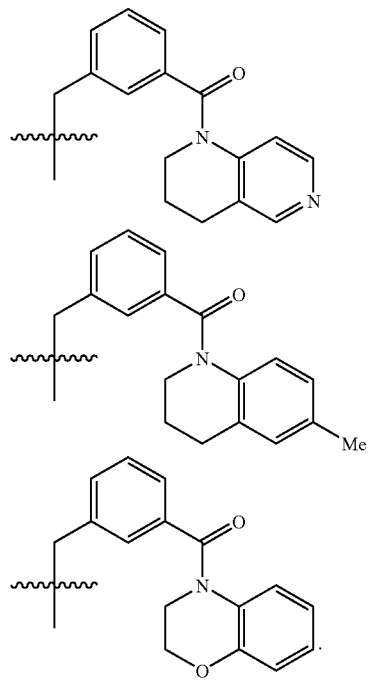

In an eighth aspect, the present invention provides a compound selected from the exemplified examples or a stereoisomer, tautomer, pharmaceutically acceptable salt, solvate, or prodrug thereof.

In a ninth aspect, the present invention provides a process for preparing compounds of formulae (VIII), (IX) or (X):

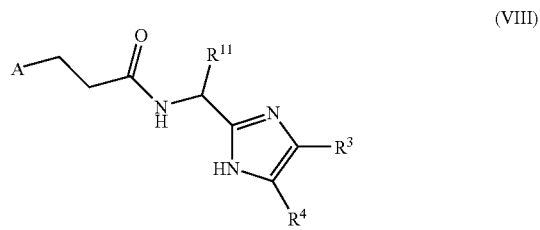

(VIII)

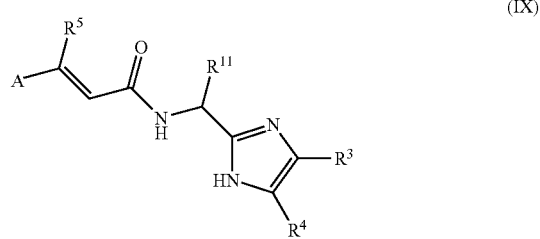

(IX)

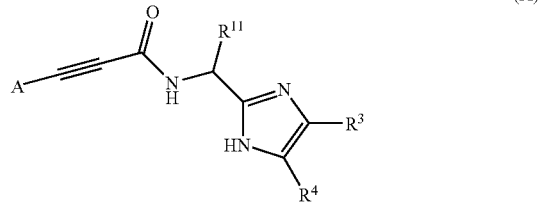

(X)

or a stereoisomer, tautomer, pharmaceutically acceptable salt, solvate, or prodrug thereof, wherein A, $R^3$, $R^4$, and $R^{11}$ are each the same as defined in the first aspect; which comprises:

contacting compounds of formula (IV)

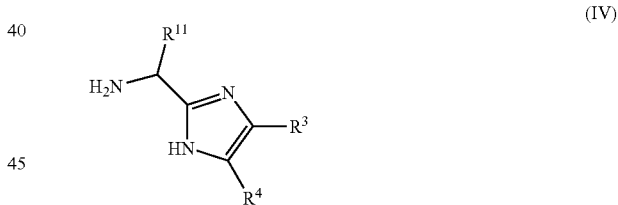

(IV)

or HCl or TFA salts thereof, wherein $R^3$, $R^4$, and $R^{11}$ are each the same as defined in the first aspect;

with carboxylic acids of formulae (V), (VI) or (VII)

$$A\text{-}(CH_2)_2CO_2H \quad (V)$$

$$A\text{-}CR^5{=}CH{-}CO_2H \quad (VI)$$

$$A\text{-}C{\equiv}C{-}CO_2H \quad (VII)$$

wherein A and $R^5$ is the same as defined in the first aspect;

alternately, contacting compounds of formula (IV) with the corresponding carbonyl halides, preferably carbonyl chlorides, or with the corresponding mixed carboxylic anhydrides of the carboxylic acids of formula (V), (VI) or (VII) in inert solvents, if appropriate, in the presence of an activating or coupling agent and/or a base to give compounds of general formulae (VIII), (IX) or (X), respectively.

In another aspect, the present invention provides a process for preparing compounds of formulae (VIIIa), (IXa) or (Xa):

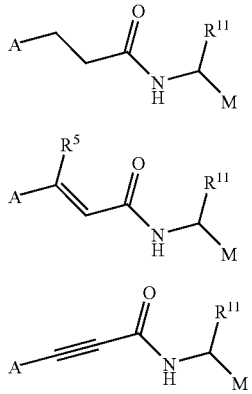

(VIIIa)

(IXa)

(Xa)

or a stereoisomer, tautomer, pharmaceutically acceptable salt, solvate, or prodrug thereof, wherein A, M and $R^{11}$ are each the same as defined in the first aspect; which comprises:

contacting compounds of formula (IVa)

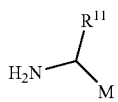

(IVa)

or HCl or TFA salts thereof, wherein M and $R^{11}$ are each the same as defined in the first aspect;

with carboxylic acids of formulae (V), (VI) or (VII)

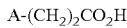 (V)

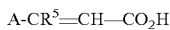 (VI)

 (VII)

wherein A and $R^5$ is the same as defined in the first aspect;

alternately, contacting compounds of formula (IVa) with the corresponding carbonyl halides, preferably carbonyl chlorides, or with the corresponding mixed carboxylic anhydrides of the carboxylic acids of formula (V), (VI) or (VII) in inert solvents, if appropriate, in the presence of an activating or coupling agent and/or a base to give compounds of general formulae (VIIIa), (IXa) or (Xa), respectively.

In a tenth aspect, the present invention provides a process for preparing compounds of formula (XII):

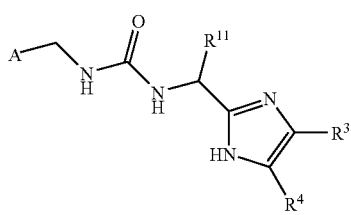

(XII)

or a stereoisomer, tautomer, pharmaceutically acceptable salt, solvate, or prodrug thereof, wherein A, $R^3$, $R^4$, and $R^{11}$ are each the same as defined in the first aspect; which comprises:

contacting compounds of formula (IV)

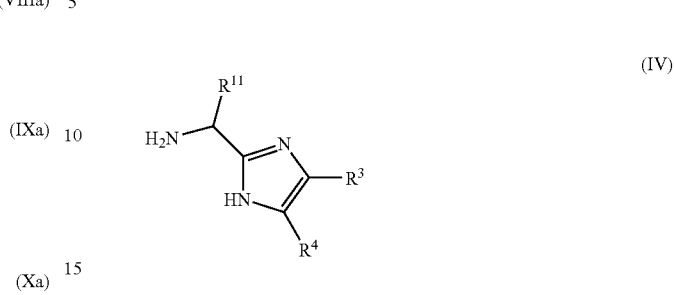

(IV)

or HCl or TFA salts thereof, wherein $R^3$, $R^4$, and $R^{11}$ are each the same as defined in the first aspect;

in an inert solvent with p-nitrochloroformate or carbonyl dimidiazole to form an activated acylamine species, which is further reacted, either in situ or after isolation, in an inert solvent, if appropriate in the presence of a base, with amines of formula $ACH_2NH_2$, wherein A is the same as defined in the first aspect.

alternately, contacting compounds of formula (IV) with isocyanate reagents of formula $ACH_2N{=}C{=}O$, wherein A is the same as defined in the first aspect, to give compounds of general formulae XII.

In another aspect, the present invention provides a process for preparing compounds of formula (XIIa):

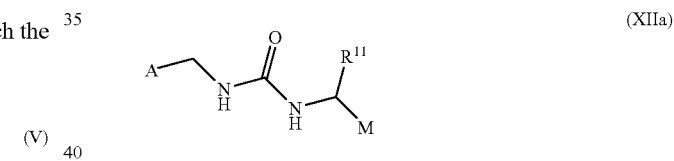

(XIIa)

or a stereoisomer, tautomer, pharmaceutically acceptable salt, solvate, or prodrug thereof, wherein A, M and $R^{11}$ are each the same as defined in the first aspect; which comprises:

contacting compounds of formula (IVa)

(IVa)

or HCl or TFA salts thereof, wherein M and $R^{11}$ are each the same as defined in the first aspect;

in an inert solvent with p-nitrochloroformate or carbonyl dimidiazole to form an activated acylamine species, which is further reacted, either in situ or after isolation, in an inert solvent, if appropriate in the presence of a base, with amines of formula $ACH_2NH_2$, wherein A is the same as defined in the first aspect.

alternately, contacting compounds of formula (IVa) with isocyanate reagents of formula $ACH_2N{=}C{=}O$, wherein A is the same as defined in the first aspect, to give compounds of general formulae XII.

In an eleventh aspect, the present invention provides a process for preparing compounds of formula (XI):

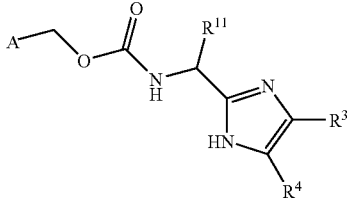

or a stereoisomer, tautomer, pharmaceutically acceptable salt, solvate, or prodrug thereof, wherein A, $R^3$, $R^4$, and $R^{11}$ are each the same as defined in the first aspect; which comprises:
  contacting compounds of formula (IV)

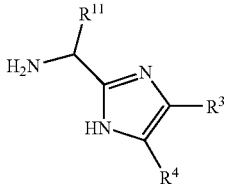

or HCl or TFA salts thereof, wherein $R^3$, $R^4$, and $R^{11}$ are each the same as defined in the first aspect;
  with chloroformate reagents of formula $ACH_2OC(O)Cl$ wherein A is the same as defined in the first aspect.
In another aspect, the present invention provides a process for preparing compounds of formula (XIa):

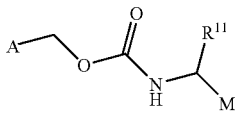

or a stereoisomer, tautomer, pharmaceutically acceptable salt, solvate, or prodrug thereof, wherein A, M and $R^{11}$ are each the same as defined in the first aspect; which comprises:
  contacting compounds of formula (IVa)

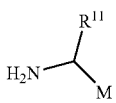

or HCl or TFA salts thereof, wherein M and $R^{11}$ are each the same as defined in the first aspect;
  with chloroformate reagents of formula $ACH_2OC(O)Cl$ wherein A is the same as defined in the first aspect.
In another embodiment the present invention includes compounds of Formula (I), or stereoisomers, tautomers, pharmaceutically acceptable salts, solvates, or prodrugs thereof, wherein:
  A is substituted with 0-1 $R^1$ and 0-3 $R^2$ and selected from: phenyl and pyridyl, M is

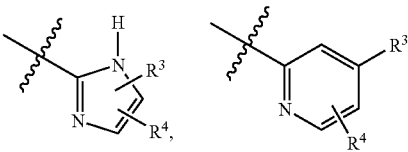

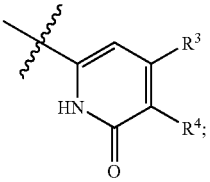

$R^1$ is, independently at each occurrence, Cl, Br, OMe, or Me;
$R^2$ is, independently at each occurrence, F, Cl, Br, Me, OMe, or a 5-7 membered heterocycle substituted with 0-2 $R^{2b}$ and selected from: pyrazolyl, triazolyl, or tetrazolyl;
  alternately, when $R^1$ and $R^2$ groups are substituents on adjacent atoms they may be taken together with the atoms to which they are attached to form a 5- to 6-membered heterocycle comprising carbon atoms and 0-4 heteroatoms selected from N, O, and $S(O)_p$;
$R^3$ is, independently at each occurrence, phenyl substituted with 0-2 $R^{3a}$, or a 5- to 12-membered heterocycle comprising: carbon atoms and 1-2 heteroatoms selected from N, O, and $S(O)_p$, wherein said heterocycle is substituted with 0-2 $R^{3a}$;
$R^{3a}$ is, independently at each occurrence, =O, F, Cl, Br, Me, CN, OH, OMe, —OC(O)(t-Bu), $CH_2OMe$, $CF_3$, COMe, $CO_2H$, $CO_2Me$, —$CH_2CO_2H$, —$(CH_2)_2CO_2H$, —$CH_2CO_2Me$, —$CH_2CO_2Et$, —$CH_2CH_2CO_2Et$, —$CH_2CN$, $NH_2$, —$CH_2NH_2$, —$CH_2NMe_2$, —NHCOMe, —$NHCO_2Me$, —$NHCO_2Et$, —$NHCH_2CH_2CO_2H$, —$NHCO_2(i\text{-}Pr)$, —$NHCO_2(i\text{-}Bu)$, —$NHCO_2(t\text{-}Bu)$, —$NHCO_2Bn$, —$NHCO_2CH_2CH_2OMe$, —$NHCO_2CH_2CH_2CH_2OMe$, —$NHCO_2CH_2CO_2H$, —$NHCO_2CH_2CH_2CO_2H$, —$NHCO_2CH_2CH_2OH$, —$NHCO_2CH_2CH_2NH_2$, —$NHCO_2CH_2$-tetrahydrofuran-2-yl, —$NHCO_2CH_2CH_2CH(Me)OMe$, —$NHCO_2CH_2CH_2C(O)NH_2$, —NHC(O)$NHCH_2CH_2$-morpholino, —NHC(O)$NHCH_2$-pyrid-4-yl, —$NHCO_2CH_2$-pyrid-4-yl, —$NHCO_2CH_2$-pyrid-3-yl, —$NHCO_2CH_2$-pyrid-2-yl, —$NHCO_2CH_2$-(piperidin-4-yl), —NHC(O)NH $CH_2CH_2$-pyrid-4-yl, —$NHCO_2CH_2CH_2$-pyrid-4-yl, —$NHCO_2CH_2CH_2$-morpholino, —$CH_2NHCO_2Me$, —NHC(O)NHMe, —NHC(O)N(Me)$_2$, —NHC(O)$NHCH_2CH_2OMe$, 4-[(1-carbamoyl-cyclopropanecarbonyl)-amino]-, —$NHSO_2Me$, —$SO_2NH_2$, —$SO_2NHMe$, —$SO_2NHCH_2CH_2OH$, —$SO_2NHCH_2CH_2OMe$, —$CONH_2$, —CONHMe, —CON(Me)$_2$, —C(O)$NHCH_2CH_2OMe$, —$CH_2CONH_2$, —CO(N-morpholino), $NHCH_2CH_2$(N-morpholino), —$NR^7R^8$, —NH(1H-imidazol-2-yl), 1H-tetrazol-5-yl, tetrazol-1-yl, pyrimidin-5-yl, or N-morpholino, or —$(CH_2)_r$-5- to-6-membered heterocycle comprising: carbon atoms and 1-4 heteroatoms selected from N, O, and $S(O)_p$, wherein said heterocycle is substituted with 0-1 $R^{3d}$;
  alternatively, two of $R^{3a}$ groups located on adjacent atoms, they can be taken together with the atoms to which they are attached to form a 5- to 10-membered heterocycle comprising: carbon atoms and 1-4 heteroatoms selected from N, O, and $S(O)_p$, wherein said heterocycle is substituted with 0-2 $R^{3d}$;

R[4] is, independently at each occurrence, H, F, Cl, Br, Me, Et, CO$_2$H, CO$_2$Me, or CO$_2$Et;

R[11] is —CH$_2$C(O)NR[8]R[9], —CH$_2$C(O)OR[a], C$_{1-6}$ alkyl substituted with 0-2 R[11c], —(CH$_2$)$_r$—C$_{3-7}$ cycloalkyl substituted with 0-2 R[11b], —(CH$_2$)$_r$-phenyl substituted with 0-2 R[11b], —(CH$_2$)$_r$-indanyl substituted with 0-2 R[11b], —(CH$_2$)$_r$-naphthyl substituted with 0-2 R[11b], or —(CH$_2$)$_r$-5- to 10-membered heteroaryl substituted with 0-2 R[11b] and selected from thiazolyl, oxazolyl, pyrazolyl, triazolyl, tetrazolyl, thiadiazolyl, isoxazolyl, imidazolyl, pyridyl, pyrimidinyl, pyrazinyl, pyridazinyl, indolyl, indazolyl, isoindolyl, indolinyl, isoindolinyl, benzimidazolyl, benzothiazolyl, benzotriazolyl, quinolinyl, isoquinolinyl, tetrahydroquinolinyl, tetrahydroisoquinolinyl, and 2,2-dioxo-2,3-dihydro-1H-2λ$^6$-benzo[c]thiophenyl; and R[11b] is, independently at each occurrence, H, =O, F, Cl, Br, CF$_3$, OMe, OEt, OCF$_3$, OCHF$_2$, CN, NH$_2$, —CH$_2$OR[a], —C(CH$_3$)$_2$OR[a], —C(O)R[a], —C(O)OR[a], —C(O)NR[7]R[8], —NR[8]C(O)R[c], —NR[8]C(O)$_2$R[c], —S(O)$_p$NR[8]R[9], —NR[8]S(O)$_p$R[c], —S(O)$_p$R[c], C$_{1-4}$ alkyl, or —CH$_2$-phenyl wherein said phenyl is substituted with 0-3 R[d].

In another embodiment the present invention includes compounds of Formula (I), or stereoisomers, tautomers, pharmaceutically acceptable salts, solvates, or prodrugs thereof, wherein:

A is substituted with 0-2 R[2] and selected from:

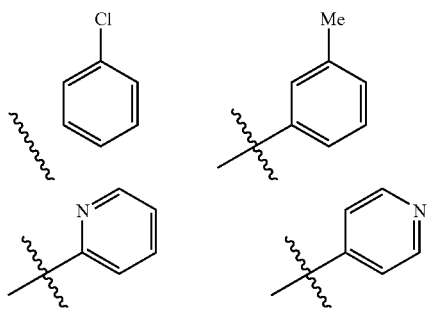

R[2] is, independently at each occurrence, F, Cl, Br, Me, CF$_3$, OMe, OEt, pyrazol-1-yl, 4-carboxy-pyrazol-1-yl, 1,2,3-triazol-1-yl, 1,2,4-triazol-1-yl, 1,2,3-triazol-2-yl, 4-carboxy-1,2,3-triazol-1-yl, 4-(ethoxycarbonyl)-1,2,3-triazol-1-yl, tetrazol-1-yl, or tetrazol-5-yl;

R[3] is, independently at each occurrence, phenyl substituted with 0-2 R[3a], or a 5- to 12-membered heterocycle substituted with 0-2 R[3a] and selected from: pyridine, pyridinone, indole, indolin-2-one, indazole, 7-azaindole, quinazoline, quinoline, 1H-quinolin-2-one, 3,4-dihydro-1H-quinolin-2-one; and R[4] is, independently at each occurrence, H, Me, F, Br, Cl, CF$_3$, CO$_2$H, CO$_2$Me, or CO$_2$Et.

In another embodiment the present invention includes compounds of Formula (I), or stereoisomers, tautomers, pharmaceutically acceptable salts, solvates, or prodrugs thereof, wherein:

A is 2-(pyrazol-1-yl)-5-chlorophenyl, 2-(4-carboxy-pyrazol-1-yl)-5-chlorophenyl, 2-(1,2,3-triazol-1-yl)-5-methylphenyl, 2-(1,2,3-triazol-1-yl)-5-chlorophenyl, 2-(1,2,3-triazol-2-yl)-5-chlorophenyl, 2-(1,2,4-triazol-1-yl)-5-chlorophenyl, 2-[(4-carboxy)-1,2,3-triazol-1-yl]-5-methylphenyl, 2-[(4-carboxy)-1,2,3-triazol-1-yl]-5-chlorophenyl, 2-[(4-ethoxycarbonyl)-1,2,3-triazol-1-yl]-5-chlorophenyl, 2-(tetrazol-1-yl)-5-methylphenyl, 2-(tetrazol-1-yl)-5-chlorophenyl, 2-(tetrazol-5-yl)-5-chlorophenyl, 2-(tetrazol-1-yl)-3-fluoro-5-chlorophenyl, or 2-(tetrazol-1-yl)-3-fluoro-5-methylphenyl, L$_1$ is —CH$_2$CH$_2$—, —CH=CH—, —C(Me)=CH—, —C≡C—, or —CH$_2$NH—, M is

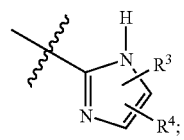

R[3] is, independently at each occurrence,

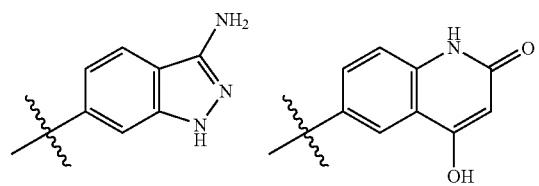

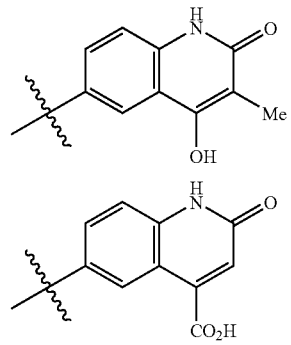

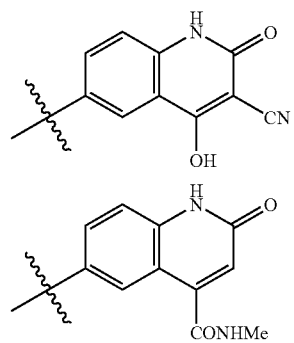

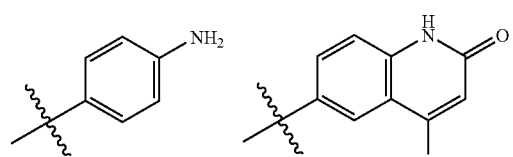

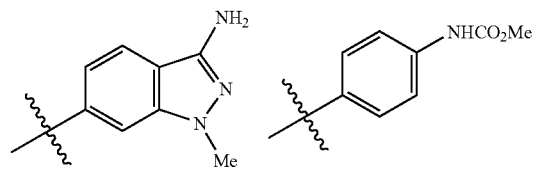

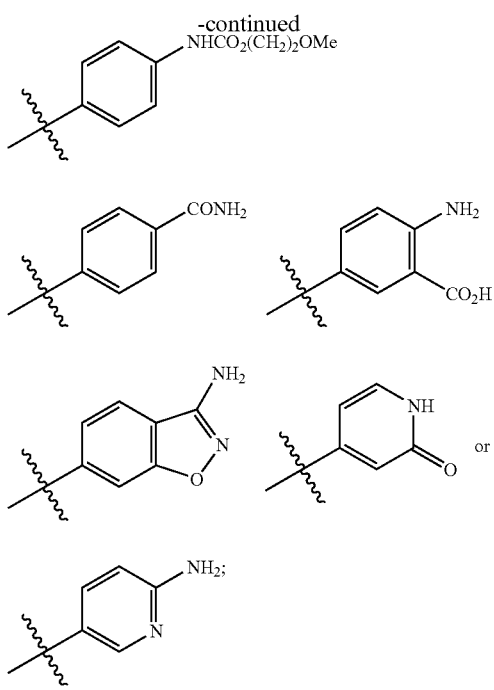

R[4] is H or Cl; and

R[11] is methyl, n-butyl, carboxymethyl, benzyl, 4-fluorobenzyl, 3-carboxy-benzyl, 3-(N,N-dimethylcarbamoyl)-benzyl, (benzyloxycarbonyl)methyl, (1-methylpyrazol-3-yl)methyl, (1-methylpyrazol-4-yl)methyl, (1-methylpyrazol-5-yl)methyl, (3-methylpyrazol-5-yl)methyl, (1-ethylpyrazol-4-yl)methyl, (1-n-propylpyrazol-4-yl)methyl, (1-isopropylpyrazol-4-yl)methyl, 1-ethylpyrazol-3-ylmethyl, 3-pyrazolylmethyl, (4-chloro-3-methyl-5-pyrazolyl)methyl, (4-chloro-1,5-dimethyl-3-pyrazolyl)methyl, (4-chloro-1,3-dimethyl-5-pyrazolyl)methyl, [1-(4-methoxybenzyl)-pyrazol-3-yl]methyl, (1,5-dimethylpyrazol-3-yl)methyl, (1,3-dimethylpyrazol-5-yl)methyl, [1-(4-methoxybenzyl)-5-methyl-pyrazol-3-yl]methyl, (3-trifluoromethylpyrazol-5-yl)methyl, [1-(4-methoxybenzyl)-3-trifluoromethylpyrazol-5-yl]methyl, [(1-methyl-5-methoxycarbonyl)-pyrazol-3-yl]methyl, [(1-methyl-5-carboxy)-pyrazol-3-yl]methyl, [(1-methyl-5-carbamoyl)-pyrazol-3-yl]methyl, [(5-methoxycarbonyl)-pyrrol-2-yl]methyl, thiazol-2-ylmethyl, thiazol-4-methyl, (2-methoxypyridin-3-yl)methyl, (6-methoxypyridin-3-yl)methyl, (4-(methoxycarbonyl)-oxazol-2-yl)methyl, morpholin-4-ylcarbonylmethyl, N-((5-methylpyrazin-2-yl)methyl)-aminocarbonylmethyl, 2-hydroxy-indan-5-ylmethyl, 4-methylpiperazin-1-ylcarbonylmethyl, 4-methylcarbonylpiperazin-1-ylcarbonylmethyl, pyrrolidin-1-ylcarbonylmethyl, 2-methoxypyrrolidin-1-ylcarbonylmethyl, aziridin-1-ylcarbonylmethyl, 2-hydroxyethylaminocarbonylmethyl, 2-methoxyethylaminocarbonylmethyl, 2-ethoxyethylaminocarbonylmethyl, bis(2-methoxyethyl)aminocarbonylmethyl, 4-dimethylaminopyrrolidin-1-ylcarbonylmethyl, 4-chlorophenylaminocarbonylmethyl, 3-chlorophenylcarbonylmethyl, N-methyl-N-benzylaminocarbonylmethyl, cyclopropylaminocarbonylmethyl, cyclopropylmethylaminocarbonylmethyl, cyclopentylaminocarbonylmethyl, (trans-2-phenylcyclopropyl)aminocarbonylmethyl, N,N-dimethylaminoethylaminocarbonylmethyl, N-((pyridin-2-yl)methyl)-aminocarbonylmethyl, N-((pyridin-3-yl)methyl)-aminocarbonylmethyl, N-((pyridin-4-yl)methyl)-aminocarbonylmethyl, N-((pyridin-2-yl)ethyl)-aminocarbonylmethyl, 1-(1,1-dioxo-1λ[6]-thiomorpholin-4-yl)carbonylmethyl, N-(tert-butoxycarbonyl)-1H-indol-3-ylmethyl, 1H-indol-3-ylmethyl, 2,2-dioxo-2,3-dihydro-1H-2λ[6]-benzo[c]thiophen-5-ylmethyl, cyclopropylmethyl, (4-hydroxy)cyclohexylmethyl or 4-oxo-cyclohexylmethyl.

In another embodiment, A is substituted with 0-1 R[1] and 0-3 R[2] and selected from: C$_{3-7}$ cycloalkyl, phenyl, naphthyl, 1,2,3,4-tetrahydronaphthyl, pyrrolidinyl, pyridyl, indazolyl, indolyl, imidazolyl, furanyl, thienyl, benzimidazolyl, benzisoxazolyl, benzothiazolyl, benzothiophenyl, 3,4-methylenedioxy-phenyl, oxazolyl, isoxazolyl, thiazolyl, isothiazolyl, and pyrazolyl.

In another embodiment, A is substituted with 0-2 R[2] and selected from:

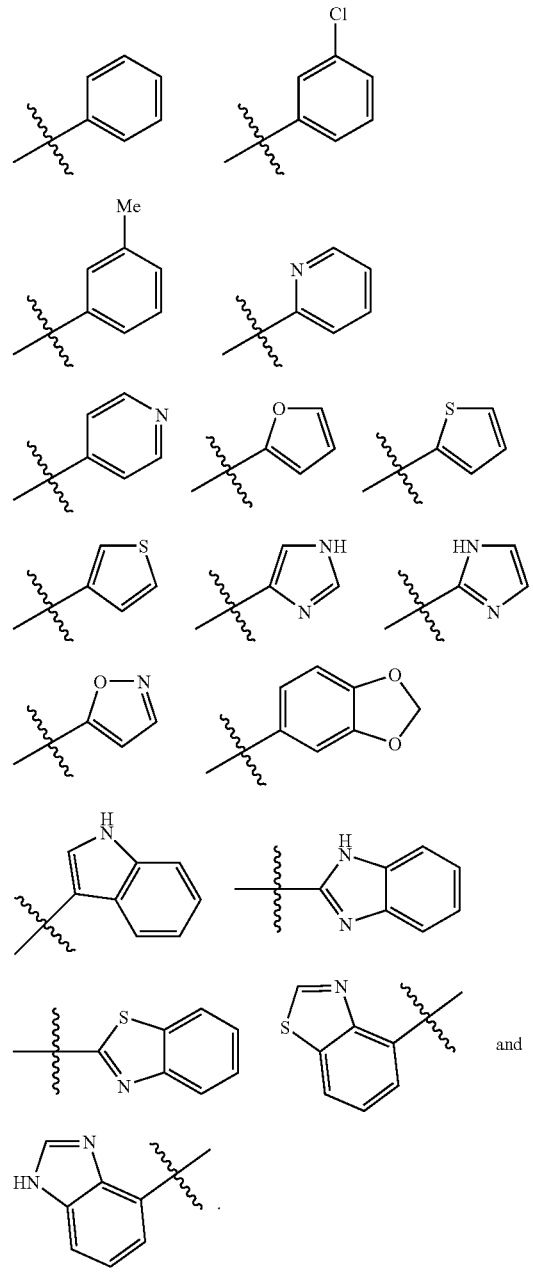

In another embodiment, A is substituted with 0-2 R² and selected from:

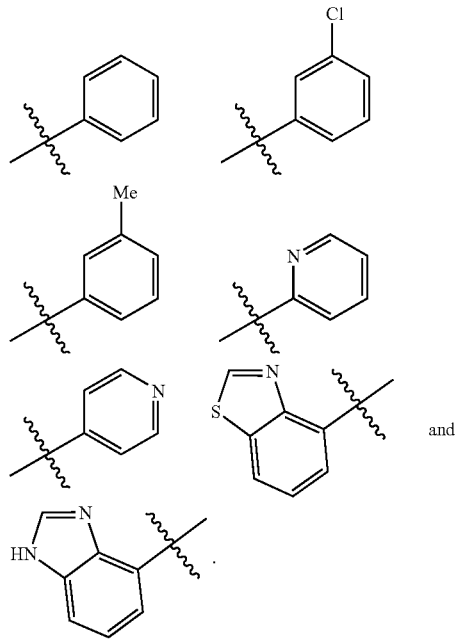

and

In another embodiment, A is phenyl, 2-fluorophenyl, 3-fluorophenyl, 2-chlorophenyl, 3-chlorophenyl, 2-bromophenyl, 3-bromophenyl, 3-methylphenyl, 2-methoxyphenyl, 3-methoxyphenyl, 3-aminomethylphenyl, 4-aminomethylphenyl, 2-carboxy-5-chlorophenyl, 2-methoxycarbonyl-5-chlorophenyl, 2-(N-(methoxycarbonyl)-amino)-5-chlorophenyl, 2-(N-(ethoxycarbonyl)-aminomethyl)-5-chlorophenyl, 2-(N-(isopropoxycarbonyl)-aminomethyl)-5-chlorophenyl, 2-(N-(tert-butoxycarbonyl)-aminomethyl)-5-chlorophenyl, 2-(N-(phenylcarbonyl)-aminomethyl)-5-chlorophenyl, 2-(N-(benzoxycarbonyl)-aminomethyl)-5-chlorophenyl, 2-((N-(3-propanoic acid)carbonyl)-aminomethyl)-5-chlorophenyl, 2-(3-methylureido)-5-chlorophenyl, 2-(3-ethylureidomethyl)-5-chlorophenyl, 2-[3-(2-ethoxycarbonyl-ethyl)-ureidomethyl]-5-chlorophenyl, 2-(3-phenylureido)methyl)-5-chlorophenyl, 2-(3-(4-chlorophenyl)ureido)methyl)-5-chlorophenyl, 2-(3-benzylureido)methyl)-5-chlorophenyl, 2-(N-(methylsulfonyl)-amino)-5-chlorophenyl, 2-(N-(methylsulfonyl)-aminomethyl)-5-chlorophenyl, 2-(N-(ethylsulfonyl)-aminomethyl)-5-chlorophenyl, 2-(N-(n-propylsulfonyl)-aminomethyl)-5-chlorophenyl, 2-(N-(isopropylsulfonyl)-aminomethyl)-5-chlorophenyl, 2-(N-(n-pentylsulfonyl)-aminomethyl)-5-chlorophenyl, 2-(N-(phenylsulfonyl)-aminomethyl)-5-chlorophenyl, 2-((N-(4-methylcarbonylaminophenyl)sulfonyl)-aminomethyl)-5-chlorophenyl, 2-(N-(4-chlorobenzylsulfonyl)-aminomethyl)-5-chlorophenyl, 2-(N-(phenethylsulfonyl)-aminomethyl)-5-chlorophenyl, 2-(N-(2-chlorophenethylsulfonyl)-aminomethyl)-5-chlorophenyl, 2-(N-(3-chlorophenethylsulfonyl)-aminomethyl)-5-chlorophenyl, 2-(N-(4-chlorophenethylsulfonyl)-aminomethyl)-5-chlorophenyl, 2-(N-(3,4-dimethyl-isoxazol-4-yl)-aminomethyl)-5-chlorophenyl, 2-(N-(3,4-dimethyl-isoxazol-4-ylsulfonyl)-aminomethyl)-5-chlorophenyl, 3-carbamoyl-phenyl, 2,4-difluorophenyl, 2,5-difluorophenyl, 2,5-dichlorophenyl, 3,5-dichlorophenyl, 5-chloro-2-fluorophenyl, 3-chloro-2-fluorophenyl, 3-chloro-4-methylphenyl, 2-methyl-5-chlorophenyl, 2-methoxy-5-chlorophenyl, 2-ethoxy-5-chlorophenyl, 2-benzyloxy-5-chlorophenyl, 2-methylthio-5-chlorophenyl, 2-ethylthio-5-chlorophenyl, 2-propylthio-5-chlorophenyl, 2-benzylthio-5-chlorophenyl, 2-methylthiomethyl-5-chlorophenyl, 2-(2-oxo-1-pyrrolidinyl)-5-chlorophenyl, 3-trifluoromethyl-2-fluorophenyl, 2-trifluoromethyl-5-chlorophenyl, 5-bromo-2-fluorophenyl, 2-amino-5-chlorophenyl, 2-aminomethyl-5-chlorophenyl, 2-methylsulfonyl-5-chlorophenyl, 2-methylsulfonamide-5-chlorophenyl, 2-phenylcarbamoyl-5-chlorophenyl, 2-(3-carboxy-N-piperidinyl)-5-chlorophenyl, 2,6-difluoro-3-methylphenyl, 2-chloro-6-fluoro-3-methylphenyl, 2-fluoro-6-chloro-3-methylphenyl, 2,6-difluoro-3-chlorophenyl, 2,3-dichloro-6-aminophenyl, 2,3-dichloro-6-nitrophenyl, 2-phenoxyphenyl, 2-phenoxy-5-chlorophenyl, 2-(N-pyrrolidinyl)-5-chlorophenyl, 2-(pyrazol-1-yl)-5-chlorophenyl, 2-(4-carboxy-pyrazol-1-yl)-5-chlorophenyl, 2-(1,2,3-triazol-1-yl)-5-methylphenyl, 2-(1,2,3-triazol-1-yl)-5-chlorophenyl, 2-(1,2,3-triazol-2-yl)-5-chlorophenyl, 2-(1,2,4-triazol-1-yl)-5-chlorophenyl, 2-[(4-carboxy)-1,2,3-triazol-1-yl]-5-methylphenyl, 2-[(4-carboxy)-1,2,3-triazol-1-yl]-5-chlorophenyl, 2-[(4-ethoxycarbonyl)-1,2,3-triazol-1-yl]-5-chlorophenyl, 2-(tetrazol-1-yl)-5-methylphenyl, 2-(tetrazol-1-yl)-5-chlorophenyl, 2-(tetrazol-5-yl)-5-chlorophenyl, 2-(5-methyl-tetrazol-1-yl)-5-chlorophenyl, 2-(tetrazol-1-yl)-3-fluoro-5-chlorophenyl, 2-(tetrazol-1-yl)-3-fluoro-5-methylphenyl, 2-(5-methyltetrazol-1-yl)-5-chlorophenyl, 2-(5-trifluoromethyl-tetrazol-1-yl)-5-chlorophenyl, 2-(2-tetrahydrofuranyl-methoxy)-5-chlorophenyl, 3,4-methylenedioxy-phenyl, cyclopentyl, 2-oxo-1-pyrrolidinyl, 2-furanyl, 2-thienyl, 3-thienyl, 5-chloro-2-thienyl, 5-chloro-3-thienyl, 2,5-dichloro-3-thienyl, 1-imidazolyl, 2-imidazolyl, 4-imidazolyl, 3-chloro-5-isoxazolyl, 4-pyridyl, 3-fluoro-2-pyridyl, 2(1H)-oxo-5-chloropyridin-1-yl, 1-indolyl, 3-indolyl, 2-benzimidazolyl, 6-chlorobenzimidazol-4-yl, 2-methyl-6-chlorobenzothiazol-4-yl or 2,6-dichlorobenzothiazol-4-yl.

In another embodiment, A is 3-chlorophenyl, 3-bromophenyl, 3-methylphenyl, 3-methoxyphenyl, 2,5-dichlorophenyl, 5-chloro-2-fluorophenyl, 5-bromo-2-fluorophenyl, 3-chloro-2-fluorophenyl, 2-methyl-5-chlorophenyl, 2-methoxy-5-chlorophenyl, 2-methylthio-5-chlorophenyl, 2-ethylthio-5-chlorophenyl, 2-propylthio-5-chlorophenyl, 2-benzylthio-5-chlorophenyl, 2-amino-5-chlorophenyl, 2-aminomethyl-5-chlorophenyl, 2,6-difluoro-3-methylphenyl, 2-chloro-6-fluoro-3-methylphenyl, 2-fluoro-6-chloro-3-methylphenyl, 2,6-difluoro-3-chlorophenyl, 2,3-dichloro-6-nitrophenyl, 5-chloro-2-thienyl, 3,4-methylenedioxyphenyl, 2-methoxycarbonyl-5-chlorophenyl, 6-chlorobenzimidazol-4-yl, 2-(1,2,3-triazol-1-yl)-5-methylphenyl, 2-(1,2,3-triazol-1-yl)-5-chlorophenyl, 2-(1,2,4-triazol-1-yl)-5-chlorophenyl, 2-(1,2,3-triazol-2-yl)-5-chlorophenyl, 2-[(4-carboxy)-1,2,3-triazol-1-yl]-5-chlorophenyl, 2-[(4-carboxy)-1,2,3-triazol-1-yl]-5-methylphenyl, 2-[(4-ethoxycarbonyl)-1,2,3-triazol-1-yl]-5-chlorophenyl, 2-(tetrazol-1-yl)-5-methylphenyl, 2-(tetrazol-1-yl)-5-chlorophenyl, 2-(tetrazol-1-yl)-3-fluoro-5-chlorophenyl, 2-(tetrazol-1-yl)-3-fluoro-5-methylphenyl, or 2-(5-methyltetrazol-1-yl)-5-chlorophenyl.

In another embodiment, $L_1$ is —CH₂CH₂—, —CH(NH₂)CH₂—, —CH(NHCOMe)CH₂—, —CH(NHCOEt)CH₂—, —CH(NHCO₂(t-Bu))CH₂—, —CH=CH—, —C(Me)=CH—, —C≡C—, —CH₂NH—, —CH(CH₂CO₂H)NH—, —CH₂O—, —NHNH—, —SCH₂—, —SO₂CH₂— or —OCH₂—.

In another embodiment, $L_1$ is —CH₂CH₂—, —CH(Me)CH₂—, —CH=CH—, —C(Me)=CH—, —C≡C—, —OCH₂—, —CH₂NH—, —CH₂O—, —SCH₂—, —SO₂CH₂—, —CH₂NH—, or —NHNH—.

In another embodiment, L₁ is —CH₂CH₂—, —CH=CH—, —C(Me)=CH—, —C≡C—, —CH₂NH—, —CH₂O—, —NHNH—, —SCH₂—, —SO₂CH₂— or —OCH₂—.

In another embodiment, L₁ is —CH₂CH₂—, —CH=CH—, —C(Me)=CH—, —C≡C—, —CH₂NH—, —CH₂O—, —NHNH—, or —SCH₂—.

In another embodiment, L₁ is —CH₂CH₂—, —CH=CH—, —C(Me)=CH—, —C≡C—, or —CH₂NH—.

In another embodiment, L₁ is —CH₂CH₂— or —CH₂NH—.

In another embodiment, L₁ is —CH₂CH₂—.

In another embodiment, L₁ is —CH₂NH—.

In another embodiment, L₁ is —CH=CH— or —C(Me)=CH—.

In another embodiment, L₁ is —C≡C—.

In another embodiment, M is

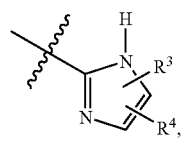 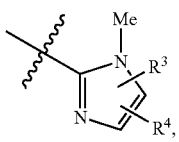

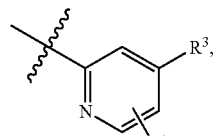 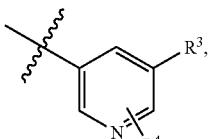

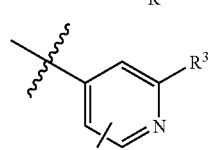 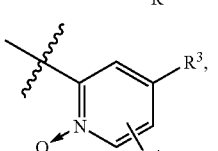

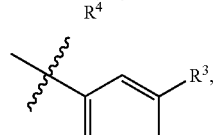 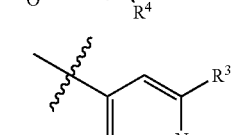

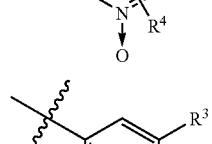 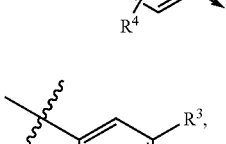

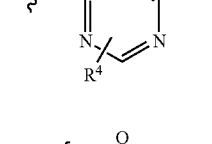 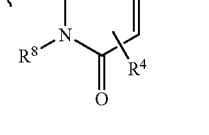

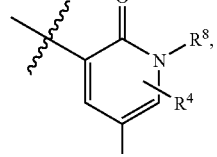 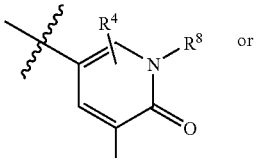

-continued

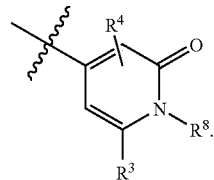

In another embodiment, M is

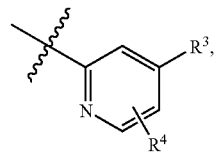 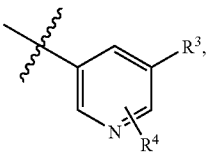

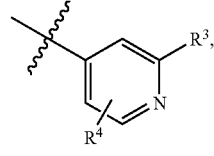 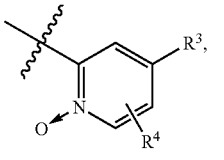

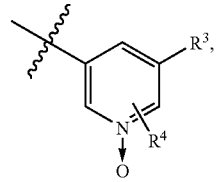 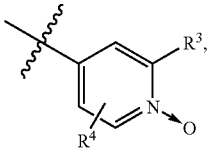

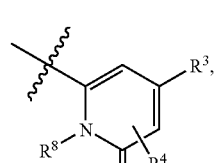 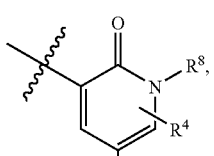

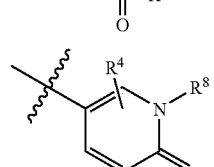 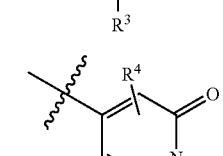

In another embodiment, M is

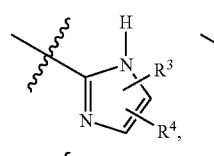 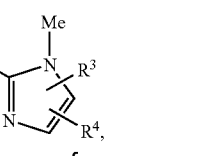

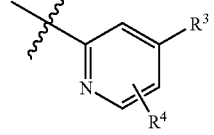 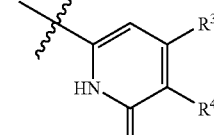

In another embodiment, M is

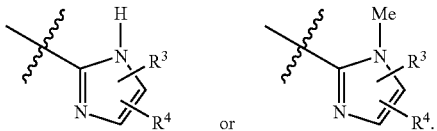  or

In another embodiment, M is

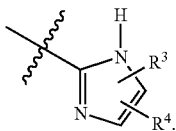

In another embodiment, M is

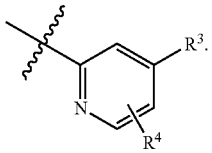

In another embodiment, M is

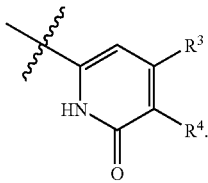

In another embodiment, $R^2$ is, independently at each occurrence, F, Cl, Br, $CF_3$, $NO_2$, $-(CH_2)_rOR^a$, $-(CH_2)_rSR^a$, $-C(O)OR^a$, $-C(O)NR^8R^9$, $-NR^8C(O)R^c$, $-NR^8C(O)OR^c$, $-NR^8C(O)NR^8R^c$, $-S(O)_pNR^8R^9$, $-NR^8SO_2R^c$, $-NR^7R^8$, $-S(O)R^c$, $-S(O)_2R^c$, $C_{1-6}$ alkyl substituted with 0-1 $R^{2a}$, or a 5-7 membered heterocycle comprising carbon atoms and 1-4 heteroatoms selected from N, O, and $S(O)_p$, wherein said heterocycle is substituted with 0-2 $R^{2b}$.

In another embodiment, $R^2$ is, independently at each occurrence, =O, F, Cl, Br, $CF_3$, Me, Et, $OR^a$, CN, $NO_2$, $NR^7R^8$, $-CH_2OMe$, $-SR^a$, $-CH_2SMe$, $-C(O)OR^a$, $-CH_2NR^7R^8$, $-SO_2NH_2$, $-SO_2Me$, $-NHSO_2R^c$, $-CH_2NHSO_2R^c$, $-C(O)NR^8R^9$, $-NHC(O)R^c$, $-CH_2NHC(O)R^c$, $-NHC(O)OR^c$, $-CH_2NHC(O)OR^c$, $-NHC(O)NHR^c$, $-CH_2NHC(O)NHR^c$, or a 5-7 membered heterocycle substituted with 0-2 $R^{2b}$ and selected from: pyrrolidinyl, 2-oxo-1-pyrrolidinyl, piperidinyl, pyrazolyl, triazolyl and tetrazolyl.

In another embodiment, $R^2$ is substituted with 0-2 $R^{2b}$ and selected from: pyrazolyl, triazolyl and tetrazolyl.

In another embodiment, $R^2$ is, independently at each occurrence, =O, F, Cl, Br, Me, $CF_3$, OMe, OEt, OPh, OBn, SMe, SEt, S(n-Pr), SBn, $-CH_2SMe$, $SO_2Me$, $NH_2$, $-CH_2NH_2$, $NO_2$, $CO_2H$, $CO_2Me$, $CONH_2$, $-CH_2NHCOPh$, $-NHCO_2Me$, $-CH_2NHCO_2Et$, $-CH_2NHCO_2(i-Pr)$, $-CH_2NHCO_2(t-Bu)$, $-CH_2NHCO_2Bn$, $-CH_2NHCO(CH_2)_2CO_2H$, $-CONHPh$, $-NHCONHMe$, $-CH_2NHCONHEt$, $-CH_2NHCONH(CH_2)_2CO_2Et$, $-CH_2NHCONHPh$, $-CH_2NHCONH(4-Cl-Ph)$, $-CH_2NHCONHBn$, $-NHSO_2Me$, $-CH_2NHSO_2Me$, $-CH_2NHSO_2Et$, $-CH_2NHSO_2(n-Pr)$, $-CH_2NHSO_2(i-Pr)$, $-CH_2NHSO_2(n-pentyl)$, $-CH_2NHSO_2Ph$, $-CH_2NHSO_2(4-NHCOMe-Ph)$, $-CH_2NHSO_2(4-Cl-Bn)$, $-CH_2NHSO_2CH_2CH_2Ph$, $-CH_2NHSO_2CH_2CH_2(2-Cl-Ph)$, $-CH_2NHSO_2CH_2CH_2(3-Cl-Ph)$, $-CH_2NHSO_2CH_2CH_2(4-Cl-Ph)$, $-CH_2NHSO_2(3,4-dimethyl-isoxazol-4-yl)$, 1-pyrrolidinyl, 2-oxo-1-pyrrolidinyl, 3-carboxy-N-piperidinyl, pyrazol-1-yl, 4-carboxy-pyrazol-1-yl, 1,2,3-triazol-1-yl, 1,2,4-triazol-1-yl, 1,2,3-triazol-2-yl, 4-carboxy-1,2,3-triazol-1-yl, 4-(ethoxycarbonyl)-1,2,3-triazol-1-yl, tetrazol-1-yl, tetrazol-5-yl, 5-Me-tetrazol-1-yl, 5-$CF_3$-tetrazol-1-yl, or $-OCH_2$(2-tetrahydrofuranyl).

In another embodiment, $R^3$ is, independently at each occurrence, phenyl substituted with 0-3 $R^{3a}$ and 0-1 $R^{3d}$, naphthyl substituted with 0-3 $R^{3a}$ and 0-1 $R^{3d}$, 1,2,3,4-tetrahydronaphthyl substituted with 0-3 $R^{3a}$ and 0-1 $R^{3d}$, or $-(CH_2)_r$-5- to 12-membered heterocycle comprising: carbon atoms and 1-4 heteroatoms selected from N, O, and $S(O)_p$, wherein said heterocycle is substituted with 0-3 $R^{3a}$ and 0-1 $R^{3d}$.

In another embodiment, $R^3$ is, independently at each occurrence, phenyl substituted with 0-2 $R^{3a}$ and 0-1 $R^{3d}$, naphthyl substituted with 0-2 $R^{3a}$ and 0-1 $R^{3d}$, 1,2,3,4-tetrahydronaphthyl substituted with 0-2 $R^{3a}$ and 0-1 $R^{3d}$, or a 5- to 12-membered heterocycle substituted with 0-2 $R^{3a}$ and 0-1 $R^{3d}$, wherein said heterocycle is selected from: thiophene, furan, thiazole, tetrazole, pyridine, pyridone, pyrimidine, pyrrole, pyrazole, indole, 2-oxindole, isoindoline, indazole, 7-azaindole, benzofuran, benzothiophene, benzimidazole, benzisoxazole, benzoxazole, quinazoline, quinoline, isoquinoline, quinoxaline, phthalazine, dihydrophthalazine, dihydroisoquinoline, dihydroquinoline, dihydroquinolinone, dihydroindole, dihydrobenzimidazole, dihydrobenzoxazine, dihydroquinazoline, dihydro-quinoxaline, benzothiazine, benzoxazine, tetrahydrobenzazepine, dihydroazabenzocycloheptene, and tetrahydroquinoline.

In another embodiment, $R^3$ is, independently at each occurrence, phenyl substituted with 0-2 $R^{32}$, naphthyl substituted with 0-2 $R^{3a}$, 1,2,3,4-tetrahydro-naphthyl substituted with 0-2 $R^{3a}$, or a 5- to 12-membered heterocycle substituted with 0-2 $R^{3a}$ and selected from: thiophene, furan, thiazole, pyridine, pyridinone, pyrimidine, pyrrole, pyrazole, indole, 2-oxindole, isoindolin-1-one, indazole, 1H-indazole-3-one, 7-azaindole, benzofuran, benzothiophene, benzimidazole, benzisoxazole, benzoxazole, quinazoline, quinoline, isoquinoline, 3H-quinazolin-4-one, phthalazine, 2H-phthalazin-1-one, 2H-3,4-dihydrophthalazin-1-one, 1H-quinolin-4-one, 1H-quinolin-2-one, 2H-3,4-dihydroisoquinolin-1-one, 3,4-dihydro-1H-quinolin-2-one, 1,3-dihydroindol-2-one, 3H-benzoxazol-2-one, 1,3-dihydrobenzimidazol-2-one, 1,4-dihydro-3,1-benzoxazin-2-one, 3,4-dihydro-1H-quinazolin-2-one, 1,3-dihydro-quinazoline-2,4-dione, 1,4-dihydro-quinoxaline-2,3-dione, 4H-benzo[1,4]thiazine-3-one, 2H-benzo[1,4]thiazin-3(4H)-one, 4H-1,4-benzoxazin-3-one, 1,3,4,5-tetrahydro-1-benzazepin-2-one, 1,3,4,5-tetrahydro-1,3-benzodiazepin-2-one, 8,9-dihydro-5H-7-oxa-5-aza-benzocyclohepten-6-one, benzimidazol-2-one, 1,3-dihydrobenzimidazol-2-one, 3H-benzoxazol-2-one, 3H-quinazolin-4-one, and 1,2,3,4-tetrahydroquinoline.

In another embodiment, $R^3$ is, independently at each occurrence, phenyl, 3-biphenyl, 4-biphenyl, 3-aminophenyl, 4-aminophenyl, 3-N,N-dimethylaminophenyl, 4-phenoxyphenyl, 4-benzyloxyphenyl, 4-(t-butoxymethyl)-phenyl, 4-methylsulfonylphenyl, 3-cyanophenyl, 4-cyanophenyl, 3-fluorophenyl, 4-fluorophenyl, 3-chlorophenyl, 4-chlorophenyl, 3-bromophenyl, 4-bromophenyl, 3-hydroxyphenyl, 4-hydroxyphenyl, 2-methoxyphenyl, 3-methoxyphenyl, 4-methoxyphenyl, 3-trifluoromethylphenyl, 4-trifluoromethylphenyl, 3-carboxyphenyl, 4-carboxyphenyl, 3-methoxycarbonylphenyl, 4-methoxycarbonylphenyl, 3-carboxymethylphenyl, 4-carboxymethylphenyl, 4-methoxycarbonylmethylphenyl, 3-ethoxycarbonylmethylphenyl, 4-ethoxycarbonylmethylphenyl, 4-ethoxycarbonylethylphenyl, 3-carbamoylphenyl, 4-carbamoylphenyl, 3-aminocarbonylmethylphenyl, 4-aminocarbonylmethylphenyl, 4-methylaminocarbonylphenyl, 4-dimethylaminocarbonylmethylphenyl, 4-amidinophenyl, 3-methylcarbonylaminophenyl, 4-methylcarbonylaminophenyl, 4-methoxycarbonylaminophenyl, 4-aminosulfonylphenyl, 3-methylsulfonylaminophenyl, 4-methylsulfonylamino, 2,4-difluorophenyl, 3-fluoro-4-cyanophenyl, 4-amino-3-carboxyphenyl, 4-amino-3-methoxycarbonylphenyl, 2,4-dichlorophenyl, 3-cyano-5-fluorophenyl, 3-fluoro-4-carbamoylphenyl, 3-carboxy-4-cyanophenyl, 3-phenyl-4-carbamoylphenyl, 4-(2-oxo-1-piperidino)-phenyl, thiazol-2-yl, thien-2-yl, 4-methoxycarbonyl-thiazol-2-yl, 4-carbamoyl-thiazol-2-yl, 1-benzyl-pyazol-4-yl, 5-phenyl-oxazol-2-yl, 5-carbamoyl-thien-2-yl, 5-carboxy-thien-2-yl, pyrid-2-yl, pyrid-3-yl, pyrid-4-yl, 6-amino-pyrid-3-yl, benzimidazol-2-yl, 6-methoxy-pyrid-3-yl, 1-methyl-benzimidazol-2-yl, benzoxazol-2-yl, benzothiazol-2-yl, 3-amino-benzisoxazol-6-yl, 3-amino-benzisoxazol-5-yl, indazol-5-yl, indazol-6-yl, 3-amino-indazol-5-yl, 3-hydroxy-indazol-5-yl, 3-amino-indazol-6-yl, 3-amino-1-methyl-indazol-6-yl, 3-amino-4-fluoro-indazol-6-yl, 3-amino-5-fluoro-indazol-6-yl, 3-amino-7-fluoro-indazol-6-yl, 4-imino-3,4-dihydro-2H-phthalazin-1-on-7-yl, 3-(5-tetrazolyl)-phenyl, 2,3-dihydro-isoindol-1-on-6-yl, quinolin-5-yl, quinolin-6-yl, quinolin-8-yl, isoquinolin-5-yl, 2H-isoquinolin-1-on-6-yl, 2,4-diaminoquinazolin-7-yl, 4-NH$_2$-quinazolin-7-yl,

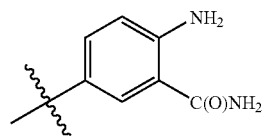

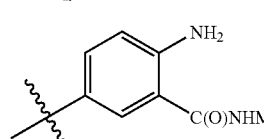

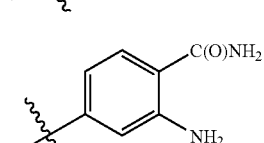

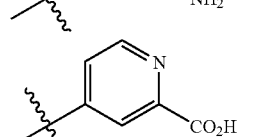

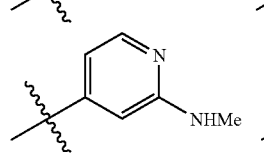

-continued

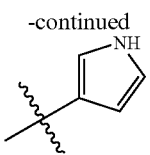

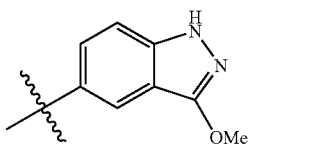

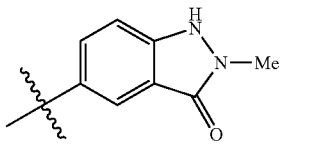

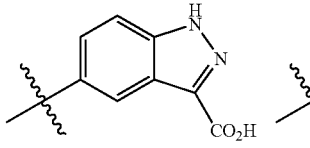
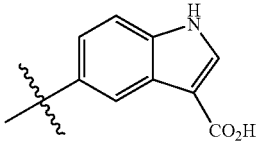

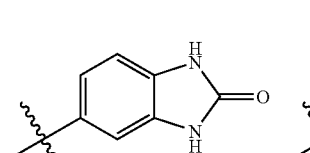
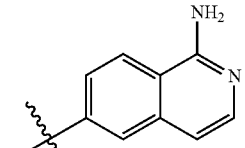

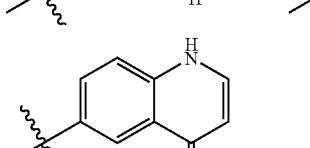

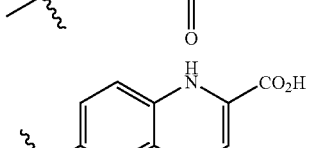

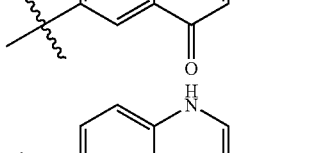

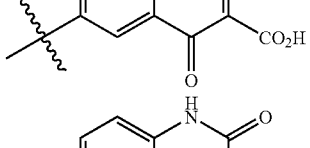

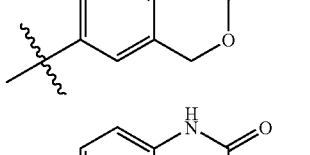

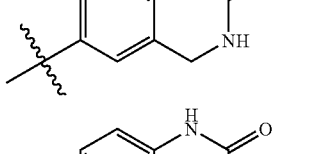

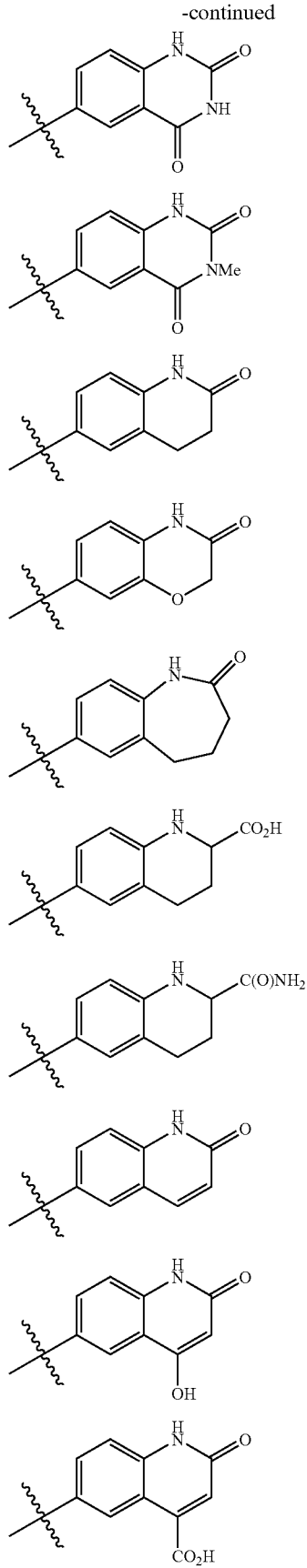
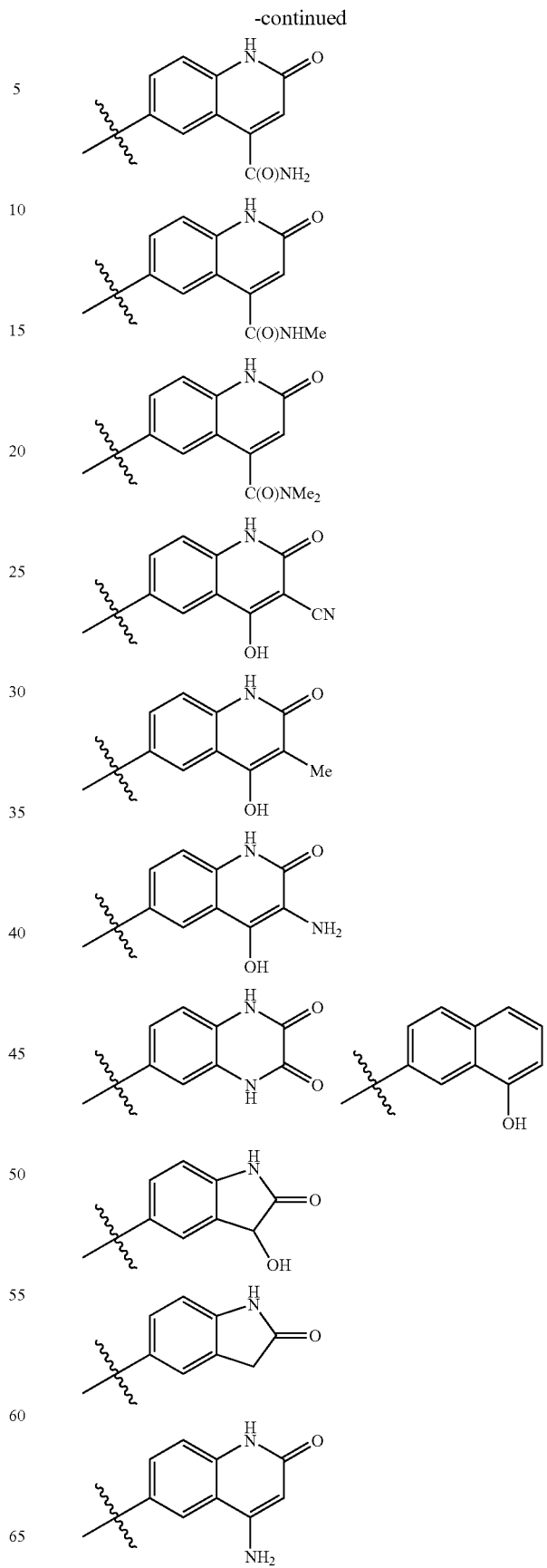

-continued
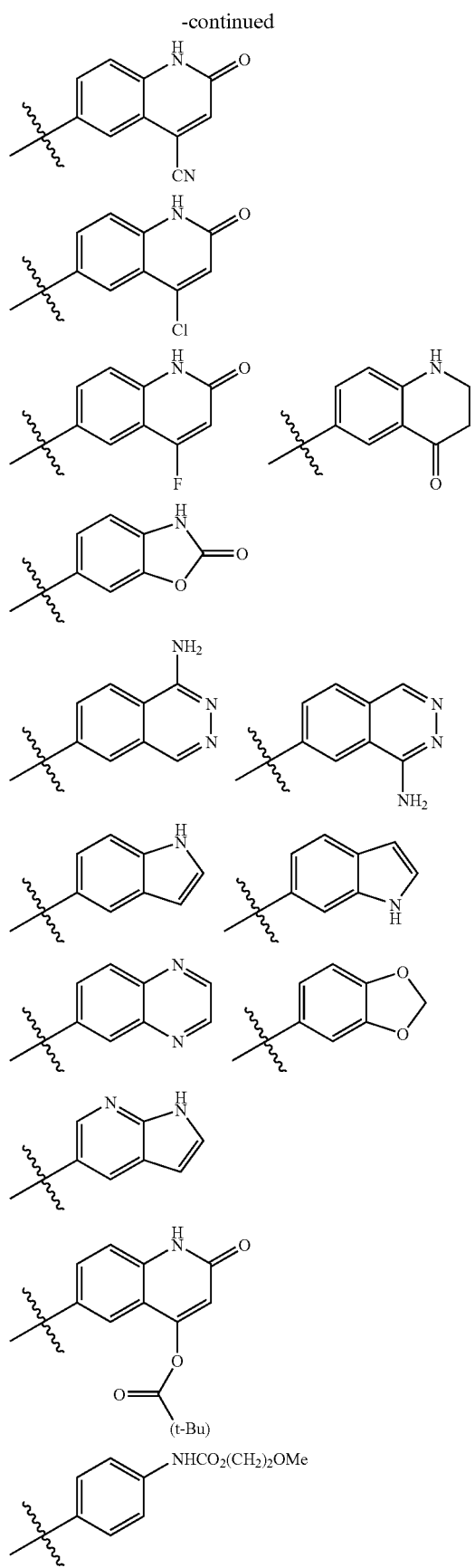
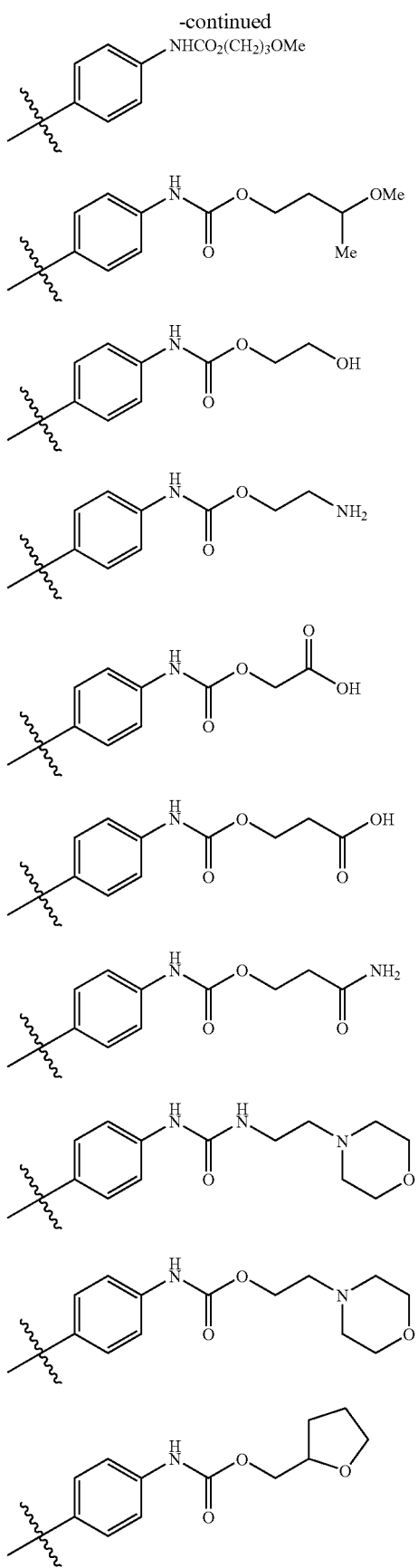

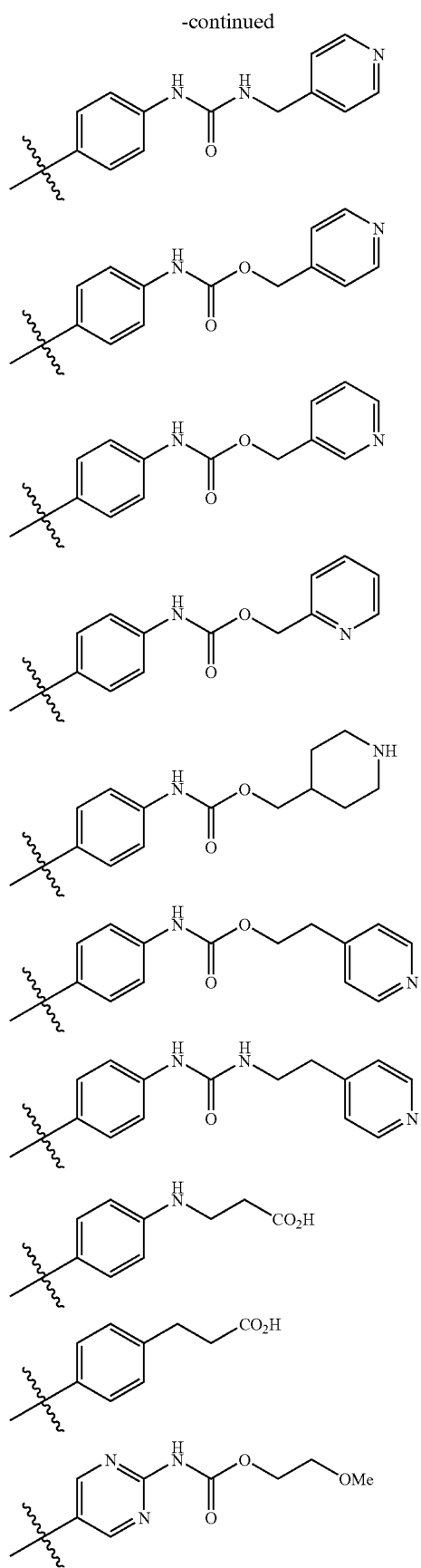
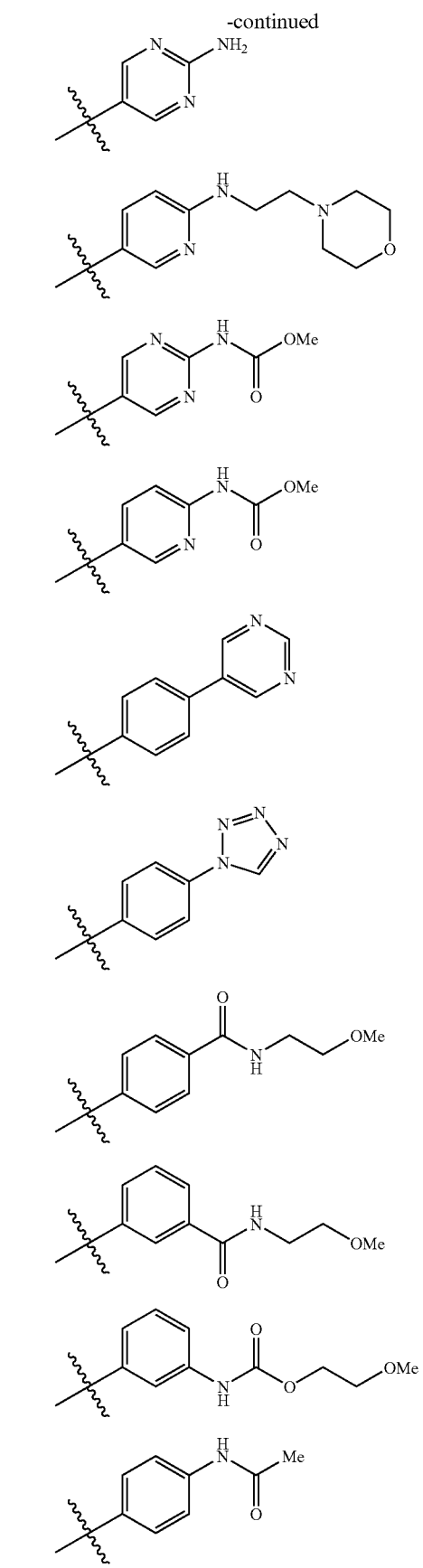

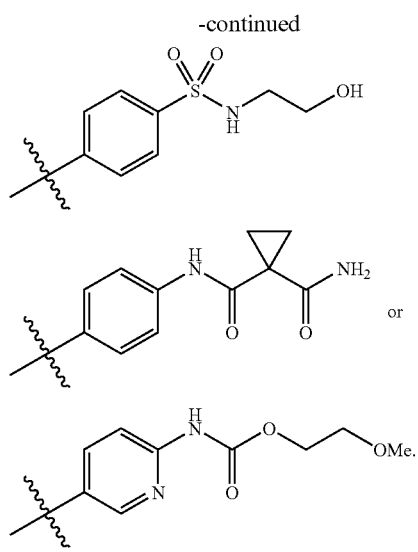
In another embodiment, $R^3$ is, independently at each occurrence,
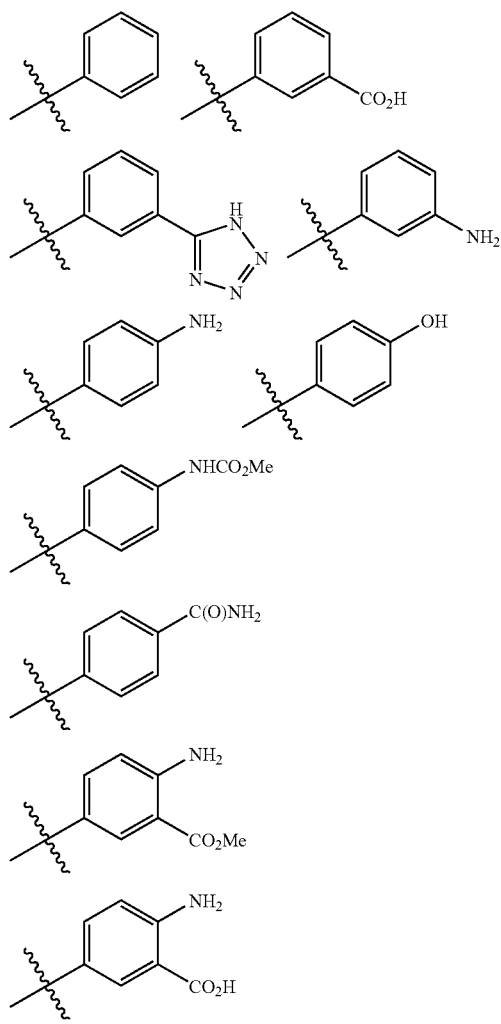
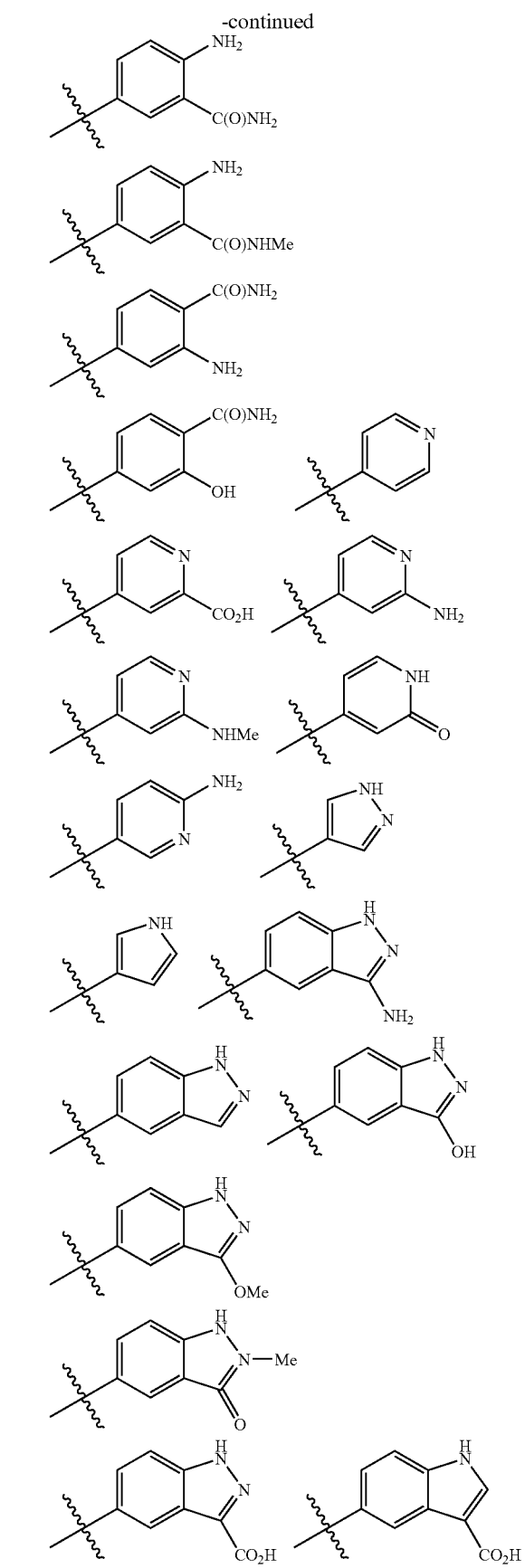

-continued
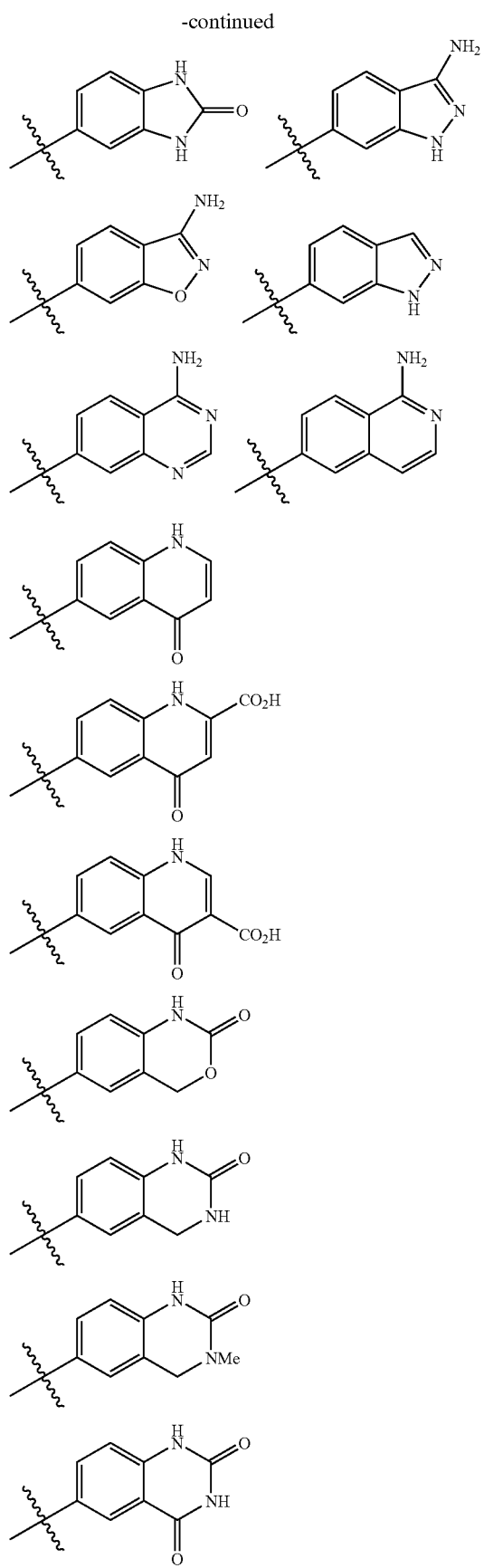
-continued
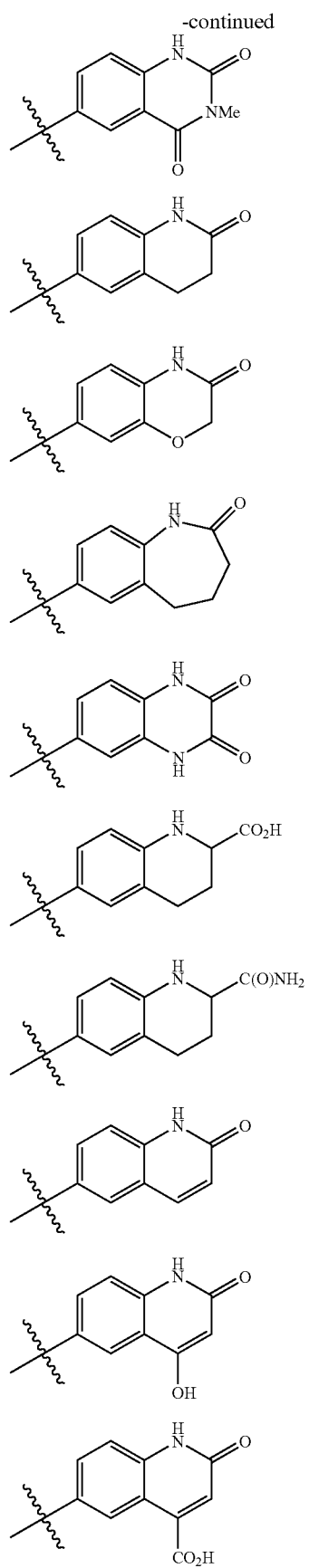

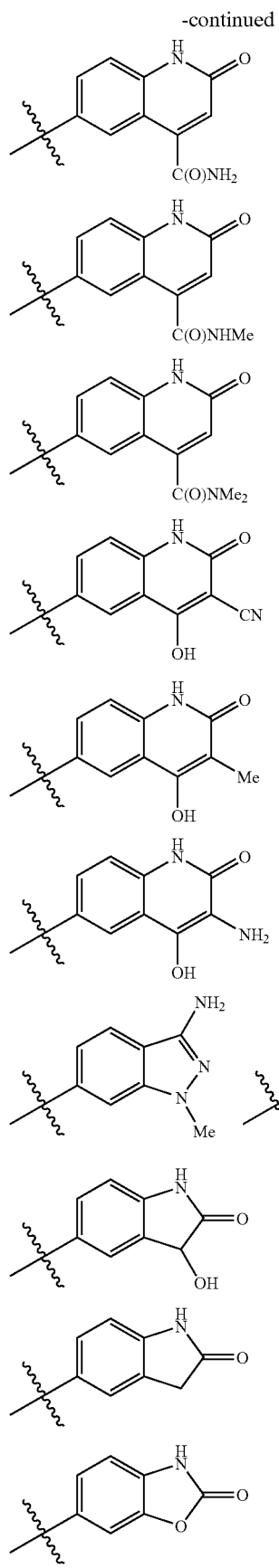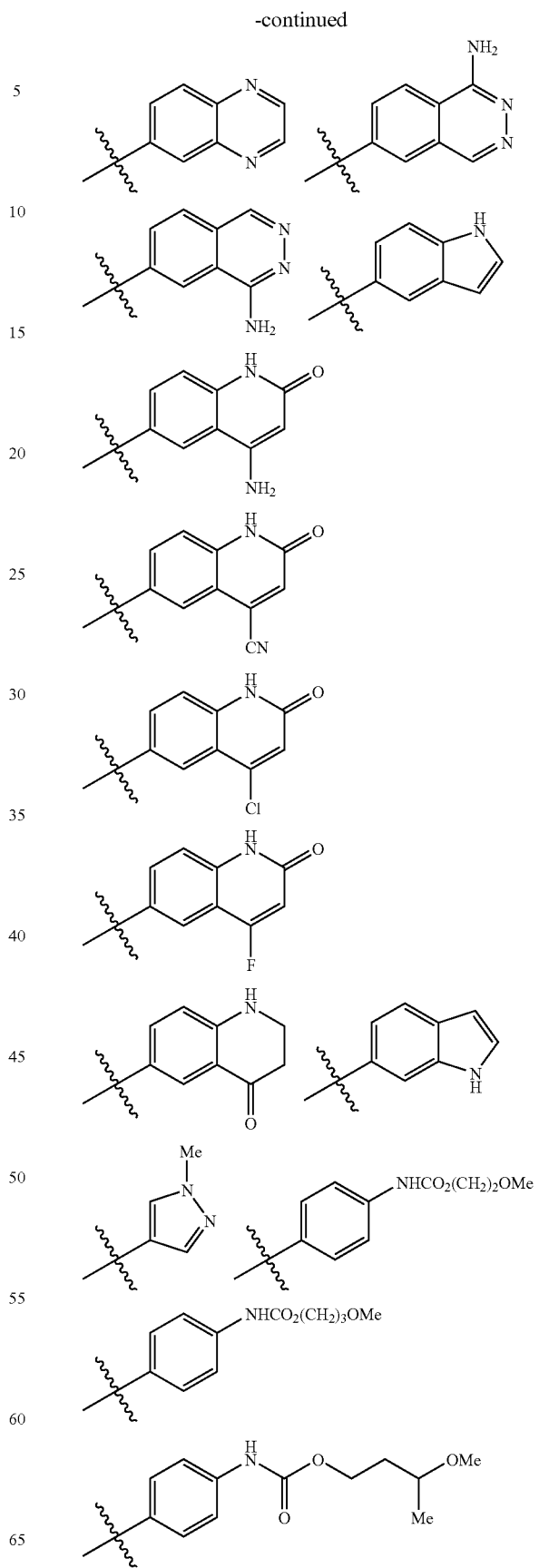

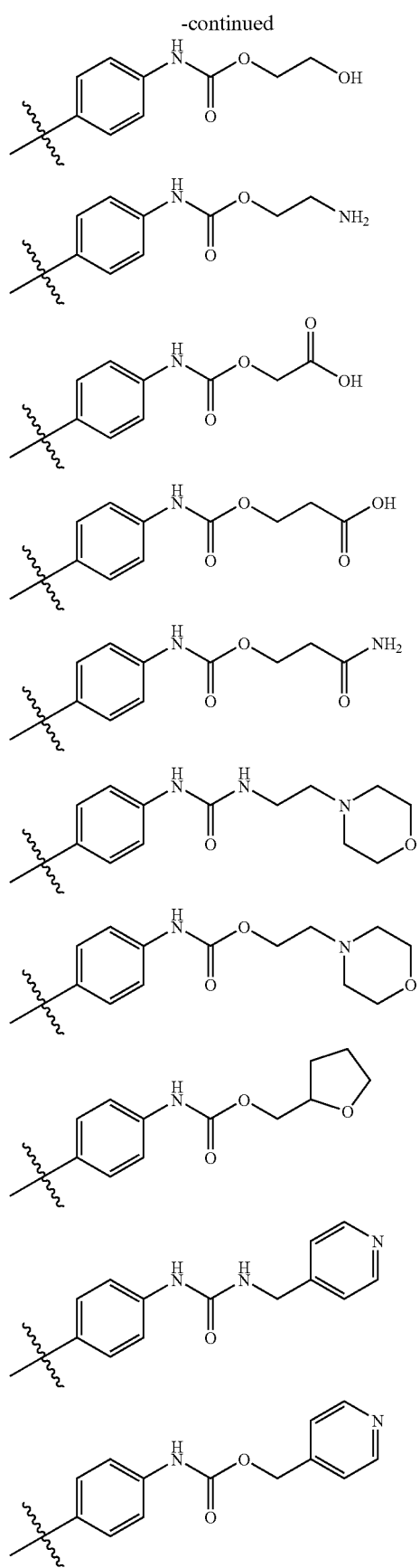
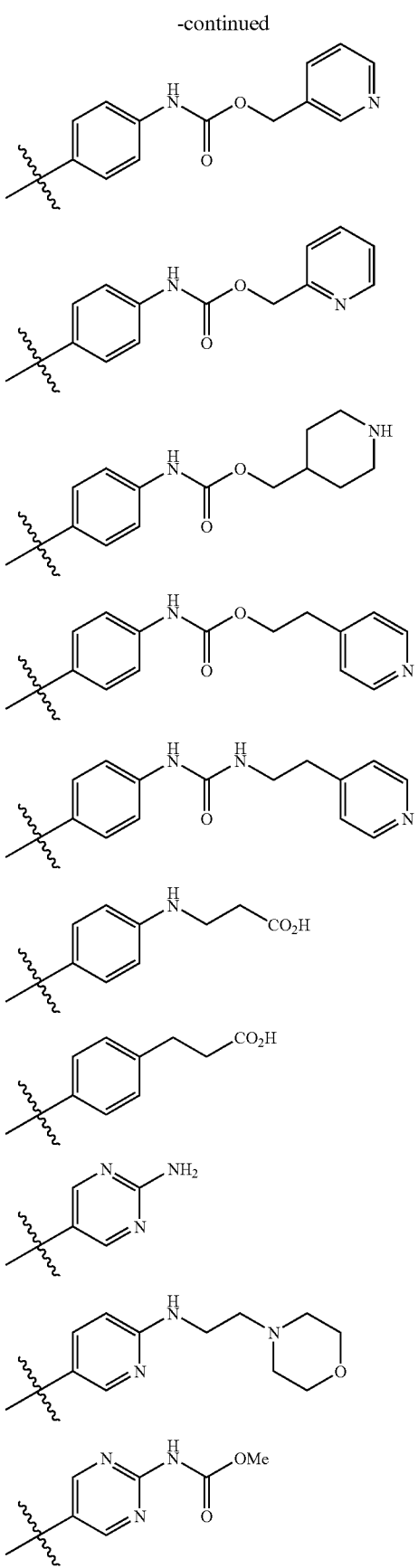

-continued
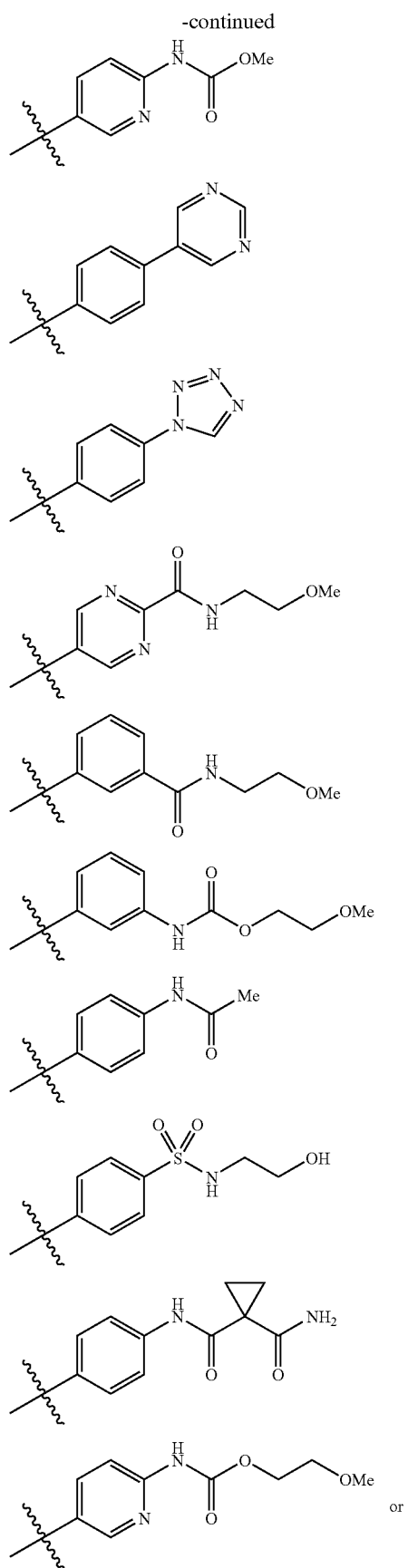
-continued
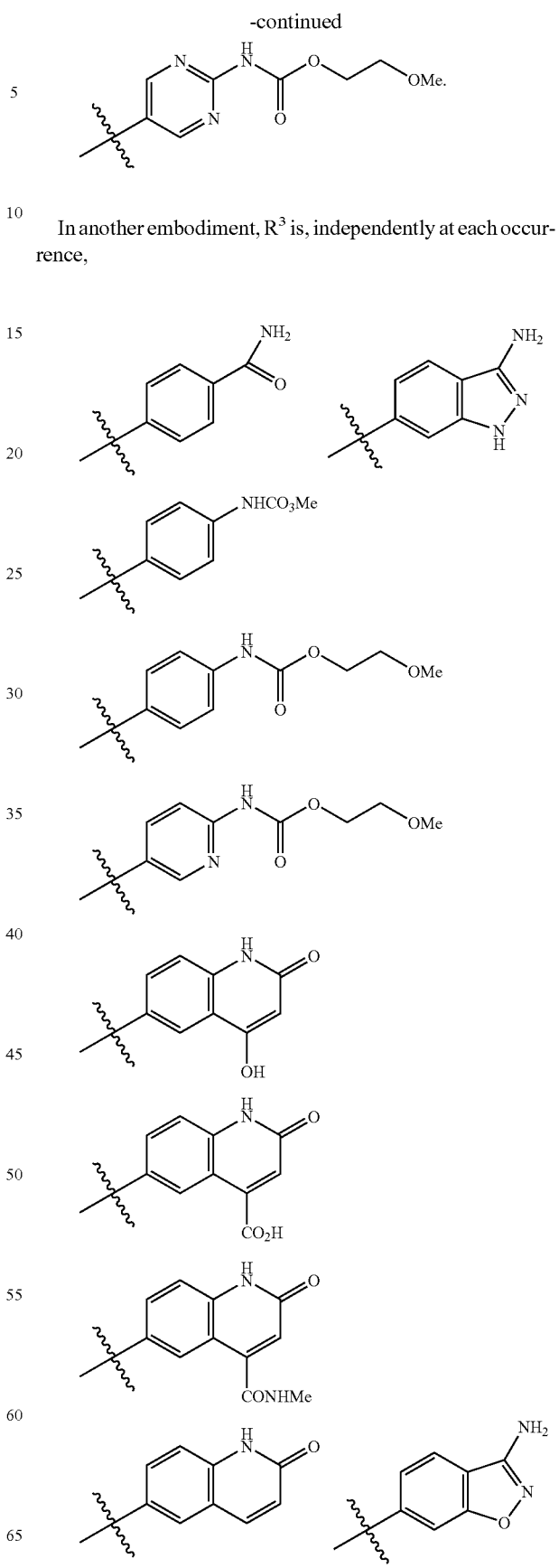
In another embodiment, $R^3$ is, independently at each occurrence, -continued

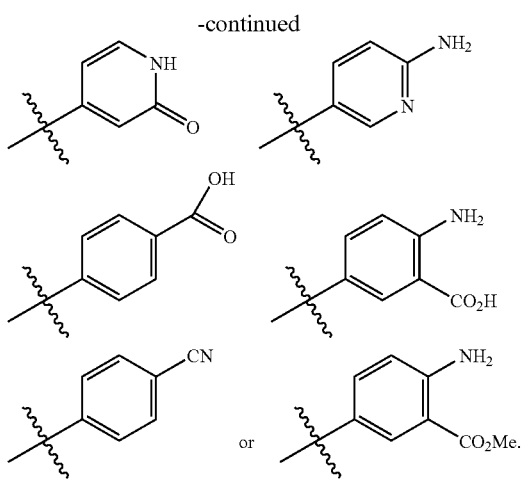

In another embodiment, $R^3$ is, independently at each occurrence,

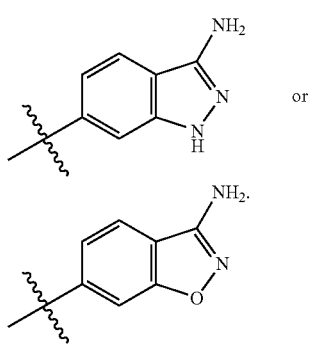

In another embodiment, $R^3$ is, independently at each occurrence,

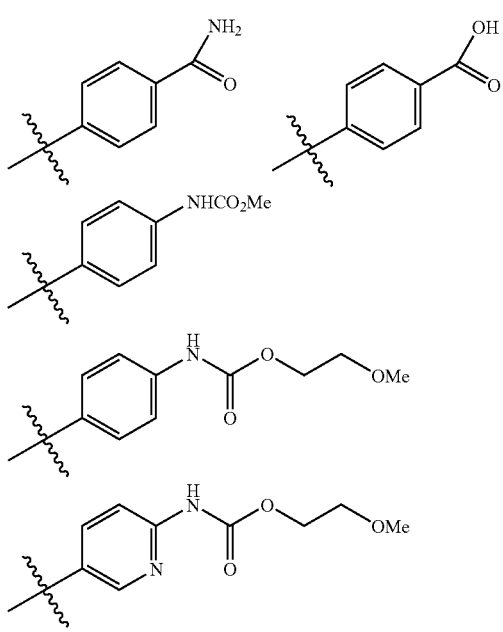

-continued

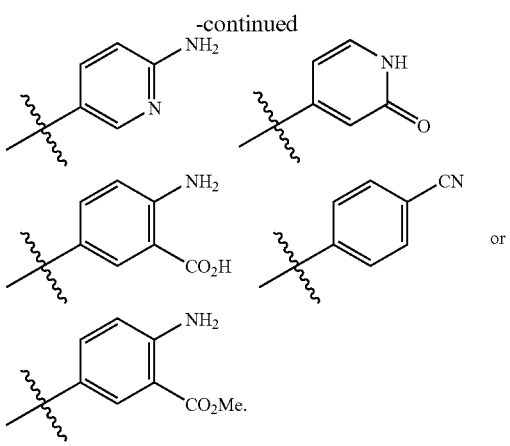

In another embodiment, $R^3$ is, independently at each occurrence,

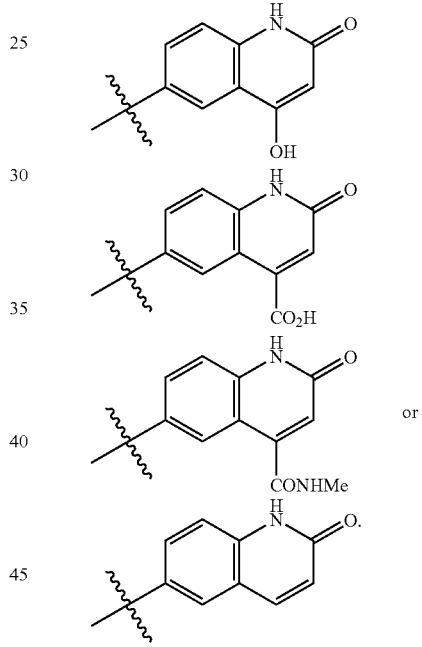

In another embodiment, $R^4$ is H, F, Cl, Br, OH, OMe, $NH_2$, Me, Et, $CF_3$, —$CH_2OH$, —$C(O)_2H$, $CO_2Me$, $CO_2Et$, —$C(O)NH_2$, —$C(O)NHMe$, —$C(O)N(Me)_2$, or —$CH_2CO_2H$.

In another embodiment, $R^4$ is H, F, Cl, Br, OMe, $NH_2$, $CF_3$, Me, Et, $CO_2H$, $CO_2Me$, or $CO_2Et$.

In another embodiment, $R^4$ is H, Me, F, Br, $C_1$, $CF_3$, $CO_2H$, $CO_2Me$, or $CO_2Et$.

In another embodiment, $R^4$ is H, Me or Cl.

In another embodiment, $R^4$ is H or Cl.

In another embodiment, $R^4$ is Cl.

In another embodiment, $R^{11}$ is $C_{1-4}$ haloalkyl, —$CH_2C(O)NR^8R^9$, —$CH_2CH_2C(O)NR^8R^9$, —$CH_2CH_2C(O)R^a$, —$CH_2C(O)OR^a$, —$CH_2CH_2C(O)OR^a$, $C_{1-6}$ alkyl substituted with 0-2 $R^{11c}$, —$(CH_2)_r$—$C_{3-7}$ cycloalkyl substituted with 0-2 $R^{11b}$, —$(CH_2)_r$-phenyl substituted with 0-2 $R^{11b}$, —$(CH_2)_r$-indanyl substituted with 0-2 $R^{11b}$, —$(CH_2)_r$-indenyl substituted with 0-2 $R^{11b}$, —$(CH_2)_r$-naphthyl substituted with 0-2 $R^{11b}$, or —$(CH_2)_r$-5- to 10-membered heterocycle comprising carbon atoms and 1-4 heteroatoms selected from N, O, and S(O)$_p$, wherein said heterocycle is substituted with 0-2 R$^{11b}$.

In another embodiment, R$^{11}$ is C$_{1-4}$ haloalkyl, —CH$_2$C(O)NR$^8$R$^9$, —CH$_2$CH$_2$C(O)NR$^8$R$^9$, —CH$_2$C(O)R$^a$, —CH$_2$CH$_2$C(O)R$^a$, —CH$_2$C(O)OR$^a$, —CH$_2$CH$_2$C(O)OR$^a$, C$_{1-6}$ alkyl substituted with 0-2 R$^{11c}$, —CH$_2$OBn, —CH$_2$SBn, —(CH$_2$)$_r$—C$_{3-7}$ cycloalkyl substituted with 0-2 R$^{11b}$, —(CH$_2$)$_r$-phenyl substituted with 0-2 R$^{11b}$, —(CH$_2$)$_r$-indanyl substituted with 0-2 R$^{11b}$, —(CH$_2$)$_r$-indenyl substituted with 0-2 R$^{11b}$, —(CH$_2$)$_r$-naphthyl substituted with 0-2 R$^{11b}$, or —(CH$_2$)$_r$-5- to 10-membered heteroaryl substituted with 0-2 R$^{11b}$ and selected from thiazolyl, oxazolyl, pyrazolyl, triazolyl, tetrazolyl, thiadiazolyl, isoxazolyl, imidazolyl, pyridyl, pyrimidinyl, pyrazinyl, pyridazinyl, indolyl, indazolyl, isoindolyl, indolinyl, isoindolinyl, benzimidazolyl, benzothiazolyl, benzotriazolyl, quinolinyl, isoquinolinyl, tetrahydroquinolinyl, tetrahydroisoquinolinyl, and 2,2-dioxo-2,3-dihydro-1H-2$\lambda^6$-benzo[c]thiophenyl.

In another embodiment, R$^{11}$ is methyl, n-propyl, n-butyl, neopentyl, cyclohexylmethyl, carboxymethyl, benzylaminocarbonylethyl, N-phenethylaminocarbonylethyl, N-benzyl-N-methylaminocarbonylethyl, N-[(pyridin-2-yl)methyl]aminocarbonylethyl, N-[(5-methylpyrazin-2-yl)methyl]aminoethyl, N-(thiazol-2-ylmethyl)aminocarbonylethyl, N-(cyclopropylmethyl)aminocarbonylmethyl, benzyl, phenethyl, 2-fluorobenzyl, 3-fluorobenzyl, 4-fluorobenzyl, 2-chlorobenzyl, 3-chlorobenzyl, 4-chlorobenzyl, 2-bromobenzyl, 3-bromobenzyl, 4-bromobenzyl, 3-carboxybenzyl, 3-carbamoylbenzyl, 3-(N-methylcarbamoyl)-benzyl, 3-(N-ethylcarbamoyl)-benzyl, 3-(N,N-dimethylcarbamoyl)-benzyl, 3-tetrazolyl-benzyl, 2-methylbenzyl, 3-methylbenzyl, 4-methylbenzyl, 3-trifluoromethylbenzyl, 4-trifluoromethylbenzyl, 2-aminobenzyl, 3-aminobenzyl, 2-nitrobenzyl, 3-nitrobenzyl, 4-nitrobenzyl, 3-methoxybenzyl, 4-methoxybenzyl, 3-difluoromethoxybenzyl, 2-trifluoromethoxybenzyl, 3-trifluoromethoxybenzyl, 2-phenoxybenzyl, 3-phenoxybenzyl, 2-benzyloxybenzyl, 3-benzyloxybenzyl, 4-benzyloxybenzyl, 4-phenylcarbonylbenzyl, 3-methoxycarbonylbenzyl, 3-methylcarbonylamino-benzyl, 2-phenylcarbonylamino-benzyl, 2-benzylcarbonylamino-benzyl, 3-benzylcarbonylamino-benzyl, 3-(benzoyl-methyl-amino)-benzyl, 3-(2-phenylethyl)carbonylamino-benzyl, 2-phenylsulfonylamino-benzyl, 3-phenylsulfonylamino-benzyl, 3-[N-methyl-N-phenylaminosulfonyl]-benzyl, 3-[benzenesulfonyl-methyl-amino]-benzyl, 3-isobutylaminocarbonylbenzyl, 3-t-butylcarbonylamino-benzyl, 3-isopentylaminocarbnoyl-benzyl, 3-(2-methylphenyl)carbamoyl-benzyl, 3-(3-methylphenyl)carbamoyl-benzyl, 3-(4-methylphenyl)carbamoyl-benzyl, 3-(4-fluorophenyl)carbamoyl-benzyl, 3-(1-naphthyl)carbamoyl-benzyl, 3-benzylcarbamoyl-benzyl, 3-(4-chlorophenyl)methylcarbamoyl-benzyl, 3-(4-methoxyphenyl)methylcarbamoyl-benzyl, 3-(2-phenylethyl)carbamoyl-benzyl, 3-[2-(4-methoxyphenyl)ethyl]carbamoyl-benzyl, 3-[2-(2-chlorophenyl)ethyl]carbamoyl-benzyl, 3-[2-(3-chlorophenyl)ethyl]carbamoyl-benzyl, 3-[2-(4-chlorophenyl)ethyl]carbamoyl-benzyl, 3-[methyl-(pyridin-2-ylethyl)]carbamoyl-benzyl 3-(3-phenylpropyl)carbamoyl-benzyl, 3-(ethyl-methyl-carbamoyl)-benzyl, 3-(isopropyl-methyl-carbamoyl)-benzyl, 3-(isobutyl-methyl-carbamoyl)-benzyl, 3-(methyl-phenyl-carbamoyl)-benzyl, 3-[(methyl-(3-methylphenyl)-carbamoyl]-benzyl, 3-[methyl-(4-methylphenyl)-carbamoyl]-benzyl, 3-(benzyl-methyl-carbamoyl)-benzyl, 3-[(3-chlorobenzyl)-methyl-carbamoyl]-benzyl, 3-[(4-chlorobenzyl)-methyl-carbamoyl]-benzyl, 3-[methyl-phenethyl-carbamoyl)]-benzyl, 3-(ethyl-phenyl-carbamoyl)-benzyl, 3-(piperidin-1-ylcarbonyl)-benzyl, 3-(4-phenyl-piperidin-1-ylcarbonyl)-benzyl, 3-(3,4-dihydro-2H-quinolin-1-ylcarbonyl)-benzyl, 3-[(2-methoxyethyl)-methyl-carbamoyl]-benzyl, 3-(4-methoxy-piperidin-1-ylcarbonyl)-benzyl, 3-(morpholin-4-ylcarbonyl)-benzyl, 3-(morpholin-4-ylsulfonyl)-benzyl, 3-[(N-(2-methoxyethyl), N-methylamino)sulfonyl]-benzyl, 3-(N,N-dimethylaminosulfonyl)-benzyl, 3-(azetidin-1-ylcarbonyl)-benzyl, 3-(3-methoxy-azetidin-1-ylcarbonyl)-benzyl, 3-(3-hydroxy-pyrrolidin-1-ylcarbonyl)-benzyl, 3-[(4-tetrahydropyranyl)methylcarbonyl]-benzyl, 3-[(2-hydroxyethyl)-methyl-carbamoyl]-benzyl, 3-(3-hydroxy-azetidin-1-ylcarbpnyl)-benzyl, 3-(4-hydroxypiperidin-1-ylcarbonyl)-benzyl, 3-[4-(N,N-dimethylamino)-piperidin-1-ylcarbonyl]-benzyl, 3-(4-methyl-piperazin-1-ylcarbonyl)-benzyl, 3-[3-(N,N-dimethylamino)-pyrrolidin-1-ylcarbonyl]-benzyl, 2-phenyl-benzyl, 3-phenyl-benzyl, 4-phenyl-benzyl, 3-phenethyl-benzyl, benzyloxymethyl, benzylthiomethyl, 1-naphthylmethyl, 2-naphthylmethyl, thiazol-4-ylmethyl, pyrid-2-ylmethyl, pyrid-3-ylmethyl, pyrid-4-ylmethyl, 1-benzyl-imidazol-4-ylmethyl, benzothiazol-2-ylmethyl, 3-[(2,6-dimethylmorpholin-4-ylcarbonyl)-benzyl, (benzyloxycarbonyl)methyl, (1-methylpyrazol-3-yl)methyl, (1-methylpyrazol-4-yl)methyl, (1-methylpyrazol-5-yl)methyl, (3-methylpyrazol-5-yl)methyl, (1-ethylpyrazol-4-yl)methyl, (1-n-propylpyrazol-4-yl)methyl, (1-isopropylpyrazol-4-yl)methyl, 1-ethylpyrazol-3-ylmethyl, 3-pyrazolylmethyl, (4-chloro-3-methyl-5-pyrazolyl)methyl, (4-chloro-1,5-dimethyl-3-pyrazolyl)methyl, (4-chloro-1,3-dimethyl-5-pyrazolyl)methyl, (4-chloro-1-methyl-3-pyrazolyl)methyl, [1-(4-methoxybenzyl)-pyrazol-3-yl]methyl, (1,5-dimethylpyrazol-3-yl)methyl, (1,3-dimethylpyrazol-5-yl)methyl, [1-(4-methoxybenzyl)-5-methylpyrazol-3-yl]methyl, (3-trifluoromethylpyrazol-5-yl)methyl, [1-(4-methoxybenzyl)-3-trifluoromethylpyrazol-5-yl]methyl, [(1-methyl-5-methoxycarbonyl)-pyrazol-3-yl]methyl, [(1-methyl-5-carboxy)-pyrazol-3-yl]methyl, [(1-methyl-5-carbamoyl)-pyrazol-3-yl]methyl, [(5-methoxycarbonyl)-pyrrol-2-yl]methyl, thiazol-2-ylmethyl, thiazol-4-methyl, (2-methoxypyridin-3-yl)methyl, (6-methoxypyridin-3-yl)methyl, (4-(methoxycarbonyl)-oxazol-2-yl)methyl, morpholin-4-ylcarbonylmethyl, (2,6-dimethyl-morpholin-4-yl)carbonylmethyl, N-((5-methylpyrazin-2-yl)methyl)-aminocarbonylmethyl, 2-hydroxy-indan-5-ylmethyl, 4-methylpiperazin-1-ylcarbonylmethyl, piperazin-1-ylcarbonylmethyl, 4-methylcarbonylpiperazin-1-ylcarbonylmethyl, pyrrolidin-1-ylcarbonylmethyl, 2-methoxypyrrolidin-1-ylcarbonylmethyl, aziridin-1-ylcarbonylmethyl, [3-(4-methoxyphenoxy)-azetidin-1-yl]carbonylmethyl, 2-hydroxyethylaminocarbonylmethyl, 2-methoxyethylaminocarbonylmethyl, 2-ethoxyethylaminocarbonylmethyl, bis(2-methoxyethyl)aminocarbonylmethyl, 4-dimethylaminopyrrolidin-1-ylcarbonylmethyl, (3-phenyl-pyrrolidin-1-yl)carbonylmethyl, (3,3-dimethyl-piperidin-1-yl)carbonylmethyl, [2-(4-pyridyl)-pyrrolidin-1-yl]carbonylmethyl, 4-chlorophenylaminocarbonylmethyl, 3-chlorophenylcarbonylmethyl, N-methyl-N-benzylaminocarbonylmethyl, cyclopropylaminocarbonylmethyl, cyclopropylmethylaminocarbonylmethyl, cyclopentylaminocarbonylmethyl, (trans-2-phenylcyclopropyl)aminocarbonylmethyl, N,N-dimethylaminoethylaminocarbonylmethyl, N-((pyridin-2-yl)methyl)-aminocarbonylmethyl, N-((pyridin-3-yl)methyl)-aminocarbonylmethyl, N-((pyridin-4-yl)methyl)-aminocarbonylmethyl, N-((pyridin-2-yl)ethyl)-aminocarbonylmethyl, N-((6-oxo-1,6-dihydropyridin-3-yl)methyl)-aminocarbonylmethyl, (1,1-dioxo-1$\lambda^6$-thiomorpholin-4-yl)carbonylmethyl, (thiomorpholin-4-yl)carbonylmethyl, N-(tert-butoxycarbonyl)-1H-indol-3- ylmethyl, 1H-indol-3-ylmethyl, 2,2-dioxo-2,3-dihydro-1H-2X$^6$-benzo[c]thiophen-5-ylmethyl, 4,4,4-trifluorobutyl, cyclopropylmethyl, (4-hydroxy)cyclohexylmethyl, 4-oxo-cyclohexylmethyl, 2-(t-butoxycarbonylamino)ethyl, 2-aminoethyl, (1,3-dihydro-isoindol-2-yl)carbonylmethyl, (4-acetyl-perhydro-1,4-diazepin-1-yl)carbonylmethyl, (4-(2-N,N-diethylaminoethyl)-perhydro-1,4-diazepin-1-yl)carbonylmethyl, (6-oxo-7,10-diaza-tricyclo[7.2.1.0$^{2,7}$]dodeca-2,4-dien-10-ylcarbonyl)methyl, (1,4-diaza-bicyclo[3.2.2]nonane-4-carbonyl)methyl, (5-t-butoxycarbonyl-2,5-diaza-bicyclo[2.2.1]heptane-2-carbonyl)methyl, (1-methyl-hexahydro-pyrrolo[1,2-a]pyrazin-2-ylcarbonyl)methyl, -continued

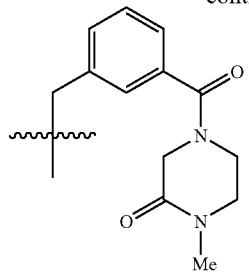

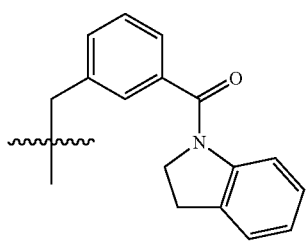

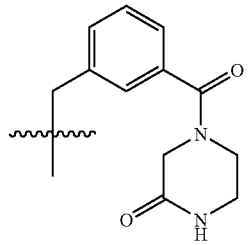

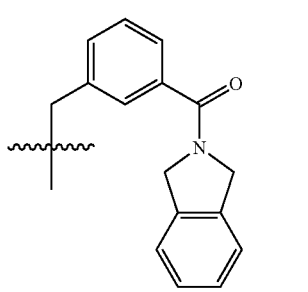

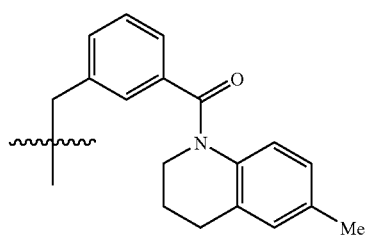

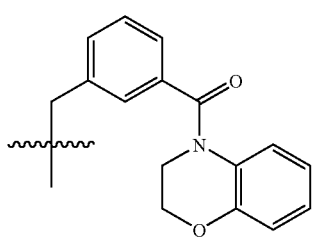

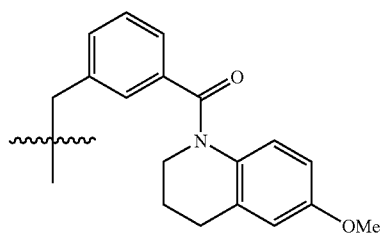

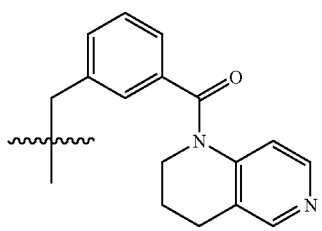

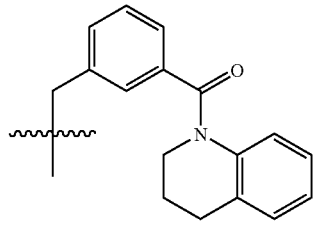

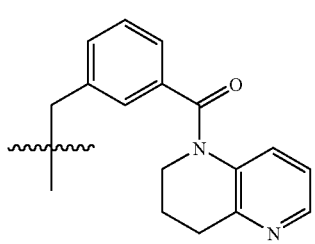

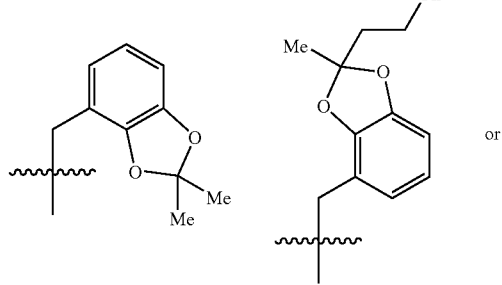

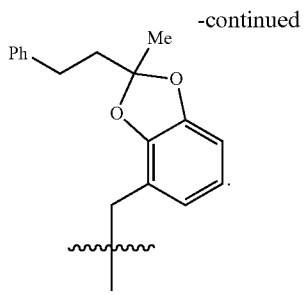

In another embodiment, $R^{11}$ is methyl, n-butyl, carboxymethyl, cyclopropylmethyl, benzyl, 4-fluoro-benzyl, (benzyloxycarbonyl)methyl, 3-carboxy-benzyl, 3-carbamoyl-benzyl, 3-(N-methylcarbamoyl)-benzyl, 3-(N,N-dimethylcarbamoyl)-benzyl, (1-methylpyrazol-3-yl)methyl, (1-methylpyrazol-4-yl)methyl, (1-ethylpyrazol-4-yl)methyl, (1-n-propylpyrazol-4-yl)methyl, (1-isopropylpyrazol-4-yl)methyl, 1-ethylpyrazol-3-ylmethyl, 3-pyrazolylmethyl, 1-(4-methoxybenzyl)-pyrazol-3-yl]methyl, (1,5-dimethylpyrazol-3-yl)methyl, (1,3-dimethylpyrazol-5-yl)methyl, [1-(4-methoxybenzyl)-5-methyl-pyrazol-3-yl]methyl, (3-trifluoromethylpyrazol-5-yl)methyl, [1-(4-methoxybenzyl)-3-trifluoromethylpyrazol-5-yl]methyl, (3-methylpyrazol-5-yl)methyl, (1-methylpyrazol-5-yl)methyl, (2-methoxypyridin-3-yl)methyl, (6-methoxypyridin-3-yl)methyl, (4-(methoxycarbonyl)-oxazol-2-yl)methyl, morpholin-4-ylcarbonylmethyl, N-((5-methylpyrazin-2-yl)methyl)-aminocarbonylmethyl, N-((pyridin-2-yl)methyl)-aminocarbonylmethyl, N-((pyridin-3-yl)methyl)-aminocarbonylmethyl, N-((pyridin-4-yl)methyl)-aminocarbonylmethyl, N-((pyridin-2-yl)ethyl)-aminocarbonylmethyl, 4-methylpiperazin-1-ylcarbonylmethyl, 4-methylcarbonylpiperazin-1-ylcarbonylmethyl, pyrrolidin-1-ylcarbonylmethyl, 2-methoxypyrrolidin-1-ylcarbonylmethyl, aziridin-1-ylcarbonylmethyl, 2-hydroxyethylaminocarbonylmethyl, 2-methoxyethylaminocarbonylmethyl, bis(2-methoxyethyl)aminocarbonylmethyl, 4-dimethylaminopyrrolidin-1-ylcarbonylmethyl, 4-chlorophenylaminocarbonylmethyl, 3-chlorophenylcarbonylmethyl, N-methyl-N-benzylaminocarbonylmethyl, cyclopropylaminocarbonylmethyl, cyclopropylmethylaminocarbonylmethyl, cyclopentylaminocarbonylmethyl, (trans-2-phenylcyclopropyl)aminocarbonylmethyl, N,N-dimethylaminoethylaminocarbonylmethyl, 1-(1,1-dioxo-1$\lambda^6$-thiomorpholin-4-yl)carbonylmethyl, N-(tert-butoxycarbonyl)-1H-indol-3-ylmethyl, 1H-indol-3-ylmethyl, 2,2-dioxo-2,3-dihydro-1H-2$\lambda^6$-benzo[c]thiophen-5-ylmethyl, (4-hydroxy)cyclohexylmethyl or 4-oxo-cyclohexylmethyl, cyclohexylmethyl, phenethyl, 2-fluorobenzyl, 3-fluorobenzyl, 2-chlorobenzyl, 3-(N-ethylcarbamoyl)-benzyl, 3-methylbenzyl, 4-methylbenzyl, 3-methoxybenzyl, 3-difluoromethoxybenzyl, 3-trifluoromethoxy-benzyl, 3-methoxycarbonylbenzyl, 3-methylcarbonylamino-benzyl, 3-benzylcarbonylamino-benzyl, 3-(benzoyl-methyl-amino)-benzyl, 3-(2-phenylethyl)carbonylamino-benzyl, 2-phenylsulfonylamino-benzyl, 3-phenylsulfonylamino-benzyl, 3-[N-methyl, N-phenylaminosulfonyl]-benzyl, 3-(benzenesulfonyl-methyl-amino)-benzyl, 3-(2-methylphenyl)carbamoyl-benzyl, 3-(3-methylphenyl)carbamoyl-benzyl, 3-(4-methylphenyl)carbamoyl-benzyl, 3-(4-fluorophenyl)carbamoyl-benzyl, 3-(1-naphthyl)carbamoyl-benzyl, 3-benzylcarbamoyl-benzyl, 3-(4-chlorophenyl)methylcarbamoyl-benzyl, 3-(4-methoxyphenyl)methylcarbamoyl-benzyl, 3-(2-phenylethyl)carbamoyl-benzyl, 3-[2-(4-methoxyphenyl)ethyl]carbamoyl-benzyl, 3-[2-(2-chlorophenyl)ethyl]carbamoyl-benzyl, 3-[2-(3-chlorophenyl)ethyl]carbamoyl-benzyl, 3-[2-(4-chlorophenyl)ethyl]carbamoyl-benzyl, 3-[methyl-(pyridin-2-ylethyl)]carbamoyl-benzyl 3-(3-phenylpropyl)carbamoyl-benzyl, 3-(ethyl-methyl-carbamoyl)-benzyl, 3-(isopropyl-methyl-carbamoyl)-benzyl, 3-(isobutyl-methyl-carbamoyl)-benzyl, 3-(methyl-phenyl-carbamoyl)-benzyl, 3-[(methyl-(3-methylphenyl)-carbamoyl]-benzyl, 3-[methyl-(4-methylphenyl)-carbamoyl]-benzyl, 3-(benzyl-methyl-carbamoyl)-benzyl, 3-[(3-chlorobenzyl)-methyl-carbamoyl]-benzyl, 3-[(4-chlorobenzyl)-methyl-carbamoyl]-benzyl, 3-[methyl-phenethyl-carbamoyl)]-benzyl, 3-(ethyl-phenyl-carbamoyl)-benzyl, 3-(piperidin-1-ylcarbonyl)-benzyl, 3-(3,4-dihydro-2H-quinolin-1-ylcarbonyl)-benzyl, 3-[(2-methoxyethyl)-methyl-carbamoyl]-benzyl, 3-(4-methoxy-piperidin-1-ylcarbonyl)-benzyl, 3-(morpholin-4-ylcarbonyl)-benzyl, 3-(morpholin-4-ylsulfonyl)-benzyl, 3-[(N-(2-methoxyethyl), N-methylamino)sulfonyl]-benzyl, 3-(N,N-dimethylaminosulfonyl)-benzyl, 3-(azetidin-1-ylcarbonyl)-benzyl, 3-(3-methoxy-azetidin-1-ylcarbonyl)-benzyl, 3-(3-hydroxy-pyrrolidin-1-ylcarbonyl)-benzyl, 3-[(4-tetrahydropyranyl)methylcarbonyl]-benzyl, 3-[(2-hydroxyethyl)-methyl-carbamoyl]-benzyl, 3-(3-hydroxy-azetidin-1-ylcarbpnyl)-benzyl, 3-(4-hydroxypiperidin-1-ylcarbonyl)-benzyl, 3-[4-(N,N-dimethylamino)-piperidin-1-ylcarbonyl]-benzyl, 3-(4-methyl-piperazin-1-ylcarbonyl)-benzyl, 3-[3-(N,N-dimethylamino)-pyrrolidin-1-ylcarbonyl]-benzyl, 1-naphthylmethyl, 2-naphthylmethyl, thiazol-4-ylmethyl, pyrid-2-ylmethyl, pyrid-3-ylmethyl, pyrid-4-ylmethyl, 1-benzyl-imidazol-4-ylmethyl, benzothiazol-2-ylmethyl, 3-[(2,6-dimethylmorpholin-1-ylcarbonyl)-benzyl, (benzyloxycarbonyl)methyl, (4-chloro-3-methyl-5-pyrazolyl)methyl, (4-chloro-1,5-dimethyl-3-pyrazolyl)methyl, (4-chloro-1,3-dimethyl-5-pyrazolyl)methyl, [(1-methyl-5-methoxycarbonyl)-pyrazol-3-yl]methyl, [(1-methyl-5-carboxy)-pyrazol-3-yl]methyl, [(1-methyl-5-carbamoyl)-pyrazol-3-yl]methyl, [(5-methoxycarbonyl)-pyrrol-2-yl]methyl, thiazol-2-ylmethyl, thiazol-4-methyl, 2-hydroxy-indan-5-ylmethyl, 2-ethoxyethylaminocarbonylmethyl, 4,4,4-trifluorobutyl, N-((6-oxo-1,6-dihydropyridin-3-yl)methyl)-aminocarbonylmethyl, (thiomorpholin-4-yl)carbonylmethyl, (2,6-dimethyl-morpholin-4-yl)carbonylmethyl, piperazin-1-ylcarbonylmethyl, (4-chloro-1-methyl-3-pyrazolyl)methyl,

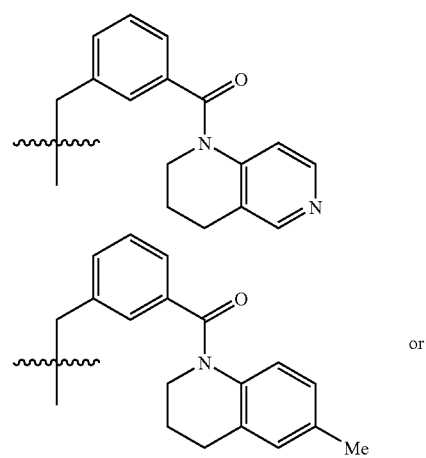

or

-continued

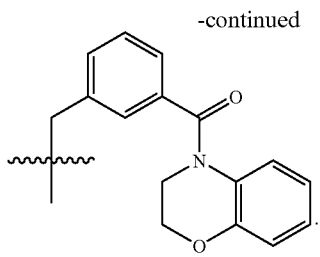

In another embodiment, $R^{11}$ is —CH$_2$C(O)NR$^8$R$^9$.

In another embodiment, $R^{11}$ is —(CH$_2$)$_r$—C$_{3-7}$ cycloalkyl substituted with 0-2 R$^{11b}$.

In another embodiment, $R^{11}$ is C$_{1-6}$ alkyl substituted with 0-2 R$^{11c}$.

In another embodiment, $R^{11}$ is —(CH$_2$)$_r$-phenyl substituted with 0-2 R$^{11b}$, —(CH$_2$)$_r$-indanyl substituted with 0-2 R$^{11b}$, —(CH$_2$)$_r$-indenyl substituted with 0-2 R$^{11b}$, —(CH$_2$)$_r$-naphthyl substituted with 0-2 R$^{11b}$, or —(CH$_2$)$_r$-5- to 10-membered heteroaryl substituted with 0-2 R$^{11b}$ and selected from thiazolyl, oxazolyl, pyrazolyl, triazolyl, tetrazolyl, thiadiazolyl, isoxazolyl, imidazolyl, pyridyl, pyrimidinyl, pyrazinyl, pyridazinyl, indolyl, indazolyl, isoindolyl, indolinyl, isoindolinyl, benzimidazolyl, benzothiazolyl, benzotriazolyl, quinolinyl, isoquinolinyl, tetrahydroquinolinyl, tetrahydroisoquinolinyl, and 2,2-dioxo-2,3-dihydro-1H-2λ$^6$-benzo[c]thiophenyl.

In another embodiment, $R^{11}$ is or —(CH$_2$)$_r$-5- to 10-membered heteroaryl substituted with 0-2 R$^{11b}$ and selected from thiazolyl, oxazolyl, pyrazolyl, triazolyl, tetrazolyl, thiadiazolyl, isoxazolyl, imidazolyl, pyridyl, pyrimidinyl, pyrazinyl, pyridazinyl, indolyl, indazolyl, isoindolyl, indolinyl, isoindolinyl, benzimidazolyl, benzothiazolyl, benzotriazolyl, quinolinyl, isoquinolinyl, tetrahydroquinolinyl, tetrahydroisoquinolinyl, and 2,2-dioxo-2,3-dihydro-1H-2λ$^6$-benzo[c]thiophenyl.

In another aspect, the present invention provides, inter alia, compounds of Formula (II):

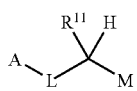

(II)

or stereoisomers, tautomers, pharmaceutically acceptable salts, solvates, or prodrugs thereof, wherein:

A is a C$_{3-10}$ carbocycle substituted with 0-1 R$^1$ and 0-3 R$^2$, or a 5- to 12-membered heterocycle comprising: carbon atoms and 1-4 heteroatoms selected from N, O, and S(O)$_p$, wherein said heterocycle is substituted with 0-1 R$^1$ and 0-3 R$^2$; provided that when A is a heterocycle containing one or more nitrogen atoms, A is not attached to L via any of the nitrogen atoms on the A ring;

L is —(CR$^5$R$^6$)$_2$C(O)NR$^{10}$—, —(CR$^5$R$^6$)$_2$NR$^{10}$C(O)—, —CR$^5$=CR$^6$C(O)NR$^{10}$—, —C≡CCONR$^{10}$—, —SC(R$^5$R$^6$)C(O)NR$^{10}$—, —OC(R$^5$R$^6$)C(O)NR$^{10}$—, —NR$^{10}$CR$^5$R$^6$C(O)NR$^{10}$—, —SO$_2$C(R$^5$R$^6$)C(O)NR$^{10}$—, —C(R$^5$R$^6$)OC(O)NR$^{10}$—, —C(R$^5$R$^6$)NHC(O)NR$^{10}$—, —NR$^{10}$C(O)NR$^{10}$CR$^5$R$^6$—, —NHNHC(O)NR$^{10}$—, —C(O)NR$^{10}$(CR$^5$R$^6$)$_2$—, or —NR$^{10}$C(O)(CR$^5$R$^6$)$_2$—;

provided that when L is —C(R$^5$R$^6$)OC(O)NR$^{10}$—, then A is other than unsubstituted phenyl;

M is a 5- to 6-membered heterocycle selected from:

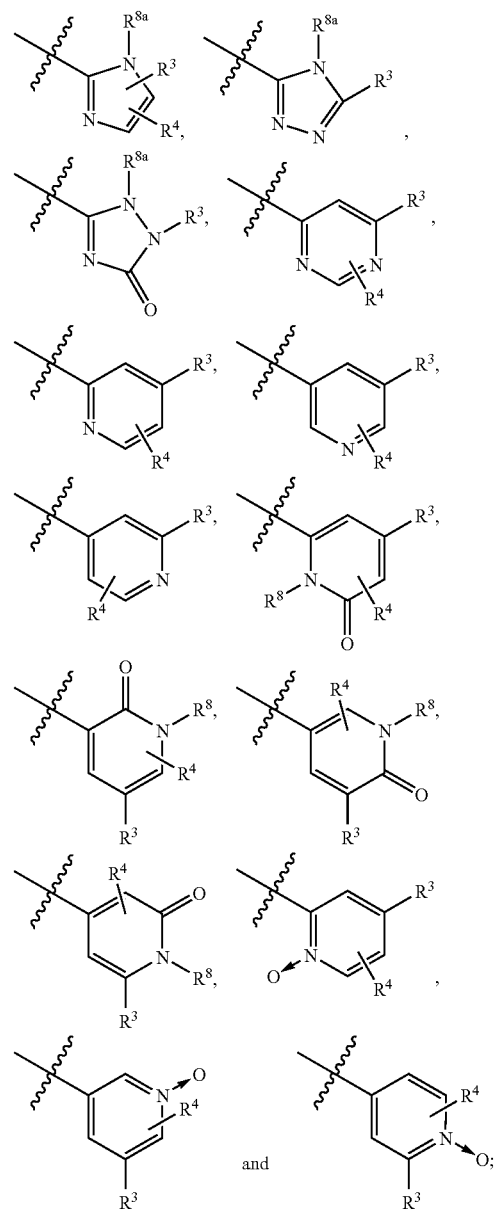

$R^1$ is, independently at each occurrence, F, Cl, Br, I, OCF$_3$, CF$_3$, —(CH$_2$)$_r$OR$^a$, —(CH$_2$)$_r$SR$^a$, CN, —(CH$_2$)$_r$NR$^7$R$^8$, —C(=NR$^8$)NR$^8$R$^9$, —C(O)NR$^8$R$^9$, —S(O)$_p$NR$^8$R$^9$, or C$_{1-6}$ alkyl substituted with 0-1 R$^{1a}$;

$R^{1a}$ is F, OCF$_3$, CF$_3$, OR$^a$, SR$^a$, CN, —NR$^7$R$^8$, —C(O)NR$^8$R$^9$, —NR$^8$C(O)R$^c$, —S(O)$_p$NR$^8$R$^9$, —NR$^8$SO$_2$R$^c$, or —(CF$_2$)$_r$CF$_3$;

$R^2$ is, independently at each occurrence, =O, F, Cl, Br, OCF$_3$, CF$_3$, CHF$_2$, CN, NO$_2$, —(CH$_2$)$_r$OR$^a$, —(CH$_2$)$_r$SR$^a$, —(CH$_2$)$_r$C(O)R$^a$, —(CH$_2$)$_r$C(O)OR$^a$, —(CH$_2$)$_r$OC(O)R$^a$, —(CH$_2$)$_r$NR$^7$R$^8$, —(CH$_2$)$_r$C(O)NR$^8$R$^9$, —(CH$_2$)$_r$NR$^8$C(O)R$^c$, —(CH$_2$)$_r$NR$^8$C(O)OR$^c$, —NR$^8$C(O)NR$^8$R$^c$, —S(O)$_p$NR$^8$R$^9$, —NR$^8$S(O)$_p$R$^c$, —S(O)R$^c$, —S(O)$_2$R$^c$, C$_{1-6}$ alkyl substituted with 0-1 R$^{2a}$, —(CH$_2$)$_r$-3-7 membered carbocycle optionally substituted with 0-2 R$^{2b}$, or —(CH$_2$)$_r$-5-7 membered heterocycle comprising carbon atoms and 1-4 heteroatoms selected from N, O, and $S(O)_p$, wherein said heterocycle is substituted with 0-2 $R^{2b}$;

alternately, when $R^1$ and $R^2$ groups are substituents on adjacent atoms they may be taken together with the atoms to which they are attached to form a 5- to 7-membered carbocycle or heterocycle comprising carbon atoms and 0-4 heteroatoms selected from N, O, and $S(O)_p$ and substituted with 0-2 $R^g$;

$R^{2a}$ is F, $OCF_3$, $CF_3$, $OR^a$, $SR^a$, CN, $-NR^7R^8$, $-C(O)NR^8R^9$, $-NR^8C(O)R^c$, $-NR^8C(O)OR^c$, $-NR^8C(O)NR^8R^c$, $-S(O)_pNR^8R^9$, $-NR^8SO_2R^c$, or $-(CF_2)_rCF_3$;

$R^{2b}$ is, independently at each occurrence, =O, F, Br, Cl, $OCF_3$, $CF_3$, $-(CH_2)_rOR^a$, $-(CH_2)_rSR^a$, $-(CH_2)_rCN$, $-(CH_2)_rNR^7R^8$, $-(CH_2)_rC(O)OR^a$, $-(CH_2)_rOC(O)R^a$, $-(CH_2)_rC(O)NR^8R^9$, $-(CH_2)_rNR^8C(O)R^c$, $-(CH_2)_rNR^8C(O)OR^c$, $-(CH_2)_rS(O)_pNR^8R^9$, $-(CH_2)_rNR^8SO_2R^c$, $C_{1-4}$ alkyl or $-(CF_2)_rCF_3$;

$R^3$ is, independently at each occurrence, $-(CH_2)_r-C_{3-10}$ carbocycle substituted with 0-3 $R^{3a}$ and 0-1 $R^{3d}$, or $-(CH_2)_r-$ 5- to 12-membered heterocycle comprising: carbon atoms and 1-4 heteroatoms selected from N, O, and $S(O)_p$, wherein said heterocycle is substituted with 0-3 $R^{3a}$ and 0-1 $R^{3d}$;

$R^{3a}$ is, independently at each occurrence, =O, $=NR^8$, F, Cl, Br, I, $OCF_3$, $CF_3$, $-(CH_2)_rCN$, $NO_2$, $-(CH_2)_rOR^{3b}$, $-(CH_2)_rSR^{3b}$, $-(CH_2)_rNR^7R^8$, $-NHC(O)NR^8R^9$, $-(CH_2)_rC(O)OR^{3b}$, $-C(O)C_{1-4}$ alkyl, $-SO_2NHR^{3b}$, $-SO_2NHCOR^{3c}$, $-SO_2NHCO_2R^{3c}$, $-CONHSO_2R^{3c}$, $-(CH_2)_rNR^8C(O)R^{3b}$, $-(CH_2)_rNR^8CO_2R^{3c}$, $-(CH_2)_rS(O)_pNR^8R^9$, $-(CH_2)_rNR^8S(O)_pR^{3c}$, $-NHSO_2CF_3$, $-S(O)R^{3c}$, $-S(O)_2R^{3c}$, $-(CH_2)_rOC(O)R^{3b}$, $-(CH_2)_rC(O)NR^8R^9$, $-(CH_2)_rOC(O)NR^8R^9$, $-NHCOCF_3$, $-NHSO_2R^{3c}$, $-CONHOR^{3b}$, $C_{1-4}$ haloalkyl, $C_{1-4}$ haloalkyloxy-, $C_{1-6}$ alkyl substituted by $R^{3e}$, $C_{2-6}$ alkenyl substituted by $R^{3e}$, $C_{1-6}$ alkynyl substituted by $R^{3e}$, $C_{3-6}$ cycloalkyl substituted by 0-1 $R^{3d}$, $-(CH_2)_r-C_{6-10}$ carbocycle substituted by 0-3 $R^{3d}$ or $-(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

alternately, when two $R^{3a}$ groups are substituted on adjacent atoms, they can be taken together with the atoms to which they are attached to form a $C_{3-10}$ carbocycle substituted with 0-2 $R^{3d}$, or a 5- to 10-membered heterocycle comprising: carbon atoms and 1-4 heteroatoms selected from N, O, and $S(O)_p$, wherein said heterocycle is substituted with 0-2 $R^{3d}$;

$R^{3b}$ is, independently at each occurrence, H, $C_{1-6}$ alkyl substituted with 0-2 $R^{3d}$, $C_{2-6}$ alkenyl substituted with 0-2 $R^{3d}$, $C_{2-6}$ alkynyl substituted with 0-2 $R^{3d}$, $-(CH_2)_r-C_{3-10}$ carbocycle substituted with 0-3 $R^{3d}$, or $-(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

$R^{3c}$ is, independently at each occurrence, $C_{1-6}$ alkyl substituted with 0-2 $R^{3d}$, $C_{2-6}$ alkenyl substituted with 0-2 $R^{3d}$, $C_{2-6}$ alkynyl substituted with 0-2 $R^{3d}$, $-(CH_2)_r-C_{3-10}$ carbocycle substituted with 0-3 $R^{3d}$, or $-(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

$R^{3d}$ is, independently at each occurrence, H, =O, F, Cl, Br, CN, $NO_2$, $-(CH_2)_rNR^7R^8$, $-(CH_2)_rOR^a$, $-C(O)R^a$, $-C(O)OR^a$, $-OC(O)R^a$, $-NR^8C(O)R^c$, $-C(O)NR^8R^9$, $-S(O)_2NR^8R^9$, $-NR^7R^8$, $-NR^8S(O)_2NR^8R^9$, $-NR^8S(O)_2R^c$, $-S(O)_pR^c$, $-(CF_2)_rCF_3$, $C_{1-4}$ alkyl substituted with 0-2 $R^e$, $C_{2-6}$ alkenyl substituted with 0-2 $R^e$, $C_{2-6}$ alkynyl substituted with 0-2 $R^e$, $-(CH_2)_r-C_{3-10}$ carbocycle substituted with 0-3 $R^d$, or $-(CH_2)_r$-5- to 10-membered heterocycle comprising: carbon atoms and 1-4 heteroatoms selected from N, O, and $S(O)_p$, wherein said heterocycle is substituted with 0-3 $R^d$;

$R^{3e}$ is, independently at each occurrence, H, $-(CH_2)_rOR^a$, F, =O, CN, $NO_2$, $-(CH_2)_rNR^7R^8$, $-C(O)R^a$, $-C(O)OR^a$, $-OC(O)R^a$, $-NR^8C(O)R^c$, $-C(O)NR^8R^9$, $-S(O)_2NR^8R^9$, $-NR^8S(O)_2NR^8R^9$, $-NR^8S(O)_2R^c$, $-S(O)_pR^c$, $-(CF_2)_rCF_3$, $-(CH_2)_r-C_{3-10}$ carbocycle substituted with 0-3 $R^d$, or $-(CH_2)_r$-5- to 10-membered heterocycle comprising: carbon atoms and 1-4 heteroatoms selected from N, O, and $S(O)_p$, wherein said heterocycle is substituted with 0-3 $R^d$;

$R^4$ is, independently at each occurrence, H, F, Cl, Br, I, $OCF_3$, $CF_3$, CN, $NO_2$, $-(CH_2)_rOR^a$, $-(CH_2)_rSR^a$, $-(CH_2)_rC(O)R^a$, $-(CH_2)_rC(O)OR^a$, $-OC(O)R^a$, $-(CH_2)_rNR^7R^8$, $-NR^8(CH_2)_rC(O)OR^a$, $-(CH_2)_rC(O)NR^8R^9$, $-(CH_2)_rNR^8C(O)R^c$, $-(CH_2)_rNR^8C(O)_2R^b$, $-(CH_2)_rNR^8C(O)NR^8R^9$, $-S(O)_pNR^8R^9$, $-NR^8S(O)_pR^c$, $-S(O)_2R^c$, or $C_{1-4}$ alkyl substituted with 0-2 $R^{4a}$;

$R^{4a}$ is, independently at each occurrence, H, F, =O, $C_{1-6}$ alkyl, $OR^a$, $SR^a$, $CF_3$, CN, $NO_2$, $-C(O)R^a$, $-C(O)OR^a$, $-NR^7R^8$, $-C(O)NR^8R^9$, $-NR^8C(O)R^c$, $-S(O)_pNR^8R^9$, $-NR^8S(O)_pR^c$, $-S(O)R^c$, or $-S(O)_2R^c$;

$R^5$ is, independently at each occurrence, H, F, $CF_3$, $-(CH_2)_rOR^a$, =O, $-(CH_2)_rNR^7R^8$, $-S(O)_pNR^8R^9$, $-(CH_2)_rCO_2R^a$, $-(CH_2)_rCONR^8R^9$, or $C_{1-4}$ alkyl;

$R^6$ is, independently at each occurrence, H, F, or $C_{1-4}$ alkyl;

$R^7$ is, independently at each occurrence, H, $C_{1-6}$ alkyl, $-(CH_2)_n-C_{3-10}$ carbocycle, $-(CH_2)_n$-(5- to 10-membered heteroaryl), $-C(O)R^c$, $-CHO$, $-C(O)_2R^c$, $-S(O)_2R^c$, $-CONR^8R^c$, $-OCONHR^c$, $-C(O)O-(C_{1-4}$ alkyl)OC(O)$-(C_{1-4}$ alkyl), or $-C(O)O-(C_{1-4}$ alkyl)OC(O)$-(C_{6-10}$ aryl); wherein said alkyl, carbocycle, heteroaryl, and aryl are substituted with 0-2 $R^f$; wherein said heteroaryl comprises: carbon atoms and 1-4 heteroatoms selected from N, O, and $S(O)_p$;

$R^8$ is, independently at each occurrence, H, $C_{1-6}$ alkyl, $-(CH_2)_n$-phenyl, or $-(CH_2)_n$-5- to 10-membered heterocycle comprising: carbon atoms and 1-4 heteroatoms selected from N, O, and $S(O)_p$; wherein said alkyl, phenyl and heterocycle are optionally substituted with 0-2 $R^f$;

alternatively, $R^7$ and $R^8$, when attached to the same nitrogen, combine to form a 5- to 10-membered heterocycle comprising: carbon atoms and 0-3 additional heteroatoms selected from N, O, and $S(O)_p$, wherein said heterocycle is substituted with 0-2 $R^f$;

$R^{8a}$ is H or $C_{1-4}$ alkyl;

$R^9$ is, independently at each occurrence, H, $C_{1-6}$ alkyl, or $-(CH_2)_n$-phenyl; wherein said alkyl and phenyl are optionally substituted with 0-2 $R^f$;

alternatively, $R^8$ and $R^9$, when attached to the same nitrogen, combine to form a 5- to 12-membered heterocycle comprising: carbon atoms and 0-2 additional heteroatoms selected from N, O, and $S(O)_p$, wherein said heterocycle is substituted with 0-2 $R^d$;

$R^{10}$ is, independently at each occurrence, H or $C_{1-6}$ alkyl substituted with 0-3 $R^{10a}$;

$R^{10a}$ is, independently at each occurrence, H, =O, $C_{1-4}$ alkyl, $OR^a$, $SR^a$, F, $CF_3$, CN, $NO_2$, $-C(O)R^a$, $-C(O)OR^a$, $-C(O)NR^8R^9$, $-NR^8C(O)R^c$, $-S(O)_pNR^8R^9$, $-NR^8S(O)_pR^c$, or $-S(O)_pR^c$;

$R^{11}$ is $C_{1-4}$ haloalkyl, $-C(O)NR^8R^9$, $-CH_2C(O)NR^8R^9$, $-CH_2CH_2C(O)NR^8R^9$, $-C(O)R^a$, $-CH_2C(O)R^a$, $-CH_2CH_2C(O)R^a$, $-C(O)OR^a$, $-CH_2C(O)OR^a$, $-CH_2CH_2C(O)OR^a$, $C_{1-6}$ alkyl substituted with 0-3 $R^{11c}$, $C_{2-6}$ alkenyl substituted with 0-3 $R^{11a}$, $C_{2-6}$ alkynyl substituted with 0-3 $R^{11a}$, —$(CR^{14}R^{15})_r$—$C_{3-10}$ carbocycle substituted with 0-3 $R^{11b}$, or —$(CR^{14}R^{15})_r$-5- to 10-membered heterocycle comprising: carbon atoms and 1-4 heteroatoms selected from N, O, and S(O)$_p$, wherein said heterocycle is substituted with 0-3 $R^{11b}$;

$R^{11a}$ is, independently at each occurrence H, =O, OR$^a$, SR$^a$, F, CF$_3$, CN, NO$_2$, —C(O)R$^a$, —C(O)OR$^a$, —NR$^7$R$^8$, —C(O)NR$^8$R$^9$, —NR$^8$C(O)R$^c$, —S(O)$_p$NR$^8$R$^9$, —NR$^8$S(O)$_p$R$^c$, —S(O)$_p$R$^c$, C$_{1-4}$ alkyl, C$_{3-6}$ cycloalkyl, C$_{1-4}$ haloalkyl, C$_{1-4}$ haloalkyloxy-, —(CH$_2$)$_r$—C$_{3-10}$ carbocycle substituted with 0-3 $R^d$, or —(CH$_2$)$_r$-5- to 10-membered heterocycle comprising carbon atoms and 1-4 heteroatoms selected from N, O, and S(O)$_p$, and substituted with 0-3 $R^d$;

$R^{11b}$ is, independently at each occurrence, H, =O, =NR$^8$, OR$^a$, —CH$_2$OR$^a$, F, Cl, Br, CN, NO$_2$, CF$_3$, OCF$_3$, OCHF$_2$, —C(CH$_3$)$_2$OR$^a$, —C(O)R$^a$, —C(O)OR$^a$, —NR$^7$R$^8$, —C(O)NR$^8$R$^9$, —NR$^7$C(O)R$^b$, —NR$^8$C(O)$_2$R$^c$, —S(O)$_p$NR$^8$R$^9$, —NR$^8$S(O)$_p$R$^c$, —S(O)$_p$R$^c$, C$_{1-6}$ alkyl, C$_{2-6}$ alkenyl, C$_{2-6}$ alkynyl, C$_{3-6}$ cycloalkyl, C$_{1-4}$ haloalkyl, C$_{1-4}$ haloalkyloxy-, —(CH$_2$)$_r$—C$_{3-10}$ carbocycle substituted with 0-3 $R^d$, or —(CH$_2$)$_r$-5- to 10-membered heterocycle comprising carbon atoms and 1-4 heteroatoms selected from N, O, and S(O)$_p$, and substituted with 0-3 $R^d$;

alternately, when two $R^{11b}$ groups are substituents on adjacent atoms they may be taken together with the atoms to which they are attached to form a 5- to 7-membered heterocycle comprising carbon atoms and 1-4 heteroatoms selected from N, O, and S(O)$_p$ and substituted with 0-2 $R^g$;

$R^{11c}$ is, independently at each occurrence H, =O, OR$^a$, SR$^a$, F, CF$_3$, CN, NO$_2$, —NR$^7$R$^8$, —NR$^8$C(O)R$^c$, —NR$^8$C(O)OR$^c$, —NR$^8$CHO, —S(O)$_p$NR$^8$R$^9$, —NR$^8$S(O)$_p$R$^c$, —S(O)$_p$R$^c$, C$_{1-4}$ alkyl, C$_{3-6}$ cycloalkyl, C$_{1-4}$ haloalkyl, C$_{1-4}$ haloalkyloxy-, —(CH$_2$)$_r$—C$_{3-10}$ carbocycle substituted with 0-3 $R^d$, or —(CH$_2$)$_r$-5- to 10-membered heterocycle comprising carbon atoms and 1-4 heteroatoms selected from N, O, and S(O)$_p$, and substituted with 0-3 $R^d$;

$R^{14}$ and $R^{15}$ are, independently at each occurrence, H, F, or C$_{1-4}$ alkyl;

$R^a$ is, independently at each occurrence, H, CF$_3$, C$_{1-6}$ alkyl, —(CH$_2$)$_r$—C$_{3-7}$ cycloalkyl, —(CH$_2$)$_r$—C$_{6-10}$ aryl, or —(CH$_2$)$_r$-5- to 10-membered heterocycle comprising carbon atoms and 1-4 heteroatoms selected from N, O, and S(O)$_p$, wherein said cycloalkyl, aryl or heterocycle groups are optionally substituted with 0-2 $R^f$;

$R^b$ is, independently at each occurrence, CF$_3$, OH, C$_{1-4}$ alkoxy, C$_{1-6}$ alkyl, —(CH$_2$)$_r$—C$_{3-10}$ carbocycle substituted with 0-2 $R^d$, or —(CH$_2$)$_r$-5- to 10-membered heterocycle comprising: carbon atoms and 1-4 heteroatoms selected from N, O, and S(O)$_p$ and substituted with 0-3 $R^d$;

$R^c$ is, independently at each occurrence, CF$_3$, C$_{1-6}$ alkyl substituted with 0-2 $R^f$, C$_{3-6}$ cycloalkyl substituted with 0-2 $R^f$, C$_{6-10}$ aryl, 5- to 10-membered heteroaryl, (C$_{6-10}$ aryl)-C$_{1-4}$ alkyl, or (5- to 10-membered heteroaryl)-C$_{1-4}$ alkyl, wherein said aryl is substituted with 0-3 $R^f$ and said heteroaryl comprises: carbon atoms and 1-4 heteroatoms selected from N, O, and S(O)$_p$ and substituted with 0-3 $R^f$;

$R^d$ is, independently at each occurrence, H, =O, =NR$^8$, OR$^a$, F, Cl, Br, I, CN, NO$_2$, —NR$^7$R$^8$, —C(O)R$^a$, —C(O)OR$^a$, —OC(O)R$^a$, —NR$^8$C(O)R$^c$, —C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl substituted with 0-2 $R^e$, C$_{2-6}$ alkenyl substituted with 0-2 $R^e$, or C$_{2-6}$ alkynyl substituted with 0-2 $R^e$;

$R^e$ is, independently at each occurrence, =O, OR$^a$, F, Cl, Br, I, CN, NO$_2$, —NR$^7$R$^8$, —C(O)R$^a$, —C(O)OR$^a$, —NR$^8$C(O)R$^c$, —C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

$R^f$ is, independently at each occurrence, H, =O, —(CH$_2$)$_r$OR$^g$, F, Cl, Br, I, CN, NO$_2$, —NR$^g$R$^g$, —C(O)R$^g$, —C(O)OR$^g$, —NR$^g$C(O)R$^g$, —C(O)NR$^g$R$^g$, —SO$_2$NR$^g$R$^g$, —NR$^g$SO$_2$NR$^g$R$^g$, —NR$^g$SO$_2$—C$_{1-4}$ alkyl, —NR$^g$SO$_2$CF$_3$, —NR$^g$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, C$_{2-6}$ alkynyl, —(CH$_2$)$_n$-phenyl, or —(CH$_2$)$_n$-5- to 10-membered heterocycle comprising carbon atoms and 1-4 heteroatoms selected from N, O, and S(O)$_p$;

$R^g$ is, independently at each occurrence, H, C$_{1-6}$ alkyl, or —(CH$_2$)$_n$-phenyl;

n, at each occurrence, is selected from 0, 1, 2, 3, and 4;
p, at each occurrence, is selected from 0, 1, and 2; and
r, at each occurrence, is selected from 0, 1, 2, 3, and 4;
provided that:
when M is a 5-membered heterocycle, L is —CHR$^6$CR$^5$R$^6$CONH—, R$^6$ is H or C$_{1-6}$ alkyl, then R$^5$ is other than NR$^7$R$^8$;
when M is an imidazole ring, L is —C(R$^5$R$^6$)NHCONH— or —CH$_2$OC(O)NH—, and R$^3$ is unsubstituted phenyl, then R$^{11}$ is other than —CH$_2$-(3-indolyl); or
when M is an imidazole ring, L-CR$^5$=CR$^6$C(O)NR$^{10}$—, A is halogen substituted phenyl, and R$^3$ is phenyl or pyridyl substituted with morpholyl which is optionally substituted, then R$^{11}$ is other than —CH$_2$—(pyridyl).

In another embodiment the present invention provides a compound wherein: L is —CH$_2$CH$_2$C(O)NR$^{10}$—, —CH(NR$^7$R$^8$)CH$_2$C(O)NH—, —CH=CHC(O)NH—, —C(R$^5$)=CHCONH—, —C≡CCONH—, —OCH$_2$C(O)NH—, —CR$^5$R$^6$NHC(O)NH—, —CH$_2$OC(O)NH—, —SCH$_2$C(O)NH—, —SO$_2$CH$_2$C(O)NH—, —CH$_2$NHC(O)NH—, or —NHNHCONH—.

In another embodiment the present invention provides a compound wherein: L is —CH$_2$CH$_2$C(O)NH—, —CH(NR$^7$R$^8$)CH$_2$CONH—, —CH=CHC(O)NH—, —C(Me)=CHCONH—, —C≡CCONH—, —OCH$_2$C(O)NH—, —SCH$_2$C(O)NH—, —SO$_2$CH$_2$CONH—, —C(R$^5$R$^6$)NHCONH—, —CH$_2$OCONH—, or —NHNHCONH—.

In another embodiment the present invention provides a compound wherein: L is —CH$_2$CH$_2$CONH—, —CH(NH$_2$)CH$_2$CONH—, —CH(NHCOMe)CH$_2$CONH—, —CH(NHCOEt)CH$_2$CONH—, —CH(NHCO$_2$(t-Bu))CH$_2$CONH—, —CH=CHCONH—, —C(Me)=CHCONH—, —C≡CCONH—, —CH$_2$NHCONH—, —CH(CH$_2$CO$_2$H)NHCONH—, —CH$_2$OCONH—, —NHNHCONH—, —SCH$_2$CONH—, —SO$_2$CH$_2$CONH— or —OCH$_2$CONH—.

In another embodiment the present invention provides a compound wherein: L is —CH$_2$CH$_2$CONH—, —CH=CHCONH—, —C(Me)=CHCONH—, —C≡CCONH—, —CH$_2$NHCONH—, —CH$_2$OCONH—, —NHNHCONH—, or —SCH$_2$CONH—.

In another embodiment the present invention provides a compound wherein: L is —CH$_2$CH$_2$CONH—, —CH=CHCONH—, —C(Me)=CHCONH—, —C≡CCONH—, or —CH$_2$NHCONH—.

In another embodiment the present invention provides a compound wherein: L is —CH$_2$CH$_2$CONH— or —CH$_2$NHCONH—.

In another embodiment the present invention provides a compound wherein: L is —CH$_2$CH$_2$CONH—.

In another embodiment the present invention provides a compound wherein: L is —CH$_2$NHCONH—.

In another embodiment the present invention provides a compound wherein: L is —CH═CHCONH— or —C(Me)═CHCONH—.

In another embodiment the present invention provides a compound wherein: L is —C≡CCONH—.

In another embodiment the present invention provides a pharmaceutical composition comprising a pharmaceutically acceptable carrier and at least one of the compounds of the present invention or a stereoisomer, tautomer, pharmaceutically acceptable salt, solvate, or prodrug thereof.

In another embodiment, the present invention provides a pharmaceutical composition, comprising: a pharmaceutically acceptable carrier and a therapeutically effective amount of at least one of the compounds of the present invention or a stereoisomer, tautomer, pharmaceutically acceptable salt, solvate or prodrug thereof.

In another embodiment, the present invention provides a novel process for making a compound of the present invention or a stereoisomer, tautomer, pharmaceutically acceptable salt, solvate or prodrug thereof.

In another embodiment, the present invention provides a novel intermediate for making a compound of the present invention or a stereoisomer, tautomer, pharmaceutically acceptable salt, solvate or prodrug thereof.

In another embodiment, the present invention provides a pharmaceutical composition further comprising additional therapeutic agent(s) selected from potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In a preferred embodiment, the present invention provides a pharmaceutical composition wherein the additional therapeutic agent is an antihypertensive agent selected from ACE inhibitors, AT-1 receptor antagonists, beta-adrenergic receptor antagonists, ETA receptor antagonists, dual ETA/AT-1 receptor antagonists, and vasopepsidase inhibitors, an antiarrythmic agent selected from IKur inhibitors, an anticoagulant selected from thrombin inhibitors, antithrombin-III activators, heparin co-factor II activators, other factor XIa inhibitors, other kallikrein inhibitors, plasminogen activator inhibitor (PAI-1) antagonists, thrombin activatable fibrinolysis inhibitor (TAFI) inhibitors, factor VIIa inhibitors, factor IXa inhibitors, and factor Xa inhibitors, or an antiplatelet agent selected from GPIIb/IIIa blockers, protease activated receptor (PAR-1) antagonists, phosphodiesterase-III inhibitors, $P2Y_1$ receptor antagonists, $P2Y_{12}$ antagonists, thromboxane receptor antagonists, cyclooxygense-1 inhibitors, and aspirin, or a combination thereof.

In a preferred embodiment, the present invention provides pharmaceutical composition, wherein the additional therapeutic agent(s) are an anti-platelet agent or a combination thereof.

In a preferred embodiment, the present invention provides a pharmaceutical composition, wherein the additional therapeutic agent is the anti-platelet agent clopidogrel.

In another embodiment the present invention provides a method for modulation of the coagulation cascade and/or contact activation system comprising administering to a patient in need of such treatment a therapeutically effective amount of at least one of the compounds of the present invention or a stereoisomer, tautomer, pharmaceutically acceptable salt, solvate or prodrug thereof.

In another embodiment, the present invention provides a novel method for treating thrombotic or thromboembolic disorders comprising: administering to a patient in need of such treatment a therapeutically effective amount of at least one of the compounds of the present invention or a stereoisomer, tautomer, pharmaceutically acceptable salt, solvate or prodrug thereof.

In another embodiment, the present invention provides a novel method, wherein the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

In another embodiment, the present invention provides a novel method, wherein the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a method for treating inflammatory disorders comprising: administering to a patient in need of such treatment a therapeutically effective amount of at least one of the compounds of the present invention or a stereoisomer, tautomer, pharmaceutically acceptable salt, solvate or prodrug thereof.

In another embodiment, the present invention provides a method, wherein the inflammatory disorder is selected from the group consisting of sepsis, acute respiratory distress syndrome, and systemic inflammatory response syndrome.

In another embodiment, the present invention provides a novel method of treating a patient in need of thromboembolic disorder treatment, comprising: administering a compound of the present invention or a stereoisomer, tautomer, pharmaceutically acceptable salt, solvate, or prodrug form thereof in an amount effective to treat a thrombotic or thromboembolic disorder.

In another embodiment, the present invention provides a method of treating a patient in need of inflammatory disorder treatment, comprising: administering a compound of the present invention or a stereoisomer, tautomer, pharmaceutically acceptable salt, solvate, or prodrug form thereof in an amount effective to treat an inflammatory disorder.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used for the treatment of a thromboembolic and/or inflammatory disorder.

In another preferred embodiment, the present invention provides a novel article of manufacture, further comprising: (d) a second container; wherein components (a) and (b) are located within the second container and component (c) is located within or outside of the second container.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used in combination with a second therapeutic agent to treat a thromboembolic and/or inflammatory disorder.

In another preferred embodiment, the present invention provides a novel article of manufacture, further comprising: (d) a second container; wherein components (a) and (b) are located within the second container and component (c) is located within or outside of the second container.

In another embodiment, the present invention provides a novel method, comprising: administering a compound of the present invention or a stereoisomer, tautomer, pharmaceutically acceptable salt, solvate, or prodrug form thereof in an amount effective to treat a thromboembolic and/or inflammatory disorder.

In another embodiment, the present invention provides a compound of the present invention for use in therapy.

In another embodiment, the present invention provides a compound of the present invention for use in therapy for treating a thromboembolic and/or inflammatory disorder.

In another embodiment, the present invention also provides the use of a compound of the present invention for the manufacture of a medicament for the treatment of a thromboembolic and/or inflammatory disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

Definitions

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention. The inventive compounds may be in the free or hydrate form.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g. n-pentyl, isopentyl, neopentyl), and the like.

Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

The term "alkoxy" or "alkyloxy" refers to an —O-alkyl group. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy, and the like. Similarly, "alkylthio" or "thioalkoxy" represents an alkyl group as defined above with the indicated number of carbon atoms attached through a sulphur bridge; for example methyl-S—, ethyl-S—, and the like.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

"Aryl" groups refer to monocyclic or polycyclic aromatic hydrocarbons, including, for example, phenyl, naphthyl, phenanthranyl, and the like. Aryl moieties are well known and described, for example, in *Hawley's Condensed Chemical Dictionary* (13 ed.), R. J. Lewis, ed., J. Wiley & Sons, Inc., New York (1997). Unless otherwise specified, "aryl", "$C_{6-10}$ aryl" or "aromatic residue" may be unsubstituted or substituted with 0 to 3 groups selected from H, OH, $OCH_3$, Cl, F, Br, I, CN, $NO_2$, $NH_2$, $N(CH_3)H$, $N(CH_3)_2$, $CF_3$, $OCF_3$, C(=O) $CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle" or "heterocyclic group" is intended to mean a stable 5, 6, or 7-membered monocyclic or bicyclic or 7, 8, 9, 10, 11, 12, 13, or 14-membered bicyclic heterocyclic ring which is saturated, partially unsaturated or fully unsaturated, and which consists of carbon atoms and 1, 2, 3 or 4 heteroatoms independently selected from N, O and S; and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, benzodioxane, and the like. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and S(O)$_p$). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a small, negatively charged species such as chloride, bromide, hydroxide, acetate, sulfate, and the like.

As referred to herein, the term "substituted" means that one or more hydrogen atoms is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative. In cases wherein there are quaternary carbon atoms on compounds of the present invention, these can be replaced by silicon atoms, provided they do not form Si—N or Si—O bond.

When any variable occurs more than one time in any constituent or formula for a compound, its definition at each occurrence is independent of its definition at every other occurrence. Thus, for example, if a group is shown to be substituted with 0-3 $R^{3a}$, then said group may optionally be substituted with up to three $R^{3a}$ groups and $R^{3a}$ at each occurrence is selected independently from the definition of $R^{3a}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, edited by H. Bundgaard, (Elsevier, 1985), and *Methods in Enzymology*, Vol. 42, at pp. 309-396, edited by K. Widder, et. al. (Academic Press, 1985);

b) *A Textbook of Drug Design and Development*, edited by Krosgaard-Larsen and H. Bundgaard, Chapter 5, "Design and Application of Prodrugs," by H. Bundgaard, at pp. 113-191 (1991);

c) H. Bundgaard, *Advanced Drug Delivery Reviews*, Vol. 8, p. 1-38 (1992);

d) H. Bundgaard, et al., *Journal of Pharmaceutical Sciences*, Vol. 77, p. 285 (1988); and e) N. Kakeya, et. al., *Chem Phar Bull.*, Vol. 32, p. 692 (1984).

Compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Preparation of Prodrugs is Well Known in the Art and Described in, for example, *Medicinal Chemistry: Principles and Practice*, ed. F. D. King, The Royal Society of Chemistry, Cambridge, UK, 1994, which is incorporated herein by reference in its entirety.

Isotopically labeled compounds of the present invention, i.e., wherein one or more of the atoms described are replaced by an isotope of that atom (e.g., C replaced by $^{13}$C or by $^{14}$C; and isotopes of hydrogen include tritium and deuterium), are also provided herein. Such compounds have a variety of potential uses, e.g., as standards and reagents in determining the ability of a potential pharmaceutical to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 98%, preferably 99%, compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates and the like. Methods of salvation are generally known in the art.

As used herein, the term "patient" encompasses all mammalian species.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor XIa and/or plasma kallikrein or to treat the disorders listed herein. When applied to a combination, the term refers to combined amounts of the active ingredients that result in the therapeutic effect, whether administered in combination, serially or simultaneously. The combination of compounds is preferably a synergistic combination. Synergy, as described, for example, by Chou and Talalay, *Adv. Enzyme Regul.* 1984, 22:27-55, occurs when the effect (in this case, prevention of thrombosis) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic and/or anti-inflammatory effect, or some other beneficial effect of the combination compared with the individual components.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th ed., 1990, which is incorporated herein by reference in its entirety.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LC-MS" for liquid chromatography mass spectrometry, "HPLC" for high pressure liquid chromatography, "RP HPLC" for reverse phase HPLC, "TLC" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "tlc" for thin layer chromatography. "α", "β", "R", "S", "E", and "Z" are stereochemical designations familiar to one skilled in the art.

| | |
|---|---|
| Me | methyl |
| Et | ethyl |
| Pr | propyl |
| i-Pr | isopropyl |
| Bu | butyl |
| i-Bu | isobutyl |
| t-Bu | tert-butyl |
| Ph | phenyl |
| Bn | benzyl |
| AcOH | acetic acid |
| MeOH | methanol |
| EtOH | ethanol |
| EtOAc | ethyl acetate |
| Et$_2$O | diethyl ether |
| i-PrOH or IPA | isopropanol |
| HOAc | acetic acid |
| BEMP | 2-t-butylimino-2-diethylamino-1,3-dimethyl-perhydro-1,3,2-diazaphosphorine |
| BOP reagent | benzotriazol-1-yloxytris(dimethyl-amino)phosphonium hexafluorophosphate |
| BBr$_3$ | boron tribromide |
| BINAP | rac-2,2'-Bis(diphenylphosphino)-1,1'-binaphthyl |
| Boc | tert-butyloxycarbonyl |
| 2MeS-ADP | 2 methylthio adenosine diphosphate |
| cDNA | complimentary DNA |
| CH$_2$Cl$_2$ | dichloromethane |
| CH$_3$CN | acetonitrile |
| Cs$_2$CO$_3$ | cesium carbonate |
| ACN | acetonitrile |
| CDI | 1,1'-carbonyldiimidazole |
| DABCO | 1,4-diazabicyclo[2.2.2]octane |
| DBAD | di-tert-butylazodicarboxylate |
| DBU | 1,8-diazabicyclo[5.4.0]undec-7-ene |
| DCE | 1,2 dichloroethane |
| DCM | dichloromethane |
| DCC | dicyclohexylcarbodiimide |
| DEAD | diethylazodicarboxyalte |
| DIBAL-H | diisobutylaluminum hydride |
| DIC or DIPCDI | diisopropylcarbodiimide |
| DIEA or DIPEA | N,N,-diisopropylethylamine |
| DMEM | Dulbecco's modified Eagle media |
| DME | 1,2-dimethoxyethane |
| DMF | dimethyl formamide |
| DMSO | dimethyl sulfoxide |
| DPPA | diphenyl phosphoryl azide |
| EDC (or EDC.HCl) or EDCI (or EDCI.HCl) or EDAC | 3-ethyl-3'-(dimethylamino)propyl-carbodiimide hydrochloride (or 1-(3-dimethylaminopropyl)-3-ethylcarbodiimide hydrochloride) |
| EDTA | ethylenediaminetetraacetic acid |
| FBS | Fetal Bovine Serum |
| HATU | O-(7-azabenzotriazol-1-yl)-N,N,N',N'-tetramethyluronium hexafluorophosphate |
| HCl | hydrochloric acid |
| HEPES | 4-(2-hydroxyethyl)piperaxine-1-ethanesulfonic acid |
| Hex | hexane |
| HOBt or HOBT | 1-hydroxybenzotriazole monohydrate |
| Hunig's base | N,N-diisopropylethyl amine |
| LAH | lithium aluminum hydride |
| LDA | Lithium diisopropylamide |
| LiHMDS | Lithium bis(trimethylsilyl) amide |
| mCPBA or m-CPBA | meta-chloroperbenzoic acid |
| NBS | N-bromosuccinimide |
| NCS | N-chlorosuccinimide |
| D-PBS | Dulbecco's Phosphate Buffered Saline |
| Pd/C | palladium on carbon |
| PCy$_3$ | tricyclohexyl phosphine |
| PPA | polyphosphoric acid |
| PPTS | pyridinium p-toluenesulfonate |
| PS | polystyrene |
| PXPd2 | bis[di-tert-butyl phosphinous chloride-kP]di-m-chlorodichlorodipalladium |
| PyBOP | (benzotriazol-1-yloxy)tripyrrolidinophosphonium hexafluorophosphate |
| SCX | Strong Cation Exchanger |
| SEM-Cl | 2-(trimethylsilyl)ethoxymethyl chloride |
| TEA | triethylamine |
| TFA | trifluoroacetic acid |
| THF | tetrahydrofuran |
| TMSBr | trimethylsilyl bromide |
| TRIS | tris (hydroxymethyl) aminomethane |
| KOAc | potassium acetate |
| K$_3$PO$_4$ | potassium phosphate |
| MgSO$_4$ | magnesium sulfate |
| NaCl | sodium chloride |
| NaH | sodium hydride |
| NaHCO$_3$ | sodium bicarbonate |
| NaOH | sodium hydroxide |
| Na$_2$SO$_3$ | sodium sulfite |
| Na$_2$SO$_4$ | sodium sulfate |
| NH$_3$ | ammonia |
| NH$_4$Cl | ammonium chloride |
| NH$_4$OH | ammonium hydroxide |
| OTs | tosylate, para-toluenesulfonate |
| PBr$_3$ | phosphorous tribromide |
| Pd$_2$(dba)$_3$ | tris(dibenzylideneacetone)dipalladium (0) |
| Pd(dppf)Cl$_2$•CH$_2$Cl$_2$ | [1,1'-bis(diphenylphosphino)ferrocene] dichloropalladium(II), complex with dichloromethane |
| Pd(Ph$_3$P)$_4$ | tetrakis(triphenylphosphine) palladium (0) |
| (Ph$_3$P)$_2$PdCl$_2$ | bis(triphenylphosphine)palladium dichloride |
| (S,S)-EtDuPhosRh(I) | (+)-1,2-bis((2S,5S)-2,5-diethyl-phospholano)benzene (cyclooctadiene)rhodium (I) trifluoromethanesulfonate |

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley-Interscience, 3$^{rd}$ Edition, 1999).

All references cited herein are hereby incorporated in their entirety herein by reference.

Compounds of this invention wherein L is —CH$_2$NHC(O)NH— can be prepared as outlined in Scheme 1. Condensation of an appropriately functionalized amine intermediate 1a with a suitably substituted benzylisocyanate 1b in a solvent such as tetrahydrofuran or methylene chloride in the presence of a base such as triethylamine, diisopropylethylamine or potassium carbonate provides ureas of formula 1c. Alternatively, ureas of formula 1c of this invention can be prepared by condensation of an amine intermediate 1a with carbonyl diimidazole in a solvent such as tetrahydrofuran or N,N-dimethylformamide followed by treatment in situ with an suitably substituted benzyl amine 1d. Urea linked compounds of this invention of formula 1c can also be prepared by condensation of amine intermediate 1a with p-nitrophenylchloroformate in the presence of a suitable base such as triethylamine, followed by treatment of the resulting p-nitrophenylcarbamate with an appropriate substituted amine 1d.

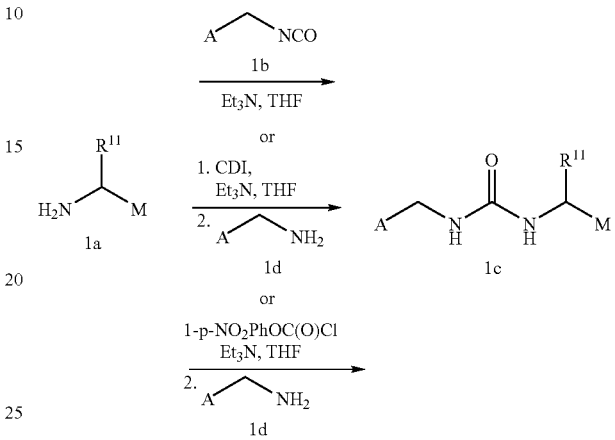

Scheme 1

Isocyanates of formula 1b used in Scheme 1 above are either commercially available or can be readily prepared from the corresponding amines 1d by treatment with phosgene or by various other methods known in the art (see for example, H. Eckert & B. Forster, *Angew. Chem. Int. Ed.* 1987, 26, 894; H. Knolker & T. Braxmeier, *Synlett,* 1997, 925; S. Porwanski et al. *Tetrahedron Lett.* 2004, 45, 5027). Amines of formula 1d are also available commercially or can be prepared by those knowledgeable in the art from a variety of easily accessible starting materials such as nitriles, aldehydes, alcohols, halides, acids and esters by methods including, but not limited to those outlined in Scheme 2.

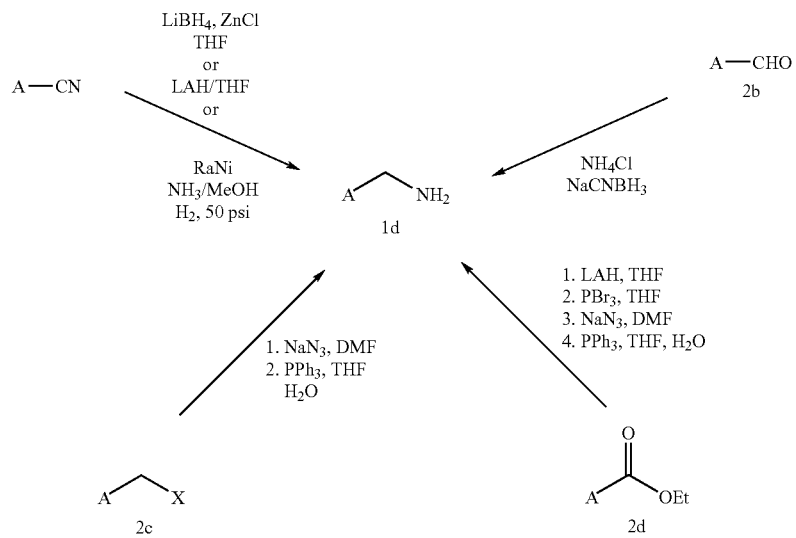

Scheme 2

Compounds of this invention wherein L is —NHNHC(O)NH— of formula 3c can be synthesized similarly as outlined in Scheme 3 by treatment of a suitably functionalized amine intermediate 1a with p-nitrochloroformate as described above followed by treatment of the resulting p-nitrophenylcarbamate 3a with a suitably substituted hydrazine of formula 3b.

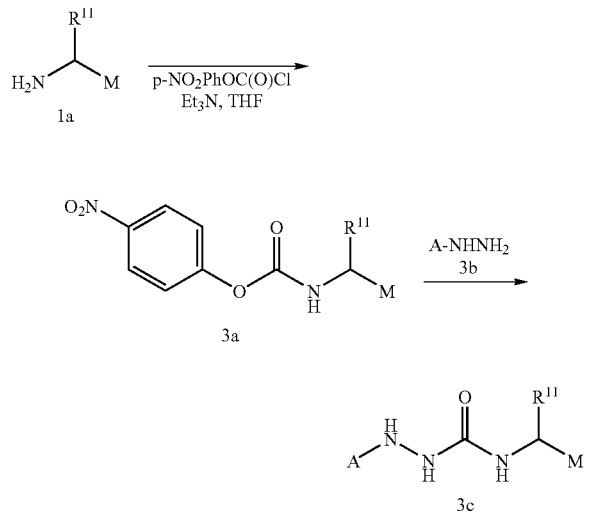

Scheme 3

Hydrazine reagents of formula 3b used to prepare compounds of this invention in Scheme 3 are commercially available or can be prepared by those knowledgeable in the art of organic synthesis by other methods. For example, when A is an aryl or heteroaryl group, the requisite hydrazine reagent is readily available via diazotization of a starting aryl or heteroarylamine 4a followed by reduction of the resulting diazonium salt with tin chloride to the corresponding arylhydrazine 4b as illustrated in Scheme 4.

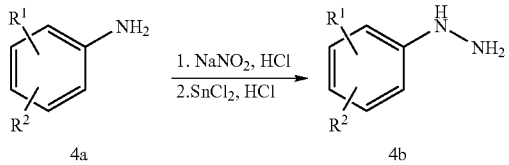

Scheme 4

Compounds of this invention wherein L is —(CH$_2$)$_2$CONH—, —CH=CHCONH—, —C≡CCONH—, —OCH$_2$CONH—, or —SCH$_2$CONH—, can be obtained by the condensation of the amine intermediate 1a shown in Scheme 1 with appropriately substituted carboxylic acid chlorides, mixed carboxylic acid anhydrides or carboxylic acids using standard amide bond forming conditions known to one skilled in the art. Reagent combinations which may be employed for the coupling of amines of formula 1a with suitably substituted carboxylic acids include, but are not limited to: BOP-reagent and triethylamine, EDCI, HOBt, and N-methylmorpholine, or HATU and Hunig's base (DIPEA). Solvents suitable for this transformation include, but are not limited to tetrahydrofuran and dimethylformamide. Coupling of amines of formula 1a with suitably substituted carboxylic acid chlorides or mixed anhydrides can be carried out in solvents such as methylene chloride or tetrahydrofuran in the presence of a base such as triethylamine, N,N-dimethyaminopyridine (DMAP) or potassium carbonate. Suitably substituted carboxylic acids (A-(CH$_2$)$_2$CO$_2$H) 5a are either commercially available, or they can be prepared from the corresponding bromides, alcohols, aldehydes, or esters as shown in Scheme 5 using methods known to one skilled in the art.

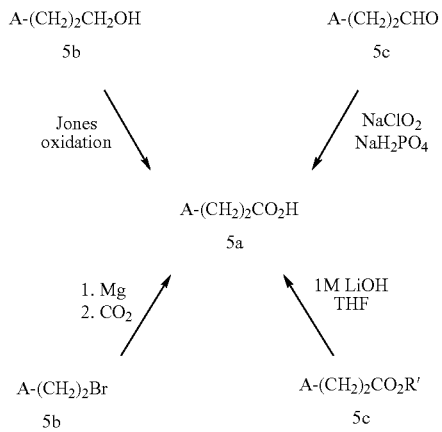

Scheme 5

Additional carboxylic acid intermediates of formulae 6a, 6b, 6c, and 6d useful for preparation of amide compounds of this invention can be prepared as outlined in Schemes 6 and 6A.

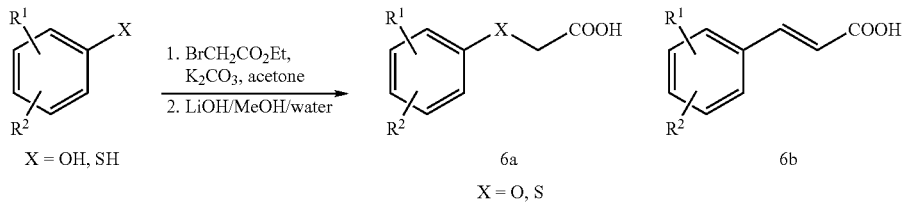

Scheme 6

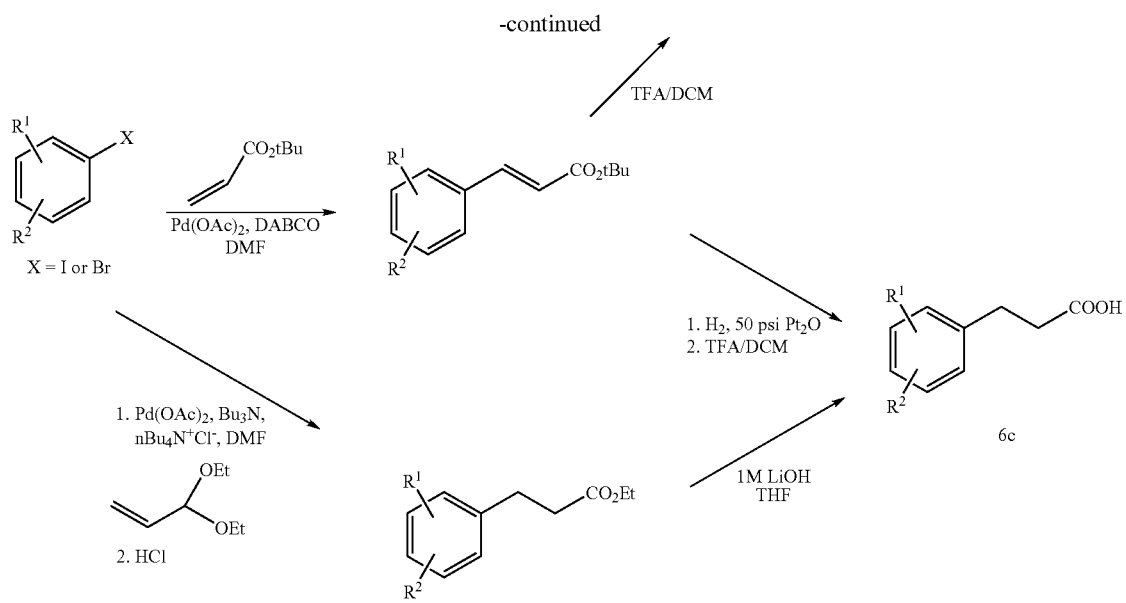

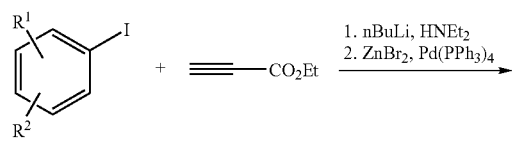

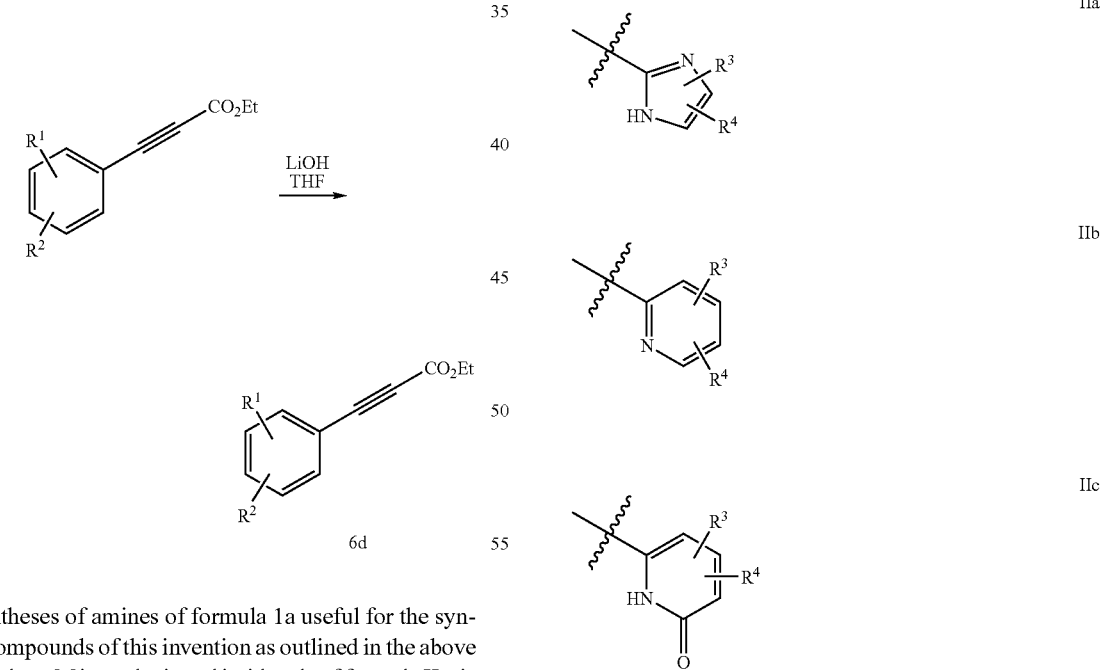

The syntheses of amines of formula 1a useful for the synthesis of compounds of this invention as outlined in the above schemes, where M is a substituted imidazole of formula IIa, is described in US patent application, 2005/282805 published Dec. 22, 2005, which is incorporated in its entirety herein by reference. Additional amines of formula 1a where in M is a substituted pyridine or pyridone of formula IIb or IIc are prepared as described in PCT patent application WO2005/123680, published Dec. 29, 2005, which is incorporated in its entirety herein by reference. Other pyridine regioisomers of IIb, along with pyrimidine analogs, can be prepared according to U.S. Provisional Application No. 60/750,416, filed Dec. 14, 2005, which is incorporated in its entirety herein by reference.

The synthesis of some representative examples of compounds of this invention are depicted in Schemes 7-10A. Substitution of other N-protected amino acids in place of Boc-Phe or Boc-Asp(OBn)-OH in Schemes 7, and 8-10A below will provide additional compounds of this invention.

Scheme 7
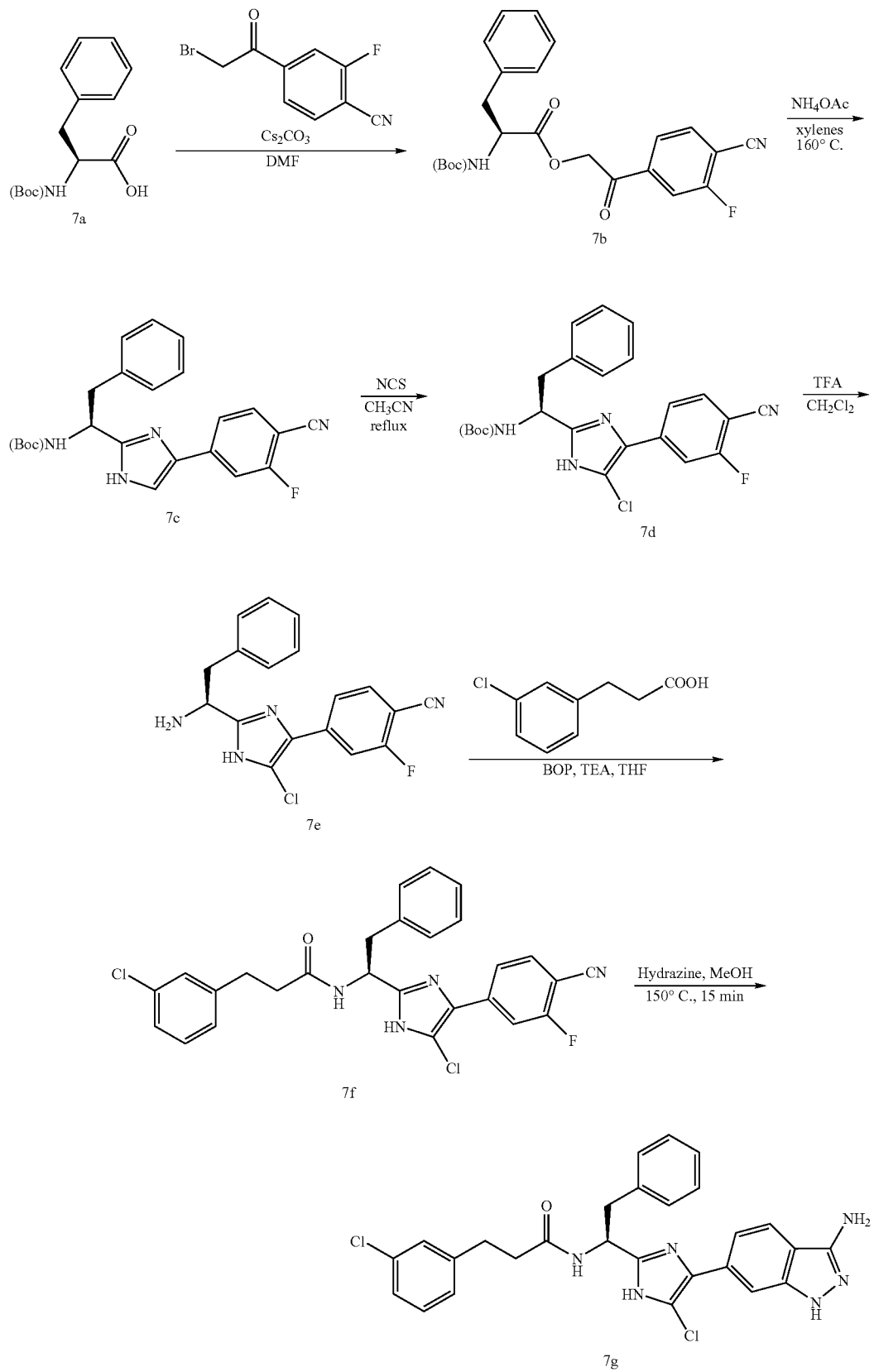

Scheme 8
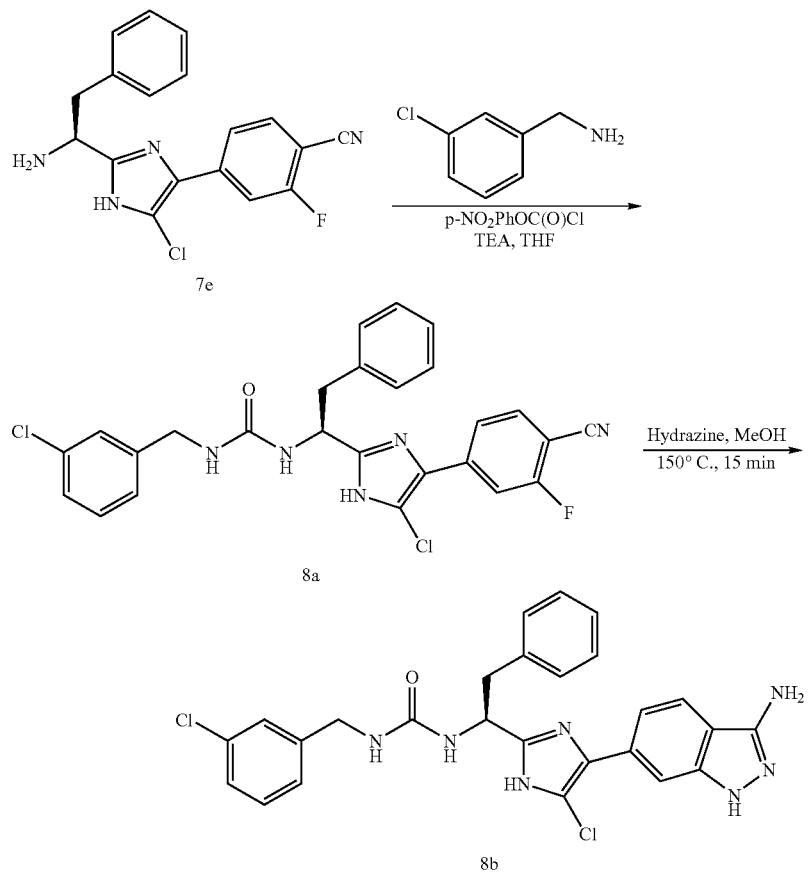
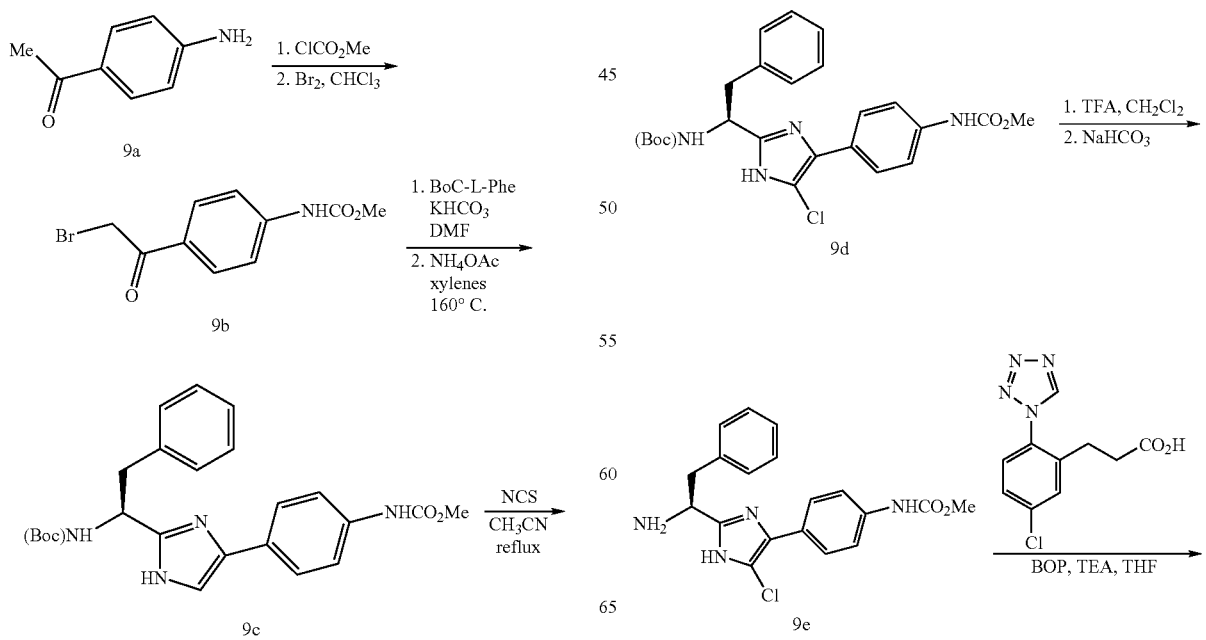

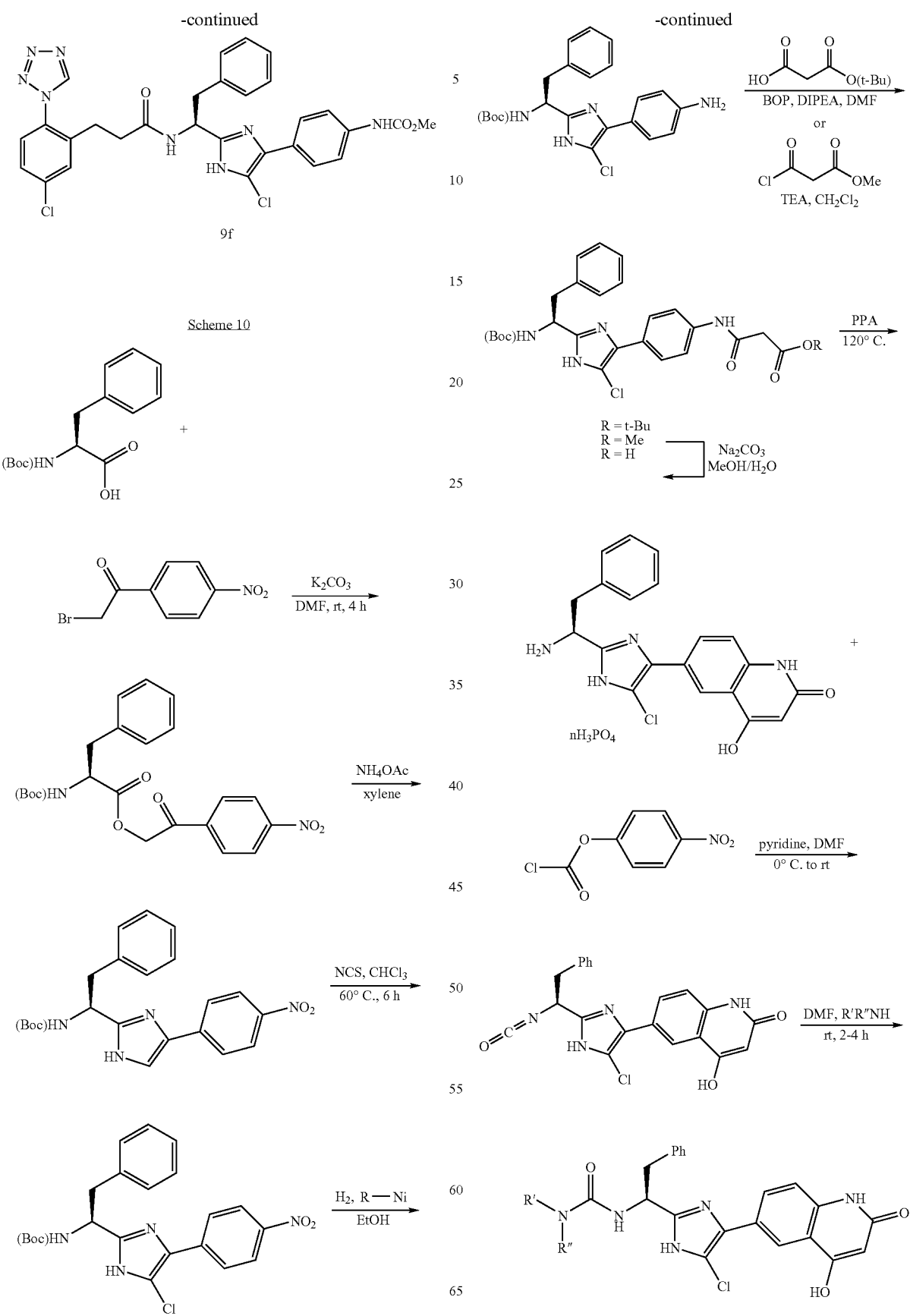

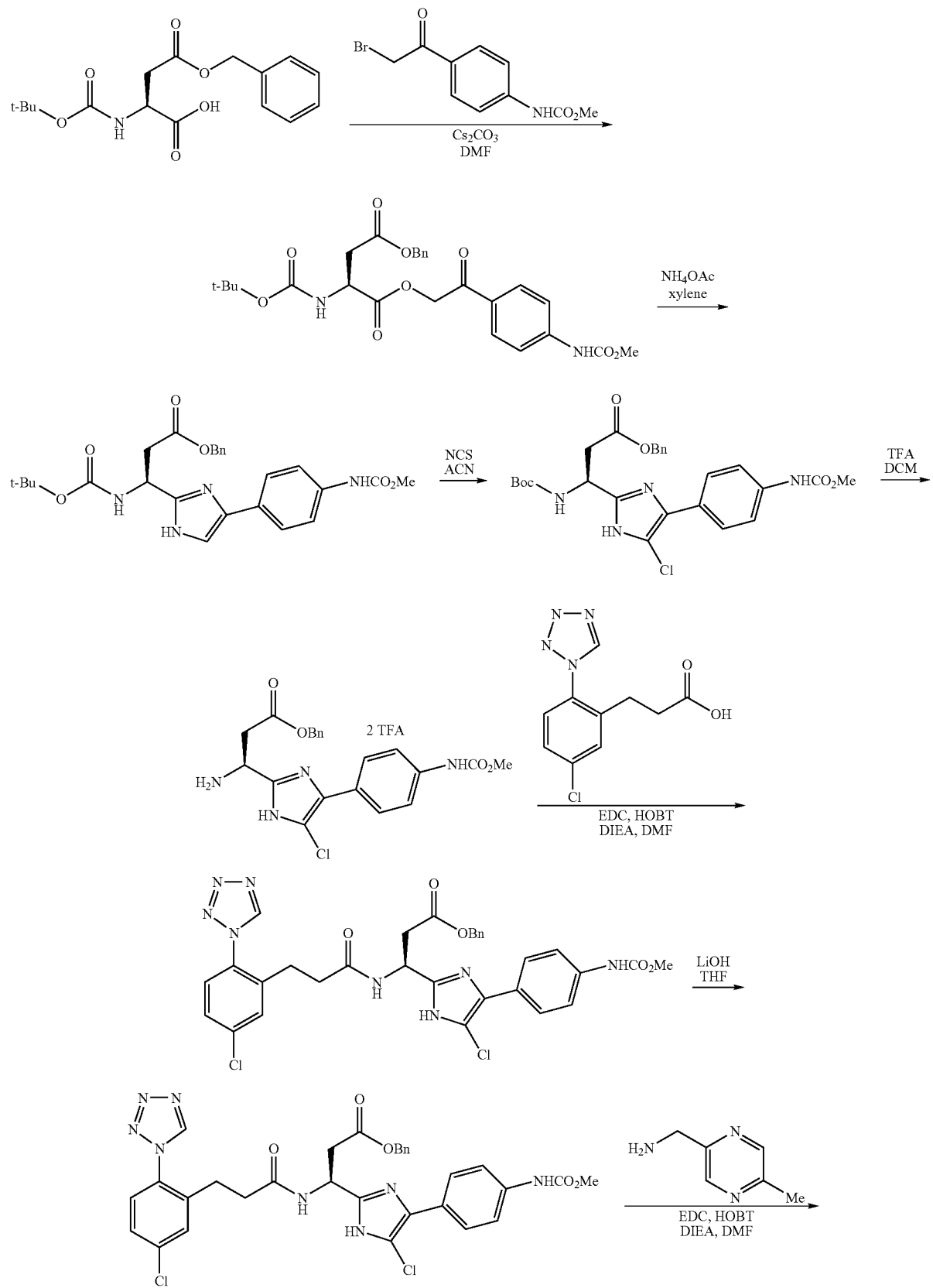

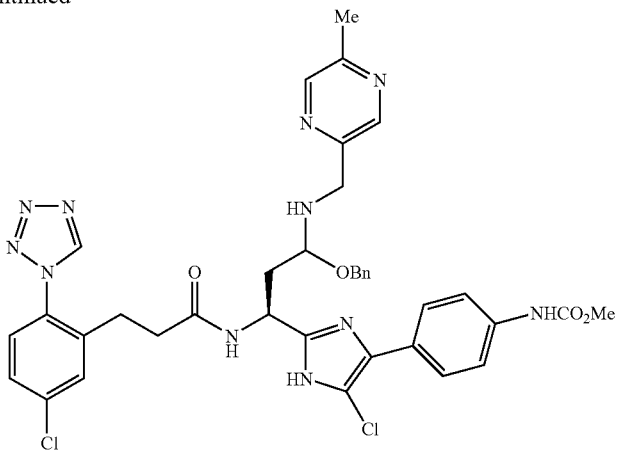

Alternately, imidazole compounds of this invention can be prepared by introduction of R³ groups via palladium-mediated coupling to an intermediate 4-bromo-5-chloroimidazole intermediate prepared as shown in Scheme 11. Alternate boronic acid or boronic ester coupling partners that are commercially available or readily synthesized by methods known to one skilled in the art may be employed in this palladium-mediated step to afford additional compounds of this invention.

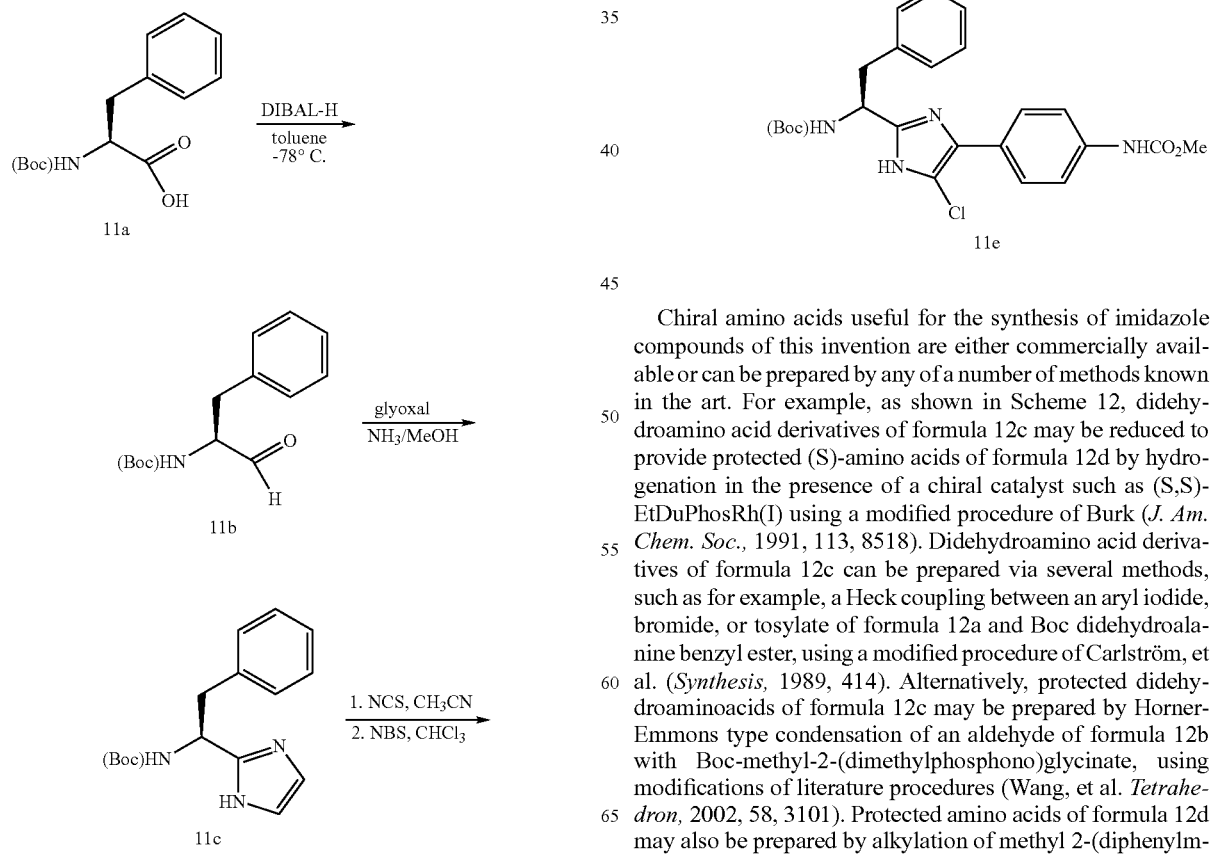

Chiral amino acids useful for the synthesis of imidazole compounds of this invention are either commercially available or can be prepared by any of a number of methods known in the art. For example, as shown in Scheme 12, didehydroamino acid derivatives of formula 12c may be reduced to provide protected (S)-amino acids of formula 12d by hydrogenation in the presence of a chiral catalyst such as (S,S)-EtDuPhosRh(I) using a modified procedure of Burk (*J. Am. Chem. Soc.,* 1991, 113, 8518). Didehydroamino acid derivatives of formula 12c can be prepared via several methods, such as for example, a Heck coupling between an aryl iodide, bromide, or tosylate of formula 12a and Boc didehydroalanine benzyl ester, using a modified procedure of Carlström, et al. (*Synthesis,* 1989, 414). Alternatively, protected didehydroaminoacids of formula 12c may be prepared by Horner-Emmons type condensation of an aldehyde of formula 12b with Boc-methyl-2-(dimethylphosphono)glycinate, using modifications of literature procedures (Wang, et al. *Tetrahedron,* 2002, 58, 3101). Protected amino acids of formula 12d may also be prepared by alkylation of methyl 2-(diphenylmethyleneamino)acetate with an appropriately substituted benzylbromide in the presence of a chiral cinchonidinium catalyst in a suitable solvent, such as methylene chloride, using a procedure similar to that described by O'Donnell, et al. (*Tetrahedron*, 1999, 55, 6347), followed by mild acidic workup and reprotection of the amino functionality with a Boc group according to methods known to one skilled in the art. Substitution of heteroaryl bromides or iodides for 12a, heteroaryl or alkyl aldehydes for 12b, and heteroarylalkyl or alkylbromides for 12c in Scheme 12 would lead to additional chiral amino acids useful for the synthesis of imidazole compounds of this invention. For example, optionally substituted pyrazole carbaldehydes may be used in place of benzaldehydes 12b to give compounds of this invention wherein $R^{11}$ is an optionally substituted pyrazolylmethyl group.

McKillop, A, Ed. Pergamon Press, New York, 1996, pp 1-300).

Representative pyridine compounds of this invention can be prepared as shown in Scheme 13. Suzuki coupling between an appropriately functionalized pyridine, such as 13a and an appropriately substituted aryl or heteroaryl boronic acid or ester 13b in the presence of a base such as anhydrous potassium carbonate in a solvent such as methanol or THF using a catalyst such as PXPd2 provides the biaryl compound. Using a modification of the procedure described by Schlosser (Schlosser, M. and Cottet, F. *Eur. J. Org. Chem.*, 2002, 24, 4181-4184), the 2-chloropyridine derivative is treated with trimethylsilyl bromide in propionitrile at

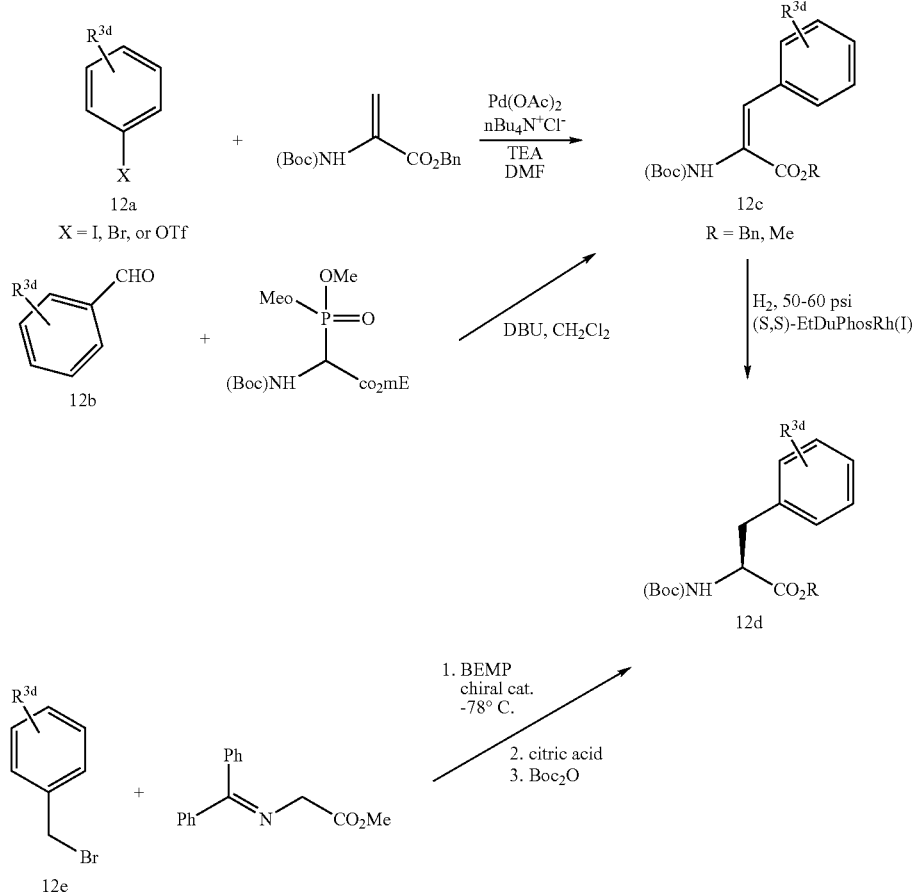

Methods for synthesis of a large variety of substituted pyridine and pyridone compounds useful as starting materials for the preparation of compounds of the present invention are well known in the art and have been extensively reviewed. (For examples of methods useful for the preparation of pyridine and pyridone starting materials see: Krohnke, F. *Synthesis*, 1976, 1.; *Pyridine and Its Derivatives*. In *The Chemistry of Heterocyclic Compounds*, Abramovitch, R. A., Ed.; John Wiley and Sons: New York, 1974; Vol 14; Supplemental 1-4.; *Comprehensive Heterocyclic Chemistry*, Vol. 2, Boulton, A. J. and McKillop, A, Eds. Pergamon Press, New York, 1984, pp 165-524; *Comprehensive Heterocyclic Chemistry*, Vol. 5, elevated temperature in a microwave to give the 2-bromopyridine derivative 13c. Metal-halogen exchange with n-butyllithium and quenching the intermediate anion with a suitable formyl source such as 1-formyl piperidine or DMF provides aldehyde 13d. Using a modification of the procedure described by Hart (Hart, D. J. et al. *J. Org. Chem.*, 1983, 48(3), 289-294), in situ generation of N-trimethylsilylaldimines from 13d and lithium bis(trimethylsilyl)amide, followed by the addition of Grignard or alkyllithium reagents give after aqueous work up the primary amine 13e. Coupling between 13e and 1b or 1d, according to Scheme 1, gives 13f. Alternately, coupling between 13e and 3b, according to Scheme 3, gives 13g. Alternately, amide coupling between 13e and 5a, 6b, 6c, or 6d employing suitable coupling reagents, such as EDCI, HOBt, and base generates 13h, 13i, and 13n. (for alternative coupling reagents see: Han, S-Y; Kim, Y-A. *Tetrahedron,* 2004, 60, 2447). The pyridine N-oxide derivatives 13j-m and 13o can be prepared by oxidation of 13f-i and 13n with a suitable oxidant such as m-chloroperbenzoic acid in chloroform. Further manipulation of functional groups on A, $R^3$, and $R^4$ using methods known to one skilled in the art of organic synthesis will give additional compounds of the invention.

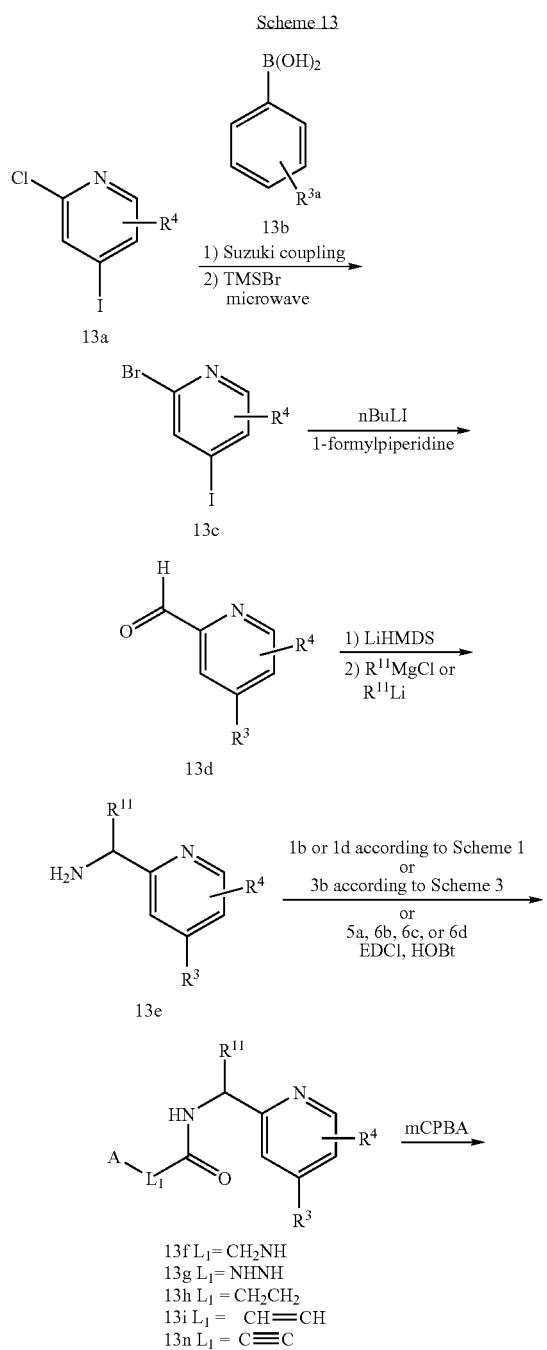

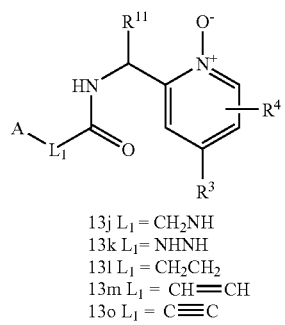

13j $L_1$ = $CH_2NH$
13k $L_1$ = NHNH
13l $L_1$ = $CH_2CH_2$
13m $L_1$ = CH=CH
13o $L_1$ = C≡C

Alternately, the $R^3$ moiety can be introduced via a Suzuki coupling strategy later in the synthesis as shown in Scheme 14. Compound 14c can be prepared in three steps according to a modified procedure described by Negi (Negi, S. et al. *Synthesis,* 1996, 991). Addition of Grignard or lithium reagents to a suitably substituted ester or Weinreb amide 14a yields ketone 14b. Condensation of 14b with hydroxylamine hydrochloride generates the oxime which can be reduced to the primary amine 14c with zinc dust and TFA. Boc protection of 14c gives 14d. Suzuki coupling between 4-chloropyridine 14d and an appropriately substituted aryl or heteroaryl boronic acid or ester 13b in the presence of a base such as anhydrous cesium carbonate, potassium fluoride, or potassium phosphate in a solvent, such as dioxane, dimethylsulfoxide, or dimethylformamide, using a catalyst such as tetrakis(triphenylphosphine)palladium(0), tris(dibenzylideneacetone)dipalladium(0) and tri-t-butylphosphonium tetrafluoroborate or $Pd(dppf)_2$ $Cl_2.CH_2Cl_2$ complex provides the biaryl compound. Boc deprotection with TFA gives 13e. Coupling between 13e and 1b or 1d, according to Scheme 1, gives 13f. Alternately, coupling between 13e and 3b, according to Scheme 3, gives 13g. Alternately, amide coupling between 13e and 5a, 6b, 6c, or 6d employing suitable coupling reagents, such as EDCI, HOBt, and base generates 13h, 13i, and 13n. (for alternative coupling reagents see: Han, S-Y; Kim, Y-A. *Tetrahedron,* 2004, 60, 2447). The pyridine N-oxide derivatives 13j-m and 13o can be prepared by oxidation of 13f-i and 13n with a suitable oxidant such as m-chloroperbenzoic acid in chloroform. Further manipulation of functional groups on A, $R^3$, and $R^4$ using methods known to one skilled in the art of organic synthesis will give additional compounds of the invention.

Scheme 14

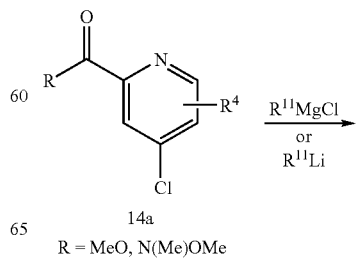

14a
R = MeO, N(Me)OMe

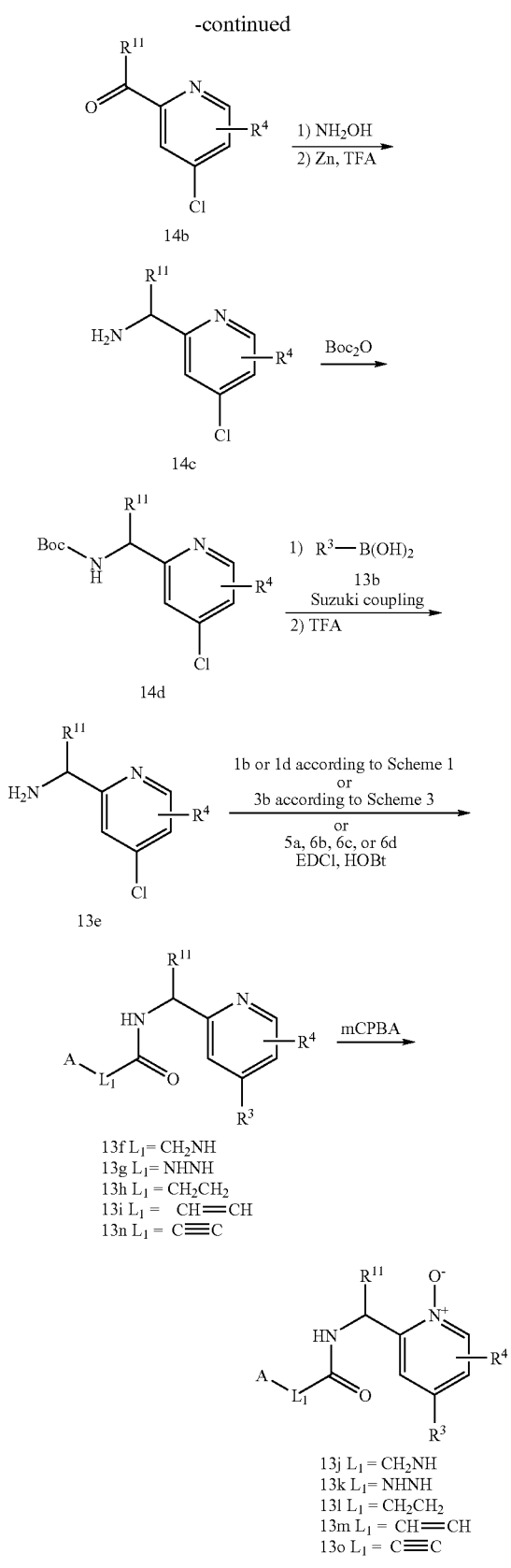

be adopted wherein an aryl halide is subjected to a palladium mediated coupling with a diboron species such as bis(pinacolato)diboron to provide the corresponding 4,4,5,5-tetramethyl-[1,3,2]dioxaborolane intermediate using the method of Ishiyama, T. et al. (J. Org. Chem. 1995, 60(23), 7508-7510). Alternately, this same intermediate can be prepared by reaction of the intermediate halide with the corresponding dialkoxyhydroborane as described by Murata et al. (J. Org. Chem. 1997, 62(19), 6458-6459). The boron pinacolate intermediates can be used in place of boronic acids for coupling to the aryl/heteroaryl halides or triflates or the boron pinacolate intermediate can be converted to the boronic acids. Alternately, the corresponding boronic acids can be prepared by metal-halogen exchange of the aryl/heteroaryl halide, quenching with a trialkoxyborate reagent, and aqueous workup to provide the boronic acids (Miyaura, N.; Suzuki, A. Chem. Review, 1995, 95, 2457).

It is also realized that the scope of intermediate synthesis can be further extended outside the use of Suzuki methodology since the precursor aryl halides or triflates described above are also precursors for Stille, Negishi, Hiyama, and Kumada-type cross coupling methodologies (Tsuji, J. Transition Metal Reagents and Catalysts: Innovations in Organic Synthesis, John Wiley & Sons, 2000; Tsuji, J. Palladium Reagents and Catalysts: Innovations in Organic Synthesis, John Wiley & Sons, 1996.)

Representative pyridone compounds of this invention can be prepared as shown in Scheme 15. Compound 15d can be prepared in two steps according to a modified procedure described by Resmini (Resmini, M. et al., Tetrahedron Asymmetry, 2004, 15, 1847). A suitably substituted amino ester 15a can be converted to the corresponding β-ketophosphonate 15b by treatment with lithium dimethylmethylphosphonate. Horner-Wadsworth-Emmons reaction of 15b and a suitably substituted aldehyde 15c in the presence of base such as potassium carbonate in a solvent such as ethanol or tetrahydrofuran gives the α,β-unsaturated ketone 15d. Condensation of 15d with 1-(ethoxycarbonylmethyl)-pyridinium chloride or 1-(carbamoylmethyl)-pyridinium chloride in the presence of ammonium acetate in a solvent such as ethanol or glacial acetic acid generates the pyridone 15e. Boc deprotection with TFA gives 15f Coupling between 15f and 1b or 1d, according to Scheme 1, gives 15g. Alternately, coupling between 15f and 3b, according to Scheme 3, gives 15h. Alternately, amide coupling between 15f and 5a, 6b, 6c, or 6d employing suitable coupling reagents, such as EDCI, HOBt, and base generates 15i, 15j, or 15k. (for alternative coupling reagents see: Han, S-Y; Kim, Y-A. Tetrahedron, 2004, 60, 2447). Further manipulation of functional groups on A and R³ using methods known to one skilled in the art of organic synthesis will give additional compounds of the invention.

Scheme 15

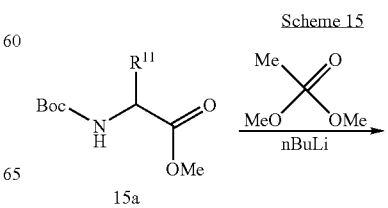

15a

In cases where suitably substituted boronic acids are not commercially available, a modification to this approach may

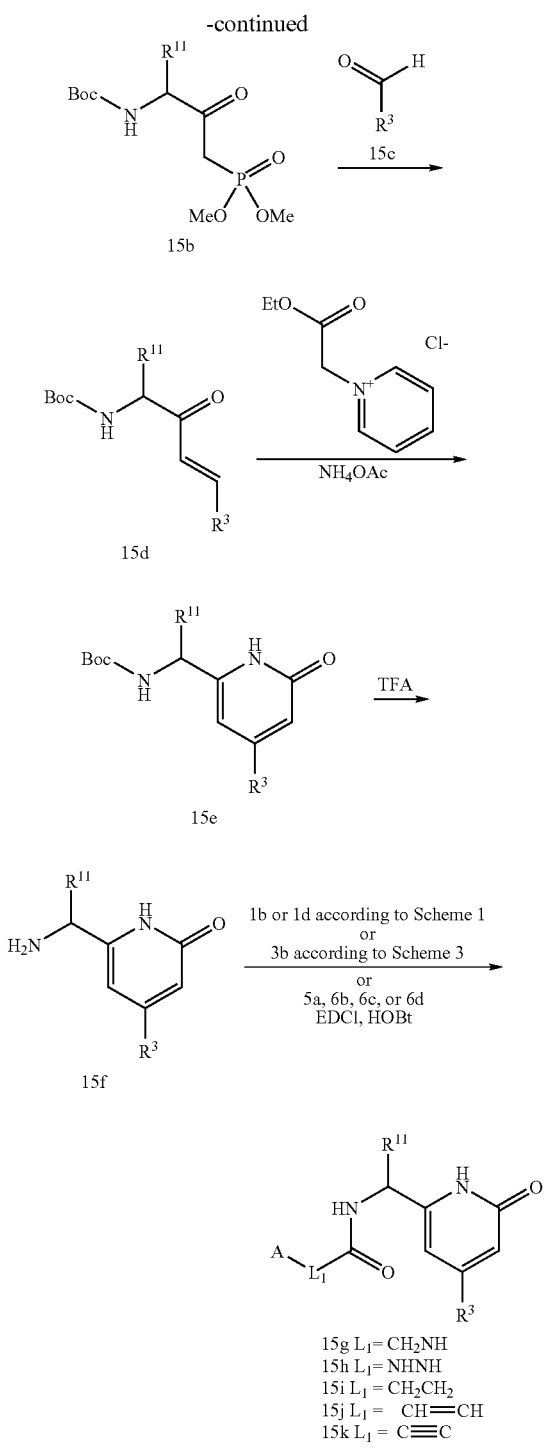

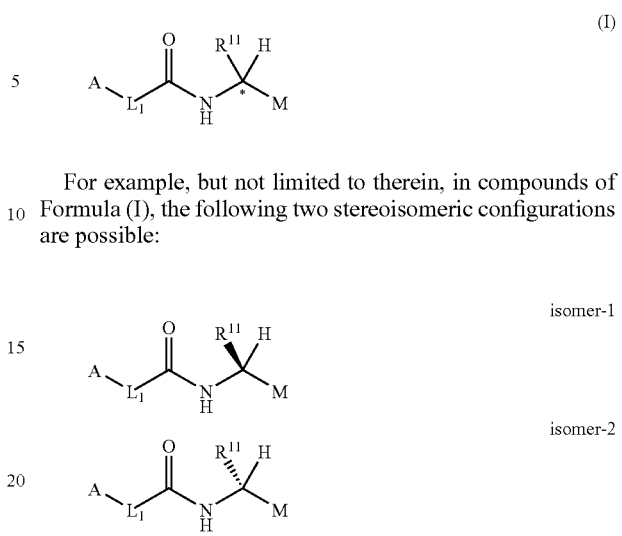

For example, but not limited to therein, in compounds of Formula (I), the following two stereoisomeric configurations are possible:

They are collectively, as well as individually, considered part of the invention. In a preferred stereoisomeric embodiment the present invention provides for a stereoisomeric configuration of isomer-1 for Formula (I) or tautomer, pharmaceutically acceptable salt, solvate, or prodrug form thereof.

Other features of the invention will become apparent in the course of the following descriptions of exemplary embodiments that are given for illustration of the invention and are not intended to be limiting thereof.

In the following experimental procedures, solution ratios express a volume relationship, unless stated otherwise. NMR chemical shifts ($\delta$) are reported in parts per million (ppm).

Products were analyzed by reverse phase analytical HPLC carried out on a Shimadzu Analytical HPLC system running DiscoveryVP software using Method A: Phenomenex Luna C18 column (4.6×50 mm or 4.6×75 mm) eluted at 4 mL/min with a 2, 4 or 8 min gradient from 100% A to 100% B (A: 10% methanol, 89.9% water, 0.1% TFA; B: 10% water, 89.9% methanol, 0.1% TFA, UV 220 nm), or Method B: Phenomenex Luna C18 column (4.6×50 mm) eluted at 4 mL/min with a 4 min gradient from 100% A to 100% B (A: 10% acetonitrile, 89.9% water, 0.1% TFA; B: 10% water, 89.9% acetonitrile, 0.1% TFA, UV 220 nm). Purification of intermediates and final products was carried out via either normal or reverse phase chromatography. Normal phase chromatography was carried out on an ISCO CombiFlash™ System using pre-packed SiO$_2$ cartridges eluted with gradients of hexanes and ethyl acetate or methylene chloride and methanol. Reverse phase preparative HPLC was carried out using a Shimadzu Preparative HPLC system running DiscoveryVP software using Method A: YMC Sunfire 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm), Method B: Phenomenex AXIA Luna 5 μm C18 30×75 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), Method C: Phenomenex Luna 5 μm C18 30×100 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), or Method D: Phenomenex Luna 5 μm C18 30×100 mm column with a 10 min It should be recognized that additional deprotection steps and further functional group manipulations of compounds obtained via Schemes 1-15 above using methods known in the art will then provide additional compounds of this invention.

The compound of the instant invention herein described may have asymmetric center(s). For example, the chiral carbon atom in Formula (I) as indicated below, exists in either as S or R configuration.

gradient at 40 mL/min from 100% A to 100% B (A: 10% methanol, 89.9% water, 0.1% TFA; B: 10% water, 89.9% methanol, 0.1% TFA, UV 220 nm). Alternatively, reverse phase preparative HPLC was carried out using a Varian ProStar Preparative HPLC System running Star 6.2 Chromatography Workstation software using Method E: Dynamax 10 μm C18 41.4×250 mm column with a 30 min gradient at 30 mL/min from 10% B to 100% B (A 98% water, 2% acetonitrile, 0.05% TFA; B: 98% acetonitrile, 2% water, 0.05% TFA, UV 254 nm). LCMS chromatograms were obtained on a Shimadzu HPLC system running DiscoveryVP software, coupled with a Waters ZQ mass spectrometer running MassLynx version 3.5 software using the same columns and conditions as utilized for analytical described above.

EXAMPLES

Example 1

N-((S)-1-(4-(3-amino-1H-indazol-6-yl)-5-chloro-1H-imidazol-2-yl)-2-phenylethyl)-3-phenylpropanamide 1A: 4-Cyano-3-fluorobenzoic acid: 4-Bromo-3-fluorobenzoic acid (7.5 g, 0.034 mol), $Zn(CN)_2$ (4.0 g, 0.034 mol) and $Pd(PPh_3)_4$ (3.95 g, 0.0034 mol) were added together with 60 mL of DMF (degassed). The mixture was heated at 90° C. under $N_2$ for 3 h. It was cooled to room temperature and filtered to remove insoluble inorganic salts (discarded). The filtrate was diluted with water and extracted with EtOAc. The EtOAc mixture was washed with water, brine, dried over $MgSO_4$, and concentrated to yield 4.5 g of the desired product with 90% purity. This material was taken into the next step without further purification. $^1$H-NMR (500 MHz, $d_4$-MeOH) δ 7.82 (m, 1H), 7.90 (m, 3H), 7.56 (d, J=10.0 Hz, 1H), 7.68 (s, 1H), 7.96 (d, J=8.4 Hz, 1H).

1B: 4-(2-Bromoacetyl)-2-fluorobenzonitrile: 1A (4.0 g of 90% pure material, 0.02 mol) was dissolved in $CH_2Cl_2$ (50 mL). To it was added dropwise oxalyl chloride over 15 minutes (2.3 mL, 0.026 mol). The mixture was stirred at rt for 1 h and then heated at reflux for 1 h under $N_2$. The solvent was removed, and the residue was redissolved in $CH_3CN$ (50 mL). This solution was cooled to −15° C., and to it was added (trimethylsilyl)diazomethane (11.5 mL of 2.0M in hexane) dropwise over 20 min. The resulting mixture was stirred at −15° C. for 1 h under $N_2$. To the mixture was added dropwise a solution of HBr in HOAc (4.25 mL of 33% wt) over 20 min, and the reaction mixture was stirred at −15° C. for 20 min. The solvent was removed, and the residue was dissolved in EtOAc, washed with water, brine, dried over $MgSO_4$, and concentrated to 3.2 g of the desired product. MS: 240.1, 242.1, $(M+H)^+$. $^1$H-NMR (400 MHz, $d_4$-MeOH) δ 2.42 (s, 2H), 7.76-7.85 (m, 3H).

1C: tert-butyl (S)-1-(4-(4-cyano-3-fluorophenyl)-1H-imidazol-2-yl)-2-phenylethylcarbamate: 1B (3.2 g 0.013 mol), L-Boc-phenylalanine (3.5 g, 0.013 mol), and $Cs_2CO_3$ (2.6 g, 0.008 mol) were added together with DMF (20 mL). The mixture was stirred at 15° C. for 1 h under $N_2$. It was diluted with 100 mL of EtOAc, washed with water, brine, dried over $MgSO_4$, concentrated, and purified by flash chromatography (120 g×2 silica, 10-55% EtOAc in hexane) to give 3.5 g of the desired ester. LC/MS: 425.3. This material was then combined with ammonium acetate (12 g) and suspended in xylenes (100 mL). The mixture was heated under $N_2$ at 150° C. for 2.5 h in a flask equipped with a Dean-Stark trap. The xylenes were removed. The residue was dissolved in EtOAc, and washed with water and brine. It was dried over $MgSO_4$, concentrated, and purified by flash chromatography (120 g×2 silica, 15-70% EtOAc in hexane) to give 2.2 g of the desired imidazole. MS: 407 $(M+H)^+$. $^1$H-NMR (400 MHz, $CDCl_3$) δ 1.39 (s, 9H), 3.30 (m, 2H), 4.86 (d, J=6.59 Hz, 1H), 5.32 (d, J=7.47 Hz, 1H), 7.14-7.24 (m, 6H), 7.53-7.61 (m, 3H).

1D: tert-butyl (S)-1-(5-chloro-4-(4-cyano-3-fluorophenyl)-1H-imidazol-2-yl)-2-phenylethylcarbamate: 1C (2.2 g, 5.4 mmol) and N-chlorosuccinimide (0.80 g, 6.7 mmol) were added together with $CH_3CN$ (100 mL). The mixture was heated at reflux for 7 h under $N_2$. The solvent was removed, and the residue was dissolved in EtOAc. It was washed with water, aqueous $NaHCO_3$, and brine, dried over $MgSO_4$, and concentrated to give 2.4 g of foam. MS: 441.3, $(M+H)^+$. $^1$H-NMR (400 MHz, $CDCl_3$) δ 1.27 (s, 9H), 3.23 (m, 2H), 4.89 (m, 1H), 5.46 (d, J=7.03 Hz, 1H), 7.07 (d, J=6.15 Hz, 2H), 7.25-7.26 (m, 5H), 7.54 (m, 1H).

1E: 4-(2-((S)-1-amino-2-phenylethyl)-5-chloro-1H-imidazol-4-yl)-2-fluorobenzonitrile: 1D (0.20 g, 0.45 mmol) was stirred with $CH_2Cl_2$ (6 mL) and TFA (1.5 mL) under $N_2$ for 0.5 h. The solvents were removed. The residue was dried under vacuum to give 0.26 g of the bis-TFA salt. MS: 340.94, $(M+H)^+$. $^1$H-NMR (400 MHz, $d_4$-MeOH) δ 3.33 (m, 2H), 4.56 (dd, J=8.57, 6.37 Hz, 1H), 7.12 (d, J=6.59 Hz, 2H), 7.25-7.30 (m, 3H), 7.67 (m, 2H), 7.81 (m, 1H).

1F. Example 1: To a THF (2 mL) solution of 1E (0.09 g, 0.26 mmol) and (E)-3-(3-chlorophenyl)acrylic acid (0.04 g, 0.26 mmol) was added BOP reagent (0.12 g, 0.26 mmol) and triethylamine (0.3 mL). The reaction mixture was stirred at rt overnight. The mixture was quenched with NaOH (1N, 50 mL) and the organics were extracted with ethyl acetate (2×50 mL), dried ($MgSO_4$) and evaporated to an oil which was used directly in the next step. The oil was dissolved in n-butanol (2 mL) and transferred into a microwave flask. To this mixture was added hydrazine (0.1 mL) and the flask was capped. The mixture was irradiated in a microwave oven at 150° C. for 15 min, cooled and purified directly by prep. reverse phase HPLC (acetonitrile:water: 0.05% TFA). Pure fractions were collected and lyophilized to a colorless powder (0.02 g). LCMS m/z 485.32 $(M+H)^+$. $^1$HNMR ($CD_3OD$, 400 MHz) δ: 7.91 (d, J=8.0 Hz, 1H), 7.67 (s, 1H), 7.42 (d, 1H), 7.27 (m, 5H), 7.17 (m, 2H), 7.01 (m, 2H), 6.91 (m, 1H), 5.75 (t. 1H), 3.60 (t, 2H), 3.20 (m, 2H), 2.29 (t, 2H).

Example 2

(E)-N-((S)-1-(4-(3-amino-1H-indazol-6-yl)-5-chloro-1H-imidazol-2-yl)-2-phenylethyl)-3-(3-chlorophenyl)acrylamide 2A. (E)-N-((S)-1-(5-chloro-4-(4-cyano-3-fluorophenyl)-1H-imidazol-2-yl)-2-phenylethyl)-3-(3-chlorophenyl)acrylamide: To a THF (10 mL) solution of 1E (0.07 g, 0.2 mmol) and (E)-3-(3-chlorophenyl)acrylic acid (0.036 g, 0.2 mmol) was added BOP reagent (0.91 g, 0.2 mmol) and triethylamine (0.3 mL). The reaction mixture was stirred at rt overnight. The mixture was quenched with NaOH (1N, 50 mL) and the organics were extracted with ethyl acetate (2×50 mL), dried ($MgSO_4$) and evaporated to an oil (0.13 g). LCMS m/z 505.22 $(M+H)^+$, 527.20 (M+Na). $^1$HNMR ($CDCl_3$, 400 MHz) δ: 7.80 (bd, 1H), 7.45 (m, 3H), 7.29-7.15 (m, 14H), 6.35 (d, J=5.6 Hz, 1H), 5.45 (m, 1H), 3.30 (m, 2H).

2B. Example 2: 2A (0.07 g), was dissolved in n-butanol (2 mL) and transferred into a microwave flask. To this mixture was added hydrazine (0.1 mL) and the flask was capped. The mixture was irradiated in a microwave oven at 150° C. for 15 min, cooled, and purified by prep. reverse phase HPLC (acetonitrile:water: 0.05% TFA). Pure fractions were collected and lyophilized to a colorless powder (0.02 g). LCMS m/z 517.35 (M+H)+. 1HNMR (CD3OD, 400 MHz) δ: 7.80 (m, 1H), 7.75-7.00 (m, 12H), 6.50 (dm, 1H), 5.30 (m, 1H), 3.20 (m, 2H).

Example 3

N-((S)-1-(4-(3-amino-1H-indazol-6-yl)-5-chloro-1H-imidazol-2-yl)-2-phenylethyl)-3-(3-methoxyphenyl)propanamide 3A. N-((S)-1-(5-chloro-4-(4-cyano-3-fluorophenyl)-1H-imidazol-2-yl)-2-phenylethyl)-3-(3-methoxyphenyl)propanamide: To a THF (5 mL) solution of 1E (0.2 g, 0.59 mmol) and 3-(3-methoxyphenyl)propanoic acid (0.10 g, 0.58 mmol) were added BOP reagent (0.26 g, 0.58 mmol) and triethylamine (0.5 mL). The reaction mixture was stirred at rt overnight, quenched with water (100 mL) and extracted with ethyl acetate (2×50 mL), washed with brine (50 mL), dried (MgSO4) and evaporated to a pale yellow oil (0.135 g). LCMS m/z 503.25 (M+H)+. 1HNMR (CDCl3, 400 MHz) δ: 7.42 (m, 3H), 7.21-6.95 (m, 7H), 6.63-6.54 (m, 3H), 5.28 (m, 1H), 3.61 (s, 3H), 3.20-3.01 (m, 2H), 2.72 (t, 2H), 2.41 (t, 2H).

3B. Example 3: The crude product from 3A (0.05 g) was treated with hydrazine (0.1 mL) in n-butanol (2 mL), irradiated in a microwave oven as described previously and purified via reverse phase HPLC (acetonitrile:water: 0.05% TFA) and lyophilized to afford the desired product as a colorless solid. (0.05 g). HPLC purity >95%. LCMS m/z 515.37 (M+H)+. 1HNMR (DMSO-d6, 400 MHz) δ: 7.86 (d, J=7.8 Hz, 1H), 7.60 (s, 1H), 7.42 (ss, J=1.5 & 7.9 Hz, 1H), 7.17-6.99 (m, 6H), 6.60 (m, 3H), 5.10 (t, 1H), 3.60 (s, 3H), 3.15-3.02 (m, 2H), 2.25 (t, 2H), 2.40 (t, 2H).

Example 4

N-((S)-1-(4-(3-amino-1H-indazol-6-yl)-5-chloro-1H-imidazol-2-yl)-2-phenylethyl)-3-m-tolylpropanamide Example 4 was prepared in a similar fashion as described above for Example 3. LCMS m/z 499.37 (M+H)+. 1HNMR (DMSO-d6, 400 MHz) δ: 8.48 (d, J=8.5 Hz, 1H), 7.88 (d, J=6.4 Hz, 1H), 7.62 (s, 1H), 7.39 (d, J=7.9 Hz, 1H), 7.25-6.92 (m, 8H), 5.21 (m, 1H), 3.20 (m, 1H), 3.05 (m, 1H), 2.70 (t, 2H), 2.40 (t, 2H), 2.23 (s, 3H).

Example 5

N-((S)-1-(4-(3-amino-1H-indazol-6-yl)-5-chloro-1H-imidazol-2-yl)-2-phenylethyl)-3-(3-chlorophenyl)propanamide Example 5 was prepared in a similar fashion described previously for Example 3. Colorless solid. HPLC purity >95%. LCMS m/z 519.33 (M+H)+; 543.34 (M+Na)+. 1HNMR (DMSO-d6, 400 MHz) δ: 7.87 (dd, J=1.5 & 9.5 Hz, 1H), 7.61 (s, 1H), 7.42 (dd, J=2.5 & 9.5 Hz, 1H), 7.17-6.95 (m, 9H), 5.07 (t, 1H), 3.10 (m, 2H), 2.73 (t, 2H), 2.40 (t, 2H).

Examples 6-12 in Table 1 were prepared in a parallel library fashion from 1E (~40 mg) in anhydrous THF (2 mL) and an equivalent amount of the appropriate acid, BOP reagent and triethylamine (0.4 mL). The reactions were stirred at rt overnight. Workup followed by hydrazine treatment and purification as described in the previous examples afforded the target compounds.

Example 6

N-{(S)-1-[4-(3-Amino-1H-indazol-6-yl)-5-chloro-1H-imidazol-2-yl]-2-phenyl-ethyl}-3-(2,4-difluoro-phenyl)-propionamide

Example 7

N-{(S)-1-[4-(3-Amino-1H-indazol-6-yl)-5-chloro-1H-imidazol-2-yl]-2-phenyl-ethyl}-3-(2-methoxy-phenyl)-propionamide

Example 8

N-{(S)-1-[4-(3-Amino-1H-indazol-6-yl)-5-chloro-1H-imidazol-2-yl]-2-phenyl-ethyl}-3-(2-chloro-phenyl)-propionamide

Example 9

N-{(S)-1-[4-(3-Amino-1H-indazol-6-yl)-5-chloro-1H-imidazol-2-yl]-2-phenyl-ethyl}-3-(3-bromo-phenyl)-propionamide

Example 10

N-{(S)-1-[4-(3-Amino-1H-indazol-6-yl)-5-chloro-1H-imidazol-2-yl]-2-phenyl-ethyl}-3-(2-fluoro-phenyl)-propionamide

Example 11

N-{(S)-1-[4-(3-Amino-1H-indazol-6-yl)-5-chloro-1H-imidazol-2-yl]-2-phenyl-ethyl}-3-(2,5-dichloro-phenyl)-propionamide

Example 12

N-{(S)-1-[4-(3-Amino-1H-indazol-6-yl)-5-chloro-1H-imidazol-2-yl]-2-phenyl-ethyl}-3-(2-bromo-phenyl)-propionamide

Example 13

N-((S)-1-(4-(3-amino-1H-indazol-6-yl)-5-chloro-1H-imidazol-2-yl)-2-phenylethyl)-2-(3-chlorophenylthio)acetamide Example 13 was prepared by the coupling (BOP reagent/TEA, THF) of commercially available 2-(3-chlorophenylthio)acetic acid and 1E followed by treatment with hydrazine in a microwave as described for Example 2. The desired product was obtained as a colorless solid following purification via reverse phase chromatography and lyophilization. LCMS m/z 537.34 (M+H)+. 1HNMR (CD3OD, 400 MHz) δ: 7.84 (d, J=7.9 Hz, 1H), 7.58 (s, 1H), 7.38 (dd, J=1.4 & 8 Hz, 1H), 7.21 (m, 1H), 7.11-7.04 (m, 8H), 5.08 (t, 1H), 3.68 (s, 2H), 3.18-3.02 (m, 2H).

Example 14

N-((S)-1-(4-(3-amino-1H-indazol-6-yl)-5-chloro-1H-imidazol-2-yl)-2-phenylethyl)-2-(3-chlorophenylsulfonyl)acetamide Example 14 was obtained by treatment of Example 13 with mCPBA (2.5 eq) in dichloromethane. Reverse phase HPLC purification followed by lyophilization of the pure fractions afforded the desired product as a colorless solid. LCMS m/z 569.28 (M+H)+. $^1$HNMR (CD$_3$OD, 400 MHz) δ: 7.98 (d, J=8.2 Hz, 1H), 7.79 (t, 1H), 7.72 (s, 2H), 7.69-7.62 (m, 2H), 7.24-7.14 (m, 7H), 5.09 (t, 1H), 4.22 (s, 2H), 3.25-3.09 (m, 2H).

Example 15

N-((S)-1-(4-(3-amino-1H-indazol-6-yl)-5-chloro-1H-imidazol-2-yl)-2-phenylethyl)-2-(3-chlorophenoxy)acetamide Example 15 was prepared from 2-(3-chlorophenoxy)acetic acid and 1E following the procedures described under Example 2 to provide Example 15 as a colorless solid. LCMS m/z 521.38 (M+H)+. $^1$HNMR (CD$_3$OD, 400 MHz) δ: 8.00 (dd, J=0.7 & 9.3 Hz, 1H), 7.74 (bs, 1H), 7.55 (dd, J=1.3 & 8.6 Hz, 1H), 7.31-7.17 (m, 6H), 7.40-7.00 (m, 2H), 6.91-6.86 (dm, J=0.3 & 8.5 Hz, 1H), 5.40 (t, J=8.3 hz, 1H), 4.60-4.50 (q, (AB), 2H), 3.28-3.20 (m, 2H).

Example 16

1-(3-chlorobenzyl)-3-((S)-1-(4-(3-amino-1H-indazol-6-yl)-5-chloro-1H-imidazol-2-yl)-2-phenylethyl)urea To a THF (3 mL) solution of the free base of 1E (0.075 g, 0.22 mmol) was added p-nitrophenylchloroformate (0.044 g, 0.22 mmol) and 3-chlorophenylbenzylamine (0.031 g, 0.22 mmol). The reaction mixture was stirred at rt overnight, quenched with water (50 mL) and extracted with ethyl acetate (2×25 mL), dried (MgSO$_4$) and evaporated to a yellow oil. LCMS m/z 508.31 (M+H)+. The oil was redissolved in methanol (2 mL) and to this solution was added hydrazine (0.5 mL). The reaction mixture was transferred into a microwave flask and irradiated in a microwave oven at 150° C. for 0.15 h. The crude product was purified via reverse phase HPLC (acetonitrile:water:0.05% TFA) to afford, after lyophilization, Example 16 as a colorless solid. LCMS m/z 520.03 (M+H)+. $^1$HNMR (CD$_3$OD, 400 MHz) δ: 7.86-7.84 (d, J=9.2 Hz, 1H), 7.63 (bs, 1H), 7.40-7.38 (dd, J=0.7 & 10.1 Hz, 1H), 7.27-7.10 (m, 9H), 5.07 (t, 1H), 4.31-4.24 (q (AB), 2H), 3.20-2.14 (m, 2H).

Examples 17-31 in Table 1 below were prepared in parallel using a similar procedure as described for Example 16.

Example 17

1-{(S)-1-[4-(3-Amino-1H-indazol-6-yl)-5-chloro-1H-imidazol-2-yl]-2-phenyl-ethyl}-3-(2,5-dichloro-benzyl)-urea Example 18

1-{(S)-1-[4-(3-Amino-1H-indazol-6-yl)-5-chloro-1H-imidazol-2-yl]-2-phenyl-ethyl}-3-(3,5-dichloro-benzyl)-urea Example 19

1-{(S)-1-[4-(3-Amino-1H-indazol-6-yl)-5-chloro-1H-imidazol-2-yl]-2-phenyl-ethyl}-3-(3-methyl-benzyl)-urea Example 20

1-{(S)-1-[4-(3-Amino-1H-indazol-6-yl)-5-chloro-1H-imidazol-2-yl]-2-phenyl-ethyl}-3-pyridin-4-ylm-ethyl-urea Example 21

(S)—N-(1-(4-(3-amino-1H-indazol-6-yl)-5-chloro-1H-imidazol-2-yl)-2-phenylethyl)-2-(3-chlorophenyl)hydrazinecarboxamide Example 22

1-{(S)-1-[4-(3-Amino-1H-indazol-6-yl)-5-chloro-1H-imidazol-2-yl]-2-phenyl-ethyl}-3-(5-chloro-2-methyl-benzyl)-urea Example 23

1-{(S)-1-[4-(3-Amino-1H-indazol-6-yl)-5-chloro-1H-imidazol-2-yl]-2-phenyl-ethyl}-3-(5-chloro-2-fluoro-benzyl)-urea Example 24

1-{(S)-1-[4-(3-Amino-1H-indazol-6-yl)-5-chloro-1H-imidazol-2-yl]-2-phenyl-ethyl}-3-(3-chloro-2-fluoro-benzyl)-urea Example 25

1-{(S)-1-[4-(3-Amino-1H-indazol-6-yl)-5-chloro-1H-imidazol-2-yl]-2-phenyl-ethyl}-3-(3-chloro-2,6-difluoro-benzyl)-urea Example 26

1-{(S)-1-[4-(3-Amino-1H-indazol-6-yl)-5-chloro-1H-imidazol-2-yl]-2-phenyl-ethyl}-3-(3-chloro-4-methyl-benzyl)-urea Example 27

1-{(S)-1-[4-(3-Amino-1H-indazol-6-yl)-5-chloro-1H-imidazol-2-yl]-2-phenyl-ethyl}-3-(6-chloro-2-fluoro-3-methyl-benzyl)-urea Example 28

1-{(S)-1-[4-(3-Amino-1H-indazol-6-yl)-5-chloro-1H-imidazol-2-yl]-2-phenyl-ethyl}-3-(2,6-difluoro-3-methyl-benzyl)-urea Example 29

1-{(S)-1-[4-(3-Amino-1H-indazol-6-yl)-5-chloro-1H-imidazol-2-yl]-2-phenyl-ethyl}-3-(2-chloro-6-fluoro-3-methyl-benzyl)-urea

Example 30

1-{(S)-1-[4-(3-Amino-1H-indazol-6-yl)-5-chloro-1H-imidazol-2-yl]-2-phenyl-ethyl}-3-(5-chloro-2-methoxy-benzyl)-urea

Example 31

1-{(S)-1-[4-(3-Amino-1H-indazol-6-yl)-5-chloro-1H-imidazol-2-yl]-2-phenyl-ethyl}-3-(2,3-dichloro-6-nitro-benzyl)-urea

Example 32

(E)-N-((S)-1-(4-(3-amino-1H-indazol-6-yl)-5-chloro-1H-imidazol-2-yl)-2-phenylethyl)-3-(thiophen-3-yl)acrylamide To a THF (10 mL) solution of 1E (0.045 g, 0.13 mmol) was added BOP reagent (0.058 g, 0.13 mmol), (E)-3-(thiophen-3-yl)acrylic acid (0.02 g, 0.13 mmol) and triethylamine (0.2 mL). The reaction mixture was stirred at rt over night. The mixture was quenched with NaOH (1N, 50 mL) and the organics were extracted with ethyl acetate (2×25 mL), dried ($MgSO_4$) and evaporated to a crude coupled oily product (0.07 g). The product was dissolved in n-butanol (2 mL) and transferred into a microwave flask. To this mixture was added hydrazine (0.1 mL) and the flask capped. The mixture was irradiated in a microwave oven at 150° C. for 0.15 min. cooled and purified directly via a prep. reverse phase HPLC. Pure fractions were collected and lyophilized to a colorless powder (0.02 g). LCMS m/z 489.03 (M+H)+. $^1$HNMR ($CD_3OD$, 400 MHz) δ: 7.73 (d, J=9 Hz, 1H), 7.70 (m, 1H), 7.57 (bs, 1H), 7.68-7.45 (bd, J=15 Hz, 1H), 7.60 (m, 1H), 7.36 (d, 1H), 7.30-7.15 (m, 7H), 6.50-6.46 (d, J=15 Hz, 1H), 5.30 (t, 1H), 3.20 (m, 2H).

Example 33

1-{(S)-1-[4-(3-amino-1H-indazol-6-yl)-5-chloro-1H-imidazol-2-yl]-2-phenyl-ethyl}-3-(3-aminomethyl-benzyl)-urea, trifluoroacetic acid salt Example 33 was prepared from commercially available tert-butyl 3-(aminomethyl)-benzylcarbamate following the procedure outlined for Example 16. $^1$HNMR ($CD_3OD$, 400 MHz) δ: 7.92 (d, J=8.5 Hz, 1H), 7.69 (bs, 1H), 7.50 (bs, J=8.6 Hz, 1H), 7.39 (t, 1H), 7.31-7.12 (m, 8H), 5.10 (t, 1H), 4.31 (d, 2H), 4.07 (s, 2H), 3.18 (m, 2H). LCMS m/z 515.3 (M+H)+.

Example 34

1-(6-amino-2,3-dichloro-benzyl)-3-{(S)-1-[4-(3-amino-1H-indazol-6-yl)-5-chloro-1H-imidazol-2-yl]-2-phenyl-ethyl}-urea, trifluoroacetic acid salt Example 34 was prepared according to the procedure described for Example 16 from commercially available (2,3-dichloro-6-nitrophenyl)methanamine hydrochloride. The nitro group was reduced with tin chloride followed by conversion to the aminoindazole and purification as previously described for Example 16. $^1$HNMR ($CD_3OD$, 400 MHz) δ: 7.96 (d, J=8.8z, 1H), 7.69 (s, 1H), 7.51 (d, J=8.7 Hz, 1H), 7.31 (d, J=8.8 Hz, 1H), 7.21-7.09 (m, 5H), 6.87 (d, J=8.8 Hz, 1H), 5.06 (t, 1H), 4.36 (s, 2H), 3.20 (m, 2H). LCMS m/z 569.2 (M+H)+.

Example 35

(S)-1-(1-(4-(3-amino-1H-indazol-6-yl)-5-chloro-1H-imidazol-2-yl)-2-phenylethyl)-3-(5-chloro-2-(trifluoromethyl)benzyl)urea, trifluoroacetic acid salt Example 35 was prepared from commercially available (5-chloro-2-(trifluoromethyl)phenyl)methanamine according to the procedure previously described for Example 16. $^1$HNMR ($CD_3OD$, 400 MHz) δ: 7.91 (d, J=8.7 Hz, 1H), 7.67 (s, 1H), 7.65 (d, J=8.3 Hz, 1H), 7.50-7.40 (m, 3H), 7.31-7.10 (m, 5H), 5.11 (t, 1H), 4.53 (q, 2H), 3.21 (m, 2H). LCMS m/z 588.1 (M+H)+.

Example 36

3-(3-{(S)-1-[4-(3-amino-1H-indazol-6-yl)-5-chloro-1H-imidazol-2-yl]-2-phenyl-ethyl}-ureidomethyl)-benzamide, trifluoroacetic acid salt Example 36 was prepared from commercially available 3-(aminomethyl)benzamide according to the procedure described for Example 16. $^1$HNMR ($CDCl_3/CD_3OD$, 400 MHz) δ: 7.71 (d, J=8.2 Hz, 3H), 7.51 (s, 1H), 7.33 (s, 5H), 7.26-7.15 (m, 3H), 7.14 (d, J=7.8 Hz, 1H), 5.12 (t, J=7.7 Hz, 1H), 4.40 (q(AB), 2H), 3.20 (m, 2H). LCMS m/z 529.2 (M+H)+.

Example 37

1-{(S)-1-[4-(3-amino-1H-indazol-6-yl)-5-chloro-1H-imidazol-2-yl]-2-phenyl-ethyl}-3-(2-aminomethyl-5-chloro-benzyl)-urea, trifluoroacetic acid salt Example 37 was prepared from tert-butyl 2-(aminomethyl)-4-chlorobenzyl-carbamate-3-(aminomethyl)benzamide (Morissette, M. M. et. al. *Bioorg. Med. Chem. Lett.* 2004, 14, 4161-4164) according to the procedure described for Example 16, followed by removal of the Boc protecting group with TFA in methylene chloride. $^1$HNMR ($CD_3OD$, 400 MHz) δ: 7.93 (d, J=8.6 Hz, 1H), 7.68 (s, 1H), 7.46 (dd, J=1.3, 8.6 Hz, 1H), 7.40 (s, 1H), 7.33 (s, 2H), 7.24-7.10 (m, 5H), 5.07 (t, J=7.6 Hz, 1H), 4.33-4.13 (m, 4H), 3.20 (m, 2H). LCMS m/z 549.12 (M+H)+.

Example 38

1-(2-amino-5-chloro-benzyl)-3-{(S)-1-[4-(3-amino-1H-indazol-6-yl)-5-chloro-1H-imidazol-2-yl]-2-phenyl-ethyl}-urea, trifluoroacetic acid salt Example 38 was prepared from 2-(aminomethyl)-4-chloroaniline according to the procedure described for Example 16. $^1$HNMR ($CD_3OD$, 400 MHz) δ: 7.84 (d, J=8.6 Hz, 1H), 7.58 (s, 1H), 7.40 (d, J=8.4 Hz, 1H), 7.21-7.05 (m, 7H), 6.93 (d, J=8.2 Hz, 1H), 4.98 (t, 1H), 4.10 (q, 2H), 3.15 (m, 2H). LCMS m/z 535.08 (M+H)+.

Example 39

1-{(S)-1-[4-(3-amino-1H-indazol-6-yl)-5-chloro-1H-imidazol-2-yl]-2-phenyl-ethyl}-3-(5-chloro-2-pyrazol-1-yl-benzyl)-urea, trifluoroacetic acid salt Example 39 was prepared from (5-chloro-2-(1H-pyrazol-1-yl)phenyl)-methanamine (prepared according to a similar procedure of Young, M. B. et. al *J. Med. Chem.* 2004, 47, 2995) according to the procedure described for Example 16. ¹HNMR (CD₃OD, 400 MHz) δ: 7.89 (m, 2H), 7.75 (d, J=1.7 Hz, 1H), 7.66 (s, 1H), 7.48 (d, J=2.2z, 1H), 7.44-7.16 (m, 8H), 6.53 (m, 1H), 5.09 (t, 1H), 4.17 (q, 2H), 3.20 (m, 2H). LCMS m/z 586.09 (M+H)⁺.

Example 40

1-{(S)-1-[4-(3-amino-1H-indazol-6-yl)-5-chloro-1H-imidazol-2-yl]-2-phenyl-ethyl}-3-(5-chloro-2-ethoxy-benzyl)-urea, trifluoroacetic acid salt 40A. (5-chloro-2-methoxyphenyl)methanamine: 40A was prepared by the LAH/THF reduction of 2-ethoxy-5-chlorobenzonitrile. ¹HNMR (CDCl₃, 400 MHz) δ: 7.24(m, 1H), 7.19 (d, J=2.6 & 8.6 Hz, 1H), 6.79 (d, J=8.7 Hz, 1H), 4.04 (t, 2H), 3.82 (s, 2H), 2.02 (bs, 2H), 1.45 (t, 3H). LCMS m/z 186.2 (M+H)⁺.

40B. Example 40 was prepared from 40A according to the procedure described for Example 16. ¹HNMR (CD₃OD, 400 MHz) δ: 7.98 (d, J=8.6 Hz, 1H), 7.70 (s, 1H), 7.53 (d, J=8.7 Hz, 1H), 7.33-7.15 (m, 7H), 6.90 (d, J=7.4 Hz, 1H), 5.12 (t, 1H), 4.82 (s, 2H), 4.11 (m, 2H), 3.20 (d, 2H), 1.48 (t, 3H). LCMS m/z 564.73 (M+H)⁺.

Example 41

1-{(S)-1-[4-(3-amino-1H-indazol-6-yl)-5-chloro-1H-imidazol-2-yl]-2-phenyl-ethyl}-3-(2-benzyloxy-5-chloro-benzyl)-urea, trifluoroacetic acid salt 41A. (2-(benzyloxy)-5-chlorophenyl)methanamine: 41A was prepared by the nucleophilic aromatic displacement of 2-fluoro-5-chlorobenzonitrile with benzylalcohol followed by reduction of the nitrile with LAH in anhydrous THF. The reaction was quenched with water (50 mL) and extracted with ethyl acetate (2×50 mL), dried (MgSO₄) and purified via silica gel column chromatography (hexane:ethyl acetate 1:1) to afford the product as a colorless solid. ¹HNMR (CDCl₃, 400 MHz) δ: 7.47 (d, J=2.5 Hz, 1H), 7.38-7.19 (m, 6H), 6.88 (d, J=8.0 Hz, 1H), 5.14 (s, 2H). LCMS m/z 244.04 (M+H)⁺.

41B. Example 41 was prepared from 41A according procedure described for Example 16. ¹HNMR (CD₃OD, 400 MHz) δ: 7.83 (d, J=8.6 Hz, 1H), 7.57 (s, 1H), 7.38-7.32 (m, 3H), 7.26-7.04 (m, 10H), 6.87 (d, J=8.4 Hz, 1H), 5.06 (s, H), 4,99 (t, 1H), 4.21 (s, 2H), 3.20 (m, 2H). LCMS m/z 626.74 (M+H)⁺.

Example 42

1-{(S)-1-[4-(3-amino-1H-indazol-6-yl)-5-chloro-1H-imidazol-2-yl]-2-phenyl-ethyl}-3-(5-chloro-2-methylsulfanyl-benzyl)-urea, trifluoroacetic acid salt 42A. (5-chloro-2-(methylthio)phenyl)methanamine: 42A was prepared by the nucleophilic aromatic displacement of 2-fluoro-5-chlorobenzonitrile with sodium thiomethoxide followed by reduction of the nitrile with LAH in anhydrous THF. The reaction was quenched with water (50 mL) and extracted with ethyl acetate (2×50 mL), dried (MgSO₄) and concentrated to a yellow oil. ¹HNMR (CDCl₃, 400 MHz) δ: 7.45 (s, 1H), 7.35-7.12 (m, 2H), 4.86 (s, 1H), 3.83 (s, 1H), 2.50 (s, 3H). LCMS m/z 188.47 (M+H)⁺.

42B. Example 42 was prepared from 42A according to the procedure described for Example 16. ¹HNMR (CD₃OD, 400 MHz) δ: 7.79 (d, =8.6 Hz, 1H), 7.56 (s, 1H), 7.34 (dd, J=8.6 & 1.2 Hz, 1H), 7.17-7.05 (m, 8H), 5.00 (t, 1H), 4.24 (q, 2H), 3.11 (m, 2H), 2.35 (s, 3H). LCMS m/z 566.62 (M+H)⁺.

Example 43

{4-[2-((S)-1-{3-[2-(tert-butoxycarbonylamino-methyl)-5-chloro-benzyl]-ureido}-2-phenyl-ethyl)-5-chloro-1H-imidazol-4-yl]-phenyl}-carbamic acid 2-methoxy-ethyl ester, trifluoroacetic acid salt 43A. {4-[2-((S)-1-amino-2-phenyl-ethyl)-5-chloro-1H-imidazol-4-yl]-phenyl}-carbamic acid 2-methoxy-ethyl ester, bis-trifluoroacetic acid salt: 43A was prepared by procedures analogous to 89A, 89B, 89C, 89F, 89G, and 89H starting from Boc-Phe in place of 84C.

43B. Example 43 was prepared according to the procedure for urea formation described for Example 16 from tert-butyl 2-(aminomethyl)-4-chlorobenzylcarbamate and 43A according to the procedure described for Example 16. ¹HNMR (CDCl₃, 400 MHz) δ: 7.32-7.20 (m, 8H), 7.18-7.10 (m, 4H), 7.00 (bs, 1H), 6.20 (bs, 1H), 5.41m (1H), 4.35 (m, 2H), 4.19 (bd, J=7.4 Hz, 4H), 3.67 (m, 2H), 3.43 (s, 3H), 3.31-3.12 (m, 2H). LCMS m/z 711.12 (M+H)⁺.

Example 44

[4-(2-{(S)-1-[3-(2-aminomethyl-5-chloro-benzyl)-ureido]-2-phenyl-ethyl}-5-chloro-1H-imidazol-4-yl)-phenyl]-carbamic acid 2-methoxy-ethyl ester, bis trifluoroacetic acid salt Removal of the Boc protecting group from Example 43 with TFA followed by reverse phase HPLC (acetonitrile/water/0.05 TFA) purification and lyophilization afforded Example 44 as a colorless solid. ¹HNMR (CD₃OD, 400 MHz) δ: 7.44-7.40 (s, 4H), 7.31 (s, 1H), 7.24 (d, J=1.1 Hz, 2H), 7.17-7.05 (m, 4H), 7.02 (d, J=8.4 Hz, 2H), 4.93 (t, 1H), 4.20 (m, 4H), 4.10 (m, 2H), 3.58 (m, 2H), 3.30 (s, 3H), 3.10 (m, 2H). LCMS m/z 611.11 (M+H)⁺.

Example 45

[4-(5-chloro-2-{(S)-1-[3-(5-chloro-2-tetrazol-1-yl-benzyl)-ureido]-2-phenyl-ethyl}-1H-imidazol-4-yl)-phenyl]-carbamic acid 2-methoxy-ethyl ester, trifluoroacetic acid salt Example 45 was prepared according to the procedure described for Example 16 from (5-chloro-2-(1H-tetrazol-1-yl)phenyl)methanamine (Young, M. B. et. al *J. Med. Chem.* 2004, 47, 2995) and 43A. Reverse phase HPLC purification and lyophilization afforded Example 45 as a colorless solid. ¹HNMR (CD₃OD, 400 MHz) δ: 9.36 (s, 1H), 7.47-7.34 (m, 7H), 7.18-7.03 (m, 5H), 4.95 (t, 1H), 4.20 (m, 2H), 4.09 (q, 2H), 3.57 (m, 2H), 3.10 (m, 2H). LCMS m/z 650.17 (M+H)⁺.

Example 46

[4-(5-chloro-2-{(S)-1-[3-(5-chloro-2-methylsulfanyl-benzyl)-ureido]-2-phenyl-ethyl}-1H-imidazol-4-yl)-phenyl]-carbamic acid 2-methoxy-ethyl ester, trifluoroacetic acid salt Example 46 was prepared from (5-chloro-2-(methylthio) phenyl)methanamine according to the procedure described for Example 45. ¹HNMR (CD₃OD, 400 MHz) δ: 7.59 (s, 4H), 7.55-7.17 (m, 8H), 5.11 (t, 1H), 4.32 (m, 2H), 3.71 (m, 2H), 3.22 (m, 2H), 2.50 (s, 3H). LCMS m/z 628.07 (M+H)$^+$.

Example 47

1-{(S)-1-[4-(3-amino-1H-indazol-6-yl)-5-chloro-1H-imidazol-2-yl]-2-phenyl-ethyl}-3-(5-chloro-2-tetrazol-1-yl-benzyl)-urea, trifluoroacetic acid salt Example 47 was prepared from (5-chloro-2-(1H-tetrazol-1-yl)phenyl)methanamine according to the procedure described for Example 16. $^1$HNMR (CD$_3$OD, 400 MHz) δ: 9.36 (s, 1H), 8.04 (d, J=8.4 Hz, 1H), 7.85 (d, J=8.6 Hz, 1H), 7.60 (s, 1H), 7.49-7.33 (m, 3H), 7.20-7.03 (m, 5H), 6.80 (d, J=8 Hz, 1H), 4.95 (t, 1H), 4.05 (q, 2H), 3.20 (m, 2H). LCMS m/z 588.12 (M+H)$^+$.

Example 48

1-{(S)-1-[4-(3-amino-1H-indazol-6-yl)-5-chloro-1H-imidazol-2-yl]-2-phenyl-ethyl}-3-(5-chloro-2-ethyl-sulfanyl-benzyl)-urea, trifluoroacetic acid salt Example 48 was prepared according to the procedure described for Example 16 from (5-chloro-2-(ethylthio)phenyl)methanamine. $^1$HNMR (CD$_3$OD, 400 MHz) δ: 7.77 (d, J=8.9 Hz, 1H), 7.55 (s, 1H), 7.33 (d, J=11.4 Hz, 1H), 7.25 (d, J=8.3 Hz, 1H), 7.18-7.05 (m, 7H), 6.10 (s, 1H), 4.98 (t, 1H), 4.26 (q, 2H), 3.09 (m, 2H), 2.83 (q, 2H), 1.17 (t, 3H). LCMS m/z 580.3 (M+H)$^+$.

Example 49

1-{(S)-1-[4-(3-amino-1H-indazol-6-yl)-5-chloro-1H-imidazol-2-yl]-2-phenyl-ethyl}-3-(5-chloro-2-propylsulfanyl-benzyl)-urea, trifluoroacetic acid salt Example 49 was prepared according to the procedure described for Example 16 from (5-chloro-2-(propylthio)phenyl)methanamine. $^1$HNMR (CD$_3$OD, 400 MHz) δ: 7.83 (d, J=8.4 Hz, 1H), 7.58 (s, 1H), 7.39 (d, J=8.6 Hz, 1H), 7.22 (d, J=8.6 Hz, 1H), 7.19-7.06 (m, 7H), 6.01 (s, 1H), 4.98 (t, 1H), 4.26 (s, 2H), 3.11 (m, 2H), 2.80 (t, 2H), 1.54 (m, 2H), 0.91 (t, 3H). LCMS m/z 594.3 (M+H)$^+$.

Example 50

1-{(S)-1-[4-(3-amino-1H-indazol-6-yl)-5-chloro-1H-imidazol-2-yl]-2-phenyl-ethyl}-3-(3-fluoro-benzyl)-urea, trifluoroacetic acid salt Example 50 was prepared according to the procedure described for Example 16 from 3-fluorobenzylamine. $^1$HNMR (CD$_3$OD, 400 MHz) δ: 7.84 (d, J=8.6 Hz, 1H), 7.59 (s, 1H), 7.40 (d, J=8.6 Hz, 1H), 7.20-7.06 (m, 6H), 6.93-6.82 (m, 3H), 4.99 (t, 1H), 4.20 (q, 2H), 3.09 (m, 2H). LCMS m/z 504.2 (M+H)$^+$.

Example 51

1-{(S)-1-[4-(3-amino-1H-indazol-6-yl)-5-chloro-1H-imidazol-2-yl]-2-phenyl-ethyl}-3-(2,5-difluoro-benzyl)-urea, trifluoroacetic acid salt Example 51 was prepared according to the procedure described for Example 16 with readily accessible 3,5-fluorobenzylamine with 1E and p-nitrophenyl-chloroformate. Treatment with hydrazine in methanol at 150° C. followed by treatment with TFA and purification via reverse phase HPLC (acetonitrile/water and 0.05% TFA), lyophilization of the pure fraction afforded Example 51 as a colorless solid. $^1$HNMR (CD$_3$OD, 400 MHz) δ: 7.84 (d, J=8.9z, 1H), 7.59 (s, 1H), 7.39 (d, J=8.6 Hz, 1H), 7.17-7.05 (m, 5H), 7.00-6.85 (m, 3H), 6.00 (s, 1H), 4.98 (t, 1H), 4.22 (q, 2H), 3.09 (m, 2H). LCMS m/z 522.3 (M+H)$^+$.

Example 52

[4-(5-chloro-2-{(S)-1-[3-(5-chloro-2-tetrazol-1-yl-benzyl)-ureido]-2-phenyl-ethyl}-1H-imidazol-4-yl)-phenyl]-carbamic acid methyl ester, trifluoroacetic acid salt 52A. {4-[2-((S)-1-tert-butoxycarbonylamino-2-phenyl-ethyl)-1H-imidazol-4-yl]-phenyl}-carbamic acid methyl ester: To a mixture of 82D (4.66 g, 0.017 mol) and L-Boc-Phe-OH (3.78 g, 0.14 mol) in DMF (350 mL) at 0° C. was added in portions Cs$_2$CO$_3$ (10.2 g, 0.31 mol). After addition, the mixture was stirred at rt under N$_2$ for 3 h. Then the mixture was filtered through a pad of Celite®. The filtrate was concentrated and dried on vacuum to provide the crude keto ester which was dissolved in toluene (250 mL), and to this solution was added NH$_4$OAc (1.65 g, 0.21 mol). The resulting mixture was stirred at reflux under N$_2$ over night. The mixture was cooled to rt, washed with water, brine and dried over anhydrous Na$_2$SO$_4$. Chromatography purification on silica gel (5% to 50% EtOAc/hexane, gradient) yielded 52A as light brown solid. LCMS m/z 437.0 (M+H)$^+$.

52B. {4-[2-((S)-1-amino-2-phenyl-ethyl)-5-chloro-1H-imidazol-4-yl]-phenyl}-carbamic acid methyl ester, bis-trifluoroacetic acid salt: To a solution of 52A (436 mg, 1.0 mmol) in CHCl$_3$ (60 mL) was added NCS (134 mg, 1.0 mmol). The mixture was stirred at 60° C. under N$_2$ for 3 h. Then the mixture was cooled to rt, washed with water, 1N HCl, brine and dried over anhydrous Na$_2$SO$_4$. Purification on prep-TLC (40% EtOAc/hexane) yielded the desired product as light brown solid. LCMS m/z 471.4 (M+H)$^+$. This intermediate was deprotected with TFA in DCM to give 52B. LCMS m/z 371.2 (M+H)$^+$.

52C. Example 52 was prepared according to the procedure described for urea formation in Example 16 by the coupling of (5-chloro-2-(1H-tetrazol-1-yl)phenyl)methanamine (prepared according to a similar procedure of Young, M. B. et al. *J. of Med. Chem.* 2004, 47, 2995), with 52B and p-nitrophenyl-chloroformate. Reverse phase HPLC purification and lyophilization afforded Example 52 as a colorless solid. $^1$HNMR (CD$_3$OD, 400 MHz) δ: 9.39 (s, 1H), 7.49-7.37 (m, 4H), 7.18-7.03 (m, 7H), 4.92 (t, 1H), 4.05 (q(AB), 2H), 3.65 (s, 3H), 3.19 (d, 2H). LCMS m/z 606.15 (M+H)$^+$.

Example 53

1-[6-(5-chloro-2-{(S)-1-[3-(5-chloro-2-tetrazol-1-yl-benzyl)-ureido]-2-phenyl-ethyl}-1H-imidazol-4-yl)-1H-indazol-3-yl]-3-(5-chloro-2-pentazol-1-yl-benzyl)-urea, trifluoroacetic acid salt Example 53 was prepared according to the procedure for urea formation described for Example 16 using excess (5-chloro-2-(1H-tetrazol-1-yl)phenyl)methanamine and (S)-6-(2-(1-amino-2-phenylethyl)-5-chloro-1H-imidazol-4-yl)-1H-indazol-3-amine. Reverse phase HPLC purification and lyophilization the bisurea product as a colorless solid. $^1$HNMR (CD$_3$OD, 400 MHz) δ: 9.51 (s, 1H), 9.40 (s, 1H), 8.29 (s, 1H), 7.71 (t, 2H), 7.51-7.30 (m, 6H), 7.21-7.05 (m, 5H), 4.99 (t, 1H), 4.31 (s, 2H), 4.07 (q(AB), 2H), 3.20 (m, 2H). LCMS m/z 823.19 (M+H)$^+$.

Example 54

1-{(S)-1-[4-(3-amino-1H-indazol-6-yl)-5-chloro-1H-imidazol-2-yl]-2-phenyl-ethyl}-3-(5-chloro-2-[1,2,4]triazol-1-yl-benzyl)-urea, trifluoroacetic acid salt Example 54 was prepared according to the procedure described for Example 16 from (5-chloro-2-(1H-1,2,4-triazol-1-yl)phenyl)methanamine. $^1$HNMR (CD$_3$OD, 400 MHz) δ: 8.66 (s, 1H), 8.13 (s, 1H), 7.87 (d, J=8.6 Hz, 1H), 7.59 (m, 1H), 7.42 (m, 2H), 7.22-7.04 (m, 7H), 4.97 (t, 1H), 4.08 (q, 1H), 3.20 (m, 2H). LCMS m/z 587.2 (M+H)$^+$.

Example 55

[4-(5-chloro-2-{(S)-1-[3-(5-chloro-2-methanesulfonyl-benzyl)-ureido]-2-phenyl-ethyl}-1H-imidazol-4-yl)-phenyl]-carbamic acid 2-methoxy-ethyl ester, trifluoroacetic acid salt Example 55 was prepared by the oxidation of Example 46 with mCPBA in dichloromethane. Reverse phase HPLC purification and lyophilization afforded Example 55 as a colorless solid. $^1$HNMR (CD$_3$OD, 400 MHz) δ: 7.94 (d, J=8.2 Hz, 1H), 7.53-7.48 (m, 6H), 7.29-7.11 (m, 5H), 5.06 (t, 1H), 4.62 (q(AB), 2H), 4.28 (m, 2H), 3.64 (m, 2H), 3.38 (s, 3H), 3.20 (d, 2H), 3.16 (s, 3H). LCMS m/z 660.14 (M+H)$^+$.

Example 56

[4-(2-{(S)-1-[3-(2-benzylsulfanyl-5-chloro-benzyl)-ureido]-2-phenyl-ethyl}-5-chloro-1H-imidazol-4-yl)-phenyl]-carbamic acid methyl ester, trifluoroacetic acid salt Example 56 was prepared according to the procedure described for Example 16 from (2-(benzylthio)-5-chlorophenyl)methanamine and 52B. Reverse phase HPLC purification and lyophilization afforded Example 56 as a colorless solid. $^1$HNMR (CD$_3$OD, 400 MHz) δ: 7.52 (m, 5H), 7.30-7.15 (m, 12H), 5.08 (t, 1H), 4.24 (q(AB), 2H), 4.06 (s, 2H), 3.74 (s, 3H), 3.20 (m, 2H). LCMS m/z 660.16 (M+H)$^+$.

Example 57

[4-(5-chloro-2-{(S)-1-[3-(5-chloro-2-methanesulfonylamino-benzyl)-ureido]-2-phenyl-ethyl}-1H-imidazol-4-yl)-phenyl]-carbamic acid 2-methoxy-ethyl ester, trifluoroacetic acid salt Example 57 was prepared from N-(2-(aminomethyl)-4-chlorophenyl)methanesulfonamide hydrochloride and 43A according to the procedure described for Example 16. Reverse phase HPLC purification and lyophilization afforded Example 57 as a colorless solid. $^1$HNMR (CDCl$_3$, 400 MHz) δ: 7.44 (bs, 4H), 7.30 (d, J=8.5 Hz, 1H), 7.23-7.03 (m, 7H), 5.00 (t, 1H), 4.23-4.17 (m, 4H), 3.57-3.54 (m, 2H), 3.30 (s, 3H), 3.10 (d, J=7.7 Hz, 2H), 2.82 (s, 3H). LCMS m/z 675.2 (M+H)$^+$.

Example 58

1-{(S)-1-[4-(3-amino-1H-indazol-6-yl)-5-chloro-1H-imidazol-2-yl]-2-phenyl-ethyl}-3-(2-benzylsulfanyl-5-chloro-benzyl)-urea, trifluoroacetic acid salt Example 58 was prepared according to the procedure described for Example 16 from (2-(benzylthio)-5-chlorophenyl)methanamine. $^1$HNMR (CD$_3$OD, 400 MHz) δ: 7.81 (d, J=9.3 Hz, 1H), 7.56 (s, 1H), 7.36 (dd, J=2.3 & 10.3 Hz, 1H), 7.21-7.04 (m, 13H), 5.01 (t, 1H), 4.29 (q(AB), 2H), 3.97 (s, 2H), 3.10 (m, 2H). LCMS m/z 642.4 (M+H)$^+$.

Example 59

[4-(5-Chloro-2-{(S)-1-[3-(5-chloro-thiophen-3-ylmethyl)-ureido]-2-phenyl-ethyl}-1H-imidazol-4-yl)-phenyl]-carbamic acid methyl ester, trifluoroacetic acid salt 59A. (5-chloro-thiophen-3-yl)-methanol: Borane-tetrahydrofuran complex (2.306 mL, 2.306 mmol) was syringed into a THF (4 mL) solution of 5-chlorothiophene-3-carboxylic acid (250 mg, 1.538 mmol). The resultant mixture was stirred at rt overnight. The reaction mixture was quenched with HCl (0.5N, 10 mL) and allowed to stir at rt for 1 h. It was further quenched with water (20 mL). The organics were extracted with EtOAc (2×20 mL), washed with NaOH (1N, 20 mL) and brine (2×15 mL), dried (Na$_2$SO$_4$), filtered and evaporated to a crude product, which was purified by silica gel chromatography (EtOAc-Hex: 0-50% EtOAc 15 min gradient) yielding 59A (188 mg) as an oil. LCMS m/z 130.8 (M−H$_2$O+H)$^+$. $^1$HNMR (CD$_3$OD, 400 MHz) δ: 4.49 (s, 2H), 6.94 (d, J=1.76 Hz, 1H), 7.09 (s, 1H).

59B. 4-bromomethyl-2-chloro-thiophene: PBr$_3$ (0.140 mL, 1.487 mmol) was syringed into a clear solution of 59A (170 mg, 1.144 mmol) in DCM (5 mL). The resultant mixture was stirred at rt for 15 min. The mixture was quenched with water (15 mL), and stirred at rt for 1 h. The organics were extracted with DCM (2×10 mL), dried (Na$_2$SO$_4$), filtered and concentrated to a colorless oil (224 mg) which was used directly in the next step. $^1$HNMR (CD$_3$OD, 400 MHz) δ: 4.48 (s, 2H), 7.02 (s, 1H), 7.27 (s, 1H).

59C. 4-azidomethyl-2-chloro-thiophene: 59B (220 mg, 1.040 mmol) was dissolved in DMF (4 mL). Sodium azide (0.366 mL, 10.40 mmol) was added to this solution. The reaction mixture was stirred at rt for 16 h. The mixture was quenched with water (30 mL), and the organics were extracted with EtOAc (25 mL), washed with brine, dried (Na$_2$SO$_4$), filtered and concentrated to a colorless oil (168 mg) which was used directly in the next step. $^1$HNMR (CD$_3$OD, 400 MHz) δ: 4.28 (s, 2H), 6.98 (d, J=4.83 Hz, 1H), 7.24 (s, 1H).

59D. 5-chloro-(thiophen-3-yl)-methylamine: 10% palladium on carbon was added to a solution of 59C (80 mg, 0.415 mmol) in MeOH (5 mL). The resultant mixture was stirred under a hydrogen balloon for 40 min. The catalyst was removed by filteration through Celite®. The filtrate was concentrated to a colorless oil. The oil was dissolved in HCl (0.5N, 7 mL), and washed with EtOAc (10 mL). The aqueous layer was basified with NaOH (1N) and extracted with EtOAc (3×10 mL). The combined extracts were washed with brine, dried (Na$_2$SO$_4$), filtered and concentrated to a colorless oil (32 mg) which was used directly in the next step. LCMS m/z 148.0 (M+H)$^+$. $^1$HNMR (CD$_3$OD, 400 MHz) δ: 3.70 (s, 2H), 6.97 (s, 1H), 7.05 (s, 1H).

59E. Example 59 was prepared according to the procedure for urea formation described for Example 16 by coupling of 59D with 52B. Purification via reverse phase HPLC (acetonitrile/water and 0.05% TFA), and lyophilization of the pure fraction afforded Example 59 as a colorless solid. LCMS m/z 544.2 (M+H)$^+$. $^1$HNMR (CD$_3$OD, 400 MHz) δ: 3.12-3.22 (m, 2H), 3.74 (s, 3H), 4.15 (q, J=13.18 Hz, 2H), 5.08 (t, J=7.69 Hz, 1H), 6.81 (s, 1H), 6.90 (s, 1H), 7.15 (d, J=6.59 Hz, 2H), 7.24 (m, 3H), 7.52 (s, 4H).

Example 60

(4-{5-chloro-2-[(S)-2-phenyl-1-(3-thiophen-3-ylmethyl-ureido)-ethyl]-1H-imidazol-4-yl}-phenyl)-carbamic acid methyl ester, trifluoroacetic acid salt Example 60 was prepared according to the procedure described for urea formation in Example 16 from thiophen-3-ylmethanamine and 52B. Purification via reverse phase HPLC (acetonitrile/water and 0.05% TFA), lyophilization of the pure fraction afforded Example 60 as a colorless solid. LCMS m/z 510.2 (M+H)$^+$. $^1$HNMR (CDCl$_3$/CD$_3$OD, 400 MHz) δ: 3.09 (d, J=7.91 Hz, 2H), 3.72 (s, 3H), 4.15-4.25 (m, 2H), 5.02 (t, J=7.91 Hz, 1H), 6.85 (d, J=5.27 Hz, 1H), 6.93 (s, 1H), 7.04 (d, J=6.59 Hz, 2H), 7.12-7.20 (m, 4H), 7.33-7.44 (m, 4H).

Example 61

(4-{5-chloro-2-[(S)-1-(3-1H-imidazol-4-yl-propionylamino)-2-phenyl-ethyl]-1H-imidazol-4-yl}-phenyl)-carbamic acid methyl ester, trifluoroacetic acid salt Example 61 was prepared according to the procedure described for 3A from commercially available 3-(1H-imidazol-4-yl)propanoic acid and 52B. Purification via reverse phase HPLC (acetonitrile/water and 0.05% TFA), lyophilization of the pure fraction afforded Example 61 as a colorless solid. LCMS m/z 493.2 (M+H)$^+$. $^1$HNMR (CD$_3$OD, 400 MHz) δ: 2.54-2.65 (m, 2H), 2.94 (d, J=5.27 Hz, 2H), 3.08-3.12 (m, 1H), 3.20-3.28 (m, 1H), 3.75 (s, 3H), 5.17-5.21 (m, 1H), 7.14-7.27 (m, 6H), 7.49-7.56 (m, 4H), 8.74 (s, 1H).

Example 62

[4-(5-chloro-2-{(S)-1-[(E)-3-(5-chloro-2-tetrazol-1-yl-phenyl)-acryloylamino]-2-phenyl-ethyl}-1H-imidazol-4-yl)-phenyl]-carbamic acid methyl ester, trifluoroacetic acid salt 62A. (E)-3-(5-chloro-2-tetrazol-1-yl-phenyl)-acrylic acid methyl ester: To a cooled (0° C.) suspension of NaH (0.262 g, 6.56 mmol) in THF (27.3 mL) was added dropwise methyl 2-(dimethoxyphosphoryl)-acetate (1.150 mL, 7.10 mmol). The resulting thick, white suspension was diluted with additional THF (15 mL) to facilitate mixing, then allowed to warm to rt and stirred at rt for 45 min. Next, a slightly cloudy blue solution of 5-chloro-2-tetrazol-1-yl-benzaldehyde (1.14 g, 5.46 mmol), prepared according to a modification of the procedure described by Howard (*J. Med. Chem.*, 2006, 49, 1346.), in THF (8 mL) was added. The yellow/green suspension was stirred vigorously. After 30 min, the reaction was poured into cold sat. ammonium chloride and extracted with EtOAc. The combined organic layers were washed with brine, dried over Na$_2$SO$_4$, filtered and concentrated to give a green/blue solid weighing 1.76 g. The solid was dissolved in EtOAc and filtered through a plug of silica gel, eluting with EtOAc. The green filtrate was concentrated to give a greenish solid weighing 1.36 g. Recrystallization from EtOAc gave an off-white solid weighing 0.476 g. Additional product was obtained by concentrating the filtrate from recrystallization, adding methanol, sonicating, and collecting the solid product by filtration. A total of 0.829 g (57%) of 62A was obtained. LCMS m/z 265.1 (M+H)$^+$; 287.2 (M+Na)$^+$. $^1$HNMR (CDCl$_3$, 500 MHz) δ: 8.80 (s, 1H), 7.78 (d, J=2.2 Hz, 1H), 7.58 (dd, J=8.8, 2.2 Hz, 1H), 7.42 (d, J=8.2 Hz, 1H), 7.25 (d, J=16.0 Hz, 1H), 6.45 (d, J=16.0 Hz, 1H), 3.78 (s, 3H).

62B. (E)-3-(5-chloro-2-tetrazol-1-yl-phenyl)-acrylic acid: To a white suspension of 62A (0.140 g, 0.529 mmol) in MeOH (3.0 mL) was added 1.0 M sodium hydroxide (1.587 ml, 1.587 mmol). The resulting suspension was stirred vigorously at rt for 2.5 h. The yellow suspension was neutralized with 1.0 N HCl (1.60 mL), and concentrated to give a beige solid. The solid was partitioned between 1.0 N HCl and EtOAc, and the layers were separated. The organic layer was washed with brine, dried over Na$_2$SO$_4$, filtered and concentrated to give 0.137 g (100%) of 62B as a white solid. LCMS m/z 251.1 (M+H)$^+$. $^1$HNMR (500 MHz, DMSO-d$_6$) δ: 12.72 (s, 1H), 9.87 (s, 1H), 8.24 (d, J=2.2 Hz, 1H), 7.77 (dd, J=8.8, 2.2 Hz, 1H), 7.73 (d, J=8.2 Hz, 1H), 6.98 (d, J=16.0 Hz, 1H), 6.70 (d, J=16.0 Hz, 1H).

Alternatively, 62B can be prepared as follows. To a cold suspension (0-5° C.) of 4-chloro-2-iodoaniline (10.0 g, 39.5 mmol) and sodium azide (7.95 g, 122 mmol) in trimethyl orthoformate (13.08 mL, 118 mmol) was added acetic acid (150 mL). The resulting clear, slightly brown solution was stirred vigorously at 0-5° C. for 30 min and then warmed to rt. A beige precipitate formed overtime and then redissolved to give a clear brown solution. After 22 h, water (400 mL) was added and the suspension was stirred vigorously for 1 h. The solid was collected by filtration, rinsed with water, air-dried, and dried under vacuum to give 11.16 g (92%) of 1-(4-chloro-2-iodo-phenyl)-1H-tetrazole as a beige solid. LCMS m/z 307.0. (M+H)$^+$. A flame-dried sealed tube vessel containing this intermediate (0.250 g, 0.816 mmol) and palladium acetate (0.018 g, 0.082 mmol) was purged with argon for several minutes. Next degassed acetonitrile (3.26 mL) was added followed by the addition of ethyl acrylate (0.133 mL, 1.224 mmol) and triethylamine (0.171 mL, 1.224 mmol). The vessel was sealed and the orange brown solution was warmed to 85° C. to give a brown suspension. After 21 h, the reaction was stopped and cooled to rt. The reaction was filtered through a 0.45 micron Glass microfibre (GMF), rinsing with acetonitrile, and the filtrate was concentrated to give a brown residue. Flash chromatography gave 0.098 g (43%) of (E)-3-(5-chloro-2-tetrazol-1-yl-phenyl)-acrylic acid ethyl ester as a pale yellow solid. LCMS m/z 279.1 (M+H)$^+$ and 281 (M+2+H)$^+$. Saponification as described above gave 62B.

62C. Example 62: To vial containing 62B (0.030 g, 0.120 mmol), the free base of 52B (0.044 g, 0.120 mmol), EDC (0.029 g, 0.150 mmol), and HOBt (0.023 g, 0.150 mmol) was added DMF (0.399 mL) and Hunig's base (0.042 mL, 0.239 mmol). The resulting clear, yellow solution was stirred at rt for 6 h. The reaction was diluted with water to give a suspension and then extracted with EtOAc (2 x). The combined organic layers were washed with 1.0 N HCl, sat. NaHCO$_3$, brine, dried over Na$_2$SO$_4$, filtered and concentrated. Purification by prep reverse phase HPLC (MeOH:water:0.1% TFA) and lyophilization gave Example 62 (0.053 g, 62%) as a fluffy off-white solid. LCMS m/z 603.1 (M+H)$^+$. $^1$HNMR (400 MHz, CD$_3$OD) δ: 9.50 (s, 1H), 7.96 (d, J=2.2 Hz, 1H), 7.65 (dd, J=8.6, 2.7 Hz, 1H), 7.55 (d, J=8.8 Hz, 1H), 7.51-7.47 (m, 4H), 7.27-7.16 (m, 5H), 7.08 (d, J=15.4 Hz, 1H), 6.71 (d, J=15.4 Hz, 1H), 5.24 (t, J=7.9 Hz, 1H), 3.74 (s, 3H), 3.30-3.20 (m, 2H).

Example 63

[4-(5-chloro-2-{(S)-1-[3-(5-chloro-2-tetrazol-1-yl-phenyl)-propionylamino]-2-phenyl-ethyl}-1H-imidazol-4-yl)-phenyl]-carbamic acid methyl ester, trifluoroacetic acid salt 63A. 3-(5-chloro-2-tetrazol-1-yl-phenyl)-propionic acid: To a suspension of 62B (0.030 g, 0.120 mmol) in MeOH (5.0 mL) was added platinum oxide (0.005 g, 0.022 mmol). Hydrogen from a balloon was bubbled through the reaction for 1-2 min and then the reaction was stirred vigorously under a hydrogen atmosphere. Additional amounts of platinum oxide (0.010 g, 0.044 mmol) were added over the course of the reaction. After 27 h, the reaction was filtered, and the filtrate was concentrated to give a brown residue. The residue was dissolved in MeOH, refiltered, and the filtrate was concentrated to give 0.025 g (83%) of 63A as a clear colorless residue. LCMS m/z 253.1 (M+H)$^+$. $^1$HNMR (400 MHz, CD$_3$OD) δ: 9.51 (s, 1H), 7.63 (d, J=2.2 Hz, 1H), 7.48 (dd, J=8.8, 2.2 Hz, 1H), 7.43 (d, J=8.8 Hz, 1H), 2.72 (t, J=7.5 Hz, 2H), 2.55 (t, J=7.5 Hz, 2H).

An alternative synthesis of 63A is as follows. To a clear, slightly green solution of 62A (0.617 g, 2.331 mmol) in EtOAc (46.6 mL) was added platinum (IV) oxide (0.106 g, 0.466 mmol). After a series of vacuum flushes, the vessel was pressurized with hydrogen to 60 psi, and the suspension was stirred vigorously. After 24 h, the reaction was stopped and the pressure was released. The reaction was filtered through a plug of Celite®/silica gel, eluting with EtOAc, to give a pale, green solution. Concentration gave a greenish-black oil weighing 0.705 g. Flash chromatography gave 0.572 g (92%) of 3-(5-chloro-2-tetrazol-1-yl-phenyl)-propionic acid methyl ester as a clear, colorless viscous oil. LCMS m/z 267.1 (M+H)$^+$. Saponification according to the procedure for 62B gave 63A.

63B. Example 63 was prepared by coupling 63A with the free base of 52B according to procedure described for 62C. LCMS m/z 605.2 (M+H)$^+$. $^1$HNMR (400 MHz, CD$_3$OD) δ: 9.43 (s, 1H), 7.54-7.48 (m, 5H), 7.43 (dd, J=8.4, 2.2 Hz, 1H), 7.38 (d, J=8.3 Hz, 1H), 7.22-7.15 (m, 3H), 7.11 (d, J=8.4 Hz, 2H), 5.11 (t, J=7.9 Hz, 1H), 3.74 (s, 3H), 3.18 (dd, J=13.6, 7.9 Hz, 1H), 3.10 (dd, J=13.6, 7.9 Hz, 1H), 2.68-2.64 (m, 2H), 2.47-2.43 (m, 2H).

Example 64

[4-(6-{1-[3-(5-methyl-2-tetrazol-1-yl-benzyl)-ureido]-2-phenyl-ethyl}-2-oxo-1,2-dihydro-pyridin-4-yl)-phenyl]-carbamic acid methyl ester 64A. {1-[4-(4-Nitro-phenyl)-6-oxo-1,6-dihydro-pyridin-2-yl]-2-phenyl-ethyl}-carbamic acid tert-butyl ester: A suspension of ((S)-3-tert-butoxycarbonylamino-2-oxo-4-phenyl-butyl)-phosphonic acid dimethyl ester (1.114 g, 3 mmol, Resmini, M. et al., *Tetrahedron Asymmetry*, 2004, 15, 1847.), 4-nitrobenzaldehyde (0.453 g, 3 mmol) and potassium carbonate (0.415 g, 3 mmol) in ethanol (60 mL) was stirred at rt for 5 h. The reaction mixture was diluted with EtOAc, washed with water, brine, and dried over Na$_2$SO$_4$, filtered and concentrated to give 1.276 g of [(E)-(S)-1-benzyl-4-(4-nitro-phenyl)-2-oxo-but-3-enyl]-carbamic acid tert-butyl ester as a yellow solid. This yellow solid was suspended in ethanol (30 mL), then 1-ethoxycarbonylmethyl-pyridinium chloride (0.605 g, 3 mmol) and ammonium acetate (4.63 g, 60 mmol) were added. The reaction mixture was stirred at rt for 10 min, then heated at 80° C. for 5 h to yield a white suspension. The reaction was cooled to rt and the solid was collected by filtration, washed with methanol, and dried in vacuo (50° C.) to give 0.85 g (62%) of 64A as a white solid. LCMS m/z 436.3 (M+H)$^+$. $^1$HNMR (400 MHz, DMSO-D$_6$) δ: 1.26 (s, 9H), 2.76-2.82 (m, 1H), 3.01-3.06 (m, 1H), 4.68-4.74 (m, 1H), 6.54-6.60 (m, 2H), 7.18-7.29 (m, 5H), 7.40 (d, J=9.2 Hz, 1H), 7.91 (d, J=8.8 Hz, 2H), 8.34 (d, J=8.8 Hz, 2H), 11.96 (s, 1H).

64B. {4-[6-(1-Amino-2-phenyl-ethyl)-2-oxo-1,2-dihydro-pyridin-4-yl]-phenyl}-carbamic acid methyl ester: To a suspension of 64A (0.956 g, 2.2 mmol) in MeOH (44 mL) were added zinc dust (1.436 g, 22 mmol) and ammonium chloride (0.235 g, 4.4 mmol). The reaction mixture was stirred at 60° C. for 2 h, filtered, and the filtrate concentrated to give the aniline. LC/MS m/z 406.3 (M+H)$^+$. The aniline was suspended in dichloromethane (10 mL), then pyridine (0.35 mL, 4.4 mmol) and methyl chloroformate (0.25 mL, 3.3 mmol) were added. The reaction mixture was stirred at rt. After 30 min, the reaction was diluted with dichloromethane, washed with water and brine, dried over Na$_2$SO$_4$, filtered, and concentrated to give a residue. To a cooled solution (0° C.) of the residue in MeOH (10 mL) was added 1 N NaOH (2 mL). After 30 min, the reaction was mixture was quenched with 1 N HCl (2.4 mL) to give a suspension. The solid was collected by filtration, washed with water, and dried in vacuo (50° C.). The filtrate was extracted with dichloromethane. The combined organic layers were dried over MgSO$_4$, filtered, and concentrated. A total of 0.7 g solid was obtained. LC/MS m/z 464.4 (M+H)$^+$. This solid was treated with 50% TFA/DCM (10 mL) at rt for 1 h and concentrated. Purification by reverse phase HPLC gave a solid. The solid was dissolved in 25% i-PrOH/CHCl$_3$, washed with sat'd NaHCO$_3$ and brine, dried over Na$_2$SO$_4$, filtered, and concentrated to give 0.45 g (56%) of 64B. The enantiomers of 64B can be separated by chiral HPLC (Chiralcel OD). LC/MS m/z 364.3 (M+H)$^+$. $^1$HNMR (500 MHz, CD$_3$OD) δ: 3.22-3.31 (m, 2H), 3.75 (s, 3H), 4.52-4.55 (m, 1H), 6.78-6.79 (m, 2H), 7.17 (d, J=7.2 Hz, 2H), 7.25-7.32 (m, 3H), 7.50-7.56 (m, 4H). Enantiomer A: [α]$_D^{25}$+30.1 (c=0.19, MeOH). Enantiomer B: [α]$_D^{25}$−340.1 (c=1.07, MeOH).

64C. Example 64 was prepared by coupling 64B (enantiomer A) and 168D according to the procedure for the urea formation described in Example 16. LCMS m/z 579.3 (M+H)$^+$. $^1$HNMR (400 MHz, DMSO-d$_6$) δ: 2.20 (s, 3H), 2.85 (dd, J=9.9 Hz, 13.7 Hz, 1H), 3.06 (dd, J=4.9 Hz, 13.7 Hz, 1H), 3.68 (s, 3H), 3.84-3.98 (m, 2H), 4.75-4.81 (m, 1H), 6.43-6.44 (m, 2H), 6.64-6.60 (m, 2H), 7.15-7.29 (m, 8H), 7.34 (d, J=7.7 Hz, 1H), 7.56 (s, 4H), 9.72 (s, 1H), 9.87 (s, 1H).

Example 65

(S)-1-(3-chloro-2-fluorobenzyl)-3-(1-(5-chloro-4-(4-hydroxy-2-oxo-1,2-dihydroquinolin-6-yl)-1H-imidazol-2-yl)-2-phenylethyl)urea, trifluoroacetic acid salt 65A. (S)-2-(4-nitrophenyl)-2-oxoethyl 2-(tert-butoxycarbonylamino)-3-phenylpropanoate: To a solution of N-Boc-(S)-phenylalanine (12.16 g, 47.5 mmol) in DMF (100 mL) was added at rt potassium carbonate (6.60 g, 47.5 mmol) and 2-bromo-1-(4-nitrophenyl)ethanone (11.6 g, 47.5 mmol). The mixture was allowed to stir at rt under nitrogen for 5 h. The reaction mixture was diluted with ethyl acetate, washed with 1N HCl and brine. The organic phase was dried over magnesium sulfate, filtered, and solvent was removed to provide a light yellow solid. ¹HNMR (400 MHz, CDCl₃) δ: 1.40 (s, 9H), 3.12 (dd, J=14.06, 7.47 Hz, 1H), 3.32 (dd, J=14.06, 5.71 Hz, 1H), 4.73 (q, J=7.03 Hz, 1H), 5.01 (d, J=8.35 Hz, 1H), 5.32 (d, J=16.26 Hz, 1H), 5.48 (d, J=16.70 Hz, 1H), 7.23-7.33 (m, 5H), 8.07 (d, J=8.79 Hz, 2H), 8.33 (d, J=8.79 Hz, 2H). LCMS: m/z 329.07 (M+H-Boc)⁺.

65B. (S)-tert-butyl 1-(4-(4-nitrophenyl)-1H-imidazol-2-yl)-2-phenylethylcarbamate: To a solution of 65A (21.6 g, 47.5 mmol) in m-xylene (250 mL) was added ammonium acetate (18.3 g, 238 mmol). The reaction was allowed to stir at 140° C. for 1 h. The reaction was cooled to rt and solvent was removed under reduced pressure. The residue was taken up into ethyl acetate, which was washed with 1N HCl, saturated sodium bicarbonate and brine. The organic phase was dried over magnesium sulfate, filtered and concentrated. The crude product was purified by flash chromatography (silica gel, ethyl acetate/hexanes 0-50% gradient) to give the pure product. ¹HNMR (400 MHz, CDCl₃) δ: 1.41 (s, 9H), 3.12-3.48 (m, 2H), 4.91 (db, J=6.59 Hz, 1H), 5.37 (d, J=7.47 Hz, 1H), 7.04-7.37 (m, 5H), 7.90 (d, J=8.79 Hz, 2H), 8.22 (d, J=8.79 Hz, 2H), 10.18 (sb, broad, 1H). LCMS: m/z 409.08 (M+H)⁺.

65C. (S)-tert-butyl 1-(5-chloro-4-(4-nitrophenyl)-1H-imidazol-2-yl)-2-phenylethylcarbamate: To a solution of 65B (11.24 g, 27.5 mmol) in chloroform (400 mL) was added at rt NCS (3.68 g, 27.5 mmol). The reaction was allowed to stir at rt for 24 h. The solvent was removed and the crude product was purified by flash chromatography (silica gel, ethyl acetate/hexanes 0-30% gradient) to give 65C as a light yellow solid. ¹HNMR (400 MHz, CDCl₃) δ: 1.36 (s, 9H), 3.06-3.42 (m, 2H), 4.94 (d, J=7.03 Hz, 1H), 5.48 (d, J=5.27 Hz, 1H), 7.11 (d, J=6.59 Hz, 2H), 7.18-7.34 (m, 3H), 7.50 (d, J=6.59 Hz, 2H), 8.17 (d, J=8.79 Hz, 2H), 11.25 (s, 1H). LCMS m/z 443.00 (M+H)⁺.

65D. (S)-tert-butyl 1-(4-(4-aminophenyl)-5-chloro-1H-imidazol-2-yl)-2-phenylethylcarbamate: To a degassed solution of 65C (7.86 g, 17.8 mmol) in EtOH/MeOH/EtOAc (150 mL/100 mL/50 mL) was added a slurry of Raney-Ni (Aldrich 2400 slurry in water, 3 mL). Hydrogen was supplied by a hydrogen balloon and the reaction was stirred at rt. After about 8 h, the reaction was complete as shown by LCMS. The reaction was degassed and purged with nitrogen. The catalyst was filtered, and the solvent was removed to give 65D as a brown solid. LCMS m/z 413.04 (M+H)⁺.

65E. (S)-methyl 3-(4-(2-(1-(tert-butoxycarbonylamino)-2-phenylethyl)-5-chloro-1H-imidazol-4-yl)phenylamino)-3-oxopropanoate: To a solution of 65D (8.15 g, 19.74 mmol) in CH₂Cl₂ (200 mL) were added TEA (4.13 ml, 29.6 mmol) and methyl 3-chloro-3-oxopropanoate (2.96 g, 21.71 mmol) at 0° C. The reaction mixture was stirred under nitrogen at 0° C. for 4 h. The reaction mixture was diluted with CH₂Cl₂, washed with 1M HCl (2×50 mL), sat NaHCO₃ (1×50 mL) and sat NaCl (1×50 mL). The organic phase was dried over Na₂SO₄, filtered and concentrated to give a light orange solid (10.1 g, 100%). ¹HNMR (400 MHz, CDCl₃) δ: 1.35 (s, 9H), 3.33 (s, broad, 2H), 3.52 (s, 2H), 3.80 (s, 3H), 4.98 (broad, 1H), 7.08-7.30 (m, 5H), 7.45-7.63 (m, 4H), 9.40 (s, 1H). LCMS m/z 513.06 (M+H)⁺.

65F. (S)-3-(4-(2-(1-(tert-butoxycarbonylamino)-2-phenylethyl)-5-chloro-1H-imidazol-4-yl)phenylamino)-3-oxopropanoic acid: To a solution of 65E (10.1 g, 19.69 mmol) in MeOH (120 mL) and water (30 mL) was added sodium carbonate (3.13 g, 29.5 mmol) at rt. The red reaction mixture was stirred under nitrogen at rt for 2 days. The reaction mixture was neutralized with 1M HCl (60 mL) and added to water (~1000 mL) to form a white precipitate, which was collected by filtration to provide 65F (8.11 g, 83%). LCMS m/z 499.02 (M+H)⁺.

65G. (S)-6-(2-(1-amino-2-phenylethyl)-5-chloro-1H-imidazol-4-yl)-4-hydroxyquinolin-2(1H)-one: To a well ground powder of 65F (2.60 g, 5.21 mmol) was added PPA (24.27 mL, 5.21 mmol) and the sticky suspension was stirred at 130° C. for 5 h resulting in a clear reaction mixture. The mixture was cooled to rt and poured carefully onto 200 mL ice-water to form a precipitate, which was collected by filtration to provide 65G (2.20 g). LCMS m/z 381.08 (M+H)⁺.

65H. (S)-6-(5-chloro-2-(1-isocyanato-2-phenylethyl)-1H-imidazol-4-yl)-4-hydroxyquinolin-2(1H)-one: To a solution of 65G (1.98 g, 5.21 mmol) in DMF (100 mL) was added sodium carbonate (2.76 g, 26.1 mmol) and 4-nitrophenyl chloroformate (1.26 g, 6.25 mmol) at 0° C. The reaction mixture was stirred under nitrogen at 0° C. for 1.5 h. Another portion of 4-nitrophenyl chloroformate (1.26 g, 6.25 mmol) was added. Stirring was continued at rt for 48 h. The reaction was filtered and filtrate was diluted with ethyl acetate, which was washed with 1M HCl (2×50 mL) and sat NaCl (1×50 mL). Solvent was removed from organic phase. The crude product was purified by flash chromatography (silica gel, eluting with MeOH/CH₂Cl₂ 0% to 20% to 20% gradient). The solvent was removed to provide a white solid. LCMS m/z 407.18 (M+H)⁺.

65I. Example 65: To a solution of (3-chloro-2-fluorophenyl)methanamine (70 mg, 0.439 mmol) in DMF (1 ml) was added pyridine (0.1 mL, 1.236 mmol) and 65H (40 mg, 0.098 mmol) at rt. The reaction mixture was stirred under nitrogen at rt for 5 h. The crude product was purified by HPLC (CH₃CN/H₂O with 0.1% TFA). The solvent was removed from the desired fraction and the product was lyophilized to give Example 65 (43.8 mg, 65.5%) as a white solid. ¹HNMR (400 MHz, CD₃OD) δ: 3.20 (dd, J=7.69, 2.42 Hz, 2H), 4.34 (dd, 2H), 5.10 (t, J=7.69 Hz, 1H), 5.95 (s, 1H), 7.07 (t, J=7.69 Hz, 1H), 7.13-7.18 (m, 3H), 7.21-7.29 (m, 3H), 7.31-7.35 (m, 1H), 7.41 (d, J=8.35 Hz, 1H), 7.84 (dd, J=8.79, 2.20 Hz, 1H), 8.21 (d, J=1.76 Hz, 1H). LCMS m/z 566.14 (M+H)⁺.

Example 66

(S)-1-(1-(5-chloro-4-(4-hydroxy-2-oxo-1,2-dihydro-quinolin-6-yl)-1H-imidazol-2-yl)-2-phenylethyl)-3-(2-fluoro-3-(trifluoromethyl)benzyl)urea, trifluoro-acetic acid salt Example 66 was prepared following a procedure similar to that described for Example 65. ¹HNMR (400 MHz, CD₃OD) δ: 3.22 (d, J=7.91 Hz, 2H), 4.38 (dd, 2H), 5.12 (t, J=7.69 Hz, 1H), 5.96 (s, 1H), 7.13-7.31 (m, 6H), 7.41 (d, J=8.79 Hz, 1H), 7.48 (t, J=7.03 Hz, 1H), 7.54 (t, J=7.25 Hz, 1H), 7.82 (dd, J=8.57, 1.98 Hz, 1H), 8.21 (d, J=1.32 Hz, 1H). LCMS m/z 600.26 (M+H)⁺.

Example 67

1-(5-Bromo-2-fluoro-benzyl)-3-{(S)-1-[5-chloro-4-(4-hydroxy-2-oxo-1,2-dihydro-quinolin-6-yl)-1H-imidazol-2-yl]-2-phenyl-ethyl}-urea, trifluoroacetic acid salt Example 67 was prepared following a procedure similar to that described for Example 65. ¹HNMR (400 MHz, CD₃OD) δ: 3.21 (d, J=7.91 Hz, 2H), 4.30 (dd, 2H), 5.09 (t, 1H), 5.95 (s, 1H), 7.00 (dd, J=9.67, 8.79 Hz, 1H), 7.15-7.23 (m, 3H), 7.28

(m, 2H), 7.36-7.43 (m, 3H), 7.83 (dd, J=8.57, 1.98 Hz, 1H) 8.21 (d, J=1.76 Hz, 1H). LCMS m/z 612.09 (M+H)$^+$.

Example 68

(S)-1-(1-(5-chloro-4-(4-hydroxy-2-oxo-1,2-dihydro-quinolin-6-yl)-1H-imidazol-2-yl)-2-phenylethyl)-3-(3-methylphenethyl)urea, trifluoroacetic acid salt Example 68 was prepared following a procedure similar to that described for Example 65. $^1$HNMR (400 MHz, CD$_3$OD) δ: 2.27 (s, 3H), 2.68 (t, J=7.03 Hz, 2H), 3.17 (d, J=7.47 Hz, 2H), 3.25-3.36 (overlapped with solvent peak, t, 2H), 5.07 (t, J=7.69 Hz, 1H), 5.95 (s, 1H), 6.89-7.02 (m, 3H), 7.08-7.31 (m, 6H), 7.41 (d, J=8.79 Hz, 1H), 7.84 (dd, J=8.79, 2.20 Hz, 1H), 8.22 (d, J=1.76 Hz, 1H). LCMS m/z 542.32 (M+H)$^+$.

Example 69

(S)-1-(1-(5-chloro-4-(4-hydroxy-2-oxo-1,2-dihydro-quinolin-6-yl)-1H-imidazol-2-yl)-2-phenylethyl)-3-(3-methoxybenzyl)urea, trifluoroacetic acid salt Example 69 was prepared following a procedure similar to that described for Example 65. $^1$HNMR (400 MHz, CD$_3$OD) δ: 3.21 (d, J=7.91 Hz, 2H), 3.73 (s, 3H), 4.25 (dd, 2H), 5.11 (t, J=7.69 Hz, 1H), 5.95 (s, 1H), 6.75-6.80 (m, 3H), 7.15-7.24 (m, 4H), 7.25-7.28 (m, J=7.03 Hz, 2H), 7.41 (d, J=8.79 Hz, 1H), 7.84 (dd, J=8.79, 2.20 Hz, 1H), 8.22 (d, J=1.76 Hz, 1H). LCMS m/z 544.24 (M+H)$^+$.

Example 70

(S)-1-(6-chloro-2-fluoro-3-methylbenzyl)-3-(1-(5-chloro-4-(4-hydroxy-2-oxo-1,2-dihydroquinolin-6-yl)-1H-imidazol-2-yl)-2-phenylethyl)urea, trifluoroacetic acid salt Example 70 was prepared following a procedure similar to that described for Example 65. $^1$HNMR (400 MHz, CD$_3$OD) δ: 2.21 (s, 3H), 3.17 (d, J=7.47 Hz, 2H), 4.40-4.50 (m, 2H), 5.06 (t, J=7.69 Hz, 1H), 5.94 (s, 1H) 7.11-7.15 (m, 4H), 7.18-7.27 (m, 3H), 7.40 (d, J=8.79 Hz, 1H), 7.81 (dd, J=8.79, 2.20 Hz, 1H), 8.20 (d, J=2.20 Hz, 1H). LCMS m/z 580.20 (M+H)$^+$.

Example 71

(S)-1-(1-(5-chloro-4-(4-hydroxy-2-oxo-1,2-dihydro-quinolin-6-yl)-1H-imidazol-2-yl)-2-phenylethyl)-3-(2-chloro-6-fluoro-3-methylbenzyl)urea, trifluoroacetic acid salt Example 71 was prepared following a procedure similar to that described for Example 65. $^1$HNMR (400 MHz, CD$_3$OD) δ: 2.33 (s, 3H), 3.17 (d, J=7.91 Hz, 2H), 4.43-4.52 (m, 2H), 5.06 (t, J=7.69 Hz, 1H), 5.94 (s, 1H), 6.97 (t, J=8.79 Hz, 1H), 7.13 (d, J=7.03 Hz, 2H), 7.17-7.27 (m, 4H), 7.40 (d, J=8.35 Hz, 1H), 7.81 (dd, J=8.79, 2.20 Hz, 1H), 8.20 (d, J=1.76 Hz, 1H). LCMS m/z 580.21 (M+H)$^+$.

Example 72

2-(2-{(S)-1-[4-(3-amino-1H-indazol-6-yl)-5-chloro-1H-imidazol-2-yl]-2-phenyl-ethylcarbamoyl}-ethyl)-4-chloro-N-phenyl-benzamide, trifluoroacetic acid salt 72A. 3-(5-chloro-2-phenylcarbamoyl-phenyl)-propionic acid: Ethyl 3-(5-chloro-2-(phenylcarbamoyl)phenyl)propanoate (0.287 g, 0.865 mmol) and lithium hydroxide (21 mg, 0.865 mmol) were stirred in THF (10 mL) with water (0.5 mL) for 2 days. The reaction was quenched with water and washed with EtOAc. The aqueous layer was acidified with 1N HCl and extracted with EtOAc (2×), dried (MgSO$_4$), and evaporated to give 72A (0.21 g, quantitative). LCMS m/z 304.3 (M+H)$^+$.

72B. Example 72 was prepared from 72A and 1E following the procedure outlined for Example 16. LCMS m/z 638.6 (M+H)$^+$. $^1$HNMR (400 MHz, CD$_3$OD) δ: 7.85 (d, J=8.0 Hz, 1H), 7.57 (m, 3H), 7.43 (dd, J=1.4 & 10.1 Hz, 1H), 7.34 (d, J=8.1 Hz, 1H), 7.31-7.02 (m, 10H), 5.09 (t, 1H), 3.2 (m, 2H), 3.00 (t, 2H), 2.55 (t, 2H).

Example 73

(S)-1-(5-chloro-2-fluorobenzyl)-3-(1-(5-chloro-4-(4-hydroxy-2-oxo-1,2-dihydroquinolin-6-yl)-1H-imidazol-2-yl)-2-phenylethyl)urea, trifluoroacetic acid salt Example 73 was prepared following a procedure similar to that described for Example 65. $^1$HNMR (400 MHz, CD$_3$OD) δ: 3.21 (d, J=7.47 Hz, 2H), 4.30 (dd, 2H), 5.09 (t, J=7.47 Hz, 1H), 5.94 (s, 1H), 7.05 (t, J=9.01 Hz, 1H), 7.16 (d, J=7.03 Hz, 2H), 7.20-7.29 (m, 5H), 7.41 (d, J=8.35 Hz, 1H), 7.84 (dd, J=8.57, 1.98 Hz, 1H), 8.22 (d, J=1.76 Hz, 1H). LCMS m/z 566.21(M+H)$^+$.

Example 74

(S)-1-(benzo[d][1,3]dioxol-5-ylmethyl)-3-(1-(5-chloro-4-(4-hydroxy-2-oxo-1,2-dihydroquinolin-6-yl)-1H-imidazol-2-yl)-2-phenylethyl)urea, trifluoroacetic acid salt Example 74 was prepared following a procedure similar to that described for Example 65. $^1$HNMR (400 MHz, CD$_3$OD) δ: 3.21 (d, J=7.47 Hz, 2H), 4.19 (dd, 2H), 5.11 (t, J=7.47 Hz, 1H), 5.89 (s, 2H), 5.95 (s, 1H), 6.65-6.72 (m, 3H), 7.16 (d, J=7.03 Hz, 2H), 7.20-7.30 (m, 3H), 7.41 (d, J=8.35 Hz, 1H), 7.83 (dd, J=8.57, 1.98 Hz, 1H), 8.22 (d, J=1.76 Hz, 1H). LCMS m/z 558.27 (M+H)$^+$.

Example 75

(S)-1-(1-(5-chloro-4-(4-hydroxy-2-oxo-1,2-dihydro-quinolin-6-yl)-1H-imidazol-2-yl)-2-phenylethyl)-3-((5-chlorothiophen-2-yl)methyl)urea, trifluoroacetic acid salt Example 75 was prepared following a procedure similar to that described for Example 65. $^1$HNMR (400 MHz, CD$_3$OD) δ: 3.20 (d, J=7.91 Hz, 2H), 4.33 (dd, 2H), 5.09 (t, J=7.69 Hz, 1H), 5.95 (s, 1H), 6.70 (d, J=3.95 Hz, 1H), 6.73-6.76 (m, 1H), 7.16 (d, J=7.03 Hz, 2H), 7.19-7.29 (m, 3H), 7.41 (d, J=8.79 Hz, 1H), 7.85 (dd, J=8.57, 1.98 Hz, 1H), 8.22 (d, J=1.76 Hz, 1H). LCMS m/z 554.31 (M+H)$^+$.

Example 76

(S)-1-(1-(5-chloro-4-(4-hydroxy-3-methyl-2-oxo-1,2-dihydroquinolin-6-yl)-1H-imidazol-2-yl)-2-phenylethyl)-3-(3-chlorobenzyl)urea, trifluoroacetic acid salt 76A. 4-nitrophenyl 3-chlorobenzylcarbamate: To a solution of (3-chlorophenyl)methanamine (600 mg, 4.24 mmol) in $CH_2Cl_2$ (10 mL) was added pyridine (0.377 mL, 4.66 mmol) and 4-nitrophenyl chloroformate (854 mg, 4.24 mmol) at 0° C. The reaction mixture was stirred under nitrogen at 0° C. overnight. The solid formed was filtered, and purified by flash chromatography (silica gel, ethyl acetate/hexane 0-20% gradient). Removal of the solvent at reduced pressure gave 76A (1235 mg, 95%) as a white solid. $^1$HNMR (400 MHz, $CDCl_3$) δ: 4.45 (d, J=6.15 Hz, 2H), 5.53 (s, 1H), 7.13-7.43 (m, 6H), 8.25 (d, J=8.79 Hz, 2H). LCMS 307.09 m/z (M+H)$^+$.

76B. N-{4-[2-((S)-1-tert-butoxycarbonylamino-2-phenyl-ethyl)-5-chloro-1H-imidazol-4-yl]-phenyl}-2-methyl-malonamic acid ethyl ester: To a solution of 65D (2.0 g, 4.84 mmol) in DMF (20 mL) were added 3-ethoxy-2-methyl-3-oxopropanoic acid (0.849 g, 5.81 mmol), DIEA (1.692 mL, 9.69 mmol) and BOP (2.57 g, 5.81 mmol) at rt. The resulted clear brown mixture was stirred under $N_2$ at rt. for 1.5 h. The reaction mixture was diluted with ethyl acetate, washed with 1.0N HCl (2×20 mL), saturated $NaHCO_3$ (1×20 mL) and brine (1×20 mL). The organic phase was dried over $MgSO_4$, filtered and concentrated. The crude product was purified by silica gel flash chromatography (ethyl acetate/hexane). Removal of the solvent at reduced pressure gave 76B (1.98 g, 76%) as a tan solid. LCMS m/z 541.07 (M+H)$^+$. $^1$HNMR (400 MHz, $CDCl_3$) δ: 1.24-1.34 (m, 12H), 1.54 (dd, J=7.25, 1.54 Hz, 3H), 3.21 (d, J=7.03 Hz, 2H), 3.51 (qd, J=7.32, 4.39 Hz, 1H), 4.23 (qd, J=7.10, 1.54 Hz, 2H), 4.98 (d, J=4.83 Hz, 1H), 5.83 (dd, J=7.25, 5.49 Hz, 1H), 7.11 (d, J=6.59 Hz, 2H), 7.19 (ddd, J=19.11, 7.03, 6.81 Hz, 3H), 7.40 (m, 4H), 7.50 (dd, J=10.77, 8.57 Hz, 2H), 7.76 (d, J=7.91 Hz, 1H), 7.82 (d, J=8.35 Hz, 1H), 8.95 (d, J=3.52 Hz, 1H).

76C. N-{4-[2-((S)-1-tert-butoxycarbonylamino-2-phenyl-ethyl)-5-chloro-1H-imidazol-4-yl]-phenyl}-2-methyl-malonamic acid: To a solution of 76B (1.98 g, 3.66 mmol) in MeOH and water was added sodium carbonate (0.582 g, 5.49 mmol). The reaction mixture was stirred under $N_2$ at rt overnight. HCl (1.0 M, 15 mmol) was added to neutralize the mixture to slightly pH~4. Some precipitate formed and was extracted with EtOAc. The organic phase was washed with brine. The solvent was removed to provide the crude acid product, which was dried and used in next step. LCMS m/z 512.99 (M+H)$^+$.

76D. 6-[2-((S)-1-amino-2-phenyl-ethyl)-5-chloro-1H-imidazol-4-yl]-4-hydroxy-3-methyl-1H-quinolin-2-one: To solid 76C (1.878 g, 3.66 mmol) was added PPA (9.71 ml, 0.00 μmol). The reaction mixture was stirred under $N_2$ at 120° C. for 3 h, then cooled to rt. The mixture was poured onto ice-water (150 mL) and neutralized with 50% NaOH to pH~5. The solvent was removed under reduced pressure, and the sticky residue was dried in vacuo to give a pale solid which was used in next step without further purification. LC-MS m/z 395.03 (M+H)$^+$.

76E. Example 76: To a solution of 76D (50 mg, 0.127 mmol) in DMF (3 mL) was added pyridine (0.053 mL, 0.652 mmol) and 76A (40 mg, 0.130 mmol) at rt. The reaction mixture was stirred under nitrogen at 60° C. for 5 h. The reaction mixture was cooled to rt and directly purified by reverse phase HPLC ($CH_3CN/H_2O$ with 0.1% TFA). The solvent was removed and the desired fraction was lyophilized to give Example 76 (29.7 mg, 33.7%) as a white solid. $^1$HNMR (400 MHz, $CD_3OD$) δ: 2.11 (s, 3H), 3.22 (d, J=7.47 Hz, 2H), 4.26 (dd, 2H), 5.11 (t, J=7.47 Hz, 1H), 7.10-7.31 (m, 9H), 7.37 (d, J=8.35 Hz, 1H), 7.76 (dd, J=8.79, 1.76 Hz, 1H), 8.21 (d, J=1.76 Hz, 1H). LCMS m/z 562.05 (M+H)$^+$.

Example 77

(S)-1-(1-(5-chloro-4-(4-hydroxy-2-oxo-1,2-dihydroquinolin-6-yl)-1H-imidazol-2-yl)-2-phenylethyl)-3-(3-chlorobenzyl)urea, trifluoroacetic acid salt Example 77 was prepared from compounds 65G and 76A following the procedure described for 76E. $^1$HNMR (400 MHz, $CD_3OD$) δ: 3.22 (d, J=7.91 Hz, 2H), 4.26 (dd, 2H), 5.11 (t, J=7.69 Hz, 1H), 5.95 (s, 1H), 7.05-7.33 (m, 9H), 7.41 (d, J=8.35 Hz, 1H), 7.84 (dd, J=8.79, 2.20 Hz, 1H), 8.22 (d, J=2.20 Hz, 1H). LCMS m/z 548.26 (M+H)$^+$.

Example 78

(S)-1-(5-chloro-2-(1H-tetrazol-1-yl)benzyl)-3-(1-(5-chloro-4-(4-hydroxy-2-oxo-1,2-dihydroquinolin-6-yl)-1H-imidazol-2-yl)-2-phenylethyl)urea, trifluoroacetic acid salt Example 78 was prepared using procedures similar to those described for Example 76. $^1$HNMR (400 MHz, $CD_3OD$) δ: 3.20 (d, J=7.47 Hz, 2H), 4.04-4.20 (dd, 2H), 5.05 (t, J=7.69 Hz, 1H), 5.95 (s, 1H), 7.10-7.32 (m, 5H), 7.37-7.52 (m, 3H), 7.56 (d, J=2.20 Hz, 1H), 7.83 (dd, J=8.79, 2.20 Hz, 1H), 8.21 (d, J=1.76 Hz, 1H), 9.48 (s, 1H). LCMS m/z 616.26 (M+H)$^+$.

Example 79

(S)—N-(1-(5-chloro-4-(4-hydroxy-2-oxo-1,2-dihydroquinolin-6-yl)-1H-imidazol-2-yl)-2-phenylethyl)-3-(1H-imidazol-4-yl)propanamide, trifluoroacetic acid salt To a solution of 65G (50 mg, 0.131 mmol) in DMF (5 mL) were added 3-(1H-imidazol-4-yl)propanoic acid (18.40 mg, 0.131 mmol), DIEA (0.115 mL, 0.656 mmol) and BOP reagent (69.7 mg, 0.158 mmol). The reaction mixture was stirred under $N_2$ at rt. for 2 h. The crude product was purified by reverse phase HPLC (MeOH/$H_2O$ with 0.1% TFA). Most of the solvent was removed from the desired fraction, and the product was lyophilized to afford Example 79 as a white solid ((7.6 mg, 7.92%). $^1$HNMR (400 MHz, $CD_3OD$) δ: 2.55-2.66 (m, 2H), 2.95 (m, 2H), 3.08-3.19 (m, 1H), 3.21-3.27 (m, 1H), 5.21 (t, J=7.69 Hz, 1H), 5.93 (s, 1H), 7.14 (s, 1H), 7.17-7.28 (m, 5H), 7.39 (d, J=8.79 Hz, 1H), 7.85 (dd, J=8.57, 1.98 Hz, 1H), 8.22 (d, J=1.76 Hz, 1H), 8.73 (s, 1H). LCMS m/z 502.99 (M+H)$^+$.

Example 80

(S,E)-N-(1-(5-chloro-4-(4-hydroxy-2-oxo-1,2-dihydroquinolin-6-yl)-1H-imidazol-2-yl)-2-phenylethyl)-3-(1H-imidazol-4-yl)acrylamide, trifluoroacetic acid salt Example 80 was prepared from 65G using the procedure similar to that described for Example 79. $^1$HNMR (400 MHz, $CD_3OD$) δ: 3.21-3.28 (m, 2H), 5.33 (t, J=7.69 Hz, 1H), 5.92

(s, 1H), 6.67 (d, J=15.82 Hz, 1H), 7.17-7.21 (m, 3H), 7.23-7.28 (m, 2H), 7.36-7.44 (m, 2H), 7.82-7.86 (m, 2H), 8.22 (d, J=1.76 Hz, 1H), 8.96 (s, 1H). LCMS m/z 500.96 (M+H)$^+$.

Example 81

(S)—N-(1-(5-chloro-4-(4-hydroxy-2-oxo-1,2-dihydroquinolin-6-yl)-1H-imidazol-2-yl)-2-phenylethyl)-3-(3-chlorophenyl)propanamide, trifluoroacetic acid salt Example 81 was prepared from 65G using the procedure similar to that described for Example 79. $^1$HNMR (400 MHz, CD$_3$OD) δ: 2.51 (t, J=7.69 Hz, 2H), 2.83 (t, J=7.91 Hz, 2H), 3.12-3.24 (m, 2H), 5.18 (t, J=7.91 Hz, 1H), 5.96 (s, 1H), 7.05 (d, J=7.47 Hz, 1H), 7.12-7.21 (m, 6H), 7.25 (t, J=7.25 Hz, 2H), 7.42 (d, J=8.79 Hz, 1H), 7.85 (dd, J=8.57, 1.98 Hz, 1H), 8.22 (d, J=2.20 Hz, 1H). LCMS m/z 547.34 (M+H)$^+$.

Example 82

(S)-methyl 4-(5-chloro-2-(1-(3-(5-chloro-2-(1H-tetrazol-1-yl)benzyl)ureido)-2-(1-methyl-1H-pyrazol-3-yl)ethyl)-1H-imidazol-4-yl)phenylcarbamate 82A. (E)-2-tert-butoxycarbonylamino-3-(1-methyl-1H-pyrazol-3-yl)-acrylic acid methyl ester: Boc-methyl-2-(dimethylphosphono)glycinate (1.620 g, 5.45 mmol) was dissolved in CH$_2$Cl$_2$ (10 mL) and stirred under nitrogen at rt. To this solution was added DBU (0.753 mL, 4.99 mmol) and the mixture was stirred for 10 min, followed by dropwise addition of a solution of 1-methyl-1H-pyrazole-3-carbaldehyde (0.5 g, 4.54 mmol) in CH$_2$Cl$_2$ (10 mL) over 15-20 min. Stirring was continued at rt overnight. The solvent was removed on a rotary evaporator and the residue was taken up in a mixture of CH$_2$Cl$_2$/EtOAc, washed with 5% citric acid and brine, then dried over anhydrous sodium sulfate, filtered and evaporated. The residue was dissolved in methylene chloride and charged to a 120 g silica gel cartridge which was eluted with a 30 min gradient from 0-60% EtOAc in hexane to provide the olefin product (0.95 g, 74.4%) as a thick viscous oil. $^1$HNMR (500 MHz, CDCl$_3$) δ: 8.49 (1H, s), 7.32 (1H, d, J=2.2 Hz), 6.50 (1H, s), 6.28 (1H, d, J=2.2 Hz), 3.94 (3H, s), 3.84 (3H, s), 1.48 (9H, s). LCMS m/z 226.1v(M+H-tBu)$^+$; 182.2 (M+H-Boc)$^+$.

82B. (S)-2-tert-butoxycarbonylamino-3-(1-methyl-1H-pyrazol-3-yl)-propionic acid methyl ester: 82A (0.95 g, 3.38 mmol) was dissolved in MeOH (15 mL) and transferred to a 250 mL hydrogenation flask. The solution was evacuated and flushed with nitrogen 3× then (S,S)-EtDuPhosRh(I) (0.1 g, 0.138 mmol) was added. The flask was connected to a hydrogenation manifold and contents evacuated and flushed with nitrogen 3× then stirred at rt under 45-50 psi H$_2$ for 3-3.5 h. An additional 20 mg of catalyst was added as described above and the reaction mixture was stirred under 55 psi H$_2$ at rt overnight. MeOH was removed on a rotary evaporator and the crude product was dissolved in methylene chloride and charged to an 80 g silica gel cartridge which was eluted with a 20 min gradient from 0-60% EtOAc in hexane to provide 82B (0.928 g, 97%) as a colorless oil. $^1$HNMR (500 MHz, CHCl$_3$) δ: 7.24 (1H, d, J=2.2 Hz), 6.00 (1H, d, J=2.2 Hz), 5.43 (1H, d, J=8.2 Hz), 4.52-4.62 (1H, m), 3.84 (3H, s), 3.72 (3H, s), 2.99-3.21 (2H, m), 1.43 (9H, s). LCMS m/z 228.2 (M+H-tBu)$^+$; 184.2 (M+H-Boc)$^+$.

82C. (S)-2-tert-butoxycarbonylamino-3-(1-methyl-1H-pyrazol-3-yl)-propionic acid: 82B (0.92 g, 3.25 mmol) was dissolved in THF (20 mL) and 1 M lithium hydroxide (5.0 mL, 5.00 mmol) and a little MeOH were added. The resulting reaction mixture was stirred for 3 days at rt under nitrogen. The reaction was diluted with a little water to dissolve small amount of solid and THF removed on a rotary evaporator. The aqueous was diluted with 5% citric acid solution to lower pH <5 and then extracted 2× with EtOAc. The combined extracts were washed with brine, dried over anhydrous Na$_2$SO$_4$, filtered and evaporated to afford 82C (0.79 g, 90%) as a white crystalline solid. $^1$HNMR (500 MHz, CDCl$_3$) δ: 7.27 (1H, d, J=2.2 Hz), 6.10 (1H, d, J=2.2 Hz), 5.49 (1H, d, J=6.6 Hz), 4.55 (1H, t, J=6.6 Hz), 3.90 (3H, s), 3.23-3.36 (1H, m), 3.10-3.24 (1H, m), 1.46 (9H, s). LCMS m/z 214.1 (M+H-tBu)$^+$; 170.2 (M+H-Boc)$^+$.

82D. methyl 4-(2-bromoacetyl)phenylcarbamate: 4-Aminoacetophenone was suspended in a 1:1 mixture of dioxane and water (150 mL), and NaOH (4.4 g, 0.11 mol) was added. The mixture was stirred until the NaOH dissolved, then cooled to 0° C. prior to dropwise addition of methylchloroformate (8.5 mL, 0.11 mol). The resulting mixture was stirred at 0° C. for an additional 10 min then at rt for 2 h, followed by standing overnight. The solvent was removed by evaporation and the residual solids were partitioned between EtOAc and water. The layers were separated and the aqueous was reextracted 2× with EtOAc. The combined organic extracts were dried over MgSO$_4$, filtered and evaporated to yield a tan powder. The crude product was suspended in EtOAc, washed 3× with 1N HCl to remove unreacted aniline, then washed with brine, dried over MgSO$_4$, filtered and evaporated to provide methyl-4-acetylphenylcarbamate as an orange/tan solid (11.2 g, 53%). A portion of this material (3 g, 15.53 mmol) was suspended in CHCl$_3$ (60 mL) and bromine (0.960 mL, 18.63 mmol) was added in small portions. About halfway through the addition, most of the starting material had dissolved in the dark orange reaction mixture. At this point, the mixture quickly decolorized with the formation of a tan precipitate. The remaining bromine was added over ~5 min, then the mixture was stirred at rt. After ~30 min, the solid product was collected by filtration and washed with CHCl$_3$ and air-dried overnight to provide the bromoketone (3.25 g, 77%) which was used without further purification. $^1$HNMR (500 MHz, DMSO-d$_6$) δ: 10.14 (1H, s), 7.95 (2H, d, J=8.8 Hz), 7.59 (2H, d, J=8.8 Hz), 4.83 (2H, s), 3.57-3.83 (3H, m).

82E. (4-{2-[(S)-1-tert-butoxycarbonylamino-2-(1-methyl-1H-pyrazol-3-yl)-ethyl]-1H-imidazol-4-yl}-phenyl)-carbamic acid methyl ester: 82C (0.79 g, 2.93 mmol) was dissolved in DMF (10 mL) and KHCO$_3$ (0.352 g, 3.52 mmol) was added. The mixture was stirred at rt under nitrogen for 0.5-1 h, then cooled in an ice bath while a solution of 82D (0.958 g, 3.52 mmol) in 5 mL DMF was added dropwise. Stirring was continued for ~2 h in an ice bath then the reaction was allowed to cool to rt and was left stirring overnight. The reaction mixture was diluted with water and extracted 2× with EtOAc. The combined extracts were washed with water and brine, then dried over anhydrous sodium sulfate, filtered and evaporated. The crude ester was taken up in Xylene (8 mL) and transferred to a 20 mL microwave vessel. Ammonium acetate (2.261 g, 29.3 mmol) was added, the tube was capped and the mixture was heated with stirring for 30 min at 160° C. in an Emrys Personal Microwave and then cooled to rt. The mixture was partitioned between EtOAc and water and phases separated. The organic layer was washed with brine and dried over anhydrous Na$_2$SO$_4$, filtered and evaporated. The residue (containing xylene) was dissolved in methylene chloride plus a little MeOH and charged to a 120 g silica gel cartridge which was eluted with a 30 min gradient from methylene chloride to 10% MeOH in methylene chloride to provide 82E (0.685 g, 53.0%) as a dark tan solid. LCMS m/z 441.3 (M+H)$^+$.

82F. (4-{2-[(S)-1-tert-butoxycarbonylamino-2-(1-methyl-1H-pyrazol-3-yl)-ethyl]-5-chloro-1H-imidazol-4-yl}-phenyl)-carbamic acid methyl ester: 82E (0.68 g, 1.544 mmol) was dissolved in a mixture of chloroform (10 mL) and acetonitrile (10 mL). To the solution was added N-chlorosuccinimide (0.247 g, 1.852 mmol). The flask was fitted with a reflux condenser and a nitrogen inlet, and the reaction was heated in a 60° C. oil bath for 4 h, cooled to rt, diluted with EtOAc then washed with water (2×) and brine, dried over anhydrous $Na_2SO_4$, filtered and evaporated. The residue was dissolved in methylene chloride and charged to an 80 g silica gel cartridge which was eluted with a 20 min gradient from methylene chloride to 10% MeOH in methylene chloride to afford 82F (0.625 g, 85%) as a orange-brown foam. $^1$HNMR (500 MHz, $CDCl_3$) δ: 11.70 (1H, s), 7.61 (2H, d, J=8.2 Hz), 7.46 (2H, d, J=8.2 Hz), 7.29 (1H, d, J=2.2 Hz), 6.71 (1H, s), 6.16 (1H, s), 5.74 (1H, s), 4.95 (1H, dd, J=12.1, 6.6 Hz), 3.89 (3H, s), 3.80 (3H, s), 3.37 (1H, d, J=13.7 Hz), 3.21 (1H, dd, J=15.1, 8.0 Hz), 1.45 (9H, s). LC/MS m/z 475.2 $(M+H)^+$.

82G. (4-{2-[(S)-1-amino-2-(1-methyl-1H-pyrazol-3-yl)-ethyl]-5-chloro-1H-imidazol-4-yl}-phenyl)-carbamic acid methyl ester, bis HCl salt: 82F (0.625 g, 1.316 mmol) was dissolved in dioxane (5 mL) and 4 N HCl in dioxane (5 ml, 20.00 mmol) was added. A thick gummy precipitate formed. Enough MeOH was added to achieve a homogeneous solution which was then stirred overnight at rt under nitrogen. A light yellow suspension was obtained, which was diluted with ether and stirred for 15-20 min, then the solid was collected by filtration, washed with ether and dried in vacuo to afford 82G (0.57 g, 97%) as a pale yellow solid. $^1$HNMR (500 MHz, DMSO-$d_6$) δ: 9.84 (1H, s), 8.73 (3H, d, J=4.9 Hz), 7.66 (2H, d, J=8.8 Hz), 7.52-7.57 (3H, m), 5.91 (1H, d, J=2.2 Hz), 4.40-4.78 (1H, m), 3.74 (3H, s), 3.67 (3H, s), 3.27-3.37 (1H, m), 3.19-3.27 (1H, m). LCMS m/z 375.2 $(M+H)^+$; 358.2 $(M+H-NH_3)^+$.

82H. Example 82: (5-Chloro-2-(1H-tetrazol-1-yl)phenyl) methanamine (24.5 mg, 0.117 mmol) was dissolved in 0.5 mL THF and treated with 40 μL TEA followed by a solution of 4-nitrophenyl chloroformate (26 mg, 0.129 mmol) in 1 mL THF. This mixture was stirred at rt under nitrogen for ~30 min. In the meantime, 82G (50 mg, 0.112 mmol) was suspended in 1 mL THF and 40 μL TEA added along with ~0.1 mL DMF. This mixture was mixed thoroughly then added as a suspension to the 4-nitrophenylcarbamate reaction mixture. The vial was rinsed with an additional 0.5 mL THF which was also added to the reaction. The whole was then stirred overnight at rt. The reaction mixture was diluted with EtOAc and washed with water (2×), 0.1 N NaOH and brine, then dried over anhydrous sodium sulfate, filtered and evaporated. The residue was redissolved in MeOH, filtered and purified by reverse phase HPLC. The fractions from main peak were evaporated to a white solid. The solid was taken up in a mixture of EtOAc and sat'd $NaHCO_3$, and phase separated. The organic layer was rewashed with more $NaHCO_3$ solution followed by brine, then dried over $Na_2SO_4$, filtered and evaporated. The residue was dissolved in a small amount of a mixture of EtOAc/$CH_2Cl_2$/MeOH and charged to a 2 mm silica gel rotor which was dried then eluted by rotary prep tlc with $CH_2Cl_2$/EtOAc/EtOH 10:10:1. The fractions from the major UV band were combined and concentrated, and the residue was dried overnight on vacuum pump to provide Example 82 (11 mg, 16.14%) as a white solid. $^1$HNMR (500 MHz, DMSO-$d_6$) δ: 12.46 (1H, s), 9.83 (1H, s), 9.76 (1H, s), 7.55-7.61 (4H, m), 7.49-7.54 (3H, m), 7.47 (1H, d, J=2.2 Hz), 6.64 (1H, d, J=8.2 Hz), 6.54 (1H, t, J=5.8 Hz), 5.82 (1H, d, J=2.2 Hz), 4.92-5.02 (1H, m), 4.02 (2H, d, J=6.0 Hz), 3.72 (3H, s), 3.66 (3H, s), 2.98-3.07 (1H, m), 2.89-2.97 (1H, m). LCMS m/z 610.4 $(M+H)^+$.

Example 83

[4-(5-chloro-2-{(S)-1-[3-(5-chloro-2-tetrazol-1-yl-benzyl)-ureido]-2-[1-(4-methoxy-benzyl)-1H-pyrazol-3-yl]-ethyl}-1H-imidazol-4-yl)-phenyl]-carbamic acid methyl ester 83A. 1-(4-methoxy-benzyl)-1H-pyrazole-3-carbaldehyde: Sodium hydride, 60% in oil (0.229 g, 5.72 mmol), was suspended in DMF (5 mL) at 0° C. under nitrogen with stirring. A solution of 1H-pyrazole-3-carbaldehyde (0.5 g, 5.20 mmol) in DMF (5 mL) was added over 5-10 minutes via syringe. The resulting mixture was stirred at 0-5° C. for 10-15 min followed by addition of 4-methoxybenzyl chloride (0.815 mL, 5.98 mmol). Stirring was continued overnight allowing ice bath to melt and the reaction to assume rt. The reaction mixture was diluted with water and extracted 3× with EtOAc. The combined extracts were washed with water and brine, then dried over anhydrous sodium sulfate, filtered and evaporated. The residue was dissolved in methylene chloride and charged to a 120 g silica gel cartridge which was eluted with a 30 min gradient from 0-40% EtOAc in hexane. The major product was 1-(4-methoxybenzyl)-1H-pyrazole-3-carbaldehyde (0.768 g, 68.3%) which was obtained as a colorless oil. $^1$HNMR (500 MHz, $CDCl_3$) δ: 9.99 (1H, s), 7.38 (1H, s), 7.22 (2H, d, J=8.2 Hz), 6.90 (2H, d, J=8.8 Hz), 6.80 (1H, d, J=2.7 Hz), 5.32 (2H, s), 3.81 (3H, s). Evaporation of the fractions from the minor peak yielded 1-(4-methoxybenzyl)-1H-pyrazole-5-carbaldehyde as a crystalline solid (0.138 g, 12.26%). $^1$HNMR (500 MHz, $CDCl_3$) δ: 9.85 (1H, s), 7.59 (1H, d, J=2.2 Hz), 7.26 (2H, d, J=8.8 Hz), 6.91 (1H, d, J=2.2 Hz), 6.83 (2H, d, J=8.8 Hz), 5.67 (2H, s), 3.77 (3H, s).

83B. Example 83: 83A was carried on to provide Example 83 following the procedures previously described for Example 82. $^1$HNMR (500 MHz, $CD_3OD$) δ: 9.50 (1H, s), 7.52-7.62 (3H, m), 7.41-7.52 (5H, m), 7.01 (2H, d, J=8.8 Hz), 6.73 (2H, d, J=8.8 Hz), 6.05 (1H, d, J=2.2 Hz), 5.15 (2H, s), 5.07 (1H, t, J=7.4 Hz), 4.04-4.20 (2H, m), 3.74 (3H, s), 3.68 (3H, s), 3.08-3.21 (2H, m). LCMS m/z 716.5 $(M+H)^+$.

Example 84

[4-(5-chloro-2-{(S)-1-[3-(5-chloro-2-tetrazol-1-yl-benzyl)-ureido]-2-[3-(morpholine-4-carbonyl)-phenyl]-ethyl}-1H-imidazol-4-yl)-phenyl]-carbamic acid methyl ester, trifluoroacetic acid salt 84A. 2-tert-butoxycarbonylamino-acrylic acid benzyl ester: Rac-serine (50 g, 0.475 mol) in dioxane (500 mL) was combined with sodium hydroxide (38 g, 0.98 mol) in water (200 mL) and cooled to 0° C. Boc anhydride (105 g, 0.48 mol) was added dropwise and the reaction was stirred at rt overnight. The reaction mixture was concentrated to remove dioxane and the aqueous layer was washed with petroleum ether. The aqueous layer was acidified to pH 4 with citric acid solution and extracted with ethyl acetate. The combined organic layers were washed with water and brine and concentrated to give N-boc-dl-serine (79 g, 81%). To this intermediate (14 g, 0.068 mol) in DMF (140 mL) was added cesium carbonate (13.2 g, 0.041 mol) and the reaction mixture was stirred at rt for 30 min under a nitrogen atmosphere. Benzyl bromide (11.7 g, 0.07 mol) was added dropwise at 0° C. and the reaction was stirred at rt overnight. The reaction mixture was quenched with water and extracted with ethyl acetate. The combined organic layers were washed with brine and concentrated. The crude product obtained was purified by flash chromatography on silica gel using chloroform as eluent to give the benzyl ester intermediate (17 g, 85%). To the benzyl ester (10 g, 0.0339 mol) in DCM (150 mL) at 0° C. under a nitrogen atmosphere was added mesyl chloride (5 g, 0.0435 mol). Triethyl amine (10 g, 0.0990 mol) was then added dropwise and the reaction was stirred at rt for 1 h. The reaction mixture was washed with 1% sodium bisulphate solution, dried over anhydrous $Na_2SO_4$, and concentrated to give 84A (10 g).

84B. 3-((E)-2-benzyloxycarbonyl-2-tert-butoxycarbonylamino-vinyl)-benzoic acid methyl ester: To 84A (10 g, 0.036 mol) dissolved in DMF (100 mL) were added methyl 3-iodobenzoate (9.5 g, 0.036 mol), palladium acetate (0.25 g, 1.08 mmol), tetrabutylammonium chloride (11 g, 0.039 mol), and triethyl amine (15 mL, 0.108 mol). The mixture was flushed with nitrogen for 1 h, then heated at 85° C. overnight. The reaction mixture was diluted with brine and extracted with ethyl acetate. The organic layer was washed with brine and concentrated. The crude product was purified by flash chromatography on silica gel eluting with 10% ethyl acetate in petroleum ether to give 84B (10 g, 67.5%).

84C. 3-((S)-2-tert-butoxycarbonylamino-2-carboxyethyl)-benzoic acid methyl ester: 84B (1 g, 0.0024 mol) in methanol (10 mL) was placed in an autoclave and the reaction mixture was degassed by flushing with nitrogen. (−)-1,2-bis((2S,5S)-2,5-diethylphospholano)benzene(cyclooctadiene) rhodium(I) trifluoromethanesulfonate (100 mg, 10 mol %) was added and the reaction mixture was again degassed by flushing with nitrogen. The reaction was placed under 55 psi of hydrogen and stirred for 2 days. The reaction mixture was filtered through Celite® and concentrated to give 0.7 g (70%) of product. To the chiral intermediate (0.6 g, 0.0014 mol) in methanol (3 mL) and ethyl acetate (3 mL) was added palladium hydroxide (0.06 g) purging the solution with nitrogen gas. The reaction mixture was stirred under a hydrogen atmosphere at rt for 4 h, then filtered through Celite® and concentrated to give 84C (0.4 g, 86%). $^1$HNMR (DMSO-$d_6$) δ: 7.85 (s 1H), 7.79 (d 1H), 7.52 (d 1H), 7.43 (m 1H), 7.18 (d, 1H), 4.03 (m, 1H), 3.84 (s, 3H), 3.08 (m, 1H), 2.88 (m, 1H), 1.23 (s, 9H). LCMS m/z 222 (M−H)$^-$.

84D. 3-{(S)-2-tert-butoxycarbonylamino-2-[2-(4-methoxycarbonylamino-phenyl)-2-oxo-ethoxycarbonyl]-ethyl}-benzoic acid methyl ester: 84C (4.0 g, 12.37 mmol) and potassium bicarbonate (1.49 g, 14.85 mmol) were dissolved in DMF (30 mL) and stirred under nitrogen at rt for 1 h. The reaction mixture was cooled to 0° C. in an ice bath, and 82D (4.04 g, 14.85 mmol) dissolved in DMF (20 mL) was added dropwise over several minutes. The reaction was stirred at 0° C. for 1 h, then warmed to rt and stirred for 1 h. The reaction was diluted with water and then extracted 3× with EtOAc. The combined extracts were washed with water and brine, dried over anhydrous $Na_2SO_4$, filtered and evaporated to afford the ketoester as a white solid. LCMS m/z 513.2 (M−H)$^-$; 515.1 (M+H)$^+$.

84E. 3-{(S)-2-tert-butoxycarbonylamino-2-[4-(4-methoxycarbonylamino-phenyl)-1H-imidazol-2-yl]-ethyl}-benzoic acid methyl ester: 84D (6.36 g, 12.37 mmol) and ammonium acetate (19.07 g, 247 mmol) were suspended in o-xylene (60 mL). The reaction mixture was heated at reflux with a Dean-Stark trap for 2 h, then allowed to cool to rt. The reaction was diluted with brine and extracted 3× with EtOAc. The combined extracts were washed with brine, dried over anhydrous $Na_2SO_4$, filtered and evaporated to leave the crude product as a red/brown solid. The residue was dissolved in methylene chloride, charged on an 80 g silica gel cartridge that had been pretreated with triethylamine in methylene chloride, and eluted with a 30 min gradient from 0-20% methanol in methylene chloride to provide the product (2.76 g, 45.2%) as a pink/brown solid. LCMS m/z 493.3 (M−H)$^-$; 495.4 (M+H)$^+$.

84F. 3-{(S)-2-tert-butoxycarbonylamino-2-[5-chloro-4-(4-methoxycarbonylamino-phenyl)-1H-imidazol-2-yl]-ethyl}-benzoic acid methyl ester: 84E was dissolved in a mixture of chloroform (40 mL) and acetonitrile (30 mL) to give a pink/red solution. Upon addition of N-chlorosuccinimide (1.12 g, 8.38 mmol), the pink/red solution turned black/brown. Conversion to the desired product was confirmed by LCMS, then the reaction mixture was diluted with water and extracted 3× with methylene chloride. The combined extracts were washed with water and brine, dried over anhydrous $Na_2SO_4$, filtered and evaporated. The residue was dissolved in methylene chloride, and purified by flash chromatography on silica gel (0-10% methanol in methylene chloride) to provide the chlorinated product (2.40 g, 80%). LCMS m/z 527.3 (M−H)$^-$; 529.4 (M+H)$^+$.

84G. 3-{(S)-2-tert-butoxycarbonylamino-2-[5-chloro-4-(4-methoxycarbonylamino-phenyl)-1H-imidazol-2-yl]-ethyl}-benzoic acid: 84F (1.28 g, 2.43 mmol) was dissolved in ethanol (12 mL) and stirred overnight with 1 M sodium hydroxide (6 mL, 6.00 mmol). The reaction mixture was diluted with water, acidified to pH 2 with 1 N aqueous hydrochloric acid, and extracted 3× with ethyl acetate. The combined extracts were washed with dilute aqueous hydrochloric acid and brine, dried over anhydrous $Na_2SO_4$, filtered and evaporated to provide the acid (1.16 g, 92%). LCMS m/z 515.4 (M+H)$^+$; 513.3 (M−H)$^-$.

84H. [4-(2-{(S)-1-tert-butoxycarbonylamino-2-[3-(morpholine-4-carbonyl)-phenyl]-ethyl}-5-chloro-1H-imidazol-4-yl)-phenyl]-carbamic acid methyl ester: 84G (0.75 g, 1.42 mmol), N-methylmorpholine (0.78 mL, 7.09 mmol), and morpholine (0.124 mL, 1.42 mmol) were combined in DMF and stirred for several minutes. EDC (0.33 g, 1.70 mmol) and HOBt (0.26 g, 1.70 mmol) were added, and the reaction mixture was stirred under nitrogen overnight. The reaction mixture was diluted with water and extracted 3× with ethyl acetate. The combined extracts were washed with water and brine, dried over anhydrous $Na_2SO_4$, filtered and evaporated to provide the amide product as a brown solid. LCMS m/z 584.4 (M+H)$^+$; 582.3 (M−H)$^-$.

84I. [4-(2-{(S)-1-amino-2-[3-(morpholine-4-carbonyl)-phenyl]-ethyl}-5-chloro-1H-imidazol-4-yl)-phenyl]-carbamic acid methyl ester, bis-trifluoroacetic acid salt: 84H (0.828 g, 1.418 mmol) was dissolved in methylene chloride (6 mL). Trifluoroacetic acid (6 mL, 78 mmol) was added and the reaction mixture was stirred at rt for 1 h. Volatiles were removed on a rotary evaporator and the crude product was triturated several times with a mixture of diethyl ether and hexanes to afford 84I as a brown solid (0.69 g, 67.9%). LCMS m/z 482.2 (M−H)$^-$; 484.1 (M+H)$^+$.

84J. Example 84: 5-Chloro-2-tetrazol-1-yl-benzylamine (0.022 g, 0.107 mmol) and triethyl amine (0.150 mL, 1.07 mmol) dissolved in THF (0.5 mL) were treated with 4-nitrophenyl chloroformate (0.022 g, 0.107 mmol) dissolved in THF (1 mL) to give a cloudy pale yellow solution that was stirred for 15 minutes. 84I was treated with sat'd aqueous $NaHCO_3$ solution, then extracted with EtOAc to obtained the corresponding free base (0.052 g, 0.107 mmol) which was dissolved in THF (2 mL) and added to the reaction mixture. The reaction was stirred at rt overnight. Volatiles were removed by rotary evaporation to leave the crude product mixture as a yellow solid. The residue purified by reverse phase HPLC (H$_2$O/CH$_3$CN/TFA 98:2:0.05). The desired compound was isolated as a yellow solid (0.0275 g, 30.7%) after evaporation of solvents. $^1$HNMR (500 MHz, DMSO-d$_6$) δ: 3.00-3.13 (m, 2H), 3.19-3.62 (m, 8H), 3.66 (s, 3H), 4.00 (d, J=6.05 Hz, 2H), 4.93-5.01 (m, 1H), 6.77 (d, J=8.80 Hz, 1H), 7.05 (s, 1H), 7.17-7.22 (m, 2H), 7.32 (t, J=7.70 Hz, 1H), 7.47 (s, 1H), 7.49-7.56 (m, 4H), 7.58 (s, 2H), 9.77 (s, 1H), 9.82 (s, 1H). LCMS m/z 719.4 (M+H)$^+$.

Examples 85-87 in Table 1 were similarly prepared using the procedures described for Example 84.

Example 85

[4-(2-{(S)-2-(3-Carbamoyl-phenyl)-1-[3-(5-chloro-2-tetrazol-1-yl-benzyl)-ureido]-ethyl}-5-chloro-1H-imidazol-4-yl)-phenyl]-carbamic acid methyl ester Example 86

(4-{5-Chloro-2-[(S)-1-[3-(5-chloro-2-tetrazol-1-yl-benzyl)-ureido]-2-(3-dimethylcarbamoyl-phenyl)-ethyl]-1H-imidazol-4-yl}-phenyl)-carbamic acid methyl ester Example 87

(4-{5-Chloro-2-[(S)-1-[3-(5-chloro-2-tetrazol-1-yl-benzyl)-ureido]-2-(3-methylcarbamoyl-phenyl)-ethyl]-1H-imidazol-4-yl}-phenyl)-carbamic acid methyl ester Example 88

3-{(S)-2-[5-chloro-4-(4-methoxycarbonylamino-phenyl)-1H-imidazol-2-yl]-2-[3-(5-chloro-2-tetrazol-1-yl-benzyl)-ureido]-ethyl}-benzoic acid, trifluoroacetic acid salt 88A. 3-{(S)-2-amino-2-[5-chloro-4-(4-methoxycarbony-lamino-phenyl)-1H-imidazol-2-yl]-ethyl}-benzoic acid methyl ester: Trifluoroacetic acid (3 ml, 38.9 mmol) was added to 84F (0.7345 g, 1.389 mmol) dissolved in methylene chloride (6 mL) to give a dark brown solution. After stirring for 30 min, volatiles were removed by rotary evaporation, leaving a black/brown solid. The residue was dissolved in ethyl acetate and washed with saturated aqueous NaHCO$_3$. The combined organic extracts were dried over anhydrous Na$_2$SO$_4$, filtered and evaporated to provide 88A (0.4166 g, 70.0%) as a dark brown solid. LCMS m/z 427.2 (M-H)$^-$; 429.1 (M+H)$^+$.

88B. 3-{(S)-2-[5-chloro-4-(4-methoxycarbonylamino-phenyl)-1H-imidazol-2-yl]-2-[3-(5-chloro-2-tetrazol-1-yl-benzyl)-ureido]-ethyl}-benzoic acid methyl ester: 5-Chloro-2-tetrazol-1-yl-benzylamine (0.204 g, 0.971 mmol) was dissolved in THF (2 mL) with triethyl amine (1.354 mL, 9.71 mmol). 4-Nitrophenyl chloroformate (0.196 g, 0.971 mmol) dissolved THF (3.5 mL) was added and the reaction mixture was stirred for 15 minutes giving a cloudy, pale yellow suspension. 88A (0.4166 g, 0.971 mmol) dissolved in THF (5 mL) was added and the reaction mixture was stirred over night. The reaction was diluted with dilute aqueous NaOH and extracted 3× with ethyl acetate. The combined organic layers were washed with dilute aqueous sodium hydroxide and brine, dried over anhydrous Na$_2$SO$_4$, and evaporated to provide the urea (0.5383 g, 83%) as a dark brown foam. LCMS m/z 662.3 (M-H)$^-$; 664.2 (M+H)$^+$.

88C. Example 88 was prepared from 88B by hydrolysis of the methyl ester using the procedure described for 84G. LCMS m/z 648.3 (M-H)$^-$; 650.1 (M+H)$^+$. $^1$HNMR (500 MHz, DMSO-d$_6$) δ: 3.08 (dd, 2H), 3.67 (s, 3H), 4.00 (d, J=5.50 Hz, 2H), 4.91-4.99 (m, 1H), 6.52 (t, J=6.05 Hz, 1H), 6.78 (d, J=8.80 Hz, 1H), 7.32-7.36 (m, 2H), 7.45 (s, 1H), 7.48-7.60 (m, 7H), 7.72-7.77 (m, 2H), 9.77 (s, 1H), 9.81 (s, 1H). $^{19}$F NMR (471 MHz, DMSO-d$_6$) δ: -74.59 (s, 3F).

Example 89

[4-(5-chloro-2-{(S)-1-[3-(5-chloro-2-tetrazol-1-yl-benzyl)-ureido]-2-[3-(morpholine-4-carbonyl)-phenyl]-ethyl}-1H-imidazol-4-yl)-phenyl]-carbamic acid 2-methoxy-ethyl ester, trifluoroacetic acid salt 89A. 3-{(S)-2-tert-butoxycarbonylamino-2-[2-(4-nitro-phenyl)-2-oxo-ethoxycarbonyl]-ethyl}-benzoic acid methyl ester: To a solution of 84C (5.75 g, 17.78 mmol) in DMF (50 mL) was added cesium carbonate (6.95 g, 21.34 mmol) and the mixture was stirred at rt under a nitrogen atmosphere for 30 min. The reaction mixture was cooled to 0° C. in an ice bath and 4-nitrophenacyl bromide (5.21 g, 21.34 mmol) in DMF (8 mL) was added via syringe over several minutes. After 30 min, the reaction mixture was warmed to rt and stirred for an additional 30 min. The reaction was diluted with water and extracted with 3× dichloromethane. The combined organic layers were washed with water and brine, dried over anhydrous Na$_2$SO$_4$, and evaporated, leaving a dark solid. Filtration from dichloromethane/methanol gave some product as an off-white solid. Additional product was purified by dissolving the remaining residue in methylene chloride and charging on a silica gel cartridge which was eluted with a 30 minute gradient from 0-10% methanol in dichloromethane to provide 89A (8.5363 g, 99%). LCMS m/z 485.1 (M-H)$^-$.

89B. 3-{(S)-2-tert-butoxycarbonylamino-2-[4-(4-nitro-phenyl)-1H-imidazol-2-yl]-ethyl}-benzoic acid methyl ester: A suspension of 89A (8.5363 g, 17.55 mmol) and ammonium acetate (27 g, 350 mmol) in o-xylene (75 mL) was heated at 145° C. for 1.5 h. After cooling to rt, the reaction mixture was diluted with brine and extracted 3× with dichloromethane. The combined organic extracts were washed with water and brine, dried over anhydrous Na$_2$SO$_4$, and evaporated to provide 89B (8.19 g, 100%). LCMS m/z 467.4 (M+H)$^+$; 465.4 (M-H)$^-$.

89C. 3-{(S)-2-tert-butoxycarbonylamino-2-[5-chloro-4-(4-nitro-phenyl)-1H-imidazol-2-yl]-ethyl}-benzoic acid methyl ester: 89B (8.19 g, 17.55 mmol) and N-chlorosuccinamide (2.80 g, 20.97 mmol) were dissolved in 100 mL of a 1:1 mixture of dichloromethane and acetonitrile, and the reaction was heated at 60° C. for 4.5 h. After cooling to rt, the reaction was diluted with water and extracted 3× with dichloromethane. The combined organic layers were washed with water and brine, dried over anhydrous Na$_2$SO$_4$, and evaporated. The resulting residue was dissolved methylene chloride, charged on a 120 g silica gel cartridge, and eluted with a 30 minute gradient from 0-10% methanol in dichloromethane to provide 89C (5.45 g, 62%). LCMS m/z 499.2 (M-H)$^-$; 501.1 (M+H)$^+$.

89D. 3-{(S)-2-tert-Butoxycarbonylamino-2-[5-chloro-4-(4-nitro-phenyl)-1H-imidazol-2-yl]-ethyl}-benzoic acid: 89C (3.0 g, 5.99 mmol) and 1 M sodium hydroxide (18 mL, 18.00 mmol) were stirred in ethanol (36 mL) overnight. The reaction was diluted with water, acidified to pH 2 with 1 N aqueous hydrochloric acid, and extracted 3× with dichloromethane. The combined organic layers were washed with water and brine, dried over anhydrous Na₂SO₄, and evaporated to give 89D (2.41 g, 83%). LCMS m/z 485.2 (M−H)⁻; 487.1 (M+H)⁺.

89E. {(S)-1-[5-chloro-4-(4-nitro-phenyl)-1H-imidazol-2-yl]-2-[3-(morpholine-4-carbonyl)-phenyl]-ethyl}-carbamic acid tert-butyl ester: 89D (2.41 g, 4.95 mmol), morpholine (0.431 ml, 4.95 mmol), and N-methylmorpholine (2.72 ml, 24.75 mmol) were combined in DMF (30 mL). EDC (1.139 g, 5.94 mmol) and HOBt (0.910 g, 5.94 mmol) were added and the reaction mixture was stirred under an atmosphere of N₂ for 1.5 h. The reaction mixture was diluted with water and extracted 3× with ethyl acetate. The combined organic layers were washed with water and brine, dried over anhydrous Na₂SO₄, and evaporated to give 89E (2.75 g, 100%). LCMS m/z 554.3 (M−H)⁻; 556.2 (M+H)⁺.

89F. {(S)-1-[4-(4-amino-phenyl)-5-chloro-1H-imidazol-2-yl]-2-[3-(morpholine-4-carbonyl)-phenyl]-ethyl}-carbamic acid tert-butyl ester: To a slurry of 89E (2.75 g, 4.95 mmol) and zinc powder (3.24 g, 49.5 mmol) in ethanol (150 mL) was added ammonium chloride (0.794 g, 14.85 mmol) dissolved in water (6 mL). The mixture was stirred at 80° C. for 3 h, then was cooled to rt. The reaction mixture was filtered through a plug of Celite® and evaporated. The resulting residue was dissolved in methylene chloride, charged on an 80 g silica gel cartridge, and eluted with a 25 minute gradient from 0-60% ethyl acetate in hexanes to provide 89F (0.6645 g, 25.5%). LCMS m/z 524.3 (M−H)⁻; 526.2 (M+H)⁺.

89G. [4-(2-{(S)-1-tert-butoxycarbonylamino-2-[3-(morpholine-4-carbonyl)-phenyl]-ethyl}-5-chloro-1H-imidazol-4-yl)-phenyl]-carbamic acid 2-methoxy-ethyl ester: 89F (0.6645 g, 1.263 mmol) was dissolved in THF (20 mL) and stirred with potassium carbonate (0.436 g, 3.16 mmol) for several minutes. The mixture was cooled to 0° C. in an ice bath and 2-methoxyethylchloroformate (0.323 ml, 2.78 mmol) was added dropwise. After 30 min, the reaction was allowed to warm to rt. After stirring 1 h, the reaction mixture was diluted with water and extracted 3× with EtOAc. The combined organic layers were washed with water and brine, dried over Na₂SO₄ and evaporated. The resulting residue was dissolved in dichloromethane and stirred over PS tris-amine resin (200 mg) overnight to remove excess chloroformate. Filtration through a plug of Celite® and evaporation gave a mixture of products, which was redissolved in dichloromethane (10 mL) and pyridine (0.202 mL, 2.500 mmol). 2-Methoxyethylchloroformate (0.232 mL, 2.000 mmol) was added and the mixture was stirred for 1.25 h. Volatiles were evaporated and the resulting residue was dissolved in methanol (12 mL) and stirred with 1 N NaOH (4 mL) for 30 min. Evaporation of the reaction mixture gave a dark red oil that was diluted with water and extracted with 3× ethyl acetate. The combined organic layers were washed with water and brine, dried over anhydrous Na₂SO₄, and evaporated to give 89G. LCMS m/z 626.3 (M−H)⁻; 628.3 (M+H)⁺.

89H. [4-(2-{(S)-1-amino-2-[3-(morpholine-4-carbonyl)-phenyl]-ethyl}-5-chloro-1H-imidazol-4-yl)-phenyl]-carbamic acid 2-methoxy-ethyl ester, bis-trifluoroacetic acid salt: 89G (0.628 g, 1 mmol) was dissolved in dichloromethane (8 mL) and stirred with trifluoroacetic acid (0.077 mL, 1.000 mmol) over night. After evaporating volatiles, the resulting brown residue was triturated several time with a mixture of ether and hexanes to give 89H as the bisTFA salt (0.5756 g, 76%). LCMS m/z 526.3 (M−H)⁻; 538.2 (M+H)⁺.

89I. Example 89: To 5-Chloro-2-tetrazol-1-yl-benzylamine (0.025 g, 0.119 mmol) dissolved in THF (0.5 mL) was added triethylamine (0.166 mL, 1.193 mmol) and then 4-nitrophenyl chloroformate (0.024 g, 0.119 mmol) dissolved in THF (1 mL). The mixture was stirred for 30 min. Meanwhile, 89H (0.098 g, 0.130 mmol) was treated with saturated aqueous NaHCO₃ and extracted with EtOAc to obtained the free base. The combined organic layers were dried over anhydrous Na₂SO₄ and evaporated to leave the free base, which was dissolved in THF (1.5 mL) and added to the reaction mixture. After stirring over night, the reaction was diluted with dilute aqueous sodium hydroxide and extracted 3× with ethyl acetate. The combined organic layers were washed with dilute aqueous sodium hydroxide and brine, dried over anhydrous Na₂SO₄, and evaporated. The resulting residue was redissolved in methanol, filtered and purified by reverse phase HPLC(HCH₃CN/H₂O/TFA) to provide Example 89 (33.4 mg, 31.9%). LCMS m/z 763.2 (M+H)⁺. ¹HNMR (500 MHz, DMSO-d₆) δ: 2.99-3.67 (m, 8H), 3.00-3.17 (m, 2H), 3.27 (s, 3H), 3.54-3.58 (m, 2H), 4.01 (d, J=5.50 Hz, 2H), 4.18-4.21 (m, 2H), 4.92-5.02 (m, 1H), 6.52 (t, J=6.32 Hz, 1H), 6.77 (d, J=8.80 Hz, 1H), 7.05 (s, 1H), 7.17-7.22 (m, 2H), 7.29-7.35 (m, 1H), 7.47 (s, 1H), 7.49-7.56 (m, 4H), 7.58 (s, 2H), 9.82 (s, 1H), 9.87 (s, 1H).

Examples 90 and 91 in Table 1 were prepared from the indicated commercially available Boc-protected amino acids following the procedures described for 84D, 84E, 84F, & 84I.

Example 90

[4-(5-chloro-2-{(S)-1-[3-(5-chloro-2-tetrazol-1-yl-benzyl)-ureido]-butyl}-1H-imidazol-4-yl)-phenyl]-carbamic acid methyl ester, trifluoroacetic acid salt (From Boc-NVa-OH): ¹HNMR (500 MHz, DMSO-d₆) δ: 0.85 (t, J=7.42 Hz, 3H), 1.13-1.31 (m, 2H), 1.59-1.75 (m, 2H), 3.66 (s, 3H), 4.05 (d, J=6.05 Hz, 2H), 4.72 (q, J=7.51 Hz, 1H), 6.49 (t, J=6.05 Hz, 1H), 6.61 (d, J=8.80 Hz, 1H), 7.49-7.55 (m, 3H), 7.57-7.61 (m, 4H), 9.77 (s, 1H), 9.84 (s, 1H), 12.51 (s, 1H). LCMS m/z 558.4 (M+H)⁺.

Example 91

[4-(5-chloro-2-{(S)-1-[3-(5-chloro-2-tetrazol-1-yl-benzyl)-ureido]-pentyl}-1H-imidazol-4-yl)-phenyl]-carbamic acid methyl ester, trifluoroacetic acid salt (From Boc-NLe-OH): ¹HNMR (400 MHz, DMSO-d₆) δ: 0.83 (t, J=7.03 Hz, 3H), 1.10-1.32 (m, 4H), 1.58-1.78 (m, J=30.32 Hz, 2H), 3.66 (s, 3H), 4.04 (d, J=5.71 Hz, 2H), 4.64-4.75 (m, 1H), 6.50 (t, J=5.71 Hz, 1H), 6.62 (d, J=8.79 Hz, 1H), 7.45-7.63 (m, 7H), 9.78 (s, 1H), 9.85 (s, 1H). LCMS m/z 572.3 (M+H)⁺.

Example 92

(S)-methyl 4-(5-chloro-2-(1-(3-(5-chloro-2-(pyrrolidin-1-yl)benzyl)ureido)-2-phenylethyl)-1H-imidazol-4-yl)phenylcarbamate, trifluoroacetic acid salt 92A. 5-chloro-2-(pyrrolidin-1-yl)benzonitrile: 5-Chloro-2-fluorobenzonitrile (0.25 g, 1.607 mmol), potassium carbonate (0.44 g, 3.18 mmol), and pyrrolidine (0.2 mL, 2.418 mmol) were combined in DMF (1.5 ml) and stirred 72 h. The reaction was partitioned with EtOAc/water and extracted with EtOAc. The combined organic layers were washed with water (100 mL) and brine (50 mL), dried (MgSO₄), and concentrated to afford 92A as a white solid (0.33 g, 94%). ¹HNMR (400 MHz, CDCl₃) δ: 1.97-2.08 (m, 4H), 3.52-3.66 (m, 4H), 6.50-6.65 (m, 1H), 7.19-7.31 (m, 1H), 7.38 (t, J=2.65 Hz, 1H). LCMS m/z 207.0 (M+H)⁺.

92B. (5-chloro-2-(pyrrolidin-1-yl)phenyl)methanamine: To 92A in 20 mL of 2M $NH_3$ in MeOH, was added Raney nickel slurry, and the reaction was stirred under 50 psi of $H_2$ for 24 h. The reaction was filtered through Celite®, concentrated and the residue dissolved in ethyl acetate and dried ($MgSO_4$). The residue obtained was partitioned in diethyl ether/1N HCl and layers separated. The aqueous layer was basified with sodium bicarbonate and extracted with ethyl acetate and dried ($MgSO_4$) to afford 92B as a yellow oil (0.23 g). LCMS m/z 211.2$(M+H)^+$. $^1$HNMR (400 MHz, $CDCl_3$) δ: 1.92 (q, J=6.48 Hz, 4H), 1.98-2.08 (m, 2H), 3.05-3.25 (m, 4H), 3.72-4.07 (m, 2H), 6.78-6.89 (m, 1H), 7.08 (dd, J=8.59, 2.53 Hz, 1H), 7.21-7.30 (m, 1H).

92C. [(S)-1-(1H-imidazol-2-yl)-2-phenyl-ethyl]-carbamic acid tert-butyl ester: To (S)-2-tert-butoxycarbonylamino-3-phenyl-propionic acid methyl ester (100.0 g, 0.35 mol) in toluene (1 L) at −78° C. was added DIBAL-H (2M solution in toluene, 322 mL, 0.64 mol) dropwise and the reaction stirred at −78° C. for 30 min. The reaction was quenched with methanol (40 mL) and the mixture was stirred with $NH_4Cl$ (350 g in 100 mL of water) for 10 min. The solution was filtered through Celite® and the aluminum salts were washed with cold ethyl acetate and water. The filtrate layers were separated and the organic layer was dried over sodium sulfate and concentrated at a temperature below 35° C. to provide ((S)-1-benzyl-2-oxo-ethyl)-carbamic acid tert-butyl ester (93 g). To this intermediate (93 g, 0.37 mol) in methanol (1 L) was added glyoxal trimeric dihydrate (39.2 g, 0.18 mol), followed by 2M $NH_3$ in methanol (838 mL) and the reaction mixture was stirred at rt for 48 h. The reaction mixture was evaporated and the crude was purified by column chromatography followed by crystallization from hexane to provide 92C as a grey solid (23 g, 23%). $^1$HNMR ($CDCl_3$, 400 MHz) δ: 9.8 (bs, 1H), 7.27 (m, 3H), 7.21 (m, 2H), 6.95 (d, 2H), 5.32, 4.91 (2d, 2H), 3.32 (d, 2H), 1.3 (s, 9H). LCMS m/z 287 $(M+H)^+$.

92D. {(S)-1-[5-bromo-1-(4-methoxy-benzyl)-1H-imidazol-2-yl]-2-phenyl-ethyl}-carbamic acid tert-butyl ester: To a solution of 92C (115.0 g, 0.49 mol) in DMF (1400 mL) at 0° C. was added p-methoxybenzyl chloride (100.4 g, 0.64 mol). The reaction mixture was stirred at rt overnight, then poured into ice cold water and extracted with ethyl acetate. The organic layer was washed with water and brine, dried over sodium sulfate and concentrated. The crude was purified by column chromatography to obtain {(S)-1-[1-(4-methoxy-benzyl)-1H-imidazol-2-yl]-2-phenyl-ethyl}-carbamic acid tert-butyl ester as a white solid (120 g, 74%). $^1$HNMR ($CDCl_3$, 400 MHz) δ: 7.21 (d, 2H), 7.02 (d, 2H), 6.78 (m, 6H), 6.6 (s, 1H), 5.08, 5.04 (2d, 1H), 4.64 (dd, 2H), 3.78 (s, 2H), 3.2 (m, 1H), 1.3 (m, 9H). LCMS m/z 407 $(M+H)^+$. To this intermediate (25 g, 60 mmol) in acetonitrile at −20° C. was added N-bromosuccinimide (8.7 g, 49 mmol) portion wise and the reaction was stirred at −20° C. for 30 min. The reaction was quenched with water and extracted with ethyl acetate. The organic layer was washed with water and brine, dried over sodium sulfate and concentrated. The crude product was purified by column chromatography to give 92D as a white solid (11 g, 38%). $^1$HNMR ($CDCl_3$, 400 MHz) δ 7.25 (d, 2H), 7.04 (d, 2H), 6.83 (m, 6H), 5.2 (s, 1H), 5.09 (m, 2H), 4.8 (d, 1H), 3.78 (s, 3H), 3.2 (m, 2H), 1.3 (m, 9H). LCMS m/z 486 $(M+H)^+$.

92E. [(S)-1-(5-bromo-1H-imidazol-2-yl)-2-phenyl-ethyl]-carbamic acid tert-butyl ester: To a solution of 92D (30 g) in anisole (100 mL) was added TFA (250 mL) and the reaction was stirred at 100° C. for 18 h. The reaction mixture was evaporated completely, basified with 5% NaOH solution and extracted with DCM. The organic layer was washed with brine, dried over sodium sulfate and concentrated. Recrystallization from hexane gave (S)-1-(5-bromo-1H-imidazol-2-yl)-2-phenyl-ethylamine as a white solid 6 (11 g, 67%). $^1$HNMR ($CD_3OD$, 400 MHz), δ 7.26 (m, 3H), 7.06 (d, 2H), 6.96 (s, 1H), 4.18 (m, 1H), 3.09 (m, 2H). LCMS m/z 266 $(M+H)^+$. To this intermediate (10 g, 37 mmol) in chloroform (250 mL) was added Boc anhydride (8.6 g, 39 mmol) dropwise at −15° C. over a period of 30 min. The reaction was warmed to 15° C. and stirred at the same temperature for 8 h. The reaction mixture was diluted with chloroform, washed with water and brine, dried over sodium sulfate and concentrated. The crude product was purified by recrystallisation from hexane to give 92E as an off-white solid (12.5 g, 91%). $^1$HNMR ($CDCl_3$, 400 MHz), δ: 10.2 (bs, 1H), 7.3 (m, 5H), 7.15 (d, 2H), 6.85 (s, 1H), 5.34 (bs, 1H), 4.84 (m, 1H), 3.28 (dd, 2H), 1.38 (s, 9H). LCMS m/z 366 $(M+H)^+$.

92F. {4-[2-((S)-1-tert-butoxycarbonylamino-2-phenyl-ethyl)-5-chloro-1H-imidazol-4-yl]-phenyl}-carbamic acid methyl ester: To 92E (4.5 g, 12.2 mmol) were added 4-(methoxycarbonylamino)-phenyl boronic acid (2.97 g, 15.0 mmol), and potassium carbonate (5 g, 36 mmol). To this mixture was added 4:1 DME/water (100 mL) that had been degassed with $N_2$. Tetrakis[(triphenyl)phosphine]palladium (0.7 g, 0.61 mmol) was added and the reaction was heated at 80° C. for 24 h. The reaction was cooled and solvents removed in vacuo. The residue was partitioned with ethyl acetate/water and the layers separated. The aqueous layer was extracted with ethyl acetate, and the combined organic layers were washed with brine and dried ($MgSO_4$). Filtration and concentration afforded {4-[2-((S)-1-tert-butoxycarbonylamino-2-phenyl-ethyl)-1H-imidazol-4-yl]-phenyl}-carbamic acid methyl ester as a yellow foam (8.1 g). LCMS m/z 437.02 $(M+H)^+$. To this intermediate (5.3 g, 12.2 mmol) in acetonitrile (60 mL) was added N-chlorosuccinimide (1.8 g, 13.4 mmol), and the reaction was heated to 55° C. for 24 h. The solvent was removed in vacuo, the residue was partitioned with ethyl acetate/saturated aqueous sodium carbonate, and the layers separated. The aqueous layer was extracted with ethyl acetate, and the combined organic layers were washed with brine and dried ($MgSO_4$). Purification by silica gel chromatography (hexane/ethyl acetate) afforded 92F (1.92 g, 33.6% over 2 steps) as a yellow foam. LCMS m/z 471.3 $(M+H)^+$. $^1$HNMR (400 MHz, $CDCl_3$) δ: 1.39 (s, 9H), 3.30 (d, J=7.07 Hz, 2H), 3.79 (s, 3H), 4.85 (d, J=7.58 Hz, 1H), 5.20 (d, J=7.58 Hz, 1H), 6.68 (s, 1H), 7.14-7.32 (m, 4H), 7.38-7.56 (m, 5H).

92G. (S)-methyl 4-(2-(1-amino-2-phenylethyl)-5-chloro-1H-imidazol-4-yl)phenylcarbamate: To 92F (2 g, 4.25 mmol) in DCM (75 mL) was added TFA (32 mL) and the mixture was stirred for 24 h. The reaction was concentrated, quenched with water, and extracted with ether (2×100 mL). The aqueous layer was basified with $NaHCO_3$ and extracted with EtOAc (2×100 mL), washed with brine (100 mL) and dried ($MgSO_4$). The organic layer was concentrated to a tan foam (0.35 g). The above ether layer was also basified with aq. $NaHCO_3$ and extracted with EtOAc (2×50 mL). The combined organic layers were washed with brine (50 mL), dried ($MgSO_4$), filtered and concentrated to afford 92G as a tan foam (1.5 g of free base). LCMS m/z 371.2 $(M+H)^+$. $^1$HNMR (400 MHz, $CD_3OD$) δ: 3.20-3.31 (m, 2H), 3.76 (s, 3H), 4.45 (dd, J=8.59, 6.57 Hz, 1H), 7.11-7.18 (m, 2H), 7.23-7.37 (m, 3H), 7.48-7.58 (m, 4H).

92H. Example 92: To a solution of 92G (36 mg, 0.097 mmol) in THF (2 mL) was added carbonyldiimidazole (17.32 mg, 0.107 mmol) and TEA (0.041 mL, 0.291 mmol), and the reaction was stirred 30 min. To this mixture was added 92B (22.50 mg, 0.107 mmol), and stirring was continued for 24 h. The reaction mixture was partitioned between EtOAc/water. The phases were separated and aqueous layer was extracted with EtOAc. The combined organic layers were washed with water and brine and dried (MgSO$_4$). Purification by reverse phase HPLC (MeOH, H$_2$O, TFA) followed by concentration of the desired fractions and lyophilization provided 92H (18 mg, 22%) as a white solid. LCMS m/z 607.3 (M+H)$^+$. $^1$HNMR (400 MHz, CD$_3$OD) δ: 2.03 (s, 4H), 2.93-3.04 (m, 1H), 3.04-3.14 (m, 1H), 3.29-3.49 (m, 4H), 3.65 (s, 3H), 4.16-4.32 (dd, J=15.79, 39.23 Hz, 2H), 4.91 (dd, J=8.46, 6.69 Hz, 1H), 7.01-7.14 (m, 5H), 7.41-7.45 (m, 5H), 7.45 (t, J=2.91 Hz, 1H), 7.50-7.53 (m, 1H), 9.25 (s, 1H).

Examples 93-98 in Table 1 were similarly prepared using the procedures described for Example 92.

Example 93

(4-{2-[(S)-1-(3-aminomethyl-benzoylamino)-2-phenyl-ethyl]-5-chloro-1H-imidazol-4-yl}-phenyl)-carbamic acid methyl ester, trifluoroacetic acid salt Colorless solid. LCMS m/z 532.92 (M+H)$^+$; $^1$HNMR (400 MHz, CD$_3$OD) δ: 3.15-3.20 (m, 2H), 3.75 (s, 3H), 4.06 (s, 2H), 4.30 (s, 2H), 5.07 (t, J=7.45 Hz, 1H), 7.13-7.16 (m, 2H), 7.19-7.32 (m, 6H), 7.32-7.41 (m, 1H), 7.48-7.56 (m, 4H).

Example 94

(4-{2-[(S)-1-(3-chloro-2,6-difluoro-benzoylamino)-2-phenyl-ethyl]-5-chloro-1H-imidazol-4-yl}-phenyl)-carbamic acid methyl ester, trifluoroacetic acid salt Colorless solid. LCMS m/z 573.83(M+H)$^+$. $^1$HNMR (400 MHz, CD$_3$OD) δ: 3.13-3.24 (m, 2H), 3.75 (s, 3H), 4.32-4.48 (m, 2H), 5.05 (t, J=7.71 Hz, 1H), 6.92-7.01 (m, 1H), 7.09-7.15 (m, 2H), 7.19-7.28 (m, 3H), 7.35-7.44 (m, 1H), 7.48-7.58 (m, 4H).

Example 95

(4-{2-[(S)-1-(3,6-dichloro-2-fluoro-benzoylamino)-2-phenyl-ethyl]-5-chloro-1H-imidazol-4-yl}-phenyl)-carbamic acid methyl ester, trifluoroacetic acid salt Colorless solid. LCMS m/z 569.85 (M+H)$^+$. $^1$HNMR (400 MHz, CD$_3$OD) δ: 2.19-2.23 (m, 3H), 3.16 (d, J=7.58 Hz, 2H), 3.75 (s, 3H), 4.38-4.51 (m, 2H), 5.05 (t, J=7.45 Hz, 1H), 7.06-7.13 (m, 4H), 7.16-7.29 (m, 3H), 7.45-7.54 (m, 4H).

Example 96

(4-{2-[(S)-1-(4-aminomethyl-benzoylamino)-2-phenyl-ethyl]-5-chloro-1H-imidazol-4-yl}-phenyl)-carbamic acid methyl ester, trifluoroacetic acid salt Colorless solid. LCMS m/z 532.91 (M+H)$^+$. $^1$HNMR (400 MHz, CD$_3$OD) δ: 3.18 (dd, J=7.45, 2.91 Hz, 2H), 3.75 (s, 3H), 4.07 (s, 2H), 4.21-4.37 (m, 2H), 5.09 (t, J=7.58 Hz, 1H), 7.14-7.18 (m, 2H), 7.20-7.30 (m, 5H), 7.34-7.38 (m, 2H), 7.50-7.56 (m, 4H).

Example 97

{4-[2-((S)-1-benzoylamino-2-phenyl-ethyl)-5-chloro-1H-imidazol-4-yl]-phenyl}-carbamic acid methyl ester, trifluoroacetic acid salt LCMS m/z 503.89 (M+H)$^+$. $^1$HNMR (400 MHz, CD$_3$OD) δ: 3.15-3.25 (m, 2H), 3.75 (s, 3H), 4.17-4.36 (m, 2H), 5.10 (t, J=7.58 Hz, 1H), 7.13-7.17 (m, 2H), 7.18-7.29 (m, 7H), 7.44-7.51 (m, 1H), 7.53 (s, 4H).

Example 98

(4-{5-chloro-2-[(S)-1-(5-chloro-2-fluoro-benzoylamino)-2-phenyl-ethyl]-1H-imidazol-4-yl}-phenyl)-carbamic acid methyl ester, trifluoroacetic acid salt LCMS m/z 555.75 (M+H)$^+$. $^1$HNMR (400 MHz, CD$_3$OD) δ: 3.09-3.21 (m, 2H), 3.75 (s, 3H), 4.21-4.42 (m, 2H), 5.01-5.12 (m, 1H), 6.99-7.05 (m, 1H), 7.11-7.27 (m, 7H), 7.46-7.50 (m, 2H), 7.51-7.57 (m, 2H).

Example 99

(4-{5-chloro-2-[(S)-1-(5-chloro-2-pyrrolidin-1-yl-benzoylamino)-2-phenyl-ethyl]-1H-imidazol-4-yl}-phenyl)-carbamic acid methyl ester, trifluoroacetic acid salt Example 99 was prepared according to the procedures outlined in Example 16. LCMS m/z 589.3 (M+H)$^+$. $^1$HNMR (400 MHz, CD$_3$OD) δ: 2.02 (s, 4H), 2.96-3.05 (m, 1H), 3.07-3.16 (m, 1H), 3.33-3.46 (m, 4H), 4.16-4.32 (m, 2H), 4.96 (dd, J=8.46, 6.69 Hz, 1H), 6.98-7.19 (m, 5H), 7.33 (dd, J=8.59, 1.26 Hz, 1H), 7.38-7.50 (m, 3H), 7.57 (s, 1H), 7.80 (d, J=7.83 Hz, 1H).

Example 100

[4-(5-chloro-2-{(S)-1-[3-(1H-imidazol-2-ylmethyl)-ureido]-2-phenyl-ethyl}-1H-imidazol-4-yl)-phenyl]-carbamic acid methyl ester, bis-trifluoroacetic acid salt Example 100 was prepared according to the procedure for urea formation described for Example 16 from (1H-imidazol-2-yl)methanamine bis-hydrochloride salt and 52B. LCMS m/z 494.3 (M+H)$^+$. $^1$HNMR (400 MHz, CD$_3$OD) δ: 3.13-3.24 (m, 2H), 3.75 (s, 3H), 4.46-4.51 (m, 1H), 4.56-4.61 (m, 1H), 5.06 (t, J=7.47 Hz, 1H), 7.15 (d, J=6.59 Hz, 2H), 7.19-7.28 (m, 3H), 7.41 (s, 2H), 7.50-7.55 (m, 4H).

Example 101

[4-(5-chloro-2-{(S)-1-[3-(3-fluoro-pyridin-2-ylmethyl)-ureido]-2-phenyl-ethyl}-1H-imidazol-4-yl)-phenyl]-carbamic acid methyl ester, bis-trifluoroacetic acid salt 101A. C-(3-fluoro-pyridin-2-yl)-methylamine, bis-hydrochloride salt: Following the procedure of Burgey, et al. (*J. Med. Chem.*, 2003, 46, 461-473), to 3-fluoropicolinonitrile (0.2 g, 1.638 mmol) and 10% palladium on carbon (50 mg, 0.470 mmol) was added ethanol (20 ml) and several drops of conc. HCl. The reaction was stirred under 35 psi of hydrogen overnight. The reaction mixture was filtered through Celite® and concentrated to give 101A as a white solid (0.37 g). LCMS m/z 127.1 (M+H)$^+$.

101B. Example 101 was prepared according to the procedure for urea formation described for Example 16 from 101A and 52B. LCMS m/z 523.3 (M+H)$^+$. $^1$HNMR (400 MHz, CD$_3$OD) δ: 3.23-3.30 (m, 2H), 3.78 (s, 3H), 4.45-4.63 (m, 2H), 5.13 (t, J=7.58 Hz, 1H), 7.14-7.22 (m, 2H), 7.23-7.34 (m, 3H), 7.40-7.47 (m, 1H), 7.51-7.62 (m, 4H), 7.63-7.70 (m, 1H), 8.36 (d, J=4.80 Hz, 1H).

Example 102

1-[4-chloro-2-(3-{(S)-1-[5-chloro-4-(4-methoxycarbonylamino-phenyl)-1H-imidazol-2-yl]-2-phenyl-ethyl}-ureidomethyl)-phenyl]-piperidine-3-carboxylic acid, trifluoroacetic acid salt 102A. 1-(4-chloro-2-cyano-phenyl)-piperidine-3-carboxylic acid ethyl ester: 5-chloro-2-fluorobenzonitrile (0.2 g, 1.286 mmol), ethyl piperidine-3-carboxylate (0.300 ml, 1.929 mmol), and potassium carbonate (0.355 g, 2.57 mmol) were combined in DMF (1 mL) and stirred overnight. The reaction mixture was partitioned with EtOAc/water/brine and extracted with EtOAc. The combined organic layers were washed with water and brine, dried (MgSO$_4$), and evaporated to afford 102A as a clear oil (0.3 g). LCMS m/z 293.2 (M+H)$^+$.

102B. 1-(2-Aminomethyl-4-chloro-phenyl)-piperidine-3-carboxylic acid ethyl ester: 102A (0.37 g, 1.327 mmol), 2M NH$_3$ in MeOH (20 mL) and a pipette of Raney nickel slurry were stirred under 50 psi of hydrogen overnight. The reaction mixture was filtered through Celite® evaporated, redissolved in EtOAc, and dried (MgSO$_4$). Filtration and evaporation gave 102B as a clear oil (0.278 g). LCMS m/z 297.3 (M+H)$^+$; 280.2 (M+H—NH$_3$)$^+$.

102C. 1-[4-chloro-2-(3-{(S)-1-[5-chloro-4-(4-methoxycarbonylamino-phenyl)-1H-imidazol-2-yl]-2-phenyl-ethyl}-ureidomethyl)-phenyl]-piperidine-3-carboxylic acid ethyl ester: 102C was prepared according to the procedure for urea formation described for Example 16 from 102B and 52B. LCMS m/z 693.4 (M+H)$^+$.

102D. Example 102: To 102C (8.3 mg, 0.012 mmol) in THF (1 mL), methanol (1 mL), and water (2 mL) was added lithium hydroxide hydrate (2.51 mg, 0.060 mmol) and the reaction was stirred overnight. After evaporating volatiles, Example 102 was purified by HPLC (MeOH, H$_2$O, TFA). LCMS m/z 665.4 (M+H)$^+$. $^1$HNMR (400 MHz, CD$_3$OD) δ: 1.22 (dd, J=15.03, 7.71 Hz, 1H), 1.70-2.01 (m, 4H), 2.88-3.14 (m, 4H), 3.29-3.40 (m, 2H), 3.66 (s, 3H), 4.07-4.40 (m, 2H), 4.96 (dd, J=8.84, 6.32 Hz, 1H), 6.94-7.17 (m, 5H), 7.34-7.49 (m, 7H).

Example 103

[4-(5-chloro-2-{(S)-1-[3-(2,5-dichloro-thiophen-3-ylmethyl)-ureido]-2-phenyl-ethyl}-1H-imidazol-4-yl)-phenyl]-carbamic acid methyl ester, trifluoroacetic acid salt 103A. 3-bromomethyl-2,5-dichloro-thiophene: Borane-THF complex (6.009 mL, 6.01 mmol) was added dropwise into a THF (5 mL) solution of 2,5-dichlorothiophene-3-carboxylic acid (296 mg, 1.502 mmol). The resultant solution was stirred at rt under argon overnight. The reaction was quenched with dilute HCl (12 mL) and stirred at rt for 1 h. The reaction was diluted with water and extracted with EtOAc (2×20 mL), washed with NaOH solution and brine, dried (Na$_2$SO$_4$), filtered and evaporated to provide (2,5-dichloro-thiophen-3-yl)-methanol, which was purified by flash chromatography. LCMS m/z 183.2 (M+H)$^+$. To a solution of this intermediate (215 mg, 1.175 mmol) in DCM (7 mL) was added PBr$_3$ (0.144 mL, 1.527 mmol) via syringe. The reaction mixture was stirred at rt under argon for 15 min, then quenched with water (18 mL) and stirred at rt for 1 h. The aqueous layer was extracted with DCM (2×10 ml) and the combined organic layers were dried (Na$_2$SO$_4$), filtered and concentrated yielding 103A (250 mg). $^1$HNMR (400 MHz, CD$_3$OD) δ: 4.47 (s, 2H), 7.02 (s, 1H).

103B. C-(2,5-dichloro-thiophen-3-yl)-methylamine: To 103A (250 mg, 1.016 mmol) in DMF (4 mL) was added sodium azide (661 mg, 10.16 mmol) and the reaction mixture was stirred at rt for 16 h. The reaction mixture was quenched with water and extracted with EtOAc. The organic layer was washed with water and brine, dried over Na$_2$SO$_4$, filtered and concentrated yielding 3-azidomethyl-2,5-dichloro-thiophene (135 mg). To a solution of this intermediate (135 mg, 0.519 mmol) in methanol (5 mL) was added 10% palladium on carbon. The reaction mixture was stirred at rt under a hydrogen balloon for 1 h. The mixture was filtered and the catalyst was washed with MeOH. The combined filtrate was concentrated and the resulting residue was dissolved in 0.25 N HCl (2 mL) and washed with EtOAc (10 mL). The aqueous layer was basified with 1N NaOH and extracted with EtOAc (5×10 mL). The combined organic layers were washed with brine, dried with Na$_2$SO$_4$, filtered and concentrated yielding 103B (41 mg). LCMS m/z 182.1 (M+H)$^+$.

103C. Example 103 was prepared according to the procedure for urea formation described for Example 16 from 103B and 52B. LCMS m/z 578.2 (M+H)$^+$. $^1$HNMR (400 MHz, CD$_3$OD) δ: 3.21 (d, J=7.47 Hz, 2H), 3.75 (s, 3H), 4.08-4.15 (m, 2H), 5.11 (t, J=7.69 Hz, 1H), 6.72 (s, 1H), 7.16 (d, J=6.59 Hz, 2H), 7.25-7.31 (m, 3H), 7.50-7.58 (m, 4H).

Examples 104 and 105

1-{(S)-1-[4-(3-amino-1H-indazol-6-yl)-5-chloro-1H-imidazol-2-yl]-2-phenyl-ethyl}-3-(5-chloro-2-phenoxy-benzyl)-urea, trifluoroacetic acid salt and 1-{(S)-1-[4-(3-amino-1H-indazol-6-yl)-5-chloro-1H-imidazol-2-yl]-2-phenyl-ethyl}-3-(2-phenoxy-benzyl)-urea, trifluoroacetic acid salt 104A. 5-chloro-2-phenoxy-benzonitrile: A mixture of 5-chloro-2-fluorobenzonitrile (0.318 g, 2.044 mmol), phenol (0.192 g, 2.044 mmol), and potassium carbonate (1.515 g, 10.96 mmol) in DMF (2 mL) was stirred overnight at rt. The reaction was quenched with water and extracted with EtOAc (2×50 mL), dried (MgSO$_4$) and evaporated to give 104A. LCMS m/z 230.2 (M+H)$^+$.

104 B and 105C. 5-chloro-2-phenoxy-benzylamine and 2-phenoxy-benzylamine: LAH (76 mg, 1.99 mmol) was added to a THF (5 mL) solution of 104A (457 mg, 1.99 mmol) and the reaction was stirred at rt overnight. After quenching the reaction with methanol (5 mL) and sodium hydroxide solution (20 mL), the mixture was extracted with EtOAc (2×50 mL), dried (MgSO$_4$), and concentrated to give a mixture of 104B, LCMS m/z 234.1 (M+H)$^+$, and 104C, LCMS m/z 200.2 (M+H)$^+$.

104D and 104E. Examples 104 and 105: The title compounds were prepared according to the procedure described for example 16 from the above describe mixture of 104B/ 104C and 1E. The compounds were separated and purified by prep. HPLC. Example 104: LCMS m/z 612.2 (M+H)$^+$. $^1$HNMR (CD$_3$OD, 400 MHz) δ: 7.98 (d, J=9.2 Hz, 1H), 7.71 (s, 1H), 7.53 (dd, J=1.4 & 8.7 Hz, 1H), 7.49-7.12 (m, 10H), 6.97 (dd, J=1.0 & 8.7z, 2H), 6.80 (d, J=8.7 Hz, 1H), 5.12 (t, 1H), 4.37 (q(AB), 2H), 3.25 (m, 2H). Example 105: LCMS m/z 578.2 (M+H)+. $^1$HNMR (CD$_3$OD, 400 MHz) δ: 7.98 (d, J=8.6 Hz, 1H), 7.70 (s, 1H), 7.53 (dd, J=1.4 & 8.7 Hz, 1H), 7.31-7.05 (m, H), 6.94 (dd, J=1.0 & 8.7 Hz, 1H), 5.12 (t, 1H), 4.39 (q(AB), 2H), 3.21 (m, 2H).

Example 106

1-{(S)-1-[4-(3-Amino-1H-indazol-6-yl)-5-chloro-1H-imidazol-2-yl]-2-phenyl-ethyl}-3-(5-chloro-2-methylsulfanylmethyl-benzyl)-urea, trifluoroacetic acid salt Example 106 was prepared according to the procedure described for Example 16 from 5-chloro-2-methylsulfanyl-methyl-benzylamine and 1E. LCMS m/z 580.3 (M+H)+. $^1$HNMR (CD$_3$OD, 400 MHz) δ: 7.87 (dd, J=0.7 & 8.6 Hz, 1H), 7.61 (s, 1H), 7.43 (dd, J=1.4 & 8.7 Hz, 1H), 7.24-6.95 (m, 8H), 5.01 (t, 1H), 4.78 (q, AB), 2H), 3.61 (s, 2H), 3.21 (m, 2H), 1.89 (s, 3H).

Example 107

1-{(S)-1-[4-(3-Amino-1H-indazol-6-yl)-5-chloro-1H-imidazol-2-yl]-2-phenyl-ethyl}-3-[5-chloro-2-(tetrahydro-furan-2-ylmethoxy)-benzyl]-urea, trifluoroacetic acid salt 107A. 5-Chloro-2-(tetrahydro-furan-2-ylmethoxy)-benzonitrile: A mixture of 5-chloro-2-fluorobenzonitrile (0.29 g, 1.86 mmol), (tetrahydrofuran-2-yl)methanol (0.19 g, 1.86 mmol) and potassium carbonate (0.81 g, 5.86 mmol) in DMF (5 mL) was stirred at rt overnight. To this mixture was added NaH (100 mg) and the reaction mixture was stirred at rt overnight. The reaction was quenched with water, extracted with EtOAc (2×), dried (MgSO$_4$), filtered and evaporated. The resulting residue was purified by flash chromatography to give 107A (0.35 g, 75%). LCMS m/z 238.2 (M+H)+.

107B. 5-Chloro-2-(tetrahydro-furan-2-ylmethoxy)-benzylamine: A small amount of Raney nickel was added to 107A (0.35 g, 1.47 mmol) in MeOH/ammonia (30 mL) solution and the reaction was stirred under 60 psi of hydrogen overnight. The reaction was filtered through Celite® and concentrated to give 107B. LCMS m/z 242.2 (M+H)+.

107C. Example 107 was prepared according to the procedure described for example 16 from 107B and 1E. LCMS m/z 620.3 (M+H)+. $^1$HNMR (CD$_3$OD, 400 MHz) δ: 7.85 (d, J=8.3 Hz, 1H), 7.60 (s, 1H), 7.40 (dd, J=1.4 & 8.4 Hz, 1H), 7.16-7.03 (m, 7H), 6.82 (d, J=8.4 Hz, 1H), 5.00 (t, 1H), 4,18 (s, 3H), 3.95-70 (m, 4H), 3.15 (m, 2H), 2.05-1.69 (m, 4H).

Example 108

[4-(5-Chloro-2-{(S)-1-[3-(5-chloro-thiophen-2-ylmethyl)-ureido]-2-phenyl-ethyl}-1H-imidazol-4-yl)-phenyl]-carbamic acid methyl ester, trifluoroacetic acid salt 108A. C-(5-chloro-thiophen-2-yl)-methylamine, trifluoroacetic acid salt: To a solution of 5-chlorothiophene-2-carbaldehyde (1.0 g, 6.82 mmol) in dichloroethane (10 mL) were added ammonium acetate (1.052 g, 13.64 mmol) and sodium triacetoxyborohydride (1.590 g, 7.50 mmol). The reaction mixture was stirred under nitrogen at rt for 2 days. The reaction was quenched with MeOH and water and then evaporated. The product was purified by prep HPLC to give 108A (142 mg, 7.96%). LCMS m/z 148.04 (M+H)+.

108B. Example 108 was prepared according to the procedure described for example 16 from 108A and 52B. LCMS m/z 544.2 (M+H)+. $^1$HNMR (400 MHz, CD$_3$OD) δ: 3.17 (d, J=7.47 Hz, 2H), 3.74 (s, 3H), 4.27-4.34 (m, 2H), 5.06 (t, J=7.69 Hz, 1H), 6.69 (d, J=3.52 Hz, 1H), 6.75 (d, J=3.95 Hz, 1H), 7.14 (d, J=6.59 Hz, 2H), 7.23 (ddd, J=14.39, 7.14, 7.03 Hz, 3H), 7.53 (s, 4H).

Example 109

[2-{(S)-1-[5-Chloro-4-(4-hydroxy-2-oxo-1,2-dihydro-quinolin-6-yl)-1H-imidazol-2-yl]-2-phenyl-ethylcarbamoyl}-1-(3-chloro-phenyl)-ethyl]-carbamic acid tert-butyl ester, trifluoroacetic acid salt To a solution of 65G (50 mg, 0.131 mmol) in DMF (1.5 mL) were added 3-(tert-butoxycarbonylamino)-3-(3-chlorophenyl)propanoic acid (50 mg, 0.167 mmol), PyBOP (100 mg, 0.192 mmol) and DIEA (0.1 ml, 0.573 mmol), and the reaction mixture was stirred under nitrogen at rt overnight. The crude product was diluted with methanol and purified by prep HPLC to give 109 (24 mg, 23.54%). LCMS m/z 662.36 (M+H)+. $^1$HNMR (400 MHz, CD$_3$OD, two diastereomers) δ: 1.35 (d, J=9.67 Hz, 9H), 2.47-2.73 (m, 2H), 3.02-3.25 (m, 2H), 4.81-5.04 (m, 1H), 5.15 (t, J=7.91 Hz, 1H), 5.96 (s, 1H), 7.02-7.34 (m, 8H), 7.41 (dd, J=8.79, 2.20 Hz, 1H), 7.85 (ddd, J=8.68, 2.09, 1.98 Hz, 1H), 8.15-8.31 (m, 1H).

Example 110

N-{(S)-1-[5-(3-Amino-1H-indazol-6-yl)-5-chloro-1H-imidazol-2-yl]-2-phenyl-ethyl}-3-(5-chloro-2-tetrazol-1-yl-phenyl)-propionamide, trifluoroacetic acid salt 110A. 6-[2-((S)-1-Amino-2-phenyl-ethyl)-5-chloro-1H-imidazol-4-yl]-1H-indazol-3-ylamine, bis trifluoroacetic acid salt: A mixture of 1D (3.0 g, 6.8 mol) and hydrazine monohydrate (3.5 mL, 72.2 mmol) in n-butanol (35 mL) was refluxed in a 120° C. oil bath for 3 h, then cooled to rt and stirred overnight. Reaction mixture was diluted with water and extracted with EtOAc. Combined extracts were washed with brine, dried over Na$_2$SO$_4$, filtered and evaporated to provide an off-white solid. LCMS m/z 453 (M+H)+. The solid was redissolved in a mixture of TFA (5 mL) and dichloromethane (7 mL) and stirred at rt for 1.5 h. The reaction was evaporated to give an orange oil which was triturated 2× with diethyl ether, then 2× with hexane. The resulting light yellow-orange solid was collected by filtration, washed with hexanes and dried in vacuo to provide the deprotected amine as its bis TFA salt (4 g, 99% over two steps). LCMS m/z 353 (M+H)+.

110B. Example 110 was prepared by coupling 63A and the free base of 110A according to the procedure described for 62C. LCMS m/z 587.2 (M+H)+. $^1$HNMR (400 MHz, methanol-D$_4$) δ: 9.44 (s, 1H), 7.95 (d, J=8.8 Hz, 1H), 7.69 (s, 1H), 7.50-7.48 (m, 2H), 7.43 (dd, J=8.8, 2.2 Hz, 1H), 7.38 (d, J=7.4 Hz, 1H), 7.24-7.11 (m, 5H), 5.12 (t, J=7.7 Hz, 1H), 3.19 (dd, J=13.2, 7.9 Hz, 1H), 3.09 (dd, J=13.6, 7.9 Hz, 1H), 2.67 (t, J=7.3 Hz, 2H), 2.45 (t, J=7.3 Hz, 2H).

Example 112

3-Amino-N-{(S)-1-[5-chloro-4-(4-hydroxy-2-oxo-1,2-dihydro-quinolin-6-yl)-1H-imidazol-2-yl]-2-phenyl-ethyl}-3-(3-chloro-phenyl)-propionamide, bis-trifluoroacetic acid salt Example 112 was prepared by treatment of Example 109 with TFA in $CH_2Cl_2$ followed by purification by prep. HPLC. LCMS m/z 562.27 $(M+H)^+$. $^1$HNMR (400 MHz, $CD_3OD$) δ: 2.83-2.93 (m, 2H), 3.04-3.14 (m, 1H), 3.16-3.24 (m, 1H), 4.60-4.68 (m, 1H), 5.17 (td, J=7.69, 3.52 Hz, 1H), 5.93 (s, 1H), 7.09-7.13 (m, 1H), 7.15-7.25 (m, 4H), 7.28-7.33 (m, 1H), 7.36-7.43 (m, 3H), 7.43-7.47 (m, 1H), 7.84 (dd, J=8.79, 1.76 Hz, 1H), 8.20 (d, J=2.20 Hz, 1H).

Example 113

N-{(S)-1-[5-Chloro-4-(4-hydroxy-2-oxo-1,2-dihydro-quinolin-6-yl)-1H-imidazol-2-yl]-2-phenyl-ethyl}-3-(5-chloro-2-tetrazol-1-yl-phenyl)-propionamide, trifluoroacetic acid salt Example 113 was prepared according to the procedure described for Example 109 from 63A and 65G. LCMS m/z 615.33 $(M+H)^+$. $^1$HNMR (400 MHz, $CD_3OD$) δ: 2.47 (t, J=7.47 Hz, 2H), 2.67 (t, J=6.81 Hz, 2H), 3.13-3.17 (m, 2H), 5.14 (t, J=7.69 Hz, 1H), 5.96 (s, 1H), 7.11-7.14 (m, 2H), 7.18-7.26 (m, 3H), 7.36-7.45 (m, 3H), 7.50 (d, J=2.20 Hz, 1H), 7.85 (dd, J=8.79, 1.76 Hz, 1H), 8.21 (d, J=2.20 Hz, 1H), 9.45 (s, 1H).

Example 114

{4-[5-Chloro-2-((S)-1-{3-[5-chloro-2-(1H-tetrazol-5-yl)-benzyl]-ureido}-2-phenyl-ethyl)-1H-imidazol-4-yl]-phenyl}-carbamic acid methyl ester, trifluoroacetic acid salt 114A. 5-(4-Chloro-2-methyl-phenyl)-1-trityl-1H-tetrazole: To 4-chloro-2-methyl-benzonitrile (4 g, 26.4 mmol) in DMF (20 mL) was added sodium azide (5.15 g, 79 mmol) and ammonium chloride (4.23 g, 79 mmol) and the reaction was heated at 85° C. overnight. The reaction was cooled to rt and additional sodium azide (3.4 g) and $NH_4Cl$ (2.8 g) was added. The reaction was heated at 24 h at 110° C., then partitioned with $Et_2O/1$ N NaOH/water and extracted with $Et_2O$. The aqueous layer was acidified and 5-(4-chloro-2-methyl-phenyl)-1H-tetrazole was collected by filtration as a white precipitate (3.45 g). LCMS m/z 195.2 $(M+H)^+$. To this intermediate (3.45 g) was added DMF (20 mL), trityl chloride (5.45 g, 19.55 mmol), and TEA (3.68 mL, 26.4 mmol) and the reaction was stirred overnight. The reaction was partitioned with EtOAc/water/brine and extracted with EtOAc. Combined organic layers were washed with water and brine, dried ($MgSO_4$), and concentrated to afford 114A (8 g). $^1$HNMR (400 MHz, $CDCl_3$) δ: 2.49 (s, 3H), 7.10-7.19 (m, 5H), 7.22-7.29 (m, 3H), 7.27-7.40 (m, 9H), 8.03 (d, J=8.84 Hz, 1H).

114B. 5-(2-Azidomethyl-4-chloro-phenyl)-1-trityl-1H-tetrazole: To 114A (4 g, 9.15 mmol) in chloroform (20 mL) was added NBS (1.711 g, 9.61 mmol) and benzoyl peroxide (30 mg, 0.124 mmol) and the reaction was heated at reflux overnight. Additional NBS and peroxide were added and the reaction was heated an addition 2 h. The reaction was cooled to rt, filtered, and purified by flash chromatography to give 5-(2-bromomethyl-4-chloro-phenyl)-1-trityl-1H-tetrazole (3.5 g, 74.1%). $^1$HNMR (400 MHz, $CDCl_3$) δ: 4.78 (s, 2H), 7.04-7.14 (m, 5H), 7.24-7.35 (m, 11H), 7.40 (d, J=2.02 Hz, 1H), 8.06 (d, J=8.34 Hz, 1H). This intermediate (1.57 g, 3.04 mmol) and sodium azide (0.198 g, 3.04 mmol) in DMF (8 mL) were stirred for two days. The reaction was partitioned with EtOAc/water/brine and extracted with EtOAc. The combined organic layers were washed with water and brine, dried ($MgSO_4$), and purified by flash chromatography to give 114B. LCMS m/z 195.2 $(M+H-N_3)^+$; 152.1 $(M+H-N_6)$.

114C. 5-Chloro-2-(1H-tetrazol-5-yl)-benzylamine: To 114B (0.153 g, 0.649 mmol) in 2M $NH_3$/MeOH (5 mL) was added a small amount of Raney nickel slurry and the reaction was stirred under 25 psi $H_2$ for 3 h, then under 50 psi $H_2$ for 1 h. The reaction was filtered and concentrated to give 114C. LCMS m/z 210.2 $(M+H)^+$; 193.2 $(M+H-NH_3)^+$.

114D. Example 114 was prepared according to the procedure for urea formation described for Example 16 from 114C and 52B. LCMS m/z 606.5 $(M+H)^+$. $^1$HNMR (400 MHz, $CD_3OD$) δ: 3.08 (d, J=7.58 Hz, 2H), 3.65 (s, 3H), 4.39 (d, J=3.28 Hz, 2H), 4.95 (t, J=7.58 Hz, 1H), 6.99-7.05 (m, 2H), 7.05-7.16 (m, 3H), 7.37 (dd, J=8.34, 2.02 Hz, 1H), 7.43 (s, 4H), 7.46 (d, J=2.27 Hz, 1H), 7.66 (d, J=8.34 Hz, 1H).

Example 115

(4-{5-Chloro-2-[(S)-2-phenyl-1-(3-thiophen-3-yl-propionylamino)-ethyl]-1H-imidazol-4-yl}-phenyl)-carbamic acid methyl ester, trifluoroacetic acid salt 3-Thiophen-3-yl-propionic acid was synthesized from (E)-3-thiophen-3-yl-acrylic acid following a literature procedure (Bonini, et al., *Eur. J. Org. Chem.*, 2004, 21, 4442-4451). This intermediate was coupled to 52B according to the procedure described for 62C to give Example 115. LCMS m/z 509.3 $(M+H)^+$. $^1$HNMR (400 MHz, $CD_3OD$) δ 2.48 (t, J=7.47 Hz, 2H), 2.84 (t, J=7.47 Hz, 2H), 3.05-3.11 (m, 1H), 3.17-3.23 (m, 1H), 3.74 (s, 3H), 5.18 (m, 1H), 6.87 (d, J=5.27 Hz, 1H), 6.92 (d, J=2.64 Hz, 1H), 7.13-7.16 (m, 2H), 7.19 (d, J=7.03 Hz, 1H), 7.21-7.26 (m, 3H), 7.51 (q, J=8.79 Hz, 4H).

Example 116

[4-(5-Chloro-2-{(S)-1-[3-(5-chloro-2-tetrazol-1-yl-phenyl)-propionylamino]-2-cyclopropyl-ethyl}-1H-imidazol-4-yl)-phenyl]-carbamic acid methyl ester, trifluoroacetic acid salt 116A. {4-[2-((S)-1-Amino-2-cyclopropyl-ethyl)-5-chloro-1H-imidazol-4-yl]-phenyl}-carbamic acid methyl ester, bis-trifluoroacetic acid salt: 116A was prepared from commercially available (S)-2-tert-butoxycarbonylamino-3-cyclopropyl-propionic acid following the procedures described for 84D, 84E, 84F, and 84I. $^1$H-NMR ($CD_3OD$, 400 MHz): 7.63 (d, 2H, J=8), 7.52 (d, 2H, J=8), 4.07 (m, 1H), 3.75 (s, 3H), 3.30 (m, 4H), 1.74 (m, 2H), 0.67 (m, 1H), 0.43 (m, 2H), 0.08 (m, 2H).

116B. Example 116 was prepared by coupling 63A with 116A according to procedure described for 62C. LCMS m/z 569 $(M+H)^+$. $^1$H-NMR ($CD_3OD$, 400 MHz): 9.47 (s, 1H), 7.60 (d, 2H, J=8), 7.55 (m, 1H), 7.54 (d, 2H, J=8), 7.40 (m, 2H), 4.96 (t, H, J=7), 3.75 (s, 3H), 3.30 (m, 3H), 2.76 (t, 2H, J=7), 2.50 (t, 2H, J=7), 1.71 (m, 2H), 0.59 (m, 1H), 0.43 (m, 2H), 0.10 (m, 1H), 0.0 (m, 1H).

Example 117

[4-(5-Chloro-2-{(S)-1-[3-(5-methyl-2-tetrazol-1-yl-phenyl)-propionylamino]-2-phenyl-ethyl}-1H-imidazol-4-yl)-phenyl]-carbamic acid methyl ester, trifluoroacetic acid salt 117A. 1-(2-Bromo-4-methyl-phenyl)-1H-tetrazole: To a solution of 2-bromo-4-methylaniline (7.50 g, 40.3 mmol) in AcOH (20 mL) were added trimethyl orthoformate (4.71 g, 44.3 mmol) and sodium azide (3.93 g, 60.5 mmol) at 0° C. The reaction mixture was stirred under nitrogen, warming from 0° C. to rt, overnight. The reaction mixture was diluted with EtOAc, washed with $H_2O$ (2×), sat'd $NaHCO_3$ and sat'd NaCl. The organic phase was dried over $MgSO_4$, filtered and concentrated. The product was purified by flash chromatography (7.90 g, 82% yield). LCMS m/z 241.11 $(M+H)^+$.

117B. 3-(5-Methyl-2-tetrazol-1-yl-phenyl)-propionic acid: To a mixture of 117A (956 mg, 4.00 mmol), 3,3-diethoxyprop-1-ene (1562 mg, 12.00 mmol), and $Bu_4NCl$ (1110 mg, 4.00 mmol) in DMF (22 mL) was added $Bu_3N$ (1480 mg, 8.00 mmol). To this mixture under $N_2$ was added $Pd(OAc)_2$ (26.9 mg, 0.12 mmol). The resulting mixture was stirred at 90° C. for 1.5 h, then cooled to rt and quenched with 2N HCl (10 mL). The resulting mixture was stirred for 20 min, then evaporated. The mixture was diluted with EtOAc, washed with water and brine, dried over $MgSO_4$, and purified by flash chromatography to provide 3-(5-Methyl-2-tetrazol-1-yl-phenyl)-propionic acid ethyl ester (695 mg, 66.8%). LCMS m/z 261.2 $(M+H)^+$. To a solution of this intermediate (690 mg, 2.65 mmol), in THF (10 mL) was added 2N LiOH (10 mL). The resulting mixture was stirred at rt for 3 h, then acidified to pH 3-4 with 2N HCl at 0° C. The mixture was concentrated and extracted with EtOAc (5×20 mL). The combined organic layers were washed with brine, dried over $MgSO_4$, and purified by prep. HPLC to give 117B (567 mg, 92%). LCMS m/z 233.2 $(M+H)^+$.

117C. Example 117 was prepared by coupling 117B with 52B according to the procedure described for 62C. LCMS m/z 585.3 $(M+H)^+$.

Example 118

N-{(S)-1-[5-Chloro-4-(4-hydroxy-2-oxo-1,2-dihydro-quinolin-6-yl)-1H-imidazol-2-yl]-2-phenyl-ethyl}-3-(5-methyl-2-tetrazol-1-yl-phenyl)-propionamide, trifluoroacetic acid salt Example 118 was prepared from 117B and 65G following the procedure described for 109. LCMS m/z 595.4 $(M+H)^+$. 1HNMR (400 MHz, $CD_3OD$) δ: 2.34 (s, 3H), 2.43 (td, J=7.47, 3.08 Hz, 2H), 2.56-2.66 (m, 2H), 3.08 (dd, J=13.62, 7.91 Hz, 1H), 3.19 (dd, J=13.62, 7.47 Hz, 1H), 5.15 (t, J=7.69 Hz, 1H), 5.94 (s, 1H), 7.12 (d, J=6.59 Hz, 2H), 7.16-7.25 (m, 6H), 7.38 (d, J=8.79 Hz, 1H), 7.83 (dd, J=8.57, 1.98 Hz, 1H), 8.19 (d, J=1.76 Hz, 1H), 9.40 (s, 1H).

Example 119

1-(3-Chloro-2,6-difluoro-benzyl)-3-{(S)-1-[5-chloro-4-(4-hydroxy-2-oxo-1,2-dihydro-quinolin-6-yl)-1H-imidazol-2-yl]-2-phenyl-ethyl}-urea, trifluoroacetic acid salt 119A. 6-[5-Chloro-2-((S)-1-isocyanato-2-phenyl-ethyl)-1H-imidazol-4-yl]-4-hydroxy-1H-quinolin-2-one: To a solution of 65G (3.81 g, 10 mmol) in DMF were added pyridine (2.426 mL, 30.0 mmol) and 4-nitrophenyl chloroformate (2.419 g, 12.00 mmol) at 0° C. The reaction mixture was stirred under nitrogen from 0° C. to rt for 4 days. Volatiles were removed under vacuum and the resulting residue was purified by flash chromatography to give 119A (0.52 g, 12.78%). LCMS m/z 409.22 $(M+H)^+$.

119B. Example 119: To a solution of (3-chloro-2,6-difluorophenyl)methanamine (50 mg, 0.282 mmol) in DMF (1 mL) were added 119A (30 mg, 0.074 mmol) and pyridine (0.1 mL, 1.236 mmol). The reaction mixture was stirred under nitrogen 2 h. The crude product was purified by prep HPLC to give Example 119. LCMS m/z 584.27 $(M+H)^+$. $^1$HNMR (400 MHz, $CD_3OD$) δ: 3.18 (d, J=7.47 Hz, 2H), 4.34-4.45 (m, J=14.94 Hz, 2H), 5.06 (t, J=7.69 Hz, 1H), 5.95 (s, 1H), 6.96 (td, J=9.01, 1.76 Hz, 1H), 7.10-7.14 (m, 2H), 7.16-7.27 (m, 3H), 7.36-7.43 (m, J=8.46, 8.46, 5.93 Hz, 2H), 7.80 (dd, J=8.79, 2.20 Hz, 1H), 8.19 (d, J=1.76 Hz, 1H). $^{19}$F NMR (376 MHz, $CD_3OD$) δ: −117.64 (s, 1F)-117.07 (s, 1F)-77.42 (s, 7F).

Examples 120 and 121

3-(3-{(S)-1-[5-Chloro-4-(4-hydroxy-2-oxo-1,2-dihydro-quinolin-6-yl)-1H-imidazol-2-yl]-2-phenyl-ethyl}-ureido)-3-(3-chloro-phenyl)-propionic acid The title compounds were prepared from 3-amino-3-(3-chlorophenyl)propanoic acid and 119A following the procedure described for 119B. The two diastereomers were separated by prep. HPLC.

Example 120

Diastereomer A (RT=1.85 min, column: Phenomenex Luna C18, 30×4.6 mm, 5µ, flow rate: 5 mL/min, MeOH/water with 0.1% TFA 0% to 100% gradient in 2 min). LCMS m/z 606.32 $(M+H)^+$. $^1$HNMR (400 MHz, $CD_3OD$) δ: 2.74 (ddd, J=19.55, 15.82, 6.81 Hz, 2H), 3.18 (d, J=7.47 Hz, 2H), 5.03 (t, J=7.47 Hz, 1H), 5.10 (t, J=6.81 Hz, 1H), 5.92 (s, 1H), 7.13 (d, J=7.03 Hz, 2H), 7.17-7.22 (m, 2H), 7.23-7.28 (m, 4H), 7.32 (s, 1H), 7.36 (d, J=8.79 Hz, 1H), 7.78 (dd, J=8.79, 1.76 Hz, 1H), 8.17 (d, J=1.76 Hz, 1H).

Example 121

Diastereomer B (RT=1.91 min, column: Phenomenex Luna C18, 30×4.6 mm, 5µ, flow rate: 5 mL/min, MeOH/water with 0.1% TFA 0% to 100% gradient in 2 min). LCMS m/z 606.31 $(M+H)^+$. $^1$HNMR (400 MHz, $CD_3OD$) δ: 2.74 (d, J=7.03 Hz, 2H), 3.12-3.23 (m, J=13.84, 13.84, 7.03 Hz, 2H), 5.05 (t, J=7.69 Hz, 1H), 5.09 (t, J=7.03 Hz, 1H), 5.93 (s, 1H), 7.11-7.15 (m, 2H), 7.16-7.21 (m, 2H), 7.21-7.29 (m, 4H), 7.30 (s, 1H), 7.40 (d, J=8.79 Hz, 1H), 7.85 (dd, J=8.57, 1.98 Hz, 1H), 8.22 (d, J=2.20 Hz, 1H).

Example 122

{(S)-1-[5-Chloro-4-(4-hydroxy-2-oxo-1,2-dihydro-quinolin-6-yl)-1H-imidazol-2-yl]-2-phenyl-ethyl}-carbamic acid 3-chloro-2,6-difluoro-benzyl ester, trifluoroacetic acid salt 122A. Carbonic acid 3-chloro-2,6-difluoro-benzyl ester 4-nitro-phenyl ester: To a solution of (3-chloro-2,6-difluorophenyl)methanol (1.50 g, 8.40 mmol) in $CH_2Cl_2$ (25 mL) were added pyridine (0.747 mL, 9.24 mmol) and 4-nitrophenyl chloroformate (1.693 g, 8.40 mmol) at 0° C. The reaction mixture was stirred under nitrogen from 0° C. to rt overnight. The reaction mixture was diluted with $CH_2Cl_2$, washed with cold 1% NaOH, 1M HCl, and brine. The organic phase was dried over $Na_2SO_4$, filtered, and evaporated to give 122A (2.82 g, 98%). $^1$HNMR (400 MHz, $CDCl_3$) δ: 5.40 (s, 2H), 6.94 (t, J=8.79 Hz, 1H), 7.39 (d, J=8.79 Hz, 2H), 7.41-7.52 (m, 1H), 8.26 (d, J=9.23 Hz, 2H). $^{19}$F NMR (376 MHz, $CDCl_3$) δ: −114.60 (s, 1F) −113.32 (s, 1F).

122B. Example 122: To a solution of 65G (75 mg, 0.197 mmol) in DMF (3 mL) were added pyridine (0.159 mL, 1.969 mmol) and 122A (67.7 mg, 0.197 mmol). The reaction mixture was stirred under a nitrogen atmosphere at 50° C. for 5 h, then cooled to rt. The crude product was purified by prep. HPLC to give Example 122 (58.6 mg, 42.5%). LCMS m/z 585.3 (M+H)$^+$. $^1$HNMR (500 MHz, $CD_3OD$) δ: 3.08-3.28 (m, 2H), 4.97 (t, J=7.70 Hz, 1H), 5.05-5.31 (m, 2H), 5.95 (s, 1H) 7.02 (t, J=9.07 Hz, 1H), 7.07-7.29 (m, 5H), 7.41 (d, J=8.80 Hz, 1H), 7.48-7.57 (m, 1H), 7.85 (d, J=7.70 Hz, 1H), 8.22 (s, 1H). $^{19}$F NMR (471 MHz, $CD_3OD$) δ: −116.84 (s, 1F)-116.11 (s, 1F)-77.43 (s, 3F).

Example 123

2,2-Dimethyl-propionic acid 6-(5-chloro-2-{(S)-1-[3-(3-chloro-2-fluoro-benzyl)-ureido]-2-phenyl-ethyl}-1H-imidazol-4-yl)-2-oxo-1,2-dihydro-quinolin-4-yl ester, trifluoroacetic acid salt To a solution of Example 65 (20.4 mg, 0.030 mmol) in $CH_2Cl_2$ (2 mL) were added pyridine (0.024 mL, 0.300 mmol) and pivaloyl chloride (5.42 mg, 0.045 mmol) at 0° C. The reaction mixture was stirred under nitrogen at 0° C. for 1 h then evaporated. The resulting residue was dissolved in MeOH/water (1:1) and allowed to sit at rt for 10 min. The crude product was purified by prep. HPLC to give Example 123 (17.5 mg, 76%). LCMS m/z 650.3 (M+H)$^+$. $^1$HNMR (400 MHz, $CD_3OD$) δ: 1.46 (s, 9H), 3.15-3.22 (m, 2H), 4.29-4.39 (m, 2H), 5.06 (t, J=7.47 Hz, 1H), 6.54 (s, 1H), 7.06 (t, J=7.69 Hz, 1H), 7.11-7.18 (m, 3H), 7.19-7.27 (m, 3H), 7.30-7.35 (m, 1H), 7.45 (d, J=8.79 Hz, 1H), 7.72 (dd, J=8.57, 1.98 Hz, 1H), 8.01 (d, J=1.76 Hz, 1H).

Example 124

N-{(S)-1-[5-Chloro-4-(4-hydroxy-2-oxo-1,2-dihydro-quinolin-6-yl)-1H-imidazol-2-yl]-2-phenyl-ethyl}-3-(3-chloro-phenyl)-3-propionylamino-propionamide, trifluoroacetic acid salt To a solution of Example 112 (11.2 mg, 0.014 mmol) in $CH_2Cl_2$ (2 mL) were added pyridine (0.011 ml, 0.142 mmol) and propionyl chloride (3.93 mg, 0.043 mmol) at 0° C. The reaction mixture was stirred under nitrogen at 0° C. for 30 min. Two drops of water were added to the reaction mixture and stirring was continued at rt overnight. The solvent was removed under vacuum and the crude product was purified by prep. HPLC to give Example 124 (7.2 mg, 69.4%). LCMS m/z 618.44 (M+H)$^+$. $^1$HNMR (400 MHz, $CD_3OD$) δ: 0.95-1.11 (m, 3H), 2.08-2.25 (m, 2H), 2.59-2.75 (m, 2H), 3.03-3.25 (m, 2H), 5.10-5.19 (m, 1H), 5.28 (t, J=7.03 Hz, 1H), 5.95 (s, 1H), 7.05-7.34 (m, 9H), 7.40 (dd, J=8.35, 3.08 Hz, 1H), 7.77-7.95 (m, 1H), 8.22 (dd, J=11.64, 1.98 Hz, 1H).

Example 125

{4-[5-Chloro-2-((S)-1-{3-[5-chloro-2-(2-oxo-pyrrolidin-1-yl)-benzyl]-ureido}-2-phenyl-ethyl)-1H-imidazol-4-yl]-phenyl}-carbamic acid methyl ester, trifluoroacetic acid salt 125A. 1-(2-Aminomethyl-4-chloro-phenyl)-pyrrolidin-2-one: To 5-chloro-2-fluorobenzonitrile (0.3 g, 1.929 mmol) and pyrrolidin-2-one (0.246 g, 2.89 mmol) in DMF (5 mL) was added NaH (0.116 g, 2.89 mmol) and the reaction was stirred overnight. The reaction mixture was partitioned with EtOAc/water/brine and extracted with EtOAc. The combined organic layers were washed with water and brine, dried ($MgSO_4$), and evaporated to give 5-Chloro-2-(2-oxo-pyrrolidin-1-yl)-benzonitrile (0.42 g). LCMS m/z 221.2 (M+H)$^+$. This intermediate was converted to 125A following the procedure described for 102B. LCMS m/z 207.2 (M+H—$NH_3$)$^+$. 1HNMR (400 MHz, CHLOROFORM-D) δ: 2.08-2.20 (m, 2H) 2.57 (t, J=7.71 Hz, 2H) 3.56 (t, J=6.69 Hz, 2H) 4.61 (s, 2H) 6.50 (d, J=8.34 Hz, 1H) 6.97 (d, J=2.27 Hz, 1H) 7.11 (dd, J=8.34, 2.27 Hz, 1H).

125B. Example 125 was prepared according to the procedure for urea formation described for Example 16 from 125A and 52B. LCMS m/z 621.5 (M+H)$^+$. $^1$HNMR (400 MHz, $CD_3OD$) δ: 2.01-2.09 (m, 2H) 2.40 (t, J=8.08 Hz, 2H) 3.11 (d, J=7.58 Hz, 2H) 3.60-3.65 (m, 2H) 3.66 (s, 3H) 4.08 (d, J=8.84 Hz, 2H) 4.98 (t, J=7.58 Hz, 1H) 7.06 (d, J=6.82 Hz, 2H) 7.09-7.25 (m, 5H) 7.27 (d, J=2.27 Hz, 1H) 7.45 (s, 4H).

Example 126

[4-(5-Chloro-2-{(S)-1-[3-(3-chloro-benzyl)-ureido]-2-phenyl-ethyl}-1H-imidazol-4-yl)-phenyl]-carbamic acid methyl ester, trifluoroacetic acid salt 126A. N,N-bis(tert-butoxycarbonyl)-2-bromo-5-chlorobenzylamine: To 1-bromo-4-chloro-2-methylbenzene (3.3 g, 16.06 mmol) in $CCl_4$ (30 mL) were added NBS (3.43 g, 19.27 mmol) and benzoyl peroxide (10 mg, 0.041 mmol). The reaction was heated 80° C. overnight, then filtered and purified by flash chromatography to give 1-bromo-2-bromomethyl-4-chloro-benzene (4.5 g). $^1$HNMR (400 MHz, $CDCl_3$) δ: 4.53 (s, 2H) 7.15 (dd, J=8.59, 2.27 Hz, 1H), 7.40-7.47 (m, 1H), 7.49 (d, J=8.59 Hz, 1H). This intermediate was combined with di-tert-butyl iminodicarbonate (3.49 g, 16.06 mmol) and cesium carbonate (5.23 g, 16.06 mmol) in DMF (16 mL) and stirred overnight. The reaction was partitioned with EtOAc/water and extracted with EtOAc. The combined organic layers were washed with water and brine, dried ($MgSO_4$), and evaporated. The resulting residue was purified by flash chromatography to give 126A (3.4 g). $^1$HNMR (400 MHz, $CDCl_3$) δ: 1.43-1.51 (m, 18H), 4.82 (s, 2H), 7.08-7.18 (m, 1H), 7.39-7.53 (m, 2H).

126B. 2-Bromo-5-chloro-benzylamine, hydrochloric acid salt: To 126A (3.4 g, 8.08 mmol) was added 4N HCl in dioxane (10 mL, 40.0 mmol) and the reaction was stirred overnight. The reaction was diluted with $Et_2O$, filtered, and evaporated to afford 126B (1.47 g). LCMS m/z 220.1 (M+H)$^+$. $^1$HNMR (400 MHz, DMSO-$d_6$) δ: 4.09 (s, 2H), 7.41 (dd, J=8.52, 2.47 Hz, 1H), 7.71 (d, J=8.79 Hz, 1H), 7.77 (d, J=2.75 Hz, 1H), 8.74 (s, 3H).

126C. [4-(2-{(S)-1-[3-(2-Bromo-5-chloro-benzyl)-ureido]-2-phenyl-ethyl}-5-chloro-1H-imidazol-4-yl)-phenyl]-carbamic acid methyl ester: 126C was prepared according to the procedure for urea formation described for Example 16 from 126B and 52B. $^1$HNMR (400 MHz, $CDCl_3$) δ: 3.30 (t, J=6.82 Hz, 2H), 3.78 (s, 3H), 4.35 (dd, J=8.72, 6.44 Hz, 2H), 4.98-5.12 (m, 1H), 6.03-6.13 (m, 1H), 6.21-6.35 (m, 1H), 7.07 (dd, J=8.21, 2.40 Hz, 1H), 7.18 (t, J=8.59 Hz, 3H), 7.23-7.29 (m, 2H), 7.42 (d, J=8.59 Hz, 1H), 7.44-7.51 (m, 2H), 7.56 (d, J=8.84 Hz, 2H), 7.77 (s, 1H).

126D. Example 126: To 126C (50 mg, 0.081 mmol) were added 3,3-diethoxyprop-1-ene (31.6 mg, 0.243 mmol), $Bu_3N$ (30.0 mg, 0.162 mmol), tetrabutylammonium bromide (26.1 mg, 0.081 mmol), DMF (1 mL) and palladium(II) acetate (0.546 mg, 2.430 µmol). The reaction was heated at 80° C. overnight. An additional aliquot of 3,3-diethoxyprop-1-ene, $Bu_3N$, tetrabutylammonium bromide, and palladium(II) acetate was added and heating was continued. The reaction mixture was evaporated, then purified by flash chromatography and prep. HPLC to give Example 126. LCMS m/z 538.5 $(M+H)^+$. $^1$HNMR (400 MHz, $CD_3OD$) δ: 3.24 (dd, J=7.58, 2.78 Hz, 2H), 3.77 (s, 3H), 4.21-4.36 (m, 2H), 5.12 (t, J=7.71 Hz, 1H), 7.12-7.21 (m, 3H), 7.20-7.35 (m, 6H), 7.49-7.62 (m, 4H).

Example 127

(4-{5-Chloro-2-[(S)-1-[3-(5-chloro-2-tetrazol-1-yl-phenyl)-propionylamino]-2-(1-methyl-1H-pyrazol-3-yl)-ethyl]-1H-imidazol-4-yl}-phenyl)-carbamic acid methyl ester, trifluoroacetic acid salt 63A was coupled to 82G according to the procedure described for 62C to give Example 127. LCMS m/z 609.5 $(M+H)^+$. $^1$HNMR (500 MHz, DMSO-$d_6$) δ: 9.72-9.80 (2H, m), 8.40 (1H, d, J=8.2 Hz), 7.57-7.59 (2H, m, J=3.3 Hz), 7.55-7.57 (1H, m), 7.49-7.54 (4H, m), 7.43 (1H, d, J=2.2 Hz), 5.79 (1H, d, J=2.2 Hz), 5.05-5.12 (1H, m), 3.70 (3H, s), 3.66 (3H, s), 3.07 (1H, dd, J=14.3, 7.1 Hz), 2.87 (1H, dd, J=14.0, 7.4 Hz), 2.56 (2H, t, J=7.4 Hz), 2.34 (2H, t, J=7.4 Hz).

Example 128

[4-(5-Chloro-2-{(S)-1-[3-(5-chloro-2-tetrazol-1-yl-phenyl)-propionylamino]-2-[1-(4-methoxy-benzyl)-1H-pyrazol-3-yl]-ethyl}-1H-imidazol-4-yl)-phenyl]-carbamic acid methyl ester, trifluoroacetic acid salt 128A. [4-(2-{(S)-1-Amino-2-[1-(4-methoxy-benzyl)-1H-pyrazol-3-yl]-ethyl}-5-chloro-1H-imidazol-4-yl)-phenyl]-carbamic acid methyl ester, di-hydrochloric acid salt: 128A was prepared from 83A following the procedure described for 82A-G. LCMS m/z 481.3 $(M+H)^+$.

128B. Example 128 was prepared by coupling 63A with 128A according to the procedure described for 62C. LCMS m/z 715.6 $(M+H)^+$. $^1$HNMR (500 MHz, DMSO-$d_6$) δ: 9.73-9.79 (2H, m), 8.40 (1H, d, J=8.2 Hz), 7.54-7.61 (3H, m), 7.48-7.54 (5H, m), 7.04 (2H, d, J=8.8 Hz), 6.76 (2H, d, J=8.8 Hz), 5.85 (1H, d, J=2.2 Hz), 5.08-5.15 (3H, m), 3.66 (3H, s), 3.65 (3H, s), 3.08 (1H, dd, J=14.3, 7.7 Hz), 2.88 (1H, dd, J=14.3, 7.1 Hz), 2.55 (2H, t, J=7.4 Hz), 2.33 (2H, t, J=7.7 Hz).

Example 129

(4-{5-Chloro-2-[(S)-1-[3-(5-chloro-2-tetrazol-1-yl-phenyl)-propionylamino]-2-(1,5-dimethyl-1H-pyrazol-3-yl)-ethyl]-1H-imidazol-4-yl}-phenyl)-carbamic acid methyl ester (4-{2-[(S)-1-Amino-2-(1,5-dimethyl-1H-pyrazol-3-yl)-ethyl]-5-chloro-1H-imidazol-4-yl}-phenyl)-carbamic acid methyl ester, bis-trifluoroacetic acid salt, was prepared from 1,5-dimethyl-1H-pyrazole-3-carbaldehyde following the procedure described for 82A-G. This intermediate was coupled with 63A according to the procedure described for 62C to provide Example 129. LCMS m/z 623.6 $(M+H)^+$. $^1$HNMR (500 MHz, DMSO-$d_6$) δ ppm 12.57 (1H, s), 9.73-9.85 (2H, m), 8.50 (1H, d, J=8.2 Hz), 7.60 (1H, d, J=2.2 Hz), 7.50-7.59 (6H, m), 5.64 (1H, s), 5.04-5.12 (1H, m), 3.67 (3H, s), 3.63 (3H, s), 3.13 (1H, dd, J=15.1, 7.4 Hz), 2.93 (1H, dd, J=15.1, 7.4 Hz), 2.57 (2H, t, J=7.7 Hz), 2.34 (2H, t, J=7.4 Hz), 2.00 (3H, s).

Example 130

(4-{2-[1-[3-(5-Chloro-2-tetrazol-1-yl-phenyl)-propionylamino]-2-(1-methyl-1H-pyrazol-4-yl)-ethyl]-1H-imidazol-4-yl}-phenyl)-carbamic acid methyl ester, trifluoroacetic acid salt 130A. (E)-2-tert-Butoxycarbonylamino-3-(1-methyl-1H-pyrazol-4-yl)-acrylic acid benzyl ester: 4-iodo-1-methyl-1H-pyrazole (0.750 g, 3.61 mmol) and 2-tert-butoxycarbonylamino-acrylic acid benzyl ester (1.00 g, 3.61 mmol) were dissolved in DMF (10 mL). To the solution was added tetra-n-butylammonium chloride (1.102 g, 3.97 mmol) and TEA (1.508 mL, 10.82 mmol). The solution was degassed by evacuating and flushing with $N_2$ (3×). Palladium(II) acetate (0.040 g, 0.180 mmol) was added, and the mixture was degassed as described above, then stirred under $N_2$ overnight at 85° C. The reaction mixture was diluted with EtOAc, and the organic layer was washed with water, 5% citric acid, and brine, then the combined organic layers were dried over anhydrous $Na_2SO_4$, filtered, and evaporated to leave a dark brown oil that was purified by flash chromatography to provide 130A as a yellow/orange oil (0.37 g, 29%).

130B. 2-tert-Butoxycarbonylamino-3-(1-methyl-1H-pyrazol-4-yl)-propionic acid: 130A (0.374 g, 1.046 mmol) was dissolved in MeOH (20 mL). The solution was evacuated and flushed with nitrogen 3×, then (S,S)-EtDuPhosRh(I) (0.038 g, 0.052 mmol) was added and the reaction was stirred for 3 d under 55 psi $H_2$ pressure. The MeOH was removed on a rotary evaporator. A mixture of the product and starting material was obtained. The material was separated from catalyst by silica gel chromatography to provide a colorless, viscous oil which was determined by NMR to be approximately a 3:1 mixture of starting material to product. This material was redissolved in 20 ml of MeOH and added to a flask containing 90 mg of 10% Pd/C (wet, Degussa) under nitrogen. The mixture was stirred and evacuated and flushed with nitrogen (3×) then stirred under a balloon of $H_2$ overnight. The catalyst was removed by filtration through a pad of Celite®, washed with MeOH, and discarded. The filtrate was evaporated. 130B (0.187 g, 66.4% yield) was obtained as a white solid after drying overnight in vacuo. LC/MS m/z 270.3 $(M+H)^+$; 214.2 (M+H-tBu)$^+$.

130C. (4-{2-[1-tert-Butoxycarbonylamino-2-(1-methyl-1H-pyrazol-4-yl)-ethyl]-1H-imidazol-4-yl}-phenyl)-carbamic acid methyl ester: 130B (0.185 g, 0.687 mmol) was dissolved in DMF (4.5 mL) and $KHCO_3$ (0.083 g, 0.824 mmol) was added. The mixture was stirred at rt for 20-30 min then cooled in an ice bath while a solution of 82D (0.224 g, 0.824 mmol) in DMF (1.5 mL) was added dropwise. The ice bath was removed after ~1 h and stirring was continued overnight at rt. The reaction mixture was diluted with EtOAc and washed with water (2×), sat'd $NaHCO_3$ and brine, then dried over anhydrous sodium sulfate, filtered and evaporated. The ketoester was redissolved in a mixture of xylene (6 mL) and EtOH (1 mL) and transferred to a 20 mL microwave vial.

Ammonium acetate (0.530 g, 6.87 mmol) was added, and the vial was capped. The reaction was heated with stirring in a microwave reactor at 160° C. for 30 min, then left standing at rt. The reaction mixture was diluted with EtOAc and washed with water and brine, then dried over anhydrous sodium sulfate, filtered and evaporated. Flash chromatography provided the imidazole product (0.203 g, 67.1%) as a light orange solid. LC/MS m/z 441.5 (M+H)$^+$.

130D. Example 130: 130C (60 mg, 0.136 mmol) was dissolved in CH$_2$Cl$_2$ (1 mL) and TFA (0.25 mL, 3.24 mmol) was added. The resulting solution was stirred overnight at rt under nitrogen, then evaporated to dryness and used without purification. The crude TFA salt of the deprotected amine was redissolved in DMF (1.5 mL) and 63A (34.4 mg, 0.136 mmol), HOBT (25.03 mg, 0.163 mmol), N-methylmorpholine (0.075 mL, 0.681 mmol) and EDC (31.3 mg, 0.163 mmol) were added. The mixture was stirred overnight at rt under a blanket of argon. The reaction mixture was diluted with EtOAc and washed with water, sat'd NaHCO$_3$ and brine, then dried over anhydrous sodium sulfate, filtered and evaporated. The residue was purified by reverse phase HPLC to provide Example 130 (32 mg, 34.1% yield) as an off-white solid. $^1$HNMR (500 MHz, DMSO-d$_6$) δ ppm 9.79 (1H, s), 9.68 (1H, s), 8.54 (1H, d, J=5.5 Hz), 7.77 (1H, s), 7.51-7.58 (2H, m), 7.39-7.51 (15H, m), 7.30 (1H, s), 7.00 (1H, s), 4.84-4.96 (1H, m), 3.62 (3H, s), 3.58 (3H, s), 2.86-3.02 (2H, m), 2.45-2.51 (2H, m), 2.30-2.36 (2H, m). LC/MS m/z 575.6 (M+H)$^+$.

Example 131

(4-{5-Chloro-2-[1-[(E)-3-(5-chloro-2-tetrazol-1-yl-phenyl)-acryloylamino]-2-(1-ethyl-1H-pyrazol-4-yl)-ethyl]-1H-imidazol-4-yl}-phenyl)-carbamic acid methyl ester, trifluoroacetic acid salt 131A. (E)-2-tert-Butoxycarbonylamino-3-(1-ethyl-1H-pyrazol-4-yl)-acrylic acid methyl ester: Boc-methyl-2-(dimethylphosphono)glycinate (0.718 g, 2.417 mmol) was dissolved in CH$_2$Cl$_2$ (5 mL) and stirred under nitrogen at rt. To this solution was added DBU (0.334 mL, 2.215 mmol), and the mixture was stirred for 10 min, followed by dropwise addition of a solution of 1-ethyl-1H-pyrazole-4-carbaldehyde (0.25 g, 2.014 mmol) in CH$_2$Cl$_2$ (5 mL) over 15-20 min. Stirring was continued at rt overnight. The reaction mixture diluted with EtOAc and washed with 5% aq. citric acid and brine, then dried over anhydrous Na$_2$SO$_4$, filtered and evaporated. The residue was purified by flash chromatography to provide 131A (0.434 g, 73.0% yield) as a colorless, sticky gum.

131B. 2-tert-Butoxycarbonylamino-3-(1-ethyl-1H-pyrazol-4-yl)-propionic acid methyl ester: 131A (0.434 g, 1.470 mmol) was dissolved in MeOH (20 mL) and transferred to a 200 mL hydrogenation flask. The solution was evacuated and flushed with nitrogen 3×, then (S,S)-EtDuPhosRh(I) (0.053 g, 0.073 mmol) was added and the reaction was stirred over the weekend under 55 psi H$_2$ pressure. The MeOH was removed on a rotary evaporator. The residue was dissolved in a small amount of methylene chloride and purified by flash chromatography to provide a ~1:1 mixture of starting material and product by $^1$H-NMR (0.286 g, 65.5% yield). This mixture was redissolved in MeOH (20 mL) and added to a flask containing 90 mg of 10% Pd/C (wet, Degussa) under nitrogen. The mixture was stirred and evacuated and flushed with nitrogen (3×) then stirred under a balloon of H$_2$ overnight. The catalyst was removed by filtration through a pad of Celite®, washed with MeOH, and discarded. The filtrate was evaporated to provide the saturated amino ester (0.284 g, 65.0% yield) as a colorless syrup after drying in vacuo overnight. $^1$HNMR (500 MHz, CDCl$_3$) δ ppm 7.27 (1H, s), 7.18 (1H, s), 5.01 (1H, d, J=7.7 Hz), 4.50 (1H, d, J=7.7 Hz), 4.12 (2H, q, J=7.1 Hz), 3.73 (3H, s), 2.95-2.99 (2H, m), 1.46 (3H, t, J=7.4 Hz), 1.44 (9H, s). LC/MS m/z 298.3 (M+H)$^+$; 242.2 (M+H-tBu)$^+$.

131C. 2-tert-Butoxycarbonylamino-3-(1-ethyl-1H-pyrazol-4-yl)-propionic acid: 131B (0.28 g, 0.942 mmol) was dissolved in THF (5.6 mL) and 1M lithium hydroxide (1.412 mL, 1.412 mmol) was added along with a small amount of MeOH. The resulting reaction mixture was stirred at rt under nitrogen for ~2 h. The reaction mixture was diluted with 5% aq. citric acid solution and extracted 2× with EtOAc. The combined extracts were washed with brine, dried over Na$_2$SO$_4$, filtered and evaporated to provide the acid (0.257 g, 96% yield) as a white solid after drying in vacuo. LC/MS m/z 284.3 (M+H)$^+$; 228.2 (M+H-tBu)$^+$.

131D. (4-{2-[1-tert-Butoxycarbonylamino-2-(1-ethyl-1H-pyrazol-4-yl)-ethyl]-1H-imidazol-4-yl}-phenyl)-carbamic acid methyl ester: This intermediate was prepared in 65% yield from 131C using the procedure described for 130C. LCMS m/z 455.4 (M+H)$^+$.

131E. (4-{2-[(S)-1-tert-Butoxycarbonylamino-2-(1-ethyl-1H-pyrazol-4-yl)-ethyl]-5-chloro-1H-imidazol-4-yl}-phenyl)-carbamic acid methyl ester: 131D (0.205 g, 0.451 mmol) was dissolved in a mixture of chloroform (10 mL) and acetonitrile (10 mL) and NCS (0.072 g, 0.541 mmol) was added. The resulting reaction mixture was heated in a 65° C. oil bath for 4 h. The reaction mixture was diluted with EtOAc and washed with water and brine, then dried over anhydrous sodium sulfate, filtered and evaporated. The residue was purified by flash chromatography to provide 131E (0.199 g, 90% yield) as an orange-brown solid. $^1$HNMR (500 MHz, CDCl$_3$) δ ppm 10.20 (1H, s), 7.54 (2H, d, J=8.8 Hz), 7.44 (2H, d, J=8.2 Hz), 7.33 (1H, s), 7.22 (1H, s), 6.68 (1H, s), 5.13 (1H, d, J=8.8 Hz), 4.70-4.82 (1H, m), 4.09 (2H, q, J=7.1 Hz), 3.80 (3H, s), 3.18 (2H, d, J=6.6 Hz), 1.42-1.46 (12H, m). LC/MS m/z 489.1 (M+H)$^+$.

131F. Example 131 was prepared from 131E and 62B in 67% yield using the procedures described for 130D followed by purification by reverse phase HPLC. $^1$HNMR (500 MHz, DMSO-d$_6$) δ ppm 12.57 (1H, s), 9.86 (1H, s), 9.78 (1H, s), 8.71 (1H, d, J=8.2 Hz), 7.93 (1H, d, J=2.2 Hz), 7.66-7.78 (2H, m), 7.54-7.61 (2H, m), 7.48-7.54 (2H, m), 7.37 (1H, s), 7.10 (1H, s), 6.77-6.91 (2H, m), 5.03 (1H, t, J=8.0 Hz), 4.00 (2H, q, J=7.1 Hz), 3.66 (3H, s), 2.96-3.08 (1H, m), 2.89 (1H, dd, J=14.6, 7.4 Hz), 1.25 (3H, t, J=7.1 Hz). LC/MS m/z 621.0 (M+H)$^+$.

Example 132

(4-{5-Chloro-2-[1-[(E)-3-(5-chloro-2-tetrazol-1-yl-phenyl)-acryloylamino]-2-(1-n-propyl-1H-pyrazol-4-yl)-ethyl]-1H-imidazol-4-yl}-phenyl)-carbamic acid methyl ester, trifluoroacetic acid salt Example 132 was prepared using the steps described for Example 131 starting from commercially available 1-n-propylpyrazole-4-carboxaldehyde. $^1$HNMR (500 MHz, DMSO-d$_6$) δ ppm 12.56 (1H, s), 9.86 (1H, s), 9.78 (1H, s), 8.71 (1H, d, J=8.2 Hz), 7.92 (1H, d, J=2.2 Hz), 7.65-7.77 (2H, m), 7.54-7.59 (2H, m), 7.47-7.54 (2H, m), 7.33 (1H, s), 7.12 (1H, s), 6.79-6.90 (2H, m), 4.97-5.11 (1H, m), 3.92 (2H, t, J=6.9 Hz), 3.66 (3H, s), 2.95-3.05 (1H, m), 2.89 (1H, dd, J=14.6, 7.4 Hz), 1.54-1.72 (2H, m), 0.68 (3H, t, J=7.4 Hz). LC/MS m/z 635.0 (M+H)$^+$.

Example 133

(4-{2-[(S)-1-[3-(5-Chloro-2-tetrazol-1-yl-phenyl)-propionylamino]-2-(1-isopropyl-1H-pyrazol-4-yl)-ethyl]-1H-imidazol-4-yl}-phenyl)-carbamic acid methyl ester, trifluoroacetic acid salt 133A. (E)-2-tert-Butoxycarbonylamino-3-(1-isopropyl-1H-pyrazol-4-yl)-acrylic acid methyl ester: The olefin product was obtained in 86% yield from 1-isopropyl-4-pyrazole carboxyaldehyde following the procedure described for 131A. $^1$HNMR (400 MHz, CDCl$_3$) δ ppm 7.70 (1H, s), 7.63 (1H, s), 7.40 (1H, s), 6.05 (1H, bs), 4.43-4.56 (1H, m), 3.82 (3H, s), 1.52 (3H, s), 1.51 (3H, s), 1.48 (9H, s). LC/MS m/z 310.4 (M+H)$^+$ 133B. 2-tert-Butoxycarbonylamino-3-(1-isopropyl-1H-pyrazol-4-yl)-propionic acid methyl ester: 133A (0.58 g, 1.875 mmol) was dissolved in MeOH (10 mL) and transferred to a 100 mL hydrogenation flask. The solution was degassed on a manifold by evacuation and flushing with N$_2$ (3×). (S,S)-EtDuPhosRh(I) (60 mg, 0.083 mmol) was then added to the flask, and the contents were stirred under 55 psi H$_2$ pressure overnight. The reaction was degassed as above and a fresh aliquot of catalyst (~35 mg) was added. The reaction was then stirred under 55 psi H$_2$ atmosphere for an additional 3-4 h. Flash chromatography provided a ~3:1 mix of product to starting material (306 mg). This mixture was redissolved in MeOH (15 mL), and hydrogenation over (S,S)-EtDuPhosRh(I) (0.036 g, 0.050 mmol) was repeated as described above. The methanol was removed on a rotary evaporator. The residue was purified by flash chromatography to provide 133B (0.178 g, 57.2% yield) as a colorless oil. LC/MS m/z 312.4 (M+H)$^+$; 256.3 (M+H-tBu)$^+$.

133C. 2-tert-Butoxycarbonylamino-3-(1-isopropyl-1H-pyrazol-4-yl)-propionic acid: 133C was obtained by saponification of 133B following the procedure described for 132C.

133D. Example 133 was prepared from 133C using the procedures described for 130C and 130D. $^1$HNMR (500 MHz, DMSO-d$_6$) δ ppm 9.77 (1H, s), 9.68 (1H, s), 8.56 (1H, s), 7.74 (1H, s), 7.50-7.57 (2H, m), 7.40-7.50 (5H, m), 7.31 (1H, s), 7.02 (1H, s), 4.84-4.95 (1H, m), 4.17-4.32 (1H, m), 3.58 (3H, s), 2.93 (2H, d, J=7.7 Hz), 2.44-2.57 (2H, m), 2.26-2.36 (2H, m), 1.19 (6H, d, J=6.6 Hz). LC/MS m/z 603.6 (M+H)$^+$.

Example 134

(4-{5-Chloro-2-[1-[(E)-3-(5-chloro-2-tetrazol-1-yl-phenyl)-acryloylamino]-2-(1-methyl-1H-pyrazol-4-yl)-ethyl]-1H-imidazol-4-yl}-phenyl)-carbamic acid methyl ester, trifluoroacetic acid salt 134A. (4-{2-[(S)-1-tert-Butoxycarbonylamino-2-(1-methyl-1H-pyrazol-4-yl)-ethyl]-5-chloro-1H-imidazol-4-yl}-phenyl)-carbamic acid methyl ester: 130C was treated with NCS using the procedure described for 131E to provide 134A in 79% yield as an light yellow solid. $^1$HNMR (500 MHz, CDCl$_3$) δ ppm 10.23 (1H, s), 7.54 (2H, d, J=8.2 Hz), 7.45 (2H, d, J=8.8 Hz), 7.32 (1H, s), 7.20 (1H, s), 6.68 (1H, s), 5.11 (1H, d, J=6.0 Hz), 4.76 (1H, q, J=7.1 Hz), 3.83 (3H, s), 3.80 (3H, s), 3.19 (2H, d, J=6.6 Hz), 1.44 (9H, s). LC/MS m/z 475.1 (M+H)$^+$.

134B. Example 134 was prepared in 64% yield from 134A and 62B using the procedures described for 130D and purified by reverse phase HPLC. $^1$HNMR (500 MHz, DMSO-d$_6$) δ ppm 12.57 (1H, s), 9.86 (1H, s), 9.78 (1H, s), 8.70 (1H, d, J=8.2 Hz), 7.93 (1H, d, J=2.2 Hz), 7.69-7.78 (2H, m), 7.55-7.61 (2H, m), 7.48-7.55 (2H, m), 7.35 (1H, s), 7.09 (1H, s), 6.78-6.91 (2H, m), 5.00-5.08 (1H, m), 3.72 (3H, s), 3.66 (3H, s), 3.01 (1H, dd, J=14.3, 7.1 Hz), 2.88 (1H, dd, J=14.6, 7.4 Hz). LC/MS m/z 607.0 (M+H)$^+$.

Example 135

(4-{2-[1-[3-(5-Chloro-2-tetrazol-1-yl-phenyl)-propionylamino]-2-(1-ethyl-1H-pyrazol-4-yl)-ethyl]-1H-imidazol-4-yl}-phenyl)-carbamic acid methyl ester, trifluoroacetic acid salt Example 135 was prepared from 131D using the procedures described for 130D. $^1$HNMR (500 MHz, DMSO-d$_6$) δ ppm 9.78 (1H, s), 9.68 (1H, s), 8.53 (1H, d, J=4.9 Hz), 7.76 (1H, s), 7.50-7.58 (2H, m), 7.40-7.50 (5H, m), 7.31(1H, s), 7.02 (1H, s), 4.84-4.95 (1H, m), 3.91 (2H, q, J=7.1 Hz), 3.58 (3H, s), 2.94 (2H, d, J=7.7 Hz), 2.44-2.56 (2H, m), 2.27-2.36 (2H, m), 1.15 (3H, t, J=7.1 Hz). LC/MS m/z 589.4 (M+H)$^+$.

Example 136

(4-{5-Chloro-2-[1-[(E)-3-(5-chloro-2-tetrazol-1-yl-phenyl)-acryloylamino]-2-(1-methyl-1H-pyrazol-3-yl)-ethyl]-1H-imidazol-4-yl}-phenyl)-carbamic acid methyl ester, trifluoroacetic acid salt A mixture of 82G (51 mg, 0.114 mmol), 62B (28.5 mg, 0.114 mmol), HOBT (20.93 mg, 0.137 mmol), N-methylmorpholine (65 μL, 0.591 mmol), and EDC (26.2 mg, 0.137 mmol) in DMF (1 mL) was stirred under argon overnight at rt. Reaction mixture was diluted with EtOAc and washed with water (2×), sat'd NaHCO$_3$ and brine, then dried over anhydrous sodium sulfate, filtered and evaporated. The residue was redissolved in MeOH, filtered and purified by reverse phase HPLC to provide Example 136 (45 mg, 54.8% yield) as a white solid. $^1$HNMR (500 MHz, DMSO-d$_6$) δ ppm 9.85 (1H, s), 9.76 (1H, s), 8.69 (1H, d, J=8.2 Hz), 7.92 (1H, d, J=2.2 Hz), 7.68-7.77 (2H, m), 7.54-7.62 (2H, m), 7.49-7.55 (2H, m), 7.47 (1H, d, J=2.2 Hz), 6.76-6.91 (2H, m), 5.87 (1H, d, J=1.6 Hz), 5.22 (1H, q, J=7.7 Hz), 3.72 (3H, s), 3.66 (3H, s), 3.15 (1H, dd, J=14.6, 7.4 Hz), 2.99 (1H, dd, J=14.3, 7.7 Hz). LC/MS m/z 607.3 (M+H)$^+$.

Example 137

(4-{5-Chloro-2-[1-[(E)-3-(5-chloro-2-tetrazol-1-yl-phenyl)-acryloylamino]-2-(1-ethyl-1H-pyrazol-3-yl)-ethyl]-1H-imidazol-4-yl}-phenyl)-carbamic acid methyl ester, trifluoroacetic acid salt 137A. (4-{2-[(S)-1-tert-Butoxycarbonylamino-2-(1-ethyl-1H-pyrazol-3-yl)-ethyl]-5-chloro-1H-imidazol-4-yl}-phenyl)-carbamic acid methyl ester: The chloroimidazole intermediate was prepared in 5 steps from 1-ethyl-3-pyrazole carboxaldehyde following the procedures described for 82A-C and 82E-F. LC/MS m/z 389.3 (M+H)$^+$.

137B. Example 137: 137A (0.2 g, 0.409 mmol) was dissolved in CH$_2$Cl$_2$ (2.5 mL) and TFA (0.6 mL, 7.79 mmol) was added. The reaction was stirred at rt under nitrogen for ~5 h. The solution was evaporated to dryness and triturated with ether/hexane to give a solid which was resuspended in ether, decanted and dried in vacuo to provide the bis-TFA salt of the deprotected amine (0.101 g, 40.0% yield) as a solid that was used without purification. LC/MS m/z 389.3 (M+H)$^+$. This intermediate (50 mg, 0.081 mmol) was dissolved in DMF (1.5 mL) and 62B (22.5 mg, 0.090 mmol), HOBT (16 mg, 0.104 mmol), N-methylmorpholine (0.050 mL, 0.455 mmol) and EDC (20 mg, 0.104 mmol) were added. The reaction mixture was stirred overnight under a blanket of argon at rt. The reaction was diluted with EtOAc and washed with water (2×), sat'd NaHCO$_3$ and brine, then dried over anhydrous sodium sulfate, filtered and evaporated. The residue was redissolved in MeOH, filtered and purified by reverse phase HPLC to provide Example 137 (20 mg, 33.5% yield) as an off-white solid. LC/MS m/z 621.1 (M+H)$^+$. $^1$HNMR (500 MHz, DMSO-d$_6$) δ ppm 9.85 (1H, s), 9.77 (1H, s), 8.70 (1H, d, J=8.2 Hz), 7.91 (1H, s), 7.67-7.79 (2H, m), 7.54-7.60 (2H, m), 7.47-7.55 (3H, m), 6.84 (2H, d, J=3.8 Hz), 5.87 (1H, d, J=2.2 Hz), 5.21 (1H, d, J=8.2 Hz), 4.00 (2H, q, J=7.1 Hz), 3.66 (3H, s), 3.15 (1H, dd, J=14.3, 7.1 Hz), 3.00 (1H, dd, J=14.3, 7.7 Hz), 1.27 (1H, t, J=7.1 Hz).

Example 138

4-{5-Chloro-2-[(S)-1-[(E)-3-(5-chloro-2-tetrazol-1-yl-phenyl)-acryloylamino]-2-(1,5-dimethyl-1H-pyrazol-3-yl)-ethyl]-1H-imidazol-4-yl}-benzamide, trifluoroacetic acid salt 138A. (S)-2-tert-Butoxycarbonylamino-3-(1,5-dimethyl-1H-pyrazol-3-yl)-propionic acid: The chiral amino acid was prepared from 1,5-dimethyl-3-pyrazolecarboxaldehyde using the procedures described for 82A-C. LCMS m/z 284.1 (M+H)$^+$; 228.1 (M+H-tBu)$^+$.

138B. [(S)-1-[4-(4-Cyano-phenyl)-1H-imidazol-2-yl]-2-(1,5-dimethyl-1H-pyrazol-3-yl)-ethyl]-carbamic acid tert-butyl ester: 138A (0.25 g, 0.882 mmol) was dissolved in DMF (5 mL) and KHCO$_3$ (0.106 g, 1.059 mmol) was added. The mixture was stirred at rt under nitrogen for ~20 min then cooled in an ice bath while a solution of 4-(2-bromoacetyl) benzonitrile (0.237 g, 1.059 mmol) in DMF (2 mL) was added dropwise. The reaction was stirred at ice bath temperature for 2 h then allowed to assume rt. The reaction mixture was diluted with EtOAc and washed with water, sat'd NaHCO$_3$ and brine, then dried over anhydrous sodium sulfate, filtered and evaporated to give the crude ketoester intermediate. This material was dissolved in a mixture of xylene (5 mL) and EtOH (1 mL) and transferred to a 20 mL microwave vial. Ammonium acetate (0.680 g, 8.82 mmol) was added and the vial was sealed. The resulting mixture was heated with stirring in a microwave reactor at 160° C. for 30 min then left at rt overnight. The reaction mixture was diluted with EtOAc and washed with water and brine, then dried over anhydrous sodium sulfate, filtered and evaporated. The residue was purified by flash chromatography to provide the imidazole as an orange foam (0.254 g, 70.8% yield). LCMS m/z 407.1 (M+H)$^+$.

138C. [(S)-1-[5-Chloro-4-(4-cyano-phenyl)-1H-imidazol-2-yl]-2-(1,5-dimethyl-1H-pyrazol-3-yl)-ethyl]-carbamic acid tert-butyl ester: 138B (0.25 g, 0.615 mmol) was dissolved in acetonitrile (10 mL) and NCS (0.099 g, 0.738 mmol) was added. The resulting mixture was stirred at reflux in an 80° C. oil bath for 4 h under N$_2$. The reaction was cooled to rt, diluted with EtOAc and washed with water and brine, then dried over anhydrous sodium sulfate, filtered and evaporated. The residue was purified by flash chromatography to provide the desired product contaminated with two minor impurities (0.248 g, 91% yield) as an orange foam. LCMS for product: m/z 441.0 (M+H)$^+$.

138D. Example 138: 138C (0.245 g, 0.556 mmol) was dissolved in CH$_2$Cl$_2$ (2 mL) and TFA (0.5 mL, 6.49 mmol) was added. The resulting dark solution was stirred overnight at rt under nitrogen. The solution was evaporated to dryness. The residue was triturated with ether to provide a tan solid that was dried in vacuo to give the bis-TFA salt of the desired amine (0.18 g, 56.9% yield) contaminated with some dichloroproduct from the previous step. A portion of this intermediate (90 mg, 0.158 mmol) was dissolved in DMF (2 mL) and 62B (39.7 mg, 0.158 mmol), HOBT (29.1 mg, 0.190 mmol), N-methylmorpholine (0.087 mL, 0.791 mmol) and EDC (36.4 mg, 0.190 mmol) were added. The reaction mixture was stirred under a blanket of argon overnight at rt. The reaction was diluted with EtOAc and washed with water, sat'd NaHCO$_3$ and brine, then dried over anhydrous sodium sulfate, filtered and evaporated. The crude product was redissolved in DMSO (2 mL) and K$_2$CO$_3$ (65.6 mg, 0.475 mmol) followed by 30% H$_2$O$_2$ (0.194 mL, 1.899 mmol) were added. The reaction was stirred overnight at rt under nitrogen. The reaction mixture was diluted with water and extracted with EtOAc. The combined extracts were washed with water and brine, then dried over anhydrous sodium sulfate, filtered and evaporated. The residue was purified by reverse phase HPLC to provide Example 138 (9.4 mg, 8.42% yield) as a light yellow solid. LC/MS m/z 591.0 (M+H)$^+$. $^1$HNMR (500 MHz, DMSO-d$_6$) δ ppm 9.85 (1H, s), 8.95 (1H, s), 7.89-8.07 (3H, m), 7.81 (2H, d, J=8.2 Hz), 7.70-7.78 (2H, m), 7.40 (1H, s), 6.91 (1H, d, J=15.9 Hz), 6.72-6.82 (1H, m), 5.31 (1H, q, J=7.5 Hz), 3.71 (3H, s), 3.28-3.41 (2H, m, J=7.7 Hz), 2.01 (3H, s).

Example 139

(E)-methyl 2-(2-(3-(5-chloro-2-(1H-tetrazol-1-yl) phenyl)acrylamido)-2-(4-chloro-5-(4-(methoxycarbonylamino)phenyl)-1H-imidazol-2-yl)ethyl)oxazole-4-carboxylate 139A. Methyl 2-(3-tert-butoxy-2-(diphenylmethyleneamino)-3-oxopropyl)oxazole-4-carboxylate: A mixture of tert-butyl 2-(diphenylmethyleneamino)acetate (1.0 g, 3.39 mmol), methyl 2-(chloromethyl)oxazole-4-carboxylate (0.594 g, 3.39 mmol) and tetrabutylammonium bromide (0.109 g, 0.339 mmol) in anhydrous DCM (25 mL) was stirred at −78° C. under an argon atmosphere, then 2-tert-butylimino-2-diethylamino-1,3-dimethylperhydrodiazaphosphorine (1.208 g, 4.40 mmol) was added dropwise. Stirring was continued while gradually warming the solution to rt over 26 h. The solvent was removed in vacuo to give a light brown oil, which was purified by flash chromatography to provide 139A as a pale yellow oil. LC/MS m/z 435 (M+H)$^+$. $^1$HNMR (CDCl$_3$, 400 MHz): 8.09 (s, 1H), 7.56 (d, 2H, J=7), 7.43 (m, 4H), 7.30 (m, 2H), 7.09 (m, 2H), 4.51 (dd, 1H, J=9, 7), 3.88 (s, 3H), 3.47 (dd, 1H, J=16, 7), 3.38 (dd, 1H, J=16, 9), 1.43 (s, 9H).

139B. Methyl 2-(2-amino-3-tert-butoxy-3-oxopropyl)oxazole-4-carboxylate: A mixture of 139A (620 mg, 1.427 mmol), 15% citric acid (25 mL) and THF (25 mL) was stirred at rt for 48 h. The reaction was poured into a separatory funnel and extracted three times with Et$_2$O. The aqueous layer was basified with 1 N NaOH to pH 9, then extracted three times with DCM. The combined organic layers were dried over MgSO$_4$ and filtered. Solvent was removed from the filtrate in vacuo to give 139B as a cloudy oil. LC/MS m/z 271 (M+H)$^+$. $^1$HNMR (CD$_3$OD, 400 MHz): 8.50 (s, 1H), 3.89 (s, 3H), 3.86 (t, 1H, J=7), 3.30 (m, 2H), 3.17 (m, 2H), 1.43 (s, 9H).

139C. 2-(tert-Butoxycarbonylamino)-3-(4-(methoxycarbonyl)oxazol-2-yl)propanoic acid: A mixture of 139B (380 mg, 1.406 mmol) and TFA (2 mL) was stirred at rt for 30 min. The cloudy solution was concentrated in vacuo to give a yellow waxy solid. This crude intermediate was taken up in water (2 mL) and THF (2 mL), di-t-butyldicarbonate (0.307 g, 1.406 mmol) was added, and as sodium bicarbonate (591 mg, 7.03 mmol) was added portionwise a small amount of gas evolution occurred. The cloudy white mixture was stirred at rt for 24 h. The reaction mixture was diluted with water and carefully neutralized with 1N HCl. Three extractions with EtOAc, drying over MgSO$_4$, filtration and removal of solvent in vacuo provided 139C as a yellow oil (440 mg). LC/MS m/z 315 (M+H)$^+$. $^1$HNMR (CDCl$_3$, 400 MHz): 8.19 (s, 1H), 6.03 (m, 1H+H$_2$O), 5.59 (m, 1H), 4.76 (m, 1H), 3.89 (s, 3H), 3.44 (m, 2H), 1.42 (s, 9H).

139D. Methyl 2-(2-(tert-butoxycarbonylamino)-3-(2-(4-(methoxycarbonylamino)phenyl)-2-oxoethoxy)-3-oxopropyl)oxazole-4-carboxylate: A mixture of 139C (440 mg, 1.400 mmol), 82D (381 mg, 1.400 mmol) and cesium carbonate (228 mg, 0.700 mmol) in DMF (5 mL) was stirred at rt for 16.5 h. The reaction mixture was diluted with EtOAc (70 mL) and the mixture was washed three times with a 10% LiCl solution. The organic solution was dried over MgSO$_4$ and filtered. Solvent was removed in vacuo to give 139D as a yellow oil (540 mg). LCMS m/z 506 (M+H)$^+$. $^1$HNMR (CDCl$_3$, 400 MHz): 8.19 (s, 1H), 7.87 (m, 3H), 7.53 (m, 2H), 5.54 (s, 1H), 5.43 (d, 1H, J=16), 5.32 (d, 1H, J=16), 4.84 (d, 1H, J=6), 3.90 (s, 3H), 3.81 (s, 4H), 3.53 (m, 1H), 1.41 (s, 9H).

139E. Methyl 2-(2-(tert-Butoxycarbonylamino)-2-(5-(4-(methoxycarbonylamino)phenyl)-1H-imidazol-2-yl)ethyl) oxazole-4-carboxylate A mixture of 139D (540 mg, 1.068 mmol) and ammonium acetate (412 mg, 5.34 mmol) in xylene (10 ml) was immersed in an oil bath preheated to 140° C. Stirring was continued for 2 h. Reaction mixture was cooled to rt, and solvent was removed in vacuo to give yellow brown oil. Flash chromatography provided the desired imidazole product as a pale tan solid, (103 mg, 20%). LCMS m/z 486 (M+H)+$^1$HNMR (CDCl$_3$, 400 MHz): 8.17 (s, 1H), 7.68 (d, 2H, J=7), 7.39 (m, 2H), 7.17 (s, 1H), 6.60 (m, 1H), 5.92 (m, 1H), 5.28 (d, 1H, J=7), 5.25 (d, 1H, J=9), 3.91 (s, 3H), 3.78 (s, 3H), 3.62 (m, 1H), 3.43 (m, 1H), 1.44 (s, 9H).

139F. Methyl 2-(2-(tert-Butoxycarbonylamino)-2-(4-chloro-5-(4-(methoxycarbonylamino)phenyl)-1H-imidazol-2-yl)ethyl)oxazole-4-carboxylate: A mixture of 139E (103 mg, 0.212 mmol) and NCS (34.0 mg, 0.255 mmol) in acetonitrile (6 mL) was stirred at reflux temperature for 3 h under argon. The reaction mixture was cooled to rt. Solvent was removed in vacuo to give a brown yellow oil. Flash chromatography gave 139F as a pale yellow powder (90 mg). LC/MS m/z 520 (M+H)$^+$. $^1$HNMR (CD$_3$OD, 400 MHz): 8.49 (s, 1H), 7.64 (d, 2H, J=8), 7.54 (d, 2H, J=8), 5.23 (m, 1H), 3.88 (s, 3H), 3.77 (s, 3H), 3.49 (m, 1H), 3.33 (m, 4H), 1.41 (s, 9H).

139G. Methyl 2-(2-amino-2-(4-chloro-5-(4-(methoxycarbonylamino)phenyl)-1H-imidazol-2-yl)ethyl)oxazole-4-carboxylate: A mixture of 139F (90 mg, 0.173 mmol) and TFA (1 mL) was stirred at rt for 30 min. Solvent was removed in vacuo. The residue was treated with saturated Na$_2$CO$_3$ solution and extracted with EtOAc. The combined organic layers were dried over MgSO$_4$ and filtered. Solvent was removed in vacuo to give 139G as a yellow oil that solidified on standing (76 mg). LC/MS m/z 420 (M+H)$^+$. $^1$HNMR (CD$_3$OD, 400 MHz): 8.38 (s, 1H), 7.53 (d, 2H, J=8), 7.43 (d, 2H, J=8), 4.79 (m, 2H, concentration dependent), 4.62 (t, 1H, J=6), 3.77 (s, 3H), 3.66 (s, 3H), 3.43 (dd, 1H, J=16, 8), 3.32 (dd, 1H, J=16, 8), 3.22 (s 2H).

139H. Example 139: A mixture of 62B (45.4 mg, 0.181 mmol), HOBT (30.5 mg, 0.199 mmol), EDC (38.2 mg, 0.199 mmol) and DIEA (0.158 ml, 0.905 mmol) in DMF (0.5 mL) was stirred at rt for 15 min. A solution of 139F (76 mg, 0.181 mmol) in DMF (1 mL) was added and stirring was continued for 19 h. The reaction mixture was diluted with EtOAc and the resulting mixture was washed with a 10% LiCl solution three times. The organic solution was dried over MgSO$_4$ and filtered. Solvent was removed in vacuo to give a reddish oil, that was purified by flash chromatography to give Example 139 as a tan solid (100 mg). LC/MS m/z 652 (M+H)$^+$. $^1$HNMR (DMSO-d$_6$, 400 MHz): 12.78 (s, 1H), 9.86 (s, 1H), 9.80 (s, 1H), 8.90 (d, 1H, J=6), 8.75 (s, 1H), 7.96 (s, 1H), 7.75 (m, 2H), 7.60 (d, 2H, J=7), 7.54 (d, 2H, J=7), 6.90 (d, 1H, J=14), 6.78 (d, 1H, J=14), 5.51 (m, 1H), 3.87 (s, 3H), 3.69 (s, 3H), 3.48 (m, 1H), 3.33 (m, 1H).

Example 140

(S,E)-methyl 4-(5-chloro-2-(1-(3-(5-chloro-2-(1H-tetrazol-1-yl)phenyl)acrylamido)-2-(4-oxocyclohexyl)ethyl)-1H-imidazol-4-yl)phenylcarbamate 140A. Ethyl 1,4-dioxaspiro[4.5]decane-8-carboxylate: A mixture of ethyl 4-oxocyclohexanecarboxylate (2 g, 11.75 mmol), ethylene glycol (0.655 mL, 11.75 mmol) and p-toluenesulfonic acid monohydrate (0.020 g, 0.118 mmol) in toluene (25 mL) was stirred at reflux temperature for 24 h. The solvent was removed in vacuo to give a light yellow liquid that was purified by vacuum distillation to give 140A as a clear liquid (1.31 g). $^1$HNMR (CDCl$_3$, 400 MHz) δ 4.13 (q, 2H, J=7), 3.94 (s, 4H), 2.33 (m, 1H), 1.92 (m, 2H), 1.79 (m, 4H), 1.58 (m, 2H), 1.25 (t, 3H, J=7).

140B. 1,4-Dioxaspiro[4.5]decan-8-ylmethanol: Lithium aluminum hydride (0.251 mL, 6.07 mmol) was added portionwise to a solution of 140A (1.3 g, 6.07 mmol) in THF (15 mL) under argon. Vigorous gas evolution occurred. Stirring was continued for 27 h, then the suspension was treated with 0.25 mL water, 0.25 mL 1N NaOH and 0.75 mL water. After 5 minutes of stirring, a white suspension formed. Filtration through Celite® and removal of solvent in vacuo from the filtrate gave 140B as a clear colorless liquid (1.01 g). $^1$HNMR (CDCl$_3$, 400 MHz) δ 3.94 (s, 4H), 3.48 (br s, 2H), 1.78 (d, 4H, J=7), 1.55 (t, 4H, J=7), 1.26 (d, 2H, J=7).

140C. 1,4-Dioxaspiro[4.5]decane-8-carbaldehyde: Pyridinium dichromate (3.31 g, 8.80 mmol) was added portionwise to a solution of 140B (1.01 g, 5.86 mmol) in DCM (5 mL) and the reaction mixture was stirred at rt for 25 h. The reaction mixture was diluted with ether (100 mL) and the chromium salts were broken up into fine granules. The brown suspension was filtered through a pad of silica gel on Celite®. The pad was washed with an additional 50 mL ether. Solvent was removed in vacuo from the filtrate to give 140C as a clear colorless liquid (490 mg). $^1$HNMR (CDCl$_3$, 400 MHz) δ 9.65 (s, 1H), 3.94 (s, 4H), 2.25 (m, 1H), 1.95 (m, 2H), 1.76 (m, 4H), 1.60 (m, 2H).

140D. (2S)-2-(4-(methoxycarbonylamino)phenyl)-2-oxoethyl 2-(tert-butoxycarbonylamino)-3-(1,4-dioxaspiro[4.5] decan-8-yl)propanoate: 140D was prepared from 140C by a series of steps similar to 82A-82E, with Cs$_2$CO$_3$ used in place of KHCO$_3$ in step 82E. LC/MS m/z 520 (M−H)$^−$. $^1$HNMR (CDCl$_3$, 400 MHz) δ 7.86 (d, 2H, J=8), 7.51 (d, 2H, J=8), 6.93 (s, 1H), 5.46 (d, 1H, J=16), 5.26 (d, 1H, J=16), 5.20 (s, 1H), 4.93 (m 1H), 4.49 (m, 1H), 3.94 (s, 4H), 3.81 (s, 3H), 1.91 (m, 1H), 1.54 (m, 9H), 1.45 (s, 9H).

140E. (S)-methyl 4-(2-(1-amino-2-(4-oxocyclohexyl) ethyl)-5-chloro-1H-imidazol-4-yl)phenylcarbamate: (S)-methyl 4-(2-(1-t-butoxycarbonylamino-2-(4-oxocyclohexyl) ethyl)-5-chloro-1H-imidazol-4-yl)phenylcarbamate was prepared from 140D by a similar procedure to 82F. This intermediate (109 mg, 0.204 mmol) and TFA (2 mL) were stirred at rt for 1.25 h. Solvent was removed in vacuo and the residue was treated with a saturated Na$_2$CO$_3$ solution and extracted with EtOAc. The combined organic layers were dried over MgSO$_4$, filtered and evaporated to give 140E as a pale yellow solid (67 mg). LC/MS m/z 390 (M+H)$^+$. $^1$HNMR (CD$_3$OD, 400 MHz) δ 7.54 (m, 2H), 7.46 (m, 2H), 4.82 (m, 5H), 3.66 (s, 3H), 2.24 (m, 1H), 2.09 (m, 4H), 1.73 (m, 2H), 1.35 (m, 3H).

140F. Example 140 was prepared from 140E and 62B by a similar procedure to 62C. LC/MS m/z 623 (M+H)$^+$. $^1$HNMR (CD$_3$OD, 400, MHz) δ 9.51 (s, 1H), 7.96 (s, 1H), 7.59 (m, 6H), 7.13 (m, 1H), 7.13 (d, 1H, J=16), 6.74 (d, 1H, J=16), 5.19 (m, 1H), 3.74 (s, 3H), 3.33 (m, 3H), 2.32 (m, 1H), 2.21 (m, 1H), 2.11 (m 2H), 1.98 (m, 2H), 1.78 (m, 2H), 1.42 (m, 2H).

Example 141

(S,E)-3-(5-chloro-2-(1H-tetrazol-1-yl)phenyl)-N-(1-(5-chloro-4-(3-cyano-4-hydroxy-2-oxo-1,2-dihydro-quinolin-6-yl)-1H-imidazol-2-yl)-2-phenylethyl) acrylamide, trifluoroacetic acid salt 141A. 6-bromo-4-hydroxy-2-oxo-1,2-dihydroquinoline-3-carbonitrile: A mixture of 6-bromo-1H-benzo[d][1,3]oxazine-2,4-dione (2.420 g, 10 mmol), ethyl 2-cyanoacetate (1.064 mmol, 10.00 mmol) and TEA (2.79 mL, 20.00 mmol) in DMF (20 mL) was heated at 150° C. for 8 h, then cooled to rt. The mixture was concentrated in vacuo, then 1N HCl was added. The resulting precipitate was collected by filtration, washed with water, and dried. The resulting solid was suspended in DCM (20 mL) and sonicated while stirring for 1 h, then filtered. The solid was dried in vacuo at 50° C. overnight to provide 141A (2.266 g, 79%). LC/MS m/z 265.0 (M+H)$^+$.

141B. 3-cyano-2,4-dihydroxyquinolin-6-ylboronic acid: A mixture of 141A (1.09 g, 4.11 mmol), 5,5,5',5'-tetramethyl-2,2'-bi(1,3,2-dioxaborinane) (1.393 g, 6.17 mmol), potassium acetate (1.211 g, 12.34 mmol), and Pd(dppf)Cl$_2$-DCM complex (0.168 g, 0.206 mmol) in DMSO (27.4 mL) was degassed by bubbling argon through the solution for 10 min, then heated at 85° C. for 10 h. The mixture was cooled to rt, then purified by reverse phase HPLC to afford 141B (0.492 g, 49%). LC/MS m/z 231.1 (M+H)$^+$.

141C. [(S)-1-(1H-Imidazol-2-yl)-2-phenyl-ethyl]-carbamic acid tert-butyl ester: To Boc-L-phenylalanine methyl ester (100.0 g, 0.35 mol) in toluene (1 mL) at –78° C. was added DIBAL-H (322 mL, 0.64 mol, 2M solution in toluene) dropwise, and the solution was stirred at –78° C. for 30 min. The reaction was quenched with methanol (40 mL) and stirred with NH$_4$Cl (350 g) in water (100 mL) for 10 min. The resulting solid was filtered through Celite® and washed with EtOAc and water. The layers were separated and the organic layer was dried over sodium sulfate and concentrated at a temperature below 35° C. To this the crude aldehyde (93 g, 0.37 mmol) in methanol (1 L) was added glyoxal trimeric dihydrate (39.2 g, 0.18 mol), followed by NH$_3$ in methanol (838 mL, 2M solution). The reaction mixture was stirred at rt for 48 h. The reaction mixture was evaporated and the resulting crude product was purified by flash chromatography followed by crystallization from hexane to give 141C (23 g, 23%) as a grey solid. LC/MS m/z 287 (M+H)$^+$. $^1$HNMR (CDCl$_3$, 400 MHz) δ 9.8 (bs, 1H), 7.27 (m, 3H), 7.21 (m, 2H), 6.95 (d, 2H), 5.32, 4.91 (2d, 2H), 3.32 (d, 2H), 1.3 (s, 9H).

141D. [(S)-1-(4-Bromo-5-chloro-1H-imidazol-2-yl)-2-phenyl-ethyl]-carbamic acid tert-butyl ester: To a suspension of 141C (5.0 g, 17 mmol) in acetonitrile (400 mL) at 0° C. was added NCS (2.3 g, 17 mmol). The reaction mixture was stirred at 0° C. for 1 h, then at rt for 1 h followed by 50° C. overnight. The reaction mixture was concentrated and the residue was dissolved in ethyl acetate, washed with water and brine, dried over sodium sulfate, and concentrated. The crude was purified by flash column chromatography to give [(S)-1-(4-chloro-1H-imidazol-2-yl)-2-phenyl-ethyl]-carbamic acid tert-butyl ester as white solid (2 g, 36%). LCMS m/z 321 (M+H)$^+$. To a solution of this intermediate (2 g, 6.20 mmol) in chloroform was added NBS (1.2 g, 6.8 mmol) and the reaction mixture was stirred at rt for 20 min. The reaction was quenched with water. The organic layer was washed with water and brine, dried over sodium sulfate and concentrated. The crude product was purified by crystallization from hexane to give 141D as an off-white solid (1.7 g, 71%). LC/MS m/z 400 (M+H)+. $^1$HNMR (CDCl$_3$, 400 MHz) δ 7.28 (m, 3H), 7.12 (d, 2H), 5.33 (d, 1H), 4.81 (d, 1H), 3.27 (dd, 2H), 1.3 (s, 9H).

141E. Example 141: A suspension of 141D (100 mg, 0.250 mmol), 141B (86 mg, 0.374 mmol), potassium carbonate (138 mg, 0.998 mmol) and bis(tri-t-butylphosphine)palladium(0) (12.75 mg, 0.025 mmol) in DME (4 mL) and water (1 mL) was heated at 140° C. in a microwave reactor for 30 min, then cooled to rt. The reaction mixture was filtered and the solid washed with MeOH. The combined filtrate was concentrated, treated with 30% TFA in DCM (3 mL) for 30 min, and evaporated. The residue was purified by reverse phase HPLC. The combined fractions were concentrated and dissolved in DMF (2 mL). To this solution were added 62B (0.024 g, 0.095 mmol), EDC (0.036 g, 0.189 mmol), HOBt (0.029 g, 0.189 mmol) and TEA (0.066 ml, 0.473 mmol). The reaction mixture was stirred at rt for 18 h. Concentration and purification by reverse phase HPLC gave Example 141 as an off-white solid (8 mg, 4.2% yield). LC/MS m/z 638.2 (M+H)$^+$. $^1$HNMR (400 MHz, CD$_3$OD) δ: 3.23-3.34 (m, 2H), 5.24-5.28 (m, 1H), 6.72 (d, J=15.4 Hz, 1H), 7.08 (d, J=15.4 Hz, 1H), 7.17-7.27 (m, 5H), 7.35 (d, J=8.8 Hz, 1H), 7.55 (d, J=8.3 Hz, 1H), 7.64 (dd, J=2.2 Hz, 8.3 Hz, 1H), 7.90 (dd, J=2.2 Hz, 8.8 Hz, 1H), 7.95 (d, J=2.2 Hz, 1H), 8.25 (d, J=2.2 Hz, 1H), 9.49 (s, 1H).

Example 142

6-(5-Chloro-2-{(S)-1-[3-(5-chloro-2-tetrazol-1-yl-phenyl)-propionylamino]-2-phenyl-ethyl}-1H-imidazol-4-yl)-2-oxo-1,2-dihydro-quinoline-4-carboxylic acid, trifluoroacetic acid salt 142A. Methyl 6-(5,5-dimethyl-1,3,2-dioxaborinan-2-yl)-2-oxo-1,2-dihydroquinoline-4-carboxylate: 142A was prepared from methyl 6-bromo-2-oxo-1,2-dihydroquinoline-4-carboxylate by a similar procedure to 141B. LCMS m/z 248.2 (M+H)$^+$. $^1$HNMR (400 MHz, CDCl$_3$) δ: 1.04 (s, 6H), 3.79 (s, 4H), 4.03 (s, 3H), 7.18 (s, 1H), 7.39 (d, J=8.3 Hz, 1H), 7.96 (dd, J=1.1 Hz, 8.3 Hz, 1H), 8.70 (s, 1H), 12.07 (bs, 1H).

142B. (S)-6-(2-(1-amino-2-phenylethyl)-5-chloro-1H-imidazol-4-yl)-2-oxo-1,2-dihydroquinoline-4-carboxylic acid: 142B was prepared from 142A by a similar procedure to the first two parts of 141E (stopping after the TFA deprotection of the amine). LC/MS m/z 409.2 (M+H)$^+$. $^1$HNMR (400 MHz, CD$_3$OD) δ: 3.31-3.42 (m, 2H), 4.59 (dd, J=6.6 Hz, 8.8 Hz, 1H), 7.14-7.16 (m, 3H), 7.24-7.33 (m, 3H), 7.44 (d, J=8.8 Hz, 1H), 7.81 (dd, J=2.2 Hz, 8.8 Hz, 1H), 8.71 (d, J=2.2 Hz, 1H).

142C. Example 142: To a solution of 63A (7.54 mg, 0.030 mmol), in DMF (0.5 mL) were added EDC (0.011 g, 0.060 mmol), HOBT (9.14 mg, 0.060 mmol), and TEA (0.021 mL, 0.149 mmol). The reaction mixture was stirred at rt for 0.5 h, then a solution of 142B (0.019 g, 0.030 mmol) in DMF (0.5 mL) was added. The reaction mixture was stirred at rt for 20 h, then concentrated and purified by reverse phase HPLC to give Example 142 (9 mg, 40%) as a green/yellow solid. LCMS m/z 643.1 (M+H)$^+$. $^1$HNMR (400 MHz, CD$_3$OD) δ

2.42-2.46 (m, 2H), 2.65-2.68 (m, 2H), 3.06-3.11 (m, 1H), 3.20 (dd, J=7.7 Hz, 13.7 Hz, 1H), 5.13 (t, J=7.7 Hz, 1H), 7.11-7.24 (m, 6H), 7.37-7.50 (m, 4H), 7.80 (dd, J=2.2 Hz, 8.8 Hz, 1H), 8.69 (d, J=2.2 Hz, 1H), 9.44 (s, 1H).

Example 143

6-(5-Chloro-2-{(S)-1-[(E)-3-(5-chloro-2-tetrazol-1-yl-phenyl)-acryloylamino]-2-phenyl-ethyl}-1H-imidazol-4-yl)-2-oxo-1,2-dihydro-quinoline-4-carboxylic acid, trifluoroacetic acid salt Example 143 was described by a similar procedure to Example 142, substituting 62B for 63A. LCMS m/z 641.1 (M+H)$^+$. $^1$HNMR (400 MHz, CD$_3$OD) δ: 3.21-3.35 (m, 2H), 5.26 (t, J=7.7 Hz, 1H), 6.72 (d, J=15.4 Hz, 1H), 7.08 (d, J=15.4 Hz, 1H), 7.15-7.28 (m, 6H), 7.44 (d, J=8.8 Hz, 1H), 7.55 (d, J=8.8 Hz, 1H), 7.64 (dd, J=2.2 Hz, 8.8 Hz, 1H), 7.80 (dd, J=2.2 Hz, 8.8 Hz, 1H), 7.95 (d, J=2.2 Hz, 1H), 8.69 (d, J=2.2 Hz, 1H), 9.50 (s, 1H).

Example 144

(S)-5-Chloro-2-(1H-tetrazol-1-yl)benzyl 1-(5-chloro-4-(4-hydroxy-2-oxo-1,2-dihydroquinolin-6-yl)-1H-imidazol-2-yl)-2-phenylethylcarbamate, trifluoroacetic acid salt 5-Chloro-2-(1H-tetrazol-1-yl)benzyl 4-nitrophenyl carbonate was prepared by a similar procedure to 122A. Example 144 was prepared from this intermediate and 65G by a similar procedure to 122B. LC/MS m/z 617.57 (M+H)$^+$. $^1$HNMR (400 MHz, CD$_3$OD) δ ppm 3.13-3.24 (m, 2H) 4.92-4.98 (m, 3H) 5.96 (s, 1H) 7.14-7.20 (m, 3H) 7.22-7.26 (m, 2H) 7.42 (d, J=8.79 Hz, 1H) 7.50-7.56 (m, 1H) 7.57-7.63 (m, 1H) 7.69 (s, 1H) 7.86 (dd, J=8.35, 1.76 Hz, 1H) 7.97 (s, 1H) 8.23 (s, 1H) 9.46 (s, 1H).

Example 145

(S)-3-(5-chloro-2-oxopyridin-1(2H)-yl)-N-(1-(5-chloro-4-(4-hydroxy-2-oxo-1,2-dihydroquinolin-6-yl)-1H-imidazol-2-yl)-2-phenylethyl)propanamide, trifluoroacetic acid salt 145A. tert-Butyl 3-(5-chloro-2-oxopyridin-1(2H)-yl)propanoate: To a solution of tert-butyl acrylate (1.187 g, 9.26 mmol) in dioxane (10 mL) was added 5-chloropyridin-2-ol (1.0 g, 7.72 mmol). The reaction mixture was stirred under nitrogen at 100° C. for 14 h. The reaction was cooled to rt and solvent was removed under reduced pressure. The crude product was purified by flash chromatography to give 145A as a white solid. LC/MS m/z 258.25 (M+H)$^+$. $^1$HNMR (500 MHz, CDCl$_3$) δ ppm 1.38 (s, 9H) 2.70 (t, J=6.32 Hz, 2H) 4.08 (t, J=6.05 Hz, 2H) 6.51 (d, J=9.35 Hz, 1H) 7.25 (dd, J=9.90, 2.75 Hz, 1H) 7.46 (d, J=2.75 Hz, 1H). $^{13}$C NMR (125 MHz, CDCl$_3$) δ ppm 27.96, 34.09, 46.77, 81.49, 112.10, 121.45, 136.27, 140.70, 160.86, 170.30.

145B. 3-(5-Chloro-2-oxopyridin-1(2H)-yl)propanoic acid: To a solution of 145A (0.36 g, 1.397 mmol) in DCM (5.0 mL) was added TFA (2.0 mL, 26.0 mmol) at rt. The reaction mixture was stirred under nitrogen at rt for 3 h, then the solvent was removed and the resulting residue was dried in vacuum to leave 145B as a solid. LC/MS m/z 202.14 (M+H)$^+$.

145C. Example 145 was prepared from 65G and 145B by a similar procedure to Example 109. LC/MS m/z 564.31 (M+H)$^+$. $^1$HNMR (500 MHz, CD$_3$OD) δ ppm 2.65-2.73 (m, 2H) 3.14 (dd, J=13.75, 8.25 Hz, 1H) 3.25 (dd, J=13.75, 7.70 Hz, 1H) 4.16 (tq, J=13.30, 6.53 Hz, 2H) 5.19 (t, J=7.70 Hz, 1H) 5.97 (s, 1H) 6.48 (d, J=9.90 Hz, 1H) 7.14-7.21 (m, 3H) 7.25 (t, J=7.15 Hz, 2H) 7.40-7.46 (m, 2H) 7.62 (d, J=2.75 Hz, 1H) 7.88 (dd, J=8.52, 1.92 Hz, 1H) 8.24 (d, J=1.65 Hz, 1H).

Example 146

(S)-6-(5-chloro-2-(1-(3-(5-methyl-2-(1H-tetrazol-1-yl)phenyl)propanamido)-2-phenylethyl)-1H-imidazol-4-yl)-2-oxo-1,2-dihydroquinolin-4-yl pivalate, trifluoroacetic acid salt To a solution of Example 118 (194 mg, 0.326 mmol) in DCM (5.0 mL) was added pivaloyl chloride (79 mg, 0.652 mmol) at 0° C., and the reaction mixture was stirred under nitrogen at 0° C. for 30 min. The solvent was evaporated and the residue was dissolved in 1:1 MeOH/water and stirred with TFA (0.5 mL) at rt for 1 h. The crude product was purified by reverse phase HPLC to give Example 146. LC/MS m/z 679.42 (M+H)$^+$. $^1$HNMR (500 MHz, CD$_3$OD) δ ppm 1.45 (s, 9H) 2.35 (s, 3H) 2.44 (t, J=7.15 Hz, 2H) 2.63 (tq, J=7.15, 6.96 Hz, 2H) 3.12 (dd, J=13.75, 7.70 Hz, 1H) 3.19 (dd, J=13.20, 7.70 Hz, 1H) 5.12 (t, J=7.70 Hz, 1H) 6.54 (s, 1H) 7.12 (d, J=6.60 Hz, 2H) 7.15-7.19 (m, 1H) 7.20-7.24 (m, 4H) 7.25 (s, 1H) 7.45 (d, J=8.80 Hz, 1H) 7.71 (dd, J=8.52, 1.92 Hz, 1H) 8.01 (d, J=2.20 Hz, 1H) 9.39 (s, 1H).

Example 147

(S)—N-(1-(5-chloro-4-(2-oxo-1,2-dihydroquinolin-6-yl)-1H-imidazol-2-yl)-2-phenylethyl)-3-(5-methyl-2-(1H-tetrazol-1-yl)phenyl)propanamide, trifluoroacetic acid salt Example 147 was prepared from 148A and 117B by a coupling procedure similar to 148B. LC/MS m/z 579.45 (M+H)$^+$. $^1$HNMR (400 MHz, CD$_3$OD) δ ppm 2.37 (s, 3H) 2.44 (t, J=7.91 Hz, 2H) 2.57-2.67 (m, 2H) 3.08-3.20 (m, 2H) 5.12 (t, J=7.91 Hz, 1H) 6.66 (d, J=9.67 Hz, 1H) 7.12 (d, J=6.59 Hz, 2H) 7.17-7.28 (m, 6H) 7.42 (d, J=8.35 Hz, 1H) 7.80 (dd, J=8.79, 2.20 Hz, 1H) 7.89 (d, J=1.76 Hz, 1H) 7.99 (d, J=9.67 Hz, 1H) 9.40 (s, 1H).

Example 148

(S,E)-3-(5-chloro-2-(1H-tetrazol-1-yl)phenyl)-N-(1-(5-chloro-4-(2-oxo-1,2,3,4-tetrahydroquinolin-6-yl)-1H-imidazol-2-yl)-2-phenylethyl)acrylamide, trifluoroacetic acid salt 148A. (S)-6-(2-(1-amino-2-phenylethyl)-5-chloro-1H-imidazol-4-yl)-3,4-dihydroquinolin-2(1H)-one, bis-trifluoroacetic acid salt: 148A was prepared by a series of steps similar to 52A and 52B, using 6-(2-bromoacetyl)-3,4-dihydroquinolin-2(1H)-one in place of 82D and K$_2$CO$_3$ in place of Cs$_2$CO$_3$. LC/MS m/z 367.46 (M+H)$^+$.

148B. Example 148: To a solution of 148A (637 mg, 1.071 mmol) in DMF (10 mL) were added 62B (268 mg, 1.071 mmol), DIEA (0.935 mL, 5.36 mmol) and EDC (246 mg, 1.285 mmol) at rt. The reaction mixture was stirred under nitrogen at rt for 3 h, then the crude product was purified by prep HPLC to give Example 148 (408.3 mg, 53.4% yield) as a white solid. LC/MS m/z 599.49 (M+H)$^+$. $^1$HNMR (400 MHz, CD$_3$OD) δ ppm 2.58 (t, J=7.47 Hz, 2H) 2.94-3.01 (m, 2H) 3.28-3.32 (m, 2H) 5.25 (t, J=7.69 Hz, 1H) 6.71 (d, J=15.82 Hz, 1H) 6.92 (d, J=8.79 Hz, 1H) 7.08 (d, J=15.38 Hz, 1H) 7.15-7.19 (m, 2H) 7.21 (d, J=7.03 Hz, 1H) 7.23-7.29 (m, 2H) 7.38-7.44 (m, 2H) 7.55 (d, J=8.35 Hz, 1H) 7.64 (dd, J=8.35, 2.20 Hz, 1H) 7.94 (d, J=1.76 Hz, 1H) 9.49 (s, 1H).

Example 149

(S,E)-methyl 4-(5-chloro-2-(1-(3-(3-chloro-2,6-difluorophenyl)acrylamido)-2-phenylethyl)-1H-imidazol-4-yl)phenylcarbamate, trifluoroacetic acid salt Example 149 was prepared from (E)-3-(3-chloro-2,6-difluoro-phenyl)-acrylic acid and 52B by a similar procedure to 3A. LC/MS m/z 571.0 (M+H)$^+$. $^1$HNMR (400 MHz, CD$_3$OD) δ ppm 3.25-3.37 (m, 2H, overlapped with solvent peak)) 3.74 (s, 3H) 5.32 (t, J=7.69 Hz, 1H) 6.97 (d, J=16.26 Hz, 1H) 7.07 (t, J=9.45 Hz, 1H) 7.16-7.24 (m, 3H) 7.24-7.32 (m, 2H) 7.46-7.51 (m, 1H) 7.53 (s, 4H) 7.57 (d, J=16.26 Hz, 1H). $^{19}$F NMR (376 MHz, CD$_3$OD) δ ppm −113.50 (s, 1F) −113.28 (s, 1F)-77.41 (s, 3.5F, TFA).

Example 150

(S,E)-3-(3-chloro-2,6-difluorophenyl)-N-(1-(5-chloro-4-(4-hydroxy-2-oxo-1,2-dihydroquinolin-6-yl)-1H-imidazol-2-yl)-2-phenylethyl)acrylamide, trifluoroacetic acid salt Example 150 was prepared from 65G and (E)-3-(3-chloro-2,6-difluoro-phenyl)-acrylic acid by a similar procedure to Example 109. LC/MS m/z 581.1 (M+H)$^+$. $^1$HNMR (400 MHz, CD$_3$OD) δ ppm 3.29-3.32 (m, 2H) 5.34 (t, J=7.69 Hz, 1H) 5.95 (s, 1H) 6.97 (d, J=16.26 Hz, 1H) 7.07 (t, J=9.45 Hz, 1H) 7.18-7.24 (m, 3H) 7.24-7.30 (m, 2H) 7.40 (d, J=8.79 Hz, 1H) 7.50 (td, J=8.68, 5.93 Hz, 1H) 7.57 (d, J=16.26 Hz, 1H) 7.86 (dd, J=8.79, 2.20 Hz, 1H) 8.23 (d, J=1.76 Hz, 1H). $^{19}$F NMR (376 MHz, CD$_3$OD) δ ppm −113.52 (s, 1F) −113.31 (s, 1F) −77.44 (s, 4.5F, TFA).

Example 151

(S,E)-3-(5-chloro-2-(1H-tetrazol-1-yl)phenyl)-N-(1-(5-chloro-4-(4-hydroxy-2-oxo-1,2-dihydroquinolin-6-yl)-1H-imidazol-2-yl)-2-phenylethyl)acrylamide, trifluoroacetic acid salt Example 151 was prepared from 65G and 62B by a similar procedure to Example 109. LC/MS m/z 613.1 (M+H)$^+$. $^1$HNMR (500 MHz, CD$_3$OD) δ ppm 3.28-3.33 (m, 2H, overlapped with solvent peak) 5.26 (t, J=7.70 Hz, 1H) 5.95 (s, 1H) 6.72 (d, J=15.40 Hz, 1H) 7.09 (d, J=15.95 Hz, 1H) 7.16-7.23 (m, 3H) 7.26 (t, J=7.42 Hz, 2H) 7.40 (d, J=8.80 Hz, 1H) 7.56 (d, J=8.25 Hz, 1H) 7.65 (dd, J=8.25, 2.20 Hz, 1H) 7.85 (dd, J=8.52, 1.92 Hz, 1H) 7.97 (d, J=2.20 Hz, 1H) 8.22 (d, J=2.20 Hz, 1H) 9.50 (s, 1H).

Example 152

(S)-methyl 4-(5-chloro-2-(1-(3-((6-chloro-1H-benzo[d]imidazol-4-yl)methyl)ureido)-2-phenylethyl)-1H-imidazol-4-yl)phenylcarbamate, trifluoroacetic acid salt 152A. 5-chloro-3-methylbenzene-1,2-diamine: 4-chloro-2-methyl-6-nitroaniline (1.3 g, 6.97 mmol) in 2M NH$_3$ in MeOH (35 mL) was hydrogenated at 50 psi H$_2$ in the presence of Raney nickel catalyst for 5 h. The reaction was filtered through Celite® and concentrated. The residue was dissolved in EtOAc and dried (MgSO$_4$), filtered and concentrated to give 152A (1.1 g) as a dark solid. LC/MS m/z 157.1 (M+H)$^+$. $^1$HNMR (400 MHz, DMSO-d$_6$) δ 2.02 (s, 3H) 4.26 (s, 2H), 4.72 (s, 2H), 6.31 (d, J=1.77 Hz, 1H), 6.43 (d, J=2.53 Hz, 1H) ppm.

152B. tert-Butyl 6-chloro-4-methyl-1H-benzo[d]imidazole-1-carboxylate: 152A (0.45 g, 2.87 mmol) was heated at 130° C. in formic acid (3 mL) in a microwave reactor for 15 min. The reaction was partitioned with EtOAc/sat'd NaHCO$_3$ and extracted with EtOAc. The combined organic layers were washed with brine and dried (MgSO$_4$). Filtration and concentration afforded a brown solid that was dissolved in DCM (15 mL) and treated with di-tertbutyldicarbonate (0.667 mL, 2.87 mmol) and triethylamine (0.801 mL, 5.75 mmol) and the reaction was stirred for 24 h. The reaction was concentrated, partitioned with EtOAc/water and extracted with EtOAc. The combined organic layers were washed with water and brine, then dried (MgSO$_4$) and purified by flash chromatography to give 152B (0.74 g, 97%) as a tan solid. $^1$HNMR (400 MHz, CDCl$_3$) δ 1.70 (s, 9H), 2.62 (s, 3H), 7.16 (d, J=1.26 Hz, 1H), 7.83 (d, J=1.52 Hz, 1H) 8.36 (s, 1H) ppm.

152C. tert-Butyl 4-(azidomethyl)-6-chloro-1H-benzo[d]imidazole-1-carboxylate: To 152D (0.74 g, 2.77 mmol) in CCl$_4$ (20 mL) was added NBS (0.494 g, 2.77 mmol) and a catalytic amount of benzoyl peroxide. The reaction was heated at reflux for 24 h, then cooled and filtered. Purification by flash chromatography afforded 1.1 g of an oily solid. LC/MS m/z 289.1 (M+H-tBu)$^+$; 245.1 (M+H-Boc)$^+$. To this intermediate in DMF (10 mL) was added sodium azide (0.180 g, 2.77 mmol) and the reaction was stirred for 24 h. The reaction was partitioned with EtOAc/water/brine and extracted with EtOAc. The combined organic layers were washed with water and brine, dried (MgSO$_4$), and purified by flash chromatography to afforded 152C (0.49 g, 57%) as a yellow oil. LC/MS m/z 308.3 (M+H)$^+$.

152D. tert-Butyl 4-(aminomethyl)-6-chloro-1H-benzo[d]imidazole-1-carboxylate: To stannous chloride dihydrate (0.539 g, 2.388 mmol) in MeOH (10 mL) was added a solution of 152C (0.49 g, 1.592 mmol) in MeOH (10 mL). After stirring for 2 h, additional stannous chloride dihydrate (0.6 g) was added and the reaction was stirred for 24 h. The reaction was concentrated and the residue was diluted with water, made basic with 10N NaOH and extracted with EtOAc. The combined organic layers were washed with brine and dried (MgSO$_4$) to afford 152D (0.3 g, 66%). LC/MS m/z 282.3 (M+H)$^+$.

152E. Example 152 was prepared by coupling of 152D and 52B by a similar procedure to Example 16, followed by removal of the Boc protecting group with 30% TFA in DCM and purification by reverse phase HPLC. LC/MS m/z 578.5 (M+H)$^+$. $^1$HNMR (400 MHz, CD$_3$OD) δ 2.99-3.08 (m, 1H), 3.08-3.15 (m, 1H), 3.65 (s, 3H), 4.40-4.56 (m, 2H), 5.02 (dd, J=8.08, 7.07 Hz, 1H), 6.99-7.07 (m, 3H), 7.07-7.15 (m, 2H), 7.35 (d, J=1.77 Hz, 1H), 7.38-7.51 (m, 4H), 7.65 (d, J=1.77 Hz, 1H), 9.14 (s, 1H).

Example 153

(S)-Methyl 4-(5-chloro-2-(1-(3-((2,6-dichlorobenzo[d]thiazol-4-yl)methyl)ureido)-2-phenylethyl)-1H-imidazol-4-yl)phenylcarbamate, trifluoroacetic acid salt Example 153 was prepared by a similar procedure to that described for 152C-E starting from commercially available 2,6-dichloro-4-methylbenzo[d]thiazole. LC/MS m/z 629.5

(M+H)⁺. ¹HNMR (400 MHz, CD₃OD) δ 3.08 (dd, J=7.58, 2.53 Hz, 2H), 3.65 (s, 3H), 4.57 (s, 2H), 4.97 (t, J=7.58 Hz, 1H), 7.02-7.06 (m, 2H), 7.09 (d, J=7.07 Hz, 1H), 7.11-7.17 (m, 2H), 7.26 (d, J=2.02 Hz, 1H), 7.41 (s, 4H), 7.76 (d, J=2.02 Hz, 1H).

Example 154

Methyl 4-(5-chloro-2-((1S)-1-(3-(5-chloro-2-(5-methyl-1H-tetrazol-1-yl)phenyl)propanamido)-2-phenylethyl)-1H-imidazol-4-yl)phenylcarbamate, trifluoroacetic acid salt 154A. 1-(2-bromo-4-chlorophenyl)-5-methyl-1H-tetrazole: To N-(2-bromo-4-chlorophenyl)acetamide (5.1 g, 20.52 mmol) in toluene (50 mL) was added PCl₅ (4.27 g, 20.52 mmol) and the reaction was heated at 100° C. for 6 h. The reaction was concentrated and the residue was dissolved in DMF (25 mL) and added to a solution of sodium azide (2.67 g, 41.0 mmol) in DMF (25 mL) at 0° C. The reaction was allowed to warm to rt and stir for 2 days. The reaction was partitioned with EtOAc/water/brine and extracted with EtOAc. The combined organic layers were washed with water and brine, dried (Na₂SO₄), and purified by flash chromatography to give 154A (5 g, 89%) as a yellow solid. LC/MS m/z 275.0 (M+H)⁺. ¹HNMR (400 MHz, CDCl₃) δ 2.49 (s, 3H) 7.37 (d, J=8.59 Hz, 1H), 7.55 (dd, J=8.34, 2.27 Hz, 1H), 7.84 (d, J=2.02 Hz, 1H).

154B. Ethyl 3-(5-chloro-2-(5-methyl-1H-tetrazol-1-yl)phenyl)propanoate: To 154A (3 g, 10.97 mmol) were added tetrabutylammonium bromide (3.2 g, 9.93 mmol), palladium (II)acetate (0.985 g, 4.39 mmol), 3,3-diethoxyprop-1-ene (3.36 mL, 21.94 mmol), tributylamine (5.22 mL, 21.94 mmol), and DMF (15 mL). The reaction was heated at 90° C. for 24 h. The reaction was cooled and stirred with 1N HCl for 15 min, then partitioned with EtOAc/brine and extracted with EtOAc. The combined organic layers were washed with water and brine, dried (MgSO₄), and purified by flash chromatography to give 154B (2.3 g, 71%) as a yellow oil. LC/MS m/z 295.3 (M+H)⁺. ¹HNMR (400 MHz, CDCl₃) δ 1.21 (t, J=7.20 Hz, 3H), 2.48 (s, 3H), 2.48-2.53 (m, 2H), 2.60-2.67 (m, 2H), 4.08 (q, 2H), 7.15 (d, J=8.34 Hz, 1H), 7.40-7.43 (m, 1H), 7.49 (d, J=2.27 Hz, 1H).

154C. 3-(5-Chloro-2-(5-methyl-1H-tetrazol-1-yl)phenyl) propanoic acid: 154B (2.3 g, 7.80 mmol) was treated with lithium hydroxide hydrate (0.327 g, 7.80 mmol) in THF (20 mL) and water (20 mL) for 24 h. The reaction was concentrated and the residue was partitioned with Et₂O/water. The aqueous layer was acidified and extracted with EtOAc. The combined organic layers were washed with brine, dried (MgSO₄), filtered and concentrated to give 154C (1.74 g, 84%) as a tan solid. LC/MS m/z 267.2 (M+H)⁺. ¹HNMR (400 MHz, CDCl₃) δ 2.47 (s, 3H), 2.56-2.68 (m, 4H), 7.16 (d, J=8.59 Hz, 1H), 7.43 (dd, J=8.34, 2.27 Hz, 1H), 7.50 (d, J=2.27 Hz, 1H).

154D. Example 154 was prepared by coupling 154D and 52B by a procedure similar to 62C using TEA in place of Hunig's base. LC/MS m/z 619.6 (M+H)⁺. ¹HNMR (400 MHz, CD₃OD) δ 2.29 (s, 3H), 2.31-2.38 (m, 2H), 2.40-2.48 (m, 2H), 2.99-3.11 (m, 2H), 3.65 (s, 3H), 5.00 (t, J=7.83 Hz, 1H), 6.99-7.03 (m, 2H), 7.08-7.16 (m, 3H), 7.25 (d, J=8.59 Hz, 1H), 7.34-7.39 (m, 1H), 7.41-7.45 (m, 5H).

Example 155

N-((S)-1-(4-(3-amino-1H-indazol-6-yl)-5-chloro-1H-imidazol-2-yl)-2-phenylethyl)-3-(5-chloro-2-(5-methyl-1H-tetrazol-1-yl)phenyl)propanamide, trifluoroacetic acid salt Example 155 was prepared by coupling 110A and 154C by a procedure similar to 62C using TEA in place of Hunig's base. LC/MS m/z 601.6 (M+H)⁺. ¹HNMR (400 MHz, CD₃OD) δ 2.30 (s, 3H), 2.31-2.37 (m, 2H), 2.41-2.50 (m, 2H), 2.95-3.05 (m, 1H), 3.05-3.13 (m, 1H), 5.01 (t, J=7.83 Hz, 1H), 6.95-7.05 (m, 2H), 7.05-7.16 (m, 3H), 7.25 (d, J=8.34 Hz, 1H), 7.32-7.41 (m, 2H), 7.43 (d, J=2.27 Hz, 1H), 7.59 (s, 1H), 7.85 (d, J=8.84 Hz, 1H).

Example 156

Methyl 4-(5-chloro-2-((1S)-1-((E)-3-(3-chlorophenyl)acrylamido)-2-(2-hydroxy-2,3-dihydro-1H-inden-5-yl)ethyl)-1H-imidazol-4-yl)phenylcarbamate, trifluoroacetic acid salt 156A. (2S)-3-(2-acetoxy-indan-5-yl)-2-(tert-butoxycarbonylamino)-propanoic acid: This intermediate was prepared in five steps as follows: 10 g (0.075 mol) of 2-indanol was cooled to 0° C. under nitrogen. To this was added 30 mL of acetyl chloride dropwise over a period of 30 min and the resulting mixture was allowed to stir at rt overnight. The reaction was concentrated using vacuum pump. The residue was dissolved in ethyl acetate and washed with 10% NaHCO₃, water, and brine then concentrated to give 2-acetoxyindane (13 g, 99%). ¹HNMR (CDCl₃, 400 MHz) δ 7.19-7.27 (m, 4H), 5.54 (m, 1H), 3.34 (m, 2H), 3.04 (dd, 2H), 2.06 (s, 3H). LC-MS: m/z 176 (M+H)⁺. A portion of this intermediate (5 g, 0.0284 mol) was taken up in 150 mL of dry acetonitrile under nitrogen and NBS (15.15 g, 0.085 mol) was added. The reaction was stirred at rt for 9 days. The reaction mixture was concentrated, dissolved in DCM, washed with water, brine solution and concentrated. The product was purified by flash column to give 2-acetoxy-5-bromo-indane (3.75 g, 52%) as an off-white solid. ¹HNMR (CDCl₃, 400 MHz) δ 7.39 (s, 1H), 7.33 (d, 1H), 7.12 (d, 1H), 5.5 (m, 1H), 3.32 (m, 2H), 3.0 (t, 2H), 2.06 (s, 3H). A mixture of the bromide (3.5 g, 0.0137 mol), 2-tert-butoxycarbonylamino-acrylic acid benzyl ester (4.94 g (0.0178 mol), tri-o-tolyl phosphine, (0.68 g, 0.00226 mol), palladium acetate (0.16 g, 0.00075 mol) and triethylamine (4.57 g, 0.045 mol) in 35 ml of dry DMF was degassed for 1 h, then heated to 110° C. overnight. The reaction was quenched with water and extracted with ethyl acetate. The extracts were washed with water and brine and concentrated. The compound was purified by flash chromatography to give (E)-3-(2-Acetoxy-indan-5-yl)-2-tert-butoxycarbonylamino-acrylic acid benzyl ester (1.7 g, 27.5%) as an off-white solid. ¹HNMR (CDCl₃, 400 MHz) δ 7.39 (s, 1H), 7.33 (d, 1H), 7.12 (d, 1H), 5.5 (m, 1H), 3.32 (m, 2H), 3.0 (t, 2H), 2.06 (s, 3H). LC-MS: m/z 451 (M+H)⁺. The olefin (14 g, 0.031 mol) was dissolved in 350 mL of methanol. The solution was degassed with nitrogen and a catalytic amount of (S,S)-Et-DUPHOS-Rh catalyst (0.67 g) was added. The solution was degassed for 30 min then stirred under 70 psi hydrogen pressure overnight. The reaction was filtered through Celite® and concentrated. The product was purified by flash chromatography to give the reduced product (12 g, 85%). ¹HNMR (CDCl₃, 400 MHz) δ 7.39 (m, 3H), 7.33 (m, 2H), 7.1 (d, 1H), 6.8 (m, 2H) 5.5 (m, 1H), 5.3 (m, 1H), 5.2 (s, 1H), 5 (d, 1H) 3.3 (m, 2H), 3.10 (d, 2H), 2.99 (t, 2H) 2.06 (s, 3H).

LC-MS: m/z 445.2 (M+1)⁺. This material was dissolved in a 1:1 ethyl acetate:methanol mixture, and palladium hydroxide (1 g, 10%) was added under nitrogen. The reaction mixture was stirred at 50 psi hydrogen pressure overnight. The catalyst was removed by filtration through Celite® and filtrate concentrated. Purification by flash chromatography provided the desired acid (2 g, 25%) as a viscous liquid. ¹HNMR (CDCl₃, 400 MHz) δ 12.5 (bs, 1H), 7.15 (m, 3H), 5.40 (m, 1H), 4.0 (m, 1H), 3.28 (m, 2H), 2.97 (m, 1H), 2.82 (m, 3H), 1.98 (s, 3H), 1.3 (s, 9H). LC-MS: m/z 363.4 (M+H)⁺.

156B. 5-((S)-2-(tert-butoxycarbonylamino)-2-(4-(4-(methoxycarbonylamino)phenyl)-1H-imidazol-2-yl)ethyl)-2,3-dihydro-1H-inden-2-yl acetate: To 156A (1.4 g, 3.85 mmol) in DMF (7 mL) was added cesium carbonate (0.628 g, 1.926 mmol), and the mixture was stirred at rt for 1 h under argon followed by addition of 82D (1.048 g, 3.85 mmol). The reaction was stirred at rt under argon overnight. The reaction mixture was filtered to remove the inorganic solid. The organic filtrate was concentrated under vacuum, and dried in vacuo to provide the crude ketoester. LCMS m/z 555.4 (M+H)⁺; 455.3 (M+H-Boc)⁺. A 100 mL flask equipped with a condenser and a Dean-Stark trap was charged with the ketoester intermediate (2.135 g, 3.85 mmol), ammonium acetate (6.53 g, 85 mmol) and xylene (50 mL). The mixture was stirred at reflux (150° C.) for 3 h, and then stirred at rt overnight. The reaction mixture was concentrated under vacuum to give a light-orange oil. The crude product was purified by flash chromatography to yield 156B (1.6 g) as a yellow foam. LCMS m/z 535.4 (M+H)⁺.

156C. 5-((S)-2-(tert-butoxycarbonylamino)-2-(5-chloro-4-(4-(methoxycarbonylamino)phenyl)-1H-imidazol-2-yl)ethyl)-2,3-dihydro-1H-inden-2-yl acetate: A mixture of 156B (1.6 g, 2.99 mmol) and NCS (0.520 g, 3.89 mmol) in acetonitrile (20 mL) was stirred at rt under argon for 5.5 h, and then held at 0° C. overnight. The reaction mixture was concentrated under vacuum. The oily crude product was purified by flash chromatography to provide the desired product (1.43 g, 84%) as a foam. LCMS m/z 569.4 (M+H)⁺.

156D. 5-((S)-2-amino-2-(5-chloro-4-(4-(methoxycarbonylamino)phenyl)-1H-imidazol-2-yl)ethyl)-2,3-dihydro-1H-inden-2-yl acetate, bis-trifluoroacetic acid salt: 156C (285 mg, 0.501 mmol) was dissolved in 8 mL of DCM/TFA (7:1) and stirred at rt under argon for 1.5 h. The reaction mixture was concentrated under vacuum and the crude deprotected amine salt was used without purification. LCMS m/z: 469.3 (M+H)⁺.

156E. 5-((S)-2-(5-chloro-4-(4-(methoxycarbonylamino)phenyl)-1H-imidazol-2-yl)-2-((E)-3-(3-chlorophenyl)acrylamido)ethyl)-2,3-dihydro-1H-inden-2-yl acetate: To a solution of (E)-3-(3-chlorophenyl)acrylic acid (36.8 mg, 0.201 mmol) in DMF (4 mL) were added BOP reagent (89 mg, 0.201 mmol) and TEA (234 μL, 1.679 mmol). The mixture was stirred at rt under argon for 30 min, then 156D (117 mg, 0.168 mmol) was added. The reaction mixture was stirred at rt under argon for 2 d. The reaction mixture was concentrated by rotary evaporation. The residue was dissolved in EtOAc, washed with water and brine, dried (Na₂SO₄) and concentrated. The residue was purified by flash chromatography to yield 156E (99 mg, 93%). LCMS m/z 633.4(M+H)⁺.

156F. Example 156: To a solution of 156E (84 mg, 0.133 mmol) in MeOH (4 mL) was added sodium hydroxide (200 μL, 0.200 mmol). The mixture was stirred at rt under argon for 2.5 h. The reaction mixture was concentrated by rotary evaporation. Purification by reverse phase HPLC and lyophilization gave the Example 156 (0.070 g, 75%) as a fluffy off-white solid. LCMS m/z 591.2 (M+H)⁺. ¹HNMR (400 MHz, CD₃OD) δ ppm: 2.79 (dd, J=16.26, 2.64 Hz, 2H), 3.04-3.13 (m, 2H), 3.27 (d, J=7.47 Hz, 2H), 3.74 (s, 3H), 4.57 (dd, J=5.71, 3.52 Hz, 1H), 5.26 (q, J=7.47 Hz, 1H), 6.69 (dd, J=15.82, 2.20 Hz, 1H), 6.96 (t, J=8.35 Hz, 1H), 7.07 (s, 1H), 7.12 (d, J=7.47 Hz, 1H), 7.37 (d, J=5.27 Hz, 2H), 7.44-7.49 (m, 2H), 7.51-7.58 (m, 5H).

Example 157

(4-{5-Chloro-2-[(S)-1-[3-(5-chloro-2-tetrazol-1-yl-phenyl)-propionylamino]-2-(2,2-dioxo-2,3-dihydro-1H-2λ⁶-benzo[c]thiophen-5-yl)-ethyl]-1H-imidazol-4-yl}-phenyl)-carbamic acid methyl ester, trifluoroacetic acid salt 157A. (S)-2-tert-Butoxycarbonylamino-3-(2,2-dioxo-2,3-dihydro-1H-2λ⁶-benzo[c]thiophen-5-yl)-propionic acid benzyl ester: This intermediate was prepared in 5 steps as follows: 4-bromo-o-xylene (50 g, 0.2703 mL) was dissolved in carbon tetrachloride (500 mL) and NBS (100 g, 0.5676 mol) was added followed by AIBN (0.89 g. 0.02 eq). The reaction mixture was refluxed vigorously for 2 h, then quenched with water. The organic layer was washed with water, and brine and concentrated. The crude product was purified by flash chromatography to give 4-bromo-1,2-bis-bromomethyl-benzene (35 g, 38%) as an off-white solid. ¹HNMR (CDCl₃, 400 MHz) δ 7.0-7.5 (m, 3H), 4.7 (m, 4H). LC-MS: m/z 343 (M+H)⁺. The dibromide (35 g, 0.1021 mol) was dissolved in 700 mL of absolute ethanol and sodium sulfide (98 g, 0.4082 mol) was added. The resulting mixture was stirred at 50° C. for 1 h, then quenched with water and extracted with ethyl acetate. The combined extracts were washed with brine and concentrated. The residue was purified by flash chromatography to give 5-bromo-1,3-dihydro-benzo[c]thiophene (7 g, 32%) as a yellow solid. ¹HNMR (CDCl₃, 400 MHz) δ 7.4 (s, 1H), 7.3 (d, 1H), 7.1 (d, 1H), 4.21 (s, 2H), 4.24 (s, 2H). LC-MS m/z 215 (M+H)⁺. A solution of this intermediate (7 g, 0.0326 mol) in 350 mL of dry DCM was cooled to –25° C. To this was added m-mCPBA (23 g, 0.1302 mol) and the reaction was slowly brought to rt and stirred for 4 h. The resulting mixture was diluted with DCM and washed with 10% NaOH solution, water, and brine then concentrated to give 5-bromo-1,3-dihydro-benzo[c]thiophene 2,2-dioxide (6.8 g, 85%) as a yellow solid. ¹HNMR (CDCl₃, 400 MHz) δ 7.54 (m, 2H), 7.21 (d, 1H), 4.33 (s, 2H), 4.37 (s, 2H). LC-MS: m/z 247 (M+H)⁺. A mixture of this bromo intermediate (10 g, 0.0405 mol), 2-tert-butoxycarbonylamino-acrylic acid benzyl ester (10 g, 0.0405 mol), palladium acetate (0.3 g, 0.0012 mol), tetra butyl ammonium chloride (2.4, 0.0446 mol) and triethylamine (5.3 g, 0.0528 mol) in dry DMF (115 mL) was degassed for 1 h and then heated to 85° C. overnight. The reaction was quenched with water and extracted with ethyl acetate. The extracts were washed with water and brine and then concentrated. Flash chromatography provided (E)-2-tert-Butoxycarbonylamino-3-(2,2-dioxo-2,3-dihydro-1H-2λ⁶-benzo[c]thiophen-5-yl)-acrylic acid benzyl ester (6 g, 33%) as a yellow solid. ¹HNMR (CDCl₃, 400 MHz) δ 7.1-7.7.5 (m, 8H), 6.5 (m, 1H), 5.30 (s, 2H), 4.35 (s, 2H), 4.37 (s, 2H), 1.40 (s, 9H). LC-MS: m/z 443.5 (M+H)⁺. The olefin (0.5 g, 0.0011 mol) was dissolved in methanol (50 mL) and DCM (25 mL). The solution was degassed with nitrogen and (S,S)-Et-DUPHOS-Rh catalyst (0.075 g) was added. Mixture was degassed for 30 min and then stirred under 70 psi hydrogen pressure for 4 days at rt. The reaction was filtered through Celite® and concentrated. The product was purified by flash chromatography to give 157A (0.2 g, 40%) as a pale yellow solid. ¹HNMR (CDCl₃, 400 MHz) δ 7.4 (m, 1H), 7.39 (m, 2H), 7.15 (d, 1H), 7.13 (d, 1H) 6.8 (s, 1H), 5.26 (d, 1H), 5.2 (d, 1H), 5.0 (d, 1H) 4.6 (q, 1H), 4.31 (s, 2H), 4.21 (s, 2H), 3.12 (m, 2H), 1.43 (s 9H). LC-MS: m/z 445.5 (M+H)$^+$.

157B. (S)-2-tert-Butoxycarbonylamino-3-(2,2-dioxo-2,3-dihydro-1H-2$\lambda^6$-benzo[c]thiophen-5-yl)-propionic acid: To a solution of 157A in MeOH (25 mL)-EtOAc (35 mL) was added palladium hydroxide on carbon (100 mg, 0.712 mmol). The solution was stirred at rt under 1 atm H$_2$ overnight. The mixture was filtered through Celite®, and the filtrate was concentrated under vacuum and dried in vacuo to provide the deprotected acid in quantitative yield. LCMS m/z 256.2 (M+H-Boc)$^+$.

157C. (4-{2-[(S)-1-tert-Butoxycarbonylamino-2-(2,2-dioxo-2,3-dihydro-1H-2$\lambda^6$-benzo[c]thiophen-5-yl)-ethyl]-1H-imidazol-4-yl}-phenyl)-carbamic acid methyl ester: 157C was prepared from 157B and 82D in 61% yield using the procedures described for 156B. LCMS m/z 527.4 (M+H)$^+$.

157D. (4-{2-[(S)-1-tert-Butoxycarbonylamino-2-(2,2-dioxo-2,3-dihydro-1H-2$\lambda^6$-benzo[c]thiophen-5-yl)-ethyl]-5-chloro-1H-imidazol-4-yl}-phenyl)-carbamic acid methyl ester: 157C was treated with NCS using the procedure described for 156C to provide the chlorinated product in 92% yield. LCMS m/z 561.3 (M+H)$^+$.

157E. (4-{2-[(S)-1-Amino-2-(2,2-dioxo-2,3-dihydro-1H-2$\lambda^6$-benzo[c]thiophen-5-yl)-ethyl]-5-chloro-1H-imidazol-4-yl}-phenyl)-carbamic acid methyl ester, bis-trifluoroacetic acid salt: 157D was deprotected with TFA in DCM as described for 157D to provide the amine as its bis-trifluoroacetic acid salt. LCMS m/z 461.2 (M+H)$^+$.

157F. Example 157: To a solution of 63A (37.8 mg, 0.150 mmol) in DMF (4 mL) were added HOAt (24.45 mg, 0.180 mmol), EDCI (34.4 mg, 0.180 mmol), and 4-methylmorpholine (165 µL, 1.497 mmol). The mixture was stirred at rt under argon for 50 min, and then 157E (69 mg, 0.150 mmol) was added. The reaction mixture was stirred at rt under argon overnight. The reaction mixture was concentrated under vacuum to remove DMF. The residue was purified by reverse phase HPLC to provide Example 157 (21 mg, 17%). LC/MS m/z 695.3 (M+H)$^+$. $^1$HNMR (400 MHz, CD$_3$OD) δ ppm: 2.45 (td, J=7.36, 3.74 Hz, 2H), 2.65 (td, J=7.36, 3.30 Hz, 2H), 3.10-3.16 (m, 1H), 3.19-3.24 (m, 1H), 3.75 (s, 3H), 4.37 (d, J=4.83 Hz, 4H), 5.15 (t, J=7.69 Hz, 1H), 7.13 (d, J=7.91 Hz, 1H), 7.20 (s, 1H), 7.25 (d, J=7.91 Hz, 1H), 7.37-7.40 (m, 1H), 7.42-7.46 (m, 1H), 7.51 (d, J=2.20 Hz, 2H), 7.53 (s, 3H), 9.44 (s, 1H).

Example 158

(4-{5-Chloro-2-[(S)-1-[3-(5-chloro-2-tetrazol-1-yl-phenyl)-propionylamino]-2-(4-fluoro-phenyl)-ethyl]-1H-imidazol-4-yl}-phenyl)-carbamic acid methyl ester, trifluoroacetic acid salt 158A. (4-{2-[(S)-1-tert-Butoxycarbonylamino-2-(4-fluoro-phenyl)-ethyl]-5-chloro-1H-imidazol-4-yl}-phenyl)-carbamic acid methyl ester: This intermediate was prepared starting from 82D and commercially available Boc-4-fluorophenylalanine using the procedures described for 156B and 156C. LCMS m/z 489.3 (M+H)$^+$.

158B. Example 158 was prepared from 158A by deprotection with TFA followed by coupling to 63A using the procedures described for 156D and 156E. LCMS m/z 623.2 (M+H)$^+$. $^1$HNMR (400 MHz, CD$_3$OD) δ ppm: 2.48 (t, J=7.25 Hz, 2H), 2.68 (t, J=7.25 Hz, 2H), 3.15 (t, J=8.57 Hz, 2H), 3.75 (s, 3H), 5.10 (t, J=7.91 Hz, 1H), 6.97 (t, J=8.13 Hz, 2H), 7.14 (dd, J=7.69, 5.49 Hz, 2H), 7.37-7.45 (m, 2H), 7.50-7.56 (m, 5H), 9.46 (s, 1H).

Example 159

(4-{5-Chloro-2-[(S)-1-[(E)-3-(5-chloro-2-tetrazol-1-yl-phenyl)-acryloylamino]-2-(4-fluoro-phenyl)-ethyl]-1H-imidazol-4-yl}-phenyl)-carbamic acid methyl ester, trifluoroacetic acid salt Example 159 was prepared from 158A and 62B as described for 158B. LCMS m/z 621.13 (M+H)$^+$. $^1$HNMR (400 MHz, CD$_3$OD) δ ppm: 3.15-3.22 (m, 1H), 3.24-3.29 (m, 1H), 3.74 (s, 3H), 5.19-5.24 (m, 1H), 6.70 (dd, J=15.82, 2.20 Hz, 1H), 6.95-7.01 (m, 2H), 7.09 (dd, J=15.60, 1.98 Hz, 1H), 7.18 (t, J=5.93 Hz, 2H), 7.48-7.57 (m, 5H), 7.62-7.66 (m, 1H), 7.96 (s, 1H), 9.50 (d, J=2.20 Hz, 1H).

Example 160

[4-(5-Chloro-2-{(S)-1-[(E)-3-(5-chloro-2-tetrazol-1-yl-phenyl)-acryloylamino]-2-phenyl-ethyl}-1-methyl-1H-imidazol-4-yl)-phenyl]-carbamic acid methyl ester, trifluoroacetic acid salt 160A. {4-[2-((S)-1-tert-Butoxycarbonylamino-2-phenyl-ethyl)-5-chloro-1H-imidazol-4-yl]-phenyl}-carbamic acid methyl ester: This compound was prepared from 84D and Boc-phenylalanine using the procedures described for 52A-B with the exception that the TFA deprotection of the Boc group was not carried out. $^1$HNMR ((DMSO, 400 MHz) δ 12.5 (s, 1H), 9.79 (s, 1H), 7.16-7.59 (m, 5H), 4.96 (m, 1H), 3.65 (s, 3H), 3.14 (m, 1H), 2.9 (m, 1H) 1.35 (s, 9H). LC-MS:m/z 470.95 (M+H)$^+$.

160B. {4-[2-((S)-1-tert-Butoxycarbonylamino-2-phenyl-ethyl)-5-chloro-1-methyl-1H-imidazol-4-yl]-phenyl}-carbamic acid methyl ester: To a solution of 160A (300 mg, 0.637 mmol) in DMF (7 mL) was added potassium carbonate (132 mg, 0.956 mmol). The mixture was stirred, and followed by addition of iodomethane (48 µl, 0.769 mmol). The reaction was stirred at rt under argon overnight. The reaction mixture was diluted with water and extracted with EtOAc. The organic extraction was washed with water and brine, dried (Na$_2$SO$_4$), filtered, and concentrated under vacuum to yield 160B. LCMS m/z 485.3 (M+H)$^+$.

160C. Example 160: To a solution of 63A (105 mg, 0.418 mmol) in DMF (4 mL) were added HOAt (56.8 mg, 0.418 mmol), EDCI (80 mg, 0.418 mmol), and 4-methylmorpholine (383 µL, 3.48 mmol). The mixture was stirred at rt under argon for 20 min, then the bis-TFA salt of the amine obtained from TFA/DCM deprotection of 160B (142 mg, 0.232 mmol) was added. The reaction mixture was stirred at rt under argon overnight. The reaction mixture was concentrated under vacuum to remove DMF. The residue was purified by reverse phase HPLC to provide Example 160. LCMS m/z 617.2 (M+H)$^+$. $^1$HNMR (400 MHz, CDCl$_3$) δ ppm: 3.40(s, 3H), 3.41-3.50 (m, 2H), 3.77 (s, 3H), 5.39-5.49 (m, 1H), 6.67 (d, J=15.39 Hz, 1H), 7.04-7.15 (m, 4H), 7.23-7.31 (m, 1H), 7.35 (d, J=8.79 Hz, 1H), 7.48-7.57 (m, 3H), 7.75-7.82 (m, 3H), 8.81 (s, 1H), 10.60 (d, J=7.70 Hz, 1H).

Example 161

(E)-N-{(S)-1-[4-(3-Amino-1H-indazol-6-yl)-5-chloro-1H-imidazol-2-yl]-2-phenyl-ethyl}-3-(5-chloro-2-tetrazol-1-yl-phenyl)-acrylamide, trifluoroacetic acid salt Example 161 was prepared from 110A and 62B by a similar procedure to Example 110. LCMS m/z 585.2 (M+H)$^+$.

Example 162

[4-(2-{(S)-1-[3-(5-Chloro-2-tetrazol-1-yl-phenyl)-propionylamino]-2-phenyl-ethyl}-pyridin-4-yl)-phenyl]-carbamic acid methyl ester, trifluoroacetic acid salt 162A. 4-Chloro-pyridine-2-carboxylic acid methyl ester (according to a modified procedure described by Varlet, D. et al, *Heterocycles*, 2000, 53(4), 797): A green suspension of 2-picolinic acid (50.0 g, 406 mmol) in thionyl chloride (200 mL) was warmed to reflux. After 41 h, the clear, red-orange solution was cooled to rt and the excess thionyl chloride was removed via rotary evaporation to obtain a red-orange liquid containing a small amount of solid. Dichloroethane (200 mL) was added, and the reaction was concentrated. The above process was repeated a second time to obtain an orange residue. Diethyl ether (1.4 L) was added to obtain a suspension and the reaction mixture was cooled to 0° C. and vigorously stirred as methanol (200 mL) was added dropwise. The resulting yellow suspension was stirred at 0° C. for 30 min and then warmed to rt and stirred for 1 h. Filtration provided a yellow solid which was washed with diethyl ether, air-dried, then dried under vacuum to obtain 21.20 g of 95% pure product. The filtrate was concentrated to dryness and diethyl ether (500 mL) was added. Sonication yielded a fine suspension which was filtered to provide a yellow solid which was washed with diethyl ether, air-dried, then dried under vacuum to produce an additional 35.5 g of 50% pure product. To a cooled (0° C.) suspension of the latter material (35.5 g) in $CH_2Cl_2$ (500 mL) was added sat. $NaHCO_3$ (300 mL). The suspension was stirred vigorously to dissolve most of the solid. The layers were separated, and the aqueous layer was extracted with $CH_2Cl_2$ (200 mL). The combined organic layers were washed with brine, dried over $MgSO_4$, filtered and concentrated to give an orange liquid weighing 28 g. Column chromatography on silica gel (0-10% ethyl acetate in $CH_2Cl_2$ and then 15:1 $CH_2Cl_2$:ethyl acetate) yielded 13.0 g of the desired product as a white solid. Neutralization of the first solid isolated above and extraction of the free base in the same manner provided an additional 17.4 g for a total of 30.4 g (44%) of 162A. $^1$H-NMR (400 MHz, $CDCl_3$) δ: 8.66 (d, J=5.2 Hz, 1H), 8.15 (d, J=2.6 Hz, 1H), 7.50 (dd, J=5.0, 2.0 Hz, 1H), 4.02 (s, 3H).

162B. 1-(4-Chloro-pyridin-2-yl)-2-phenyl-ethanone: To a cooled (−40° C.) solution of 162A (14.5 g, 84.5 mmol) in THF (192 mL) was added rapidly via cannula a cooled (−40° C.), pale brown solution of 0.6 M benzylmagnesium chloride (142 mL, 84.5 mmol) in THF. The resulting, clear orange solution was stirred at −40° C. for 1 h and then the reaction was quenched with glacial acetic acid (5.4 mL, 93 mmol). The reaction was allowed to warm to rt. The reaction was partitioned between ethyl acetate and sat. $NaHCO_3$. The layers were separated and the aqueous layer was extracted with ethyl acetate. The combined organic layers were washed with brine, dried over $Na_2SO_4$, filtered, and concentrated to give 21.6 g red-brown liquid. Column chromatography on silica gel (1.5:1 $CH_2Cl_2$:hexane) gave 162B (10.1 g, 52%) as an orange liquid. $^1$H-NMR (500 MHz, $CDCl_3$) δ: 8.63 (d, J=5.5 Hz, 1H), 8.03 (d, J=2.2 Hz, 1H), 7.46 (dd, J=5.0, 2.2 Hz, 1H), 7.34-7.28 (m, 4H), 7.27-7.22 (m, 1H), 4.52 (s, 2H). MS 232.1 $(M+H)^+$.

162C. 1-(4-Chloropyridin-2-yl)-2-phenylethanamine: To a clear, yellow solution of 162B (3.96 g, 17.1 mmol) in methanol (34 mL) was added hydroxylamine hydrochloride (3.56 g, 51.3 mmol). The suspension was stirred at rt. Over time the hydroxylamine hydrochloride went into solution. After 14 h the reaction was concentrated to produce a yellow solid. The solid was dissolved in ethyl acetate and washed with sat. $NaHCO_3$. The layers were separated and the aqueous layer was extracted with ethyl acetate. The combined organic layers were washed with brine, dried over $Na_2SO_4$, filtered, and concentrated to yield the oxime as a pink solid weighing 4.13 g.

162D. [(S)-1-(4-Chloro-pyridin-2-yl)-2-phenyl-ethyl]-carbamic acid tert-butyl ester: To a cooled (0° C.) solution of 162C (15 g, 0.064 mol) in dichloromethane (150 mL) was added DMAP (0.78 g, 0.0064 mol) followed by the portion-wise addition of $Boc_2O$ (16.9 g, 0.0775 mol). The reaction mixture was allowed to warm to rt and stirred overnight. The reaction mixture was concentrated. Flash chromatography gave 162D (9.0 g, 43%) as a white solid. The enantiomers were separated by SFC (Supercritical Fluid Chromatography) using Chiralpak AS. Enantiomer B, following Boc-deprotection and conversion of the amine to the o-methyl-mandelic amide, was determined by $^1$HNMR to possess the (S)-absolute configuration. LCMS m/z 333.2 $(M+H)^+$. $^1$HNMR (400 MHz, $CDCl_3$) δ: 8.45 (d, J=5.3 Hz, 1H), 7.22-7.16 (m, 4H), 6.99-6.91 (m, 3H), 5.62-5.58 (m, 1H), 4.97-4.93 (m, 1H), 3.19-3.14 (m, 1H), 3.06 (dd, J=13.2, 7.5 Hz, 1H), 1.41 (bs, 9H).

162E. {4-[2-((S)-1-Amino-2-phenyl-ethyl)-pyridin-4-yl]-phenyl}-carbamic acid methyl ester: To a flame-dried round-bottom flask was added 162D (0.300 g, 0.901 mmol), 4-(methoxycarbonylamino)phenylboronic acid (0.264 g, 1.352 mmol), $Cs_2CO_3$ (0.441 g, 1.352 mmol), $Pd_2\,dba_3$ (0.041 g, 0.045 mmol), and tri-tert-butylphosphine tetrafluoroborate (0.031 g, 0.108 mmol). The flask was purged with argon for several minutes and then degassed. 1,4-Dioxane (4.51 mL) was added. The reaction mixture was stirred at rt for 1 h and then warmed to 90° C. After 3.5 h the reaction was stopped and cooled to rt. The resulting gray/black suspension was filtered through a 0.45 micron GMF to give an orange filtrate. Concentration followed by flash chromatography gave a white foam weighing 0.363 g. LCMS m/z 448.3 $(M+H)^+$. This intermediate was dissolved in 15% TFA/$CH_2Cl_2$ (20 mL) to give a clear, slightly yellow solution. After 1 h, the reaction was concentrated, redissolved in $CH_2Cl_2$ and concentrated to give a clear, yellow oil. The oil was dissolved in $CH_2Cl_2$ and washed with sat'd $NaHCO_3$ and brine, dried over $MgSO_4$, filtered, and concentrated to give 162E (0.248 g, 79%) as a white foam. LCMS m/z 348.2 $(M+H)^+$. $^1$HNMR (400 MHz, $CDCl_3$) δ: 8.61 (d, J=5.3 Hz, 1H), 7.53 (d, J=8.8 Hz, 2H), 7.48 (d, J=8.8 Hz, 2H), 7.37-7.35 (m, 2H), 7.30-7.26 (m, 2H), 7.23-7.17 (m, 3H), 6.83 (bs, 1H), 4.29 (dd, J=8.3, 5.7 Hz, 1H), 3.80 (s, 3H), 3.18 (dd, J=13.2, 5.3 Hz, 1H), 2.93 (dd, J=13.2, 8.8 Hz, 1H), 1.80 (s, 3H).

162F. Example 162 was prepared by coupling 162E and 63A according to the procedure described for 62C. LCMS m/z 582.3 $(M+H)^+$. $^1$HNMR (500 MHz, DMSO-$d_6$) δ: 9.96 (s, 1H), 9.72 (s, 1H), 8.60 (d, J=5.5 Hz, 1H), 8.54 (d, J=8.2 Hz, 1H), 7.78-7.72 (m, 4H), 7.63 (d, J=8.8 Hz, 2H), 7.50-7.49 (m, 2H), 7.44 (dd, J=8.2, 2.2 Hz, 1H), 7.20 (t, J=7.1 Hz, 2H), 7.16-7.12 (m, 3H), 5.18-5.14 (m, 1H), 3.69 (s, 3H), 3.13-3.09 (m, 1H), 3.10-2.96 (m, 1H), 2.52-2.47 (m, 2H), 2.37-2.34 (m, 2H).

Example 163

[4-(2-{(S)-1-[(E)-3-(5-Chloro-2-tetrazol-1-yl-phenyl)-acryloylamino]-2-phenyl-ethyl}-pyridin-4-yl)-phenyl]-carbamic acid methyl ester, trifluoroacetic acid salt Example 163 was prepared by coupling 162C and 62B according to the procedure described for 62C. LCMS m/z 580.3 (M+H)+; 582 (M+2+H)+. $^1$HNMR (500 MHz, DMSO-$d_6$) δ: 9.96 (s, 1H), 9.83 (s, 1H), 8.84 (d, J=8.2 Hz, 1H), 8.62 (d, J=5.5 Hz, 1H), 7.96 (d, J=2.2 Hz, 1H), 7.79-7.75 (m, 4H), 7.74 (dd, J=8.8, 2.2 Hz, 1H), 7.70 (d, J=8.8 Hz, 1H), 7.62 (d, J=8.8 Hz, 2H), 7.26-7.23 (m, 2H), 7.20-7.15 (m, 3H), 6.85 (d, J=15.4 Hz, 1H), 6.80 (d, J=15.4 Hz, 1H), 5.31-5.28 (m, 1H), 3.68 (s, 3H), 3.18 (dd, J=13.8, 5.8 Hz, 1H), 3.10 (dd, J=13.8, 8.8 Hz, 1H).

Example 164

1-[4-Chloro-2-((E)-2-{(S)-1-[5-chloro-4-(4-methoxycarbonylamino-phenyl)-1H-imidazol-2-yl]-2-phenyl-ethylcarbamoyl}-vinyl)-phenyl]-1H-pyrazole-4-carboxylic acid, trifluoroacetic acid salt 164A. 1-(4-Chloro-2-formyl-phenyl)-1H-pyrazole-4-carboxylic acid ethyl ester: A suspension of 5-chloro-2-fluorobenzaldehyde (0.950 g, 5.99 mmol), ethyl 1H-pyrazole-4-carboxylate (0.840 g, 5.99 mmol), and cesium carbonate (1.952 g, 5.99 mmol) in DMSO (5.99 mL) was heated at 75° C. After 30 min, the reaction was cooled to rt and filtered through a 0.45 micron GMF filter, eluting with EtOAc. The filtrate was diluted with EtOAc and washed with water, brine, dried over $Na_2SO_4$, filtered and concentrated to give a yellow solid weighing 1.80 g. Trituration from EtOAc gave 164A (0.649 g, 39%) as a white solid. LCMS m/z 279 (M+H)+. $^1$HNMR (400 MHz, CDCl$_3$) δ: 10.00 (s, 1H), 8.31 (s, 1H), 8.16 (d, J=4.8 Hz, 1H), 8.01 (d, J=2.6 Hz, 1H), 7.67 (dd, J=8.6, 2.4 Hz, 1H), 7.47 (d, J=8.4 Hz, 1H), 4.36 (q, J=7.3 Hz, 2H), 1.39 (t, J=7.3 Hz, 3H).

164B. 1-[2-((E)-2-tert-Butoxycarbonyl-vinyl)-4-chloro-phenyl]-1H-pyrazole-4-carboxylic acid ethyl ester: To a suspension of NaH (9.04 mg, 0.226 mmol) in THF (0.404 mL) was added dropwise tert-butyl 2-(dimethoxyphosphoryl)acetate (0.048 mL, 0.242 mmol). The slightly cloudy reaction mixture was stirred at rt for 45 min and then cooled to 0° C. Next a solution of 164A (0.045 g, 0.161 mmol) in THF (2 mL) was added. After 30 min, the reaction was quenched with saturated NH$_4$Cl and extracted with EtOAc. The combined organic layers were washed with brine, dried over $Na_2SO_4$, filtered and concentrated. Flash chromatography gave 164B (0.0248 g, 41%) as a white solid. LCMS m/z 321.2 (M-C$_4$H$_8$+H)+. $^1$HNMR (400 MHz, CDCl$_3$) δ: 8.15 (s, 1H), 8.10 (s, 1H), 7.71 (d, J=2.2 Hz, 1H), 7.45 (dd, J=8.4, 2.2 Hz, 1H), 7.40 (d, J=16.2 Hz, 1H), 7.38 (d, J=8.3 Hz, 1H), 6.36 (d, J=15.8 Hz, 1H), 4.34 (q, J=7.0 Hz, 2H), 1.49 (s, 9H), 1.37 (t, J=7.0 Hz, 3H).

164C. 1-[2-((E)-2-Carboxy-vinyl)-4-chloro-phenyl]-1H-pyrazole-4-carboxylic acid ethyl ester: A clear, colorless solution of 164B (0.024 g, 0.064 mmol) in dichloromethane (2.55 mL) and TFA (0.30 mL, 3.89 mmol) was stirred at rt. After 6 h, the reaction was concentrated to give a residue which was used in the next step without further purification. LCMS m/z 321.2 (M+H)+.

164D. 1-[4-Chloro-2-((E)-2-{(S)-1-[5-chloro-4-(4-methoxycarbonylamino-phenyl)-1H-imidazol-2-yl]-2-phenyl-ethylcarbamoyl}-vinyl)-phenyl]-1H-pyrazole-4-carboxylic acid ethyl ester: The amide was prepared by coupling 164C and the free base of 52B according to the procedure described for 62C. LCMS m/z 673.3 (M+H)+. $^1$HNMR (500 MHz, CD$_3$OD) δ: 9.36 (s, 1H), 8.39 (s, 1H), 8.10 (s, 1H), 7.85 (d, J=1.4 Hz, 1H), 7.56-7.46 (m, 6H), 7.26-7.23 (m, 3H), 7.19-7.16 (m, 3H), 6.66 (d, J=15.4 Hz, 1H), 5.24 (t, J=7.7 Hz, 1H), 4.30 (q, J=7.2 Hz, 2H), 3.74 (s, 3H), 3.30-3.26 (m, 1H), 3.21 (dd, J=13.2, 7.7 Hz, 1H) 1.33 (t, J=7.2 Hz, 3H).

164E. Example 164 was prepared by saponification of 164D according to the procedure described in 62B. LCMS m/z 645.2 (M+H)+. $^1$HNMR (500 MHz, DMSO-$d_6$) δ: 12.51 (s, 1H), 9.72 (s, 1H), 8.67 (d, J=8.2 Hz, 1H), 8.52 (s, 1H), 8.04 (s, 1H), 7.73 (d, J=2.2 Hz, 1H), 7.55 (dd, J=8.2, 2.2 Hz, 1H), 7.51-7.49 (m, 3H), 7.45 (d, J=8.8 Hz, 2H), 7.19-7.16 (m, 2H), 7.13-7.08 (m, 3H), 7.00 (d, J=15.4 Hz, 1H), 6.71 (d, J=15.4 Hz, 1H), 5.15-5.10 (m, 1H), 3.60 (s, 3H), 3.14 (dd, J=13.8, 6.9 Hz, 1H), 2.98 (dd, J=13.8, 8.2 Hz, 1H).

Example 165

2-Amino-5-(5-chloro-2-{(S)-1-[(E)-3-(5-chloro-2-tetrazol-1-yl-phenyl)-acryloylamino]-2-phenyl-ethyl}-1H-imidazol-4-yl)-benzoic acid methyl ester, bis-trifluoroacetic acid salt 165A. 2-Amino-5-(5,5-dimethyl-1,3,2-dioxaborinan-2-yl)-benzoic acid methyl ester: To a flame-dried, round-bottom flask equipped with a condenser was added 2-Amino-5-bromo-benzoic acid methyl ester (0.7 g, 3.0 mmol), Pd(dppf) Cl$_2$.CH$_2$Cl$_2$ complex (0.106 g, 0.130 mmol), KOAc (1.28 g, 13.0 mmol), and bis(neopentyl glycolato)diboron (1.08 g, 4.78 mmol). Next degassed DMSO (29 mL) was added and the reaction was stirred at 80° C. After 5 h, the reaction was cooled to rt, diluted with EtOAc (100 mL), washed with water, brine, dried over $Na_2SO_4$, filtered and concentrated. Column chromatography on silica gel (gradient elution 0-20% EtOAc/Hexane) gave 165A (0.858 g, 75%) as a white solid. $^1$HNMR (400 MHz, CDCl$_3$) δ: 1.01 (s, 6H), 3.74 (s, 4H), 3.86 (s, 3H), 5.91 (bs, 2H), 6.63 (d, J=8.3 Hz, 1H), 7.66-7.68 (m, 1H), 8.33 (s, 1H). MS 196.1 (M-C$_5$H$_8$+H)+.

165B. 2-Amino-5-[2-((S)-1-amino-2-phenyl-ethyl)-5-chloro-1H-imidazol-4-yl]-benzoic acid methyl ester, tris-trifluoroacetic acid salt: A suspension of 141D (0.300 g, 0.749 mmol), 165A (0.394 g, 1.497 mmol), potassium carbonate (0.414 g, 2.99 mmol), and bis(tri-tert-butylphosphine)palladium(0) (0.019 g, 0.037 mmol) in DME (3.99 mL) and water (0.998 mL) was heated in a microwave reactor at 140° C. for 15 min to give a brown biphasic mixture. The reaction was partitioned between EtOAc and water and the layers were separated. The organic layer was washed with brine, dried over $Na_2SO_4$, filtered, and concentrated to give a brown oil. Flash chromatography gave a pale orange foam (0.116 g) which was dissolved in 30% TFA/CH$_2$Cl$_2$ (5 mL) to give a clear, orange brown solution. After 30 min, the reaction was concentrated to give a brown oil which was purified by reverse phase HPLC, followed by lyophilization from acetonitrile/water to give 165B (0.119 g, 22%) as an off-white lyophilate. LCMS m/z 371.1 (M+H)+. $^1$HNMR (500 MHz, CD$_3$OD) δ: 8.04 (d, J=2.2 Hz, 1H), 7.52 (dd, J=8.8, 2.2 Hz, 1H), 7.32-7.25 (m, 3H), 7.13 (d, J=7.7 Hz, 2H), 6.81 (d, J=8.8 Hz, 1H), 4.52 (dd, J=9.0, 6.3 Hz, 1H), 3.86 (s, 3H), 3.36 (dd, J=13.2, 8.8 Hz, 1H), 3.30-3.26 (m, 1H).

165C. Example 165 was prepared by coupling 165B with 62B according to the procedure described in 62C. LCMS m/z 603.2 (M+H)+. $^1$HNMR (500 MHz, CD$_3$OD) δ: 9.50 (s, 1H), 8.04 (d, J=2.2 Hz, 1H), 7.96 (s, 1H), 7.65 (dd, J=8.2, 2.2 Hz, 1H), 7.56 (d, J=8.8 Hz, 1H), 7.50 (dd, J=8.8, 2.2 Hz, 1H), 7.28-7.25 (m, 2H), 7.22-7.19 (m, 1H), 7.16 (d, J=7.2 Hz, 2H), 7.09 (d, J=15.4 Hz, 1H), 6.82 (d, J=8.8 Hz, 1H), 6.71 (d, J=15.4 Hz, 1H), 5.23 (t, J=7.7 Hz, 1H), 3.87 (s, 3H), 3.28-3.25 (m, 2H).

Example 166

2-Amino-5-(5-chloro-2-{(S)-1-[(E)-3-(5-chloro-2-tetrazol-1-yl-phenyl)-acryloylamino]-2-phenyl-ethyl}1H-imidazol-4-yl)-benzoic acid, bis-trifluoroacetic acid salt 166A. 2-Amino-5-[2-((S)-1-amino-2-phenyl-ethyl)-5-chloro-1H-imidazol-4-yl]-benzoic acid, tri-hydrochloric acid salt: To a clear, yellow solution of 165B (0.089 g, 0.125 mmol) in MeOH (1.248 mL) was added 1.0 N NaOH (0.749 mmol). The solution was stirred at rt for 1 h and then at 50° C. for 5 h. The reaction was cooled to rt and stirred overnight. The reaction was concentrated, redissolved in water, acidified with 1.0 N HCl, and extracted with EtOAc. The combined organic layers were washed with brine, dried over $Na_2SO_4$, filtered and concentrated to give 166A in quantitative yield as an orange/brown solid. LC/MS m/z 357.1 $(M+H)^+$.

166B. Example 166 was prepared by coupling 166A with 62B according to the procedure described in 62C. LC/MS m/z 589.2 $(M+H)^+$. $^1$HNMR (400 MHz, $CD_3OD$) δ: 9.50 (s, 1H), 8.09 (d, J=2.2 Hz, 1H), 7.96 (d, J=2.2 Hz, 1H), 7.65 (dd, J=8.4, 2.2 Hz, 1H), 7.56 (d, J=8.4 Hz, 1H), 7.49 (dd, J=8.6, 2.4 Hz, 1H), 7.29-7.25 (m, 2H), 7.22-7.16 (m, 3H), 7.09 (d, J=15.8 Hz, 1H), 6.81 (d, J=8.8 Hz, 1H), 6.71 (d, J=15.4 Hz, 1H), 5.24 (t, J=7.7 Hz, 1H), 3.30-3.26 (m, 2H).

Example 167

(E)-N-{(S)-1-[4-(3-Amino-1H-indazol-6-yl)-5-chloro-1H-imidazol-2-yl]-2-phenyl-ethyl}-3-(5-chloro-3-fluoro-2-tetrazol-1-yl-phenyl)-acrylamide, trifluoro acetic acid salt 167A. 1-(4-Chloro-2-fluoro-6-iodo-phenyl)-1H-tetrazole: To a cold suspension (0-5° C.) of 4-chloro-2-fluoro-6-iodoaniline (1.50 g, 5.53 mmol) and sodium azide (1.114 g, 17.13 mmol) in trimethyl orthoformate (1.832 mL, 16.58 mmol) was added acetic acid (21.01 mL). The suspension was stirred vigorously at 0-5° C. for 30 min and then warmed to rt. A clear, light brown solution formed. After 7 days, water (100 mL) was added to give a suspension. After 1 h of stirring the solid was collected and rinsed with water, air-dried, then dried under vacuum to give an off-white solid. Trituration from $CH_2Cl_2$ gave 167A (0.380 g, 21%) as a white solid. LC/MS m/z 325.0 $(M+H)^+$. $^1$HNMR (400 MHz, $CDCl_3$) δ: 8.81 (s, 1H), 7.86 (t, J=1.8 Hz, 1H), 7.40 (dd, J=8.8, 2.2 Hz, 1H). $^{19}$F NMR (376 MHz, $CDCl_3$) δ: −112.52.

167B. (E)-3-(5-Chloro-3-fluoro-2-tetrazol-1-yl-phenyl)-acrylic acid: 167B was prepared from 167A according to the Heck coupling and saponification procedures described in 62B. LCMS m/z 269 $(M+H)^+$.

167C. Example 167 was prepared by coupling 167B with the free base of 110A according to the procedure described in 62C. LCMS m/z 603.2 $(M+H)^+$. $^1$HNMR (400 MHz, $CD_3OD$) δ: 9.55 (s, 1H), 7.94 (d, J=8.4 Hz, 1H), 7.83 (s, 1H), 7.68-7.64 (m, 2H), 7.49 (dd, J=8.8, 1.3 Hz, 1H), 7.26-7.22 (m, 2H), 7.19-7.16 (m, 3H), 6.93 (d, J=15.8 Hz, 1H), 6.75 (d, J=15.8 Hz, 1H), 5.23 (t, J=7.7 Hz, 1H), 3.30-3.22 (m, 2H). $^{19}$F NMR (376 MHz, $CD_3OD$) δ: −120.62, −77.19.

Example 168

(S)-1-(1-(4-(3-amino-1H-indazol-6-yl)-5-chloro-1H-imidazol-2-yl)-2-phenylethyl)-3-(5-methyl-2-(1H-tetrazol-1-yl)benzyl)urea 168A. 5-methyl-2-(1H-tetrazol-1-yl)benzoic acid: A solution of 2-amino-5-methylbenzoic acid (2.5 g, 16.54 mmol), trimethyl orthoformate (5.48 mL, 49.6 mmol), and sodium azide (3.23 g, 49.6 mmol) in acetic acid (56 mL) was stirred at rt for 2 h, then filtered. The white solid was washed with acetic acid and air-dried to give 168A (2.73 g, 81%) as a white solid. LC/MS m/z 205.2 $(M+H)^+$. $^1$HNMR (400 MHz, $CD_3OD$) δ: 2.52 (s, 3H), 7.46 (d, J=8.2 Hz, 1H), 7.61 (dd, J=1.6 Hz, 8.2 Hz, 1H), 7.98 (d, J=1.6 Hz, 1H), 9.42 (s, 1H).

168B. (5-methyl-2-(1H-tetrazol-1-yl)phenyl)methanol: Borane in THF (1 M, 20 mL) was syringed into a THF (50 mL) solution of 168A (2.73 g, 13.37 mmol). The reaction mixture was allowed to stir at rt for 3 days. The cloudy reaction mixture was cooled to 0° C., quenched with 1 N HCl (50 mL) and stirred at rt for 1 h. Water (100 mL) was added and the mixture was extracted with EtOAc. The combined organic layers were filtered, and the filtrate was washed with 1N NaOH solution and brine, dried ($Na_2SO_4$), filtered, and evaporated to give 168B as a white solid (1.35 g, 53%). LC/MS m/z 191.1 $(M+H)^+$. $^1$HNMR ($CDCl_3$, 400 MHz) δ 2.47 (s, 3H), 2.85 (bs, 1H), 4.48 (s, 2H), 7.31-7.36 (m, 2H), 7.47 (s, 1H), 9.05 (s, 1H).

168C. 1-(2-(azidomethyl)-4-methylphenyl)-1H-tetrazole: $PBr_3$ (0.870 mL, 9.23 mmol) was added to a solution of 168B (1.35 g, 7.10 mmol) in DCM (47 mL). The resulting cloudy mixture was stirred for 10 min, then quenched with water (50 mL) and stirred at rt for 1 h. The aqueous layer was extracted with DCM, and the combined organic layers were dried ($MgSO_4$), filtered, and concentrated to a white solid. To this intermediate dissolved in DMF (47 mL) was added sodium azide (4.61 g, 71.0 mmol) and the reaction mixture was stirred at rt for 16 h. The reaction was quenched with water (200 mL) and a white solid precipitated out of solution. The aqueous phase was extracted with EtOAc, and the combined organic layers were washed with brine, dried over $Na_2SO_4$, filtered, and concentrated. The crude oil was dissolved in DMF (5 mL). Addition of water (50 mL) gave a white precipitate that was collected by filtration, washed with water, and dried to give 168C (1.2 g, 79%) as a white solid. LC/MS m/z 216.2 $(M+H)^+$. $^1$HNMR ($CDCl_3$, 400 MHz) δ 2.50 (s, 3H), 4.26 (s, 2H), 7.30-7.40 (m, 3H), 7.47 (s, 1H), 8.89 (s, 1H).

168D. (5-methyl-2-(1H-tetrazol-1-yl)phenyl)methanamine: To a solution of 168C (1.2 g, 5.58 mmol) in ethanol (28 mL) was added 5% palladium on carbon. The reaction mixture was stirred at rt under an $H_2$ balloon for 1 h, then filtered. The solid was washed with MeOH and the combined filtrates were concentrated. The resulting oil was dissolved in 1N HCl (25 mL) and washed with EtOAc. The aqueous layer was made basic with NaOH (1.5 g) and extracted with EtOAc. The combined organic layers were washed with brine, dried over $MgSO_4$, filtered and concentrated. The crude product was purified by reverse phase HPLC to give a white solid that was dissolved in EtOAc and washed with 1N NaOH. The aqueous layer was extracted with EtOAc, and the combined organic layers were dried over $MgSO_4$, filtered, and concentrated to give 168D (0.300 g, 28%) as a white solid. LC/MS 190.2 (M+H)⁺. ¹HNMR (CDCl₃, 400 MHz) δ 1.28 (bs, 2H), 2.46 (s, 3H), 3.65 (s, 2H), 7.25-7.31 (m, 2H), 7.40 (s, 1H), 9.20 (s, 1H).

168E. Example 168 was prepared from 168D and 110A by a similar procedure to Example 16. The crude product was purified by reverse phase HPLC to give a TFA salt that was dissolved in MeOH and basified with NH₄OH, concentrated, filtered, washed with water, and dried to give Example 168 (0.03 g, 25%) as an off-white solid. LC/MS m/z 568.3 (M+H)⁺. ¹HNMR (400 MHz, CD₃OD) δ: 2.39 (s, 3H), 3.09-3.20 (m, 2H), 4.04-4.13 (m, 2H), 5.00-5.04 (m, 1H), 7.13-7.34 (m, 9H), 7.53 (s, 1H), 7.70 (d, J=8.2 Hz, 1H), 9.40 (s, 1H).

Example 169

(S,E)-benzyl 3-(3-(5-chloro-2-(1H-tetrazol-1-yl)phenyl)acrylamido)-3-(5-chloro-4-(4-(methoxycarbonylamino)phenyl)-1H-imidazol-2-yl)propanoate 169A. (S)-4-benzyl 1-(2-(4-(methoxycarbonylamino)phenyl)-2-oxoethyl) 2-(tert-butoxycarbonylamino)succinate: A mixture of Boc-Asp(OBn)—OH (10 g, 30.9 mmol), 82D (8.42 g, 30.9 mmol), and cesium carbonate (5.04 g, 15.46 mmol) in DMF (60 mL) was stirred at rt overnight. The reaction mixture was diluted with EtOAc and washed with 10% LiCl solution. The combined organic layers were dried over MgSO₄ and purified by flash chromatography to give the desired product (13.4 g, 84%). LC/MS m/z 515.3 (M+H)⁺.

169B. (S)-benzyl 3-(tert-butoxycarbonylamino)-3-(4-(4-(methoxycarbonyl amino) phenyl)-1H-imidazol-2-yl)propanoate: A mixture of 169A (13.4 g, 26.0 mmol) and ammonium acetate (20.07 g, 260 mmol) in xylene (60 mL) was heated at reflux for 2 h. The reaction mixture was diluted with EtOAc and washed with brine. The combined organic layers were dried over MgSO₄ and purified by flash chromatography to give 169B (7.8 g, 61%). LC/MS m/z 495.4 (M+H)⁺.

169C. (S)-benzyl 3-(tert-butoxycarbonylamino)-3-(5-chloro-4-(4-(methoxy carbonyl amino)phenyl)-1H-imidazol-2-yl)propanoate: A mixture of 169B (7.64 g, 15.45 mmol) and NCS (2.063 g, 15.45 mmol) in acetonitrile (300 mL) was stirred at 80° C. under argon for 4 h. The reaction mixture was concentrated and purified by flash chromatography to give 169C (6.8 g, 83%). LC/MS m/z 529.2 (M+H)⁺.

169D. (S)-benzyl 3-amino-3-(5-chloro-4-(4-(methoxycarbonylamino) phenyl)-1H-imidazol-2-yl)propanoate: A solution of 50% TFA in DCM (total volume 25 mL) was added to 169C (3.0 g, 5.67 mmol) and the resulting solution was stirred at rt for 30 min. The mixture was concentrated to give 169D (2.4 g, 99%). LC/MS m/z 429.3 (M+H)⁺.

169E. Example 169: To a solution of 62B (1.286 g, 5.13 mmol) in DMF (50 mL) were added EDC (1.967 g, 10.26 mmol), HOBT (1.571 g, 10.26 mmol) and DIEA (3.58 mL, 20.52 mmol) and the mixture was stirred at rt for 15 min. To this solution was added 169D (2.2 g, 5.13 mmol) and the reaction was stirred at rt under argon overnight. The reaction mixture was diluted with EtOAc, washed with 10% LiCl solution, and dried over MgSO₄ to give the crude product. The crude product was purified by flash chromatography to give Example 169 (3.1 g, 91%). LC/MS m/z 661.3 (M+H)⁺. ¹HNMR (500 MHz, CD₃OD) δ ppm 9.41 (s, 1H) 7.84 (s, 1H) 7.53-7.59 (m, 1H) 7.45-7.52 (m, 3H) 7.39-7.44 (m, 2H) 7.11-7.19 (m, 5H) 7.03 (d, J=15.40 Hz, 1H) 6.56 (d, J=15.40 Hz, 1H) 5.37-5.43 (m, 1H) 4.97-5.06 (m, 2H) 3.65 (s, 3H) 3.20 (m, 3H) 3.03-3.10 (m, 1H) 2.87-2.99 (m, 1H).

Example 170

(S,E)-3-(3-(5-chloro-2-(1H-tetrazol-1-yl)phenyl)acrylamido)-3-(5-chloro-4-(4-(methoxycarbonylamino)phenyl)-1H-imidazol-2-yl)propanoic acid To a solution of Example 169 (1.8 g, 2.72 mmol) in THF (12 mL) and water (10 mL) was added lithium hydroxide (0.130 g, 5.44 mmol) and the mixture was stirred at rt overnight. The reaction mixture was concentrated, diluted with brine, acidified with 2 N HCl and extracted with EtOAc. The crude product was purified by flash chromatography to give Example 170 (450 mg, 29%). LC/MS m/z 571.0 (M+H)⁺. ¹HNMR (500 MHz, CD₃OD) δ ppm 9.40 (s, 1H) 7.85 (d, J=2.20 Hz, 1H) 7.36-7.60 (m, 6H) 7.03 (d, J=15.40 Hz, 1H) 6.60 (d, J=15.40 Hz, 1H) 5.35 (t, J=7.15 Hz, 1H) 3.64 (s, 3H) 3.32 (m, 4H) 2.93-3.01 (m, 1H) 2.84-2.90 (m, 1H).

Example 171

(S)-benzyl 3-(3-(5-chloro-2-(1H-tetrazol-1-yl)phenyl)propanamido)-3-(5-chloro-4-(4-(methoxycarbonylamino)phenyl)-1H-imidazol-2-yl)propanoate To a solution of 63A (500 mg, 1.979 mmol) in DMF (20 mL) were added EDC (759 mg, 3.96 mmol), HOBT (606 mg, 3.96 mmol) and DIEA (1.383 mL, 7.92 mmol). The reaction mixture was stirred at rt for 15 min under argon. To this mixture was added 169D (849 mg, 1.979 mmol) and the reaction was stirred at rt under argon overnight. The mixture was diluted with EtOAc and washed with 10% LiCl. The combined organic layers were dried over MgSO₄ and concentrated to give a crude product that was purified by flash chromatography to yield Example 171 (280 mg, 22%). LC/MS m/z 663.3 (M+H)⁺. ¹HNMR (500 MHz, CD₃OD) δ ppm 9.40 (s, 1H) 7.39-7.53 (m, 5H) 7.25-7.36 (m, 2H) 7.09-7.23 (m, 5H) 5.27 (t, J=7.15 Hz, 1H) 4.94-5.04 (m, 2H) 3.66 (s, 3H) 3.21 (m, 3H) 2.92-2.99 (m, 1H) 2.82 (dd, J=16.50, 7.15 Hz, 1H) 2.62 (t, J=7.42 Hz, 2H) 2.29-2.42 (m, 2H).

Example 172

(S)-3-(3-(5-chloro-2-(1H-tetrazol-1-yl)phenyl)propanamido)-3-(5-chloro-4-(4-(methoxycarbonylamino)phenyl)-1H-imidazol-2-yl)propanoic acid Example 172 was prepared from Example 171 by a similar procedure to Example 170. LC/MS m/z 573.3 (M+H)⁺. ¹HNMR (500 MHz, CD₃OD) δ ppm 9.40 (s, 1H) 7.49-7.54 (m, 3H) 7.47 (d, J=2.20 Hz, 1H) 7.42 (d, J=8.80 Hz, 2H) 7.31-7.35 (m, 1H) 7.27-7.30 (m, 1H) 5.21 (t, J=7.15 Hz, 1H) 3.66 (s, 3H) 3.22 (m, 3H) 2.83-2.93 (m, 1H) 2.69-2.80 (m, 1H) 2.65 (t, J=7.42 Hz, 2H) 2.39 (t, J=7.42 Hz, 2H).

Example 173

(S)-methyl 4-(5-chloro-2-(1-(3-(5-chloro-2-(1H-tetrazol-1-yl)phenyl)propanamido)-3-((5-methylpyrazin-2-yl)methylamino)-3-oxopropyl)-1H-imidazol-4-yl)phenyl carbamate To a solution of Example 172 (100 mg, 0.174 mmol) in DMF (5 mL) were added EDC (66.9 mg, 0.349 mmol), HOBT (53.4 mg, 0.349 mmol) and DIEA (0.122 mL, 0.698 mmol) and the reaction was stirred at rt under argon for 15 min. To this mixture was added (5-methylpyrazin-2-yl) methanamine (21.48 mg, 0.174 mmol) and the reaction was stirred under argon overnight. The reaction mixture was diluted with EtOAc and washed with 10% LiCl. The combined organic layers were dried over $MgSO_4$ and concentrated. The resulting residue was purified by flash chromatography to give Example 173 (15 mg, 13%). LC/MS m/z 678.6 $(M+H)^+$. $^1$HNMR (500 MHz, DMSO-$d_6$) δ ppm 9.79 (s, 1H) 9.76 (s, 1H) 8.55 (t, J=5.77 Hz, 1H) 8.29-8.39 (m, 3H) 7.62 (d, J=2.20 Hz, 1H) 7.49-7.59 (m, 7H) 5.24-5.32 (m, 1H) 4.29 (dd, J=11.00, 5.50 Hz, 2H) 3.66 (s, 3H) 2.82 (dd, J=14.85, 8.25 Hz, 1H) 2.53-2.62 (m, 3H) 2.40 (s, 3H) 2.34 (t, J=7.70 Hz, 2H).

Example 174

(S)-methyl 4-(5-chloro-2-(1-(3-(5-chloro-2-(1H-tetrazol-1-yl)phenyl)propanamido)-3-morpholino-3-oxopropyl)-1H-imidazol-4-yl)phenyl carbamate, trifluoroacetic acid salt To a solution of Example 172 (50 mg) in DMF (5 mL) were added pyBOP (46 mg) and DIEA (0.061 mL) and the reaction was stirred at rt under argon overnight. The reaction mixture was diluted with EtOAc and washed with 10% LiCl. The crude product was purified by reverse phase HPLC to give Example 174. LC/MS m/z 642.3 $(M+H)^+$. $^1$HNMR (500 MHz, $CD_3OD$) δ ppm 9.43 (s, 1H) 7.43-7.55 (m, 5H) 7.28-7.39 (m, 2H) 5.29 (t, 1H) 3.67 (s, 3H) 3.59 (t, J=4.67 Hz, 2H) 3.52 (q, J=4.95 Hz, 2H) 3.38-3.47 (m, 4H) 3.22 (m, 3H) 2.96-3.05 (m, 1H) 2.82-2.92 (m, 1H) 2.66 (t, J=7.42 Hz, 2H) 2.41 (t, J=7.15 Hz, 2H).

Example 175

(S,E)-methyl 4-(5-chloro-2-(1-(3-(5-chloro-2-(1H-tetrazol-1-yl)phenyl)acrylamido)-3-morpholino-3-oxopropyl)-1H-imidazol-4-yl)phenylcarbamate, trifluoroacetic acid salt Example 175 was prepared from Example 170 by a similar procedure to Example 174. LC/MS m/z 640.4 $(M+H)^+$. $^1$HNMR (500 MHz, $CD_3OD$) δ ppm 9.41 (s, 1H) 7.85 (d, J=2.20 Hz, 1H) 7.37-7.60 (m, 6H) 7.04 (d, J=15.95 Hz, 1H) 6.60 (d, J=15.40 Hz, 1H) 5.41 (t, J=6.87 Hz, 1H) 3.64 (s, 3H) 3.57 (m, 2H) 3.48-3.54 (m, 2H) 3.46 (m, 2H) 3.40-3.44 (m, 2H) 3.32 (m, 3H) 3.06-3.14 (dd, J=16.50, 7.70 Hz, 1H) 2.95 (dd, J=16.22, 6.32 Hz, 1H).

Example 176

(S,E)-methyl 4-(5-chloro-2-(1-(3-(5-chloro-2-(1H tetrazol-1-yl)phenyl)acrylamido)-3-((5-methylpyrazin-2-yl)methylamino)-3-oxopropyl)-1H-imidazol-4-yl)phenyl carbamate, trifluoroacetic acid salt Example 176 was prepared from Example 170 by a similar procedure to Example 173. LC/MS m/z 676.3 $(M+H)^+$. $^1$HNMR (500 MHz, DMSO-$d_6$) δ ppm 12.61 (s, 1H) 9.86 (s, 1H) 9.77 (s, 1H) 8.58-8.72 (m, 2H) 8.35 (d, J=19.25 Hz, 2H) 7.94 (d, J=2.20 Hz, 1H) 7.69-7.79 (m, 2H) 7.56-7.63 (m, 2H) 7.51 (d, J=8.80 Hz, 2H) 6.85-6.93 (m, 1H) 6.76-6.82 (m, 1H) 5.39 (d, J=7.15 Hz, 1H) 4.31 (dd, J=5.50, 2.75 Hz, 2H) 3.66 (s, 3H) 2.86-2.94 (m, 1H) 2.71 (dd, J=15.12, 6.32 Hz, 1H) 2.39 (s, 3H).

Example 177

(S,E)-3-(5-chloro-2-(1H-tetrazol-1-yl)phenyl)-N-(1-(5-chloro-4-(4-cyanophenyl)-1H-imidazol-2-yl)-3-((5-methylpyrazin-2-yl)methylamino)-3-oxopropyl) acrylamide 177A: (S)-3-tert-Butoxycarbonylamino-3-[5-(4-cyanophenyl)-1H-imidazol-2-yl]-propionic acid benzyl ester: A mixture of Boc-Asp(OBn)—OH (5 g, 0.015 mol) and cesium carbonate (5 g, 0.015 mol) in dry DMF (25 mL) was stirred for 30 min. The reaction was cooled to 0° C. and 2-bromo-4'-cyanoacetophenone (3.5 g, 0.015 mol) in dry DMF (12.5 mL) was added dropwise and stirred for 30 minutes at 0° C. and at rt for 2 h. The reaction was quenched with water, extracted with ethyl acetate, washed with brine, dried over anhydrous $Na_2SO_4$ and concentrated. The crude material was purified by flash chromatography to provide the ketoester intermediate. (5.5 g, 76%) $^1$HNMR ($CDCl_3$, 400 MHz) δ 7.9 (d, 2H), 7.8 (d, 2H), 7.3 (m, 5H), 5.6 (d, 1H), 5.3 (dd, 2H), 5.2 (s, 2H), 4.8 (d, 1H), 3.1 (d, 1H), 3.0 (d, 1H), 1.45 (s, 9H). LCMS m/z 466 $(M+H)^+$. A mixture of the ketoester (5.5 g, 0.012 mol) and $NH_4OAc$ (18.2 g, 0.23 mol) in xylene (160 mL) was refluxed at 170° C. using a Dean Stark apparatus for 4 h. The reaction was concentrated, and the residue was taken up in ethyl acetate, washed with water, brine, dried over anhydrous $Na_2SO_4$ and concentrated to provide the crude imidazole product (3.9 g, 75%). $^1$HNMR ($CDCl_3$, 400 MHz) δ 7.7 (d, 2H), 7.6 (d, 2H), 7.3 (m, 5H), 6.0 (d, 1H), 5.2 (m, 3H), 3.2 (d, 1H), 3.0 (d, 1H), 1.45 (s, 9H). LCMS m/z 446 $(M+H)^+$.

177B: (S)-3-tert-Butoxycarbonylamino-3-[5-chloro-4-(4-cyano-phenyl)-1H-imidazol-2-yl]-propionic acid benzyl ester: To a solution of 177A (2.8 g, 6.2 mmol) in dry acetonitrile (70 mL), N-chlorosuccinimide (0.85 g, 6.3 mmol) was added and the mixture was refluxed at 95° C. overnight. The solvent was evaporated, and the residue was taken in ethyl acetate, washed with water, brine, dried over anhydrous $Na_2SO_4$ and concentrated. Purification by flash chromatography provided 177B. (2 g, 66%). $^1$HNMR ($CDCl_3$, 400 MHz) δ 11.0 (bs, 1H), 7.7 (d, 2H), 7.6 (d, 2H), 7.3 (m, 5H), 5.2 (m, 3H), 3.2 (d, 1H), 3.0 (d, 1H), 1.45 (s, 9H). LCMS m/z 480 $(M+H)^+$.

177C: (S)-3-tert-Butoxycarbonylamino-3-[5-(4-cyanophenyl)-1H-imidazol-2-yl]-propionic acid: To a solution of 177B (2 g, 4.15 mmol) in THF (20 mL), a solution of LiOH (0.4 g, 0.016 mol) in water (20 mL) was added, and the mixture was stirred for 4 h. THF was evaporated and the aq.layer was washed with ethyl acetate. The aq.layer was then acidified with citric acid and extracted with ethyl acetate and concentrated. The solid obtained was crystallized using hexane to provide the acid.(1.2 g, 75%). $^1$HNMR ($CD_3OD$, 400 MHz) δ 7.9 (d, 2H), 7.8 (d, 2H), 5.1 (m, 1H), 2.9 (dd, 2H), 1.45 (s, 9H). LCMS m/z 390 $(M+H)^+$.

177D. (S)-tert-butyl 1-(5-chloro-4-(4-cyanophenyl)-1H-imidazol-2-yl)-3-((5-methylpyrazin-2-yl)methylamino)-3-oxopropylcarbamate: 177D was prepared from 177C by a similar procedure to Example 173. LC/MS m/z 496.3 $(M+H)^+$.

177E. (S)-3-amino-3-(5-chloro-4-(4-cyanophenyl)-1H-imidazol-2-yl)-N-((5-methylpyrazin-2-yl)methyl)propanamide: 177E was prepared from 177D by a similar procedure to 169D. LC/MS m/z 396.0 $(M+H)^+$.

177F. Example 177 was prepared from 177E and 62B by a similar procedure to 169E and purified by flash chromatography. LC/MS m/z 628.0 (M+H)+. $^1$HNMR (500 MHz, CD$_3$OD) δ ppm 9.86 (s, 1H) 8.74 (d, J=7.70 Hz, 1H) 8.66 (t, J=5.77 Hz, 1H) 8.37 (s, 1H) 8.30 (s, 1H) 7.86-7.98 (m, 5H) 7.69-7.80 (m, 2H) 6.87-6.92 (m, 1H) 6.77-6.82 (m, 1H) 5.41 (d, J=7.15 Hz, 1H) 4.24-4.39 (m, 2H) 2.87-2.96 (m, 1H) 2.71-2.79 (m, 1H) 2.37 (s, 3H).

Examples 178, 179 and 180 in Table 1 were prepared from 62B and the indicated commercially available aldehydes by similar procedures to 82A-F and 82H.

Example 178

(S,E)-methyl 4-(5-chloro-2-(1-(3-(5-chloro-2-(1H-tetrazol-1-yl)phenyl)acrylamido)-2-(6-methoxypyridin-3-yl)ethyl)-1H-imidazol-4-yl)phenylcarbamate (6-methoxypyridine-3-carboxaldehyde). LC/MS m/z 634.3 (M+H)+. $^1$HNMR (500 MHz, CD$_3$OD) δ ppm 9.37 (s, 1H) 7.84-7.88 (m, 1H) 7.81 (d, J=2.20 Hz, 1H) 7.57 (dd, J=8.80, 2.20 Hz, 1H) 7.48-7.53 (m, 1H) 7.40-7.45 (m, 3H) 7.36-7.40 (m, 2H) 6.94 (d, J=15.40 Hz, 1H) 6.75-6.80 (m, 1H) 6.56 (d, J=15.40 Hz, 1H) 5.12 (t, J=7.42 Hz, 1H) 3.79 (s, 3H) 3.59-3.64 (m, 3H) 3.15-3.22 (m, 4H) 3.02-3.09 (m, 1H).

Example 179

(S,E)-tert-butyl 3-(2-(3-(5-chloro-2-(1H-tetrazol-1-yl)phenyl)acrylamido)-2-(5-chloro-4-(4-(methoxycarbonylamino)phenyl)-1H-imidazol-2-yl)ethyl)-1H-indole-1-carboxylate (N-Boc-indole-3-carboxaldehyde). LC/MS m/z 742.4 (M+H)+. $^1$HNMR (500 MHz, CD$_3$OD) δ ppm 9.39 (s, 1H) 7.96 (d, J=7.70 Hz, 1H) 7.86 (d, J=2.20 Hz, 1H) 7.54 (dd, J=8.52, 2.47 Hz, 1H) 7.40-7.47 (m, 2H) 7.37 (s, 4H) 7.22 (s, 1H) 7.16 (t, J=7.42 Hz, 1H) 7.08 (t, J=7.42 Hz, 1H) 7.01 (d, J=15.40 Hz, 1H) 6.63 (d, J=15.40 Hz, 1H) 5.20 (t, J=7.42 Hz, 1H) 3.63 (s, 3H) 3.24-3.29 (m, 2H) 3.20 (m, 3H) 1.45-1.51 (m, 9H).

Example 180

(S,E)-methyl 4-(5-chloro-2-(1-(3-(5-chloro-2-(1H-tetrazol-1-yl)phenyl)acrylamido)-2-(2-methoxypyridin-3-yl)ethyl)-1H-imidazol-4-yl)phenylcarbamate (2-methoxypyridine-3-carboxaldehyde). LC/MS m/z 634.0 (M+H)+. $^1$HNMR (500 MHz, DMSO-d$_6$) δ ppm 12.58 (s, 1H) 9.83 (s, 1H) 9.77 (s, 1H) 8.69 (d, J=8.80 Hz, 1H) 7.98 (dd, J=4.95, 2.20 Hz, 1H) 7.90 (d, J=2.20 Hz, 1H) 7.67-7.76 (m, 2H) 7.53-7.58 (m, 2H) 7.48-7.53 (m, 2H) 7.37 (d, J=7.15 Hz, 1H) 6.83 (dd, J=7.15, 2.20 Hz, 1H) 6.77 (m, 2H) 5.26-5.33 (m, 1H) 3.81-3.86 (m, 3 H) 3.63-3.69 (s, 3H) 3.14 (dd, J=14.02, 6.32 Hz, 1H) 2.96-3.03 (dd, J=14.02, 6.32 Hz, 1H).

Example 181

1-{(S)-1-[5-Chloro-4-(4-cyano-phenyl)-1H-imidazol-2-yl]-2-phenyl-ethyl}-3-(5-chloro-2-tetrazol-1-yl-benzyl)-urea, trifluoroacetic acid salt 181A. (S)-4-(2-(1-amino-2-phenylethyl)-5-chloro-1H-imidazol-4-yl)benzonitrile, bis TFA salt: This material was prepared from L-Boc-Phe-OH and 4-(2-Bromo-acetyl)-benzonitrile following the procedures described in 52A-B. LCMS m/z 323.3 (M+H)+.

181B. Example 181 was prepared from (5-chloro-2-(1H-tetrazol-1-yl)phenyl)methanamine (Young, M. B. et. al *J. Med. Chem.* 2004, 47, 2995) and the free base of 181A using the urea formation procedure described in Example 16. LC/MS m/z 558.2 (M+H)+. $^1$HNMR (CD$_3$OD) δ 9.37 (s, 1H), 7.72-7.66 (m, 4H), 7.46-7.34 (m, 3H), 7.16-7.03 (m, 6H), 4.94 (t, 1H), 4.05 (q(AB), 2H), 3.10 (m, 2H).

Example 182

4-(5-Chloro-2-{(S)-1-[3-(5-chloro-2-tetrazol-1-yl-phenyl)-propionylamino]-2-phenyl-ethyl}-1H-imidazol-4-yl)-benzamide, trifluoroacetic acid salt 182A. N-{(S)-1-[5-Chloro-4-(4-cyano-phenyl)-1H-imidazol-2-yl]-2-phenyl-ethyl}-3-(5-chloro-2-tetrazol-1-yl-phenyl)-propionamide: The intermediate nitrile was prepared from 63A and 181A by a similar procedure to that described for 63B.

182B. Example 182: 182A was dissolved in DMSO and excess potassium carbonate (5 g) was added followed by hydrogen peroxide (4 mL). The reaction mixture was stirred at rt overnight, then quenched with water and extracted with EtOAc. The combined organic layers were dried (MgSO$_4$), filtered, and evaporated to give a yellow oil that was purified by reverse phase HPLC to give Example 182 as a white solid. LC/MS m/z 575.2 (M+H)+. $^1$HNMR (CD$_3$OD) δ 9.45 (s, 1H), 7.94 (d, J=8.6 Hz, 2H), 7.78 (d, J=8.4 Hz, 2H), 7.53 (d, J=2.1 Hz, 1H), 7.46-7.38 (m, 2H), 7.24-7.12 (m, 4H), 5.18 (t, 1H), 3.22 (m, 1H), 3.11 (m, 1H), 2.21 (m, 2H), 2.48 (m, 2H).

Example 183

[4-(5-Chloro-2-{(S)-1-[3-(5-chloro-2-phenylcarbamoyl-phenyl)-propionylamino]-2-phenyl-ethyl}-1H-imidazol-4-yl)-phenyl]-carbamic acid methyl ester, trifluoroacetic acid salt 183A. 3-(5-Chloro-2-phenylcarbamoyl-phenyl)-propionic acid: A mixture of palladium acetate (0.022 g, 0.1 mmol), 2-iodo-4-chlorobenzamide (0.954 g, 2.67 mmol), 3,3-diethoxyprop-1-ene (0.693 g, 5.32 mmol), tetrabutylammonium bromide (0.86 g, 2.67 mmol), and tributylamine (0.984 g, 5.32 mmol) in DMF (25 mL) was heated at 80° C. overnight. The reaction was quenched with 1N HCl (50 mL) and stirred at rt for 1 h. The mixture was extracted with EtOAc and the combined organic layers were washed with 1N HCl, dried (MgSO$_4$), filtered, and evaporated to give an oil. This residue was purified by flash chromatography to give 3-(5-chloro-2-phenylcarbamoyl-phenyl)-propionic acid ethyl ester (0.287 g, 32%). LC/MS m/z 332.3 (M+H)+. This intermediate (0.278 g, 0.865 mmol) was stirred with LiOH (21 mg, 0.865 mmol) in THF (10 mL) and water (0.5 mL) for 2 d. The mixture was diluted with water and washed with EtOAc. The aqueous layer was acidified with 1N HCl and extracted with EtOAc. The combined organic layers were dried (MgSO$_4$), filtered, evaporated, and purified by reverse phase HPLC to give 183A. LC/MS m/z 304.3 (M+H)+. $^1$HNMR (CDCl$_3$) δ 7.68 (d, J=8.0 Hz, 2H), 7.48 (d, J=8.2 Hz, 1H), 7.41-7.25 (m, H), 7.15 (t, 1H), 4.00 (bs, 1H), 3.11 (t, 2H), 2.80 (tm, 2H).

183B. Example 183: 183A was coupled to 52B by a similar procedure to that described for 1F to give Example 183. LC/MS m/z 656.3 (M+H)+. $^1$HNMR (CDCl$_3$) δ 9.52 (bs, 1H), 7.65 (d, J=7.9 Hz, 2H), 7.40 (d, J=8.6 Hz, 2H), 7.33-7.26 (m, 4H), 7.16-6.93 (m, 8H), 5.21 (q, 1H), 3.13 (m, 2H), 2.97 (m, 1H), 2.81 (m, 1H), 2.50 (m, 2H), 2.11 (bs, 3H).

Example 184

4-Chloro-2-((E)-2-{(S)-1-[5-chloro-4-(4-methoxy-carbonylamino-phenyl)-1H-imidazol -2-yl]-2-phenyl-ethylcarbamoyl}-vinyl)-benzoic acid methyl ester 184A. (E)-3-(5-chloro-2-(methoxycarbonyl)phenyl) acrylic acid: 184A was prepared from methyl-2-iodo-4-chloro-benzoate and tert-butylacrylate by a similar procedure to 183A followed by treatment with TFA in DCM. LC/MS m/z 241.1 (M+H)$^+$. $^1$HNMR (CDCl$_3$) δ 8.54 (d, J=15.9 Hz, 1H), 7.96 (d, J=8.4 Hz, 1H), 7.59 (d, J=2.1 Hz, 1H), 7.45 (dd, J=2.3 & 10.6 Hz, 1H), 7.33 (d, J=15.9 Hz, 1H), 3.94 (s, 3H), 2.75 (bs, 1H).

184B. Example 184: 184A was coupled to 52B by a similar procedure to that described for 1F. Example 184 was purified by flash chromatography. LC/MS m/z 593.2 (M+H)$^+$. $^1$HNMR (CDCl$_3$) δ 8.26 (d, J=15.6 Hz, 1H), 7.90 (d, J=8.4 Hz, 1H), 7.75 (bs, 1H), 7.57 (bm, 3H), 7.46 (bd, J=8.4 Hz, 2H), 7.39 (dd, J=2.1 & 8.4 Hz, 1H), 7.26-7.16 (m, 5H), 6.36 (d, J=15.4 Hz, 1H), 5.26 (t, 1H), 3.78 (s, 3H), 3.27 (m, 2H).

Example 185

4-Chloro-2-((E)-2-{(S)-1-[5-chloro-4-(4-methoxy-carbonylamino-phenyl)-1H-imidazol-2-yl]-2-phenyl-ethylcarbamoyl}-vinyl)-benzoic acid Example 185 was prepared by hydrolysis of Example 184 with LiOH/THF/methanol and water. LC/MS m/z 579.2 (M+H)$^+$. $^1$HNMR (CD$_3$OD) δ 8.35 (d, J=15.7 Hz, 1H), 7.99 (d, J=8.5 Hz, 1H), 7.70 (d, J=1.1 Hz, 1H), 7.56 (s, 3H), 7.51 (dd, J=2.1 & 8.4 Hz, 1H), 7.33-7.21 (m, 4H), 6.57 (d, J=15.7 Hz, 1H), 5.33 (t, 1H), 3.77 (s, 3H), 3.3 (m, 2H).

Example 186

[4-(5-Chloro-2-{(S)-1-[(E)-3-(5-chloro-2-[1,2,3] triazol-1-yl-phenyl)-acryloylamino]-2-phenyl-ethyl}-1H-imidazol-4-yl)-phenyl]-carbamic acid methyl ester, trifluoroacetic acid salt 186A and 186B. (E)-3-(5-chloro-2-[1,2,3]triazol-2-yl-phenyl)-acrylic acid: and (E)-3-(5-Chloro-2-[1,2,3]triazol-1-yl-phenyl)-acrylic acid and 1H-1,2,3-triazole (0.684 g, 9.84 mmol) was dissolved in DMF (20 mL). To this solution was added 5-chloro-2-fluorobenzaldehyde (1.56 g, 9.84 mmol) and excess potassium carbonate (4.26 g, 30.84 mmol). The reaction mixture was stirred at rt overnight, quenched with water (100 mL) and the organics were extracted with EtOAc (2×100 mL), washed with brine (50 mL) and dried (MgSO$_4$). The triazole addition products were obtained as a mixture of regioisomers which were inseparable. The crude mixture was treated with tert-butyl 2-(diethoxyphosphoryl)acetate (1.078 g, 4.27 mmol), and NaH (0.103 g, 4.07 mmol), and the reaction mixture was stirred at room temperature overnight. The reaction mixture was quenched with water and extracted with EtOAc (2×100 mL), dried (MgSO$_4$) and evaporated to a yellow oil. Redissolved in DCM (2 mL) and charged to a silica gel flash column which was eluted with 10% EtOAc in hexane followed by a gradient form 10-50% EtOAc in hexane. The faster eluting product is the 2-substituted triazole analog which was obtained as a colorless oil which gradually solidified (909 mg). $^1$HNMR (CDCl$_3$) δ: 7.91 (s, 2H), 7.82 (d, J=15.9 Hz, 1H), 7.74 (d, J=2.3 Hz, 1H), 7.70 (d, J=7.6 Hz, 1H), 7.49 (dd, J=2.3 & 8.6 Hz, 1H), 6.40 (d, J=15.9 Hz, 1H), 1.52 (s, 9H) ppm. Treatment of this ester with TFA afforded (E)-3-(5-chloro-2-[1,2,3]triazol-2-yl-phenyl)-acrylic acid 186A. $^1$HNMR (CDCl$_3$/MeOD) δ: 7.99 (d, J=15.9, 1H), 7.86 (s, 2H), 7.68 (m, 2H), 7.47 (d, J=2.3, 8.8 Hz, 1H), 6.37 (d, J=15.9 Hz, 1H) ppm. The slower eluting product from the flash column described above corresponded to the 1-substituted 1,2,3-triazole tert-butyl ester analog (60 mg solid). $^1$HNMR (CDCl$_3$) δ: 7.82 (d, J=0.9 Hz, 1H), 7.71 (d, J=1.0 Hz, 1H), 7.68 (d, J=2.2 Hz, 1H), 7.44 (dd, J=2.2 & 8.5 Hz, 1H), 7.38 (d, J=8.5 Hz, 1H), 7.16 (d, J=15.9 Hz, 1H), 6.31 (d, J=15.6 Hz, 1H), 1.41 (s, 9H) ppm. This compound was treated with TFA to afford the (E)-3-(5-Chloro-2-[1,2,3]triazol-1-yl-phenyl)-acrylic acid derivative 186B. $^1$HNMR (CDCl$_3$/CD$_3$OD) δ: 7.95 (d, J=13.3, 1H), 7.82 (d, J=2.0, 2H), 7.58 (dd, J=2.3 & 8.6 Hz, 1H), 7.48 (d, J=8.8 Hz, 1H), 7.31 (d, J=15.9 Hz, 1H), 6.45 (d, J=15.9 Hz, 1H) ppm.

186C. Example 186 was prepared via the coupling of 186B and 52B by a similar procedure to that described for 1F. LC/MS m/z 602.2 (M+H)$^+$. $^1$HNMR (CD$_3$OD) δ 8.15 (d, J=1.0 Hz, 1H), 7.839 (m, 2H), 7.53 (dd, J=2.3 & 8.5z, 1H), 7.43 (s, 5H), 7.19-7.06 (m, 4H), 7.049 (d, J=15.6 Hz, 1H), 6.61 (d, J=15.8 Hz, 1H), 5.13 (t, 1H), 3.62 (s, 3H), 3.20 (m, 2H).

Example 187

(E)-N-{(S)-1-[4-(3-Amino-1H-indazol-6-yl)-5-chloro-1H-imidazol-2-yl]-2-phenyl-ethyl}-3-(5-chloro-2-[1,2,3]triazol-1-yl-phenyl)-acrylamide, trifluoroacetic acid salt Example 187 was prepared from 186B and 110A using a coupling procedure similar to that described for 1F. LC/MS m/z 584.2 (M+H)$^+$. $^1$HNMR (CD$_3$OD) δ 8.25 (s, 1H), 7.96 (m, 3H), 7.69 (s, 1H), 7.62 (dd, J=2.4 & 8.4 Hz, 1H), 7.52-7.46 (m, 2H), 7.26-7.24 (m, 7.23-7.17 (3H0, 7.13 (d, J=15.7 Hz, 1H), 6.73 (d, J=15.7 Hz, 1H), 5.26 (t, 1H), 3.20 (m, 2H).

Example 188

(E)-N-{(S)-1-[4-(3-Amino-1H-indazol-6-yl)-5-chloro-1H-imidazol-2-yl]-2-phenyl-ethyl}-3-(5-chloro-2-[1,2,3]triazol-2-yl-phenyl)-acrylamide, trifluoroacetic acid salt Example 188 was prepared from 186A and 110A by am amide coupling procedure similar to that described for 1F. LC/MS m/z 584.2 (M+H)$^+$. $^1$HNMR (CD$_3$OD) δ 7.91-7.85 (m, 3H), 7.75 (d, J=2.3 Hz, 1H), 7.63-7.40 (m, 5H), 7.21-7.10 (m, 6H), 6.59 (d, J=15.7 hz, 1H), 5.19 (t, 1H), 3.20 (m, 2H).

Example 189

[4-(5-Chloro-2-{(S)-1-[3-(5-chloro-2-tetrazol-1-yl-phenyl)-propynoylamino]-2-phenyl-ethyl}-1H-imidazol-4-yl)-phenyl]-carbamic acid methyl ester, trifluoroacetic acid salt 189A. 3-(5-chloro-2-(1H-tetrazol-1-yl)phenyl)propiolic acid: In a 250 mL round bottom flask was added diisopropylamine (0.68 mL, 4.82 mmol) and THF (20 mL). The solution stirred under nitrogen and cooled to −78° C. To this solution was added nBuLi (2.5N, 1.98 mL, 0.482 mmol) via syringe, and the solution was stirred for 0.25 h. A solution of ethylpropiolate in THF (2 mL) was then added, and the reaction mixture was stirred at −78° C. for 2 h, followed by addition of a THF (10 mL) solution of ZnBr$_2$ (1N, 0.48 mmol). The reaction turned red. Separately, 1-(4-chloro-2-iodophenyl)-1H-tetrazole (1.17 g, 3.82 mmol) was dissolved in THF (10 mL) and cooled to −78° C. To this solution was cannulated the ethylpropiolate zincate generated above, followed by addition of 0.03 g of tetrakistriphenylphosphine palladium catalyst. The reaction mixture was stirred at this temperature and allowed to gradually warmed to rt, then stirred for 24 h. After a dilute HCl (1N, 100 mL) aqueous quench, the organics were extracted with EtOAc (2×100 mL), dried (MgSO$_4$) and evaporated to a reddish brown oil. Purification via silica-gel column chromatography afforded the product as the ethyl ester (150 mg, 11%). $^1$HNMR (CDCl$_3$) δ: 9.22 (s, 1H), 7.74 (d, J=2.3 hz, 1H), 7.70 (d, J=8.6 Hz, 1H), 7.61 (dd, J=2.3 & 8.6 Hz, 1H), 4.25 (q, 2H), 1.23 (t, 3H) ppm. LCMS m/z 277.3 (M+H)$^+$. Hydrolysis of the ester with LiOH/THF/MeOH/water afforded the desired acid 189A (97 mg). $^1$HNMR (CDCl$_3$ containing MeOD) δ: 9.41 (s, 1H), 7.81 (d, J=2.3 Hz, 1H), 7.77 (d, J=8.7 Hz, 1H), 7.68 (dd, J=2.3 &8.5 Hz, 1H) ppm. LCMS m/z 249.2 (M+H)$^+$.

189B. Example 189 was prepared by coupling 189A and 52B by a similar procedure to that described for 1F. LC/MS m/z 601.4 (M+H)$^+$. $^1$HNMR (CD$_3$OD) δ 9.72 (s, 1H), 7.92 (m, 1H), 7.77 (s, 2H), 7.57-7.48 (m, 4H), 7.29-7.12 (m, 5H), 5.23 (t, 1H), 3.75 (s, 3H), 3.20 (m, 2H).

Example 190

3-(5-Chloro-2-tetrazol-1-yl-phenyl)-propynoic acid {(S)-1-[4-(3-amino-1H-indazol-6-yl)-5-chloro-1H-imidazol-2-yl]-2-phenyl-ethyl}-amide, trifluoroacetic acid salt Example 190 was prepared from 189A and 110A by a similar procedure to that described for 1F. LC/MS m/z 583.2 (M+H)$^+$. $^1$HNMR (CD$_3$OD) δ 9.72 (s, 1H), 9.14 (s, 1H), 8.02 (m, 3H), 7.95-7.15 (m, 10H), 5.31 (t, 1H), 3.20 (m, 2H).

Example 191

3-(5-Chloro-2-tetrazol-1-yl-phenyl)-propynoic acid {(S)-1-[5-chloro-4-(4-cyano-phenyl)-1H-imidazol-2-yl]-2-phenyl-ethyl}-amide, trifluoroacetic acid salt Example 191 was prepared from 63A and 181A by a similar procedure to that described for 1F. LC/MS m/z 557.2 (M+H)$^+$. $^1$HNMR (CDCl$_3$) δ 8.84 (s, 1H), 7.70 (m, 3H), 7.38-7.31 (m, 2H), 7.30-7.19 (m, 5H), 7.11 (d, J=8.5 Hz, 1H), 6.34 (bd, 1H), 5.07 (q, 21H), 3.22 (m, 2H), 2.68 (t, 2H), 2.40 (t, 2H).

Example 192

(S)-methyl 4-(2-(1-(3-(2-amino-5-chlorobenzyl)ureido)-2-phenylethyl)-5-chloro-1H-imidazol-4-yl)phenylcarbamate, bis-trifluoroacetic acid salt 192A. tert-Butyl 2-(aminomethyl)-4-chlorophenylcarbamate: To a solution of Boc-2-amino-5-chlorobenzylalcohol (5.0 g, 19.40 mmol) and diphenylphosphoryl azide (4.18 mL, 19.40 mmol) in dry toluene (100 mL) at 0° C. was added DBU (3.22 mL, 21.34 mmol) and the reaction was stirred at rt for 14 h (*J. Med. Chem.* 2002, 45, 2388-2409). After concentrating, the resulting residue was dissolved in EtOAc, washed with sat'd NaHCO$_3$ and brine, dried over sodium sulfate, filtered, and concentrated. This azide intermediate was dissolved in MeOH (75 mL) and treated with stannous chloride (8.76 g, 38.8 mmol) under a nitrogen atmosphere. After stirring for 48 h, the excess MeOH was removed under reduced pressure an the residue diluted with cold water (75 mL). The mixture was then made basic with 1N NaOH solution and stirring was continued for 15 min. The mixture was diluted with water and extracted with EtOAc. The combined organic extracts were washed with brine, dried over sodium sulfate, filtered, and concentrated to give 192A (2.55 g, 51.2%) as an amber oil. LC/MS m/z 527 (M+H)$^+$. $^1$HNMR (400 MHz, DMSO-d6) δ 1.45 (s, 9H), 3.75 (s, 2H), 7.22 (dd, J=8.52, 2.47 Hz, 1H), 7.27 (d, J=2.75 Hz, 1H), 7.73 (d, J=8.79 Hz, 1H).

192B. Example 192: The Boc-protected title compound was prepared from 192A and 52B according to the urea coupling procedure described in Example 16. This intermediate was treated with 1:1 TFA/DCM for 1 h to remove the Boc group and give t Example 192. LCMS m/z 553.1 (M+H)$^+$. $^1$HNMR (400 MHz, DMSO-d6) δ 2.95-3.18 (m, 2H), 3.66 (s, 3H), 4.04 (s, 1H), 4.99 (m, 1H), 6.54 (m, 1H), 6.70 (d, J=8.24 Hz, 1H) 6.79 (d, J=9.34 Hz, 1H) 7.03-7.27 (m, 7H) 7.50-7.57 (m, 4H) 9.78 (s, 1H).

Example 193

(S)-methyl 4-(5-chloro-2-(1-(3-(5-chloro-2-(3-methylureido)benzyl)ureido)-2-phenylethyl)-1H-imidazol-4-yl)phenylcarbamate, trifluoroacetic acid salt To a solution of Example 192 (100 mg, 0.181 mmol) and N-methylmorpholine (19.87 μL, 0.181 mmol) in THF (5 mL) at room temperature, methyl isocyanate (10.31 mg, 0.181 mmol) was added. After stirring for 15 h, the mixture was concentrated and purified by reverse phase HPLC to afford Example 193 as a pale yellow solid (23 mg, 20%). LCMS m/z 608.2. $^1$HNMR (400 MHz, DMSO-d6) δ 2.61 (s, 3H), 2.96-3.17 (m, 2H), 3.67 (s, 3H), 4.10 (d, J=6.05 Hz, 2H), 5.01 (m, 1H), 6.17 (s, 1H), 6.55 (t, J=6.05 Hz, 1H), 6.74 (d, J=8.25 Hz, 1H), 7.07-7.26 (m, 7H), 7.49-7.60 (m, 4H), 7.78 (d, J=8.25 Hz, 1H), 8.23 (s, 1H), 9.78 (s, 1H).

Example 194

[4-Chloro-2-(3-{(S)-1-[5-chloro-4-(4-methoxycarbonylamino-phenyl)-1H-imidazol-2-yl]-2-phenyl-ethyl}-ureidomethyl)-phenyl]-carbamic acid methyl ester, trifluoroacetic acid salt To a solution of Example 192 (100 mg, 0.181 mmol) and pyridine (29.2 μL, 0.361 mmol) in THF (5 mL) at rt, methyl chloroformate (34.1 mg, 0.361 mmol) was added. After stirring for 16 h, the reaction mixture was concentrated. The residue was dissolved in MeOH (3 mL), cooled to 0° C., and treated with 1N NaOH (0.5 mL). After 30 minutes, brine (5 mL) was added, and the mixture extracted with EtOAc. The combined organic extract was washed with brine, dried over sodium sulfate, and concentrated. Purification by reverse phase HPLC afforded Example 194 as a pale yellow solid (27 mg, 23%). LCMS m/z 611.2. $^1$HNMR: (400 MHz, DMSO) δ 2.93-3.13 (m, 2H), 3.62 (s, 3H), 3.67 (s, 3H), 4.03-4.18 (m, 2H), 5.00 (q, J=7.70 Hz, 1H), 6.60 (t, J=6.05 Hz, 1H), 6.76 (d, J=8.79 Hz, 1H), 7.08-7.29 (m, 7H), 7.48-7.62 (m, 5H), 9.52 (s, 1H) 9.78 (s, 1H) 12.54 (s, 1H).

Example 195

(S)-methyl 4-(5-chloro-2-(1-(3-(5-chloro-2-(methyl-sulfonamido)benzyl)ureido)-2-phenylethyl)-1H-imidazol-4-yl)phenylcarbamate, trifluoroacetic acid salt To a solution of Example 192 (100 mg, 0.181 mmol) and pyridine (29.2 μL, 0.361 mmol) in THF (5 mL) at room temperature, methanesulfonyl chloride (41.4 mg, 0.361 mmol) was added with stirring. After 15 h, the mixture was concentrated and purified by reverse phase HPLC to give Example 195 as a pale yellow solid (24 mg, 21%). LCMS m/z 629.2. $^1$HNMR (400 MHz, DMSO-d6) δ 2.95 (s, 3H), 2.97-3.13 (m, 2H), 3.67 (s, 3H), 4.17-4.23 (m, 2H), 4.99 (m, 1H), 6.61 (t, J=6.05 Hz, 1H), 6.81 (d, J=8.24 Hz, 1H), 7.07-7.25 (m, 5H), 7.31 (s, 3H), 7.48-7.60 (m, 4H), 9.66 (s, 1H), 9.78 (s, 1H).

Examples 196-204 in Table 1 were prepared according to the following general procedure: Tetrakis(triphenylphosphine)palladium (0) (14.42 mg, 0.012 mmol) was added to a degassed solution of DME/H$_2$O (4:1, 3 mL) containing 141D (50 mg, 0.125 mmol), the appropriate boronic acid or boronate (0.187 mmol), and potassium carbonate (69.0 mg, 0.499 mmol) under a blanket of argon. The mixture was heated under microwave irradiation at 150° C. for 15 min. Afterward, the reaction mixture was partitioned between EtOAc and water. The separated organic extract was washed with brine, dried over sodium sulfate, filtered, and concentrated. Boc-deprotection was carried out by subsequent treatment with 50% TFA/DCM for 1 h. Afterwards, the solvent was removed and the residue dissolved with EtOAc and stirred with saturated sodium bicarbonate solution. After 15 minutes, the organic layer was separated, washed with brine, dried over sodium sulfate, filtered, and concentrated. The free amine thus obtained, 62B (31.3 mg, 0.125 mmol), and 1-hydroxybenzotriazole hydrate (20.23 mg, 0.150 mmol) were dissolved in DMF (3 mL) at room temperature with stirring. Then, EDCI (35.9 mg, 0.187 mmol) and N-methylmorpholine (27.4 μL, 0.250 mmol) were added, respectively, and stirring continued. After 14 h, the reaction mixture was poured into a biphasic mixture of EtOAc and brine/water. The organic layer was separated, washed with brine, dried over sodium sulfate, filtered, and concentrated. Final products were purified by reverse phase HPLC.

Example 196

4-(5-Chloro-2-{(S)-1-[(E)-3-(5-chloro-2-tetrazol-1-yl-phenyl)-acryloylamino]-2-phenyl-ethyl}-1H-imidazol-4-yl)-N-methyl-benzamide, trifluoroacetic acid salt

Example 197

(E)-N-((S)-1-{5-Chloro-4-[6-(2-morpholin-4-yl-ethylamino)-pyridin-3-yl]-1H-imidazol-2-yl}-2-phenyl-ethyl)-3-(5-chloro-2-tetrazol-1-yl-phenyl)-acrylamide, bis trifluoroacetic acid salt

Example 198

(E)-N-((S)-1-{5-Chloro-4-[5-(morpholine-4-carbonyl)-pyridin-3-yl]-1H-imidazol-2-yl}-2-phenyl-ethyl)-3-(5-chloro-2-tetrazol-1-yl-phenyl)-acrylamide, bis trifluoroacetic acid salt

Example 199

(E)-N—[(S)-1-(4-1,3-Benzodioxol-5-yl-5-chloro-1H-imidazol-2-yl)-2-phenyl-ethyl]-3-(5-chloro-2-tetrazol-1-yl-phenyl)-acrylamide, trifluoroacetic acid salt

Example 200

4-(5-Chloro-2-{(S)-1-[(E)-3-(5-chloro-2-tetrazol-1-yl-phenyl)-acryloylamino]-2-phenyl-ethyl}-1H-imidazol-4-yl)-benzoic acid methyl ester, trifluoroacetic acid salt

Example 201

3-[4-(5-Chloro-2-{(S)-1-[(E)-3-(5-chloro-2-tetrazol-1-yl-phenyl)-acryloylamino]-2-phenyl-ethyl}-1H-imidazol-4-yl)-phenyl]-propionic acid ethyl ester, trifluoroacetic acid salt

Example 202

3-(5-Chloro-2-{(S)-1-[(E)-3-(5-chloro-2-tetrazol-1-yl-phenyl)-acryloylamino]-2-phenyl-ethyl}-1H-imidazol-4-yl)-benzoic acid methyl ester, trifluoroacetic acid salt

Example 203

(E)-N-{(S)-1-[4-(6-Amino-pyridin-3-yl)-5-chloro-1H-imidazol-2-yl]-2-phenyl-ethyl}-3-(5-chloro-2-tetrazol-1-yl-phenyl)-acrylamide, bis trifluoroacetic acid salt

Example 204

(E)-N-{(S)-1-[5-Chloro-4-(6-methoxy-pyridin-3-yl)-1H-imidazol-2-yl]-2-phenyl-ethyl}-3-(5-chloro-2-tetrazol-1-yl-phenyl)-acrylamide, bis trifluoroacetic acid salt

Example 205

(S,E)-2-methoxyethyl 5-(5-chloro-2-(1-(3-(5-chloro-2-(1H-tetrazol-1-yl)phenyl)acrylamido)-2-phenyl-ethyl)-1H-imidazol-4-yl)pyridin-2-ylcarbamate, trifluoroacetic acid salt 205A. 2-Methoxyethyl 5-bromopyridin-2-ylcarbamate: 2-amino-5-bromopyridine (5.0 g, 28.9 mmol) and pyridine (3.51 mL, 43.3 mmol) were added to DCM (50 mL) at 0° C. 2-Methoxyethyl chloroformate (6.01 g, 34.7 mmol) was slowly added and the mixture was allowed to come to rt and stirred for 48 h. The resulting suspension was poured into saturated sodium bicarbonate solution with stirring. The solids were collected by filtration, washed with water several times, and dried under vacuum to give 205A as a white solid (6.38 g, 80%). LC/MS m/z 275 (M+H)$^+$. $^1$HNMR (400 MHz, DMSO-d$_6$) δ 3.27 (s, 3H), 3.50-3.59 (m, 2H), 4.17-4.30 (m, 2H), 7.79 (d, J=8.84 Hz, 1H), 7.95 (d, J=2.53 Hz, 1H), 8.36 (d, J=2.53 Hz, 1H), 10.39 (s, 1H).

205B. 2-Methoxyethyl 5-(5,5-dimethyl-1,3,2-dioxaborinan-2-yl)pyridin-2-ylcarbamate: 206A (1.0 g, 3.64 mmol), 5,5,5',5'-tetramethyl-2,2'-bi(1,3,2-dioxaborinane) (1.232 g, 5.45 mmol), potassium acetate (1.070 g, 10.91 mmol), and Pd(dppf)Cl$_2$ (0.150 g, 0.182 mmol) were added to dioxane (36.4 mL) with stirring. Argon was bubbled through this mixture for 15 min before heating it at 85° C. for 16 h. After cooling to rt, the mixture was partitioned between EtOAc and water. The separated organic layer was washed with brine, dried over sodium sulfate, filtered, and concentrated to leave a beige solid. Purification by flash chromatography gave 205B as a light beige solid (509 mg, 45%). LC/MS m/z 241 (M+H)$^+$ for boronic acid. $^1$HNMR (400 MHz, DMSO) δ 0.94 (s, 6H) 3.23-3.30 (m, 4H) 3.69-3.83 (m, 4H) 4.14-4.33 (m, 3H) 7.74-7.85 (m, 1H) 7.89-8.00 (m, 1H) 8.47 (s, 1H) 10.30 (s, 1H).

205C. Example 205 was prepared from 205B according to the general procedure described above for Examples 196-204. LCMS m/z 648.2 (M+H)$^+$. $^1$HNMR (400 MHz, CD$_3$OD) δ 3.05-3.17 (m, 2H), 3.29 (s, 3H), 3.54-3.58 (m, 2H), 4.20-4.24 (m, 2H), 5.13 (m, 1H), 6.61 (d, J=15.39 Hz, 1H), 6.97 (d, J=15.39 Hz, 1H), 7.04-7.11 (m, 3H), 7.14 (t, J=7.15 Hz, 1H), 7.44-7.47 (m, 1H), 7.55 (dd, J=8.24, 2.20 Hz, 1H), 7.77-7.93 (m, 3H), 8.39 (d, J=2.75 Hz, 1H) 9.40 (s, 1H).

Example 206

(S)-methyl 4-(2-(1-(3-(2-(aminomethyl)-5-chlorophenyl)propanamido)-2-phenylethyl)-5-chloro-1H-imidazol-4-yl)phenylcarbamate, bis-trifluoroacetic acid salt 206A. (4-Chloro-2-iodophenyl)methanol: borane-tetrahydrofuran complex (52.0 mL, 52 mmol) was added into a solution of 4-chloro-2-iodobenzoic acid (8.47 g, 30 mmol) in THF (60 mL) at 0° C. under nitrogen atmosphere, dropwise via an addition funnel over 1 h. The mixture was stirred at rt for 60 h before quenching with 1M HCl (75 mL). After stirring for 1 h, the solution was further diluted with water (75 mL) and extracted with EtOAc. The combined organic extracts were washed with 1N NaOH and brine, dried over sodium sulfate, filtered, and concentrated to leave 206A (8.0 g, 99%) as a white solid. LC/MS m/z 267 (M−H)−. $^1$HNMR (400 MHz, DMSO) δ 4.38 (s, 2H) 5.52 (s, 1H) 7.40-7.52 (m, 2H) 7.86 (d, J=2.20 Hz, 1H).

206B. tert-Butyl 4-chloro-2-iodobenzylcarbamate: To a stirred solution of 206A (8.0 g, 29.8 mmol) and DPPA (9.84 g, 35.8 mmol) in dry toluene (50 mL) at 0° C. was added DBU (4.94 mL, 32.8 mmol). The mixture gradually came to room temperature and was stirred at rt for 20 h. The mixture was washed with water and 5% HCl. The organic layer was washed further with brine, dried over sodium sulfate, filtered, and concentrated in vacuo to leave a colorless oil. This intermediate in MeOH (15 mL) was added dropwise to a suspension of stannous chloride dihydrate (10.09 g, 44.7 mmol) in methanol (40 mL) with vigorous stirring. After 5 h, the excess MeOH was removed, ice water was added, and the suspension was made basic with 1N NaOH. The mixture was extracted with Et$_2$O and EtOAc. NaCl was added to the aqueous layer and it was extracted again with E$_2$O. The combined organic extracts were dried over sodium sulfate, filtered, and concentrated to leave the benzyl amine intermediate as a white solid. LC/MS m/z 267 (M+H)$^+$. This intermediate was dissolved in THF (75 mL) and treated with DMAP (0.364 g, 2.98 mmol) followed by di-tert-butyl dicarbonate (7.80 g, 35.8 mmol) at 0° C. After stirring for 15 h, the reaction mixture was partitioned between EtOAc and water. The aqueous layer was extracted with EtOAc and the combined organic extracts were washed with brine, dried over sodium sulfate, filtered, and concentrated. The resulting oil was purified by flash chromatography 206B as an amber oil (4.8 g, 44%). LC/MS m/z 368 (M+H)$^+$.

206C. 3-(2-((tert-Butoxycarbonylamino)methyl)-5-chlorophenyl)propanoic acid: To a mixture of 206B (4.70 g, 12.79 mmol), 3,3-diethoxyprop-1-ene (1.958 ml, 12.79 mmol), palladium(II) acetate (0.287 g, 1.279 mmol), and tetrabutylammonium bromide (4.12 g, 12.79 mmol) in DMF (50 mL) was added tributylamine (3.04 ml, 12.79 mmol) under a nitrogen atmosphere. The mixture stirred at 90° C. for 16 h. After cooling to rt, 1M HCl (20 mL) was added and stirring was continued for 30 min. The solution was partitioned between EtOAc and brine/water. The organic layer was washed further with brine, dried over sodium sulfate, filtered, and concentrated to leave a brown oil. This intermediate was dissolved in THF (50 mL) and treated with lithium hydroxide monohydrate (1.610 g, 38.4 mmol) dissolved in water (10 mL). The reaction was heated at 60° C. for 36 h. The reaction mixture was cooled to rt and concentrated to dryness under vacuum to give 206C. LC/MS m/z 314 (M+H)$^+$.

206D. Example 206: 206C (3.0 g, 9.56 mmol), 52B (3.55 g, 9.56 mmol), and 1-hydroxybenzotriazole hydrate (1.292 g, 9.56 mmol) were added to DMF (50 mL). Then EDCI (2.199 g, 11.47 mmol) and N-methylmorpholine (2.102 mL, 19.12 mmol) were added and the mixture was stirred for 20 h. The mixture was partitioned between EtOAc and brine/water. The organic layer was washed further with brine, dried over sodium sulfate, filtered, and concentrated. The crude material was purified by flash chromatography. This material was treated with 50% TFA/DCM for 1 h before concentrating. Purification by reverse phase HPLC afforded Example 206 as a white solid (366 mg, 68%). LCMS m/z 566.2 (M+H)$^+$. $^1$HNMR (400 MHz, DMSO) δ 2.44 (t, J=7.42 Hz, 2H), 2.79 (t, J=7.42 Hz, 2H), 3.07-3.18 (m, 2H), 3.67 (s, 3H), 4.03 (d, J=5.50 Hz, 2H), 5.09 (m, 1H), 7.08-7.25 (m, 5H), 7.28-7.41 (m, 2H), 7.54 (m, 4H), 8.11 (m, 1H), 8.55 (d, J=8.79 Hz, 1H), 9.77 (s, 1H).

Example 207

1-[2-((E)-2-{(S)-1-[4-(3-Amino-1H-indazol-6-yl)-5-chloro-1H-imidazol-2-yl]-2-phenyl-ethylcarbamoyl}-vinyl)-4-chloro-phenyl]-1H-[1,2,3]triazole-4-carboxylic acid ethyl ester 207A: 1-azido-4-chloro-2-iodobenzene. 2-amino-5-chloro-iodobenzene (1.75 g, 6.71 mmol was added to cold (0° C.) TFA (10 ml). Water (5 mL) was added and the reaction mixture was stirred at this temperature for 0.5 h. To this solution was added an aqueous solution of sodium nitrite (0.5 g, 0.5 mmol) dropwise. After stirring at this temperature for an additional 0.5 h, an aqueous solution of excess sodium azide (2 g) was added dropwise. The reaction mixture was stirred at this temperature for 2 h then filtered. The residue was washed with excess water (500 mL) and dried under nitrogen to afford the desired product as a grayish white solid (1.45 g). $^1$HNMR (CDCl$_3$) δ: 7.80 (s, 1H), 7.40 (dd, J=2.4 & 8.7 Hz, 1H), 7.09 (d, J=8.6 Hz, 1H) ppm.

207B. 1-(4-Chloro-2-iodo-phenyl)-1H-[1,2,3]triazole-4-carboxylic acid ethyl ester: 207A (1.45 g) was stirred in a sealed tube with toluene (5 mL) and excess ethylpropiolate (7 mL) and heated under microwave irradiation at 100° C. for ~1.5 h. The vessel was cooled and the contents were dissolved in ethylacetate (50 ml) and filtered through a Celite® pad. The filtrate was concentrated and the residue was purified by flash chromatography to afford the desired 4-ethylester regioisomer as the major product (1.047 g). $^1$HNMR (CDCl$_3$) δ: 8.41

(s, 1H), 8.05 (d, J=2.2 Hz, 1H), 7.56 (dd, J=2.2 & 8.4 Hz, 1H), 7.43 (d, J=8.5 Hz, 1H), 4.54 q, 2H), 1.50 (t, 3H) ppm. LCMS m/z 378.0 (M+H)+.

207C. 1-[2-((E)-2-Carboxy-vinyl)-4-chloro-phenyl]-1H-[1,2,3]triazole-4-carboxylic acid ethyl ester: 207B (0.28 g) was dissolved in 1 mL of DMF. The mixture was degassed for 0.5 h, followed by the addition of tert-butylacrylate (4 mL), tributylamine (0.214 mL), palladium on carbon (10%, 0.5 g) and cat. Pd(OAc)$_2$. The reaction vessel was sealed and heated to 100° C. overnight, then was cooled and diluted with ethylacetate (100 mL) and filtered through a pad of Celite®. The filtrate was washed with water (100 mL) and the organic layer separated, and concentrated to afford the desired product (0.3 µg). $^1$HNMR (CDCl$_3$) δ: 8.22 (s, 1H), 7.69 (d, J=2.2 Hz, 1H), 7.46 (dd, J=2.2 & 8.5 Hz, 1H), 7.37 (d, J=8.5 Hz, 1H), 7.15 (d, J=15.8 Hz, 1H), 6.34 (d, J=15.8 Hz, 1H), 4.43 (q, 2H), 1.39 (s, 9H) 1.37 (t, 3H) ppm. LCMS m/z 378.1 (M+H)+; 322 (M+H-tBu)+. The crude ester was dissolved in DCM (5 mL) and TFA (2 mL) was added. The reaction mixture was stirred at rt for 1 h, then concentrated and quenched with water (100 mL), extracted with DCM (2×100 mL), and dried (MgSO$_4$) and evaporated to afford the acid as a colorless solid (0.206 g). $^1$HNMR (CDCl$_3$) δ: 8.37 (s, 1H), 7.81 d, J=2.3 Hz, 1H), 7.57 (dd, J=2.3, 8.5 Hz, 1H), 7.56 (d, J=8.4 Hz, 1H), 7.32 (d, J=15.8 Hz, 1H), 6.47 (d, J=15.9 Hz, 1H), 4.50 (q, 2H), 1.43 (t, 3H) ppm. LCMS m/z 322.2 (M+H)+.

207D. Example 207 was prepared from 207C and 110A using a procedure similar to that described for 1F and purified via reverse phase HPLC followed by lyophilization to afford Example 207 as colorless solid. $^1$HNMR (CD$_3$OD) δ: 8.84 (s, 1H), 7.95 (m, 2H), 7.70-7.48 (m, 4H0, 7.27-7.16 (m, 5H), 7.12 (d, J=15.7 Hz, 1H), 6.74 (d, J=15.7 Hz, 1H), 5.26 (t, 1H), 4.43 (q, 2H), 3.22 (m, 2H), 1.38 (t, 3H) ppm. LCMS m/z 656.2 (M+H)+.

Example 208

1-[2-((E)-2-{(S)-1-[4-(3-Amino-1H-indazol-6-yl)-5-chloro-1H-imidazol-2-yl]-2-phenyl-ethylcarbamoyl}-vinyl)-4-chloro-phenyl]-1H-[1,2,3]triazole-4-carboxylic acid 207D was hydrolyzed with LiOH (0.1 g) in methanol (5 ml) and water (0.5 ml). The reaction mixture was concentrated and directly purified via reverse phase HPLC and lyophilized to afford Example 208 as a colorless solid. $^1$HNMR (CD$_3$OD) δ: 8.80(s, 1H), 7.95 (m, 2H), 7.69 (s, 1H), 7.64 (dd, J=2.3 & 8.5 Hz, 1H), 7.56 (d, J=8.5 Hz, 1H), 7.51 (dd, J=1.4 & 8.3 Hz, 1H), 7.26-7.16 (m, 5H), 7.15 (d, J=15.7 Hz, 1H), 6.73 (d, J=15.7 Hz, 1H), 5.24 (t, 1H), 3.22 (m, 2H) ppm. LCMS m/z 628.1 (M+H)+.

Example 209

1-[4-Chloro-2-((E)-2-{(S)-1-[5-chloro-4-(4-methoxycarbonylamino-phenyl)-1H-imidazol-2-yl]-2-phenyl-ethylcarbamoyl}-vinyl)-phenyl]-1H-[1,2,3]triazole-4-carboxylic acid ethyl ester Example 209 was prepared from 52B and 207C using a procedure similar to that described for 1F. Purification via reverse phase HPLC and lyophilization afforded the desired product as a colorless solid. LCMS m/z 674.2 (M+H)+. $^1$HNMR (CH$_3$OD) δ: 8.83 (s, 1H), 7.93 (d, J=2.2 Hz, 1H), 7.64 (dd, J=2.3 & 8.5 Hz, 1H), 7.56 (d, J=8.5 Hz, 1H), 7.51 (s, 4H), 7.27-7.15 (m, 5H), 7.12 (d, J=15.7 Hz, 1H), 6.72 (d, J=15.7 Hz, 1H), 5.26 (t, 1H), 4.43 (q, 2H), 3.74 (s, 3H), 3.26 (m, 2H), 1.40 (t, 3H) ppm.

Example 210

1-[4-Chloro-2-((E)-2-{(S)-1-[5-chloro-4-(4-methoxycarbonylamino-phenyl)-1H-imidazol-2-yl]-2-phenyl-ethylcarbamoyl}-vinyl)-phenyl]-1H-[1,2,3]triazole-4-carboxylic acid Example 210 was prepared from Example 209 using the procedure described for Example 208. LCMS m/z 646.2 (M+H)+. $^1$HNMR (CH$_3$OD) δ: 8.79 (s, 1H), 7.94 (d, J=2.2 Hz, 1H), 7.64 (dd, J=2.3 & 8.5 Hz, 1H), 7.549 (d, J=8.5 Hz, 1H), 7.49 (s, 4H), 7.28-7.15 (m, 5H), 7.14 (d, J=15.7 Hz, 1H), 6.72 (d, J=15.8 Hz, 1H), 5.26 (t, 1H), 3.74 (s, 3H), 3.24 (m, 2H) ppm.

Example 211

6-(5-Chloro-2-{(S)-1-[(E)-3-(5-chloro-2-tetrazol-1-yl-phenyl)-acryloylamino]-2-phenyl-ethyl}-1H-imidazol-4-yl)-2-oxo-1,2-dihydro-quinoline-4-carboxylic acid methylamide, trifluoroacetic acid salt 211A. 6-[2-((S)-1-Amino-2-phenyl-ethyl)-5-chloro-1H-imidazol-4-yl]-2-oxo-1,2-dihydro-quinoline-4-carboxylic acid methylamide, bis-trifluoroacetic acid salt: To a brown suspension of the Boc-protected precursor to 142B, (0.033 g, 0.065 mmol) in DMF (0.3 mL) was added 1,1'-carbonyldiimidazole (0.013 g, 0.078 mmol). The reaction was stirred at rt for 5 min, warmed to 85° C. for 30 min, and then cooled to rt. Next triethylamine (0.027 mL, 0.195 mmol) and methylamine hydrochloride (4.38 mg, 0.065 mmol) were added and the reaction mixture was stirred at rt for 2 h. Water was added, and the reaction was filtered. The solid was washed with water and air-dried to give 0.020 g of the amide as a brown solid. LCMS m/z 522.4 (M+H)+. This brown solid was treated with 30% TFA/DCM (1 mL) for 30 min and then concentrated. Purification by reverse phase HPLC (MeOH, water, 0.1% TFA) gave 211A (0.025 g, 59%) as a yellow solid. LCMS m/z 422.1 (M+H)+. $^1$HNMR (400 MHz, CD$_3$OD) δ: 2.98 (s, 3H), 3.28-3.40 (m, 2H), 4.54-4.58 (m, 1H), 6.70 (s, 1H), 7.13-7.15 (m, 2H), 7.24-7.32 (m, 3H), 7.44 (d, J=8.8 Hz, 1H), 7.84 (dd, J=1.7 Hz, 8.8 Hz, 1H), 8.09 (d, J=2.2 Hz, 1H).

211B. Example 211 was prepared by coupling 211A with 62B according to the procedure described in 62C. LCMS m/z 654.2 (M+H)+. $^1$HNMR (500 MHz, DMSO-d$_6$) δ: 2.81 (d, J=5.0 Hz, 3H), 3.05 (dd, J=8.3 Hz, 13.8 Hz, 1H), 3.20 (dd, J=6.6 Hz, 13.8 Hz, 1H), 5.18-5.22 (m, 1H), 6.54 (s, 1H), 6.76-6.85 (m, 2H), 7.14-7.25 (m, 5H), 7.39 (d, J=8.3 Hz, 1H), 7.69-7.78 (m, 3H), 7.91 (d, J=2.2 Hz, 1H), 8.04 (s, 1H), 8.68-8.71 (m, 1H), 8.81 (d, J=8.3 Hz, 1H), 9.84 (s, 1H), 12.03 (s, 1H), 12.76 (s, 1H).

Examples 212-219 in Table 1 were prepared in a library format according to the following general procedure: Example 206 (15.9 mg, 0.020 mmol) was dissolved in DCM and added to the appropriate pre-weighed isocyanate, chloroformate, sulfonyl chloride or anhydride (2.5 eq., 0.050 mmol) in 1 dram vials. DIPEA (3 eq., 0.060 mmol) was added and the reactions were stirred overnight. The solvent was removed in a SpeedVac and the products were purified by reverse phase HPLC.

Example 212

{4-[5-Chloro-2-((S)-1-{3-[5-chloro-2-(ethoxycarbonylamino-methyl)-phenyl]-propionylamino}-2-phenyl-ethyl)-1H-imidazol-4-yl]-phenyl}-carbamic acid methyl ester

Example 213

(4-{5-Chloro-2-[(S)-1-(3-{5-chloro-2-[(3-ethyl-ureido)-methyl]-phenyl}-propionylamino)-2-phenyl-ethyl]-1H-imidazol-4-yl}-phenyl)-carbamic acid methyl ester

Example 214

N-[4-Chloro-2-(2-{(S)-1-[5-chloro-4-(4-methoxycarbonylamino-phenyl)-1H-imidazol-2-yl]-2-phenyl-ethylcarbamoyl}-ethyl)-benzyl]-succinamic acid

Example 215

(4-{5-Chloro-2-[(S)-1-(3-{5-chloro-2-[(propane-2-sulfonylamino)-methyl]-phenyl}-propionylamino)-2-phenyl-ethyl]-1H-imidazol-4-yl}-phenyl)-carbamic acid methyl ester

Example 216

{4-[5-Chloro-2-((S)-1-{3-[5-chloro-2-(methane-sulfonylamino-methyl)-phenyl]-propionylamino}-2-phenyl-ethyl)-1H-imidazol-4-yl]-phenyl}-carbamic acid methyl ester

Example 217

{4-[5-Chloro-2-((S)-1-{3-[5-chloro-2-(ethanesulfonylamino-methyl)-phenyl]-propionylamino}-2-phenyl-ethyl)-1H-imidazol-4-yl]-phenyl}-carbamic acid methyl ester

Example 218

(4-{5-Chloro-2-[(S)-1-(3-{5-chloro-2-[(propane-1-sulfonylamino)-methyl]-phenyl}-propionylamino)-2-phenyl-ethyl]-1H-imidazol-4-yl}-phenyl)-carbamic acid methyl ester

Example 219

3-{3-[4-Chloro-2-(2-{(S)-1-[5-chloro-4-(4-methoxycarbonylamino-phenyl)-1H-imidazol-2-yl]-2-phenyl-ethylcarbamoyl}-ethyl)-benzyl]-ureido}-propionic acid ethyl ester Examples 220-242 in Table 1 were prepared in a library format from carboxylic acid Example 170 and the appropriate commercially available amines using the following procedure. The acid was dissolved in dried DMF (20 mL) and HATU and DIPEA were added. The mixture was stirred for 2 minutes and the solution was then added into amines. The reactions were stirred for 6 hours at which point LC-MS showed that the reactions were complete. The samples were transferred into 96 deep-well plate and purified by reverse phase HPLC.

Example 220

[4-(5-Chloro-2-{(S)-2-(4-chloro-benzylcarbamoyl)-1-[(E)-3-(5-chloro-2-tetrazol-1-yl-phenyl)-acryloylamino]-ethyl}-1H-imidazol-4-yl)-phenyl]-carbamic acid methyl ester

Example 221

(4-{5-Chloro-2-[(S)-1-[(E)-3-(5-chloro-2-tetrazol-1-yl-phenyl)-acryloylamino]-2-(2-methoxy-ethylcarbamoyl)-ethyl]-1H-imidazol-4-yl}-phenyl)-carbamic acid methyl ester

Example 222

[4-(5-Chloro-2-{(S)-2-(3-chloro-benzylcarbamoyl)-1-[(E)-3-(5-chloro-2-tetrazol-1-yl-phenyl)-acryloylamino]-ethyl}-1H-imidazol-4-yl)-phenyl]-carbamic acid methyl ester

Example 223

[4-(2-{(S)-3-Azetidin-1-yl-1-[(E)-3-(5-chloro-2-tetrazol-1-yl-phenyl)-acryloylamino]-3-oxo-propyl}-5-chloro-1H-imidazol-4-yl)-phenyl]-carbamic acid methyl ester

Example 224

[4-(5-Chloro-2-{(S)-1-[(E)-3-(5-chloro-2-tetrazol-1-yl-phenyl)-acryloylamino]-3-oxo-3-pyrrolidin-1-yl-propyl}-1H-imidazol-4-yl)-phenyl]-carbamic acid methyl ester

Example 225

(4-{5-Chloro-2-[(S)-1-[(E)-3-(5-chloro-2-tetrazol-1-yl-phenyl)-acryloylamino]-3-(4-methyl-piperazin-1-yl)-3-oxo-propyl]-1H-imidazol-4-yl}-phenyl)-carbamic acid methyl ester

Example 226

[4-(2-{(S)-2-(Benzyl-methyl-carbamoyl)-1-[(E)-3-(5-chloro-2-tetrazol-1-yl-phenyl)-acryloylamino]-ethyl}-5-chloro-1H-imidazol-4-yl)-phenyl]-carbamic acid methyl ester

Example 227

(4-{5-Chloro-2-[(S)-1-[(E)-3-(5-chloro-2-tetrazol-1-yl-phenyl)-acryloylamino]-3-((R)-2-methoxy-pyrrolidin-1-yl)-3-oxo-propyl]-1H-imidazol-4-yl}-phenyl)-carbamic acid methyl ester

Example 228

[4-(2-{(S)-2-[Bis-(2-methoxy-ethyl)-carbamoyl]-1-[(E)-3-(5-chloro-2-tetrazol-1-yl-phenyl)-acryloylamino]-ethyl}-5-chloro-1H-imidazol-4-yl)-phenyl]-carbamic acid methyl ester

Example 229

[4-(2-{(S)-3-(4-Acetyl-piperazin-1-yl)-1-[(E)-3-(5-chloro-2-tetrazol-1-yl-phenyl)-acryloylamino]-3-oxo-propyl}-5-chloro-1H-imidazol-4-yl)-phenyl]-acetic acid methyl ester

Example 230

(4-{5-Chloro-2-[(S)-1-[(E)-3-(5-chloro-2-tetrazol-1-yl-phenyl)-acryloylamino]-3-((R)-3-dimethylamino-pyrrolidin-1-yl)-3-oxo-propyl]-1H-imidazol-4-yl}-phenyl)-carbamic acid methyl ester

Example 231

[4-(5-Chloro-2-{(S)-1-[(E)-3-(5-chloro-2-tetrazol-1-yl-phenyl)-acryloylamino]-2-[(pyridin-4-ylmethyl)-carbamoyl]-ethyl}-1H-imidazol-4-yl)-phenyl]-carbamic acid methyl ester

Example 232

[4-(5-Chloro-2-{(S)-1-[(E)-3-(5-chloro-2-tetrazol-1-yl-phenyl)-acryloylamino]-2-cyclopropylcarbamoyl-ethyl}-1H-imidazol-4-yl)-phenyl]-carbamic acid methyl ester

Example 233

[4-(5-Chloro-2-{(S)-1-[(E)-3-(5-chloro-2-tetrazol-1-yl-phenyl)-acryloylamino]-2-cyclopentylcarbamoyl-ethyl}-1H-imidazol-4-yl)-phenyl]-carbamic acid methyl ester

Example 234

(4-{5-Chloro-2-[(S)-1-[(E)-3-(5-chloro-2-tetrazol-1-yl-phenyl)-acryloylamino]-2-(cyclopropylmethyl-carbamoyl)-ethyl]-1H-imidazol-4-yl}-phenyl)-carbamic acid methyl ester

Example 235

(4-{5-Chloro-2-[(S)-1-[(E)-3-(5-chloro-2-tetrazol-1-yl-phenyl)-acryloylamino]-2-((1S,2R)-2-phenyl-cyclopropylcarbamoyl)-ethyl]-1H-imidazol-4-yl}-phenyl)-carbamic acid methyl ester

Example 236

(4-{5-Chloro-2-[(S)-1-[(E)-3-(5-chloro-2-tetrazol-1-yl-phenyl)-acryloylamino]-2-(2-ethoxy-ethylcarbamoyl)-ethyl]-1H-imidazol-4-yl}-phenyl)-carbamic acid methyl ester

Example 237

(4-{5-Chloro-2-[(S)-1-[(E)-3-(5-chloro-2-tetrazol-1-yl-phenyl)-acryloylamino]-2-(2-hydroxy-ethylcarbamoyl)-ethyl]-1H-imidazol-4-yl}-phenyl)-carbamic acid methyl ester

Example 238

(4-{5-Chloro-2-[(S)-1-[(E)-3-(5-chloro-2-tetrazol-1-yl-phenyl)-acryloylamino]-2-(2-dimethylamino-ethylcarbamoyl)-ethyl]1H-imidazol-4-yl}-phenyl)-carbamic acid methyl ester

Example 239

[4-(5-Chloro-2-{(S)-1-[(E)-3-(5-chloro-2-tetrazol-1-yl-phenyl)-acryloylamino]-2-[(pyridin-2-ylmethyl)-carbamoyl]-ethyl}-1H-imidazol-4-yl)-phenyl]-carbamic acid methyl ester

Example 240

[4-(5-Chloro-2-{(S)-1-[(E)-3-(5-chloro-2-tetrazol-1-yl-phenyl)-acryloylamino]-2-[(pyridin-3-ylmethyl)-carbamoyl]-ethyl}-1H-imidazol-4-yl)-phenyl]-carbamic acid methyl ester

Example 241

(4-{5-Chloro-2-[(S)-1-[(E)-3-(5-chloro-2-tetrazol-1-yl-phenyl)-acryloylamino]-2-(2-pyridin-2-yl-ethyl-carbamoyl)-ethyl]-1H-imidazol-4-yl}-phenyl)-carbamic acid methyl ester

Example 242

(4-{5-Chloro-2-[(S)-1-[(E)-3-(5-chloro-2-tetrazol-1-yl-phenyl)-acryloylamino]-3-(1,1-dioxo-1$\lambda^6$-thio-morpholin-4-yl)-3-oxo-propyl]-1H-imidazol-4-yl}-phenyl)-carbamic acid methyl ester

Example 243

(S,E)-methyl 4-(4-chloro-2-(1-(3-(5-chloro-2-(1H-tetrazol-1-yl)phenyl)acrylamido)-2-(4-hydroxycyclohexyl)ethyl)-1H-imidazol-4-yl)phenylcarbamate A mixture of Example 140 (20 mg, 0.032 mmol) and sodium borohydride (2.4 mg, 0.064 mmol) in ethanol (1 mL) was stirred at rt for 66 h. Solvent was removed in vacuo. The residue was treated with a 1N NaOH solution and extracted three times with EtOAc. The combined organic layers were dried over $MgSO_4$ and filtered. Solvent was removed in vacuo to give a yellow oily solid. Normal phase preparative HPLC (0 to 100% EtOAc-hexane) gave Example 243 as a pale yellow solid (7.9 mg) LCMS: m/z 627 (M+H)$^+$; $^1$HNMR (CD$_3$OD, 400 MHz): 9.41 (s, 0.5H), 9.39 (s, 0.5H), 7.87 (s, 1H), 7.49 (m, 6H), 7.31 (m, 1H), 7.02 (d, 1H, J=14), 6.64 (d, 1H, J=14), 5.00 (m, 1H), 3.65 (s, 3H), 3.35 (m, 1H), 3.30 (m, 4H), 2.65 (m, 1H), 2.40 (m, 1H), 1.74 (m, 4H), 1.10 (m, 4H).

Example 244

3-[4-(5-Chloro-2-{(S)-1-[(E)-3-(5-chloro-2-tetrazol-1-yl-phenyl)-acryloylamino]-2-phenyl-ethyl}-1H-imidazol-4-yl)-phenyl]-propionic acid Tetrakis(triphenylphosphine)palladium (0) (0.014 g, 0.012 mmol) was added to a degassed solution of DME/H$_2$O (4:1, 4 mL) containing 141D (0.1 g, 0.250 mmol), 4-(3-ethoxy-3-oxopropyl)phenylboronic acid (0.111 g, 0.499 mmol), and potassium carbonate (0.207 g, 1.497 mmol) under a blanket of argon. The mixture was heated at 150° C. under microwave irradiation for 30 min. The cooled solution was partitioned between EtOAc (10 mL) and H$_2$O (10 mL). The aqueous layer was extracted with EtOAc (2×5 mL). The combined organic extracts were washed with brine, dried over sodium sulfate and Florosil™, filtered, and concentrated to leave crude a brown oil. This material was treated with 50% TFA/

DCM for 1 h. The reaction mixture was partitioned between EtOAc (10 mL) and saturated sodium bicarbonate solution and stirred for 15 min. The organic layer was separated, washed with brine, dried over sodium sulfate, filtered, and concentrated. The residue was dissolved in DMF (3 mL), and 62B (0.094 g, 0.374 mmol), 1-Hydroxybenzotriazole hydrate (0.057 g, 0.374 mmol), EDC (0.072 g, 0.374 mmol), and N-methylmorpholine (0.055 mL, 0.499 mmol) were added. The mixture was stirred overnight at rt. The reaction mixture was partitioned between EtOAc and water/brine (1:1). The organic extract was dried over sodium sulfate, filtered, and concentrated. The ester was hydrolyzed by dissolution in MeOH (5 mL) and treatment with 1M sodium hydroxide (0.499 mL, 0.499 mmol). After 1 h, the reaction mixture was evaporated to remove solvent, further diluted with water (5 mL), and acidified with 1.0 M HCl (2.0 mL). The suspension was extracted with EtOAc (3×5 mL). The combined organic extracts were dried over sodium sulfate, filtered, and concentrated. Purification by reverse phase prep. HPLC and lyophilizaiton provided Example 244 as the TFA salt (6.32 mg, 3.49% yield) as a white solid. $^1$HNMR (400 MHz, DMSO-d$_6$) δ ppm 2.51 (t, J=7.69 Hz, 2H) 2.82 (t, J=7.47 Hz, 2H) 3.04-3.17 (m, 2H) 5.13 (t, J=7.69 Hz, 1H) 6.61 (d, J=15.38 Hz, 1H) 6.97 (d, J=15.82 Hz, 1H) 7.03-7.11 (m, 3H) 7.11-7.21 (m, 4H) 7.44 (dd, J=1.86, 8.35 Hz, 3H) 7.52-7.57 (m, 1H) 7.86 (d, J=2.64 Hz, 1H) 9.39 (s, 1H). LC/MS: m/z 602 (M+H)$^+$.

Example 245

(4-{5-Chloro-2-[(S)-1-[3-(5-chloro-2-tetrazol-1-yl-phenyl)-propynoylamino]-2-(1-methyl-1H-pyrazol-3-yl)-ethyl]-1H-imidazol-4-yl}-phenyl)-carbamic acid methyl ester Example 245 was prepared from 189A and 82G using the procedure described for the synthesis of 1F. $^1$HNMR (CD$_3$OD, 400 MHz) δ: 9.63 (s, 1H), 7.839 (m, 1H), 7.67 (s, 2H), 7.51 (d, J=8.5 Hz, 2H), 7.43 (d, 2H0, 7.34 (d, J=1.2 Hz, 1H), 5.90 (d, J=2.2 Hz, 1H), 3.73 (s, 3H), 3.67 (s, 3H), 3.15 (m, 2H)ppm. LCMS m/z 605.0 (M+H)$^+$.

Example 246

(4-{5-Chloro-2-[(S)-1-[(E)-3-(5-chloro-2-tetrazol-1-yl-phenyl)-acryloylamino]-2-(1,5-dimethyl-1H-pyrazol-3-yl)-ethyl]-1H-imidazol-4-yl}-phenyl)-carbamic acid methyl ester Example 246 was prepared in 62% yield as described for Example 129 by substituting 62B in place of 63A in that procedure. $^1$H NMR (500 MHz, DMSO-d$_6$) δ ppm 12.66 (1H, s), 9.85 (1H, s), 9.78 (1H, s), 8.81 (1H, d, J=7.7 Hz), 7.92 (1H, d, J=2.2 Hz), 7.69-7.79 (2H, m), 7.55-7.60 (2H, m), 7.49-7.55 (2H, m), 6.87-6.94 (1H, m), 6.75-6.82 (1H, m), 5.70 (1H, s), 5.20 (1H, q, J=7.7 Hz), 3.66 (3H, s), 3.65 (3H, s), 3.21 (1H, dd, J=15.1, 7.4 Hz), 3.03-3.10 (1H, m), 2.01 (3H, s). LC/MS m/z 621.1 (M+H)$^+$.

Example 247

(4-{5-Chloro-2-[(S)-1-[(E)-3-(5-methyl-2-tetrazol-1-yl-phenyl)-acryloylamino]-2-(1,5-dimethyl-1H-pyrazol-3-yl)-ethyl]-1H-imidazol-4-yl}-phenyl)-carbamic acid methyl ester Example 247 was prepared in 67% yield as described for Example 246 by substitution of (E)-3-(5-methyl-2-tetrazol-1-yl-phenyl)-acrylic acid for 62B. $^1$H NMR (500 MHz, DMSO-d$_6$) d ppm 12.66 (1H, s), 9.82 (1H, s), 9.78 (1H, s), 8.81 (1H, s), 7.67 (1H, s), 7.55-7.61 (2H, m), 7.52 (3H, d, J=7.7 Hz), 7.42-7.48 (1H, m), 6.85-6.95 (1H, m), 6.72 (1H, d, J=15.4 Hz), 5.71 (1H, s), 5.15-5.25 (1H, m), 3.66 (3H, s), 3.66-3.66 (3H, s), 3.21 (1H, dd, J=15.4, 7.1 Hz), 3.06 (1H, dd, J=15.1, 7.4 Hz), 2.44 (3H, s), 2.01 (3H, s). LC/MS m/z 601.1 (M+H)$^+$.

Example 248

(E)-N-{(S)-1-[5-Chloro-4-(2-oxo-1,2-dihydro-pyridin-4-yl)-1H-imidazol-2-yl]-2-phenyl-ethyl}-3-(5-chloro-2-tetrazol-1-yl-phenyl)-acrylamide, trifluoroacetic acid salt 248A. (S)-1-[5-Chloro-4-(2-fluoro-pyridin-4-yl)-1H-imidazol-2-yl]-2-phenyl-ethylamine: 248A was prepared from 141D and commercially available 2-fluoropyridin-4-ylboronic acid by a procedure similar to that described for 141E, using K$_3$PO$_4$ in place of K$_2$CO$_3$ and dioxane in place of DME/water. LC/MS m/z 317.2 (M+H)$^+$.

248B. 4-[2-((S)-1-Amino-2-phenyl-ethyl)-5-chloro-1H-imidazol-4-yl]-pyridin-2-ol: A suspension of 248A (110 mg, 0.202 mmol) in 1N sodium hydroxide (4.0 mL, 4.00 mmol) was heated in a microwave reactor at 160° C. for 25 min. The solvent was removed under reduced pressure to give 248B (63.6 mg, 100%). LC/MS m/z 315.2 (M+H)$^+$.

248C. Example 248 was prepared from 248B and 62B by a similar procedure to 62C. LC/MS m/z 547.1 (M+H)$^+$. $^1$H NMR (400 MHz, CD$_3$OD) δ ppm 3.16-3.26 (m, 2H) 5.23 (t, J=7.69 Hz, 1H) 6.71 (d, J=15.38 Hz, 1H) 6.84-6.91 (m, 2H) 7.08 (d, J=15.38 Hz, 1H) 7.12-7.21 (m, 3H) 7.24 (t, J=7.03 Hz, 2H) 7.49-7.60 (m, 2H) 7.61-7.70 (m, 1H) 7.96 (s, 1H) 9.50 (s, 1H).

Examples 249-253 were prepared from 141D and the appropriate commercially available boronic acid or boronic ester by a procedure similar to that described for 141E, followed by reaction of the resulting amine with 62B according to the procedure described for 62C.

Example 249

4-(5-Chloro-2-{(S)-1-[(E)-3-(5-chloro-2-tetrazol-1-yl-phenyl)-acryloylamino]-2-phenyl-ethyl}-1H-imidazol-4-yl)-benzoic acid, trifluoroacetic acid salt LC/MS m/z 574 (M+H)$^+$. $^1$H NMR (400 MHz, CD$_3$OD) δ 3.04-3.18 (m, 2H), 5.10-5.21 (m, 1H), 6.61 (d, J=15.82 Hz, 1H), 6.97 (d, J=15.82 Hz, 1H), 7.02-7.18 (m, 5H), 7.45 (d, J=8.79 Hz, 1H), 7.54 (dd, J=8.35, 2.20 Hz, 1H), 7.63 (d, J=8.35 Hz, 2H), 7.86 (d, J=2.20 Hz, 1H), 7.94 (d, J=8.35 Hz, 2H), 9.39 (s, 1H).

Example 250

(E)-N-{(S)-1-[5-Chloro-4-(2,4-dichloro-phenyl)-1H-imidazol-2-yl]-2-phenyl-ethyl}-3-(5-chloro-2-tetrazol-1-yl-phenyl)-acrylamide, trifluoroacetic acid salt LC/MS m/z 564 (M+H)$^+$. $^1$H NMR (400 MHz, CD$_3$OD) δ 3.22-3.35 (m, 2H), 5.22 (t, J=8.13 Hz, 1H), 7.01 (d, J=15.82 Hz, 1H), 7.06 (d, J=6.59 Hz, 2H), 7.10-7.20 (m, 3H), 7.35 (dd, J=8.35, 2.20 Hz, 1H), 7.43-7.48 (m, 2H), 7.51-7.59 (m, 3H), 7.86 (d, J=2.20 Hz, 1H), 9.40 (s, 1H).

Example 251

4-(5-Chloro-2-{(S)-1-[(E)-3-(5-chloro-2-tetrazol-1-yl-phenyl)-acryloylamino]-2-phenyl-ethyl}-1H-imidazol-4-yl)-benzamide, trifluoroacetic acid salt LC/MS m/z 573 (M+H)$^+$. $^1$H NMR (400 MHz, CD$_3$OD) δ ppm 2.99-3.10 (m, 1H) 3.21 (dd, J=13.74, 6.60 Hz, 1H) 5.15-5.30 (m, J=7.70 Hz, 1H) 6.73-6.93 (m, 2H) 7.11-7.29 (m, 5H) 7.39 (s, 1H) 7.68-7.83 (m, 4H) 7.89-8.00 (m, 4H) 8.82 (d, J=8.25 Hz, 1H) 9.84 (s, 1H).

Example 252

(E)-N—[(S)-1-(5-Chloro-4-pyridin-3-yl-1H-imidazol-2-yl)-2-phenyl-ethyl]-3-(5-chloro-2-tetrazol-1-yl-phenyl)-acrylamide, bis-trifluoroacetic acid salt LC/MS m/z 531 (M+H)$^+$. $^1$H NMR (400 MHz, CD$_3$OD) δ 3.07-3.15 (m, 1H) 3.21-3.28 (m, 1H) 5.12 (t, J=7.69 Hz, 1H) 6.60 (d, J=15.38 Hz, 1H) 6.96 (d, J=15.38 Hz, 1H) 7.03-7.18 (m, 5H) 7.42-7.47 (m, 1H) 7.51-7.57 (m, 1H) 7.75 (dd, J=8.35, 5.27 Hz, 1H) 7.84 (d, J=2.20 Hz, 1H) 8.40-8.57 (m, 2H) 8.88 (d, J=1.76 Hz, 1H) 9.38 (s, 1H).

Example 253

(E)-N-{(S)-1-[5-Chloro-4-(1H-pyrrolo[2,3-b]pyridin-5-yl)-1H-imidazol-2-yl]-2-phenyl-ethyl}-3-(5-chloro-2-tetrazol-1-yl-phenyl)-acrylamide, bis-trifluoroacetic acid salt LC/MS m/z 570 (M+H)$^+$. $^1$H NMR (400 MHz, CD$_3$OD) δ ppm 3.06-3.16 (m, 2H) 5.15 (t, J=7.69 Hz, 1H) 6.52 (d, J=3.52 Hz, 1H) 6.61 (d, J=15.82 Hz, 1H) 6.97 (d, J=15.82 Hz, 1H) 7.04-7.11 (m, 3H) 7.12-7.19 (m, 2H) 7.37-7.48 (m, 2H) 7.50-7.56 (m, 1H) 7.85 (d, J=2.20 Hz, 1H) 8.22 (d, J=2.20 Hz, 1H) 8.33 (d, J=2.20 Hz, 1H) 9.39 (s, 1H).

Example 254

(S,E)-methyl 4-(5-chloro-2-(1-(3-(5-chloro-2-(1H-tetrazol-1-yl)phenyl)acrylamido)ethyl)-1H-imidazol-4-yl)phenylcarbamate, trifluoroacetic acid salt 254A. {4-[2-((S)-1-tert-Butoxycarbonylamino-ethyl)-1H-imidazol-4-yl]-phenyl}-carbamic acid methyl ester: 254A was prepared from (S)-2-(tert-butoxycarbonylamino)propanoic acid and 82D by a similar procedure to that described for 82E using Cs$_2$CO$_3$ in place of KHCO$_3$. LC/MS m/z 361 (M+H)$^+$.

254B. (S)-methyl 4-(2-(1-aminoethyl)-5-chloro-1H-imidazol-4-yl)phenylcarbamate, bis-trifluoroacetic acid salt: 254B was prepared from 254A by a similar procedure as that described for 52B. LC/MS m/z 295 (M+H)$^+$.

254C. Example 254 was prepared from 254B and 62B by a procedure similar to 62C. LC/MS m/z 527 (M+H)$^+$. $^1$H NMR (400 MHz, DMSO-d$_6$) δ 1.42 (d, J=6.60 Hz, 3H), 3.66 (s, 3H), 5.00-5.11 (m, 1H), 6.72-6.94 (m, 2H), 7.49-7.64 (m, 4H), 7.68-7.83 (m, 3H), 7.91 (d, J=2.20 Hz, 1H), 8.67 (d, J=7.70 Hz, 1H), 9.78 (s, 1H), 9.86 (s, 1H).

Example 255

1-[4-Chloro-2-((E)-2-{(S)-1-[5-chloro-4-(2-oxo-1,2-dihydro-pyridin-4-yl)-1H-imidazol-2-yl]-2-phenyl-ethylcarbamoyl}-vinyl)-phenyl]-1H-1,2,3-triazole-4-carboxylic acid ethyl ester, trifluoroacetic acid salt Example 255 was prepared by coupling 248B and 207C by a similar procedure to 62C. LC/MS m/z 618 (M+H)$^+$. $^1$H NMR (400 MHz, CD$_3$OD) δ 1.28 (t, J=6.87 Hz, 3H) 3.02-3.16 (m, 2H) 4.31 (q, J=7.15 Hz, 2H) 5.06-5.17 (m, 1H) 6.60 (d, J=15.39 Hz, 1H) 6.67-6.75 (m, 2H) 6.94-7.18 (m, 7H) 7.36 (d, J=7.70 Hz, 1H) 7.41-7.48 (m, 1H) 7.49-7.55 (m, 1H) 7.84 (d, J=2.20 Hz, 1H) 8.74 (s, 1H).

Example 256

1-[4-Chloro-2-((E)-2-{(S)-1-[5-chloro-4-(2-oxo-1,2-dihydro-pyridin-4-yl)-1H-imidazol-2-yl]-2-phenyl-ethylcarbamoyl}-vinyl)-phenyl]-1H-1,2,3-triazole-4-carboxylic acid, trifluoroacetic acid salt Example 256 was prepared by treating Example 255 with 1N NaOH (1.0 mL) for 2 h. The mixture was diluted with water and acidified with 1.0 M HCl. The suspension was extracted with EtOAc and the combined organic extracts were dried over sodium sulfate, filtered, and concentrated. The crude reaction material was diluted with MeOH and purified by reverse phase HPLC. LC/MS m/z 590 (M+H)$^+$. $^1$H NMR (400 MHz, CD$_3$OD) δ 2.99-3.17 (m, 2H) 5.12 (t, J=7.69 Hz, 1H) 6.59 (d, J=15.82 Hz, 1H) 6.69-6.77 (m, 2H) 6.96-7.19 (m, 6H) 7.38 (d, J=7.91 Hz, 1H) 7.42-7.48 (m, 1H) 7.49-7.56 (m, 1H) 7.83 (d, J=2.20 Hz, 1H) 8.69 (s, 1H).

Example 257

(E)-N—[(S)-1-[4-(3-Amino-1H-indazol-6-yl)-1H-imidazol-2-yl]-2-(4-chloro-1,5-dimethyl-1H-pyrazol-3-yl)-ethyl]-3-(5-chloro-2-tetrazol-1-yl-phenyl)-acrylamide, trifluoroacetic acid salt 257A. [(S)-1-[4-(4-Cyano-3-fluoro-phenyl)-1H-imidazol-2-yl]-2-(1,5-dimethyl-1H-pyrazol-3-yl)-ethyl]-carbamic acid tert-butyl ester: (S)-2-tert-Butoxycarbonylamino-3-(1,5-dimethyl-1H-pyrazol-3-yl)-propionic acid was prepared from commercially available 1,5-dimethyl-1H-pyrazole-3-carbaldehyde according to procedures similar to 82A-C. LC/MS m/z 284.2 (M+H)$^+$. This intermediate was condensed with 1B and the resulting intermediate was treated with NH$_4$OAc by a procedure similar to that described for 1C to give 257A. LC/MS m/z 425.4 (M+H)$^+$.

257B. 6-{2-[(S)-1-Amino-2-(4-chloro-1,5-dimethyl-1H-pyrazol-3-yl)-ethyl]-1H-imidazol-4-yl}-1H-indazol-3-ylamine, bis-trifluoroacetic acid salt: 257A (0.495 g, 1.166 mmol) was dissolved in ACN (20 mL) and NCS (0.171 g, 1.283 mmol) was added. The resulting solution was stirred under nitrogen at 80° C. for 4 h then left standing at rt overnight. The reaction mixture was diluted with EtOAc and washed with water and brine, then dried over anhydrous sodium sulfate, filtered and evaporated. The crude product was redissolved in ethanol (5 mL) and hydrazine (0.5 mL, 15.93 mmol) was added. The resulting dark solution was heated at 150° C. for 20 min in a microwave reactor, then evaporated to remove EtOH. The crude product was partitioned between EtOAc and water and extracted with EtOAc. The combined organic extracts were washed with brine, and dried over Na$_2$SO$_4$. The solution was filtered and evaporated, and the resulting residue was purified by reverse phase HPLC to give [(S)-1-[4-(3-amino-1H-indazol-6-yl)-1H-imidazol-2-yl]-2-(4-chloro-1,5-dimethyl-1H-pyrazol-3-yl)-ethyl]-carbamic acid tert-butyl ester. LC/MS m/z 471.1 (M+H)$^+$. $^1$H NMR (500 MHz, DMSO-d$_6$) δ ppm 8.05 (1H, s), 7.85 (1H, d, J=8.2 Hz), 7.67 (2H, s), 7.35 (1H, d, J=8.2 Hz), 4.96-5.14 (1H, m), 3.74 (3H, s), 3.31 (2H, d, J=6.6 Hz), 2.02 (3H, s), 1.33 (9H, s). This intermediate was treated with TFA in DCM to give 257B as an off-white solid. LC/MS m/z 371.1 (M+H)$^+$.

257C. Example 257 was prepared from 62B and 257B by a similar procedure to 62C. LC/MS m/z 603.0 (M+H)$^+$.

Example 258

(E)-N-{(S)-1-[4-(3-Amino-1H-indazol-6-yl)-5-chloro-1H-imidazol-2-yl]-2-phenyl-ethyl}-3-[5-chloro-2-(5-trifluoromethyl-tetrazol-1-yl)-phenyl]-acrylamide, trifluoroacetic acid salt 258A. (E)-3-[5-Chloro-2-(5-trifluoromethyl-tetrazol-1-yl)-phenyl]-acrylic acid tert-butyl ester: To PPh$_3$ (2.483 g, 9.47 mmol) and CCl$_4$ (15 mL) cooled to 0° C. were added TEA (0.605 mL, 4.34 mmol) and TFA (0.274 mL, 3.55 mmol) and the solution was stirred for 10 min before 4-chloro-2-iodoaniline (1 g, 3.95 mmol) was added and the reaction was heated at reflux overnight. The reaction mixture was cooled to rt and evaporated. The resulting residue was dissolved in hexanes, filtered, and concentrated. The resulting yellow oil was dissolved in AcOH (15 mL). Sodium azide (0.7 g, 10.77 mmol) was added and the reaction was heated at 70° C. for 3 h. The solvent was removed under vacuum and the resulting residue was purified by flash chromatography to give a mixture of 1-(4-chloro-2-iodo-phenyl)-5-trifluoromethyl-1H-tetrazole and N-(4-chloro-2-iodo-phenyl)-2,2,2-trifluoro-acetamide. For the tetrazole intermediate, $^1$H NMR (400 MHz, CHLOROFORM-D) δ ppm 7.35 (d, J=8.34 Hz, 1H) 7.59 (dd, J=8.59, 2.27 Hz, 1H) 8.06 (d, J=2.27 Hz, 1H). This mixture of 1-(4-chloro-2-iodo-phenyl)-5-trifluoromethyl-1H-tetrazole (0.4 g, 1.068 mmol) and N-(4-chloro-2-iodo-phenyl)-2,2,2-trifluoro-acetamide (0.2 g, 0.572 mmol) was dissolved in DMF (2 mL) and degassed. K$_2$CO$_3$ (0.4 g, 2.89 mmol), DABCO (4.55 mg, 0.041 mmol), palladium(II) acetate (4.80 mg, 0.021 mmol), and tert-butyl acrylate (1 mL, 6.89 mmol) were added and the mixture was heated at 110° C. in a sealed tube overnight. The reaction mixture was evaporated and purified by flash chromatography to give 258A as a brown oil. LC/MS m/z 375.3 (M+H)$^+$. $^1$H NMR (400 MHz, Chloroform-d) δ ppm 1.46 (s, 9H) 6.36 (d, J=15.94 Hz, 1H) 6.81 (d, J=15.39 Hz, 1H) 7.33 (d, J=8.79 Hz, 1H) 7.58 (dd, J=8.24, 2.20 Hz, 1H) 7.83 (d, J=2.20 Hz, 1H).

258B. (E)-3-[5-Chloro-2-(5-trifluoromethyl-tetrazol-1-yl)-phenyl]-acrylic acid: To 258A (0.35 g, 0.934 mmol) in dioxane (4 mL) was added 4N HCl in dioxane (8 mL) and the solution was stirred for 2 days. Solvent was removed under vacuum and 258B was obtained as a tan solid. LC/MS m/z 319.2 (M+H)$^+$. $^1$H NMR (400 MHz, DMSO-d$_6$) δ ppm 6.71-6.76 (d, J=15.912 Hz, 1H) 6.79-6.86 (d, J=15.91 Hz, 1H) 7.83-7.87 (dd, J=8.34, 2.27 Hz, 1H) 7.88-7.93 (d, J=8.59 Hz, 1H) 8.33 (d, J=2.27 Hz, 1H) 12.76 (bs, 1H).

258C. Example 258 was prepared from 258B and 110A by a similar procedure to 62C. LC/MS m/z 653.2 (M+H)$^+$. $^1$H NMR (400 MHz, CD$_3$OD) δ ppm 3.17-3.24 (m, 2H) 5.23 (t, J=7.97 Hz, 1H) 6.71-6.77 (d, J=15.39 Hz, 1H) 6.77-6.84 (d, J=15.39 Hz, 1H) 7.13-7.21 (m, 3H) 7.21-7.28 (m, 2H) 7.48 (d, J=9.89 Hz, 1H) 7.61-7.65 (d, J=8.79 Hz, 1H) 7.66-7.73 (m, 2H) 7.93 (d, J=8.79 Hz, 1H) 8.04 (d, J=2.20 Hz, 1H).

Example 259

(E)-N-{(S)-1-[5-(3-Amino-1,2-benzisoxazol-6-yl)-5-chloro-1H-imidazol-2-yl]-2-phenyl-ethyl}-3-(5-chloro-2-tetrazol-1-yl-phenyl)-acrylamide, trifluoroacetic acid salt 259A. {(S)-1-[5-Chloro-4-(4-cyano-3-fluoro-phenyl)-1-(2-trimethylsilanyl-ethoxymethyl)-1H-imidazol-2-yl]-2-phenyl-ethyl}-carbamic acid tert-butyl ester: To a suspension of sodium hydride (60% dispersion; 0.091 g, 2.268 mmol) in DMF (4.54 mL) ID (1.0 g, 2.268 mmol) was added in portions over a 20 min period. Gas evolution was observed and the resulting orange-brown suspension was stirred vigorously for 1.5 h. To resulting clear, orange solution was added SEM-Cl (0.421 mL, 2.382 mmol) to give a yellow suspension. After 30 min, the reaction was quenched with water and extracted with EtOAc (2×). The combined organic layers were washed with brine, dried over Na$_2$SO$_4$, filtered and concentrated to give a pale, yellow solid weighing 1.26 g. Purification by column chromatography on silica gel (gradient elution 0-25% EtOAc/Hex) gave a 0.929 g (72%) of 259A as a white solid). LCMS m/z 571.3 (M+H)$^+$ and 573.3 (M+2+H)$^+$. $^1$H NMR (400 MHz, CDCl$_3$) δ: 7.94 (dd, J=8.1, 1.5 Hz, 1H), 7.90 (dd, J=10.8, 1.5 Hz, 1H), 7.65 (dd, J=8.1, 6.8 Hz, 1H), 7.26-7.19 (m, 3H), 7.15-7.12 (m, 2H), 5.31-5.28 (m, 2H), 5.18-5.13 (m, 1H), 4.92 (d, J=11.4 Hz, 1H), 3.40-3.35 (m, 2H), 3.28-3.21 (m, 2H), 1.40 (s, 9H), 0.90-0.76 (m, 2H), −0.03 (s, 9H). $^{19}$F NMR (376 MHz, CDCl$_3$) δ: −106.35.

259B. {(S)-1-[4-(3-Amino-1,2-benzisoxazol-6-yl)-5-chloro-1-(2-trimethylsilanyl-ethoxymethyl)-1H-imidazol-2-yl]-2-phenyl-ethyl}-carbamic acid tert-butyl ester: A modification of the procedure described by Palermo (*Tetrahedron Letters*, 1996, 37 (17), 2885.) was used. To a flame-dried flask containing a suspension of potassium tert-butoxide (0.913 g, 8.13 mmol) in DMF (16.27 mL) was added acetohydroxamic acid (0.610 g, 8.13 mmol). The resulting suspension was stirred vigorously at RT for 40 min and then 259A (0.929 g, 1.627 mmol) was added. The resulting yellow suspension was stirred vigorously at rt for 19 h. The reaction was poured onto ice, diluted with water and sat. NH$_4$Cl, and extracted with EtOAc (2×). The combined organic layers were washed with brine, dried over Na$_2$SO$_4$, filtered and concentrated to approximately 100 mL of EtOAc. Methanol (50 mL) was added and the reaction was stirred for 3 h and then concentrated to give a clear, viscous yellow oil weighing 1.10 g. Purification by column chromatography on silica gel (gradient elution 0-100% EtOAc:Hex) gave 0.712 g (75%) of 259B as a white foam. LCMS m/z 584.3 (M+H)$^+$ and 586.3 (M+2+H)$^+$. $^1$H NMR (500 MHz, CDCl$_3$) δ: 8.05 (s, 1H), 7.94 (dd, J=8.2, 1.1 Hz, 1H), 7.57 (d, J=8.2 Hz, 1H), 7.27-7.16 (m, 5H), 5.45-5.41 (m, 1H), 5.29 (d, J=11.6 Hz, 1H), 5.19-5.15 (m, 1H), 4.92 (d, J=11.0 Hz, 1H), 4.42 (d, 2H, NH$_2$), 3.45-3.37 (m, 2H), 3.35-3.23 (m, 2H), 1.40 (s, 9H), 0.91-0.85 (m, 1H), 0.82-0.76 (m, 1H), −0.03 (s, 9H).

259C. 6-[2-((S)-1-Amino-2-phenyl-ethyl)-5-chloro-1H-imidazol-4-yl]-1,2-benzisoxazol-3-ylamine: A clear, colorless solution of 259B (0.547 g, 0.936 mmol) and PPTS (0.259 g, 1.030 mmol) in MeOH (1.873 mL) was warmed to 60° C. for 8 h. The reaction was concentrated to give a white solid, and the solid was partitioned between water and EtOAc. The layers were separated and the aqueous layer was extracted with EtOAc (1×). The combined organic layers were washed with brine, dried over Na$_2$SO$_4$, filtered and concentrated to give a clear, colorless residue 0.525 g. LCMS m/z 454.4 (M+H)$^+$. The residue was dissolved in 20% TFA/CH$_2$Cl$_2$ (40 mL) to give a clear, colorless solution. After 30 min the reaction was concentrated. Purification by prep reverse phase HPLC (MeOH:water:0.1% TFA) gave a clear, residue weighing 0.339 g. LCMS m/z 354.4 (M+H)$^+$ and 356.3 (M+2+H)$^+$. $^1$H NMR (500 MHz, MeOD$_4$) δ: 7.81 (d, J=8.2 Hz, 1H), 7.62 (s, 1H), 7.54 (dd, J=8.2, 1.1 Hz, 1H), 7.32-7.25 (m, 3H), 7.15 (d, J=8.2 Hz, 2H), 4.59 (dd, J=9.4, 6.3 Hz, 1H), 3.39 (dd, J=13.2, 9.4 Hz, 1H), 3.34-3.32 (m, 1H). This residue was partitioned between EtOAc and sat. NaHCO$_3$ and the layers separated. The aqueous layer was extracted with EtOAc (1×). The combined organic layers were washed with brine, dried over Na$_2$SO$_4$, filtered, and concentrated to 0.213 g (64%) of 259C as a pale, yellow foam.

259D. Example 259 was prepared as the TFA salt by coupling 62B with 259C according to the procedure described in 62C. LCMS m/z 586.5 (M+H)$^+$ and 588.4 (M+2+H)$^+$ and 590.4 (M+4+H)$^+$. $^1$H NMR (500 MHz, DMSO-d$_6$) δ: 9.84 (s, 1H), 8.82 (d, J=8.2 Hz, 1H), 7.92 (d, J=2.2 Hz, 1H), 7.86 (d, J=8.2 Hz, 1H), 7.74 (dd, J=8.8, 2.2 Hz, 1H), 7.70 (d, J=8.8 Hz, 1H), 7.66 (s, 1H), 7.58 (d, J=8.2 Hz, 1H), 7.26-7.23 (m, 2H), 7.19-7.15 (m, 3H), 6.84 (d, J=16.0 Hz, 1H), 6.78 (d, J=16.0 Hz, 1H), 5.21 (dd, J=15.1, 8.0 Hz, 1H), 3.22 (d, J=13.7, 6.6 Hz, 1H), 3.06 (dd, J=13.2, 8.2 Hz, 1H).

Example 260

N-{(S)-1-[5-(3-Amino-1,2-benzisoxazol-6-yl)-5-chloro-1H-imidazol-2-yl]-2-phenyl-ethyl}-3-(5-chloro-2-tetrazol-1-yl-phenyl)-propionamide, trifluoroacetic acid salt Example 260 was prepared as the TFA salt by coupling 63A with 259C according to the procedure described in 62C. LCMS m/z 588.4 (M+H)$^+$ and 590.4 (M+2+H)$^+$ and 592.4 (M+4+H)$^+$. $^1$H NMR (400 MHz, CD$_3$OD) δ: 9.44 (s, 1H), 7.80 (d, J=8.4 Hz, 1H), 7.61 (s, 1H), 7.53 (dd, J=8.4, 1.3 Hz, 1H), 7.50 (d, J=2.2 Hz, 1H), 7.43 (dd, J=8.4, 2.2 Hz, 1H), 7.38 (d, J=8.8 Hz, 1H), 7.25-7.15 (m, 3H), 7.13-7.10 (m, 2H), 5.14 (t, J=7.9 Hz, 1H), 3.20 (dd, J=13.6, 7.9 Hz, 1H), 3.11 (dd, J=13.6, 7.9 Hz, 1H), 2.69-2.65 (m, 2H), 2.46 (t, J=7.0 Hz, 2H).

The following additional examples in Table 1 were prepared using a combination of the methods described above and other methods known to one skilled in the art of organic synthesis which should be apparent to the skilled practioner.

Example 261

(E)-N-{(S)-1-[5-(3-Amino-1-methyl-1H-indazol-6-yl)-5-chloro-1H-imidazol-2-yl]-2-phenyl-ethyl}-3-(5-chloro-2-tetrazol-1-yl-phenyl)-acrylamide Example 262

6-(5-Chloro-2-{(S)-1-[(E)-3-(5-chloro-2-tetrazol-1-yl-phenyl)-acryloylamino]-2-phenyl-ethyl}-1H-imidazol-4-yl)-2-oxo-1,2-dihydro-quinoline-4-carboxylic acid amide Example 263

[4-(5-Chloro-2-{1-[(E)-3-(5-chloro-2-tetrazol-1-yl-phenyl)-acryloylamino]-2-thiazol-2-yl-ethyl}-1H-imidazol-4-yl)-phenyl]-carbamic acid methyl ester Example 264

(4-{5-Chloro-2-[1-[(E)-3-(5-chloro-2-tetrazol-1-yl-phenyl)-acryloylamino]-2-(2-methyl-2H-pyrazol-3-yl)-ethyl]-1H-imidazol-4-yl}-phenyl)-carbamic acid methyl ester Example 265

(4-{5-Chloro-2-[1-[(E)-3-(5-chloro-2-tetrazol-1-yl-phenyl)-acryloylamino]-2-(5-methyl-2H-pyrazol-3-yl)-ethyl]-1H-imidazol-4-yl}-phenyl)-carbamic acid methyl ester Example 266

[4-(5-Chloro-2-{2-(4-chloro-5-methyl-2H-pyrazol-3-yl)-1-[(E)-3-(5-chloro-2-tetrazol-1-yl-phenyl)-acryloylamino]-ethyl}-1H-imidazol-4-yl)-phenyl]-carbamic acid methyl ester Example 267

(4-{5-Chloro-2-[(S)-1-[(E)-3-(5-chloro-2-tetrazol-1-yl-phenyl)-acryloylamino]-2-(6-oxo-1,6-dihydro-pyridin-3-yl)-ethyl]-3H-imidazol-4-yl}-phenyl)-carbamic acid methyl ester 267A. (4-{2-[(S)-1-Amino-2-(6-methoxy-pyridin-3-yl)-ethyl]-5-chloro-3H-imidazol-4-yl}-phenyl)-carbamic acid methyl ester was prepared from commercially available 6-methoxypyridine-3-carboxyaldehyde by similar procedures to 82A-F. To a solution of this intermediate (50 mg, 0.124 mmol) in CHCl$_3$ (5 mL) was added TMS-I (0.017 mL, 0.124 mmol) and the reaction was heated at 60° C. for 72 h. The reaction mixture was quenched with methanol and evaporated. The resulting residue was washed with sodium sulfite and purified by reverse phase HPLC to give 267A. LC/MS m/z 388.2 (M+H)$^+$.

267B. Example 267: The title compound was prepared from 267A and 62B by a similar procedure to 62E. LC/MS m/z 620.3 (M+H)$^+$.

Example 268

[4-(5-Chloro-2-{(S)-1-[(E)-3-(5-chloro-2-tetrazol-1-yl-phenyl)-acryloylamino]-3-oxo-3-piperazin-1-yl-propyl}-1H-imidazol-4-yl)-phenyl]-carbamic acid methyl ester Example 268 was prepared from Example 170 by a similar procedure to Example 174 using piperazine in place of morpholine. LC/MS m/z 639.2 (M+H)$^+$.

Example 269

6-(5-Chloro-2-{(S)-2-(4-chloro-1-methyl-1H-pyrazol-3-yl)-1-[(E)-3-(5-chloro-2-tetrazol-1-yl-phenyl)-acryloylamino]-ethyl}-1H-imidazol-4-yl)-2-oxo-1,2-dihydro-quinoline-4-carboxylic acid, trifluoroacetic acid salt Example 269 was prepared by hydrolysis of Example 270 with NaOH in MeOH. LCMS m/z 679.1 (M+H)$^+$. $^1$H NMR (400 MHz, CD$_3$OD) δ: 3.27-3.31 (m, 2H), 3.80 (s, 3H), 5.37-5.41 (m, 1H), 6.74 (d, J=15.7 Hz, 1H), 7.10 (d, J=15.7

Hz, 1H), 7.16 (s, 1H), 7.47 (d, J=8.8 Hz, 1H), 7.56 (d, J=8.8 Hz, 1H), 7.59 (s, 1H), 7.65 (dd, J=2.2 Hz, 8.8 Hz, 1H), 7.86 (dd, J=2.2 Hz, 8.8 Hz, 1H), 7.97 (d, J=2.2 Hz, 1H), 8.71 (d, J=2.2 Hz, 1H), 9.51 (s, 1H).

Example 270

6-(5-Chloro-2-{(S)-2-(4-chloro-1-methyl-1H-pyrazol-3-yl)-1-[(E)-3-(5-chloro-2-tetrazol-1-yl-phenyl)-acryloylamino]-ethyl}-1H-imidazol-4-yl)-2-oxo-1,2-dihydro-quinoline-4-carboxylic acid methyl ester, trifluoroacetic acid salt Example 270 was prepared as the TFA salt according to the following sequence. Imidazole formation according to the procedure described in 82E, by replacing 82D with 271B. Chlorination of the imidazole and pyrrazole rings by a similar procedure to 82F. Deprotection of the Boc group according to the procedure described in 1E. Amide coupling according to the procedure described in 62C gave Example 270. LC/MS m/z 693.3 (M+H)$^+$. $^1$H NMR (400 MHz, CD$_3$OD) δ: 3.28-3.34 (m, 2H), 3.81 (s, 3H), 4.01 (s, 3H), 5.38-5.41 (m, 1H), 6.74 (d, J=15.7 Hz, 1 H), 7.10 (d, J=15.7 Hz, 1H), 7.15 (s, 1H), 7.47 (d, J=8.3 Hz, 1H), 7.56 (d, J=8.3 Hz, 1H), 7.60 (s, 1H), 7.65 (dd, J=2.2 Hz, 8.3 Hz, 1H), 7.87 (dd, J=2.2 Hz, 8.3 Hz, 1H), 7.97 (d, J=2.2 Hz, 1H), 8.65 (d, J=2.2 Hz, 1H), 9.51 (s, 1H).

Example 271

6-{2-[(S)-1-[(E)-3-(5-Chloro-2-tetrazol-1-yl-phenyl)-acryloylamino]-2-(1-methyl-1H-pyrazol-3-yl)-ethyl]1H-imidazol-4-yl}-2-oxo-1,2-dihydro-quinoline-4-carboxylic acid, trifluoroacetic acid salt 271A. 6-Acetyl-2-oxo-1,2-dihydro-quinoline-4-carboxylic acid methyl ester: 271A was prepared according to the procedure described in 274A, replacing 1-(4-chloro-2-iodophenyl)-1H-tetrazole with 6-bromo-2-oxo-1,2-dihydro-quinoline-4-carboxylic acid methyl ester. LCMS m/z 246.2.0 (M+H)$^+$. $^1$H NMR (400 MHz, CDCl$_3$) δ: 2.68 (s, 3H), 4.05 (s, 3H), 7.34 (s, 1H), 7.47 (d, J=8.8 Hz, 1H), 8.19 (dd, J=1.7 Hz, 8.8 Hz, 1H), 9.08 (d, J=1.7 Hz, 1H), 12.23 (s, 1H).

271B. 6-(2-Bromo-acetyl)-2-oxo-1,2-dihydro-quinoline-4-carboxylic acid methyl ester: To a refluxing suspension of copper(II) bromide (0.730 g, 3.27 mmol) in ethyl acetate (6.0 mL) was added a suspension of 271A (0.444 g, 1.635 mmol) in chloroform (6.0 mL). After 5 h, the reaction was cooled to rt and concentrated. The residue was dissolved in DMF and then water was added to give a brown suspension. The solid was collected by filtration, washed with water, and air-dried. The solid was suspended in chloroform, sonicated, and filtered to give a 271B (0.43 g, 60%, 74% pure by HPLC) as a brown solid. LCMS m/z 324.0 (M+H)$^+$ and 326.0 (M+2+H)$^+$. $^1$H NMR (400 MHz, DMSO-d$_6$) δ: 3.95 (s, 3H), 4.89 (s, 2H), 7.01 (d, J=2.2 Hz, 1H), 7.44 (d, J=8.8 Hz, 1H), 8.16 (dd, J=2.2 Hz, 8.8 Hz, 1H), 8.78 (d, J=2.2 Hz, 1H), 12.47 (s, 1H).

271C. Example 271 was prepared as the TFA salt according to the following sequence. Imidazole formation according to the procedure described in 82E, by replacing 82D with 271B. Deprotection of the Boc group according to the procedure described in 1E. Hydrolysis of the ester according to the procedure described in 62B. Amide coupling according to the procedure described in 62C gave Example 271. LCMS m/z 611.3 (M+H)$^+$. $^1$HNMR (400 MHz, CD$_3$OD) δ: 3.31-3.48 (m, 2H), 3.81 (s, 3H), 5.40-5.44 (m, 1H), 6.12 (d, J=2.2 Hz, 1H), 6.75 (d, J=15.4 Hz, 1H), 7.14 (d, J=15.4 Hz, 1H), 7.20 (s, 1H), 7.49-7.51 (m, 2H), 7.58 (d, J=8.2 Hz, 1H), 7.68 (dd, J=2.2 Hz, 8.8 Hz, 1H), 7.77 (s, 1H), 7.86 (dd, J=2.2 Hz, 8.8 Hz, 1H), 7.99 (d, J=2.2 Hz, 1H), 8.68 (d, J=2.2 Hz, 1H), 9.51 (s, 1H).

Examples 272 and 273 in Table 1 were prepared by a similar procedure to Example 164.

Example 272

1-[2-((E)-2-{(S)-1-[4-(3-Amino-1H-indazol-6-yl)-5-chloro-1H-imidazol-2-yl]-2-phenyl-ethylcarbamoyl}-vinyl)-4-chloro-phenyl]-1H-pyrazole-4-carboxylic acid Example 273

1-[2-(2-{(S)-1-[4-(3-Amino-1H-indazol-6-yl)-5-chloro-1H-imidazol-2-yl]-2-phenyl-ethylcarbamoyl}-ethyl)-4-chloro-phenyl]-1H-pyrazole-4-carboxylic acid Example 274

[4-(5-Chloro-2-{(S)-1-[(E)-3-(5-chloro-2-tetrazol-1-yl-phenyl)-but-2-enoylamino]-2-phenyl-ethyl}-1H-imidazol-4-yl)-phenyl]-carbamic acid methyl ester, trifluoroacetic acid salt 274A. 1-(5-Chloro-2-tetrazol-1-yl-phenyl)-ethanone: A flame-dried flask containing 1-(4-chloro-2-iodophenyl)-1H-tetrazole (2.15 g, 7.01 mmol), from the alternative synthesis of 62B, and bis(triphenylphosphine)palladium(II) chloride (0.246 g, 0.351 mmol) was purged with argon. Next, degassed toluene (23.38 mL) and tributyl(1-ethoxyvinyl)tin (2.61 mL, 7.72 mmol) were added. The resulting suspension was warmed to reflux to give a clear, yellow-orange solution. After 1.5 h, the dark suspension was cooled to rt, filtered through a 0.45 micron glass membrane filter, eluting with EtOAc, and concentrated to give a clear, orange-brown liquid. A heterogeneous mixture of this liquid in a 1:1 THF: 1.0 N HCl (100 mL) was stirred vigorously. After 3 h, EtOAc was added and the layers were separated. The organic layer was washed with saturated KF and the resulting suspension was filtered to remove the solid. The layers were separated and the organic layer was washed with brine, dried over Na$_2$SO$_4$, filtered, and concentrated to give a black solid. Purification by flash chromatography gave 274A (1.14 g, 73%) as an off-white solid. LCMS m/z 223.0 (M+H)$^+$ and 225.0 (M+2+H)$^+$. $^1$H NMR (400 MHz, CDCl$_3$) δ: 8.92 (s, 1H), 7.84 (d, J=2.2 Hz, 1H), 7.70 (dd, J=8.4, 2.2 Hz, 1H), 7.46 (d, J=8.4 Hz, 1H), 2.46 (s, 3H).

274B. (E)-3-(5-Chloro-2-tetrazol-1-yl-phenyl)-but-2-enoic acid: A 3:1 E-enolate:Z-enolate mixture, separable by reverse phase hplc, was prepared by reacting 274A and tert-butyl 2-(dimethoxyphosphoryl)acetate according to the procedure for 62A. Deprotection of the E-enolate according to the procedure for 1E gave 274B. LCMS m/z 265.0 (M+H)$^+$. $^1$H NMR (400 MHz, CD$_3$OD) δ: 9.48 (s, 1H), 7.64 (dd, J=8.8, 2.2 Hz, 1H), 7.61 (d, J=8.8 Hz, 1H), 7.60 (d, J=1.8 Hz, 1H), 5.71-5.70 (m, 1H), 2.11 (d, J=1.1 Hz, 3H).

274C. Example 274 was prepared as the TFA salt by coupling 274B with the free base of 52B according to procedure described for 62C. LCMS m/z 617.2 (M+H)$^+$. $^1$H NMR (500 MHz, CD$_3$OD) δ: 9.43 (s, 1H), 7.63 (dd, J=8.2, 2.2 Hz, 1H), 7.59 (d, J=8.2 Hz, 1H), 7.56 (d, J=2.2 Hz, 1H), 7.53 (bs, 4H), 7.29-7.26 (m, 2H), 7.22-7.19 (m, 1H), 7.15 (d, J=7.2 Hz, 2H), 5.85 (d, J=1.1 Hz, 1H), 5.18 (t, J=8.0 Hz, 1H), 3.75 (s, 3H), 3.27-3.17 (m, 2H), 1.96 (d, J=1.1 Hz, 3H).

Example 275

[4-(5-Chloro-2-{(S)-1-[(Z)-3-(5-chloro-2-tetrazol-1-yl-phenyl)-but-2-enoylamino]-2-phenyl-ethyl}-1H-imidazol-4-yl)-phenyl]-carbamic acid methyl ester Example 275 was prepared by the procedures described for 274B and 274C, using the Z-enolate produced in 274B. LCMS m/z 617.2 (M+H)$^+$.

Example 276

[4-(2-{(S)-1-[(E)-3-(5-Chloro-2-tetrazol-1-yl-phenyl)-acryloylamino]-2-phenyl-ethyl}-5-methyl-1H-imidazol-4-yl)-phenyl]-carbamic acid methyl ester, trifluoroacetic acid salt 276A. [(S)-1-(5-Methyl-1H-imidazol-2-yl)-2-phenyl-ethyl]-carbamic acid tert-butyl ester: A mixture of ((S)-1-Benzyl-2-oxo-ethyl)-carbamic acid tert-butyl ester (7.25 g, 29.0 mmol), pyruvic aldehyde (40% in water, 15 mL, 98 mmol) and 7N ammonia (50 mL) in 20 mL MeOH was allowed to stir at rt overnight. Solvent was removed under vacuum to leave a crude product as a brown solid. LC/MS m/z 302.3 (M+H)$^+$.

276B. [(S)-1-(4-Bromo-5-methyl-1H-imidazol-2-yl)-2-phenyl-ethyl]-carbamic acid tert-butyl ester: To the crude product from 276A dissolved in chloroform (250 mL) was added NBS (5.22 g, 29 mmol) at 0° C. After stirring for 3 h, the reaction mixture was washed with water, brine, and dried over sodium sulfate, filtered, and solvent was removed under vacuum. The crude product was passed through a pad of silica gel eluting with 3:7 ethyl acetate:hexanes to give the desired product. LC/MS m/z 382.2 (M+H)$^+$. $^1$H NMR (400 MHz, CDCl$_3$) d ppm 1.35 (s, 9H) 2.06 (s, 3H) 3.15-3.27 (m, 2H) 4.79 (q, J=7.03 Hz, 1H) 5.37 (d, J=7.91 Hz, 1H) 7.09 (d, J=6.59 Hz, 2H) 7.17-7.27 (m, 3H) 10.20 (s, br, 1H).

276C. {4-[2-((S)-1-tert-Butoxycarbonylamino-2-phenyl-ethyl)-5-methyl-1H-imidazol-4-yl]-phenyl}-carbamic acid methyl ester: To a solution of 276B (510 mg, 1.341 mmol) in DME (15 mL) were added 4-(methoxycarbonylamino)-phenylboronic acid (392 mg, 2.012 mmol) and sodium carbonate (355 mg, 3.35 mmol). The mixture was degassed and purged with nitrogen, and bis(tri-t-butylphosphine)palladium(0) (34.3 mg, 0.067 mmol) was added at rt. The reaction mixture was stirred under nitrogen at 85° C. for 12 h. The mixture was filtered and solvent was removed from the filtrate to leave 276C as the crude product. LC/MS m/z 451.2 (M+H)$^+$.

276D. {4-[2-((S)-1-Amino-2-phenyl-ethyl)-5-methyl-1H-imidazol-4-yl]-phenyl}-carbamic acid methyl ester, bis-trifluoroacetic acid salt: 276D was prepared from 276C by a similar procedure to 1E. LC/MS m/z 351.2 (M+H)$^+$.

276E. Example 276: The title compound was prepared from 276D and 62B by a similar procedure to 62E. LC/MS m/z 583.0 (M+H)$^+$. $^1$H NMR (500 MHz, CD$_3$OD) δ ppm 2.36 (s, 3H) 3.24-3.35 (m, 1H, over lapped with solvent peak) 3.42 (dd, J=13.75, 7.70 Hz, 1H) 3.75 (s, 3H) 5.28 (t, J=8.25 Hz, 1H) 6.72 (d, J=15.95 Hz, 1H) 7.12 (d, J=15.40 Hz, 1H) 7.18 (d, J=7.15 Hz, 2H) 7.26 (t, J=7.15 Hz, 1H) 7.28-7.34 (m, 2H) 7.36 (d, J=8.80 Hz, 2H) 7.54-7.62 (m, 3H) 7.68 (dd, J=8.25, 2.20 Hz, 1H) 7.97 (d, J=2.20 Hz, 1H) 9.51 (s, 1H).

Example 277

[4-(2-{(S)-1-[3-(5-Chloro-2-tetrazol-1-yl-phenyl)-propionylamino]-2-phenyl-ethyl}-5-methyl-1H-imidazol-4-yl)-phenyl]-carbamic acid methyl ester, trifluoroacetic acid salt Example 277 was prepared from 276D and 63A by a similar procedure to 62C. LC/MS m/z 585.1 (M+H)$^+$. $^1$H NMR (500 MHz, CD$_3$OD) δ ppm 2.36 (s, 3H) 2.50-2.56 (td, J=7.15, 2.75 Hz, 2H) 2.67 (td, J=7.15, 2.75 Hz, 2H) 3.21 (dd, J=13.75, 8.80 Hz, 1H) 3.31 (dd, J=13.75, 8.80 Hz, 1H, overlapped with solvent peak) 3.76 (s, 3H) 5.16 (t, J=8.25 Hz, 1H) 7.12 (d, J=6.60 Hz, 2H) 7.21-7.30 (m, 3H) 7.36 (d, J=8.25 Hz, 2H) 7.42 (d, J=8.25 Hz, 1H) 7.47 (dd, J=8.25, 2.20 Hz, 1H) 7.52 (d, J=2.20 Hz, 1H) 7.60 (d, J=8.25 Hz, 2H) 9.46 (s, 1H).

Example 278

[4-(2-{(S)-1-[(E)-3-(5-Chloro-2-tetrazol-1-yl-phenyl)-acryloylamino]-2-phenyl-ethyl}-1H-imidazol-4-yl)-phenyl]-carbamic acid methyl ester, trifluoroacetic acid salt {4-[2-((S)-1-Amino-2-phenyl-ethyl)-1H-imidazol-4-yl]-phenyl}-carbamic acid methyl ester, bis-trifluoroacetic acid salt, was prepared by TFA/DCM de-protection of 52A. Example 278 was prepared from this intermediate and 62B following a similar procedure to 62C. LC/MS m/z 569 (M+H)$^+$. $^1$H NMR (400 MHz, DMSO) δ ppm 3.20-3.40 (m, 2H) 3.67 (s, 3H) 5.24-5.34 (m, J=7.03 Hz, 1H) 6.75-6.91 (m, 2H) 7.17-7.23 (m, 3H) 7.24-7.30 (m, 2H) 7.54 (d, J=8.35 Hz, 2H) 7.62-7.66 (m, 2H) 7.71-7.80 (m, 2H) 7.94 (d, J=2.20 Hz, 1H) 8.98 (s, 1H) 9.85 (s, 1H).

Example 279

[4-(5-Chloro-2-{(S)-1-[3-(5-chloro-2-tetrazol-1-yl-phenyl)-propynoylamino]-ethyl}-1H-imidazol-4-yl)-phenyl]-carbamic acid methyl ester, trifluoroacetic acid salt Example 279 was prepared from 189A and 254B by a similar procedure to 62C. LC/MS m/z 525 (M+H)$^+$. $^1$H NMR (400 MHz, DMSO) δ 1.42 (d, J=7.03 Hz, 3H), 3.66 (s, 3H), 4.96-5.06 (m, 1H), 7.50-7.63 (m, 5H), 7.86-7.88 (m, J=3.52 Hz, 1H), 8.02 (d, J=1.76 Hz, 1H), 9.39 (d, J=7.47 Hz, 1H), 9.79 (s, 1H) 10.01 (s, 1H).

Example 280

[4-(5-Chloro-2-{(S)-1-[(E)-3-(5-chloro-2-tetrazol-1-yl-phenyl)-acryloylamino]-ethyl}-1H-imidazol-4-yl)-phenyl]-carbamic acid 2-methoxy-ethyl ester, trifluoroacetic acid salt 280A. [4-(2-Bromo-acetyl)-phenyl]-carbamic acid 2-methoxy-ethyl ester: To a stirring solution of 1-(4-aminophenyl)ethanone (1.0 g, 7.40 mmol) and pyridine (0.898 mL, 11.10 mmol) in THF (20 mL), 2-methoxyethyl carbonochloridate (1.128 g, 8.14 mmol) was added. The reaction mixture stirred overnight. The reaction mixture was taken up in EtOAc, washed with water followed by brine, dried over sodium sulfate, filtered, and concentrated to leave a tan solid. This material was dissolved in chloroform and treated with bromine (0.457 mL, 8.88 mmol) at rt. After stirring for 1 h, the reaction mixture was concentrated. LC/MS showed both the desired product and a bis-brominated side-product; this material was carried forward without purification.

280B. (S)-2-tert-Butoxycarbonylamino-propionic acid 2-[4-(2-methoxy-ethoxycarbonylamino)-phenyl]-2-oxo-ethyl ester: To a stirring solution of (S)-2-(tert-butoxycarbonylamino)propanoic acid (1.317 g, 6.96 mmol) in DMF (15 mL) at rt, cesium carbonate (1.360 g, 4.18 mmol) was added. After 30 minutes, 280A (2.2 g, 3.48 mmol) dissolved in DMF (10 mL) was added dropwise and the mixture stirred at rt overnight. The reaction mixture was partitioned between EtOAc and water:brine (1:1). The organic extract was washed with brine, dried over sodium sulfate, filtered, and concentrated to give a yellow solid. LC/MS m/z 351 (M−H)⁻.

280C. Example 280: The title compound was prepared by imidazole formation from 280B by a similar procedure to that described for 82E, chlorination by a similar procedure to 1D, removal of the Boc group using TFA/DCM by a similar procedure to 1E, and subsequent amide coupling with 62B by a similar procedure to 62C. LC/MS m/z 571 (M+H)⁺. ¹H NMR (400 MHz, DMSO-d₆) δ 1.42 (d, J=7.15 Hz, 3H), 3.27 (s, 3H), 3.50-3.61 (m, 2H), 4.18-4.25 (m, 2H), 4.97-5.11 (m, 1H), 6.73-6.84 (m, 1H), 6.85-6.98 (m, 1H), 7.48-7.64 (m, 4H), 7.70-7.79 (m, 2H), 7.91 (d, J=2.20 Hz, 1H), 8.67 (d, J=8.25 Hz, 1H), 9.80-9.93 (m, 2H), 12.48-12.65 (s, 1H).

Example 281

(4-{5-Chloro-2-[1-[(E)-3-(5-chloro-2-tetrazol-1-yl-phenyl)-acryloylamino]-2-(1H-pyrazol-3-yl)-ethyl]-1H-imidazol-4-yl}-phenyl)-carbamic acid methyl ester, trifluoroacetic acid salt Example 281 was prepared using the steps described for Example 131 starting from commercially available 1H-pyrazole-3-carbaldehyde. LC/MS m/z 593.1 (M+H)⁺. ¹H NMR (500 MHz, DMSO-d₆) δ ppm 9.86 (1H, s), 9.78 (1H, s), 8.72 (1H, d, J=8.2 Hz), 7.92 (1H, d, J=2.2 Hz), 7.68-7.77 (2H, m), 7.54-7.61 (2H, m), 7.48-7.54 (2H, m), 7.46 (1H, s), 6.77-6.89 (2H, m), 5.90 (1H, d, J=2.2 Hz), 5.19-5.28 (1H, m), 3.66 (3H, s), 3.22 (1H, dd, J=14.3, 7.7 Hz), 3.07 (1H, dd, J=14.6, 7.4 Hz).

Example 282

(E)-3-(5-Chloro-2-tetrazol-1-yl-phenyl)-but-2-enoic acid {(S)-1-[4-(3-amino-1H-indazol-6-yl)-5-chloro-1H-imidazol-2-yl]-2-phenyl-ethyl}-amide, trifluoroacetic acid salt Example 282 was prepared by coupling 274B and 110A by a similar procedure to 62C. LC/MS m/z 599.2 (M+H)⁺.

Example 283

[4-(6-{(S)-1-[(E)-3-(5-Chloro-2-tetrazol-1-yl-phenyl)-acryloylamino]-2-phenyl-ethyl}-2-oxo-1,2-dihydro-pyridin-4-yl)-phenyl]-carbamic acid methyl ester, trifluoroacetic acid salt Example 283 was prepared by coupling 64B (enantiomer A) and 62B by a similar procedure to 62C. LC/MS m/z 596.3 (M+H)⁺.

Example 284

[4-(2-{(S)-3-tert-Butoxycarbonylamino-1-[(E)-3-(5-chloro-2-tetrazol-1-yl-phenyl)-acryloylamino]-propyl}-5-chloro-1H-imidazol-4-yl)-phenyl]-carbamic acid methyl ester, trifluoroacetic acid salt 284A. {(S)-3-Benzyloxycarbonylamino-3-[4-chloro-5-(4-methoxycarbonylamino-phenyl)-1H-imidazol-2-yl]-propyl}-carbamic acid tert-butyl ester: 284A was prepared from 82D and (S)-2-benzyloxycarbonylamino-4-tert-butoxycarbonylamino-butyric acid by similar procedures to 82E-F. LC/MS m/z 558.3 (M+H)⁺. ¹H NMR (500 MHz, CD₃OD) δ ppm 7.50 (d, J=8.80 Hz, 2H) 7.40 (m, 3H) 7.15-7.27 (m, 4H) 4.98 (q, J=12.65 Hz, 2H) 4.67 (t, J=7.42 Hz, 1H) 3.64 (s, 3H) 3.20 (m, 4H) 2.95-3.09 (m, 2H) 1.95-1.86 (m, 2H) 1.31 (s, 9H).

284B. {4-[2-((S)-1-Amino-3-tert-butoxycarbonylamino-propyl)-5-chloro-1H-imidazol-4-yl]-phenyl}-carbamic acid methyl ester: To a degassed solution of 284A (1.42 g, 2.54 mmol) was added palladium on carbon (0.014 g, 0.127 mmol) and the reaction was stirred at rt under a hydrogen balloon for 5 min. The reaction was filtered through a pad of Celite® and evaporated to give 284B. LC/MS m/z 424.3 (M+H)⁺. ¹H NMR (500 MHz, CD₃OD) δ ppm 7.50 (d, J=8.25 Hz, 2H) 7.39 (d, J=8.80 Hz, 2H) 3.82 (t, J=7.15 Hz, 1H) 3.61 (s, 3H) 3.21 (s, 1H) 3.20 (m, 1H) 2.98 (dd, J=13.20, 6.60 Hz, 2H) 2.55-2.54 (s, 3H) 1.81 (dd, J=13.20, 6.60 Hz, 2H) 1.28 (s, 9H).

284C. Example 284 was prepared from 284B and 62B by a similar procedure to 62C. LC/MS m/z 656.3 (M+H)⁺. ¹H NMR (500 MHz, DMSO-d₆) δ ppm 12.57 (s, 1H) 9.86 (s, 1H) 9.79 (s, 1H) 7.91 (s, 1H) 7.69-7.77 (m, 2H) 7.57-7.61 (m, 2H) 7.51-7.55 (m, 2H) 6.87-6.93 (m, 1H) 6.80-6.86 (m, 1H) 6.77 (t, J=5.50 Hz, 1H) 5.00 (q, J=7.70 Hz, 1H) 3.66 (s, 3H) 2.83-2.98 (m, 2H) 1.94-2.02 (m, 1H) 1.81-1.92 (m, 1H) 1.35 (s, 9H).

Example 285

[4-(2-{(S)-3-Amino-1-[(E)-3-(5-chloro-2-tetrazol-1-yl-phenyl)-acryloylamino]-propyl}-5-chloro-1H-imidazol-4-yl)-phenyl]-carbamic acid methyl ester, bis-trifluoroacetic acid salt Example 285 was prepared from Example 284 by treatment with TFA in DCM to remove the Boc protecting group. LC/MS m/z 556.2 (M+H)⁺.

Examples 286-299 in Table 1 were prepared in a library format from carboxylic acid Example 170 and the appropriate commercially available amines using the following procedure. The acid was dissolved in dried DMF (20 mL) and HATU and DIPEA were added. The mixture was stirred for 2 min and the solution was then added into amines. The reactions were stirred for 6 hours at which point LC-MS showed that the reactions were complete. The samples were transferred into 96 deep-well plate and purified by reverse phase HPLC.

Example 287

(4-{5-Chloro-2-[(S)-1-[(E)-3-(5-chloro-2-tetrazol-1-yl-phenyl)-acryloylamino]-3-(2,6-dimethyl-morpholin-4-yl)-3-oxo-propyl]-1H-imidazol-4-yl}-phenyl)-carbamic acid methyl ester

Example 288

[4-(5-Chloro-2-{(S)-1-[(E)-3-(5-chloro-2-tetrazol-1-yl-phenyl)-acryloylamino]-3-oxo-3-thiomorpholin-4-yl-propyl}-1H-imidazol-4-yl)-phenyl]-carbamic acid methyl ester

Example 289

(4-{5-Chloro-2-[(S)-1-[(E)-3-(5-chloro-2-tetrazol-1-yl-phenyl)-acryloylamino]-3-(3,3-dimethyl-piperidin-1-yl)-3-oxo-propyl]-1H-imidazol-4-yl}-phenyl)-carbamic acid methyl ester

Example 290

(4-{5-Chloro-2-[(S)-1-[(E)-3-(5-chloro-2-tetrazol-1-yl-phenyl)-acryloylamino]-3-(1,3-dihydro-isoindol-2-yl)-3-oxo-propyl]-1H-imidazol-4-yl}-phenyl)-carbamic acid methyl ester

Example 291

[4-(2-{(S)-3-(4-Acetyl-perhydro-1,4-diazepin-1-yl)-1-[(E)-3-(5-chloro-2-tetrazol-1-yl-phenyl)-acryloylamino]-3-oxo-propyl}-5-chloro-1H-imidazol-4-yl)-phenyl]-carbamic acid methyl ester

Example 292

(4-{5-Chloro-2-[(S)-1-[(E)-3-(5-chloro-2-tetrazol-1-yl-phenyl)-acryloylamino]-3-oxo-3-(2-pyridin-4-yl-pyrrolidin-1-yl)-propyl]-1H-imidazol-4-yl}-phenyl)-carbamic acid methyl ester

Example 293

[4-(5-Chloro-2-{(S)-1-[(E)-3-(5-chloro-2-tetrazol-3-yl-phenyl)-acryloylamino]-3-[3-(4-methoxy-phenoxy)-azetidin-1-yl]-3-oxo-propyl}-1H-imidazol-4-yl)-phenyl]-carbamic acid methyl ester

Example 294

(1S,4S)-5-{(S)-3-[5-Chloro-4-(4-methoxycarbonylamino-phenyl)-1H-imidazol-2-yl]-3-[(E)-3-(5-chloro-2-tetrazol-1-yl-phenyl)-acryloylamino]-propionyl}-2,5-diaza-bicyclo[2.2.1]heptane-2-carboxylic acid tert-butyl ester

Example 295

(4-{5-Chloro-2-[(S)-1-[(E)-3-(5-chloro-2-tetrazol-1-yl-phenyl)-acryloylamino]-3-oxo-3-(8-oxo-1,5,6,8-tetrahydro-2H,4H-1,5-methano-pyrido[1,2-a][1,5]diazocin-3-yl)-propyl]-1H-imidazol-4-yl}-phenyl)-carbamic acid methyl ester

Example 296

[4-(5-Chloro-2-{(S)-1-[(E)-3-(5-chloro-2-tetrazol-1-yl-phenyl)-acryloylamino]-3-[4-(2-diethylamino-ethyl)-perhydro-1,4-diazepin-1-yl]-3-oxo-propyl}-1H-imidazol-4-yl)-phenyl]-carbamic acid methyl ester

Example 297

(4-{5-Chloro-2-[(S)-1-[(E)-3-(5-chloro-2-tetrazol-1-yl-phenyl)-acryloylamino]-3-(1-methyl-hexahydro-pyrrolo[1,2-a]pyrazin-2-yl)-3-oxo-propyl]-1H-imidazol-4-yl}-phenyl)-carbamic acid methyl ester

Example 298

(4-{5-Chloro-2-[(S)-1-[(E)-3-(5-chloro-2-tetrazol-1-yl-phenyl)-acryloylamino]-3-oxo-3-((1S,5R)-8-oxo-1,5,6,8-tetrahydro-2H,4H-1,5-methano-pyrido[1,2-a][1,5]diazocin-3-yl)-propyl]-3H-imidazol-4-yl}-phenyl)-carbamic acid methyl ester

Example 299

(4-{5-Chloro-2-[(S)-1-[(E)-3-(5-chloro-2-tetrazol-1-yl-phenyl)-acryloylamino]-3-(1,4-diaza-bicyclo[3.2.2]non-4-yl)-3-oxo-propyl]-1H-imidazol-4-yl}-phenyl)-carbamic acid methyl ester Table 1 below summarizes representative examples of the compounds in the present invention synthesized as described above.

TABLE 1

| Ex. No. | Structure | $(M + H)^+$ |
| --- | --- | --- |
| 1 | 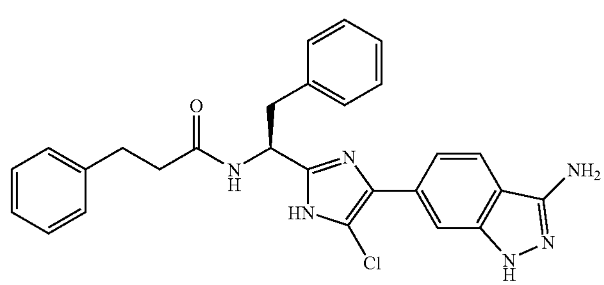 | 485.32 |

TABLE 1-continued

| Ex. No. | Structure | (M + H)+ |
|---------|-----------|----------|
| 2 | 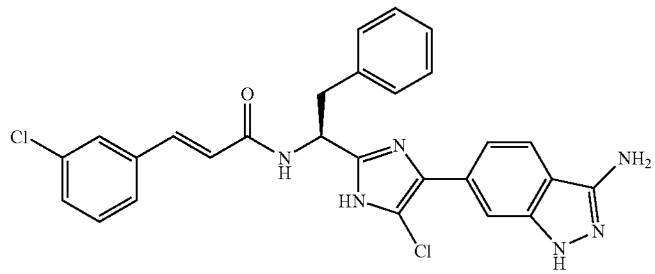 | 517.35 |
| 3 | 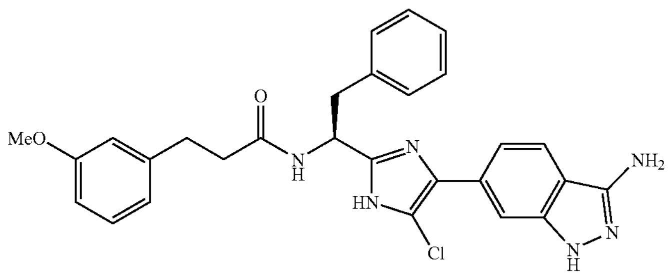 | 515.37 |
| 4 | 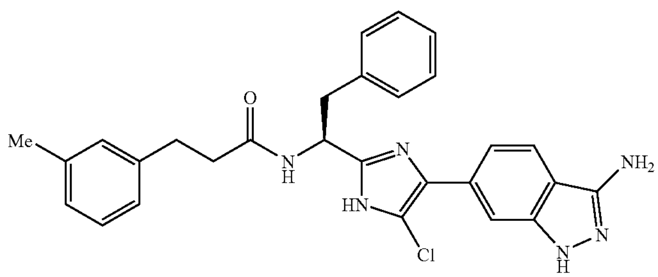 | 499.37 |
| 5 | 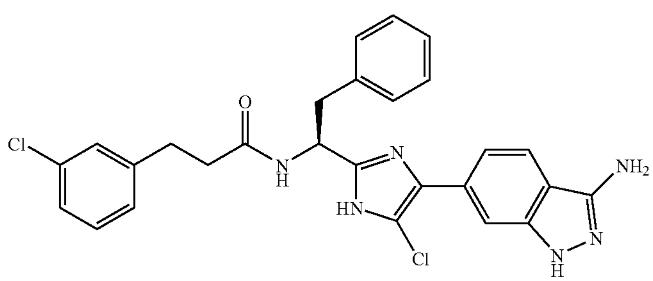 | 519.33 |
| 6 | 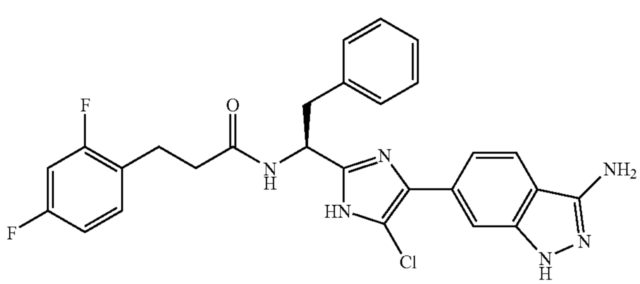 | 521.34 |

TABLE 1-continued

| Ex. No. | Structure | (M + H)+ |
|---|---|---|
| 7 | 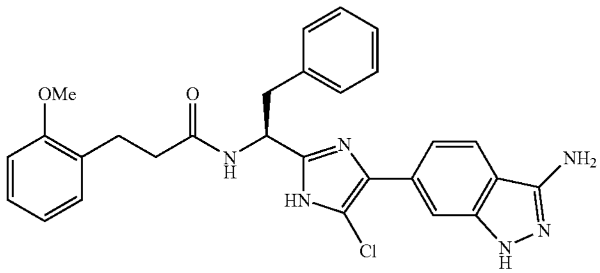 | 515.38 |
| 8 | 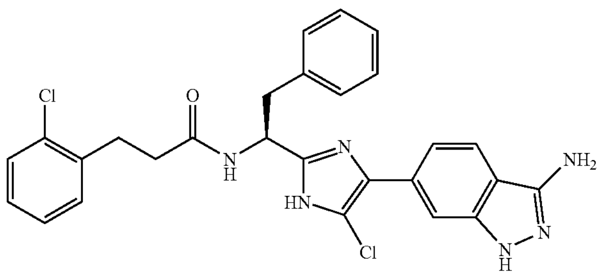 | 519.36 |
| 9 | 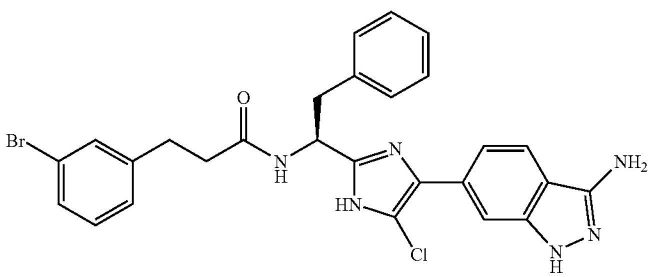 | 564.37 |
| 10 | 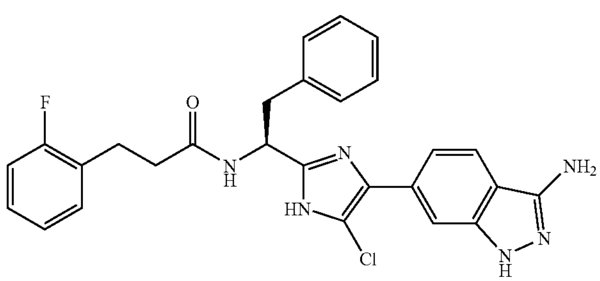 | 503.36 |
| 11 | 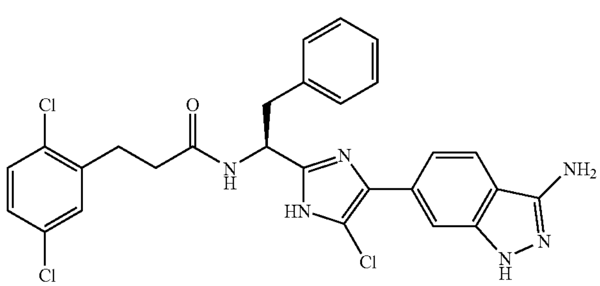 | 553.98 |

TABLE 1-continued

| Ex. No. | Structure | (M + H)+ |
|---|---|---|
| 12 | 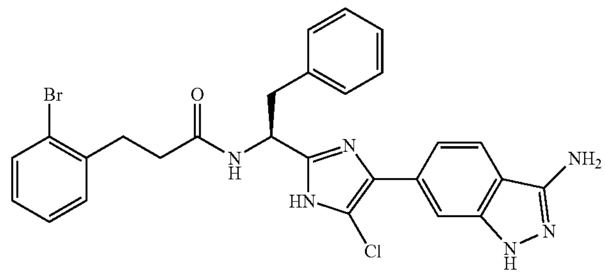 | 563.34 |
| 13 | 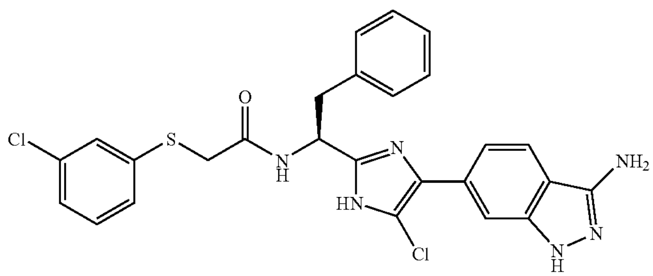 | 537.34 |
| 14 | 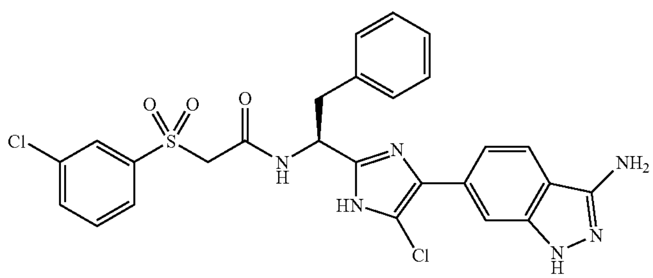 | 569.28 |
| 15 | 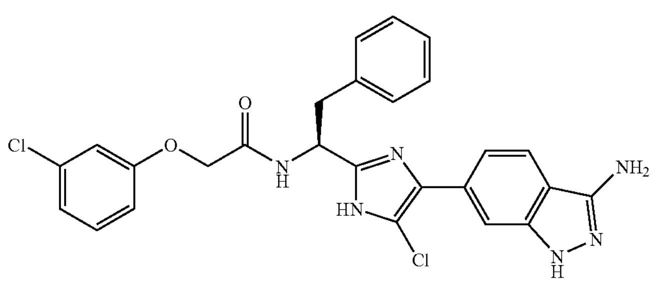 | 521.38 |
| 16 | 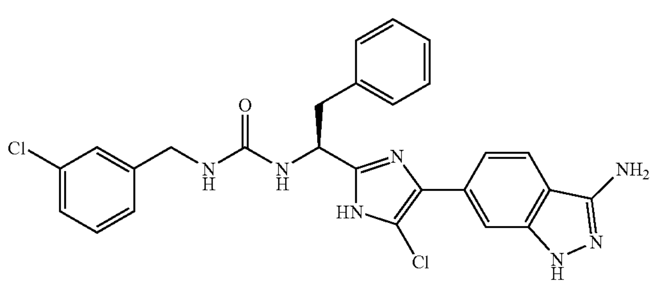 | 520.03 |

TABLE 1-continued

| Ex. No. | Structure | (M + H)+ |
|---|---|---|
| 17 | 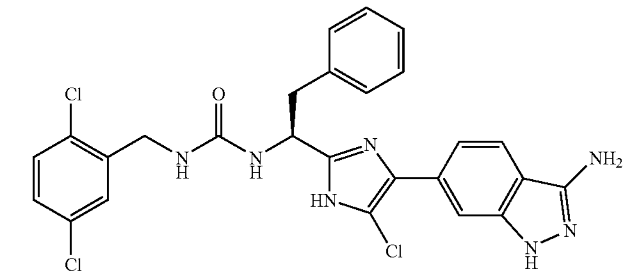 | 554.35 |
| 18 | 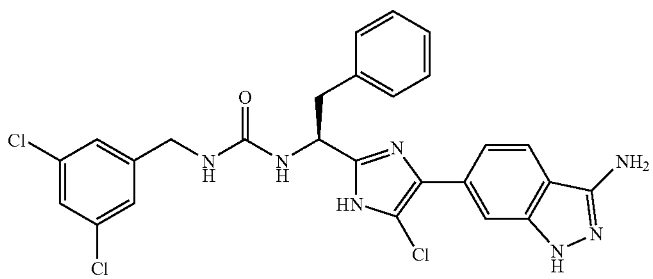 | 554.96 |
| 19 | 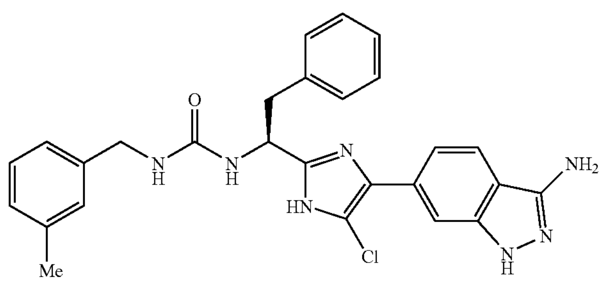 | 499.93 |
| 20 | 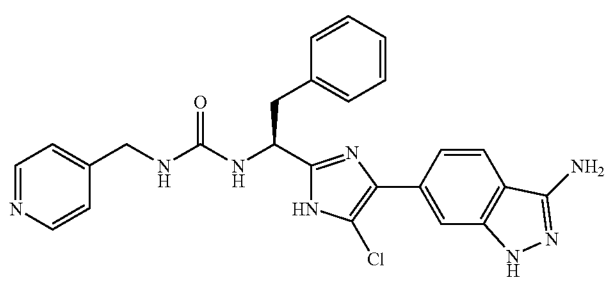 | 487.43 |
| 21 | 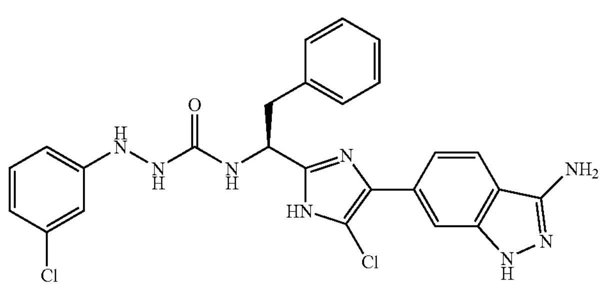 | 521.38 |

TABLE 1-continued

| Ex. No. | Structure | (M + H)+ |
|---|---|---|
| 22 | 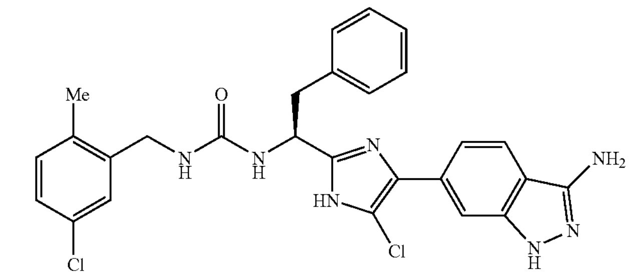 | 534.31 |
| 23 | 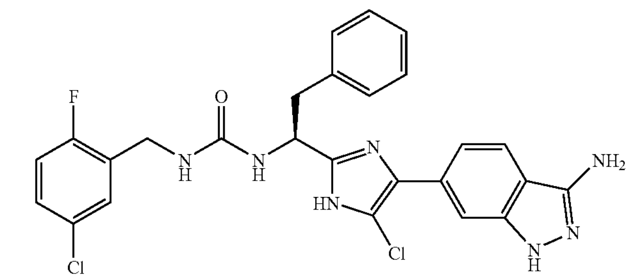 | 538.29 |
| 24 | 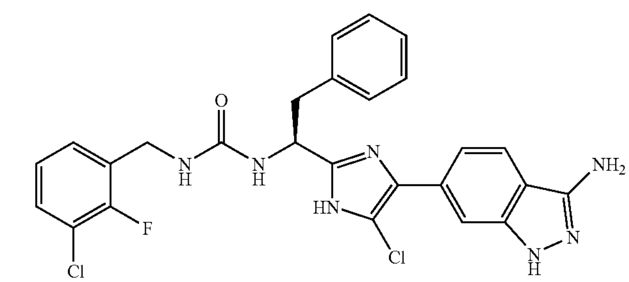 | 537.97 |
| 25 | 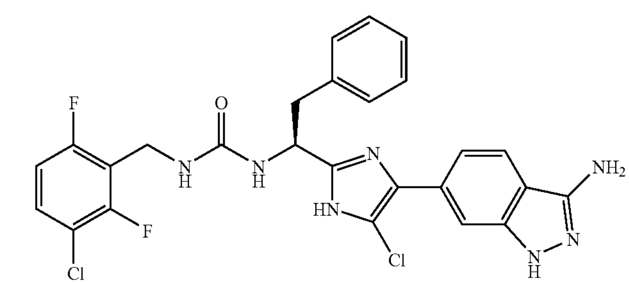 | 556.29 |
| 26 | 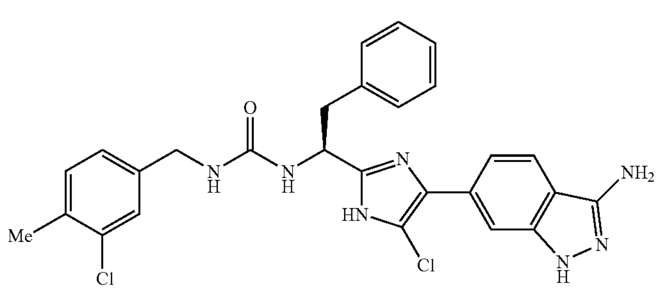 | 534.31 |

TABLE 1-continued

| Ex. No. | Structure | (M + H)+ |
|---|---|---|
| 27 | 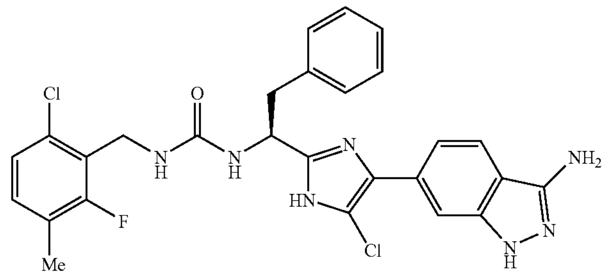 | 552.23 |
| 28 | 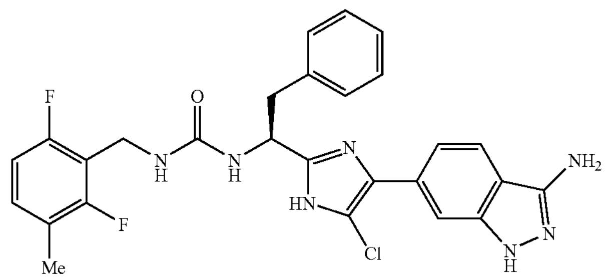 | 536.28 |
| 29 | 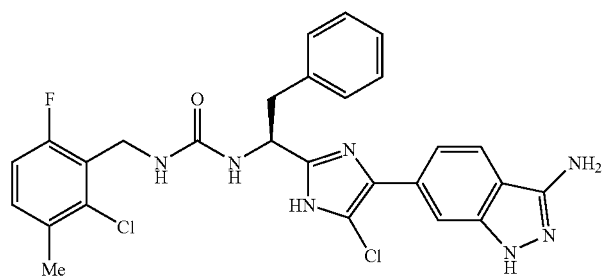 | 552.22 |
| 30 | 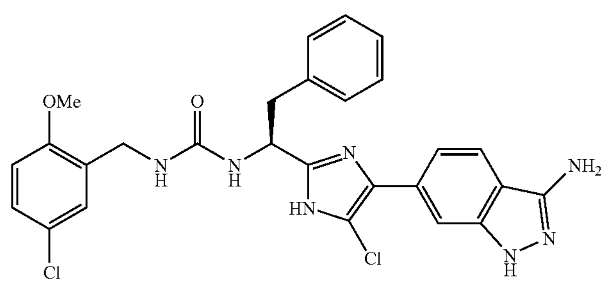 | 549.92 |
| 31 | 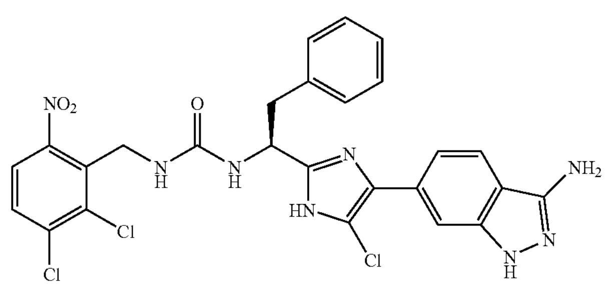 | 598.83 |

TABLE 1-continued

| Ex. No. | Structure | (M + H)+ |
|---|---|---|
| 32 | 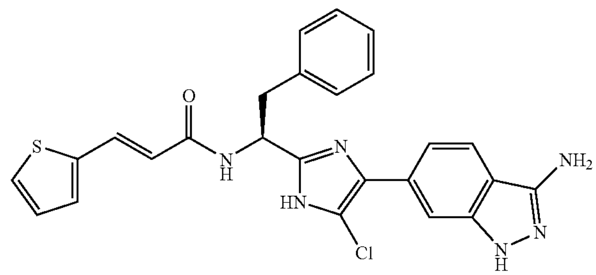 | 489.03 |
| 33 | 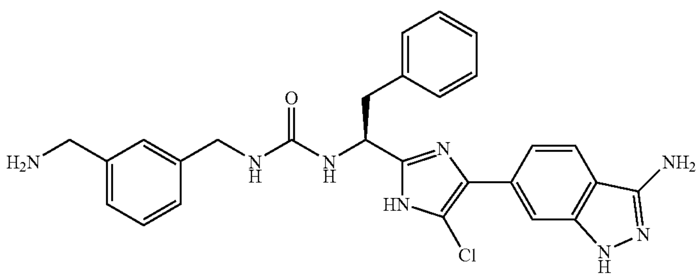 | 515.3 |
| 34 | 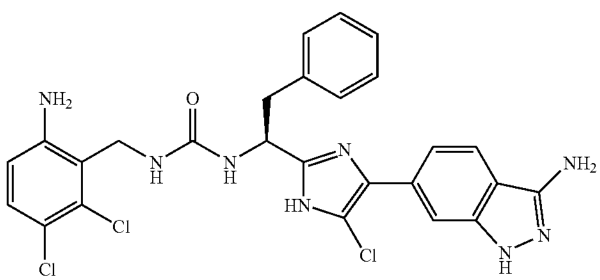 | 569.2 |
| 35 | 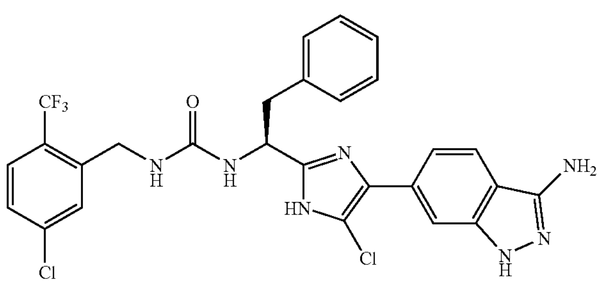 | 588.1 |
| 36 | 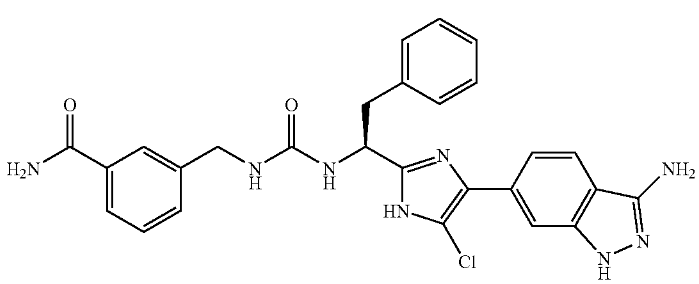 | 529.2 |

TABLE 1-continued

| Ex. No. | Structure | (M + H)+ |
|---|---|---|
| 37 | 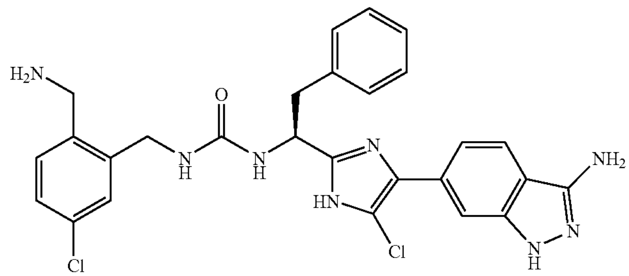 | 549.1 |
| 38 | 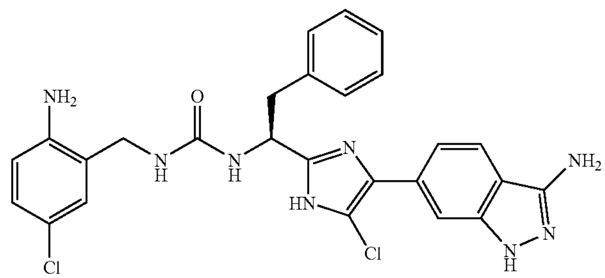 | 535.1 |
| 39 | 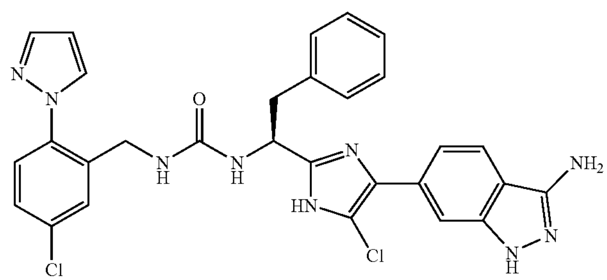 | 586.1 |
| 40 | 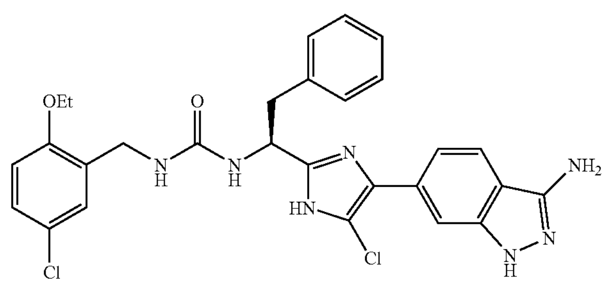 | 564.7 |
| 41 | 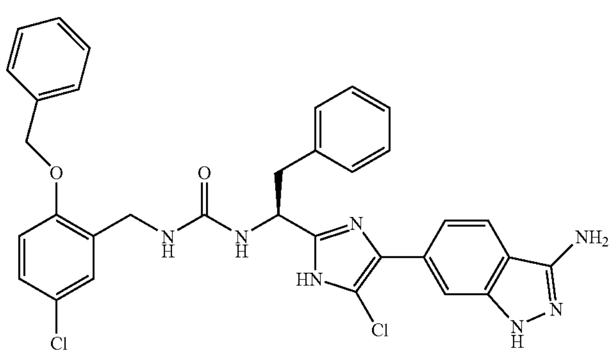 | 626.7 |

TABLE 1-continued

| Ex. No. | Structure | (M + H)+ |
|---|---|---|
| 42 | 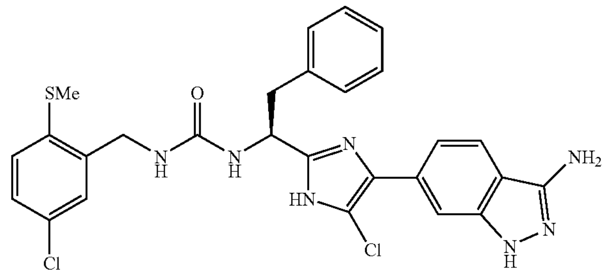 | 566.6 |
| 43 | 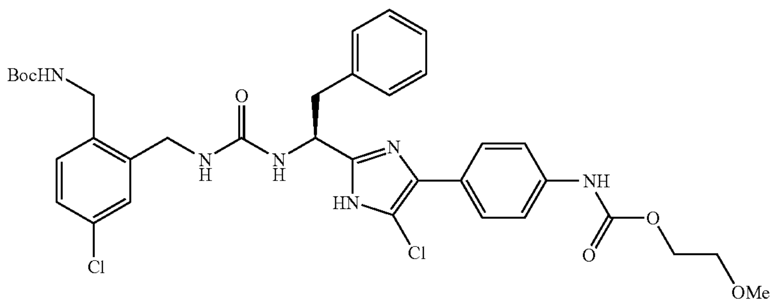 | 711.1 |
| 44 | 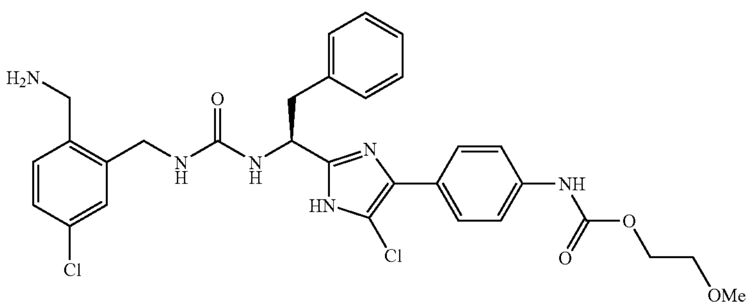 | 611.1 |
| 45 | 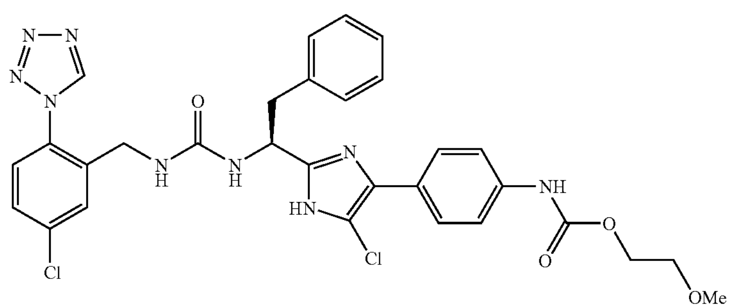 | 650.2 |
| 46 | 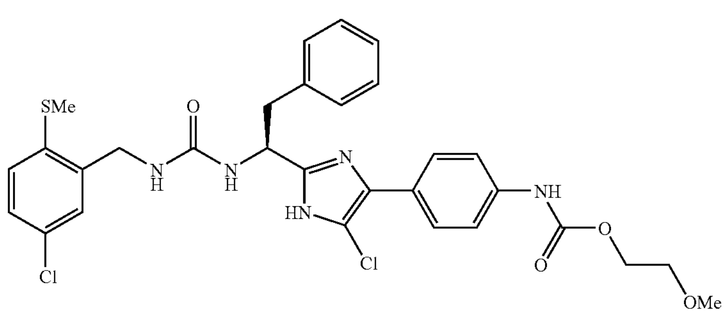 | 628.1 |

TABLE 1-continued

| Ex. No. | Structure | (M + H)+ |
| --- | --- | --- |
| 47 | 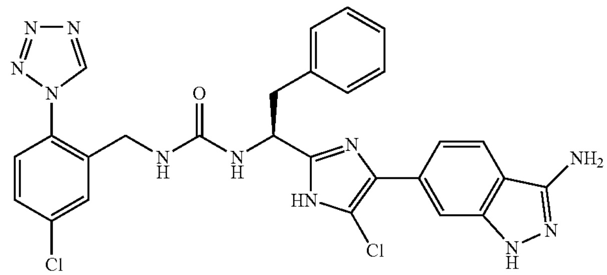 | 588.1 |
| 48 | 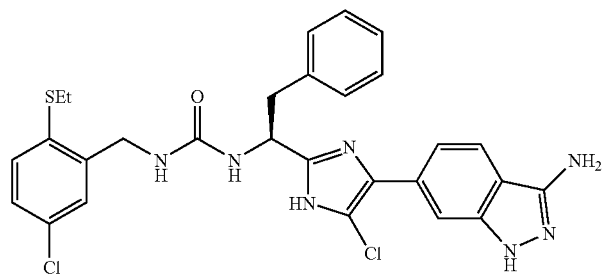 | 580.3 |
| 49 | 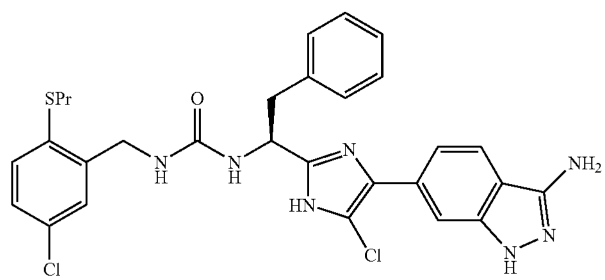 | 594.3 |
| 50 | 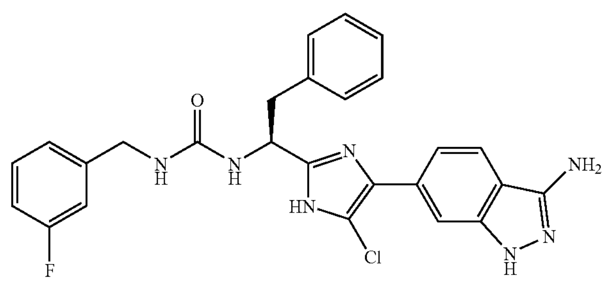 | 504.2 |
| 51 | 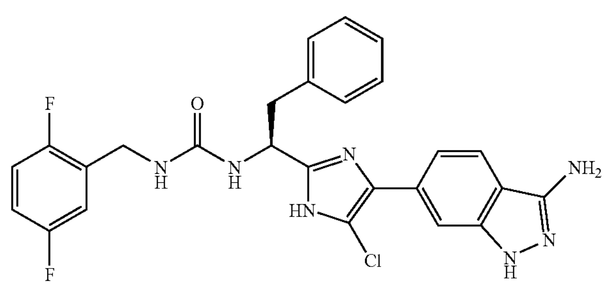 | 522.3 |

TABLE 1-continued

| Ex. No. | Structure | (M + H)+ |
|---|---|---|
| 52 | 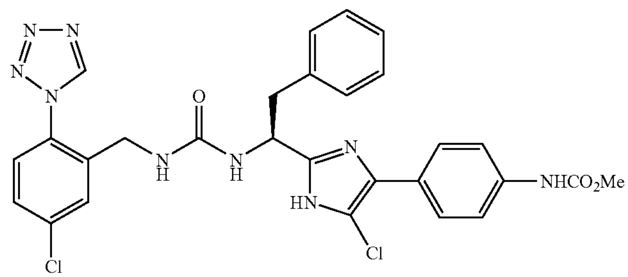 | 606.15 |
| 53 | 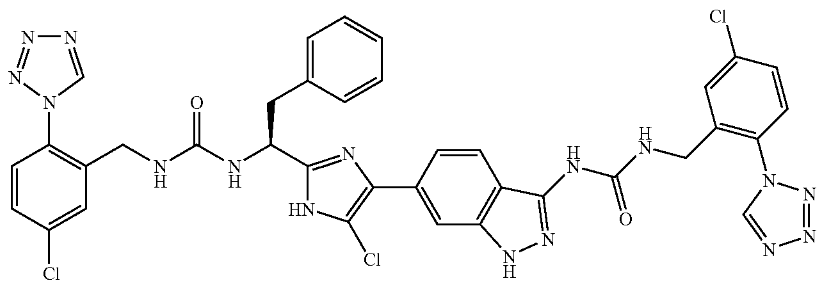 | 823.19 |
| 54 | 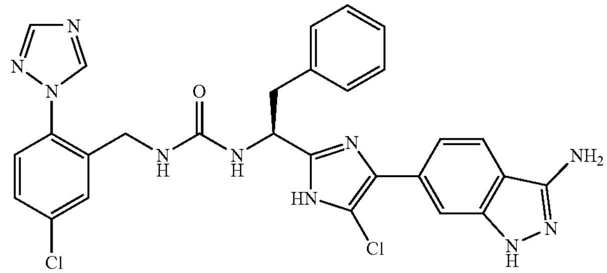 | 587.2 |
| 55 | 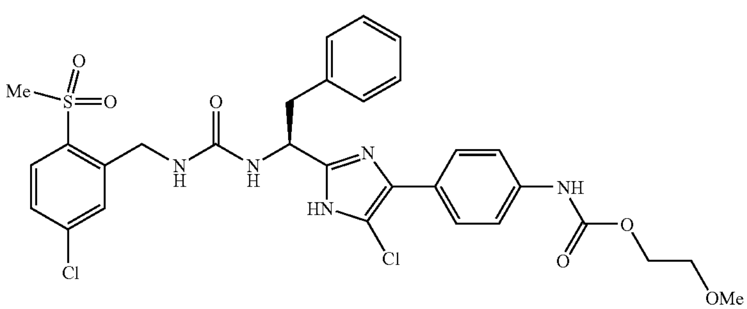 | 660.14 |
| 56 | 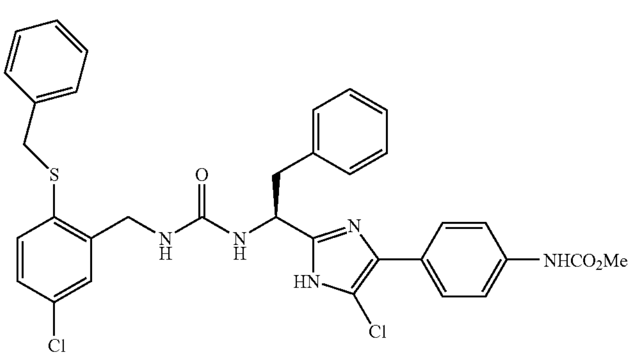 | 660.16 |

TABLE 1-continued
| Ex. No. | Structure | (M + H)+ |
|---|---|---|
| 57 | 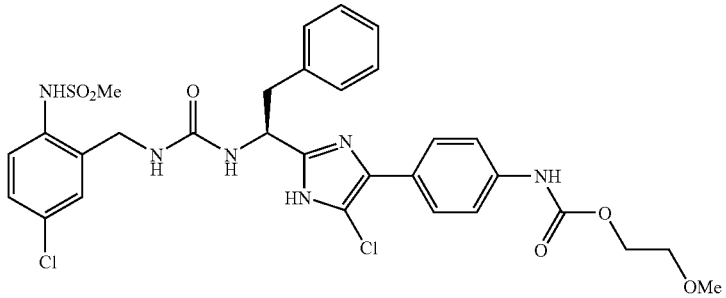 | 675.2 |
| 58 | 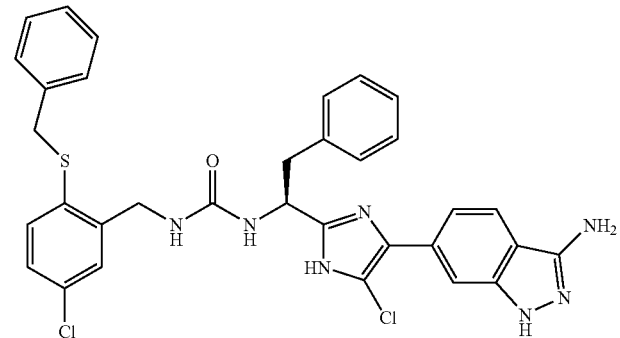 | 642.4 |
| 59 | 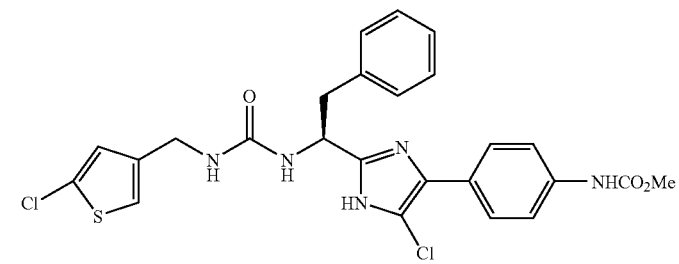 | 544.2 |
| 60 | 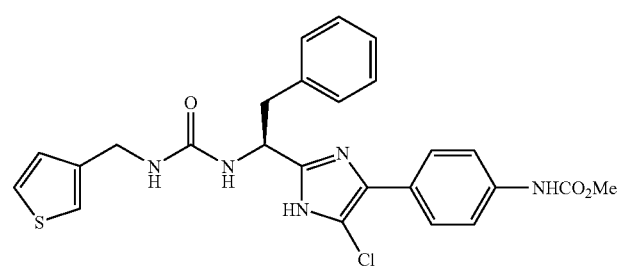 | 510.2 |
| 61 | 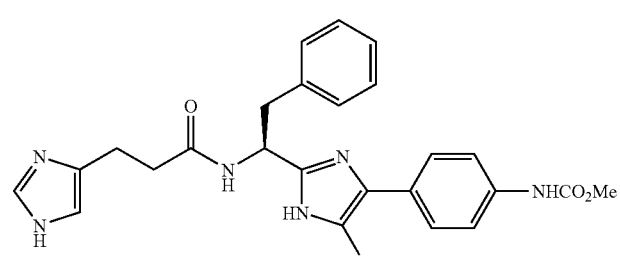 | 493.2 |

TABLE 1-continued

| Ex. No. | Structure | (M + H)+ |
|---|---|---|
| 62 | 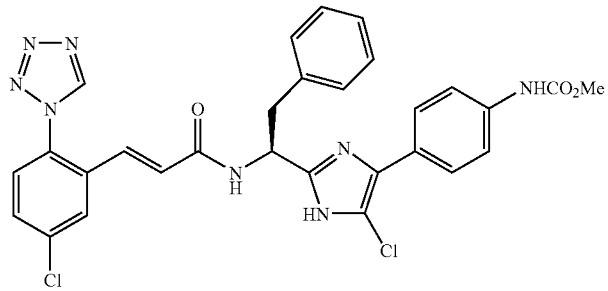 | 603.1 |
| 63 | 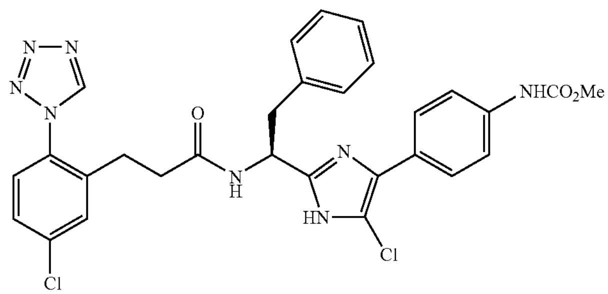 | 605.2 |
| 64 | 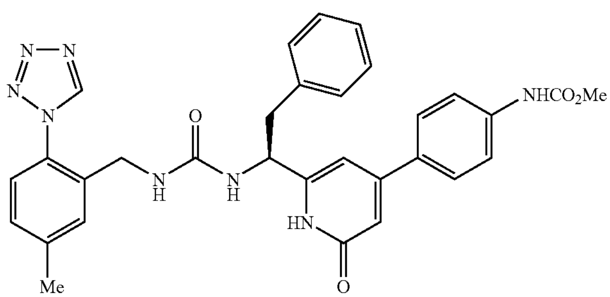 | 579.3 |
| 65 | 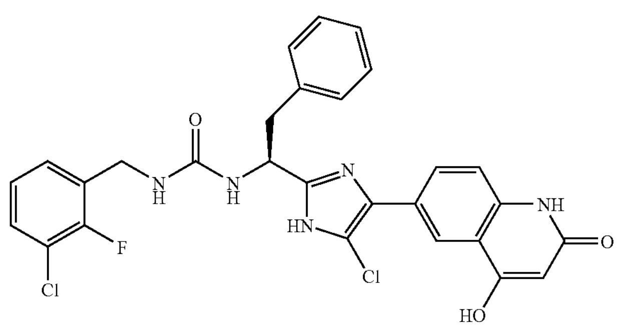 | 566.14 |
| 66 | 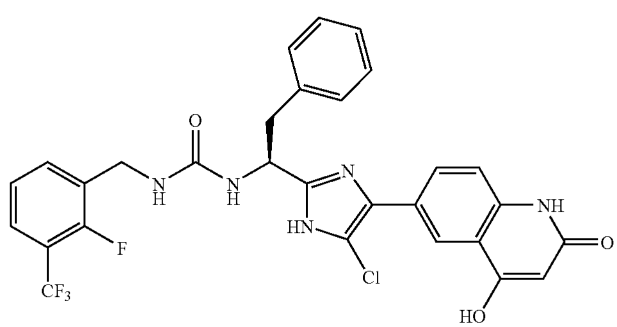 | 600.26 |

TABLE 1-continued

| Ex. No. | Structure | (M + H)+ |
|---|---|---|
| 67 | 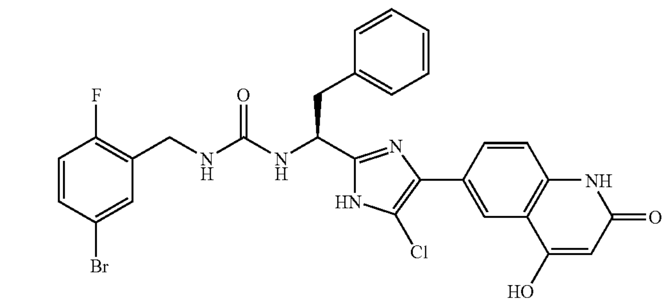 | 612.09 |
| 68 | 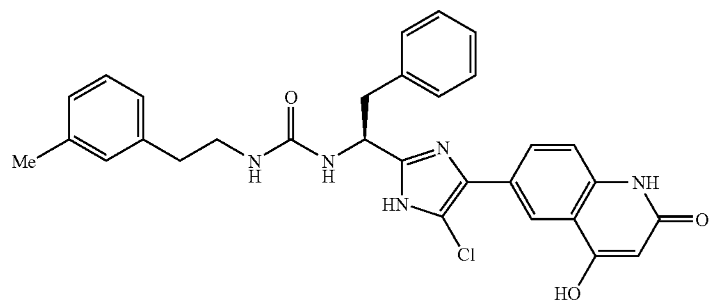 | 542.32 |
| 69 | 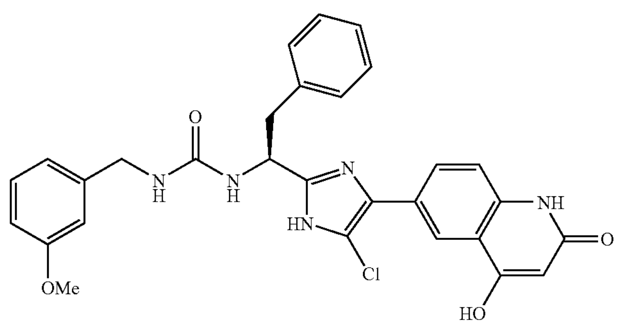 | 544.24 |
| 70 | 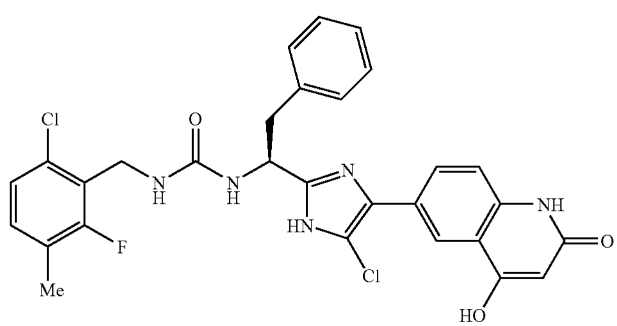 | 580.20 |
| 71 | 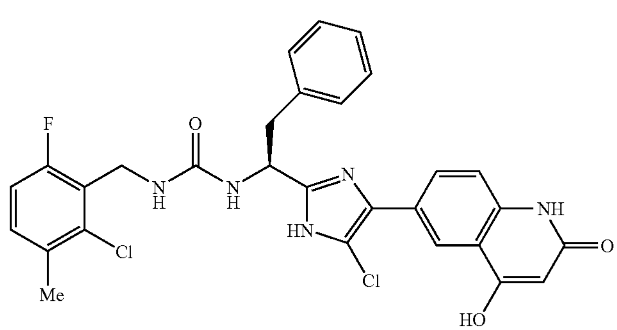 | 580.21 |

TABLE 1-continued
| Ex. No. | Structure | (M + H)+ |
|---|---|---|
| 72 | 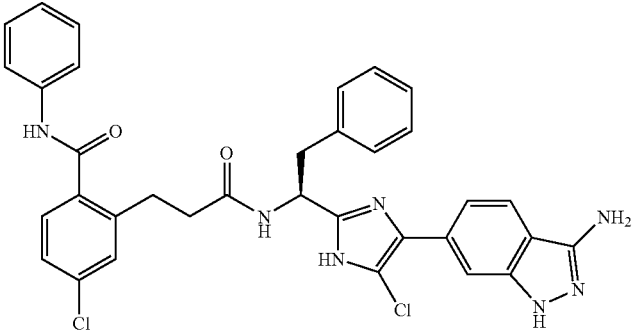 | 638.3 |
| 73 | 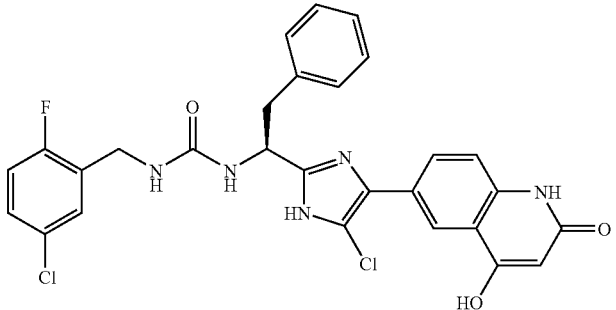 | 566.21 |
| 74 | 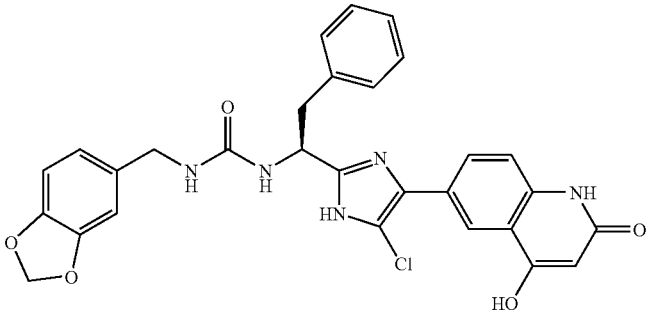 | 558.27 |
| 75 | 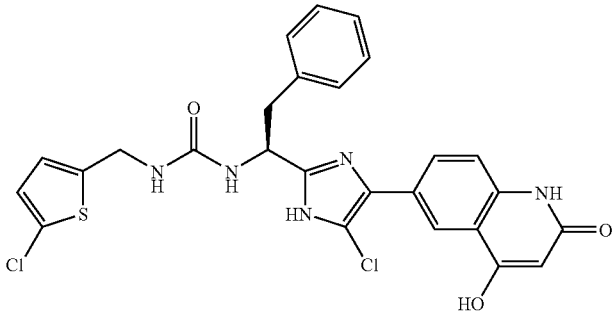 | 554.31 |

TABLE 1-continued

| Ex. No. | Structure | (M + H)+ |
|---|---|---|
| 76 | 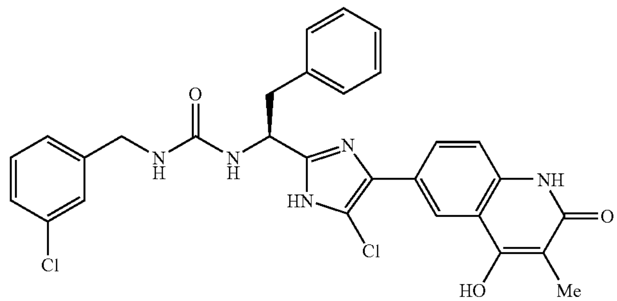 | 562.05 |
| 77 | 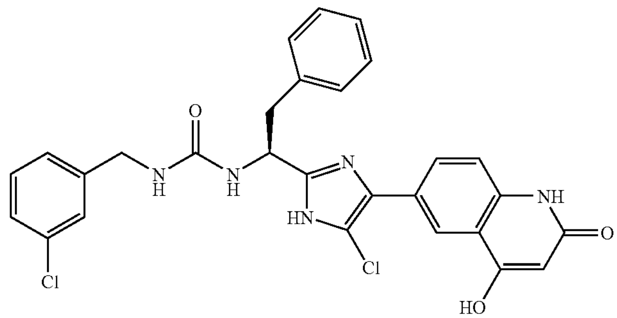 | 548.26 |
| 78 | 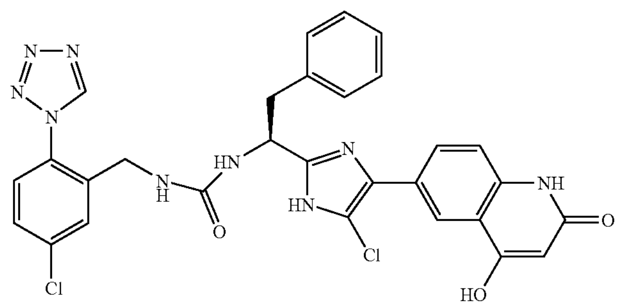 | 616.26 |
| 79 | 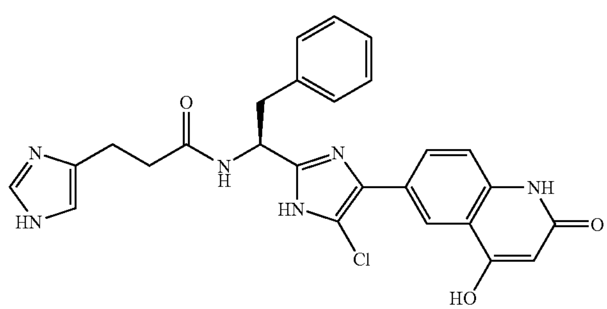 | 502.99 |
| 80 | 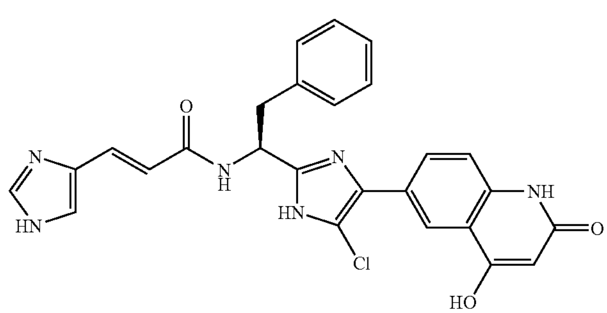 | 500.96 |

TABLE 1-continued
| Ex. No. | Structure | (M + H)+ |
|---|---|---|
| 81 | 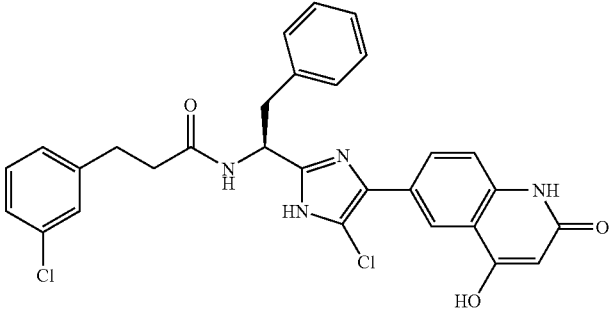 | 547.34 |
| 82 | 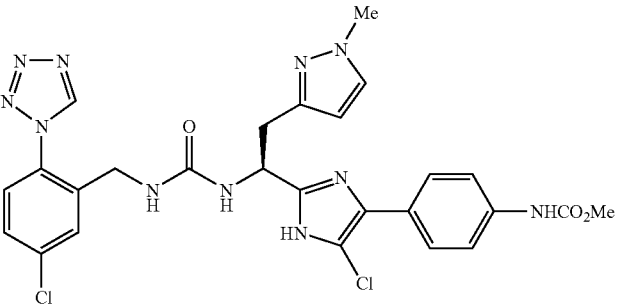 | 610.4 |
| 83 | 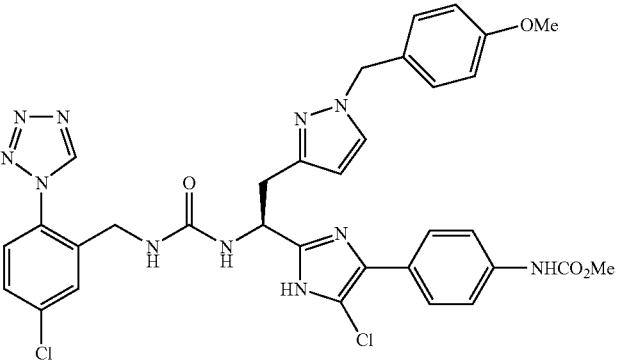 | 716.5 |
| 84 | 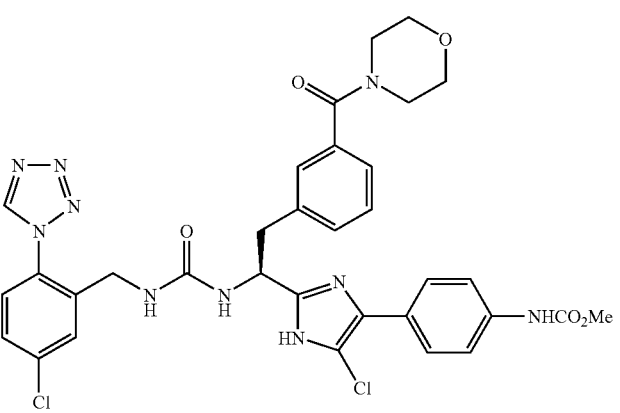 | 719.4 |

TABLE 1-continued

| Ex. No. | Structure | (M + H)+ |
|---|---|---|
| 85 | 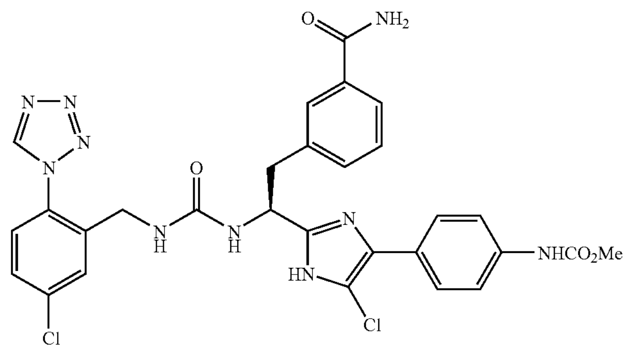 | 649.2 |
| 86 | 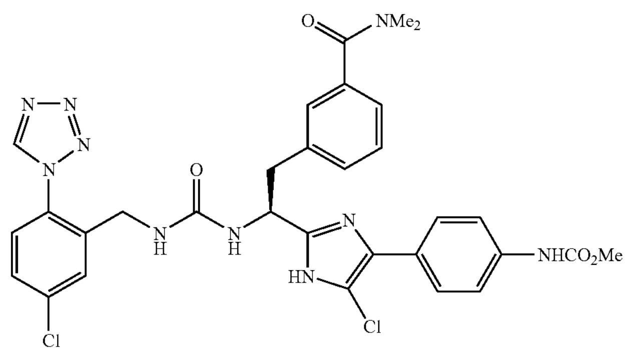 | 677.2 |
| 87 | 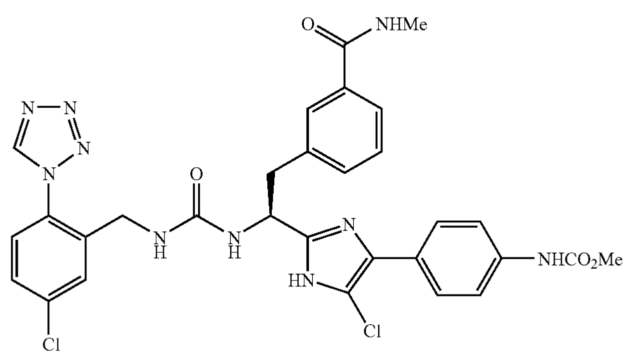 | 663.2 |
| 88 | 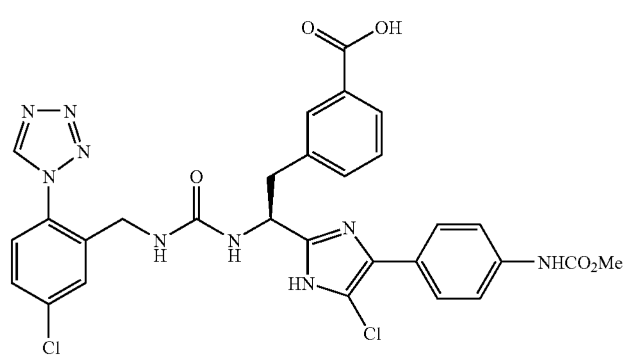 | 650.1 |

| Ex. No. | Structure | (M + H)+ |
| --- | --- | --- |
| 89 | 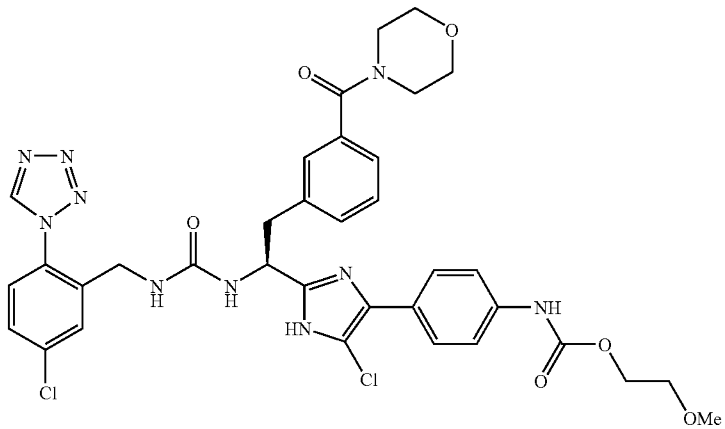 | 763.2 |
| 90 | 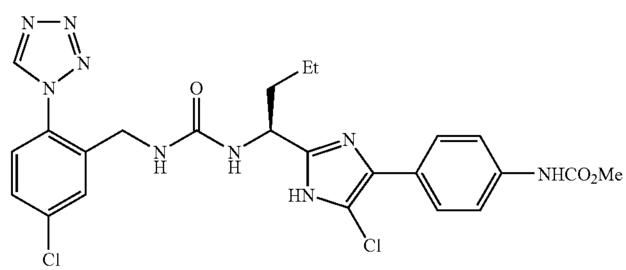 | 558.4 |
| 91 | 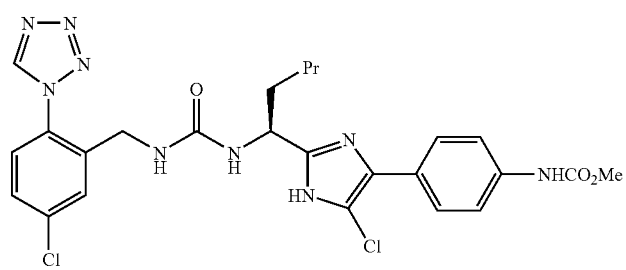 | 572.3 |
| 92 | 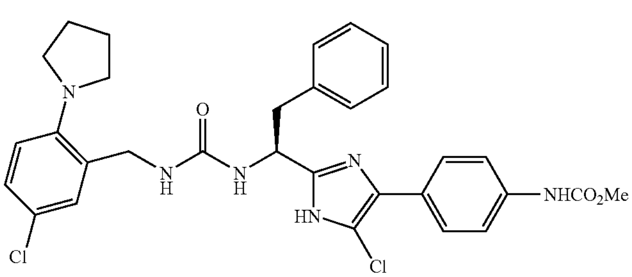 | 607.3 |
| 93 | 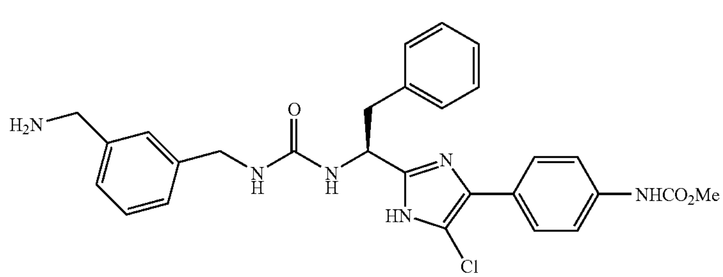 | 532.92 |

TABLE 1-continued

| Ex. No. | Structure | (M + H)+ |
|---|---|---|
| 94 | 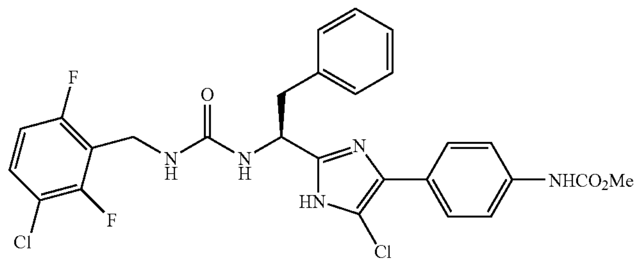 | 573.83 |
| 95 | 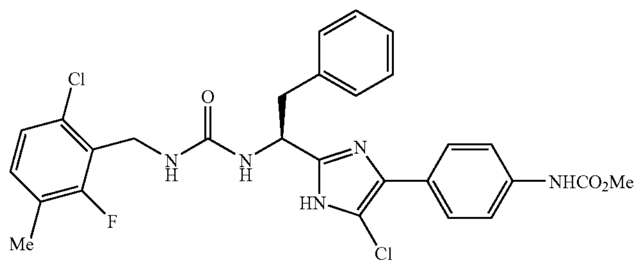 | 569.85 |
| 96 | 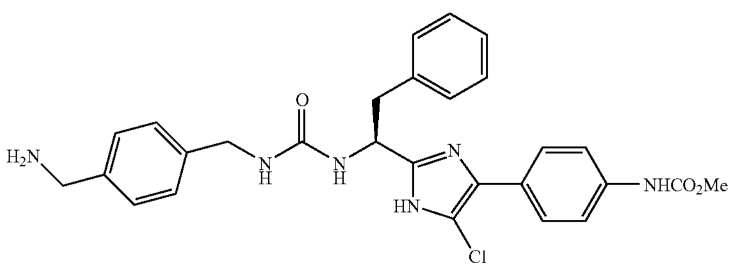 | 532.91 |
| 97 | 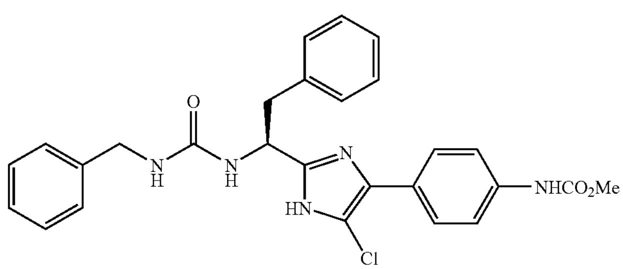 | 503.89 |
| 98 | 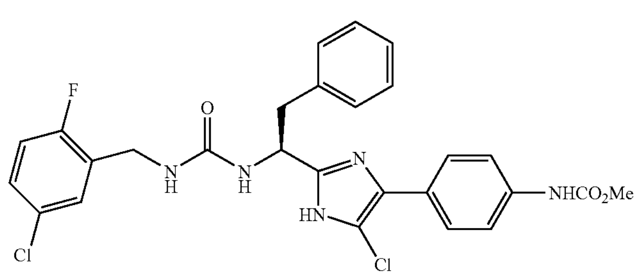 | 555.75 |

TABLE 1-continued
| Ex. No. | Structure | (M + H)+ |
|---|---|---|
| 99 | 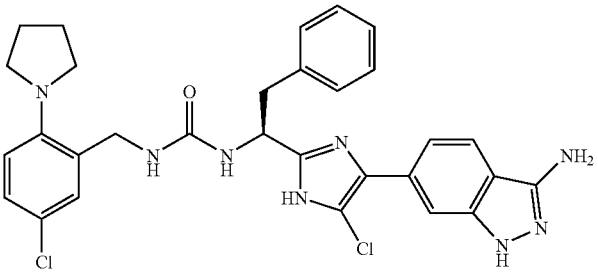 | 589.3 |
| 100 | 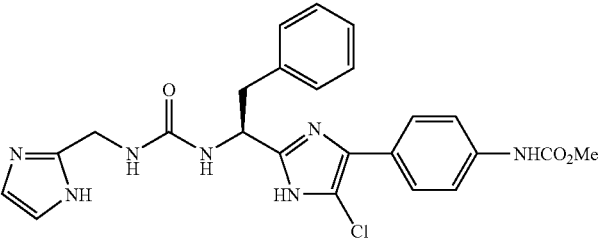 | 494.3 |
| 101 | 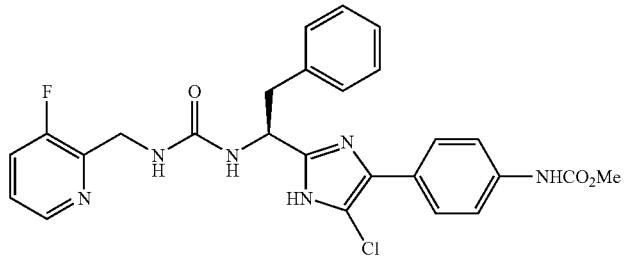 | 523.3 |
| 102 | 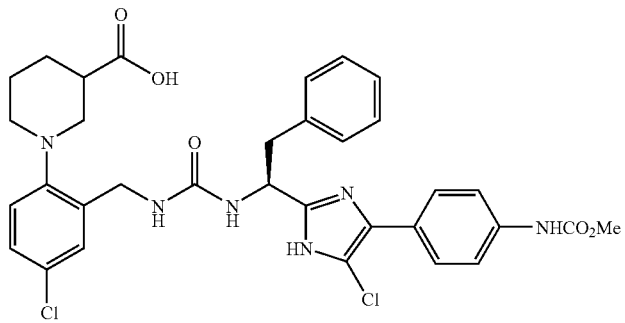 | 665.4 |
| 103 | 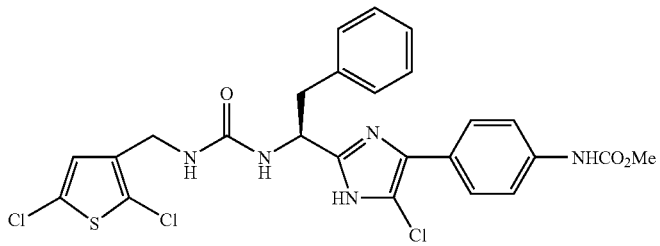 | 578.2 |

TABLE 1-continued

| Ex. No. | Structure | (M + H)+ |
|---|---|---|
| 104 | 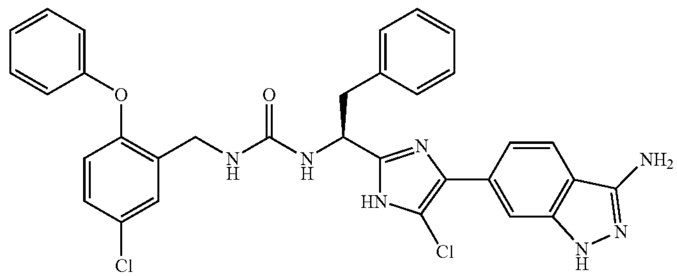 | 612.2 |
| 105 | 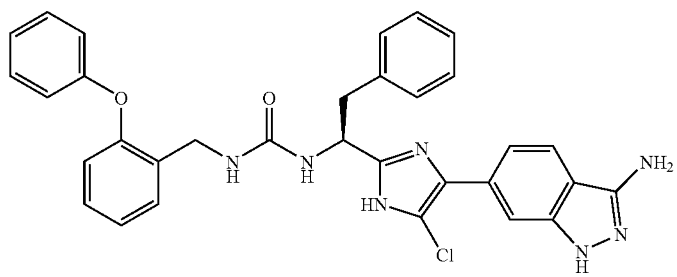 | 578.2 |
| 106 | 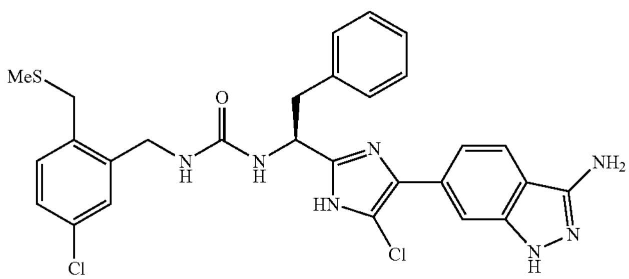 | 580.3 |
| 107 | 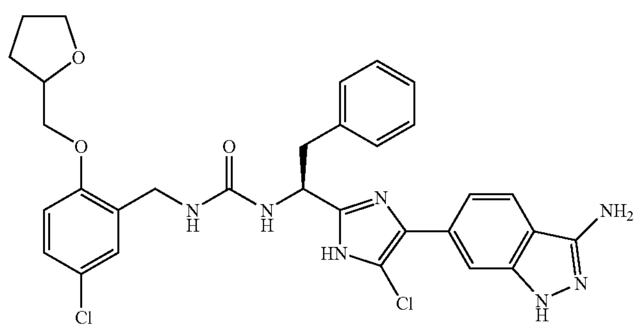 | 620.3 |
| 108 | 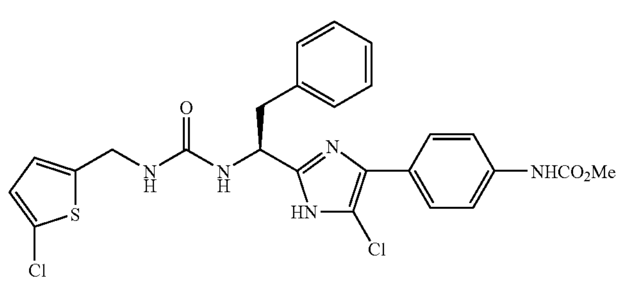 | 544.2 |

TABLE 1-continued
| Ex. No. | Structure | (M + H)+ |
|---|---|---|
| 109 | 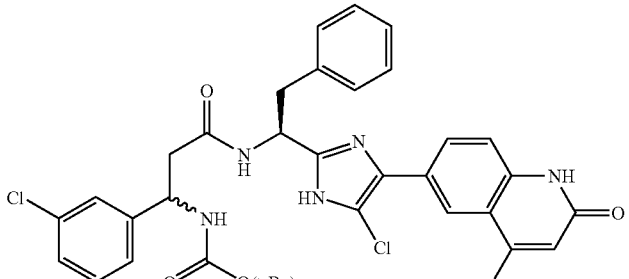 | 662.36 |
| 110 | 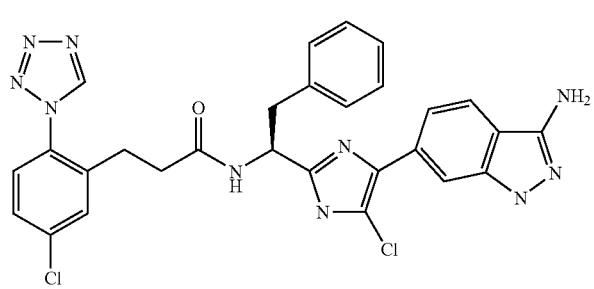 | 587.2 |
| 112 | 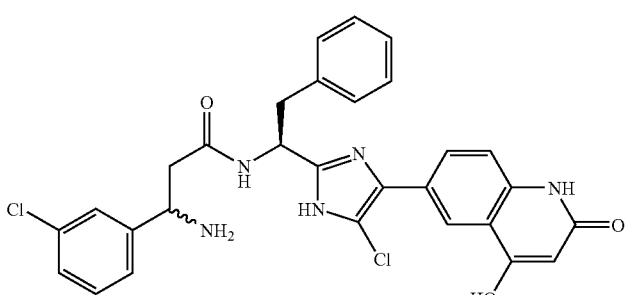 | 562.27 |
| 113 | 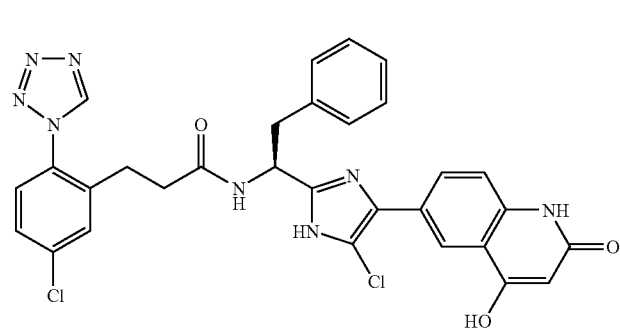 | 615.33 |
| 114 | 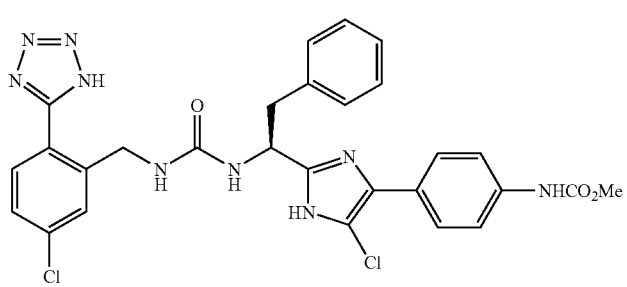 | 606.5 |

TABLE 1-continued
| Ex. No. | Structure | (M + H)+ |
|---|---|---|
| 115 | 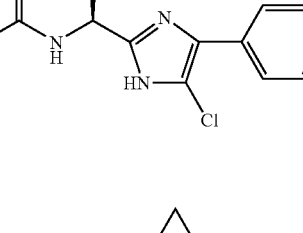 | 509.3 |
| 116 | 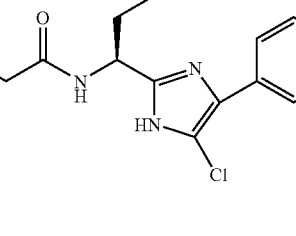 | 569 |
| 117 | 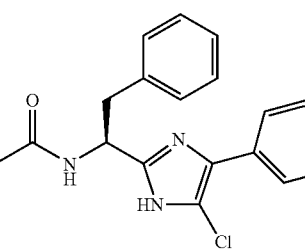 | 585.3 |
| 118 | 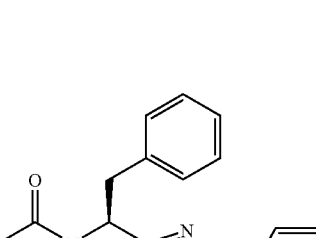 | 595.4 |
| 119 | 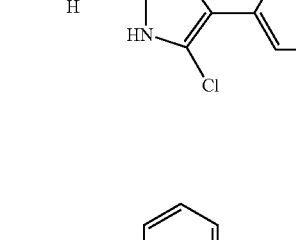 | 584.27 |

TABLE 1-continued
| Ex. No. | Structure | (M + H)+ |
|---|---|---|
| 120 | 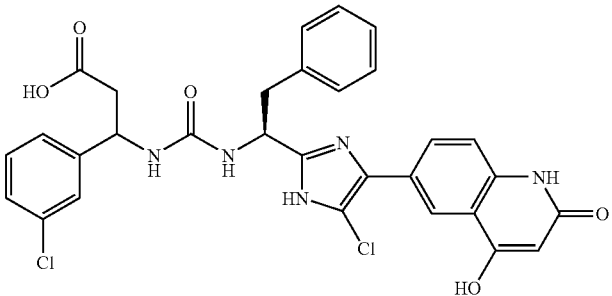 | 606.32 |
| 121 | 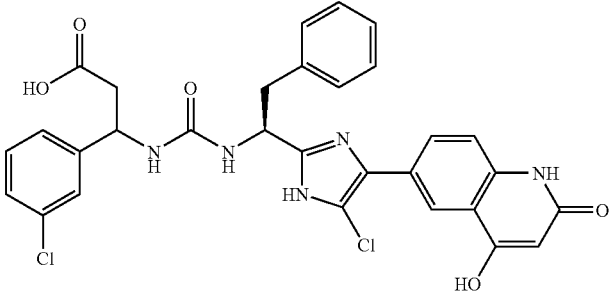 | 606.31 |
| 122 | 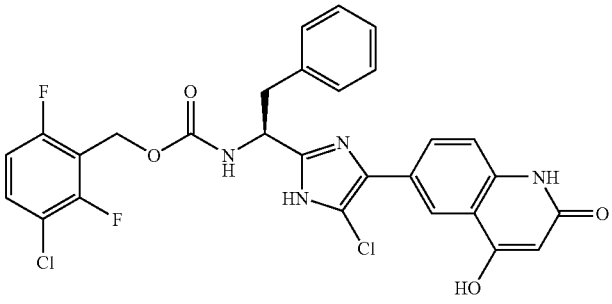 | 585.3 |
| 123 | 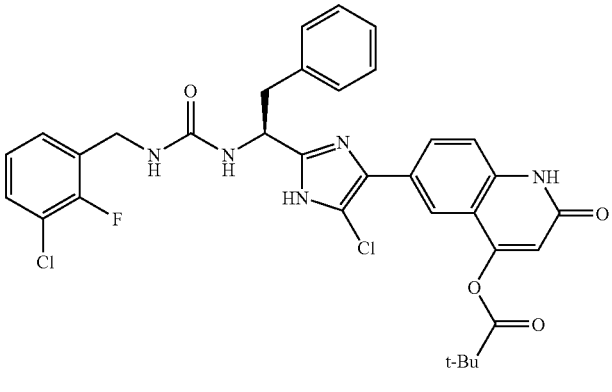 | 650.3 |

TABLE 1-continued

| Ex. No. | Structure | (M + H)+ |
|---|---|---|
| 124 | 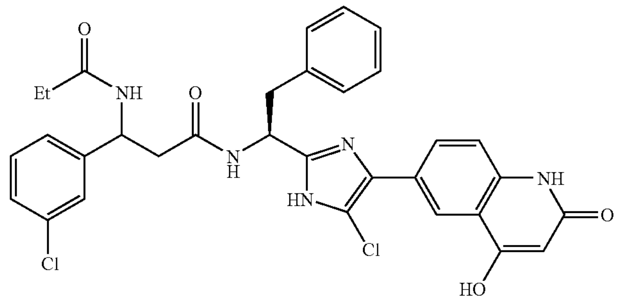 | 618.4 |
| 125 | 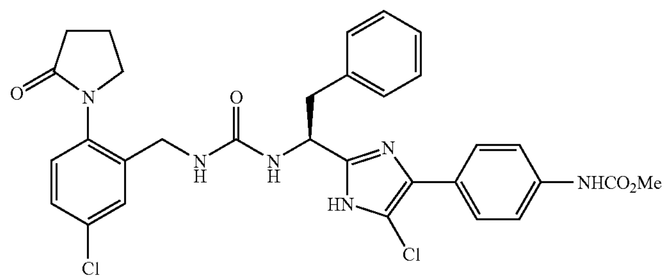 | 621.5 |
| 126 | 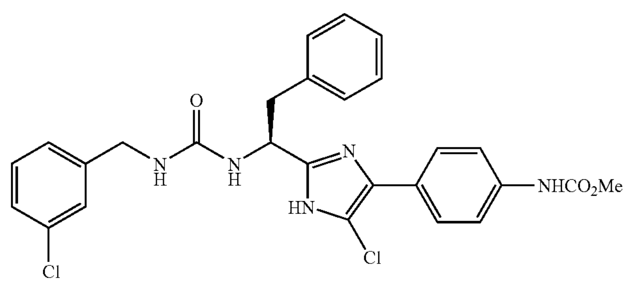 | 538.5 |
| 127 | 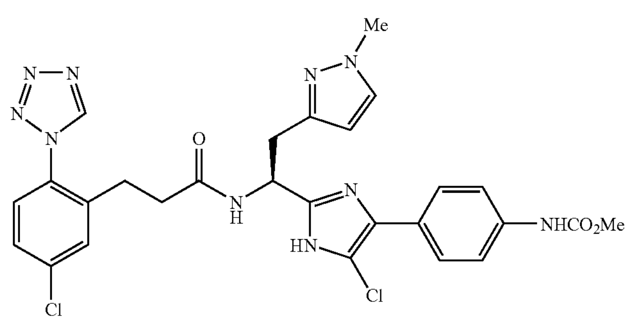 | 609.5 |
| 128 | 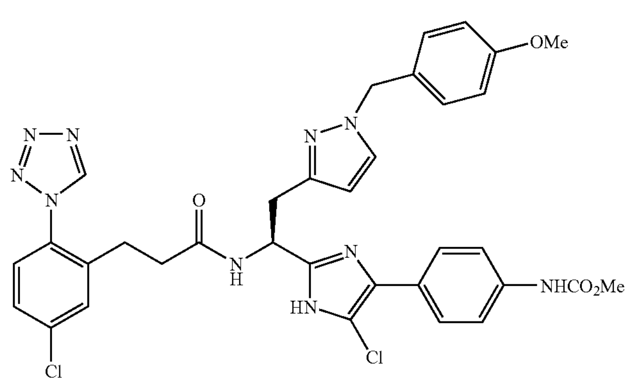 | 715.6 |

TABLE 1-continued
| Ex. No. | Structure | (M + H)+ |
|---|---|---|
| 129 | 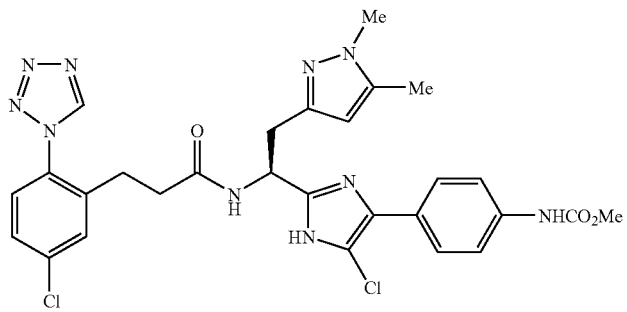 | 623.6 |
| 130 | 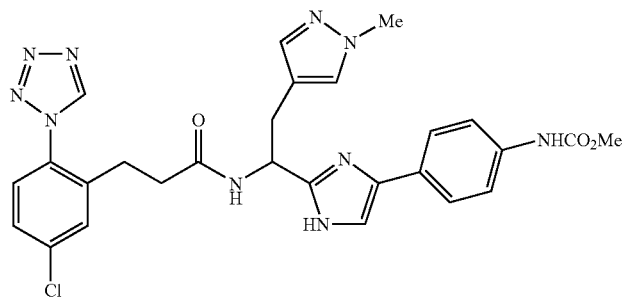 | 575.6 |
| 131 | 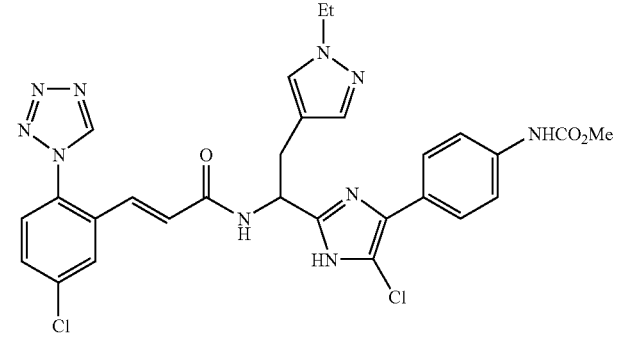 | 621.0 |
| 132 | 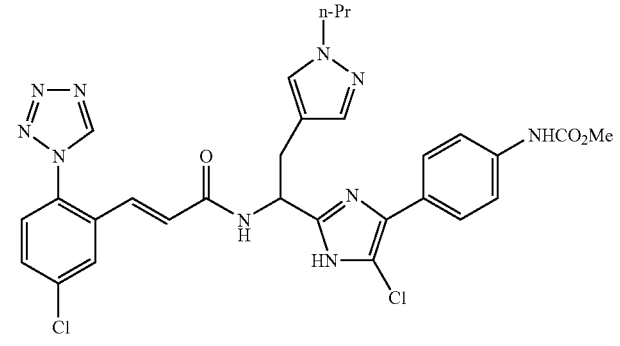 | 635.0 |

TABLE 1-continued

| Ex. No. | Structure | (M + H)+ |
| --- | --- | --- |
| 133 | 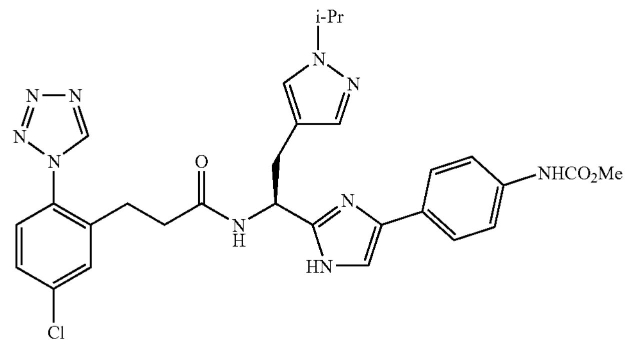 | 603.6 |
| 134 | 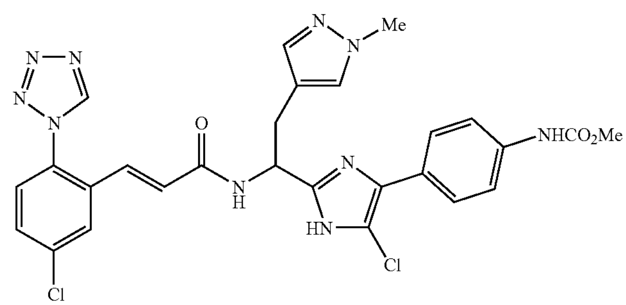 | 607.0 |
| 135 | 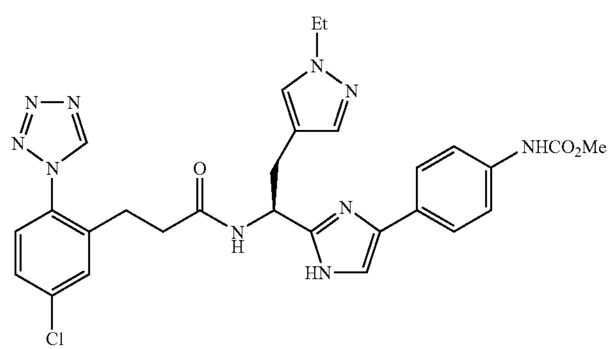 | 589.4 |
| 136 | 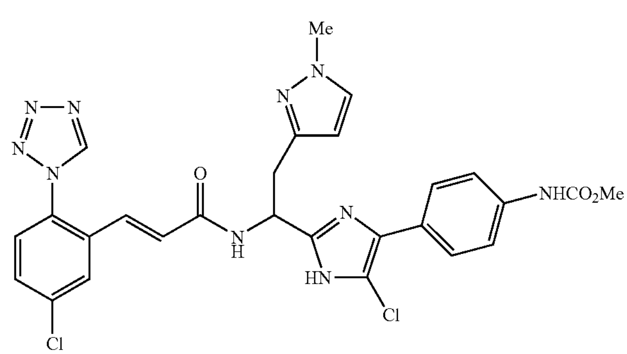 | 607.3 |

TABLE 1-continued
| Ex. No. | Structure | (M + H)+ |
|---|---|---|
| 137 | 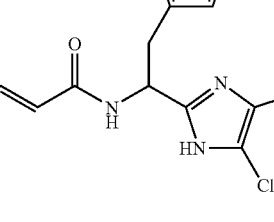 | 621.1 |
| 138 | 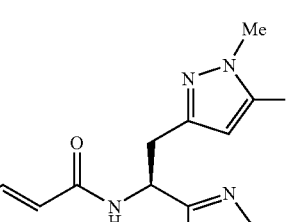 | 591.0 |
| 139 | 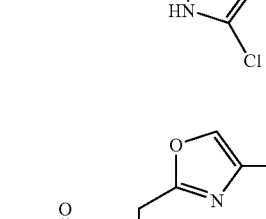 | 652.1 |
| 140 | 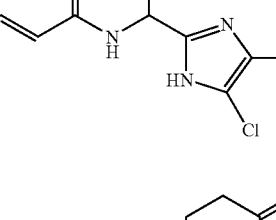 | 623.0 |
| 141 | 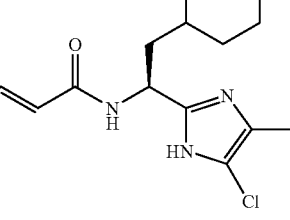 | 638.2 |

TABLE 1-continued

| Ex. No. | Structure | (M + H)+ |
|---|---|---|
| 142 | 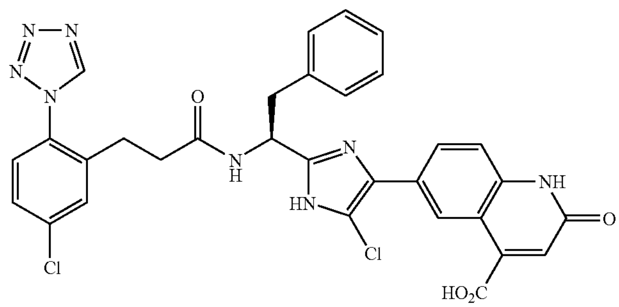 | 643.3 |
| 143 | 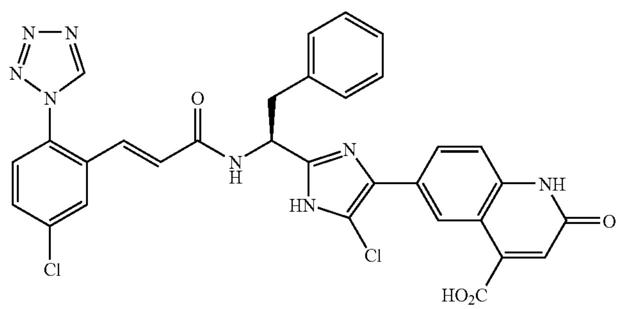 | 641.2 |
| 144 | 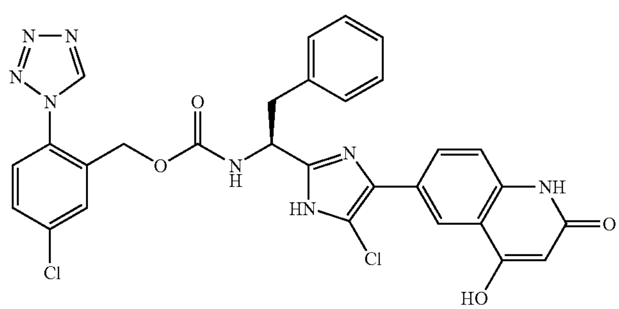 | 617.6 |
| 145 | 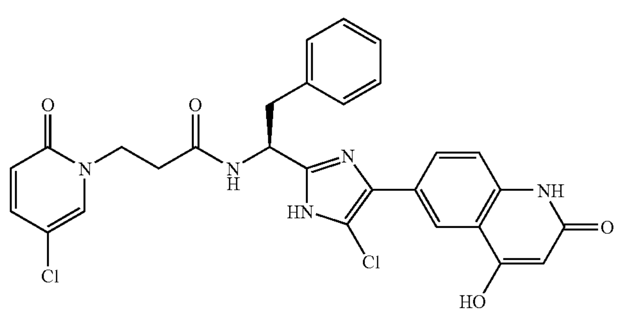 | 564.3 |

TABLE 1-continued
| Ex. No. | Structure | (M + H)+ |
|---|---|---|
| 146 | 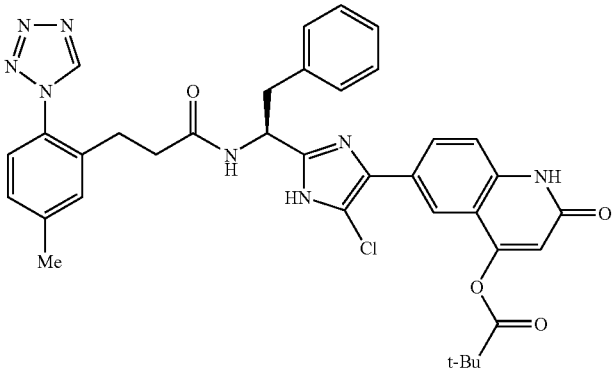 | 679.4 |
| 147 | 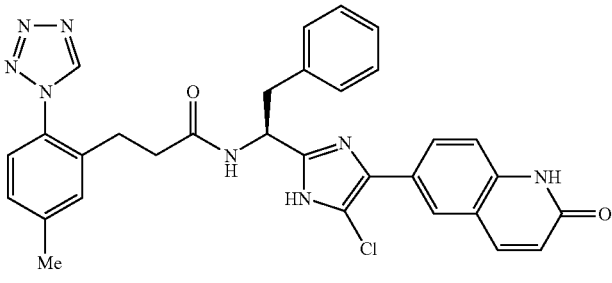 | 579.5 |
| 148 | 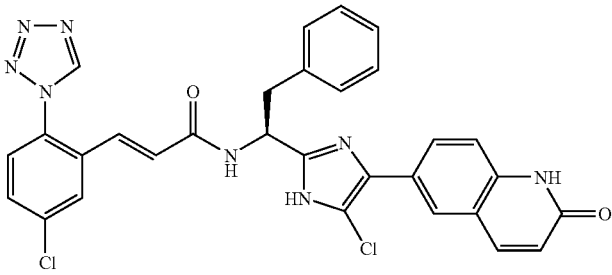 | 599.5 |
| 149 | 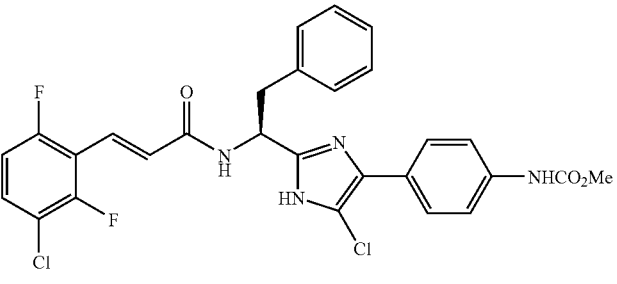 | 571.0 |
| 150 | 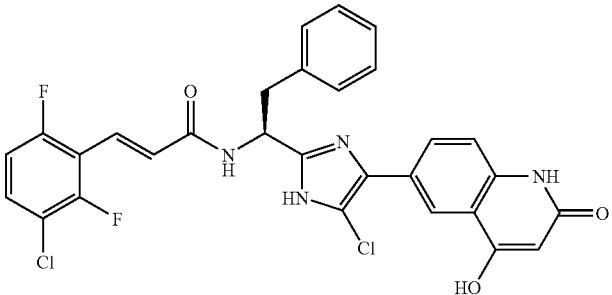 | 581.1 |

TABLE 1-continued

| Ex. No. | Structure | (M + H)+ |
|---|---|---|
| 151 | 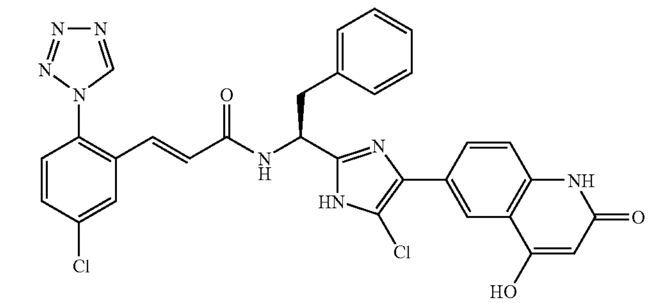 | 613.1 |
| 152 | 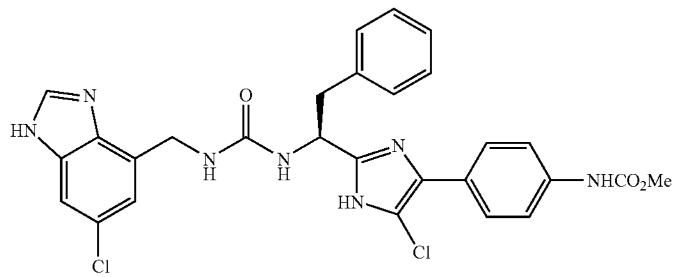 | 578.5 |
| 153 | 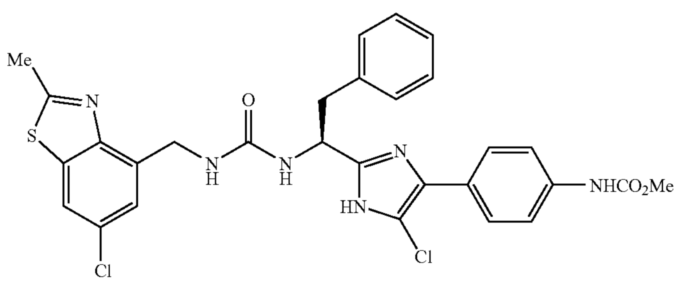 | 629.5 |
| 154 | 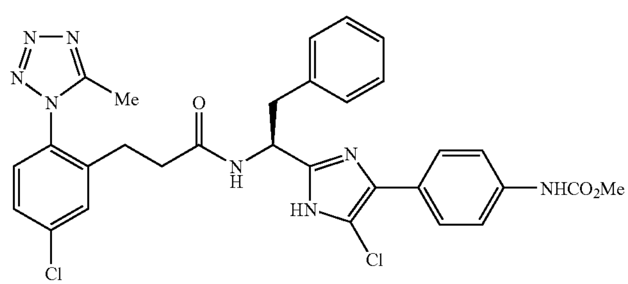 | 619.6 |
| 155 | 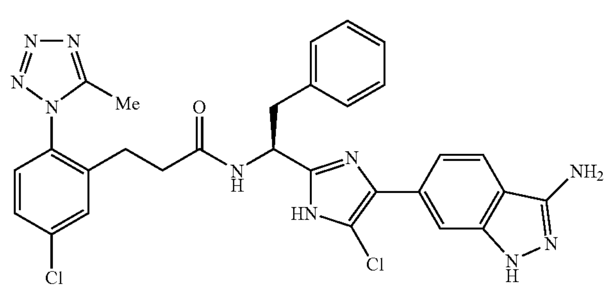 | 601.6 |

TABLE 1-continued
| Ex. No. | Structure | (M + H)+ |
|---|---|---|
| 156 | 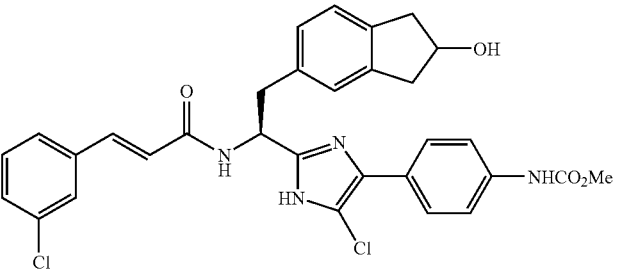 | 591.2 |
| 157 | 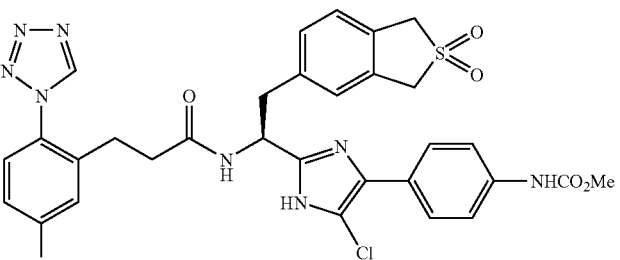 | 695.14 |
| 158 | 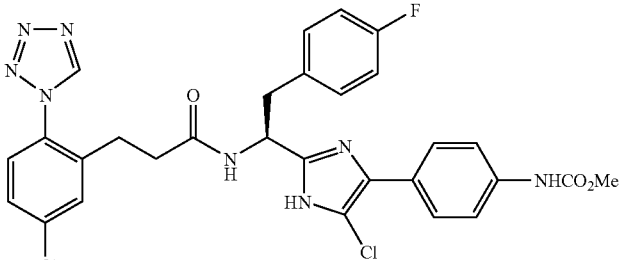 | 623.15 |
| 159 | 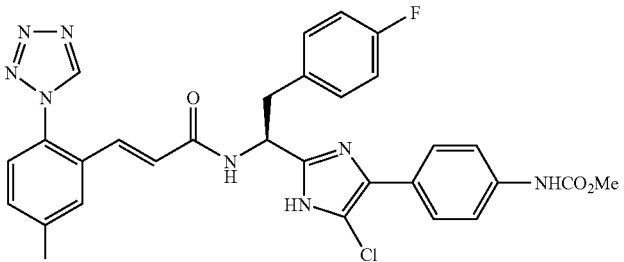 | 621.13 |
| 160 | 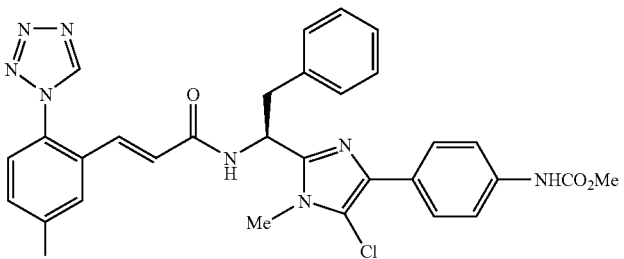 | 617.16 |

| Ex. No. | Structure | (M + H)+ |
|---|---|---|
| 161 | 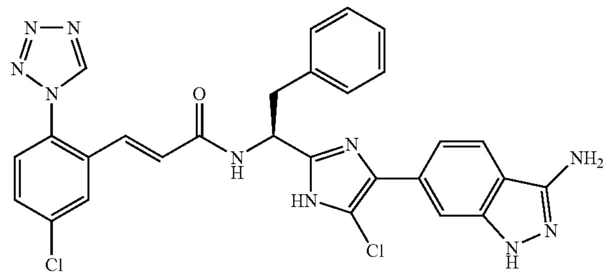 | 585.2 |
| 162 | 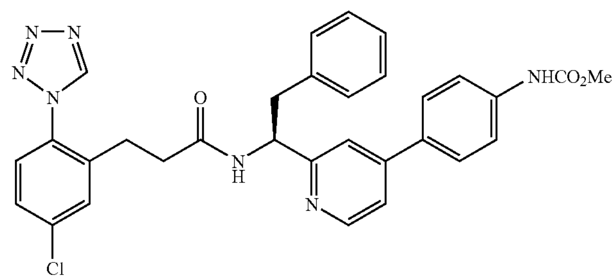 | 582.3 |
| 163 | 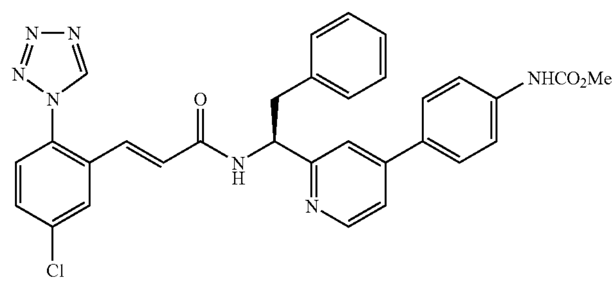 | 580.3 |
| 164 | 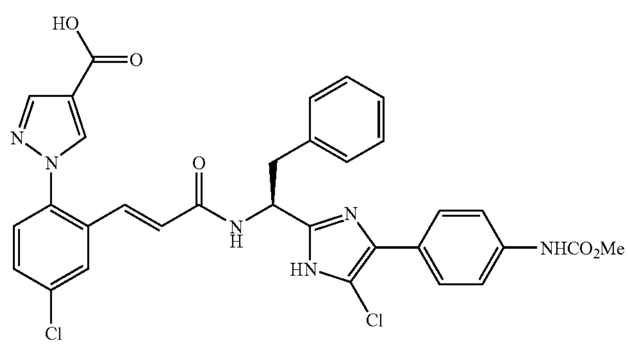 | 645.2 |
| 165 | 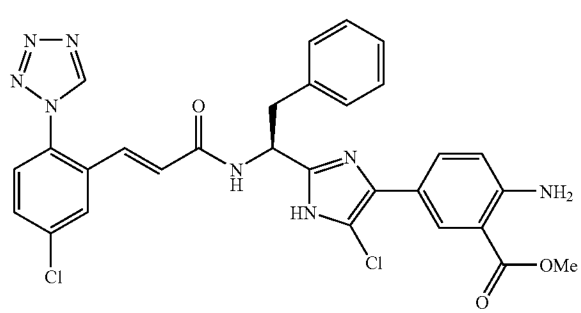 | 603.2 |

TABLE 1-continued

| Ex. No. | Structure | (M + H)+ |
|---|---|---|
| 166 | 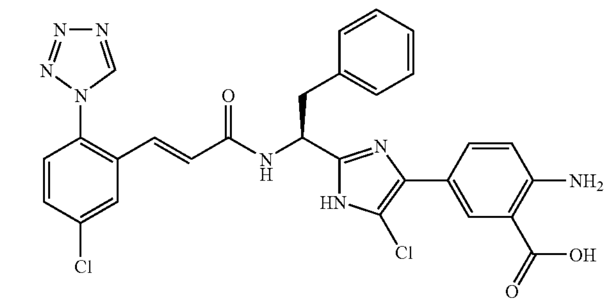 | 589.2 |
| 167 | 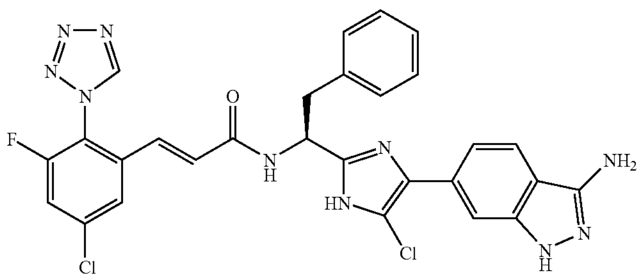 | 603.2 |
| 168 | 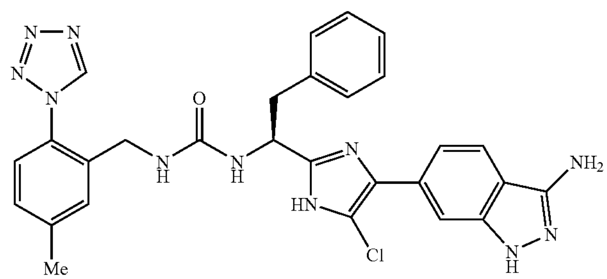 | 568.3 |
| 169 | 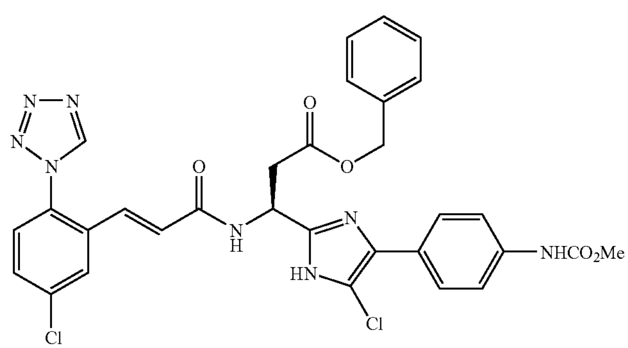 | 661.3 |
| 170 | 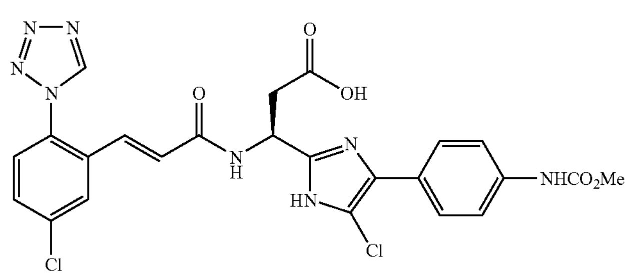 | 571.0 |

TABLE 1-continued

| Ex. No. | Structure | (M + H)+ |
|---|---|---|
| 171 | 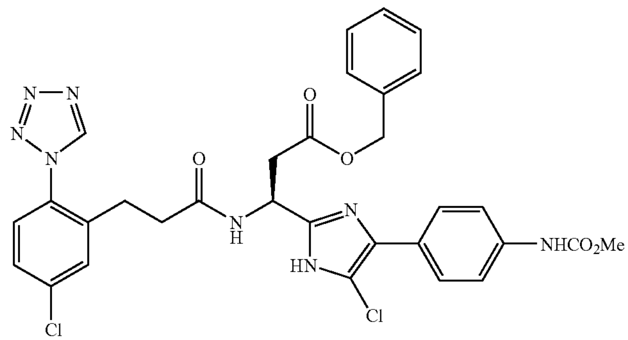 | 663.3 |
| 172 | 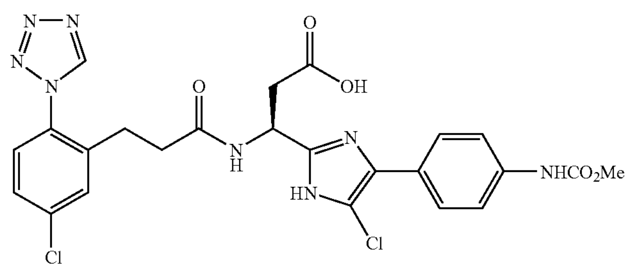 | 573.3 |
| 173 | 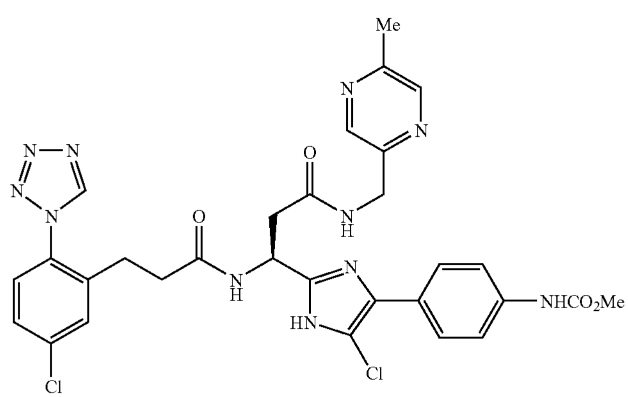 | 678.6 |
| 174 | 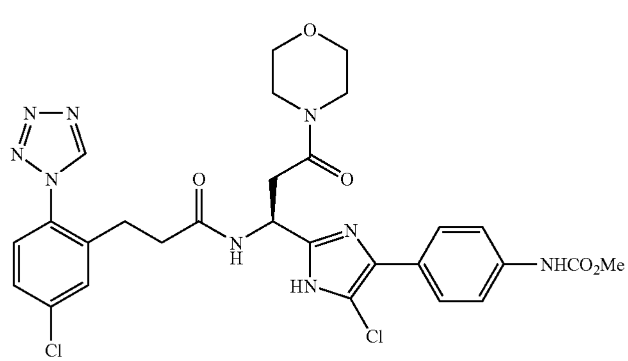 | 642.3 |

TABLE 1-continued
| Ex. No. | Structure | (M + H)+ |
|---|---|---|
| 175 | 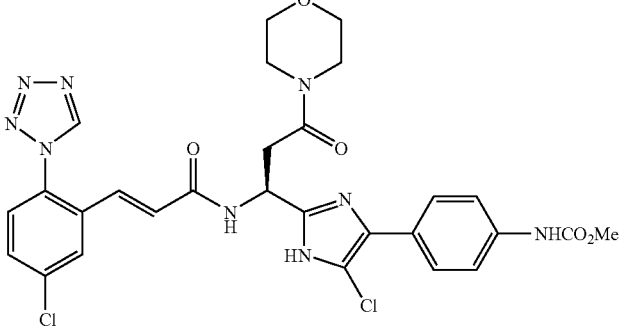 | 640.4 |
| 176 | 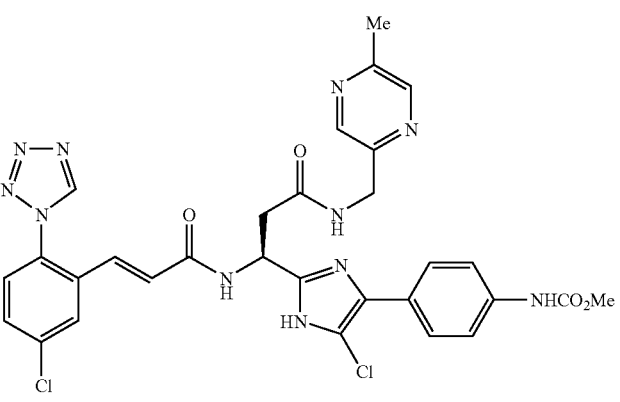 | 676.3 |
| 177 | 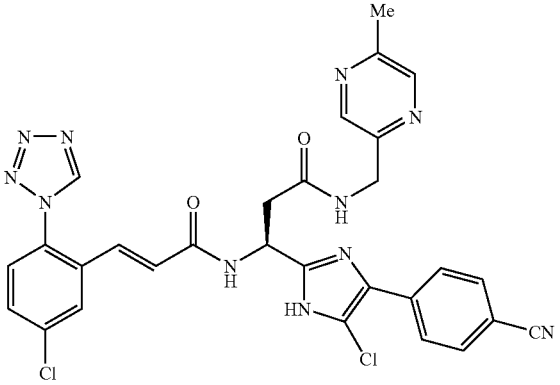 | 628.0 |
| 178 | 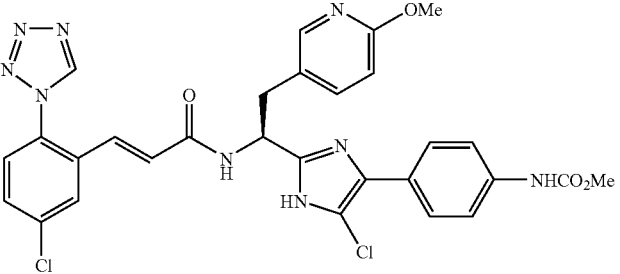 | 634.3 |

TABLE 1-continued
| Ex. No. | Structure | (M + H)+ |
|---|---|---|
| 179 | 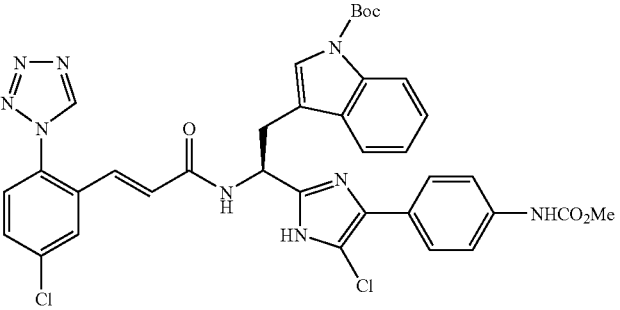 | 742.4 |
| 180 | 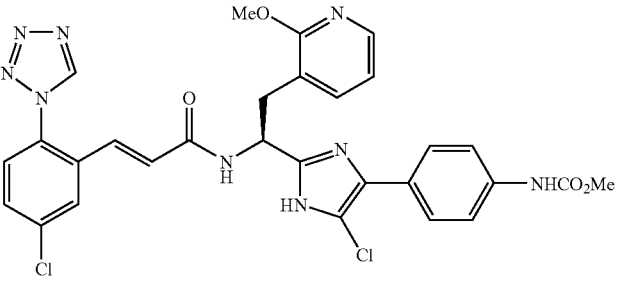 | 634.0 |
| 181 | 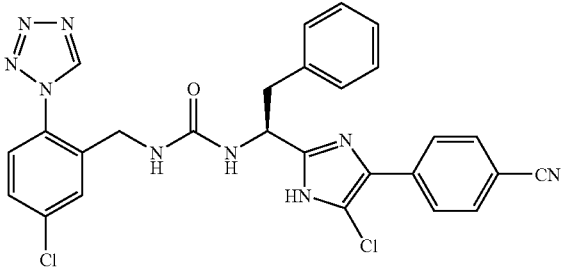 | 558.2 |
| 182 | 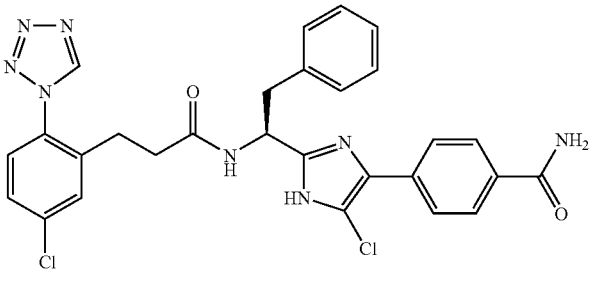 | 575.2 |
| 183 | 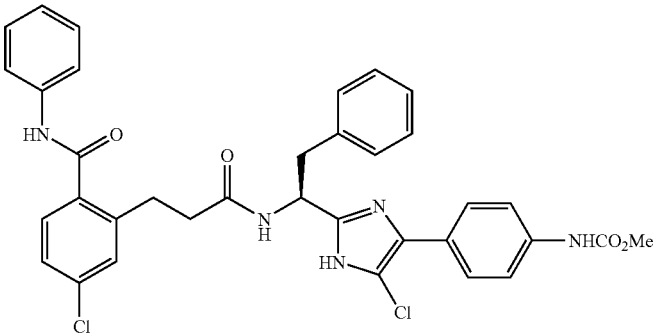 | 656.3 |

TABLE 1-continued

| Ex. No. | Structure | (M + H)+ |
|---|---|---|
| 184 | 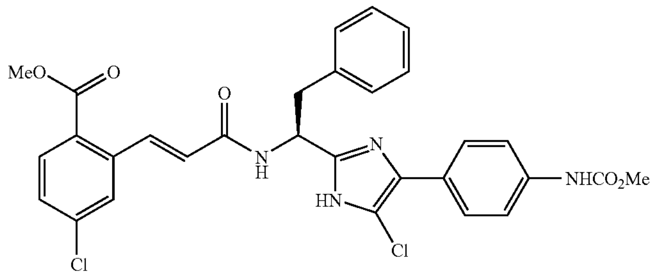 | 593.2 |
| 185 | 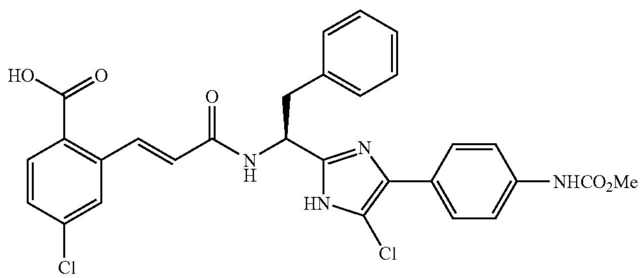 | 579.2 |
| 186 | 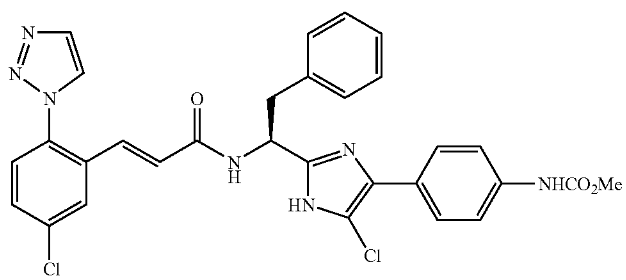 | 602.2 |
| 187 | 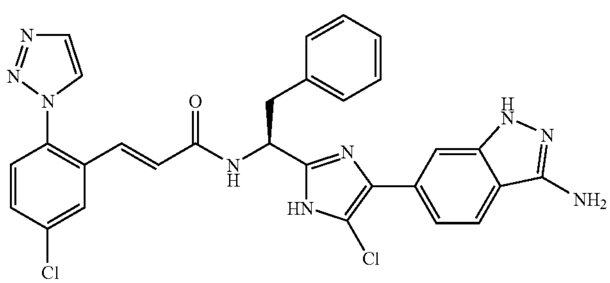 | 584.2 |
| 188 | 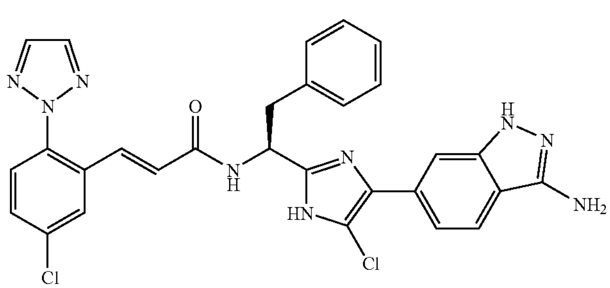 | 584.2 |

TABLE 1-continued

| Ex. No. | Structure | (M + H)+ |
|---|---|---|
| 189 | 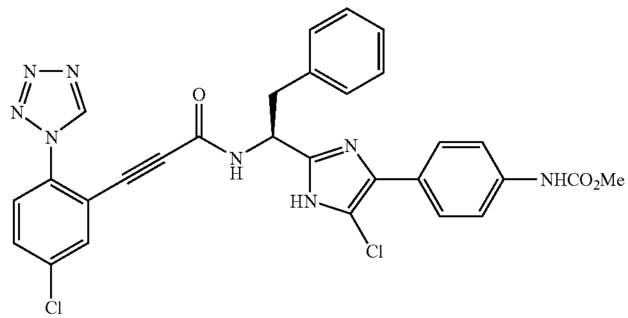 | 601.4 |
| 190 | 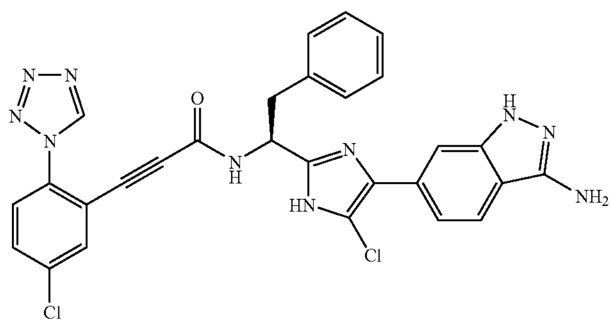 | 583.2 |
| 191 | 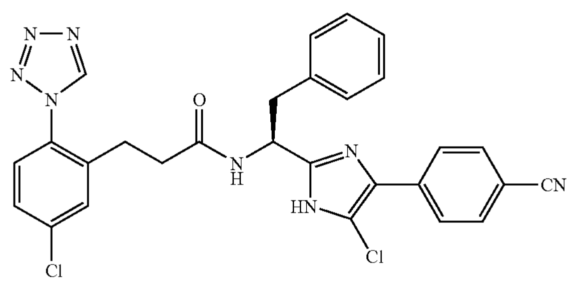 | 557.2 |
| 192 | 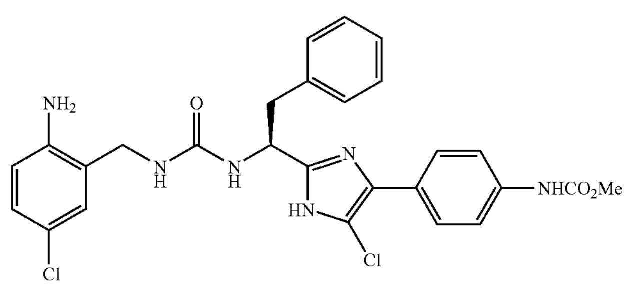 | 553.2 |
| 193 | 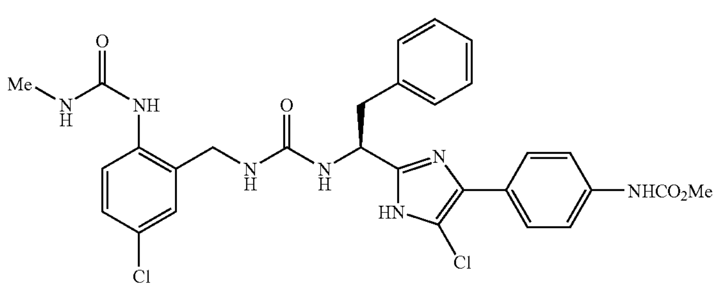 | 610.2 |

TABLE 1-continued

| Ex. No. | Structure | (M + H)+ |
|---|---|---|
| 194 | 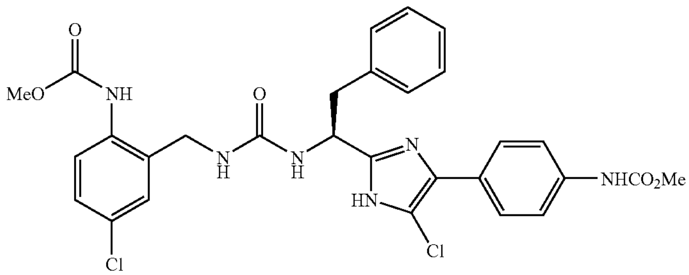 | 611.2 |
| 195 | 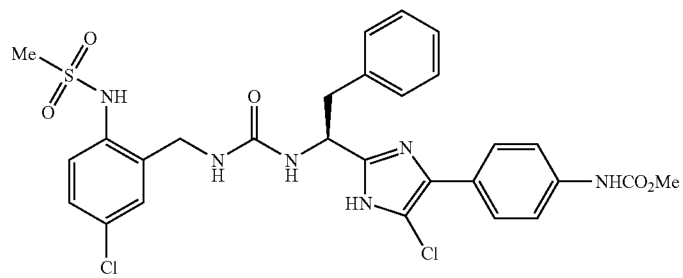 | 631.1 |
| 196 | 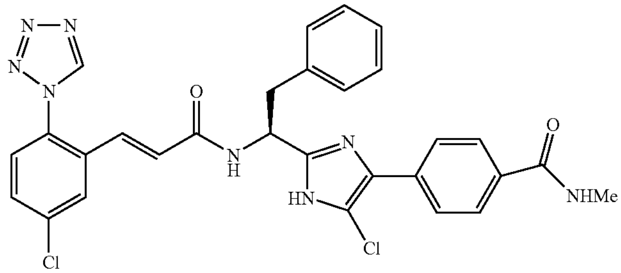 | 26.71 |
| 197 | 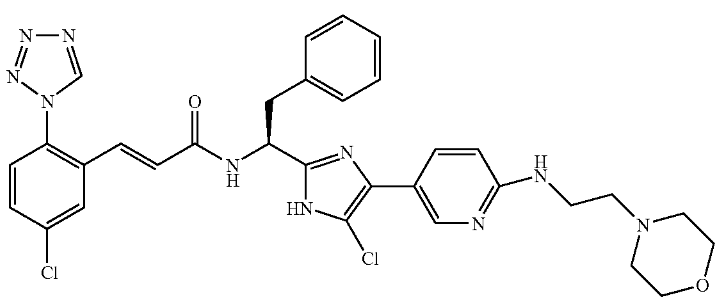 | 659.2 |
| 198 | 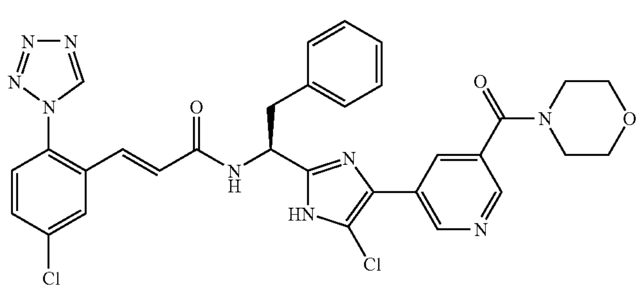 | 644.2 |

TABLE 1-continued

| Ex. No. | Structure | (M + H)+ |
|---|---|---|
| 199 | 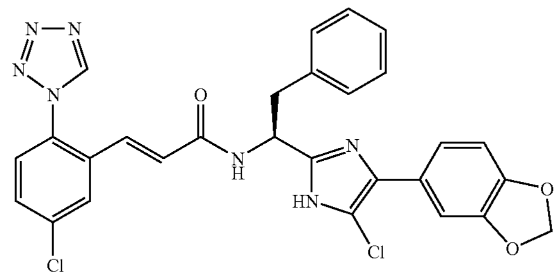 | 574.1 |
| 200 | 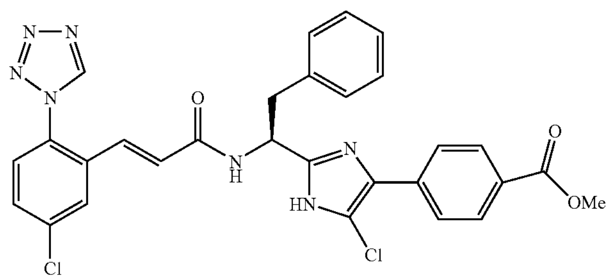 | 588.1 |
| 201 | 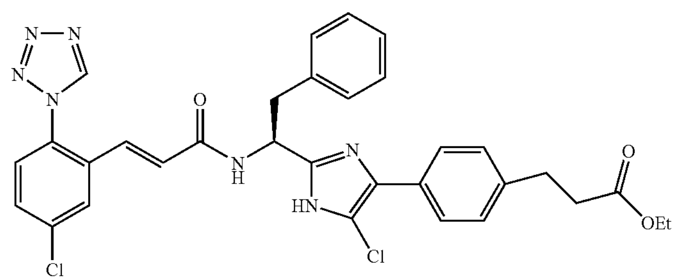 | 630.2 |
| 202 | 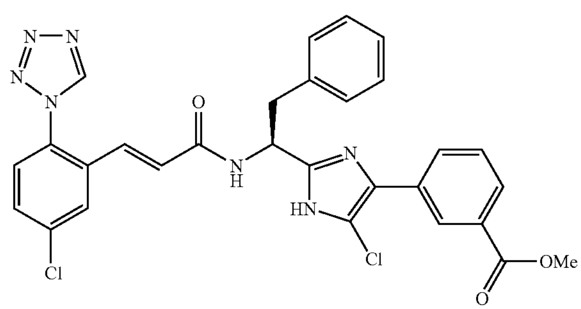 | 588.1 |
| 203 | 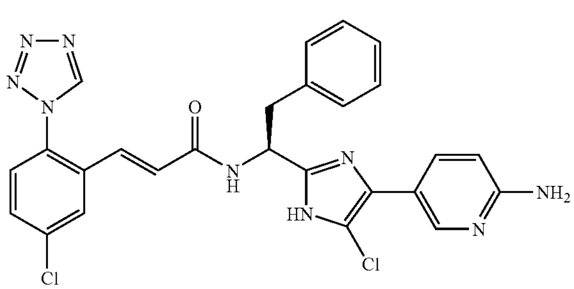 | 546.1 |

TABLE 1-continued
| Ex. No. | Structure | (M + H)+ |
|---|---|---|
| 204 | 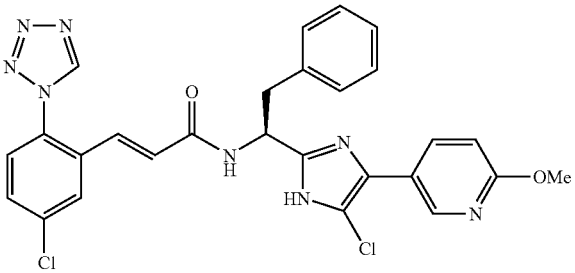 | 561.1 |
| 205 | 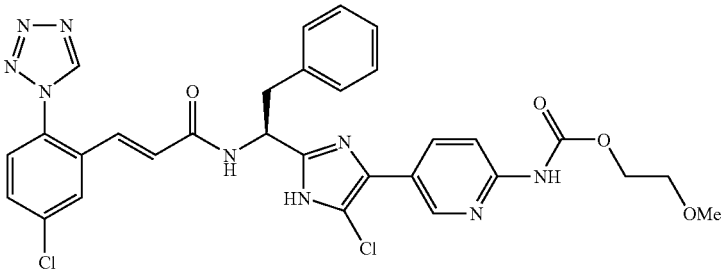 | 648.2 |
| 206 | 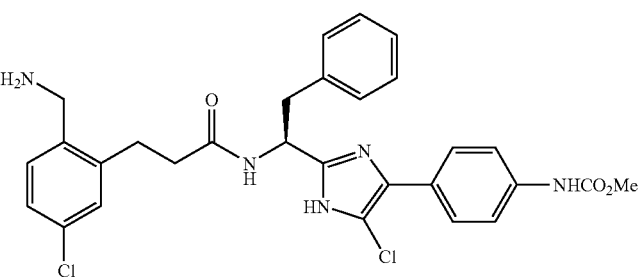 | 566.2 |
| 207 | 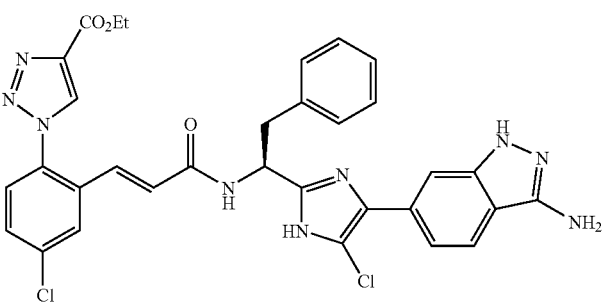 | 656.2 |
| 208 | 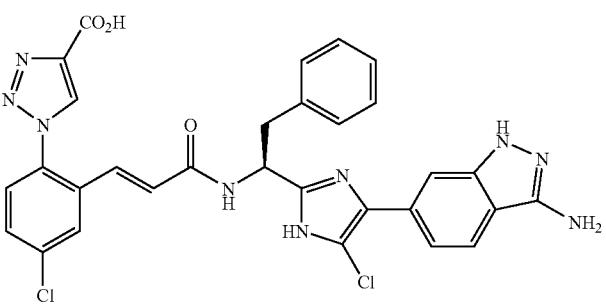 | 628.1 |

| Ex. No. | Structure | (M + H)+ |
|---|---|---|
| 209 | 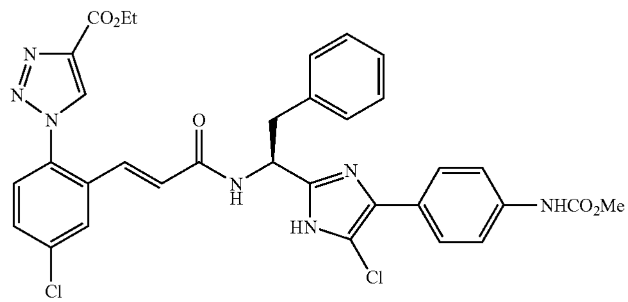 | 674.2 |
| 210 | 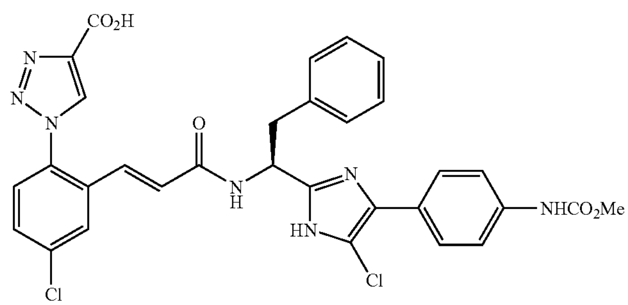 | 646.2 |
| 211 | 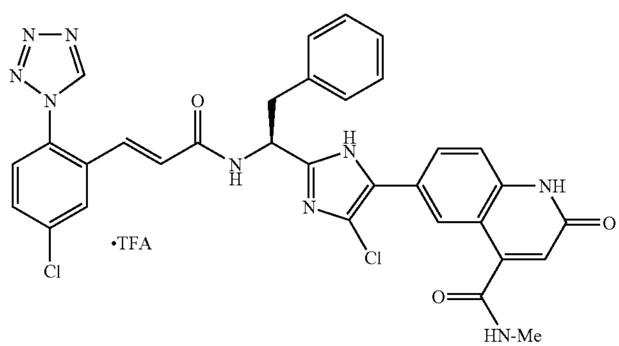 | 654.2 |
| 212 | 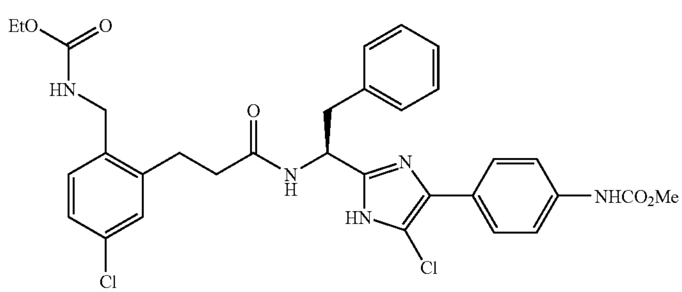 | 638.1 |
| 213 | 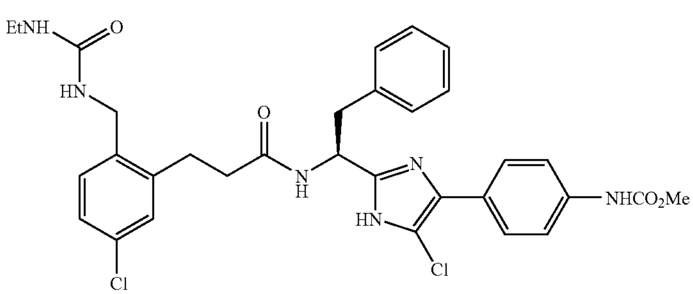 | 637.2 |

TABLE 1-continued

| Ex. No. | Structure | (M + H)+ |
| --- | --- | --- |
| 214 | 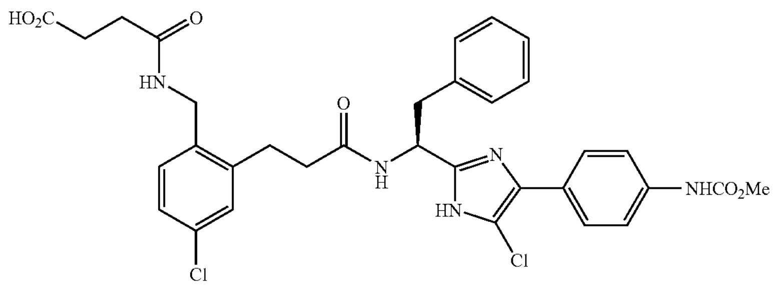 | 666.2 |
| 215 | 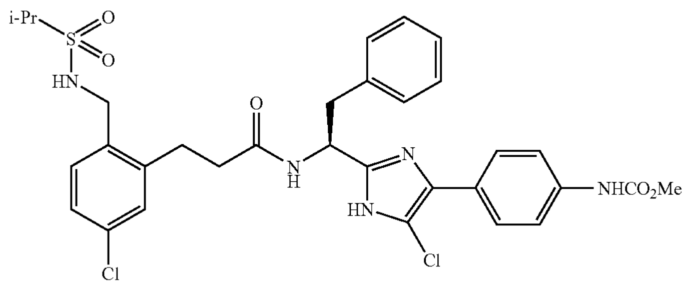 | 672.2 |
| 216 | 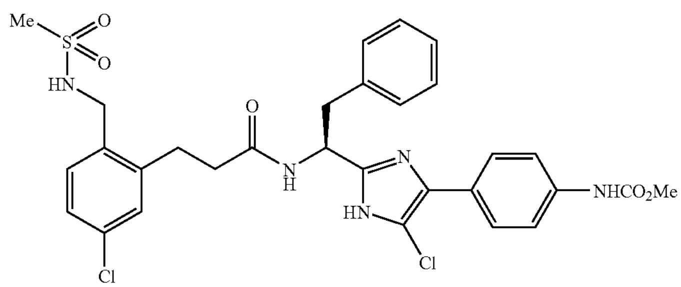 | 644.1 |
| 217 | 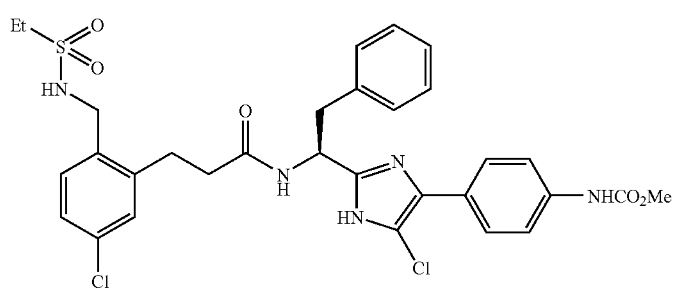 | 648.1 |
| 218 | 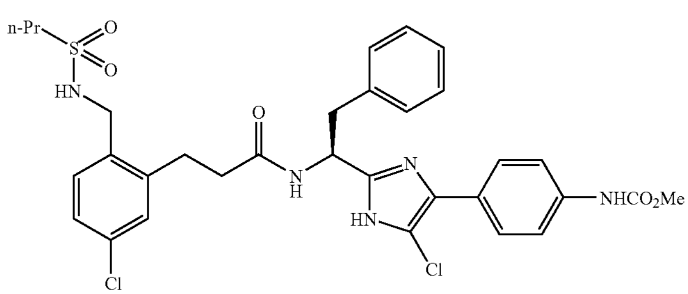 | 672.1 |

TABLE 1-continued
| Ex. No. | Structure | (M + H)+ |
|---|---|---|
| 219 | 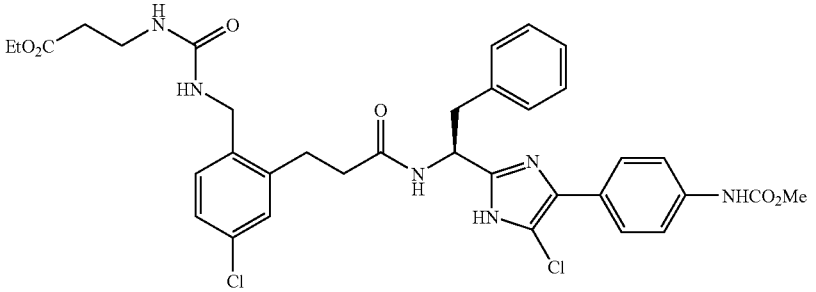 | 709.2 |
| 220 | 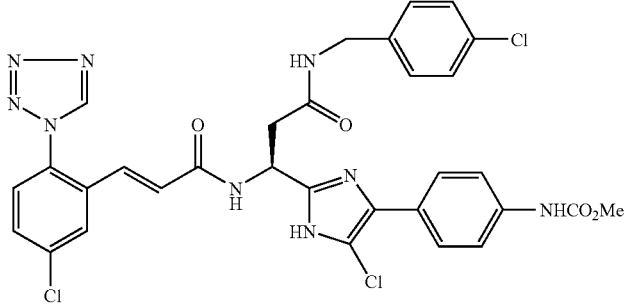 | 694.2 |
| 221 | 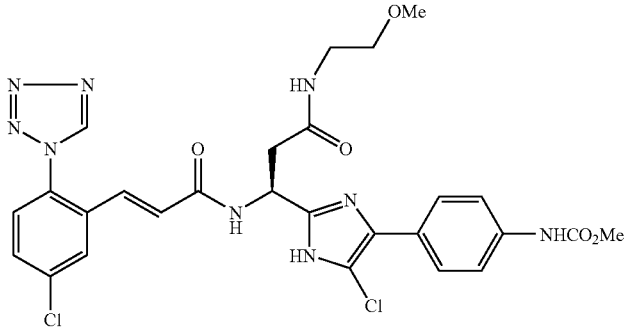 | 628.23 |
| 222 | 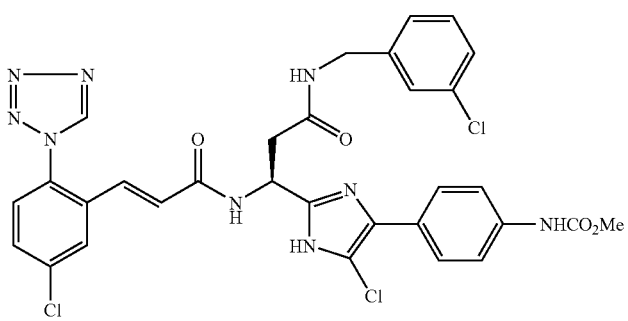 | 694.2 |
| 223 | 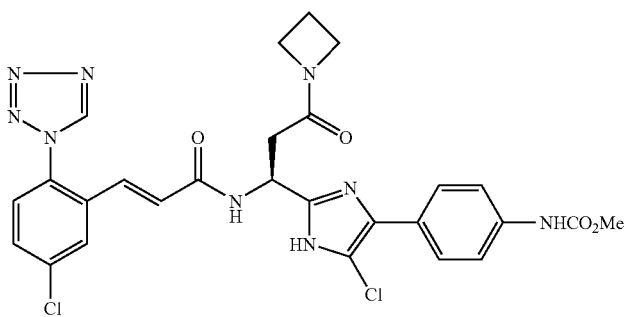 | 610.2 |

TABLE 1-continued

| Ex. No. | Structure | (M + H)+ |
|---|---|---|
| 224 | 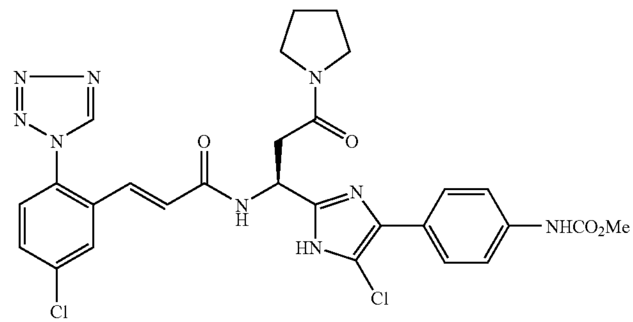 | 624.2 |
| 225 | 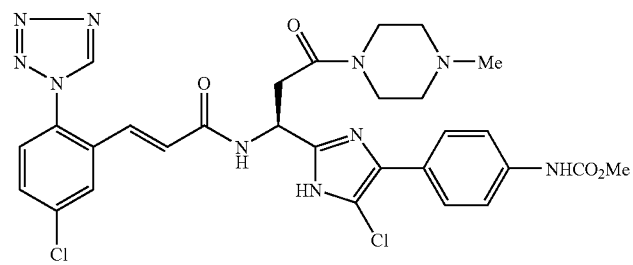 | 653.2 |
| 226 | 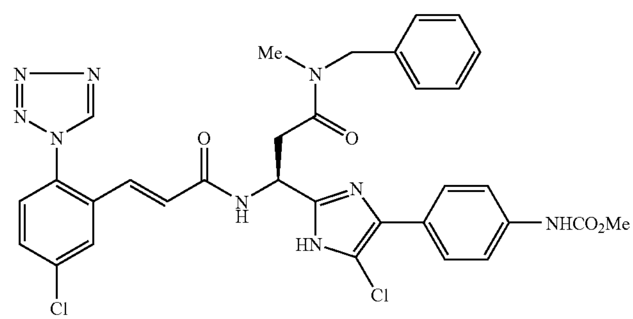 | 672.3 |
| 227 | 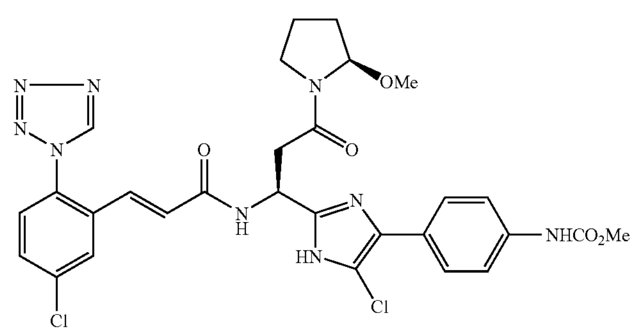 | 666.1 |
| 228 | 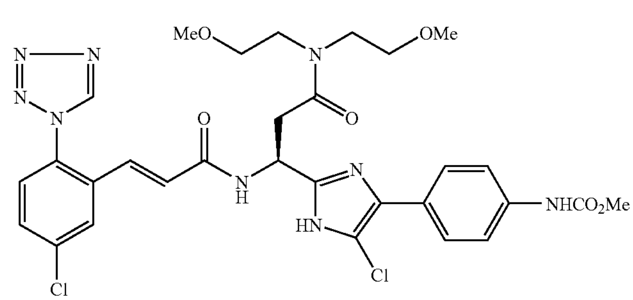 | 686.2 |

TABLE 1-continued

| Ex. No. | Structure | (M + H)+ |
|---|---|---|
| 229 | 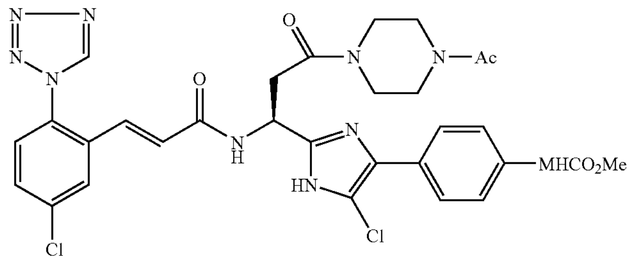 | 681.23 |
| 230 | 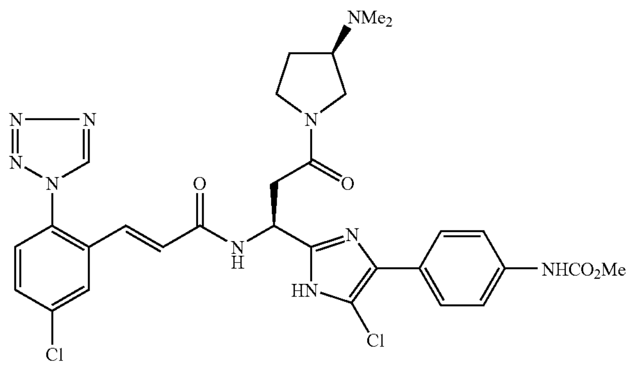 | 667.3 |
| 231 | 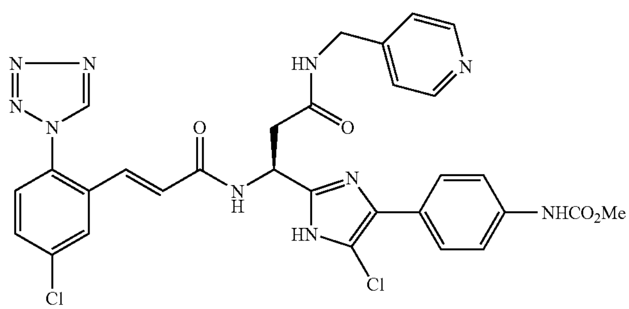 | 661.5 |
| 232 | 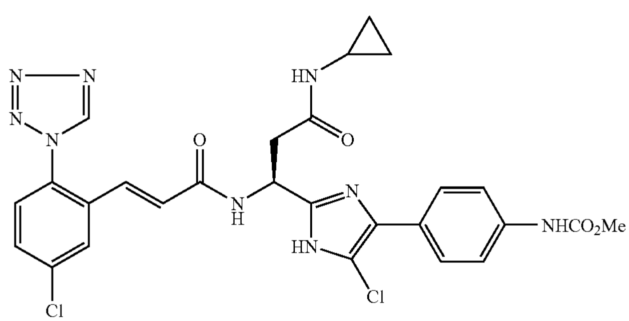 | 610.5 |
| 233 | 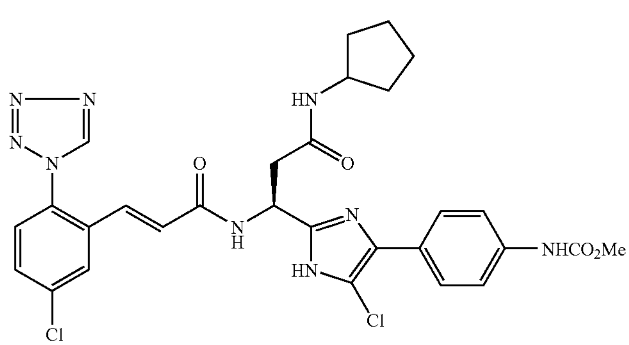 | 638.5 |

TABLE 1-continued

| Ex. No. | Structure | (M + H)+ |
|---|---|---|
| 234 | 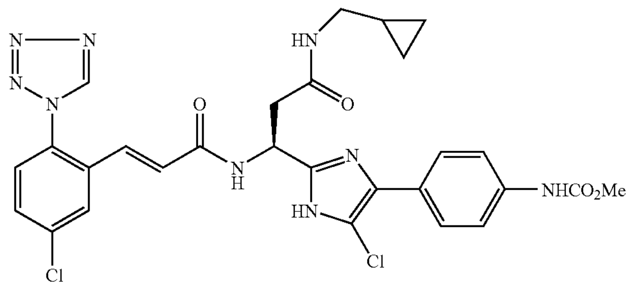 | 624.5 |
| 235 | 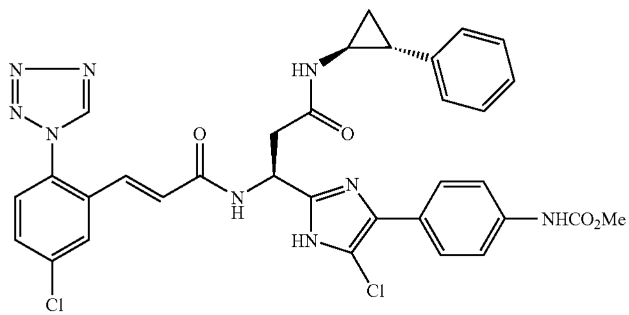 | 686.5 |
| 236 | 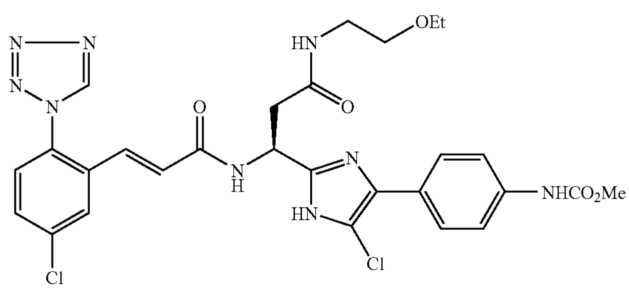 | 642.5 |
| 237 | 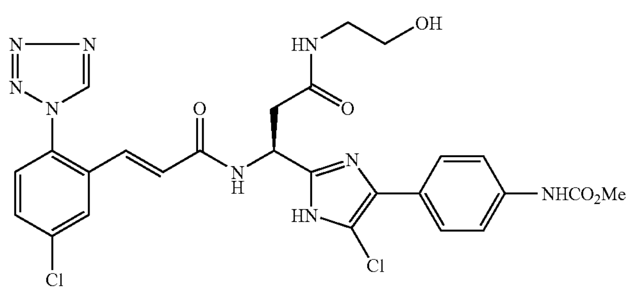 | 614.4 |
| 238 | 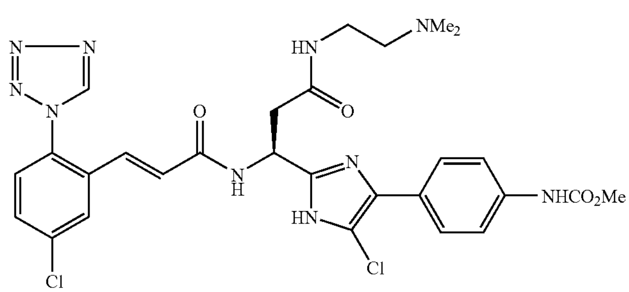 | 641.4 |

TABLE 1-continued
| Ex. No. | Structure | (M + H)+ |
|---|---|---|
| 239 | 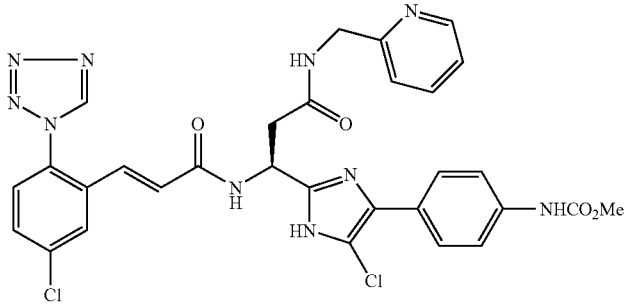 | 661.4 |
| 240 | 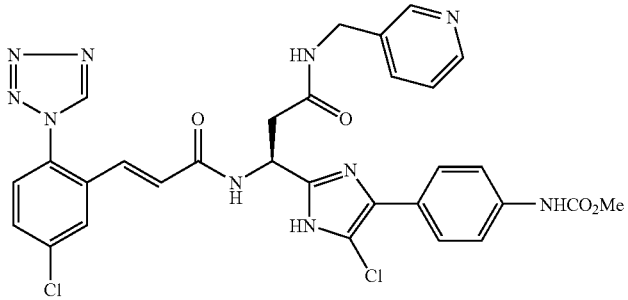 | 661.4 |
| 241 | 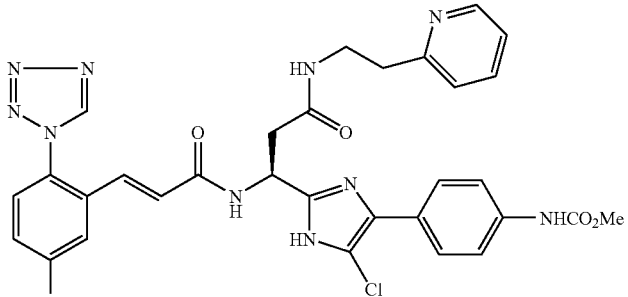 | 675.5 |
| 242 | 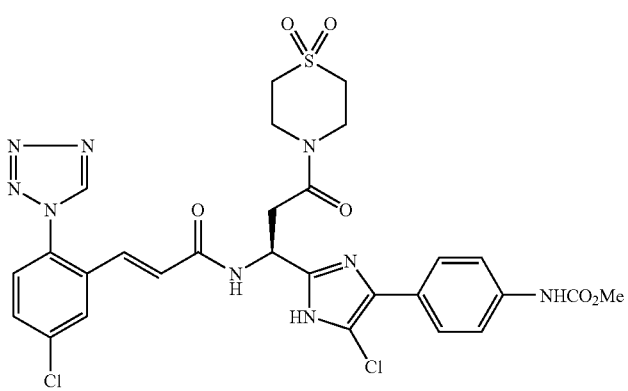 | 688.4 |

TABLE 1-continued

| Ex. No. | Structure | (M + H)+ |
|---|---|---|
| 243 | 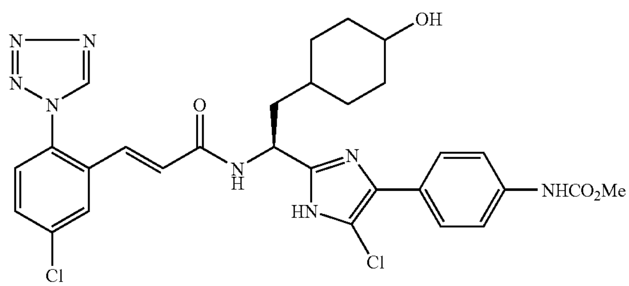 | 627.5 |
| 244 | 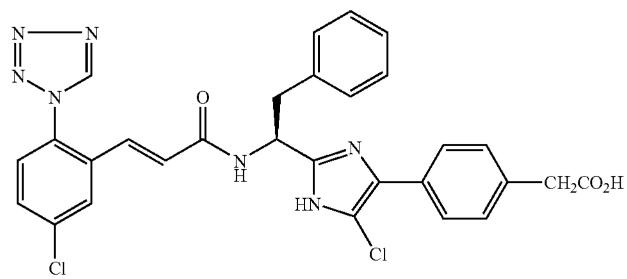 | 602 |
| 245 | 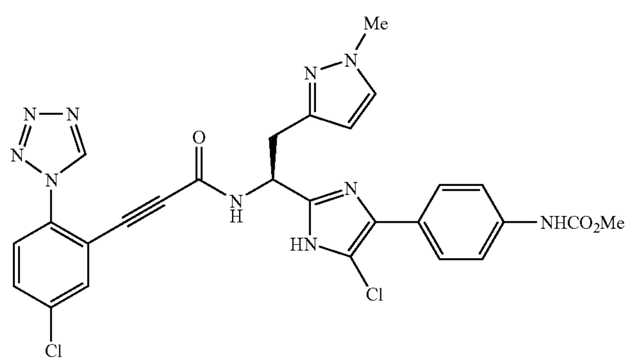 | 605.0 |
| 246 | 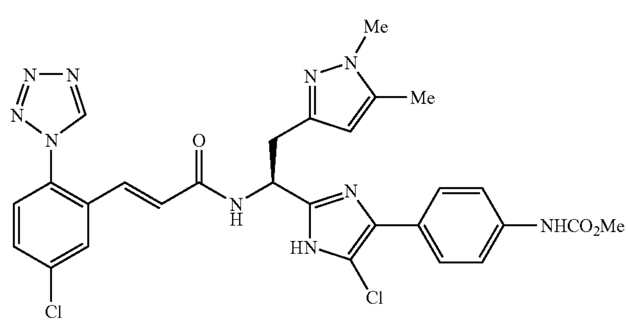 | 621.1 |
| 247 | 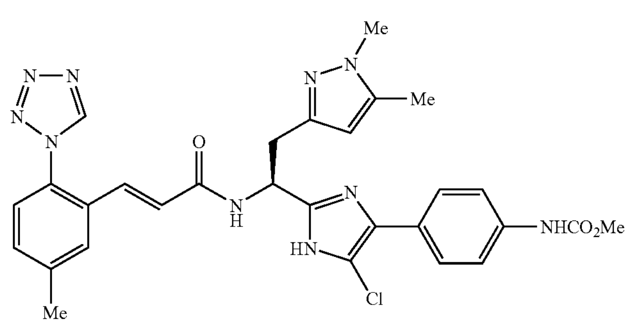 | 601.1 |

TABLE 1-continued

| Ex. No. | Structure | (M + H)+ |
|---|---|---|
| 248 | 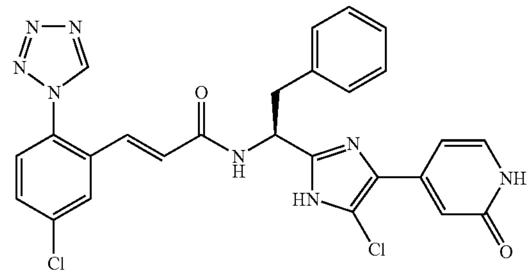 | 547.1 |
| 249 | 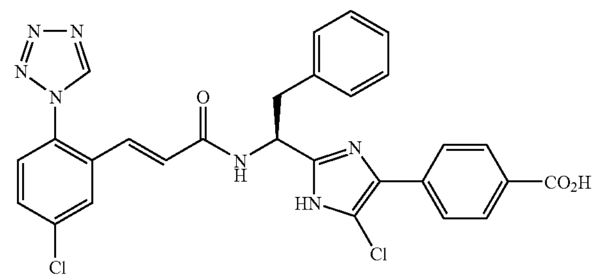 | 574 |
| 250 | 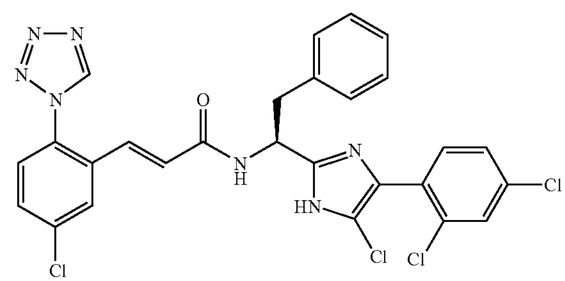 | 564 |
| 251 | 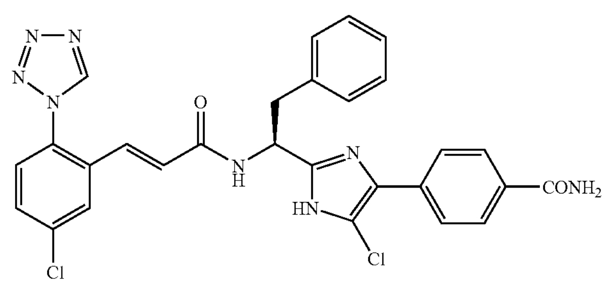 | 573 |
| 252 | 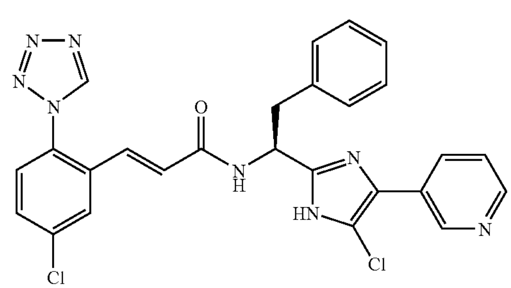 | 531 |

TABLE 1-continued

| Ex. No. | Structure | (M + H)+ |
|---|---|---|
| 253 | 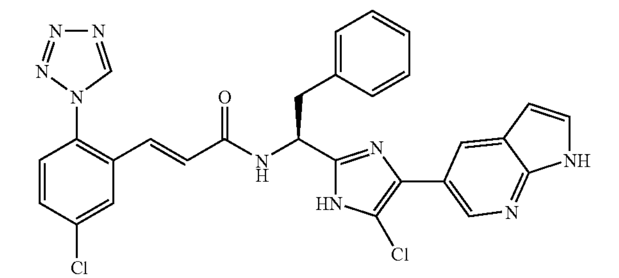 | 570 |
| 254 | 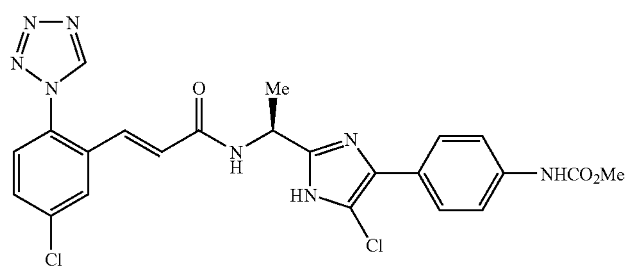 | 527 |
| 255 | 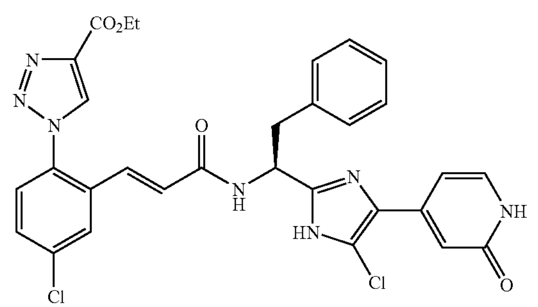 | 618 |
| 256 | 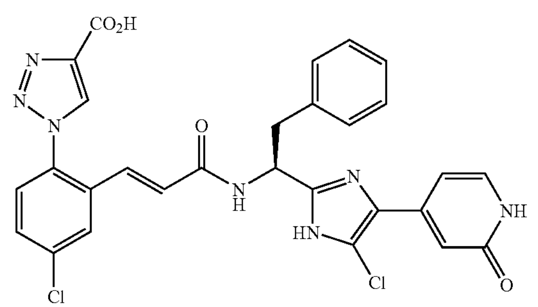 | 590 |
| 257 | 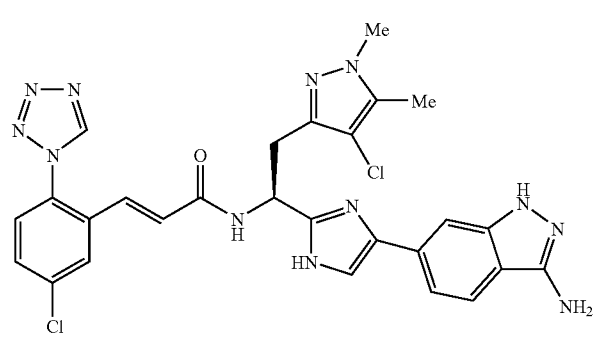 | 603.0 |

TABLE 1-continued

| Ex. No. | Structure | (M + H)+ |
| --- | --- | --- |
| 258 | 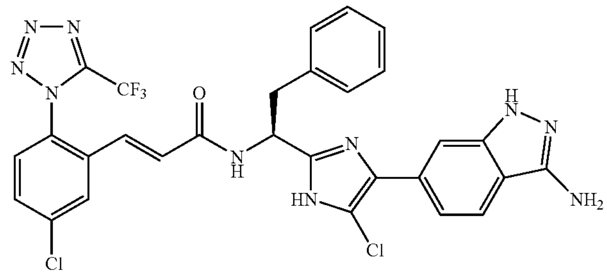 | 653.2 |
| 259 | 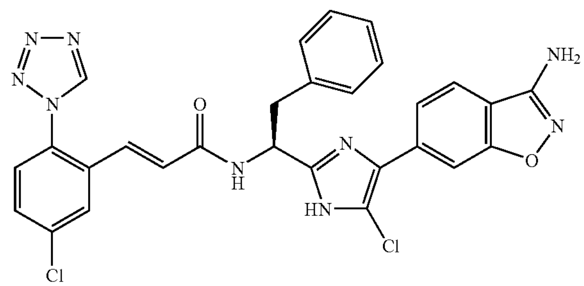 | 586.5 |
| 260 | 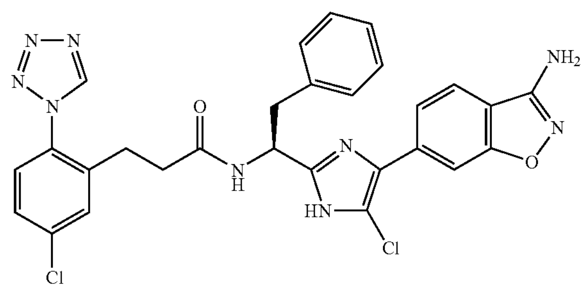 | 588.4 |
| 261 | 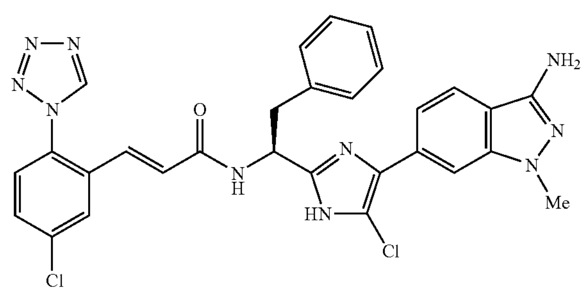 | 599.2 |
| 262 | 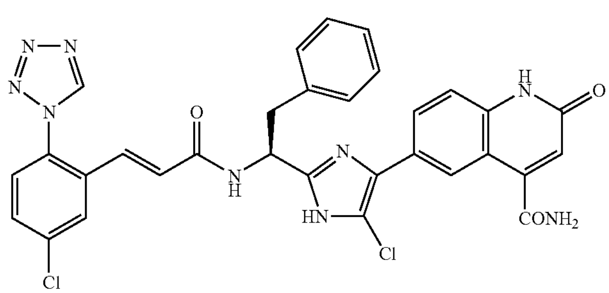 | 640.4 |

TABLE 1-continued

| Ex. No. | Structure | (M + H)+ |
|---------|-----------|----------|
| 263 | 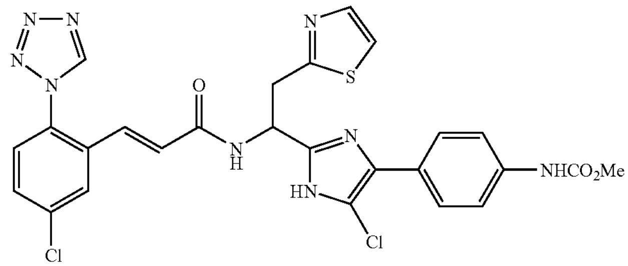 | 609.9 |
| 264 | 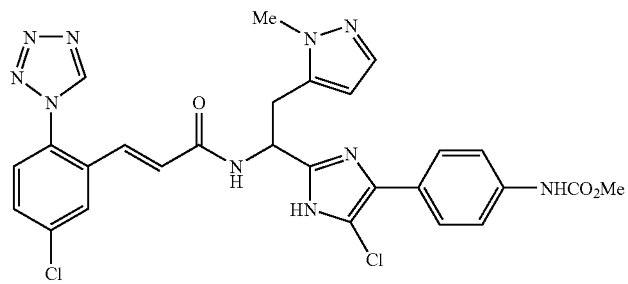 | 607.0 |
| 265 | 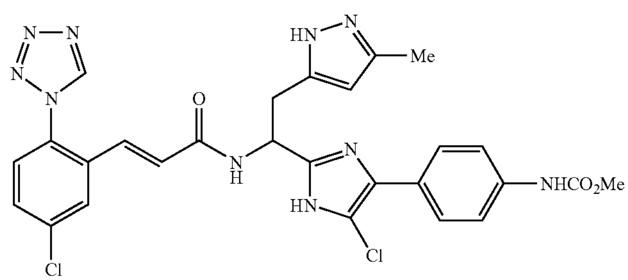 | 607.4 |
| 266 | 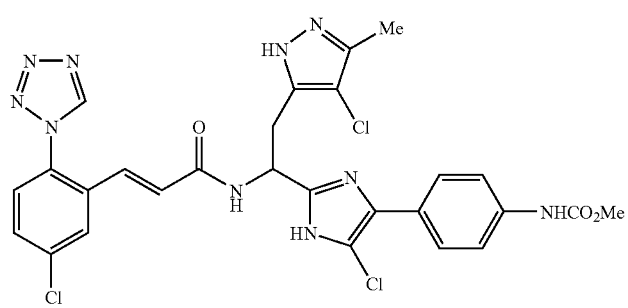 | 643.5 |
| 267 | 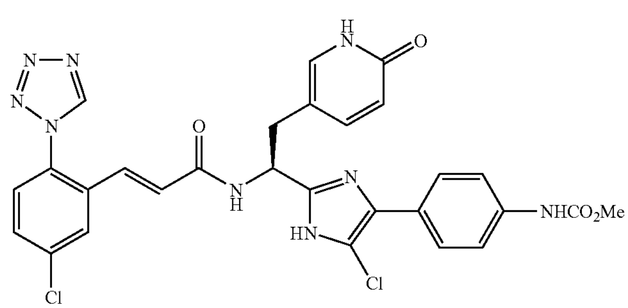 | 620.3 |

TABLE 1-continued

| Ex. No. | Structure | (M + H)+ |
|---|---|---|
| 268 | 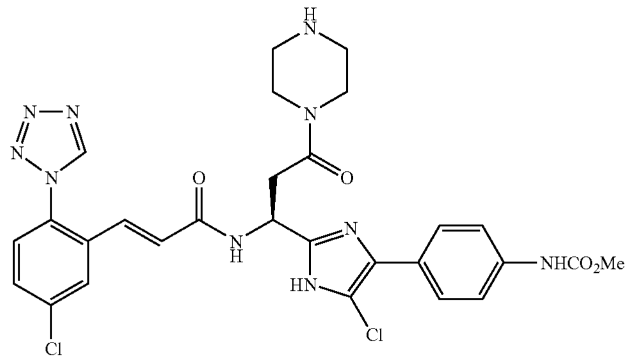 | 639.2 |
| 269 | 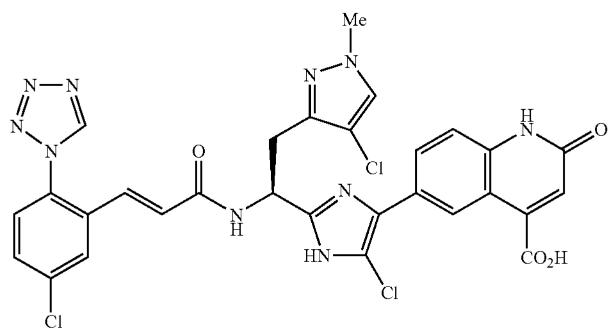 | 679.1 |
| 270 | 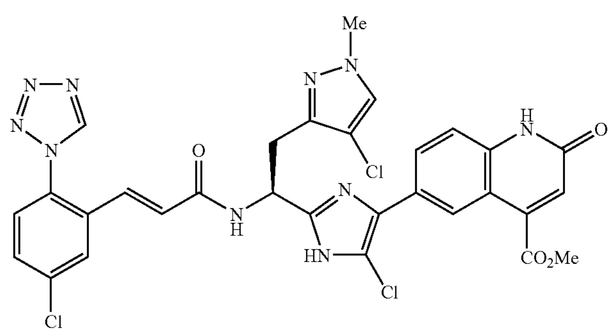 | 693.3 |
| 271 | 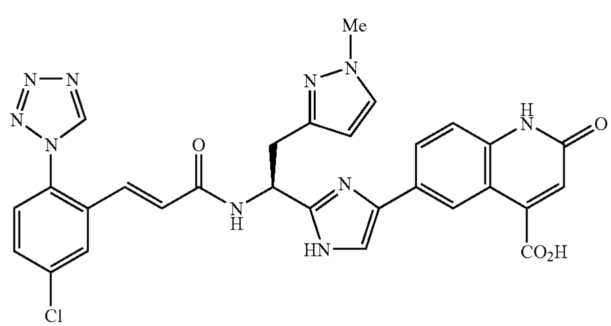 | 611.3 |

TABLE 1-continued
| Ex. No. | Structure | (M + H)+ |
|---|---|---|
| 272 | 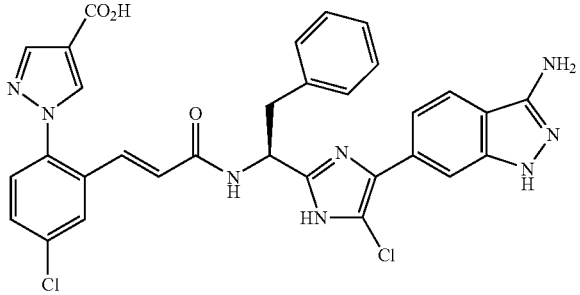 | 627.2 |
| 273 | 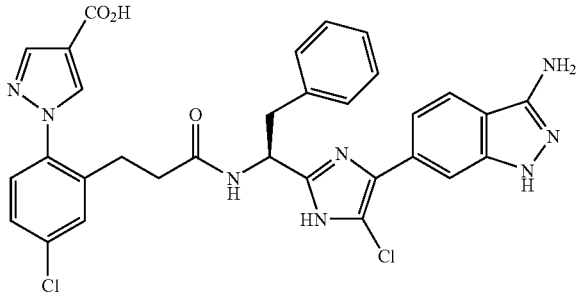 | 629.2 |
| 274 | 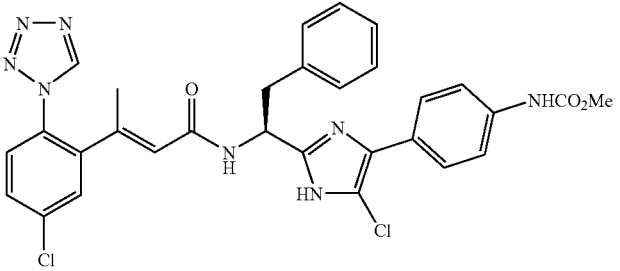 | 617.2 |
| 275 | 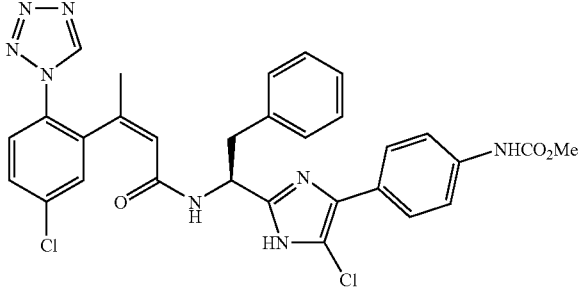 | 617.2 |
| 276 | 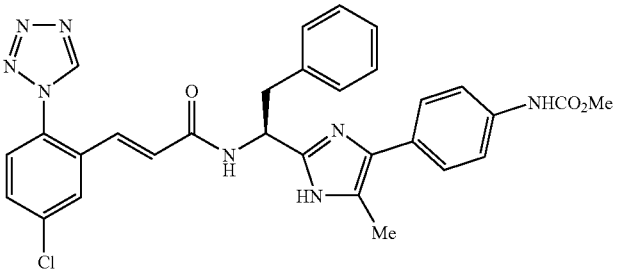 | 583.0 |

TABLE 1-continued

| Ex. No. | Structure | (M + H)+ |
|---|---|---|
| 277 | 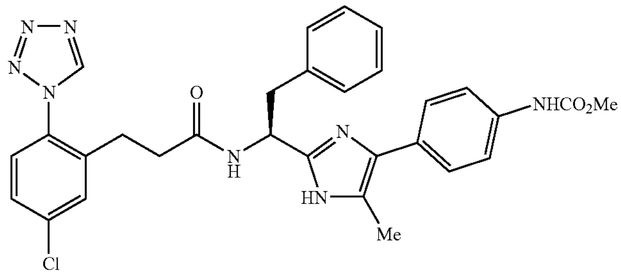 | 585.1 |
| 278 | 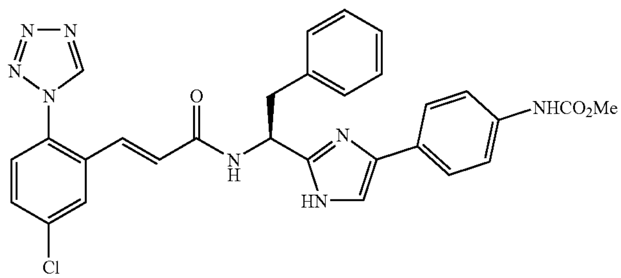 | 569 |
| 279 | 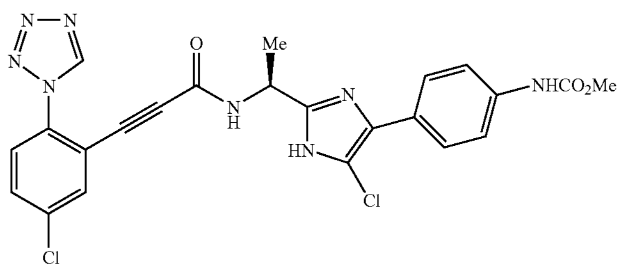 | 525 |
| 280 | 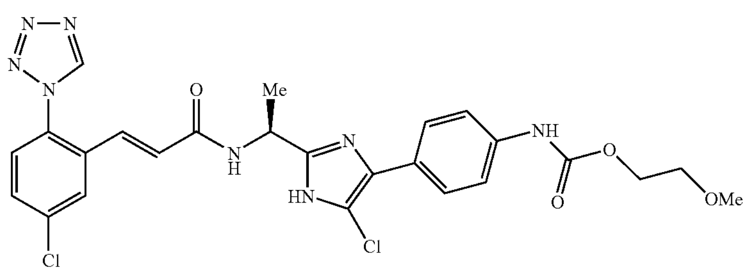 | 571 |
| 281 | 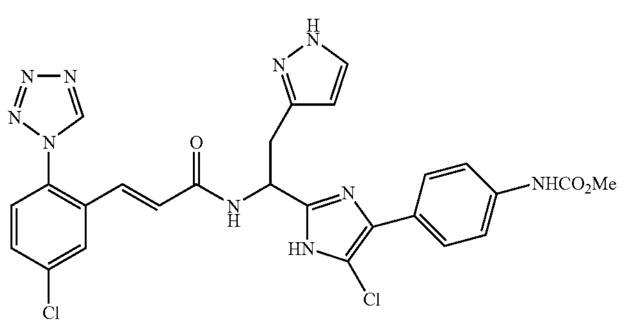 | 593.1 |

TABLE 1-continued

| Ex. No. | Structure | (M + H)+ |
|---|---|---|
| 282 | 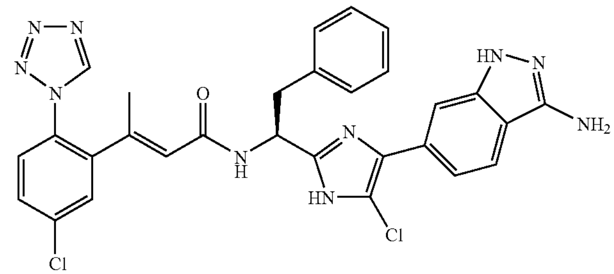 | 599.2 |
| 283 | 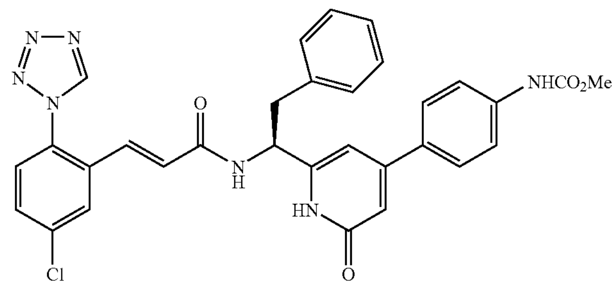 | 596.3 |
| 284 | 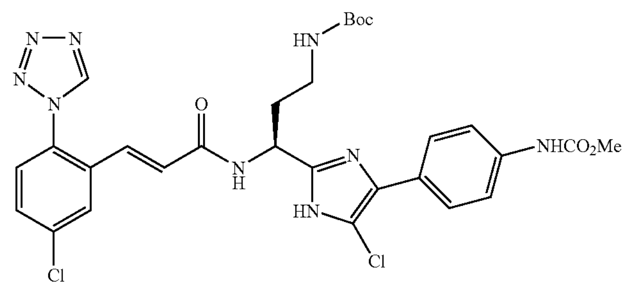 | 656.3 |
| 285 | 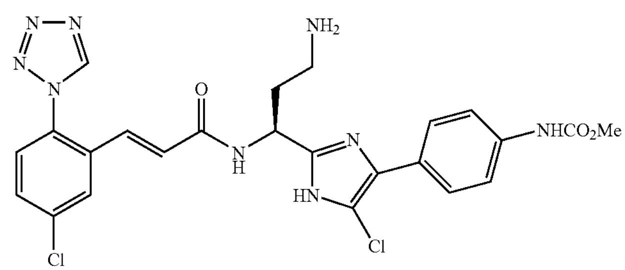 | 556.2 |
| 286 | 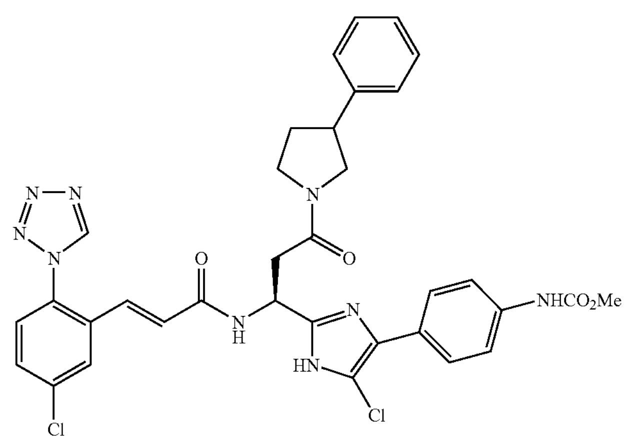 | 700.16 |

TABLE 1-continued
| Ex. No. | Structure | (M + H)+ |
|---|---|---|
| 287 | 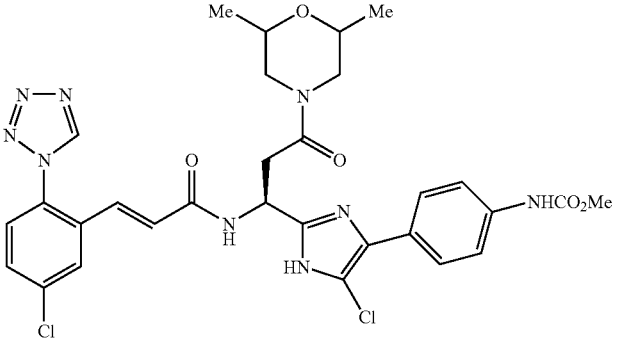 | 668.11 |
| 288 | 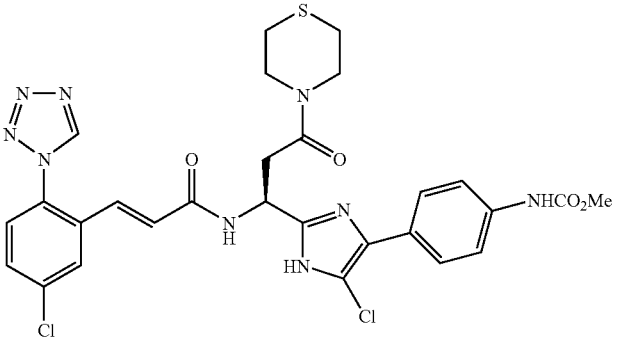 | 656.1 |
| 289 | 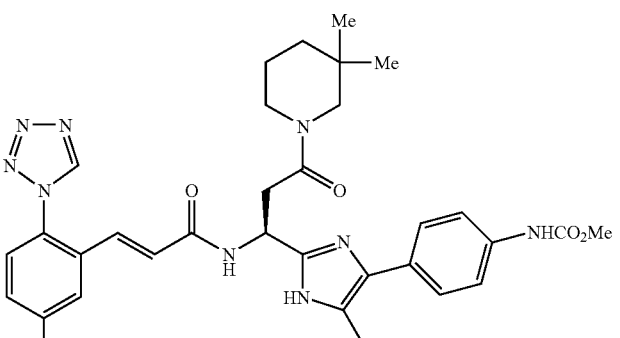 | 666.21 |
| 290 | 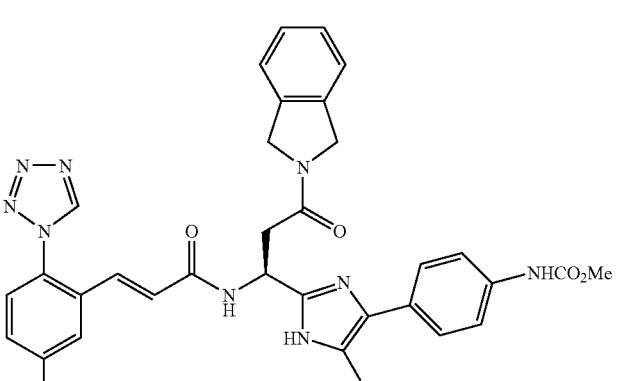 | 672.15 |

TABLE 1-continued
| Ex. No. | Structure | (M + H)+ |
|---|---|---|
| 291 | 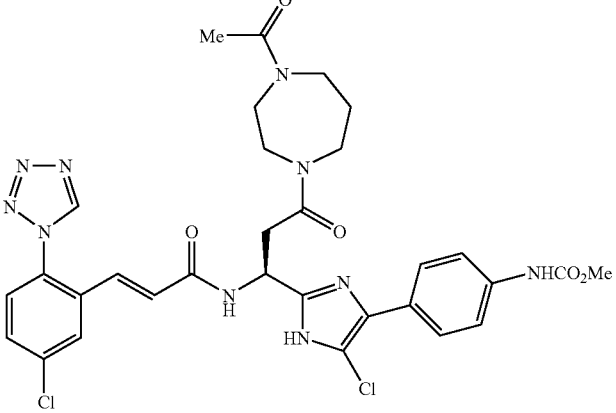 | 695.19 |
| 292 | 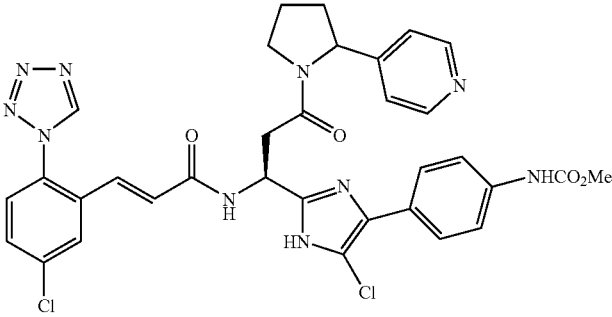 | 701.18 |
| 293 | 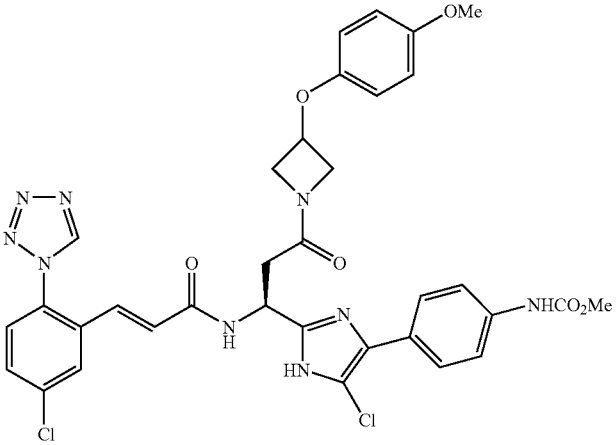 | 732.16 |
| 294 | 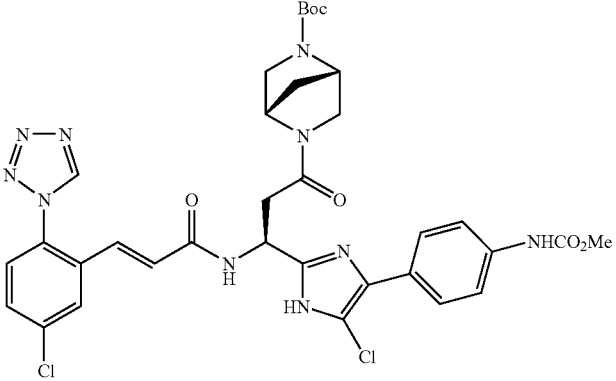 | 751.21 |

TABLE 1-continued

| Ex. No. | Structure | (M + H)+ |
|---|---|---|
| 295 | 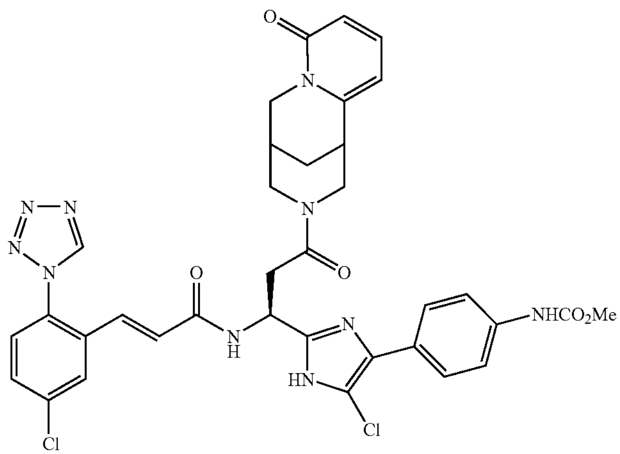 | 743.17 |
| 296 | 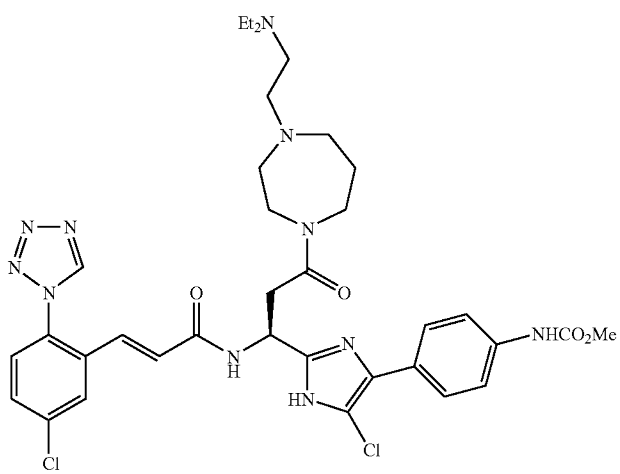 | 752.26 |
| 297 | 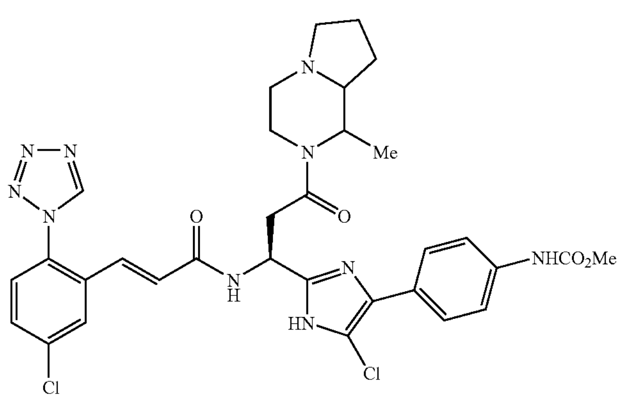 | 693.22 |

TABLE 1-continued

| Ex. No. | Structure | (M + H)+ |
|---|---|---|
| 298 | 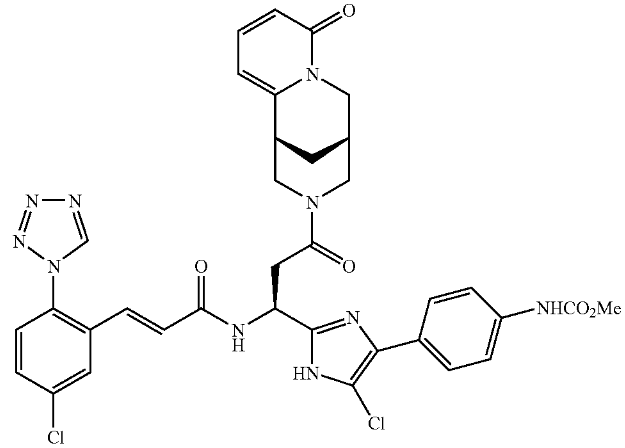 | 743.14 |
| 299 | 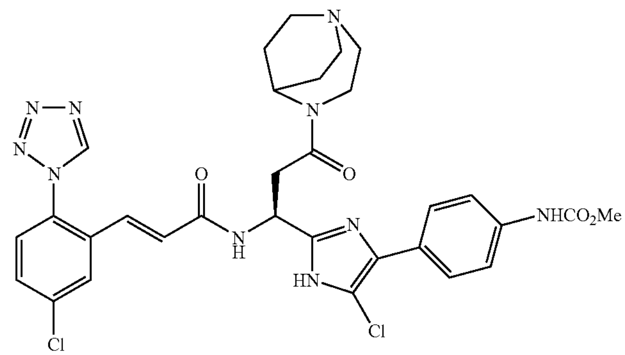 | 679.2 |

Utility

The compounds of this invention are inhibitors of factor XIa and are useful as anticoagulants for the treatment or prevention of thromboembolic disorders in mammals (i.e., factor XIa-associated disorders). In general, a thromboembolic disorder is a circulatory disease caused by blood clots (i.e., diseases involving fibrin formation, platelet activation, and/or platelet aggregation). The term "thromboembolic disorders" as used herein includes arterial cardiovascular thromboembolic disorders, venous cardiovascular or cerebovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of serine proteases involved in the coagulation cascade and/or contact activation system, more specifically, inhibition of the coagulation factors: factor XIa, factor VIIa, factor IXa, factor Xa, plasma kallikrein or thrombin.

The term "thrombosis", as used herein, refers to formation or presence of a thrombus (pl. thrombi); clotting within a blood vessel which may cause ischemia or infarction of tissues supplied by the vessel. The term "embolism", as used herein, refers to sudden blocking of an artery by a clot or foreign material which has been brought to its site of lodgment by the blood current. The term "thromboembolism", as used herein, refers to obstruction of a blood vessel with thrombotic material carried by the blood stream from the site of origin to plug another vessel. The term "stroke", as used herein, refers to embolic stroke or atherothrombotic stroke arising from occlusive thrombosis in the carotid communis, carotid interna, or intracerebral arteries.

The compounds of this invention also are inhibitors of plasma kallikrein and are useful as anti-inflammatory agents for the treatment or prevention of diseases associated with an activation of the contact activation system (i.e., plasma kallikrein associated disorders). In general, a contact activation system disorder is a disease caused by activation of blood on artificial surfaces, including prosthetic valves or other implants, indwelling catheters, stents, cardiopulmonary bypass, hemodialysis, microorganism (e.g., bacteria, virus), or other procedures in which blood is exposed to an artificial surface that promotes contact activation, blood clots (i.e., diseases involving fibrin formation, platelet activation, and/or platelet aggregation). Contact activation can also occur on cell surfaces, cellular receptors or extracellular matrices. Diseases of the contact activation system also include systemic inflammatory response syndrome, sepsis, acute respiratory distress syndrome, hereditary angioedema or other inherited or acquired deficiencies of contact activation components or their inhibitors (plasma kallikrein, factor XIIa, high molecular weight kininogen, C1-esterase inhibitor). It may also include acute and chronic inflammations of joints, vessels, or other mammalian organs.

The effectiveness of compounds of the present invention as inhibitors of the coagulation factors XIa, VIIa, IXa, Xa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin), which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 75-200 pM (Haematologic Technologies) and the synthetic substrate S-2366 (pyroGlu-Pro-Arg-pNA; Chromogenix) at a concentration of 0.0002-0.00025 M. In general, preferred compounds of the present invention, such as the particular compounds disclosed in the above examples, have been identified to be active and exhibit $K_i$'s of equal to or less than 15 µM in the Factor XIa assay, thereby demonstrating the utility of the compounds of the present invention as especially effective inhibitors of coagulation Factor XIa. More preferred compounds have $K_i$'s of equal to or less than 5 µM, preferably equal to or less than 1 µM, more preferably equal to or less than 0.5 µM.

Factor VIIa determinations were made in 0.005 M calcium chloride, 0.15 M sodium chloride, 0.05 M HEPES buffer containing 0.5% PEG 8000 at a pH of 7.4. Determinations were made using purified human Factor VIIa (Haematologic Technologies) or recombinant human Factor VIIa (Novo Nordisk) at a final assay concentration of 2-5 nM, recombinant soluble tissue factor at a concentration of 18-35 nM and the synthetic substrate H-D-Ile-Pro-Arg-pNA (S-2288; Chromogenix or BMPM-2; AnaSpec) at a concentration of 0.001 M. In general, compounds tested in the Factor VIIa assay are considered to be active if they exhibit a $K_i$ of equal to or less than 15 µM.

Factor IXa determinations were made in 0.005 M calcium chloride, 0.1 M sodium chloride, 0.05 M TRIS base and 0.5% PEG 8000 at a pH of 7.4. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Ph'Gly-Arg-AMC; CenterChem) at a concentration of 0.0004-0.0005 M. In general, compounds tested in the Factor IXa assay are considered to be active if they exhibit a $K_i$ of equal to or less than 15 µM.

Factor Xa determinations were made in 0.1 M sodium phosphate buffer at a pH of 7.4 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA; Chromogenix) at a concentration of 0.0002-0.0003 M. In general, compounds tested in the Factor Xa assay are considered to be active if they exhibit a $K_i$ of equal to or less than 15 µM.

Plasma kallikrein determinations were made in 0.1 M sodium phosphate buffer at a pH of 7.4 containing 0.2 M sodium chloride and 0.5% PEG 8000. Determinations were made using purified human kallikrein (Enzyme Research Laboratories) at a final assay concentration of 200 µM and the synthetic substrate S-2302 (H-(D)-Pro-Phe-Arg-pNA; Chromogenix) at a concentration of 0.00008-0.0004 M. The Km value used for calculation of Ki was 0.00005 to 0.00007 M. In general, Compounds tested in the plasma kallikrein assay are considered to be active if they exhibit a $K_i$ of equal to or less than 15 µM.

Thrombin determinations were made in 0.1 M sodium phosphate buffer at a pH of 7.4 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; Chromogenix) at a concentration of 0.0002 M. In general, compounds tested in the thrombin assay are considered to be active if they exhibit a $K_i$ of equal to or less than 15 µM.

In general, preferred compounds of the present invention have demonstrated $K_i$ values of equal to or less than 15 µM in at least one of the above assays, thereby confirming the utility of the compounds of the present invention as effective inhibitors of the coagulation cascade and/or contact activation system, and useful as anticoagulants for the prevention or treatment of thromboembolic disorders in mammals and/or as anti-inflammatory agents for the prevention or treatment of inflammatory disorders in mammals.

The Michaelis constant, $K_m$, for substrate hydrolysis by each protease was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance or fluorescence change versus time) were measured. The following relationships were used to calculate $K_i$ values:

$$(v_o-v_s)/v_s=I/(K_i(1+S/K_m)) \text{ for a competitive inhibitor with one binding site; or}$$

$$v_s/v_o=A+((B-A)/1+((IC_{50}/(I)^n))) \text{ and}$$

$$K_i=IC_{50}/(1+S/K_m) \text{ for a competitive inhibitor}$$

where:
$v_o$ is the velocity of the control in the absence of inhibitor;
$v_s$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme: inhibitor complex;
S is the concentration of substrate; and
$K_m$ is the Michaelis constant for the substrate.

The effectiveness of compounds of the present invention as antithrombotic agents can be determined using relevant in vivo thrombosis models, including In Vivo Electrically-induced Carotid Artery Thrombosis Models and In Vivo Rabbit Arterio-venous Shunt Thrombosis Models.

In Vivo Electrically-induced Carotid Artery Thrombosis (ECAT) Model:

The rabbit ECAT model, described by Wong et al. (*J Pharmacol Exp Ther* 2000, 295, 212-218), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to the initiation of thrombosis. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid $E_{max}$ equation (DeltaGraph; SPSS Inc., Chicago, Ill.).

In Vivo Rabbit Arterio-venous (AV) Shunt Thrombosis Model

The rabbit AV shunt model, described by Wong et al. (Wong, P. C. et al. *J Pharmacol Exp Ther* 2000, 292, 351-357), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm). The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by a nonlinear least square regression program using the Hill sigmoid $E_{max}$ equation (DeltaGraph; SPSS Inc., Chicago, Ill.).

The anti-inflammatory effect of these compounds can be demonstrated in an Evans Blue dye extravasation assay using C1-esterase inhibitor deficient mice. In this model, mice are dosed with a compound of the present invention, Evans Blue is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors).

The utility of the compounds of the current invention to reduce or prevent the morbidity and/or mortality of sepsis can be assessed by injecting a mammalian host with bacteria or viruses or extracts there of and compounds of the present invention. Typical read-outs of the efficacy include changes in the LD50 and blood pressure preservation.

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

The compounds of the present invention can be administered alone or in combination with one or more additional therapeutic agents. These include other anti-coagulant or coagulation inhibitory agents, anti-platelet or platelet inhibitory agents, anti-inflammatory agents, thrombin inhibitors, or thrombolytic or fibrinolytic agents.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Compounds which can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVENOX™), synthetic pentasaccharide, direct acting thrombin inhibitors including hirudin and argatroban, as well as other factor VIIa inhibitors, factor IXa inhibitors, factor Xa inhibitors (e.g., Arixtra™, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granule-content secretion of platelets. Such agents include, but are not limited to, the various known non-steroidal anti-inflammatory drugs (NSAIDS) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDS, aspirin (acetylsalicylic acid or ASA), and piroxicam are preferred. Other suitable platelet inhibitory agents include glycoprotein IIb/IIIa antagonists (e.g., tirofiban, eptifibatide, abciximab, and integrelin), thromboxane-A2-receptor antagonists (e.g., ifetroban), thromboxane-A-synthetase inhibitors, phosphodiesterase-III (PDE-III) inhibitors (e.g., dipyridamole, cilostazol), and PDE-V inhibitors (such as sildenafil), protease-activated receptor 1 (PAR1) antagonists (e.g., SCH-530348, SCH-203099, SCH-529153 and SCH-205831), and pharmaceutically acceptable salts or prodrugs thereof.

Other examples of suitable anti-platelet agents for use in combination with the compounds of the present invention, with or without aspirin, ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include clopidogrel, ticlopidine, prasugrel, and AZD-6140, and pharmaceutically acceptable salts or prodrugs thereof. Ticlopidine and clopidogrel are also preferred compounds since they are known to be more gentle than aspirin on the gastro-intestinal tract in use. Clopidogrel is an even more preferred agent.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors IXa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable anti-arrhythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); $K^+$ channel openers such as $I_{Ach}$ inhibitors, and $I_{Kur}$ inhibitors (e.g., compounds such as those disclosed in WO01/40231).

Examples of suitable antihypertensive agents for use in combination with the compounds of the present invention include alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; angiotensin-converting enzyme (ACE) inhibitors (e.g., captopril, lisinopril, fosinopril, enalapril, ceranopril, cilazopril, delapril, pentopril, quinapril, ramipril, lisinopril), angiotensin AT-1 receptor antagonists (e.g., irbesartan, losartan, valsartan); ET-A receptor antagonists (e.g., sitaxsentan, atrsentan and compounds disclosed in U.S. Pat. Nos. 5,612, 359 and 6,043,265); Dual ET-A/AT-1 antagonist (e.g., compounds disclosed in WO 00/01389); neutral endopeptidase (NEP) inhibitors; vasopepsidase inhibitors (dual ACE/NEP inhibitors, e.g., omapatrilat gemopatrilat, nitrates) and β-blockers (for example propanolol, nadolo, or carvedilol).

Examples of suitable calcium channel blockers (L-type or T-type) for use in combination with the compounds of the present invention include diltiazem, verapamil, nifedipine, amlodipine and mybefradil.

Examples of suitable cardiac glycosides for use in combination with the compounds of the present invention include digitalis and ouabain.

Examples of suitable diruetics for use in combination with the compounds of the present invention include: chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone.

Examples of suitable mineralocorticoid receptor antagonists for use in combination with the compounds of the present invention include sprionolactone and eplirinone.

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DPP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protein tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-obesity agents for use in combination with the compounds of the present invention include orlistat, aP2 inhibitors (such as those disclosed in WO00/59506), and cannabinoid receptor CB1 antagonists (e.g., rimonabant, AVE-1625, SR-147778, and CP-945598).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable holesterol/lipid lowering agents and lipid profile therapies for use in combination with the compounds of the present invention include HMG-CoA reductase inhibitors (e.g., pravastatin, lovastatin, simvastatin, fluvastatin, atorvsatatin, rosuvastatin, and other statins), sequestrants (e.g., cholestyramine and colestipol), nicotonic acid, fenofibric acid derivatives (e.g., gemfibrozil, clofibrat, fenofibrate and benzafibrate), probucol, choesterol absorption inhibitors, and cholesterol ester transfer protein inhibitors (e.g., CP-529414).

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each. A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 μM against the target protease and greater than or equal to 0.1 μM against the other proteases, may also be used in diagnostic assays involving the quantitation of thrombin, Factor VIIa, IXa, Xa, XIa, and/or plasma kallikrein in serum samples. For example, the amount of Factor XIa in serum samples could be determined by careful titration of protease activity in the presence of the relevant chromogenic substrate, S2366, with a potent and selective Factor XIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof, and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 0.1 to 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to 100 milligrams of the compound of the present invention and about 0.1 to 7.5 milligrams of the second anticoagulant, per kilogram of patient body weight. For a tablet dosage form, the compounds of this invention generally may be present in an amount of about 5 to 100 milligrams per dosage unit, and the second anti-coagulant in an amount of about 1 to 50 milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolyic agent when administered alone may be reduced by about 50-80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

What is claimed is:

1. A compound of Formula (I):

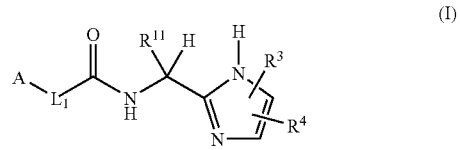

or a stereoisomer, a tautomer, or a pharmaceutically acceptable salt wherein:

A is phenyl substituted with 0-1 $R^1$ and 0-3 $R^2$;

$L_1$ is —$CH_2CH_2$—, —CH=CH—, —C(Me)=CH—, or —C≡C—;

$R^1$ is, independently at each occurrence, F, Cl, Br, I, $OCF_3$, $CF_3$, —$(CH_2)_rOR^a$, —$(CH_2)_rSR^a$, CN, —$(CH_2)_r$ $NR^7R^8$, —C(=NH)$NH_2$, —C(O)$NR^8R^9$, —S(O)$_p$ $NR^8R^9$, or $C_{1-6}$ alkyl;

$R^2$ is, independently at each occurrence, F, Cl, Br, $OCF_3$, $CF_3$, $CHF_2$, CN, $NO_2$, $OR^a$, $NR^7R^8$, —$CH_2$OMe, —$SR^a$, —$CH_2$SMe, —C(O)$OR^a$, —$CH_2NR^7R^8$, —$SO_2NH_2$, —$SO_2$Me, —$NHSO_2R^c$, —$CH_2NHSO_2R^c$, —C(O)$NR^8R^9$, —NHC(O)$R^c$, —$CH_2$NHC(O)$R^c$, —NHC(O)$OR^c$, —$CH_2$NHC(O)$OR^c$, —NHC(O) $NHR^c$, —$CH_2$NHC(O)$NHR^c$, —$(CH_2)_r$-3-7 membered carbocycle optionally substituted with 0-2 $R^{2b}$, or —$(CH_2)_r$-5-7 membered heterocycle comprising carbon atoms and 1-4 heteroatoms selected from the group consisting of N, O, and $S(O)_p$, wherein said heterocycle is substituted with 0-2 $R^{2b}$;

$R^{2b}$ is, independently at each occurrence, =O, F, Br, Cl, $OCF_3$, $CF_3$, $-(CH_2)_rOR^a$, $-(CH_2)_rSR^a$, $-(CH_2)_rCN$, $-(CH_2)_rNR^7R^8$, $-CH_2)_rC(O)OR^a$, or $C_{1-4}$ alkyl;

$R^3$ is $-(CH_2)_r-C_{3-10}$ carbocycle substituted with 0-3 $R^{3a}$, or $-(CH_2)_r$-5- to 10-membered heterocycle comprising: carbon atoms and 1-4 heteroatoms selected from N, O, and $S(O)_p$, wherein said heterocycle is substituted with 0-3 $R^{3a}$;

$R^{3a}$ is, independently at each occurrence, selected from the group consisting of: =O, F, Cl, Br, I, $OCF_3$, $CF_3$, $-(CH_2)_rCN$, $NO_2$, $-(CH_2)_rOR^{3b}$, $-(CH_2)_rSR^{3b}$, $-(CH_2)_rNR^7R^8$, $-NHC(O)NR^8R^9$, $-(CH_2)_rC(O)OR^{3b}$, $-C(O)C_{1-4}$ alkyl, $-SO_2NHR^{3b}$, $-(CH_2)_rNHC(O)R^{3b}$, $-(CH_2)_rNHCO_2R^{3c}$, $-(CH_2)_rOC(O)R^{3b}$, $-(CH_2)_rC(O)NR^8R^9$, $-NHSO_2R^{3c}$, $C_{1-4}$ haloalkyl, $C_{1-4}$ haloalkyloxy-, $C_{1-6}$ alkyl, $C_{2-6}$ alkenyl, $C_{1-6}$ alkynyl, and $-(CH_2)_r$-5- to 6-membered heterocycle comprising: carbon atoms and 1-4 heteroatoms selected from N, O, and $S(O)_p$;

$R^{3b}$ is, independently at each occurrence, H or $C_{1-6}$ alkyl substituted with 0-2 $R^{3d}$;

$R^{3c}$ is, independently at each occurrence, $C_{1-6}$ alkyl substituted with 0-2 $R^{3d}$, $-(CH_2)_r$-phenyl, or $-(CH_2)_r$-5- to 6-membered heterocycle comprising: carbon atoms and 1-4 heteroatoms selected from N, O, and $S(O)_p$;

$R^{3d}$ is, independently at each occurrence, H, F, Cl, Br, CN, $NO_2$, $-(CH_2)_rNR^7R^8$, $-(CH_2)_rOR^a$, or $-C(O)OR^a$;

$R^4$ is selected from the group consisting of: H, F, Cl, Br, I, $OCF_3$, $CF_3$, CN, $NO_2$, $-(CH_2)_rOR^a$, $-(CH_2)_rSR^a$, $-(CH_2)_rC(O)OR^a$, $-(CH_2)_rNR^7R^8$, and $C_{1-4}$ alkyl;

$R^7$ is, independently at each occurrence, H, $C_{1-6}$ alkyl, or $-(CH_2)_n$-phenyl;

$R^8$ is, independently at each occurrence, H, $C_{1-6}$ alkyl, or $-(CH_2)_n$-phenyl;

alternatively, $R^7$ and $R^8$, when attached to the same nitrogen, combine to form a 5- to 6-membered heterocycle comprising: carbon atoms and 0-3 additional heteroatoms selected from N, O, and $S(O)_p$;

$R^9$ is, independently at each occurrence, H, $C_{1-6}$ alkyl, or $-(CH_2)_n$-phenyl;

alternatively, $R^8$ and $R^9$, when attached to the same nitrogen, combine to form a 5- to 6-membered heterocycle comprising: carbon atoms and 0-2 additional heteroatoms selected from N, O, and $S(O)_p$;

$R^{11}$ is $-(CH_2)_r-C_{3-10}$ carbocycle substituted with 0-3 $R^{11b}$;

$R^{11b}$ is, independently at each occurrence, selected from the group consisting of: H, =O, $OR^a$, $-(CH_2OR^a$, F, Cl, Br, CN, $NO_2$, $CF_3$, $OCF_3$, $OCHF_2$, $-C(CH_3)_2OR^a$, $-C(O)R^a$, $-C(O)OR^a$, $-NR^7R^8$, $-C(O)NR^8R^9$, $-NR^7C(O)R^b$, $-NR^8C(O)_2R^c$, $-S(O)_pNR^8R^9$, $-NR^8S(O)_pR^c$, and $C_{1-6}$ alkyl;

$R^a$ is, independently at each occurrence, H, $CF_3$, $C_{1-6}$ alkyl, or benzyl;

$R^b$ is, independently at each occurrence, $CF_3$, OH, $C_{1-4}$ alkoxy, $C_{1-6}$ alkyl, $-(CH_2)_r-C_{3-10}$ carbocycle, or $-(CH_2)_r$-5- to 10-membered heterocycle comprising: carbon atoms and 1-4 heteroatoms selected from N, O, and $S(O)_p$;

$R^c$ is, independently at each occurrence, $CF_3$ or $C_{1-6}$ alkyl substituted with 0-2 $R^f$;

$R^f$ is, independently at each occurrence, H, =O, $-(CH_2)_rOR^g$, F, Cl, Br, I, CN, $NO_2$, $-NR^gR^g$, $-C(O)R^g$, $-C(O)OR^g$, $-NR^gC(O)R^g$, $-C(O)NR^gR^g$, or $-SO_2NR^gR^g$;

$R^g$ is, independently at each occurrence, H, $C_{1-6}$ alkyl, or $-(CH_2)_n$-phenyl;

n, at each occurrence, is selected from 0, 1, 2, 3, and 4;

p, at each occurrence, is selected from 0, 1, and 2; and r, at each occurrence, is selected from 0, 1, 2, 3, and 4.

2. The compound according to claim 1, wherein:

$R^1$ is, independently at each occurrence, F, Cl, Br, I, $OCF_3$, $CF_3$, $OCH_3$, $CH_3$, Et, $NH_2$, $-C(=NH)NH_2$, $-C(O)NH_2$, $-CH_2NH_2$ or $-SO_2NH_2$;

$R^2$ is, independently at each occurrence, F, Cl, Br, $CF_3$, $NO_2$, $OR^a$, $NR^7R^8$, $-CH_2OMe$, $-SR^a$, $-CH_2SMe$, $-C(O)OR^a$, $-C(O)NR^8R^9$, $-NHC(O)R^c$, $-CH_2NHC(O)R^c$, $-NHC(O)OR^c$, $-CH_2NHC(O)OR^c$, $-NHC(O)NHR^c$, $-CH_2NHC(O)NHR^c$, or a 5-7 membered heterocycle comprising carbon atoms and 1-4 heteroatoms selected from N, O, and $S(O)_p$, wherein said heterocycle is substituted with 0-2 $R^{2b}$;

$R^3$ is phenyl substituted with 0-2 $R^{3a}$, naphthyl substituted with 0-2 $R^{3a}$, 1,2,3,4-tetrahydronaphthyl substituted with 0-2 $R^{3a}$, or a heterocycle substituted with 0-2 $R^{3a}$ and said heterocycle is selected from the group consisting of: pyridine, pyridone, pyrimidine, indole, 2-oxindole, isoindoline, isoindolin-1-one, indazole, 1H-indazole-3-one, benzimidazole, benzisoxazole, benzoxazole, quinoline, isoquinoline, dihydroisoquinoline, dihydroquinoline, dihydroquinolinone, dihydroindole, dihydrobenzimidazole, dihydrobenzoxazine, and tetrahydroquinoline;

$R^{3a}$ is, independently at each occurrence, selected from the group consisting of: =O, F, Cl, Br, Me, CN, OH, OMe, $-OC(O)(t-Bu)$, $-CH_2OMe$, $CF_3$, COMe, $CO_2H$, $CO_2Me$, $-CH_2CO_2H$, $-(CH_2)_2CO_2H$, $-CH_2CO_2Me$, $-CH_2CO_2Et$, $-CH_2CH_2CO_2Et$, $-CH_2CN$, $NH_2$, $-CH_2NH_2$, $-CH_2NMe_2$, $-NHCOMe$, $-NHCO_2Me$, $-NHCO_2Et$, $-NHCH_2CH_2CO_2H$, $-NHCO_2(i-Pr)$, $-NHCO_2(i-Bu)$, $-NHCO_2(t-Bu)$, $-NHCO_2Bn$, $-NHCO_2CH_2CH_2OMe$, $-NHCO_2CH_2CH_2CH_2OMe$, $-NHCO_2CH_2CO_2H$, $-NHCO_2CH_2CH_2CO_2H$, $-NHCO_2CH_2CH_2OH$, $-NHCO_2CH_2CH_2NH_2$, $-NHCO_2CH_2$-tetrahydrofuran-2-yl, $-NHCO_2CH_2CH_2CH(Me)OMe$, $-NHCO_2CH_2CH_2C(O)NH_2$, $-NHC(O)NHCH_2CH_2$-morpholino, $-NHC(O)NHCH_2$-pyrid-4-yl, $-NHCO_2CH_2$-pyrid-4-yl, $-NHCO_2CH_2$-pyrid-3-yl, $-NHCO_2CH_2$-pyrid-2-yl, $-NHCO_2CH_2$-(piperidin-4-yl), $-NHC(O)NHCH_2CH_2$-pyrid-4-yl, $-NHCO_2CH_2CH_2$-pyrid-4-yl, $-NHCO_2CH_2CH_2$-morpholino, $-CH_2NHCO_2Me$, $-NHC(O)NHMe$, $-NHC(O)N(Me)_2$, $-NHC(O)NHCH_2CH_2OMe$, $-NHSO_2Me$, $-SO_2NH_2$, $-SO_2NHMe$, $-SO_2NHCH_2CH_2OH$, $-SO_2NHCH_2CH_2OMe$, $-CONH_2$, $-CONHMe$, $-CON(Me)_2$, $-C(O)NHCH_2CH_2OMe$, $-CH_2CONH_2$, $-CO(N$-morpholino), $-NHCH_2CH_2(N$-morpholino), $-NR^7R^8$, $-NH(1H$-imidazol-2-yl), 1H-tetrazol-5-yl, tetrazol-1-yl, pyrimidin-5-yl, N-morpholino, and $-(CH_2)_r$-5- to 6-membered heterocycle comprising: carbon atoms and 1-4 heteroatoms selected from N, O, and $S(O)_p$;

$R^4$ is selected from the group consisting of: H, F, Cl, Br, OH, OMe, $NH_2$, Me, Et, $CF_3$, $-CH_2OH$, $-C(O)_2H$, $CO_2Me$, $CO_2Et$, $-C(O)NH_2$, $-C(O)NHMe$, $-C(O)N(Me)_2$, and $-CH_2CO_2H$; and R¹¹ is —(CH₂)ᵣ—C₃₋₇ cycloalkyl substituted with 0-2 R¹¹ᵇ, —(CH₂)ᵣ-indanyl substituted with 0-2 R¹¹ᵇ, —(CH₂)ᵣ-indenyl substituted with 0-2 R¹¹ᵇ, —(CH₂)ᵣ-phenyl substituted with 0-2 R¹¹ᵇ, or —(CH₂)ᵣ-naphthyl substituted with 0-2 R¹¹ᵇ.

3. The compound according to claim 1, wherein:

R¹ is, independently at each occurrence, F, Cl, Br, CF₃, NH₂, —CH₂NH₂, —C(=NH)NH₂, —C(O)NH₂, —SO₂NH₂, SRᵃ, ORᵃ, or C₁₋₆ alkyl;

R² is, independently at each occurrence, selected from the group consisting of: =O, F, Cl, Br, CF₃, Me, Et, ORᵃ, CN, NO₂, NR⁷R⁸, —CH₂OMe, —SRᵃ, —CH₂SMe, —C(O)ORᵃ, —CH₂NR⁷R⁸, —SO₂NH₂, —SO₂Me, —NHSO₂Rᶜ, —CH₂NHSO₂Rᶜ, —C(O)NR⁸R⁹, —NHC(O)Rᶜ, —CH₂NHC(O)Rᶜ, —NHC(O)ORᶜ, —CH₂NHC(O)ORᶜ, —NHC(O)NHRᶜ, —CH₂NHC(O)NHRᶜ, and a heterocycle substituted with 0-2 R²ᵇ and said heterocycle selected from: pyrrolidinyl, 2-oxo-1-pyrrolidinyl, piperidinyl, pyrazolyl, triazolyl, and tetrazolyl;

R³ᵃ is, independently at each occurrence, selected from the group consisting of: =O, F, Cl, Br, Me, CN, OH, OMe, —OC(O)(t-Bu), CH₂OMe, CF₃, COMe, CO₂H, CO₂Me, —CH₂CO₂H, —(CH₂)₂CO₂H, —CH₂CO₂Me, —CH₂CO₂Lt, —CH₂CH₂CO₂Lt, —CH₂CN, NH₂, —CH₂NH₂, —CH₂NMe₂, —NHCOMe, —NHCO₂Me, —NHCO₂Lt, —NHCH₂CH₂CO₂H, —NHCO₂(i-Pr), —NHCO₂(i-Bu), —NHCO₂(t-Bu), —NHCO₂Bn, —NHCO₂CH₂CH₂OMe, —NHCO₂CH₂CH₂CH₂OMe, —NHCO₂CH₂CO₂H, —NHCO₂CH₂CH₂CO₂H, —NHCO₂CH₂CH₂OH, —NHCO₂CH₂CH₂NH₂, —NHCO₂CH₂-tetrahydrofuran-2-yl, —NHCO₂CH₂CH₂CH(Me)OMe, —NHCO₂CH₂CH₂C(O)NH₂, —NHC(O)NHCH₂CH₂-morpholino, —NHC(O)NHCH₂-pyrid-4-yl, —NHCO₂CH₂-pyrid-4-yl, —NHCO₂CH₂-pyrid-3-yl, —NHCO₂CH₂-pyrid-2-yl, —NHCO₂CH₂-(piperidin-4-yl), —NHC(O)NH CH₂CH₂-pyrid-4-yl, —NHCO₂CH₂CH₂-pyrid-4-yl, —NHCO₂CH₂CH₂-morpholino, —CH₂NHCO₂Me, —NHC(O)NHMe, —NHC(O)N(Me)₂, —NHC(O)NHCH₂CH₂OMe, 4-[(1-carbamoyl-cyclopropanecarbonyl)-amino]-, —NHSO₂Me, —SO₂NH₂, —SO₂NHMe, —SO₂NHCH₂CH₂OH, —SO₂NHCH₂CH₂OMe, —CONH₂, —CONHMe, —CON(Me)₂, —C(O)NHCH₂CH₂OMe, —CH₂CONH₂, —CO(N-morpholino), —NHCH₂CH₂(N-morpholino), —NR⁷R⁸, —NH(1H-imidazol-2-yl), 1H-tetrazol-5-yl, tetrazol-1-yl, pyrimidin-5-yl, N-morpholino, and —(CH₂)ᵣ-5- to 6-membered heterocycle comprising: carbon atoms and 1-4 heteroatoms selected from N, O, and S(O)ₚ;

R⁴ is, independently at each occurrence, selected from the group consisting of: H, F, Cl, Br, OMe, NH₂, CF₃, Me, Et, CO₂H, CO₂Me, and CO₂Et;

R¹¹ is —(CH₂)ᵣ—C₃₋₇ cycloalkyl substituted with 0-2 R¹¹ᵇ, —(CH₂)ᵣ-phenyl substituted with 0-2 R¹¹ᵇ, —(CH₂)ᵣ-indanyl substituted with 0-2 R¹¹ᵇ, —(CH₂)ᵣ-indenyl substituted with 0-2 R¹¹ᵇ, or —(CH₂)ᵣ-naphthyl substituted with 0-2 R¹¹ᵇ;

R¹¹ᵇ is, independently at each occurrence, selected from the group consisting of: H, =O, F, Cl, Br, CF₃, OH, OMe, OEt, —CH₂OH, —C(CH₃)₂OH, —CH₂OMe, O(i-Pr), OCF₃, OCHF₂, CN, OPh, OBn, NO₂, NH₂, and C₁₋₆ alkyl.

4. The compound according to claim 1, wherein:
A is

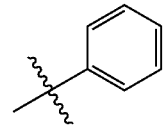

substituted with 0-2 R²,

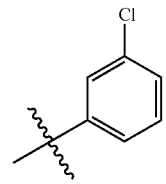

substituted with 0-2 R², or

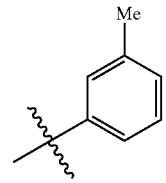

substituted with 0-2 R²;

R² is, independently at each occurrence, selected from the group consisting of: F, Cl, Br, Me, CF₃, OMe, OEt, OPh, OBn, SMe, SEt, S(n-Pr), SBn, —CH₂SMe, SO₂Me, NH₂, —CH₂NH₂, NO₂, CO₂H, CO₂Me, CONH₂, —CH₂NHCOPh, —NHCO₂Me, —CH₂NHCO₂Et, —CH₂NHCO₂(i-Pr), —CH₂NHCO₂(t-Bu), —CH₂NHCO₂Bn, —CH₂NHCO(CH₂)₂C₀₂H, —CONHPh, —NHCONHMe, —CH₂NHCONHEt, —CH₂NHCONH(CH₂)₂CO₂Et, —CH₂NHCONHPh, —CH₂NHCONH(4-Cl-Ph), —CH₂NHCONHBn, —NHSO₂Me, —CH₂NHSO₂Me, —CH₂NHSO₂Et, —CH₂NHSO₂(n-Pr), —CH₂NHSO₂(i-Pr), —CH₂NHSO₂(n-pentyl), —CH₂NHSO₂Ph, —CH₂NHSO₂(4—NHCOMe-Ph), —CH₂NHSO₂(4-Cl-Bn), —CH₂NHSO₂CH₂CH₂Ph, —CH₂NHSO₂CH₂CH₂(2-Cl-Ph), —CH₂NHSO₂CH₂CH₂(3-Cl-Ph), —CH₂NHSO₂CH₂CH₂(4-Cl-Ph), —CH₂NHSO₂(3,4-dimethyl-isoxazol-4-yl), 1-pyrrolidinyl, 2-oxo-1-pyrrolidinyl, 3-carboxy-N-piperidinyl, pyrazol-1-yl, 4-carboxy-pyrazol-1-yl, 1,2,3-triazol-1-yl, 1,2,4-triazol-1-yl, 1,2,3-triazol-2-yl, 4-carboxy-1,2,3-triazol-1-yl, 4-(ethoxycarbonyl)-1,2,3-triazol-1-yl, tetrazol-1-yl, tetrazol-5-yl, 5-Me-tetrazol-1-yl, 5-CF₃-tetrazol-1-yl, and —OCH₂(2-tetrahydrofuranyl);

R³ is phenyl substituted with 0-2 R³ᵃ, naphthyl substituted with 0-2 R³ᵃ, 1,2,3,4-tetrahydro-naphthyl substituted with 0-2 R³ᵃ, or a heterocycle substituted with 0-2 R³ᵃ and said heterocycle is selected from the group consisting of: pyridine, pyridinone, pyrimidine, indole, 2-oxindole, isoindoline, isoindolin-1-one, indazole, 1H-indazole-3-one, benzimidazole, benzisoxazole, benzoxazole, quinoline, isoquinoline, 1H-quinolin-4- one, 1H-quinolin-2-one, 2H-3,4-dihydroisoquinolin-1-one, 3,4-dihydro-1H-quinolin-2-one, 1,3-dihydroindol-2-one, 3H-benzoxazol-2-one, and 1,2,3,4-tetrahydroquinoline; and R⁴ is, independently at each occurrence, selected from the group consisting of: H, Me, F, Br, Cl, CF₃, CO₂H, CO₂Me, and CO₂Et.

5. The compound according to claim 1, wherein:

A is selected from the group consisting of: phenyl, 2-fluorophenyl, 3-fluorophenyl, 2-chlorophenyl, 3-chlorophenyl, 2-bromophenyl, 3-bromophenyl, 3-methylphenyl, 2-methoxyphenyl, 3-methoxyphenyl, 3-aminomethylphenyl, 4-aminomethylphenyl, 2-carboxy-5-chlorophenyl, 2-methoxycarbonyl-5-chlorophenyl, 2-(N-(methoxycarbonyl)-amino)-5-chlorophenyl, 2-(N-(ethoxycarbonyl)-aminomethyl)-5-chlorophenyl, 2-(N-(isopropoxycarbonyl)-aminomethyl)-5-chlorophenyl, 2-(N-(tert-butoxycarbonyl)-aminomethyl)-5-chlorophenyl, 2-(N-(phenylcarbonyl)-aminomethyl)-5-chlorophenyl, 2-(N-(benzoxycarbonyl)-aminomethyl)-5-chlorophenyl, 2-((N-(3-propanoic acid)carbonyl)-aminomethyl)-5-chlorophenyl, 2-(3-methylureido)-5-chlorophenyl, 2-(3-ethylureidomethyl)-5-chlorophenyl, 2-[3-(2-ethoxycarbonyl-ethyl)-ureidomethyl]-5-chlorophenyl, 2-(3-phenylureido)methyl)-5-chlorophenyl, 2-(3-(4-chlorophenyl)ureido)methyl)-5-chlorophenyl, 2-(3-benzylureido)methyl)-5-chlorophenyl, 2-(N-(methylsulfonyl)-amino)-5-chlorophenyl, 2-(N-(methylsulfonyl)-aminomethyl)-5-chlorophenyl, 2-(N-(ethylsulfonyl)-aminomethyl)-5-chlorophenyl, 2-(N-(n-propylsulfonyl)-aminomethyl)-5-chlorophenyl, 2-(N-(isopropylsulfonyl)-aminomethyl)-5-chlorophenyl, 2-(N-(n-pentylsulfonyl)-aminomethyl)-5-chlorophenyl, 2-(N-(phenylsulfonyl)-aminomethyl)-5-chlorophenyl, 2-((N-(4-methylcarbonylaminophenyl)sulfonyl)-aminomethyl)-5-chlorophenyl, 2-(N-(4-chlorobenzylsulfonyl)-aminomethyl)-5-chlorophenyl, 2-(N-(phenethylsulfonyl)-aminomethyl)-5-chlorophenyl, 2-(N-(2-chlorophenethylsulfonyl)-aminomethyl)-5-chlorophenyl, 2-(N-(3-chlorophenethylsulfonyl)-aminomethyl)-5-chlorophenyl, 2-(N-(4-chlorophenethylsulfonyl)-aminomethyl)-5-chlorophenyl, 2-(N-(3,4-dimethyl-isoxazol-4-yl)-aminomethyl)-5-chlorophenyl, 2-(N-(3,4-dimethyl-isoxazol-4-ylsulfonyl)-aminomethyl)-5-chlorophenyl, 3-carbamoyl-phenyl, 2,4-difluorophenyl, 2,5-difluorophenyl, 2,5-dichlorophenyl, 3,5-dichlorophenyl, 5-chloro-2-fluorophenyl, 3-chloro-2-fluorophenyl, 3-chloro-4-methylphenyl, 2-methyl-5-chlorophenyl, 2-methoxy-5-chlorophenyl, 2-ethoxy-5-chlorophenyl, 2-benzyloxy-5-chlorophenyl, 2-methylthio-5-chlorophenyl, 2-ethylthio-5-chlorophenyl, 2-propylthio-5-chlorophenyl, 2-benzylthio-5-chlorophenyl, 2-methylthiomethyl-5-chlorophenyl, 2-(2-oxo-1-pyrrolidinyl)-5-chlorophenyl, 3-trifluoromethyl-2-fluorophenyl, 2-trifluoromethyl-5-chlorophenyl, 5-bromo-2-fluorophenyl, 2-amino-5-chlorophenyl, 2-aminomethyl-5-chlorophenyl, 2-methylsulfonyl-5-chlorophenyl, 2-methylsulfonamide-5-chlorophenyl, 2-phenylcarbamoyl-5-chlorophenyl, 2-(3-carboxy-N-piperidinyl)-5-chlorophenyl, 2,6-difluoro-3-methylphenyl, 2-chloro-6-fluoro-3-methylphenyl, 2-fluoro-6-chloro-3-methylphenyl, 2,6-difluoro-3-chlorophenyl, 2,3-dichloro-6-aminophenyl, 2,3-dichloro-6-nitrophenyl, 2-phenoxyphenyl, 2-phenoxy-5-chlorophenyl, 2-(N-pyrrolidinyl)-5-chlorophenyl, 2-(pyrazol-1-yl)-5-chlorophenyl, 2-(4-carboxy-pyrazol-1-yl)-5-chlorophenyl, 2-(1,2,3-triazol-1-yl)-5-methylphenyl, 2-(1,2,3-triazol-1-yl)-5-chlorophenyl, 2-(1,2,3-triazol-2-yl)-5-chlorophenyl, 2-(1,2,4-triazol-1-yl)-5-chlorophenyl, 2-[(4-carboxy)-1,2,3-triazol-1-yl]-5-methylphenyl, 2-[(4-carboxy)-1,2,3-triazol-1-yl]-5-chlorophenyl, 2-[(4-ethoxycarbonyl)-1,2,3-triazol-1-yl]-5-chlorophenyl, 2-(tetrazol-1-yl)-5-methylphenyl, 2-(tetrazol-1-yl)-5-chlorophenyl, 2-(tetrazol-5-yl)-5-chlorophenyl, 2-(5-methyl-tetrazol-1-yl)-5-chlorophenyl, 2-(tetrazol-1-yl)-3-fluoro-5-chlorophenyl, 2-(tetrazol-1-yl)-3-fluoro-5-methylphenyl, 2-(5-methyltetrazol-1-yl)-5-chlorophenyl, 2-(5-trifluoromethyl-tetrazol-1-yl)-5-chlorophenyl, and 2-(2-tetrahydrofuranyl-methoxy)-5-chlorophenyl;

R³ is selected from the group consisting of: phenyl, 3-biphenyl, 4-biphenyl, 3-aminophenyl, 4-aminophenyl, 3-N,N-dimethylaminophenyl, 4-phenoxyphenyl, 4-benzyloxyphenyl, 4-(t-butoxymethyl)-phenyl, 4-methylsulfonylphenyl, 3-cyanophenyl, 4-cyanophenyl, 3-fluorophenyl, 4-fluorophenyl, 3-chlorophenyl, 4-chlorophenyl, 3-bromophenyl, 4-bromophenyl, 3-hydroxyphenyl, 4-hydroxyphenyl, 2-methoxyphenyl, 3-methoxyphenyl, 4-methoxyphenyl, 3-trifluoromethylphenyl, 4-trifluoromethylphenyl, 3-carboxyphenyl, 4-carboxyphenyl, 3-methoxycarbonylphenyl, 4-methoxycarbonylphenyl, 3-carboxymethylphenyl, 4-carboxymethylphenyl, 4-methoxycarbonylmethylphenyl, 3-ethoxycarbonylmethylphenyl, 4-ethoxycarbonylmethylphenyl, 4-ethoxycarbonylethylphenyl, 3-carbamoylphenyl, 4-carbamoylphenyl, 3-aminocarbonylmethylphenyl, 4-aminocarbonylmethylphenyl, 4-methylaminocarbonylphenyl, 4-dimethylaminocarbonylmethylphenyl, 4-amidinophenyl, 3-methylcarbonylaminophenyl, 4-methylcarbonylaminophenyl, 4-methoxycarbonylaminophenyl, 4-aminosulfonylphenyl, 3-methylsulfonylaminophenyl, 4-methylsulfonylamino, 2,4-difluorophenyl, 3-fluoro-4-cyanophenyl, 4-amino-3-carboxyphenyl, 4-amino-3-methoxycarbonylphenyl, 2,4-dichlorophenyl, 3-cyano-5-fluorophenyl, 3-fluoro-4-carbamoylphenyl, 3-carboxy-4-cyanophenyl, 3-phenyl-4-carbamoylphenyl, 4-(2-oxo-1-piperidino)-phenyl, 1-benzyl-pyazol-4-yl, pyrid-2-yl, pyrid-3-yl, pyrid-4-yl, 6-amino-pyrid-3-yl, 6-methoxy-pyrid-3-yl, benzoxazol-2-yl, 3-amino-benzisoxazol-6-yl, 3-amino-benzisoxazol-5-yl, indazol-5-yl, indazol-6-yl, 3-amino-indazol-5-yl, 3-hydroxy-indazol-5-yl, 3-amino-indazol-6-yl, 3-amino-1-methyl-indazol-6-yl, 3-amino-4-fluoro-indazol-6-yl, 3-amino-5-fluoro-indazol-6-yl, 3-amino-7-fluoro-indazol-6-yl, 3-(5-tetrazolyl)-phenyl, 2,3-dihydro-isoindol-1-on-6-yl, quinolin-5-yl, quinolin-6-yl, quinolin-8-yl,

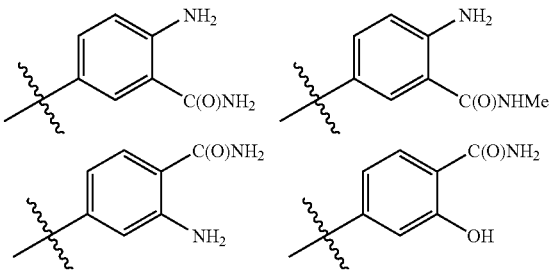

-continued
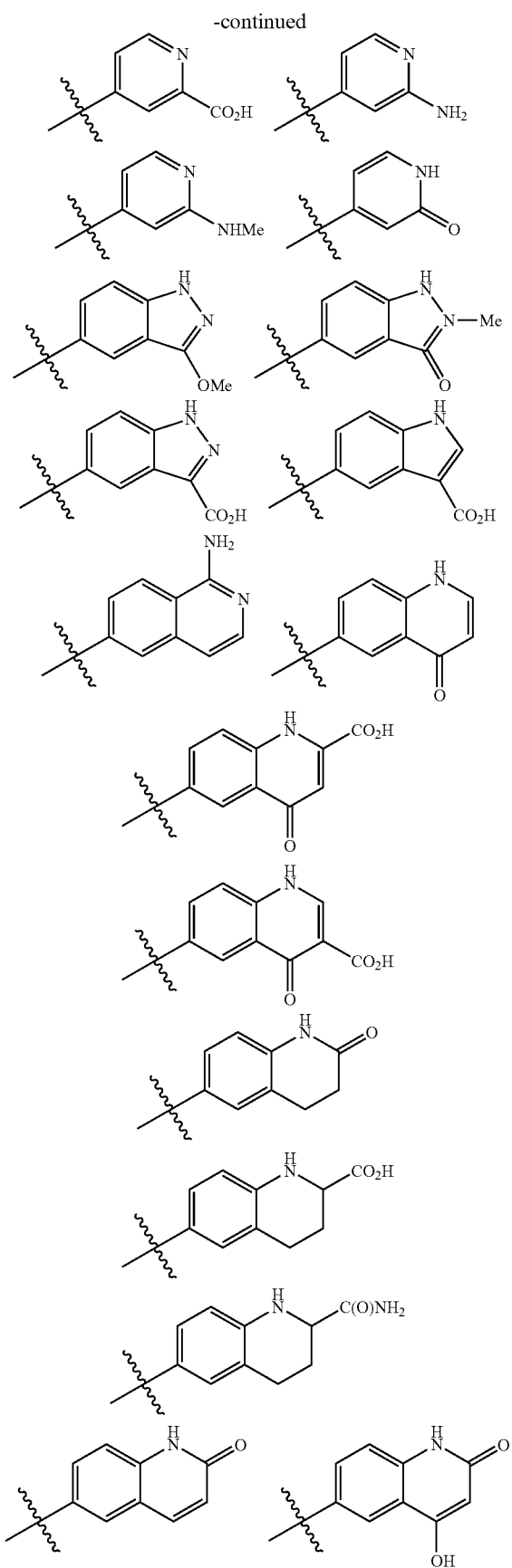
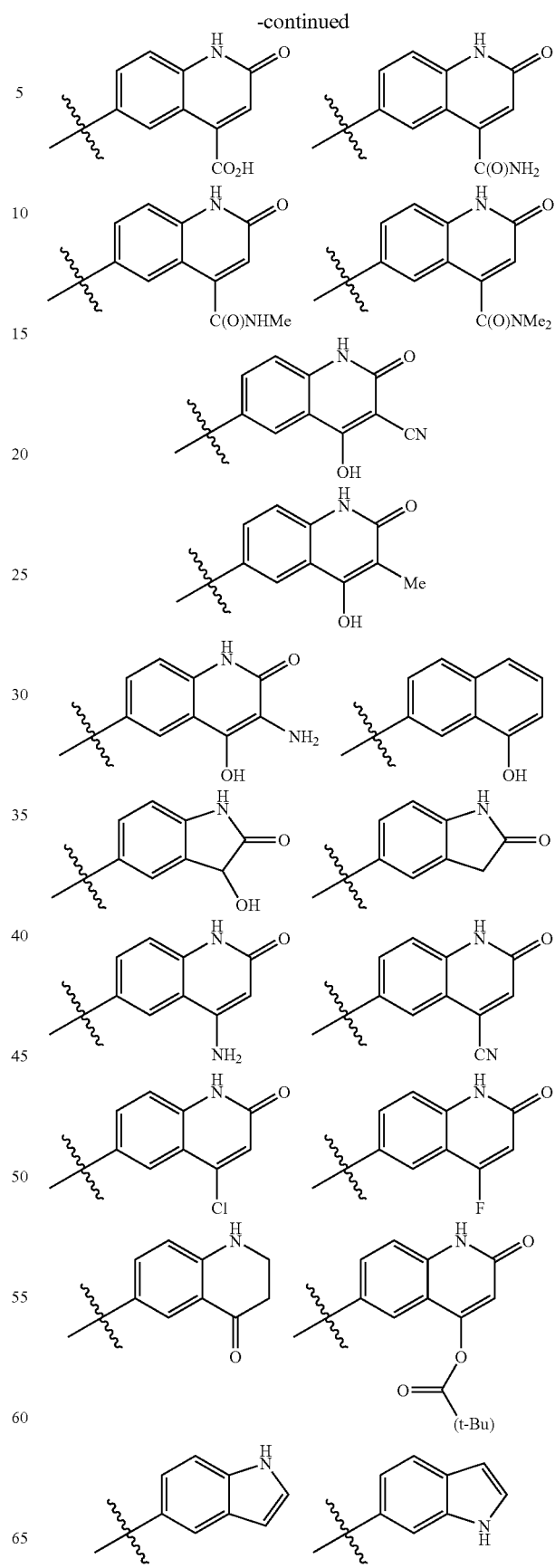

-continued
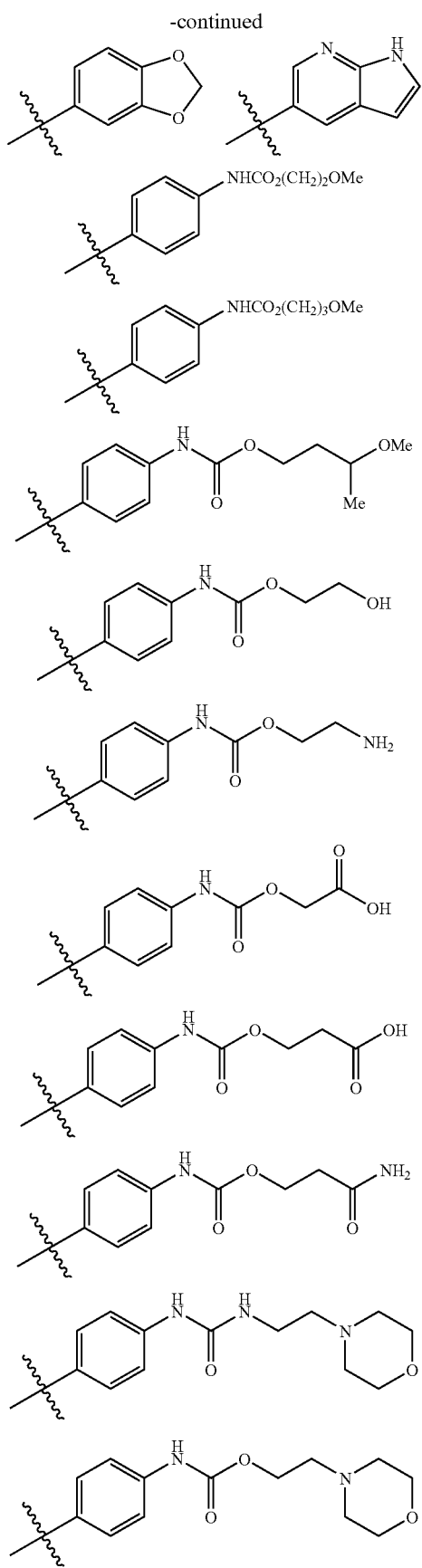
-continued
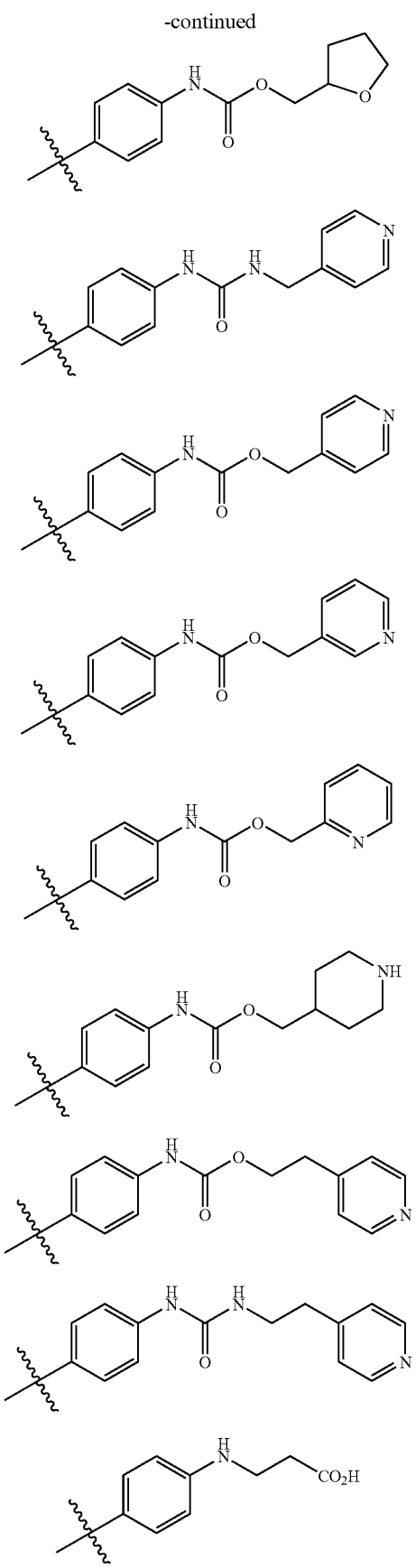

-continued

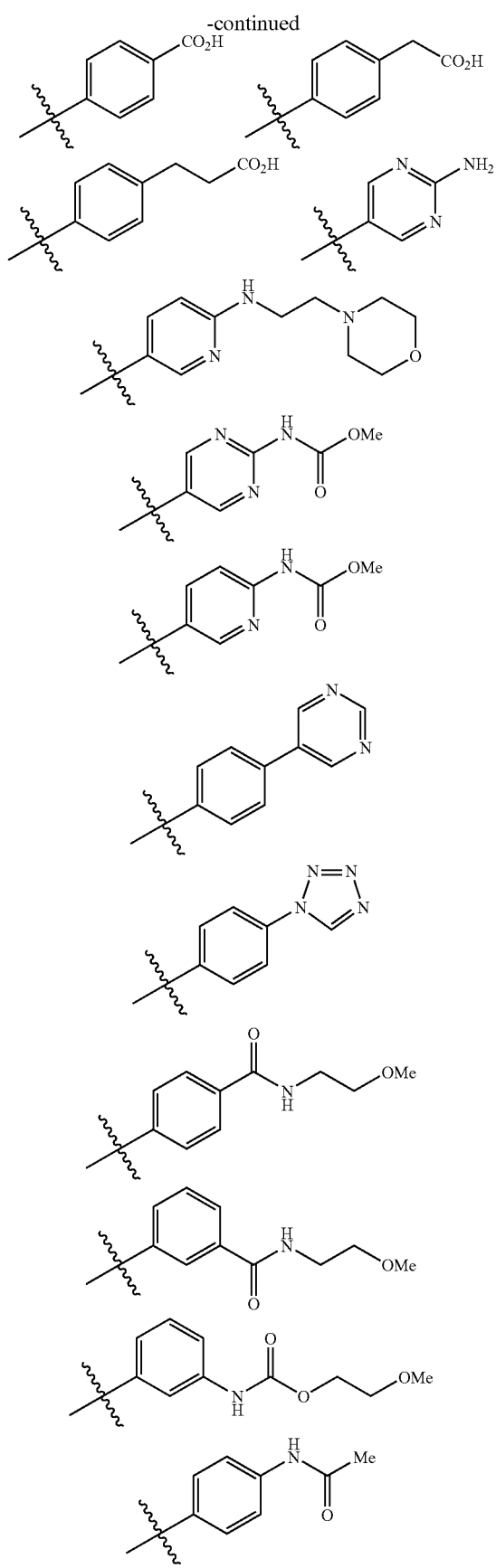

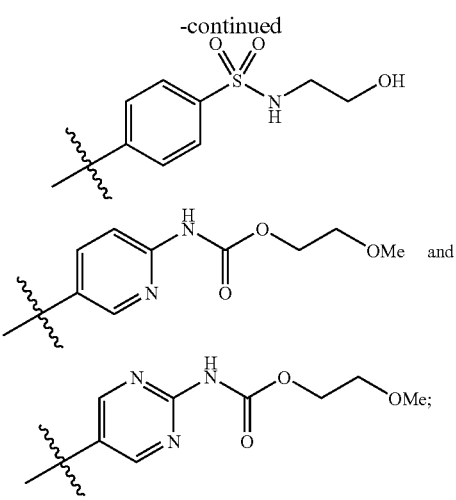

$R^4$ is selected from the group consisting of: H, Me, F, Br, Cl, $CF_3$, $CO_2H$, $CO_2Me$, and $CO_2Et$; and $R^{11}$ is selected from the group consisting of: cyclohexylmethyl, benzyl, phenethyl, 2-fluorobenzyl, 3-fluorobenzyl, 4-fluorobenzyl, 2-chlorobenzyl, 3-chlorobenzyl, 4-chlorobenzyl, 2-bromobenzyl, 3-bromobenzyl, 4-bromobenzyl, 3-carboxybenzyl, 3-carbamoylbenzyl, 3-(N-methylcarbamoyl)-benzyl, 3-(N-ethylcarbamoyl)-benzyl, 3-(N,N-dimethylcarbamoyl)-benzyl, 2-methylbenzyl, 3-methylbenzyl, 4-methylbenzyl, 3-trifluoromethylbenzyl, 4-trifluoromethylbenzyl, 2-aminobenzyl, 3-aminobenzyl, 2-nitrobenzyl, 3-nitrobenzyl, 4-nitrobenzyl, 3-methoxybenzyl, 4-methoxybenzyl, 3-difluoromethoxybenzyl, 2-trifluoromethoxybenzyl, 3-trifluoromethoxybenzyl, 3-methoxycarbonylbenzyl, 3-methylcarbonylaminobenzyl, 3-isobutylaminocarbonyl-benzyl, 3-t-butylcarbonylamino-benzyl, 3-isopentylaminocarbnoyl-benzyl, 3-(ethyl-methyl-carbamoyl)-benzyl, 3-(isopropyl-methyl-carbamoyl)-benzyl, 3-(isobutyl-methyl-carbamoyl)-benzyl, 3-[(2-methoxyethyl)-methyl-carbamoyl]-benzyl, N-methylamino)sulfonyl]-benzyl, 3-(N,N-dimethylaminosulfonyl)-benzyl, and 3-[(2-hydroxyethyl)-methyl-carbamoyl]-benzyl.

6. The compound according to claim 1, wherein:

A is selected from the group consisting of: 3-chlorophenyl, 3-bromophenyl, 3-methylphenyl, 3-methoxyphenyl, 2,5-dichlorophenyl, 5-chloro-2-fluorophenyl, 5-bromo-2-fluorophenyl, 3-chloro-2-fluorophenyl, 2-methyl-5-chlorophenyl, 2-methoxy-5-chlorophenyl, 2-methylthio-5-chlorophenyl, 2-ethylthio-5-chlorophenyl, 2-propylthio-5-chlorophenyl, 2-benzylthio-5-chlorophenyl, 2-amino-5-chlorophenyl, 2-aminomethyl-5-chlorophenyl, 2,6-difluoro-3-methylphenyl, 2-chloro-6-fluoro-3-methylphenyl, 2-fluoro-6-chloro-3-methylphenyl, 2,6-difluoro-3-chlorophenyl, 2,3-dichloro-6-nitrophenyl, 3,4-methylenedioxyphenyl, 2-methoxycarbonyl-5-chlorophenyl, 2-(1,2,3-triazol-1-yl)-5-methylphenyl, 2-(1,2,3-triazol-1-yl)-5-chlorophenyl, 2-(1,2,4-triazol-1-yl)-5-chlorophenyl, 2-(1,2,3-triazol-2-yl)-5-chlorophenyl, 2-[(4-carboxy)-1,2,3-triazol-1-yl]-5-chlorophenyl, 2-[(4-carboxy)-1,2,3-triazol-1-yl]-5-methylphenyl, 2-[(4-ethoxycarbonyl)-1,2,3-triazol-1-yl]-5-chlorophenyl, 2-(tetrazol-1-yl)-5-methylphenyl, 2-(tetrazol-1-yl)-5-chlorophenyl, 2-(tetrazol-1-yl)-3-fluoro-5-chlorophenyl, 2-(tetrazol-1-yl)-3-fluoro-5-methylphenyl, and 2-(5-methyltetrazol-1-yl)-5-chlorophenyl;
$R^3$ is selected from the group consisting of:
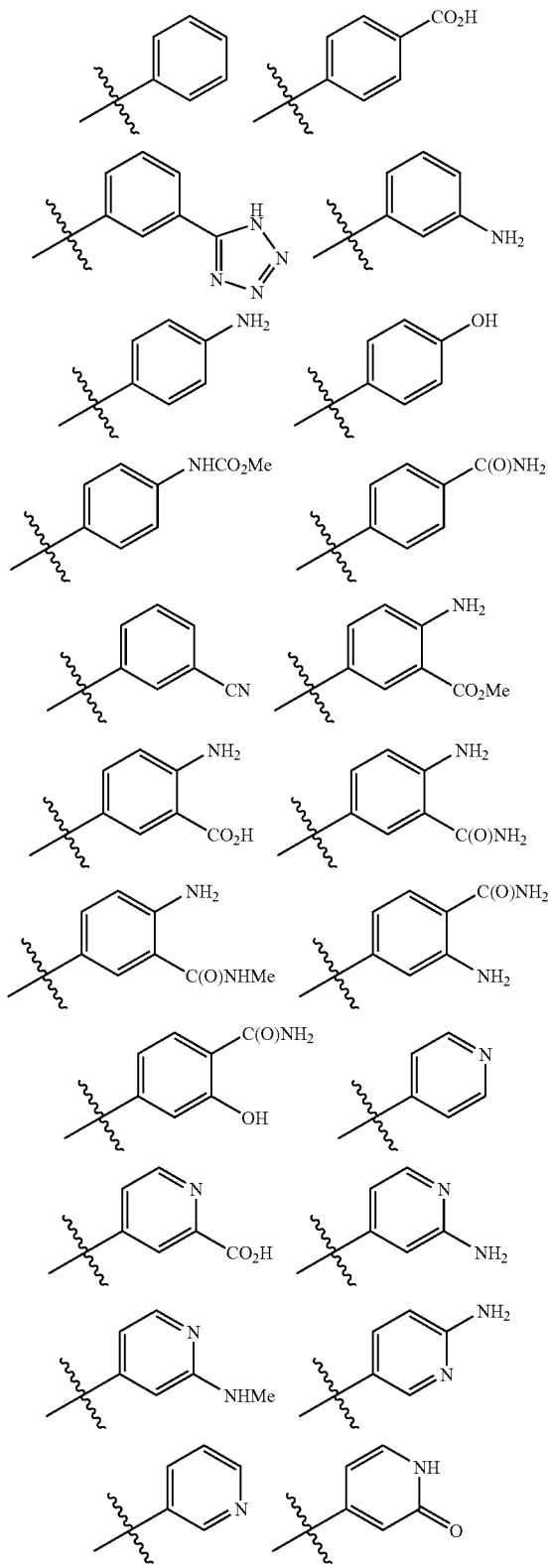
-continued
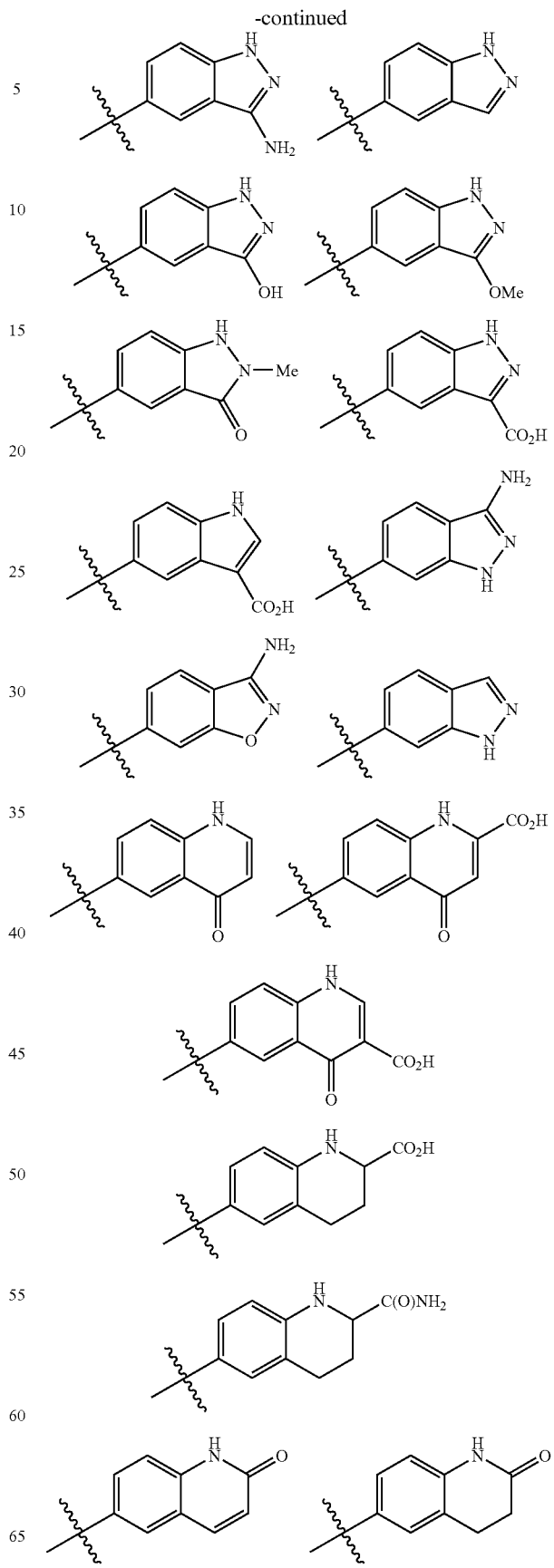

-continued
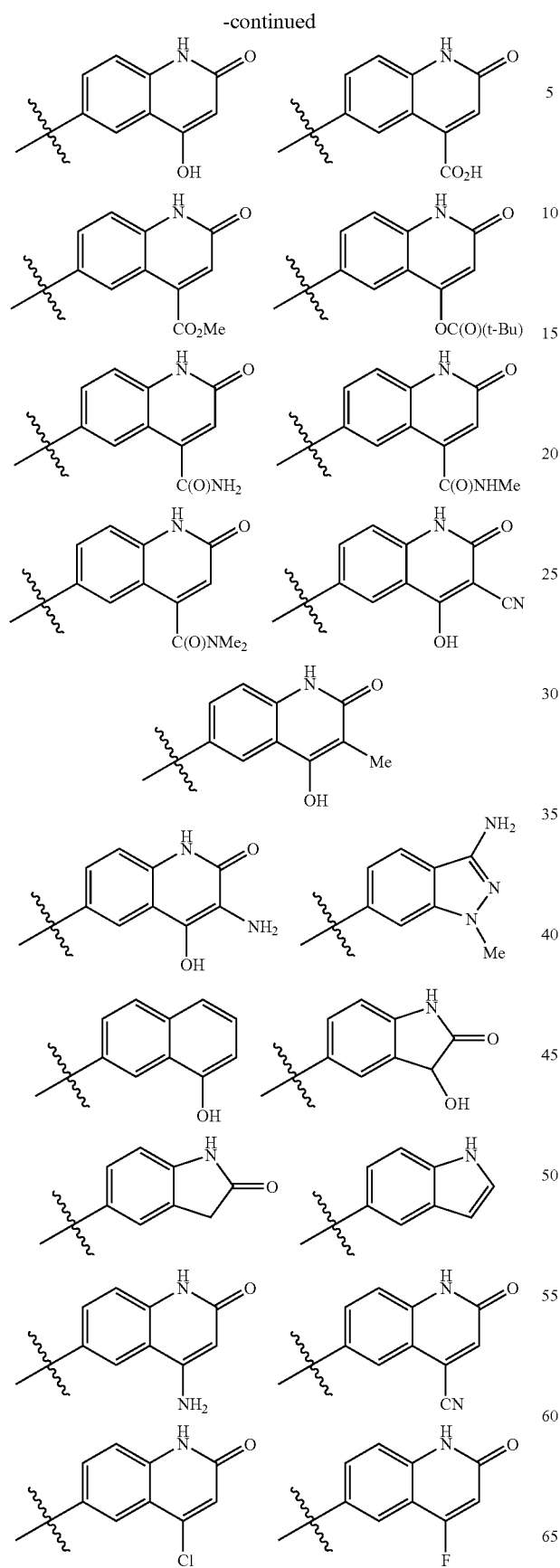
-continued
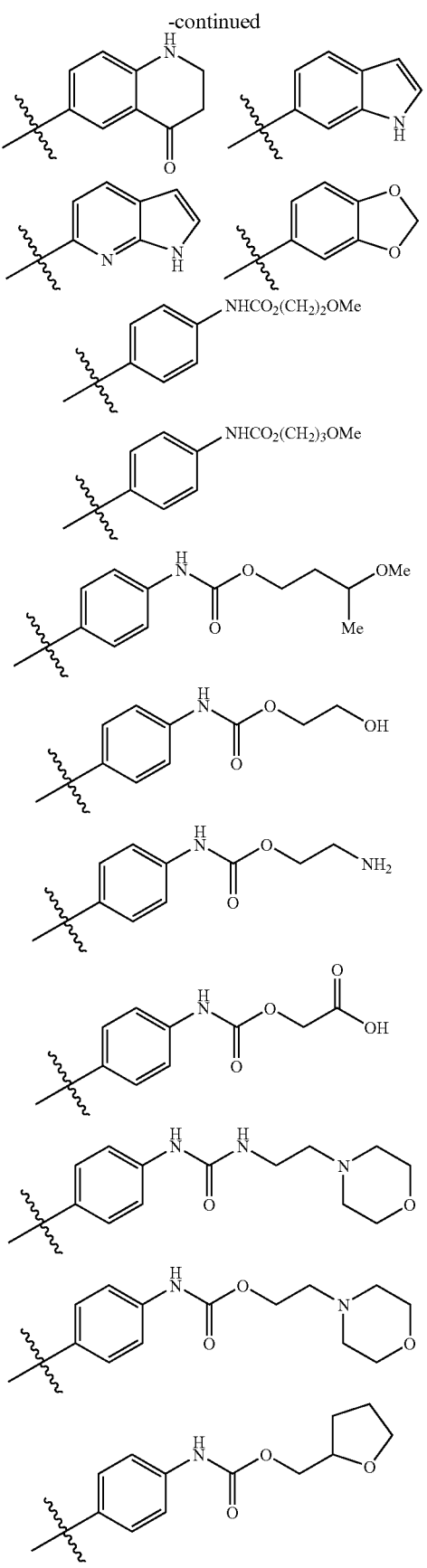

-continued
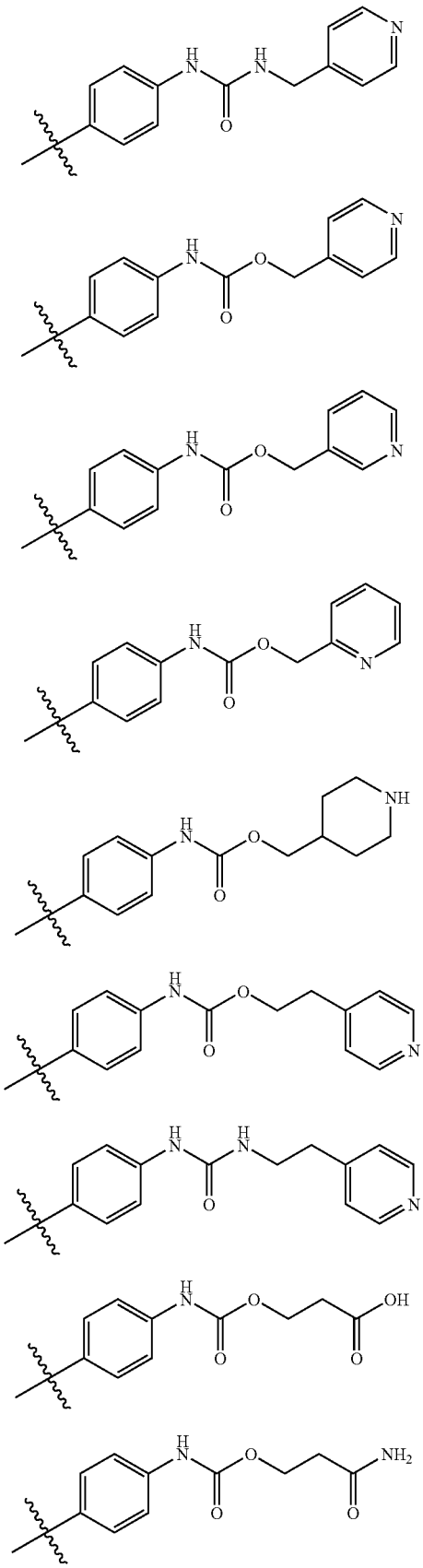
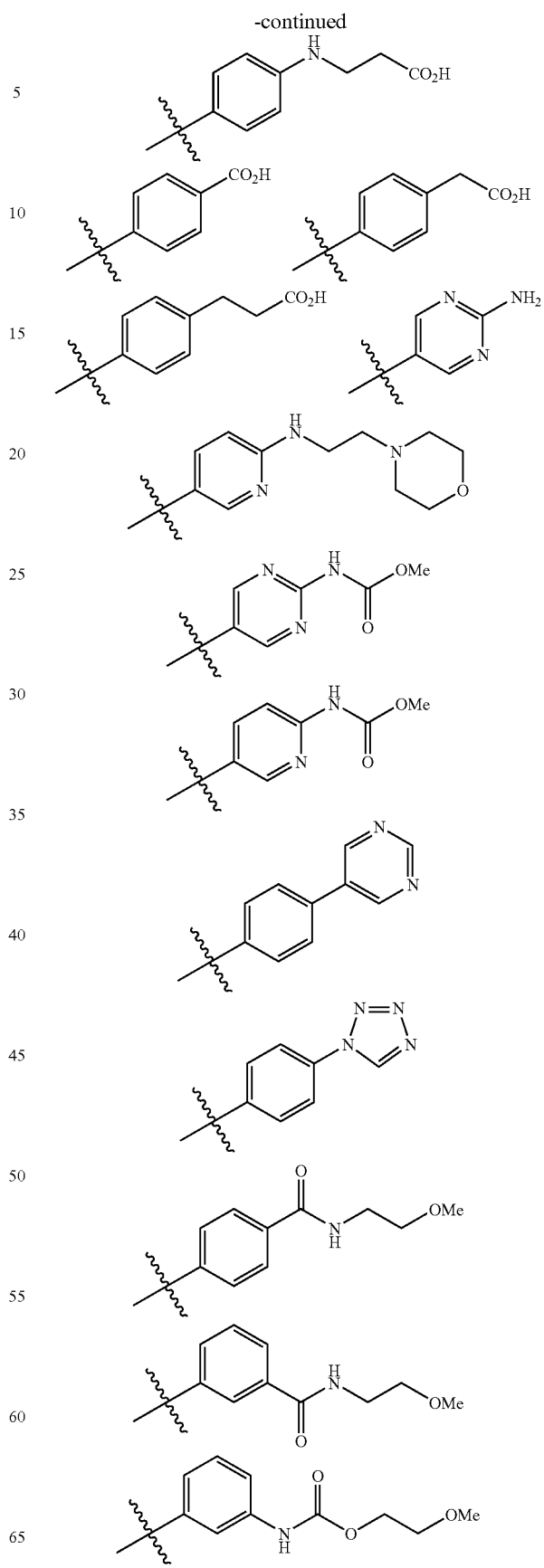

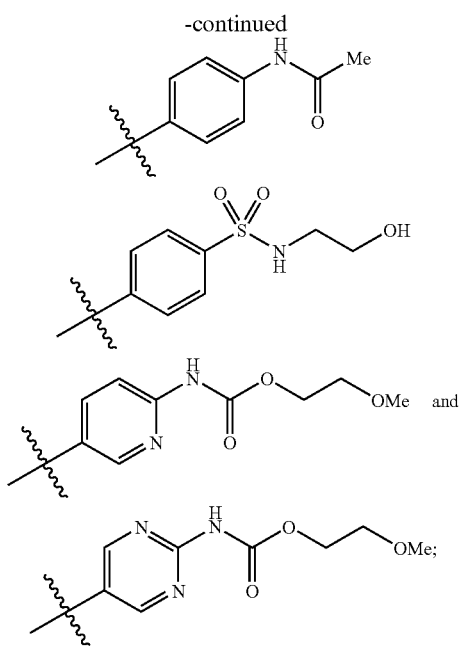

R[4] is selected from the group consisting of H, Me and Cl; and

R[11] is selected from the group consisting of: cyclopropylmethyl, benzyl, 4-fluoro-benzyl, 3-carboxy-benzyl, 3-carbamoyl-benzyl, 3-(N-methylcarbamoyl)-benzyl, 3-(N,N-dimethylcarbamoyl)-benzyl, 4-oxo-cyclohexylmethyl, cyclohexylmethyl, phenethyl, 2-fluorobenzyl, 3-fluorobenzyl, 2-chlorobenzyl, 3-(N-ethylcarbamoyl)-benzyl, 3-methylbenzyl, 4-methylbenzyl, 3-methoxybenzyl, 3-difluoromethoxybenzyl, 3-trifluoromethoxybenzyl, 3-methoxycarbonylbenzyl, 3-methylcarbonylamino-benzyl, 3-(ethyl-methyl-carbamoyl)-benzyl, 3-(isopropyl-methyl-carbamoyl)-benzyl, 3-(isobutyl-methyl-carbamoyl)-benzyl, 3-[(2-methoxyethyl)-methyl-carbamoyl]-benzyl, N-methylamino)sulfonyl]-benzyl, 3-(N,N-dimethylaminosulfonyl)-benzyl, 3-[(2-hydroxyethyl)-methyl-carbamoyl]-benzyl, 1-naphthylmethyl, and 2-naphthylmethyl.

7. A compound is selected from the group consisting of:

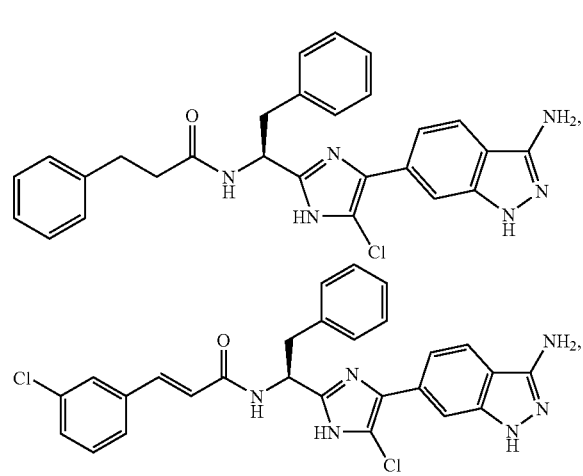

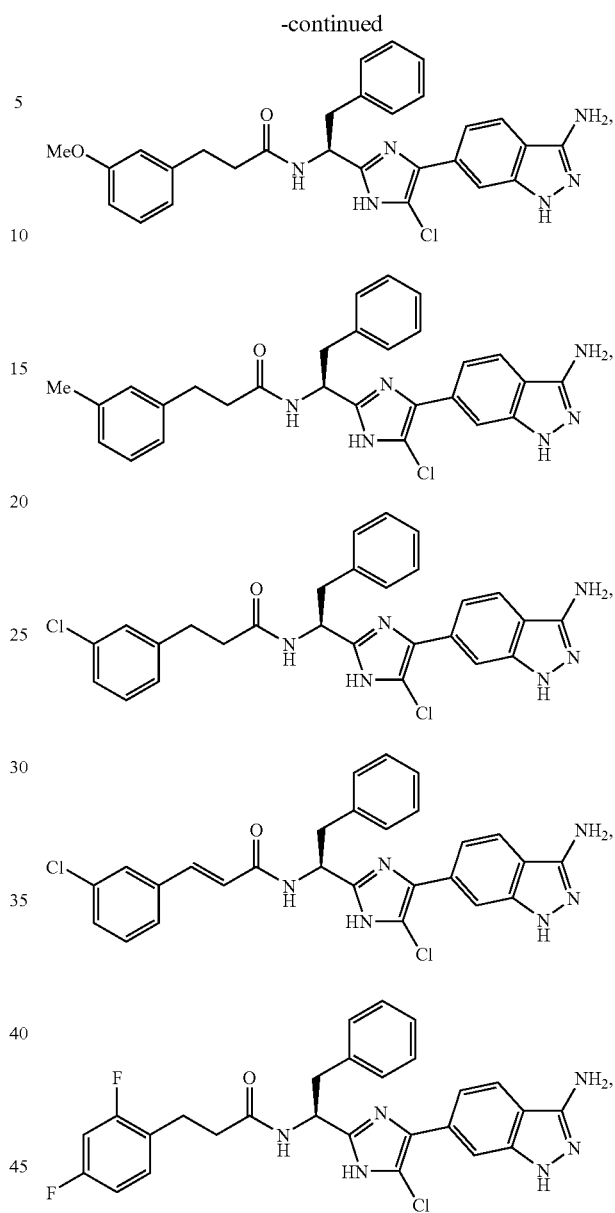

-continued

395
-continued
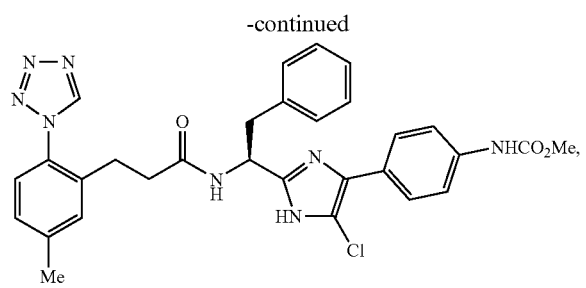
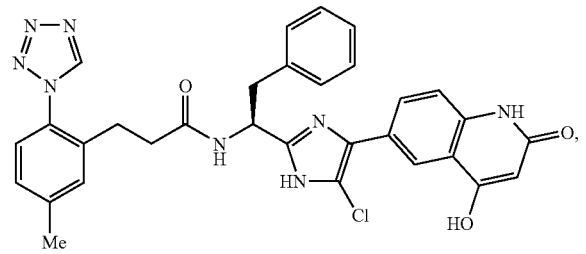
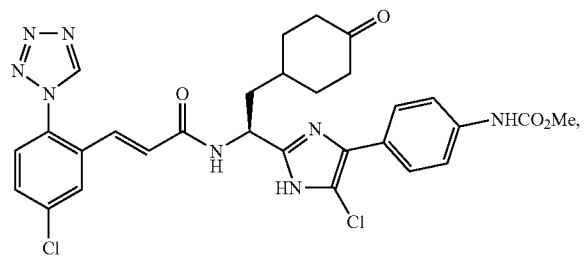
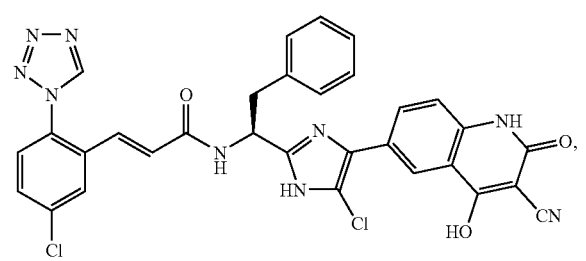
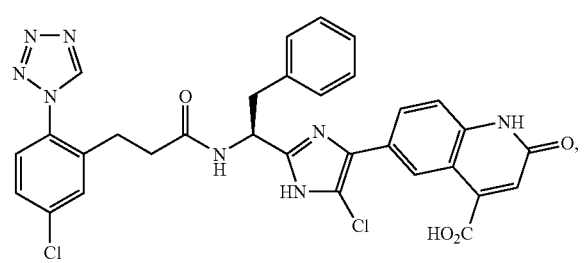
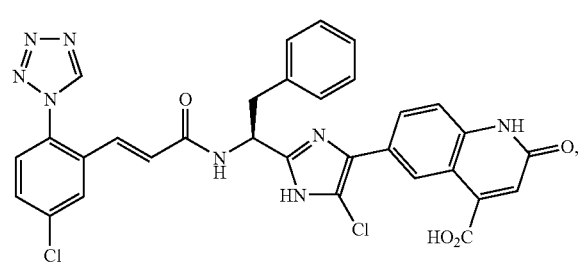
396
-continued
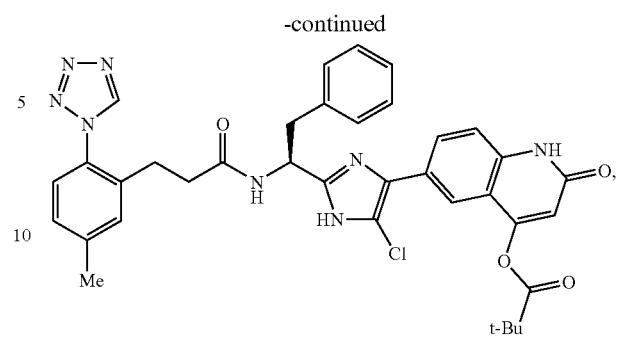
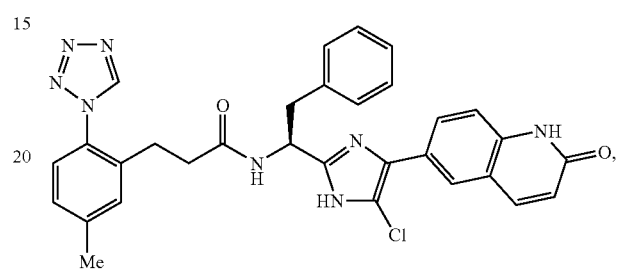
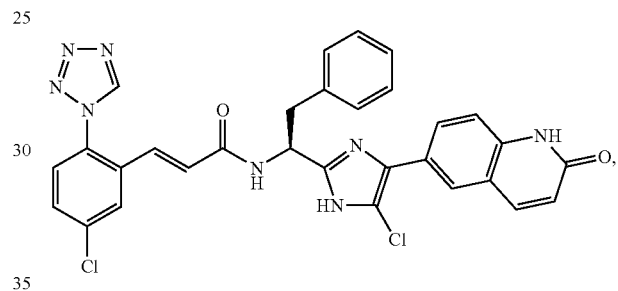
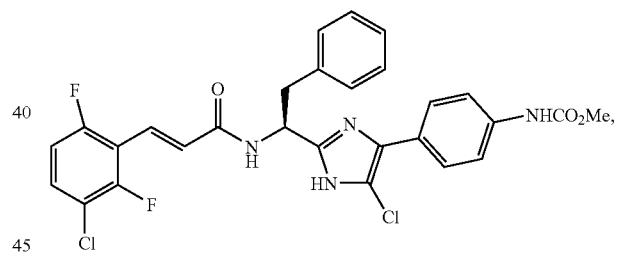
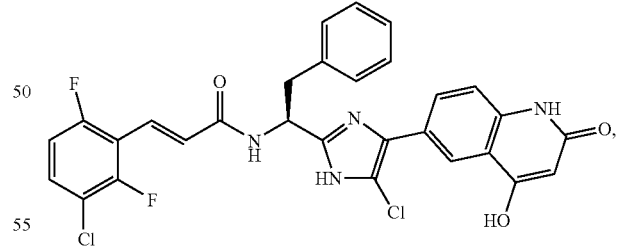
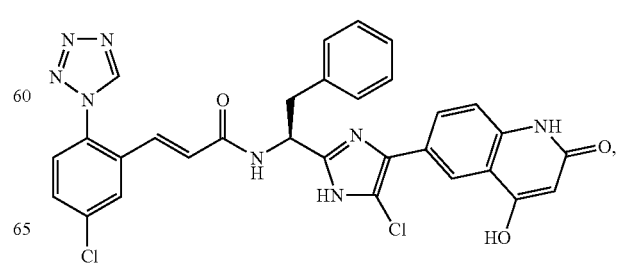

-continued
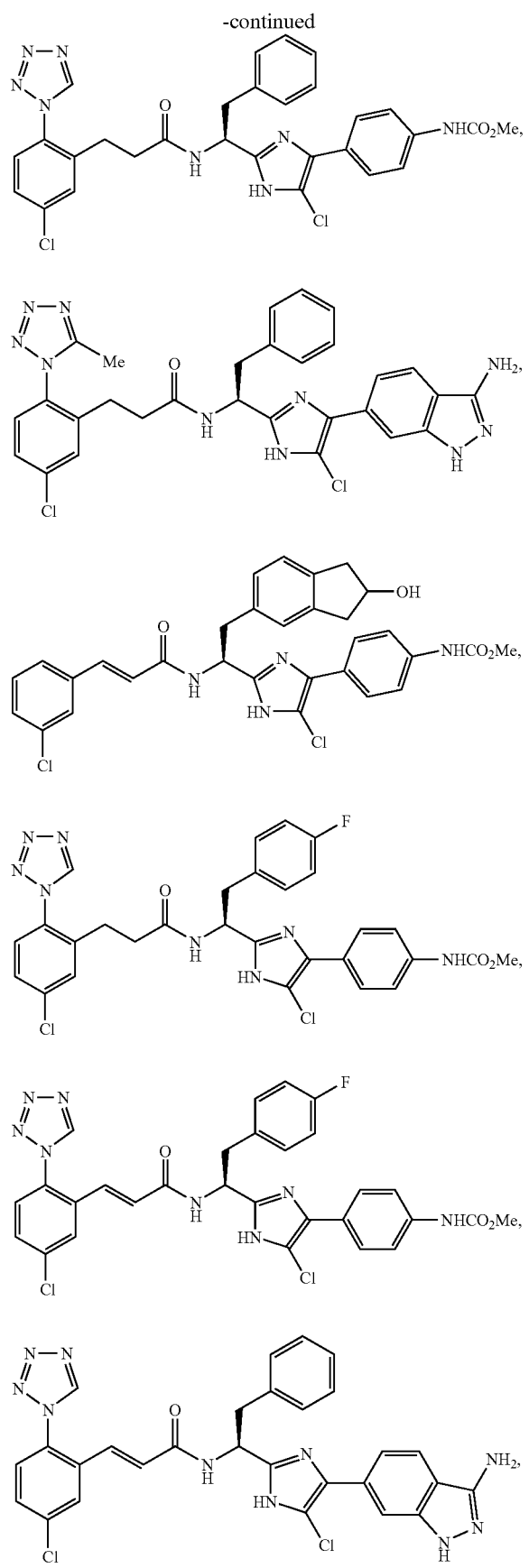
-continued
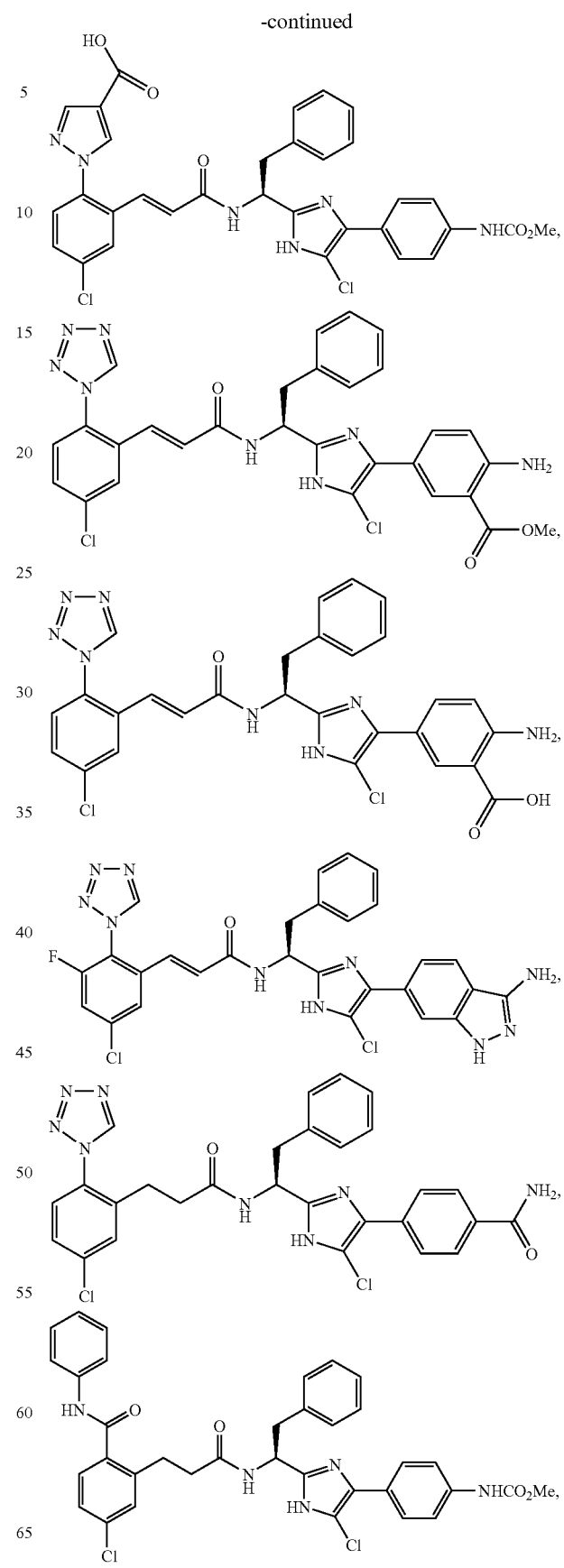

-continued
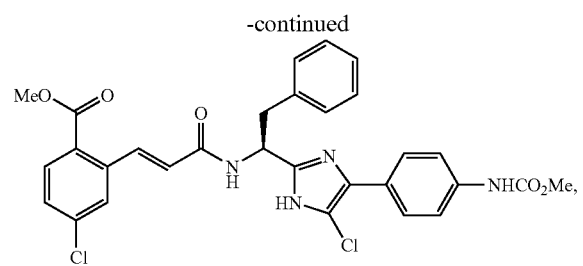
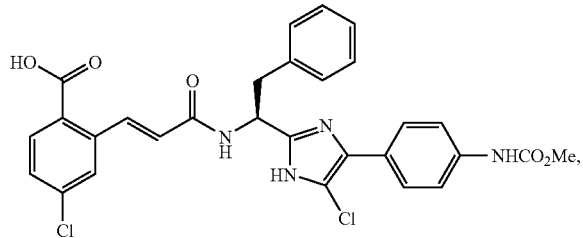
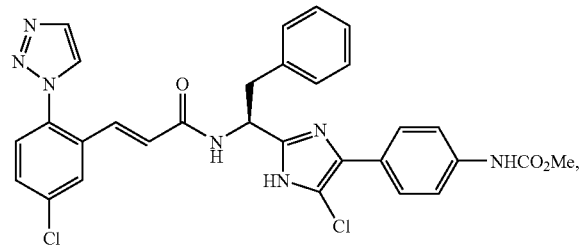
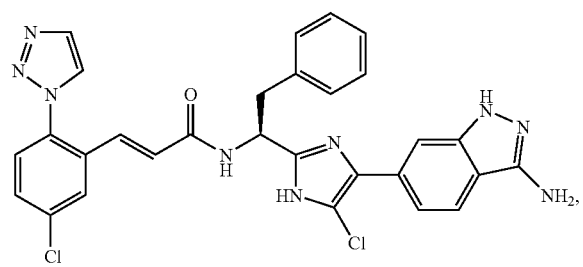
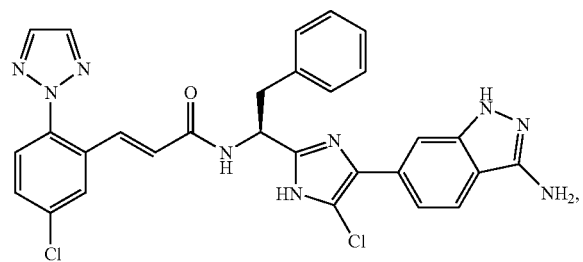
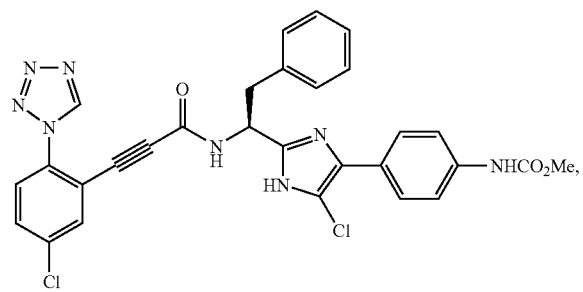
-continued
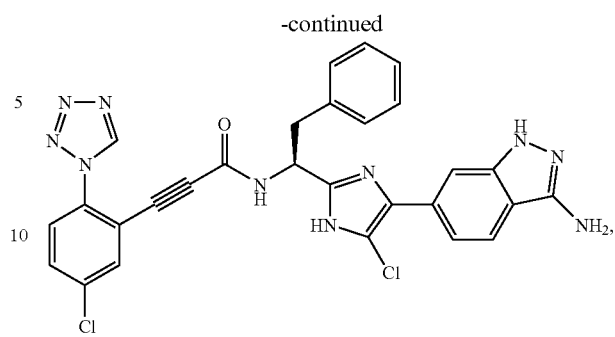
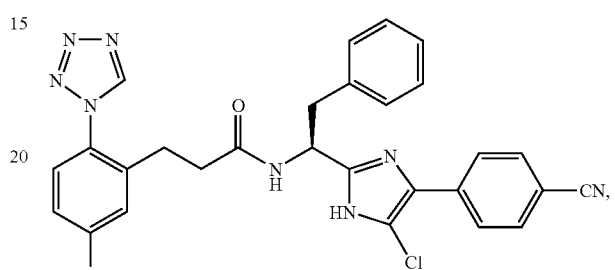
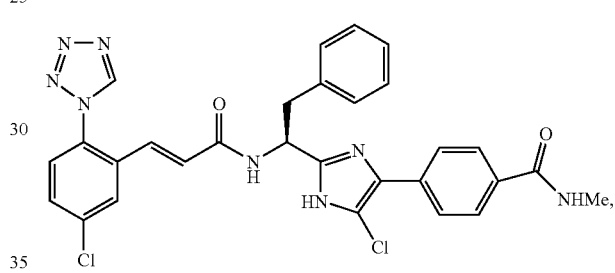
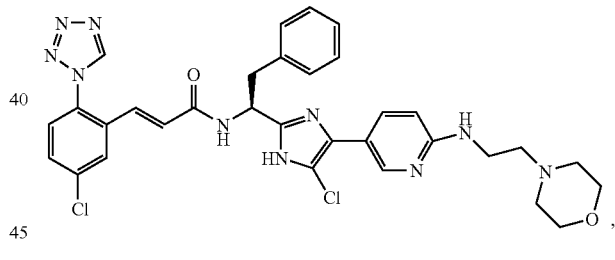
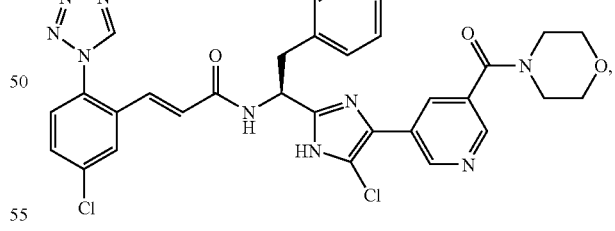
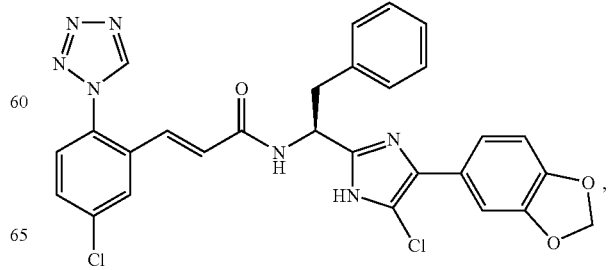

401
-continued
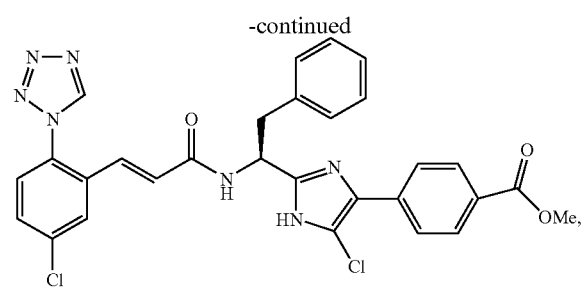
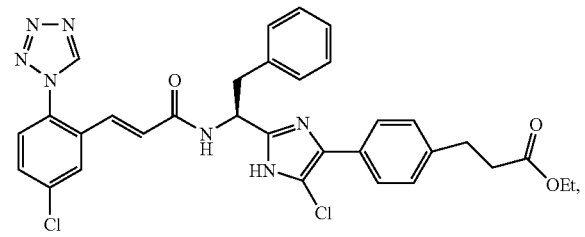
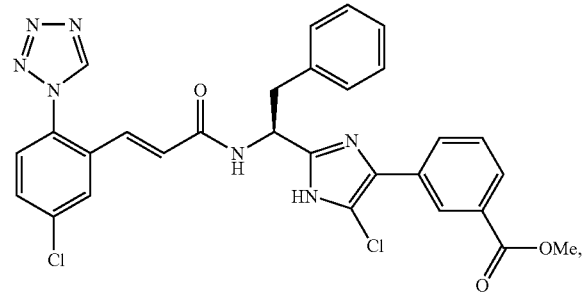
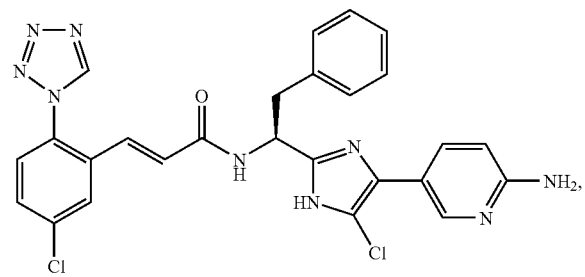
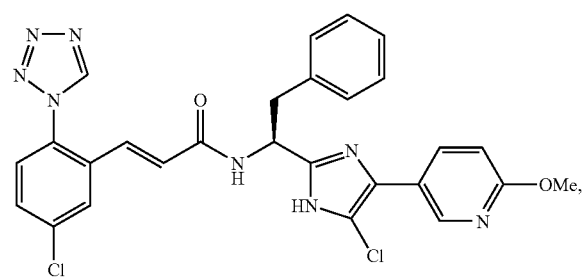
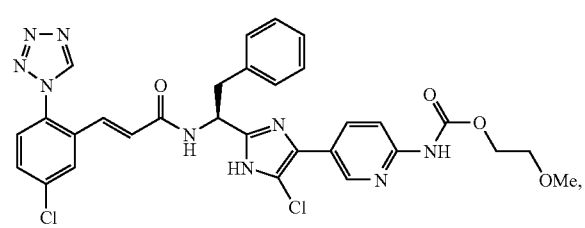
402
-continued
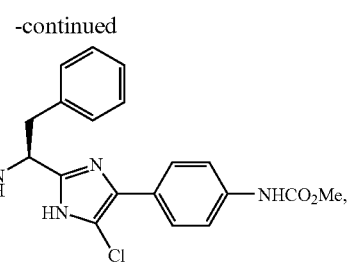
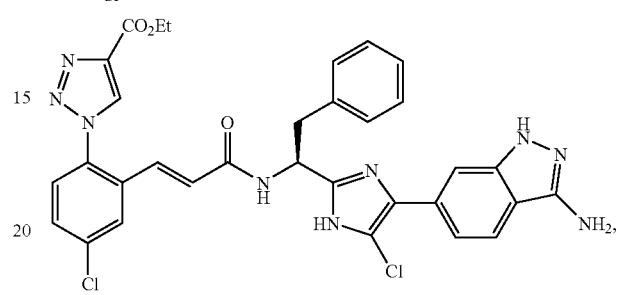
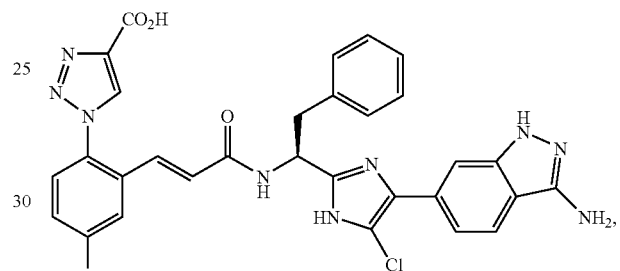
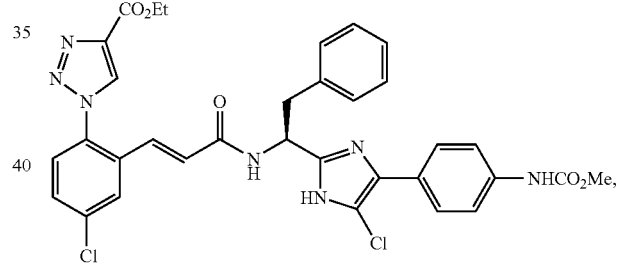
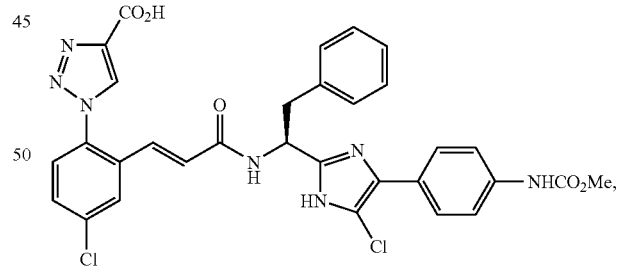
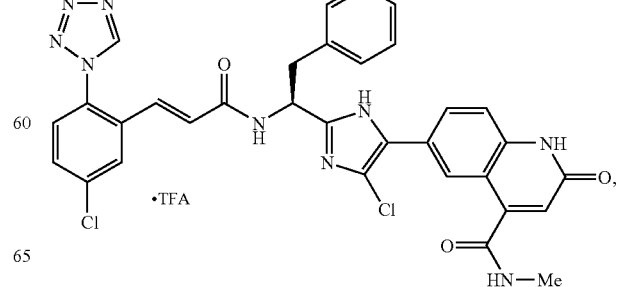

403
-continued
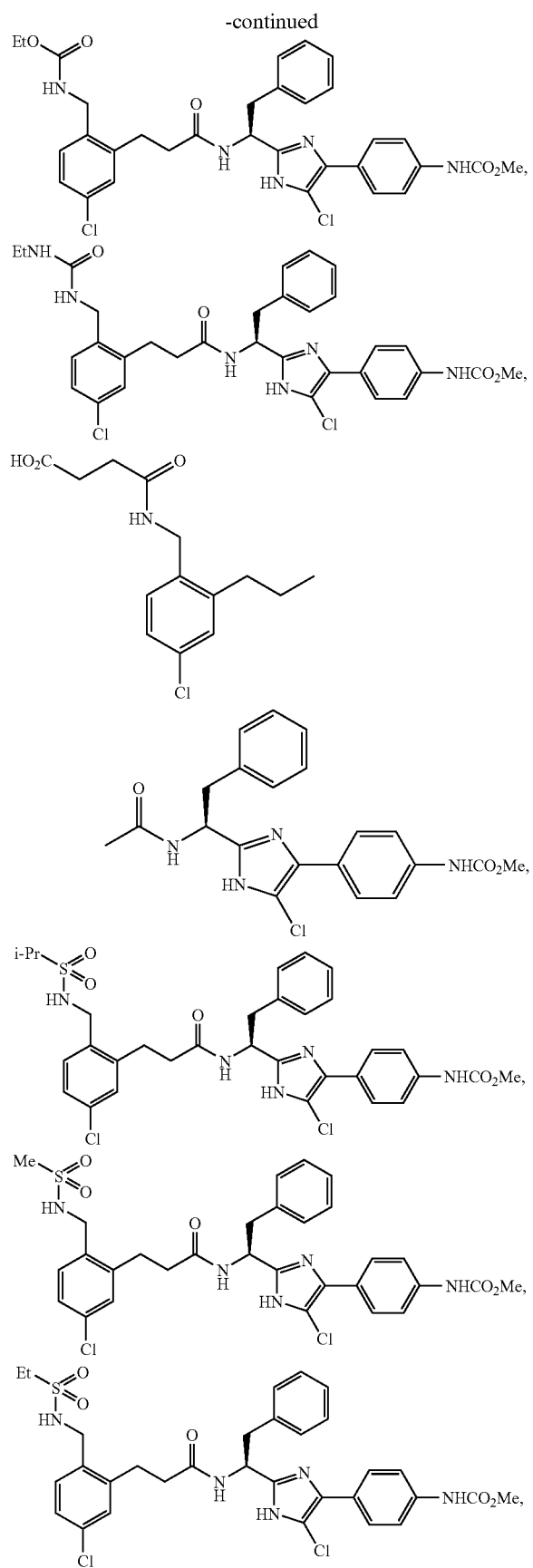
404
-continued
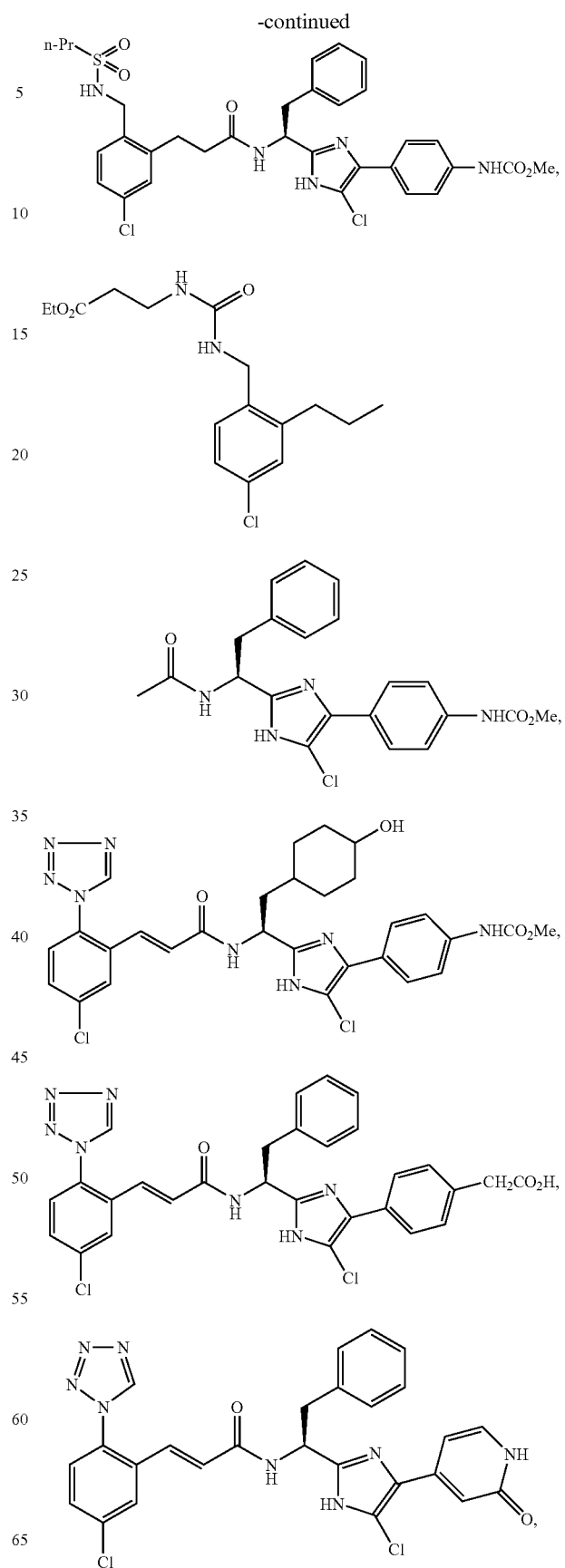

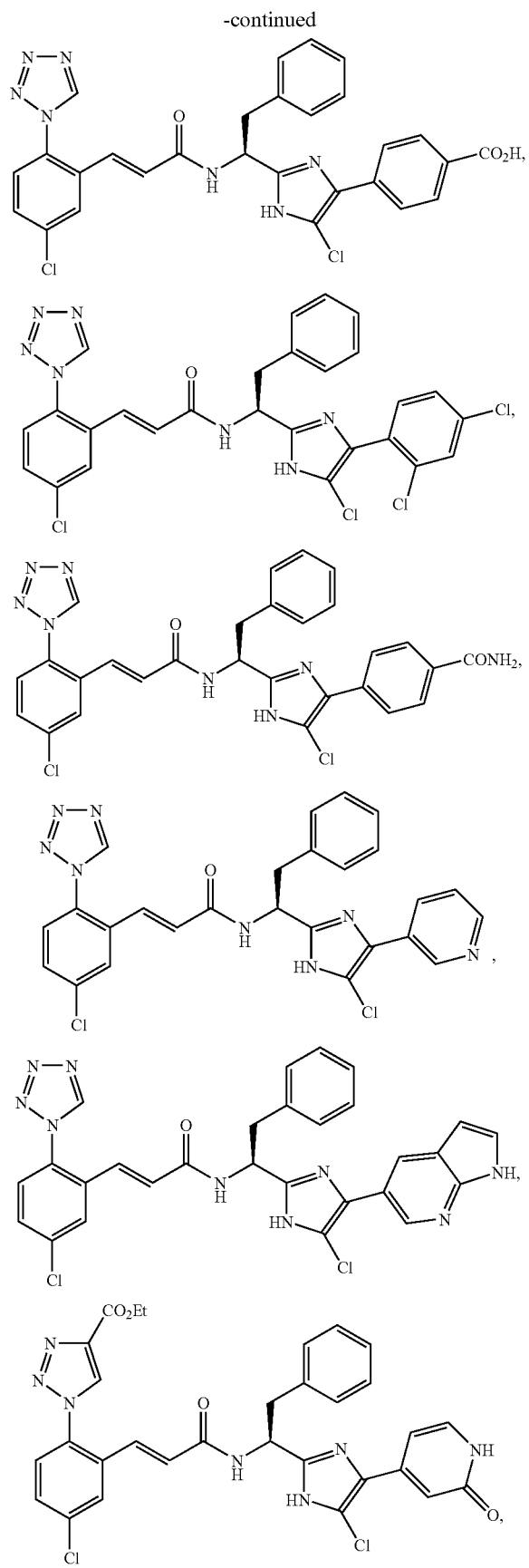
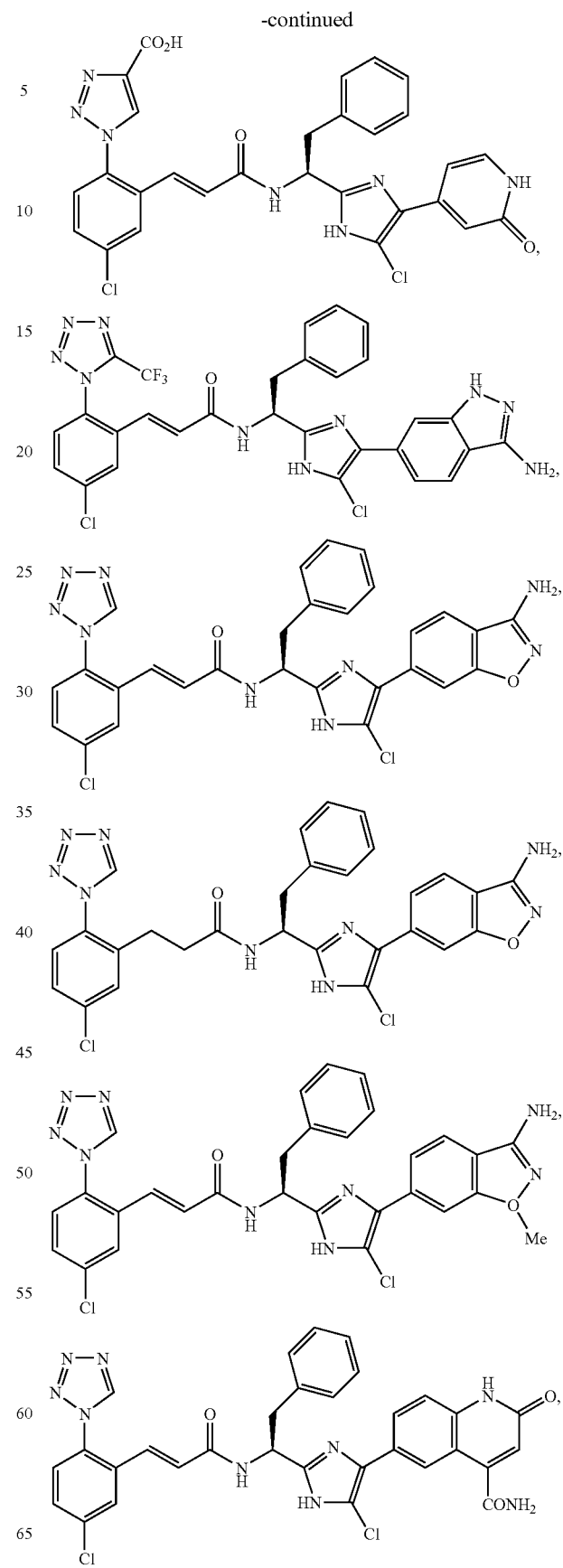

-continued

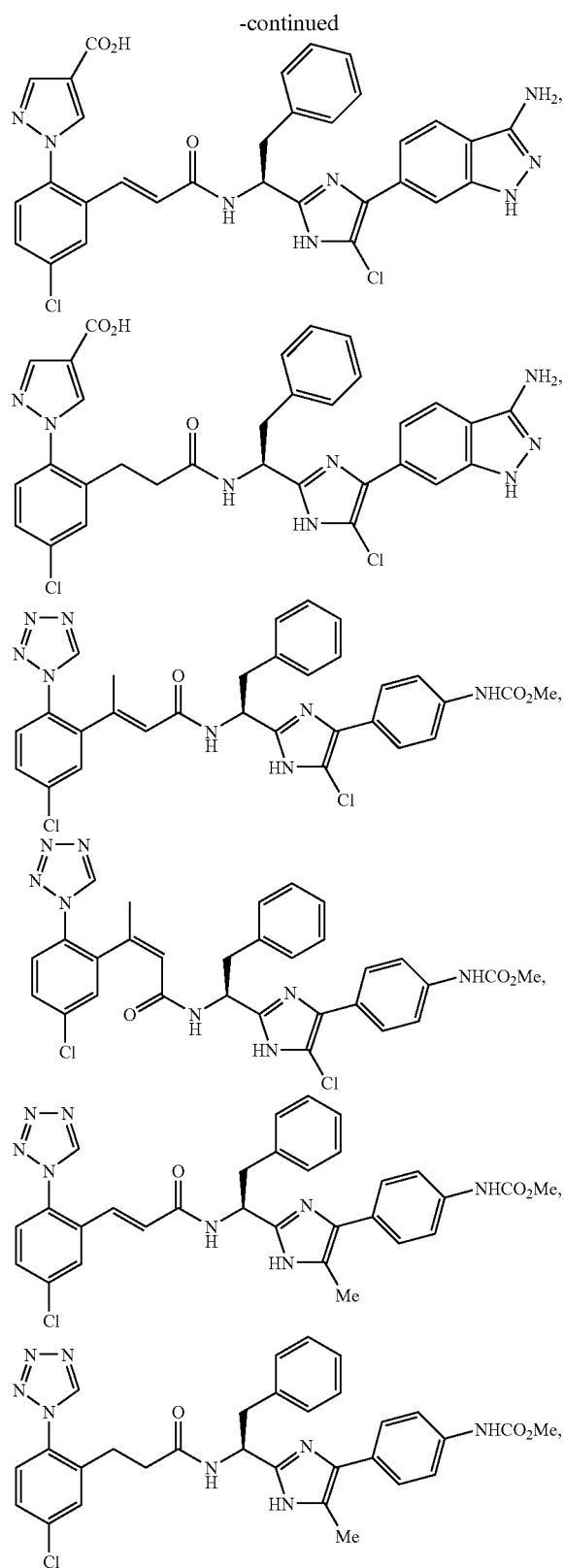

-continued

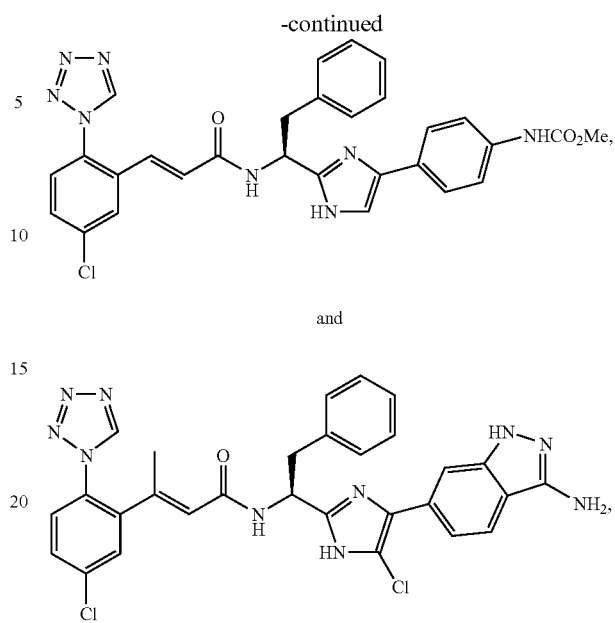

and or a stereoisomer, a tautomer, or a pharmaceutically acceptable salt thereof.

8. A pharmaceutical composition, comprising: a pharmaceutically acceptable carrier and a compound of claim 1, or a stereoisomer, a tautomer, or a pharmaceutically acceptable salt thereof.

9. A pharmaceutical composition, comprising: a pharmaceutically acceptable carrier and a compound of claim 2, or a stereoisomer, a tautomer, or a pharmaceutically acceptable salt thereof.

10. A pharmaceutical composition, comprising: a pharmaceutically acceptable carrier and a compound of claim 3, or a stereoisomer, a tautomer, or a pharmaceutically acceptable salt thereof.

11. A pharmaceutical composition, comprising: a pharmaceutically acceptable carrier and a compound of claim 4, or a stereoisomer, a tautomer, or a pharmaceutically acceptable salt thereof.

12. A pharmaceutical composition, comprising: a pharmaceutically acceptable carrier and a compound of claim 5, or a stereoisomer, a tautomer, or a pharmaceutically acceptable salt thereof.

13. A pharmaceutical composition, comprising: a pharmaceutically acceptable carrier and a compound of claim 6, or a stereoisomer, a tautomer, or a pharmaceutically acceptable salt thereof.

14. A pharmaceutical composition, comprising: a pharmaceutically acceptable carrier and a compound of claim 7, or a stereoisomer, a tautomer, or a pharmaceutically acceptable salt thereof.

* * * * *

UNITED STATES PATENT AND TRADEMARK OFFICE
CERTIFICATE OF CORRECTION

PATENT NO.      : 7,626,039 B2                                        Page 1 of 2
APPLICATION NO. : 11/610027
DATED           : December 1, 2009
INVENTOR(S)     : Donald J. P. Pinto et al.

It is certified that error appears in the above-identified patent and that said Letters Patent is hereby corrected as shown below:

Column 1, First Page (Title)
Line 2, "AYRLPROPYNAMIDE" should read -- ARYLPROPYNAMIDE --.

Column 1
Line 2, "AYRLPROPYNAMIDE" should read -- ARYLPROPYNAMIDE --.

Column 373
Line 6, "—CH$_2$)$_r$C(O)OR$^a$" should read -- —(CH$_2$)$_r$C(O)OR$^a$, --;
Line 17, "—CH$_2$)$_r$NHCO$_2$R$^{3c}$" should read -- —(CH$_2$)$_r$NHCO$_2$R$^{3c}$, --;
Line 31, "—CH$_2$)$_r$OR$^a$," should read -- —(CH$_2$)$_r$OR$^a$, --;
Line 33, "—CH$_2$)$_r$OR$^a$," should read -- —(CH$_2$)$_r$OR$^a$, --; and
Line 53, "—(CH$_2$OR$^a$," should read -- —CH$_2$OR$^a$, --.

Column 375
Line 26, "—CH$_2$CO$_2$Lt," should read -- —CH$_2$CO$_2$Et, --;
Line 26, "—CH$_2$CH$_2$CO$_2$Lt," should read -- —CH$_2$CH$_2$CO$_2$Et, --; and
Line 28, "—NHCO$_2$Lt," should read -- —NHCO$_2$Et, --.

Column 376
Line 41, "—CH$_2$NHCO(CH$_2$)$_2$C$_{02}$H," should read -- —CH$_2$NHCO(CH$_2$)$_2$CO$_2$H, --.

Column 406

Line 46-56, " 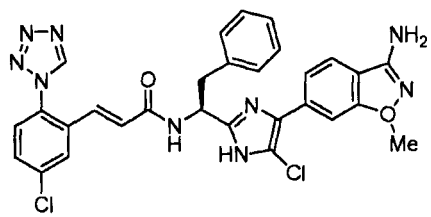 " should read

Signed and Sealed this

Eighth Day of June, 2010

David J. Kappos
*Director of the United States Patent and Trademark Office*

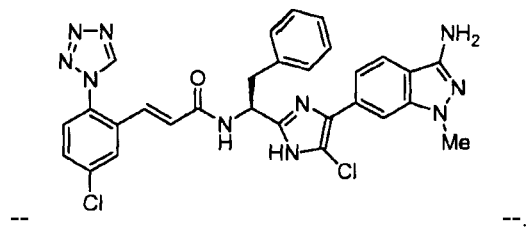
-- -- .